United States Patent [19]
Stinchcomb et al.

[11] Patent Number: 5,817,796
[45] Date of Patent: Oct. 6, 1998

[54] C-MYB RIBOZYMES HAVING 2'-5'-LINKED ADENYLATE RESIDUES

[76] Inventors: Dan T. Stinchcomb, 7203 Old Post Rd.; Kenneth Draper, 4619 Cloud Ct.; James McSwiggen, 4866 Franklin Dr.; Thale Jarvis, 3720 Smuggler Pl., all of Boulder, Colo. 80301

[21] Appl. No.: 435,628

[22] Filed: May 5, 1995

Related U.S. Application Data

[60] Division of Ser. No. 373,124, Jan. 13, 1995, Pat. No. 5,646,042, and a continuation-in-part of Ser. No. 987,132, Dec. 7, 1992, abandoned, Ser. No. 245,466, May 18, 1994, abandoned, and Ser. No. 192,943, Feb. 7, 1994, which is a continuation of Ser. No. 936,422, Aug. 26, 1992, abandoned.

[51] Int. Cl.$^6$ .............................. C07H 21/04; C12Q 1/68
[52] U.S. Cl. ...................... 536/24.5; 536/23.1; 536/23.2; 435/6; 435/91.31; 435/172.3
[58] Field of Search ................................ 435/91.31, 91.1, 435/6, 172.1, 172.3; 536/23.1, 23.2, 24.5, 25.2; 514/44

[56] References Cited

U.S. PATENT DOCUMENTS

| | | | |
|---|---|---|---|
| 4,987,071 | 1/1991 | Cech | 435/91.31 |
| 5,098,890 | 3/1992 | Gewirtz et al. | 514/44 |
| 5,168,053 | 12/1992 | Altman | 514/44 |
| 5,213,580 | 5/1993 | Slepian et al. | 623/1 |
| 5,328,470 | 7/1994 | Nabel et al. | 604/101 |
| 5,532,130 | 7/1996 | Alul | 435/6 |
| 5,583,032 | 12/1996 | Torrence et al. | 435/91.1 |

FOREIGN PATENT DOCUMENTS

| | | |
|---|---|---|
| 2106819 | 9/1993 | Canada . |
| 0519463 | 12/1991 | European Pat. Off. . |
| 9103162 | 3/1991 | WIPO . |
| 9115580 | 10/1991 | WIPO . |
| 9118624 | 12/1991 | WIPO . |
| 9118625 | 12/1991 | WIPO . |
| 9118913 | 12/1991 | WIPO . |
| 9200080 | 1/1992 | WIPO . |
| 9207065 | 4/1992 | WIPO . |
| 9220348 | 11/1992 | WIPO . |
| 9302654 | 2/1993 | WIPO . |
| 9308845 | 5/1993 | WIPO . |
| 9309789 | 5/1993 | WIPO . |
| 9315187 | 8/1993 | WIPO . |
| 9323569 | 11/1993 | WIPO . |
| 9402595 | 2/1994 | WIPO . |

OTHER PUBLICATIONS

Gewirtz et al. PNAS 93: 3161–3163, 1996.

Rojanasa Kul Adv. Drug Delivery Revs. 18:115–131, 1996.

Akhtar and Juliano, "Cellular Uptake and Intracellular Fate of AntiSense Oligonucleotides," *Trends Cell Biol.* 2:139–144 (1992).

Alitalo et al., "Aberrant Expression of An Amplified c-myb oncogene in two cell lines from a colon carcinoma," *Proc. Natl. Acad. Sci. USA* 81:4534–4538 (1984).

Anfossi et al., "An oligomer complementary to c-myb-encoded mRNA inhibits proliferation of human myeloid leukemia cell lines," *Proc. Natl. Acad. Sci. USA* 86:3379–3383 (1989).

Austin et al., "Intimal Proliferation of Smooth Muscle Cells as an Explanation for Recurrent Coronary Artery Stenosis After Percutaneous Transluminal Coronary Angioplasty," *J. Am. Coll. Cardiol.* 6:369–375 (1985).

Banskota et al., "Insulin, Insulin–Like Growth Factor I and Platelet–Derived Growth Factor Interact Additively in the Induction of the Protooncogene c-myc and Cellular Proliferation in Cultured Bovine Aortic Smooth Muscle Cells," *Molec. Endocrinol.*, 3:1183–1190 (1989).

Barinaga, "Gene Therapy for Clogged Arteries Passes Test in Pigs," *Science* 265–738 (1994).

Belknap et al., "Transcriptional Regulation in Vascular Cells; Genetically Modified Animals," *J. Cell. Biochem.* S18A:277 (1994).

Bennett et al., "Cationic Lipids Enhance Cellular Uptake and Activity of Phosphoropthioate Antisense Oligonucleotides," *Mol. Pharmacology* 41:1023–1033 (1992).

Biotech Abstracts Act. #91–00050 EP 388758 (Sep. 26, 90).

Biro et al., "Inhibitory Effects of Antisense Oligodeoxynucleotides targeting c-myc mRNA on smooth muscle cell proliferation and migration," *Pro. Natl. Acad. Sci. USA*, 90:654–658 (1993).

Blam et al., "Addition of Growth Hormone Secretion Signal to Basic Fibroblast Growth Factors Results in Cell Transformation and Secretion of Aberrant Forms of the Protein," *Oncogene* 3:129–136 (1988).

Brown et al., "Expression of the c-myb Proto–oncogene in Bovine Vascular Smooth Muscle Cells," *J. Biol. Chem.* 267:4625–4630 (1992).

Bywater et al., "Expression of Recombinant Platelet–Derived Growth Factor A–Chain and B–Chaim Homodimers in Rat Cells and Human Fibroblastic Reveals Differences in Protein Processing and Autocrine Effects," *Mol. Cell Biol.* 8:2753–2762 (1988).

Calabretta et al., "Normal and Leukemic Hematopoietic Cells Manifest Differential Sensitivity to Inhibitory Effects of c-myb Antisense Oligodeoxynucleotides: An in vitro study relevant to bone marrow purging," *Proc. Natl. Acad. Sci. USA*, 88:2351–2355 (1991).

Califf et al., "Restenosis: The Clinical Issues," in *Textbook of Interventional Cardiology*, E.J. Topol, ed.. W. B. Saunders, Philadelphia, pp. 363–394 (1990).

Cameron and Jennings, "Specific Gene Suppression by Engineered Ribozymes in Monkey Cells." *Proc. Natl. Acad. Sci. USA* 86:9139 (1989).

Carter, "Adeno–Associated Virus Vectors," *Curr Opi. Biotech.* 3:533–539 (1992).

Castanatto et al., "Antisense Catalytic RNAs as Therapeutic Agents," *Adv. in Pharmacol.* 25:289–317 (1984).

(List continued on next page.)

*Primary Examiner*—John L. LeGuyader
*Attorney, Agent, or Firm*—Lyon & Lyon LLP

[57] ABSTRACT

Enzymatic nucleic acid molecules which cleave c-myb RNA or other RNAs associated with restenosis or cancer.

3 Claims, 24 Drawing Sheets

OTHER PUBLICATIONS

Chen, "Multitarget–Ribozyme Directed to Cleave at up to Nine Highly Conserved HIV–1 env RNA Regions inhibits HIV–1 Replication–Potential Effectiveness Against Most Presently Sequenced HIV–1 Isolates," *Nucleic Acids Res.* 20:4581–4589 (1992).

Chomcyzynski and Sacchi, "Single Step Method of RNA Isolation by Acid Guanidinum Thiocyanate–Phenol–Chloroform Extraction," *Analytical Biochem.* 162:156–159 (1987).

Chowrira and Burke, "Extensive Phosphorothioate Substitution Yields Highly Active and Nuclease–Resistant Hairpin Ribozymes," *Nucleic Acids Res.* 20:2835–2840 (1992).

Chowrira et al., "In Vitro and in Vivo Comparison of Hammerhead Hairpin, and Hepatitis Delta Virus Self–Processing Ribozyme Cassettes," *J. Biol. Chem.* 269:25856–25864 (1994).

Chuat and Galibert, "Can Ribozymes be Used to Regulate Procaryote Gene Expression?" *Biochem. and Biophys. Res. Comm.* 162–1025 (1989).

Cleary et al. "Cloning and Structural Analysis of cDNAs For bcl–2 And A Hybrid bcl–2/Immunoglobulin Transcript Resulting From the t(14;18) Traslocation," *Cell* 47:199–28 (1986).

Clowes et al., "Kinetics of Cellular Proliferation After Arterial Injury," *Lab Invest.* 49:327–333 (1983).

Collins and Olive, "Reaction Conditions and Kinetics of Self–Cleavage of a Ribozyme Derived From *Neurospora* VS RNA," *Biochemistry* 32:2795–2799 (1993).

Cotten et al., "High–Efficiency Receptor–Mediated Delivery of Small and Large (48 kilobase Gene Constructs Using the Endosome–Disruption Activity of Defective or Chemically Inactivated Adenovirus Particles," *Proc. Natl. Acad. Sci. USA* 89:6094–6098 (1992).

Cotten et al. "Transferrin–Polycation–Mediated Introduction of DNA into Human Leukemic Cells: Stimulation by Agents that Affect the Survival of Transfected DNA or Modulate Transfetrin Receptor Levels" (Abstract) *Proc. Acad. Sci. USA* 87:4033–4037 (1990).

Cotten et al., "Chicken Adenovirus (CELO Virus) Particles Augment Receptor–Mediated DNA Delivery to Mammalian Cells and Yield Exceptional Levels of Stable Transformants," *J. Virol.* 67:3777–3785 (1993).

Cristiano et al., "Hepatic Gene Therapy: Adenovirus Enhancement of Receptor–Mediated Gene Delivery and Expression in Primary Hepatocytes," *Proc. Natl. Acad. Sci. USA* 90:2122–2126 (1993).

Curiel et al., "Adenovirus Enhancement of Transferrin––Polylysine–Mediated Gene Delivery," *Proc. Natl. Acad. Sci. USA*, 88:8850–8854 (1991).

Dropulic et al., "Functional Characterization of a U5 Ribozyme: Intracellular Suppression of Human Immunodeficiency Virus Type I Expression," *J Virol.* 66:1432–1441 (1992).

Ege et al., "Enhancement of DNA–Mediated Gene Transfer by Inhibitors of Autophagic–Lysosomal Function," *Exp. Cell Res.* 155:9–16 (1984).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 1990).

Ferguson et al., "Compensation for Treating Wounds to Inhibit Scar Tissue—Contains Agent Esp. Antibody, Which Selectively Neutralises Fibrotic Growth Factors," WPI Acc#92:3659974/44.

Ferns et al., "Inhibition of Neointimal Smooth Muscle Accumulation After Angioplasty by an Antibody to PDGF," *Science* 253:1129–1132 (1991).

Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–2872 (1993).

Garratt et al., "Differential Histopathology of Primary Atherosclerotic and Restenotic Lesions in Coronary Arteries and Saphenous Vein Bypass Grafts: Analysis of Tissue Obtained From 73 Patients by Directional Atherectomy," *J. Am. Coll. Cardio.* 17:442–428 (1991).

Goldberg et al., "Vascular Smooth Muscle Cell Kinetics: A New Assay for Studying Patterns of Cellular Proliferation in vivo," *Science* 205:920–922 (1979).

Griffin and Baylin, "Expression of the c–myb Oncogene in Human Small Cell Lung Carcinoma," *Cancer Res.* 45:272–275 (1985).

Grotendorst et al., "Attachment of Smooth Muscle Cells to Collagen and Their Migration Toward Platelet–Derived Growth Factor," *Proc. Natl. Acad. Sci. USA* 78:3669–3672 (982).

Guerrier–Takada et al., "The RNA Moiety of Ribonuclease P Is the Catalytic Subunit of the Enzyme," *Cell* 35:849 (1983).

Hajjar et al., "Tumor Necrosis Factor–Mediated Release of Platelet–Derived Growth Factor From Cultured Endothelial Cells," *J. Exp. Med.* 166:235–245 (1987).

Hampel and Tritz, "RNA Catalytic Properties of the Minimum (–)s TRSV Sequence," *Biochemistry* 28:4929–4933 (1989).

Hampel et al., "'Hairpin'Catalytic RNA Model: Evidence for Helices and Sequence Requirement for Substrate RNA," *Nucleic Acids Research* 18:299–304 (1990).

Harris et al., "Receptor–Mediated Gene Transfer to Airway Epithelial Cells in Primary Culture," *Am. J. Respir. Cell Mol. Biol.*, 9:441–447 (1993).

Haseloff and Gerlach, "Simple RNA Enzymes with New and Highly Specific Endoribonuclease Activities," *Nature* 334:585–591 (1988).

Herschlag, "Implications of Ribozyme Kinetics for Targeting the Cleavage of Specific RNA Molecules in vivo: More Isn't Always Better," *Proc. Natl. Acad. Sci. USA* 88:6921–5 (1991).

Hertel et al., "Numbering System for the Hammerhead," *Nucleic Acids Res.* 20:3252 (1992).

Higashiyama et al., "A Heparin–Biding Growth Factor Secreted by Macrophage–Like Cells That is Related to EFG," *Science* 251:936–939 (1991).

Jaeger et al., "Improved Predictions of Secondary Structures for RNA," *Proc. Natl. Acad. Sci. USA* 86:7706–7710 (1989).

Jeffries and Symons, "A Catalytic 13–mer Ribozyme," *Nucleic Acids Research* 17:1371 (1989).

Kashani–Sabet et al., "Reversal of the Malignant Phenotype by an Anti–ras Ribozyme," *Antisense Research & Development* 2:3–15 (1992).

Kaye et al., "Structure and Expression of the Human L–myc Gene Reveal a Complex Pattern Of Alternative mRNA Processing," *Mol. Cell. Biol.* 8:186–195 (1988).

Kindy and Sonenshein, "Regulation of Oncogene Expression in Cultured Aortic Smooth Muscle Cells," *J. Biol. Chem.* 261:12865–12868 (1986).

Klagsbrun and Edelman, "Biological and Biochemical Properties of Fibroblast Growth Factors," *Arteriosclerosis* 9:269–278 (1989).

Koizumi et al., "Ribozymes Designed to inhibit Transformation of NIH3T3 Cells by the Activated c–Ha–ras Gene," *Gene* 117:179 (1992).

Komuro et al., "Endothelin stimulates c–fos and c–myc expression and proliferation of vascular smooth muscle cells," *FEBS Letters* 238:249–252 (1988).

Kunapuli et al., "Molecular Cloning of Human Angiotensinogen cDNA and Evidence for the Presence of Its mRNA in Rat Heart—DNA Sequence," *Circ. Res.* 60:786–790 (1987).

Lieber et al., "Stable High–Level Gene Expression in Mammalian Cells by T7 Phage $NA Polymerase," *Methods Enzymol.* 217:47–66 (1993).

L'Huillier et al., "Cytoplasmic Delivery of Ribozymes Leads to Efficient Reduction in αLactalbumin mRNA Levels in C1271 Mouse," *Embo J.* 11:4411–4418 (1992).

Lindner and Reidy, "Proliferation of Smooth Muscle Cells After Vascular Injury is Inhibited by an Antibody Against Basic Fibroblast Growth Factor," *Proc. Natl. Acad. Sci. USA* 88:3739–3743 (1991).

Lisziewicz et al., "Inhibition of Human Immunodeficiency Virus Type 1 Replication by Regulated Expression of a Polymeric Tat Activation RNA Decoy as a Strategy for Gene Therapy in Aids," *Proc. Natl. Acad. Sci. U.S.A.* 90:8000–8004 (1993).

Majello et al., "Human c–myb Protooncogene: Nucleotide Sequence of cDNA and Organization of the Genomic Locus," *Proc. Natl. Acad. Sci. USA,* 83:9636–9640 (1986).

Mamone et al., "Design of Hammerhead Ribozymes Targeted to Sequences in HIV, HSV and the RAT ANF Gene," Abstract of Keystone, CO (May 27, 1992).

McGrath et al., "Structure and Organization of the Human Ki–ras Protooncogene And a Related Processed Pseudogene," 304:501–506 (1983).

Melani et al., "Inhibition of Proliferation by c–myb, Antisense Oligodeoxynucleotide in Colon Adenocarcinoma Cell Lines that Express c–myb, " *Cancer Res.* 51:2897–2901 (1991).

Milligan and Uhlenbeck, "Synthesis of Small RNAs Using T7 RNA Polymerase," *Methods Enzymol.* 180:51–62 (1989).

Minvielle et al., "A Novel Calcitonin Carboxyl–Terminal Peptide Produced in Medullary Thyroid Carcinoma by Alternative RNA Processing of the Calcitonin–Calcitonin Gene–Related Peptide Gene" *J. Biol. Chem.* 266:24627–24631 (1991).

Nabel et al., "Site–Specific Gene Expression in Vivo by Direct Gene Transfer Into the Arterial Wall," *Science* 249:1285–1288 (1990).

Nabel et al., Recombinant Platelet–Derived Growth Factor B Gene Expression in Porcine Arteries Induces Intimal Hyperplasia in Vivo, *J. Clin. Invest.* 91:1822–1829 (1993).

Ohno et al., "Gene Therapy for Vascular Smooth Muscle Cell Proliferation After Arterial Injury," *Science* 265:781–784 (1994).

Ohkawa et al., *Nucleic Acids Symp. Ser.* 27:15–6 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Ortigao et al., "Antisense Effects of Oligodeoxynucleotides with Inverted Terminal Internucleotidic Linkages: A Minimal Modification Protecting Against Nucleolytic Degradation," *Antisense Research and Development* 2:129–146 (1992).

Pavco et al., "Regulation of Self–Splicing Reactions by Antisence RNA," Abstract of Keystone, CO (May 27, 1992).

Perreault et al., "Mixed Deoxyribo–and Ribo–Oligonucleotides with Catalytic Activity," *Nature* 344:565–568 (1990).

Perrotta and Been, "Cleavage of Oligoribonucleotides by a Ribozyme Derived from the Hepatitis σVirus RNA Sequence," *Biochemistry* 31:16 (1992).

Pieken et al., "Kinetic Characterization of Ribonuclease–Resistant 2'–Modified Hammerhead Ribozymes," *Science* 253:314–317 (1991).

Popoma et al., "Clinical Trials of Restenosis After Coronary Angioplasty," *Circulation* 84:1426–1436 (1991).

Raines et al., "Interleukin–1 Mitogenic Activity for Fibroblasts and Smooth Muscle Cell Is Due to PDGF–AA," *Science* 243:393–396 (1989).

Raschella et al., "Inhibition of Proliferation by c–myb Antisense RNA and Oligodeoxynucleotides in Transformed Neuroectodermal Cell Lines," *Cancer Res.* 52:4221–4226 (1992).

Ratajczak et al., "In Vivo Treatment of Human Leukemia in a scid Mouse Model With c–myb Antisense Oligodeoxynucleotides," *Proc. Natl. Acad. Sci. USA* 89:11823–11827 (1992).

Riessen et al., "Arterial Gene Transfer Using Pure DNa Applied Directly to a Hydrogel–Coated Angioplasty Balloon,"*Human Gene Therapy* 4:749–758 (1993).

Ross et al., "A Platelet–Dependent Serum Factor That Stimulates the Proliferation of Arterial Smooth Muscle Cells In Vitro," *Proc. Natl. Acad. Sci. USA* 71:1207–1210 (1974).

Rossi et al., *J. Cell Biochem.* Suppl 14A:D428 (1990).

Rossi et al., "Ribozymes as Anti–HIV–1 Therapeutic Agents: Principles, Applications, and Problems," *Aids Research and Human Retroviruses* 8:183 (1992).

Ruben et al., "Isolation of a rel–related human cDNA that potentially encodes the 65–kD subunit of NF, Kappba B," *Science* 251:5000 (1991).

Ruben et al., "Isolation of a rel–related human cDNA that potentially encodes the 65–kD subunit of NF, Kappba B," *Science* 254:5028 (1991).

Saville and Collins, "RNA–Mediated Ligation of Self–Cleavage Products of a *Neurospora* Mitochondrial Plasmid Transcript," *Proc. Natl. Acad. Sci. USA* 88:8826–8830 (1991).

Saville and Collins, "A Site–Specific Self–Cleavage Reaction Performed by a Novel RNA in Neurospora Mitochondria," *Cell* 61:685–696 (1990).

Sarver et al., "Ribozymes as Potential Anti–HIV–1 Therapeutic Agents," *Science* 247:1222–1225 (1990).

Sarver et al., "Catalytic RNAs (Ribozymes): A New Frontier in Biomedical Applications," *AIDS Res. Revs.* 2:259 (1992).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical Synthesis of biologically active oligoribonucleotides using β–cyanoethyl protected ribonucleoside phosphoramidites," *Nucl Acids Res.* 18: 5433–5441 (1990).

Semba, "A v–erbB–Related Protooncogene, C–erB–2 Is Distinct From the c–erB–1/Epidermal Growth Factor–Receptor Gene and Is Amplified in A Human Salivary Gland Adenocarcinoma," *Proc. Natl. Acad. Sci. USA* 82:6497–6501 (1985).

Seth et al., "Mechanism of Enhancement of DNA Expression Consequent to Cointernalization of a Replication–Deficient Adenovirus and Unmodified Plasmid dDNA," *J. Virol.*, 68:933–940 (1994).

Sessa et al., "Molecular Cloning and Expression of a cDNA Encoding Endothelial Cell Nitric Oxide Synthase," *J. Biol. Chem.* 267:15274–15276 (1992).

Shi et al., "Downregulation of c–myc Expression by Antisense Oligonucleotides Inhibits Proliferation of Human Smooth Muscle Cell," *Circulation* 88:1190–1195 (1993).

Simons et al., "Antisense c–myb Oligonucleotides Inhibit Intimal Arterial Smooth Muscle Cell Accumulation in vivo," *Nature* 359:67–70 (1992).

Simons et al., "Relation Between Activated Smooth Muscle Cells in Coronary–Artery Lesions and Restenosis After Atherectomy," *New Engl. J. Med.* 328:608–613 (1993).

Sioud and Drulica, "Prevention of Human Immunodeficiency Virus Type 1 Integrase Expression in *Escherichia coli* by a Ribozyme," *Proc. Natl. Acad. Sci. USA* 88:7303 (1991).

Sjolund et al., "Arterial Smooth Muscle Cells Express Platelet–Derived Growth Factor (PDGF) A Chain mRNA, Secrete a PDGF–Like Mitogen, and Bind Exogenous PDGF in a Phenotype–and Growth State–Dependent Manner" *J. Cell. Biol.* 106:403–413 (1988).

Slamon et al., "Studies of the Human c–myb Gene and Its Products In Human Acute Leukemias," *Science* 233:3467–351 (1986).

Slamon et al., "Expression of Cellular Oncogenes in Human Malignancies," *Science* 224:256–262 (1984).

Steele et al., "Balloon Angioplasty—Natural History of the Pathophysiological Response to Injury in a Pig Model," *Cir. Res.* 57:105–112 (1985).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–30 (1991).

Ten Dijke et al., "Recombinant Transforming Growth factor Type Beta–3 Biological Activities and Receptor–Binding Properties in Isolated Bone Cells," *Mol. Cell Biol.* 10:4473–4479 (1990).

Tessler et al, "Basic Fibroblast Growth Factor Accumulates in the Nuclei of Vairous BFGF–Producing Cell Types" *J. Cell Physiol.* 145:310–317 (1990).

Thiele et al., "Regulation of c–myb Expression in Human Neuroblastoma Cells During Retinoic Acid–Induced Differentiation," *Mol. Cell. Biol.* 8:1677–1683 (1988).

Thompson et al., "Molecular Quantification of Residual Disease in Chronic Myelogenous Leukemia After Bone Marrow Transplantation ," *Blood* 79:1692–1635 (1995).

Torelli et al., "Expression of c–myb Protoncogene and Other Cell Cycle–Related Genes in Normal and Neoplastic Human Colonic Mucosa," *Cancer Res.* 47:5266–5269 (1987).

Torrence et al., "Targeting RNA for degradation with a (2'–5') oligoadenylate–antisense chimera," *Proc. Natl. Acad. Sci. USA* 90:1300–1304 (1993).

Uhlenbeck, "A Small Catalytic Oligoribonucleotide," *Nature* 327:596–600 (1987).

Usman et al., "Chemical modification of hammerhead ribozymes: activity and nuclease resistance," *Nucleic Acids Symposium Series* 31:163–164 (1994).

Usman and Cedergren, "Exploiting the chemical synthesis of RNA," *Trends In Biochem. Sci.* 17:334–339 (1992).

Usman et al., "Automated Chemical Synthesis of Long Oligoribonucleotides Using 2'–O–Silylated Ribonucleoside 3'–O–Phosphoramidtes on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Ventura et al., "Activation of HIV–Specific Ribozyme Activity by Self–Cleavage," *Nucleic Acids Res.* 21:3249–55 (1993).

Weerasinghe et al., "Resistance to Human Immunodeficiency Virus Type 1 (HIV–1) Infection in Human $CD4^+$ Lymphocyte–Derived Cell Lines Conferred by Using Retroviral Vectors Expressing an HIV–1 RNA–Specific Ribozyme," *Journal of Virology* 65:5531–4 (1994).

Wagner et al., "Gene inhibition using antisense oligodeoxynucleotides," *Nature* 372:333–335 (1994).

Weiser et al., "The Growth–Related Transcription Factor OCT–1 is Expressed as a Function of Vascular Smooth Muscle Cell Modulation," *J. Cell. Biochem.* S18A:282 (1994).

Westin et al., "Alternative Splicing of the Human c–myb Gene ," *Oncogenes* 5:1117–1124 (1990).

Willard et al., Willard et al., "Recombinant Adenovirus in an Efficient Vector for In Vivo Gene Transfer and can be Preferentially Directed at Vascular Endothelium or Smooth Muscle Cells," *Circulation—Abstracts from the 6th Scientific Sessions*, New Orleans Convention Center, New Orleans, Louisiana, Nov. 16–19 1992.

Woolf et al., "Specificity of Antisense Oligonucleotides in vivo," *Pro. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. U S A* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zenke et al., "Receptor–mediated Endocytosis of Transferrin–Polycation Conjugates: An Efficient Way to Introduce DNA into Hematopoietic Cells" (Abstract), *Proc. Natl. Acad. Sci. USA* 87:3655–3659 (1990).

Zhou et al., "Synthesis of Function mRNA in Mammalian ells by Bacteriophage T3 RNA Polymerase," *Mol. Cell. Biol.* 10:4529–4537(1990).

HEPATITIS DELTA VIRUS RIBOZYME

Fig. 6
RNase H Assay
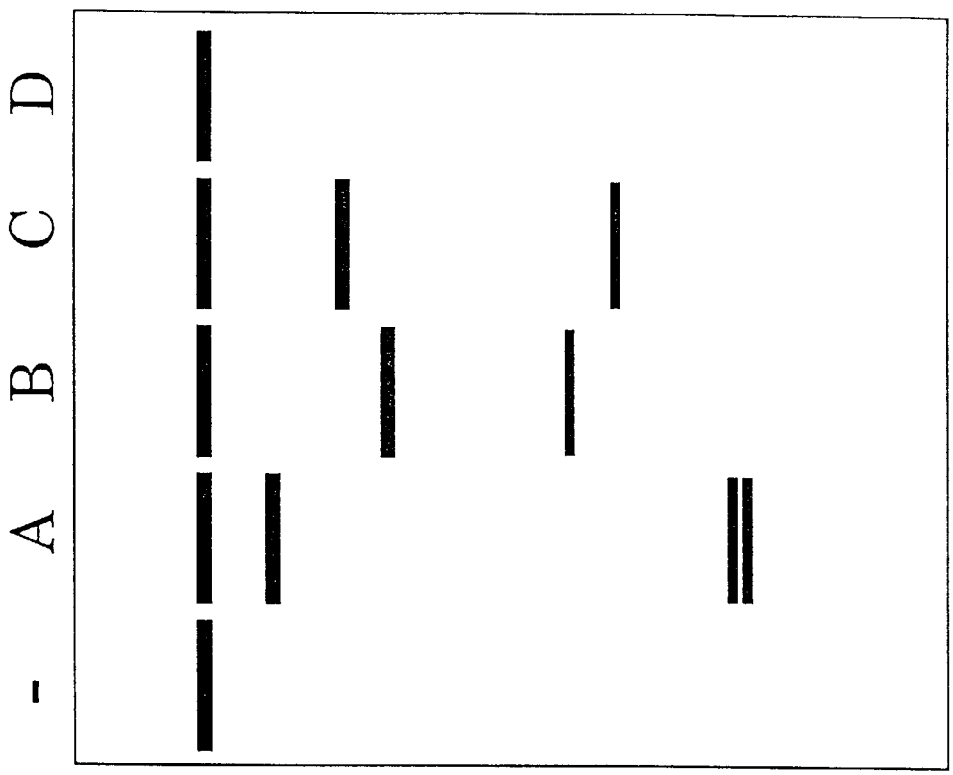
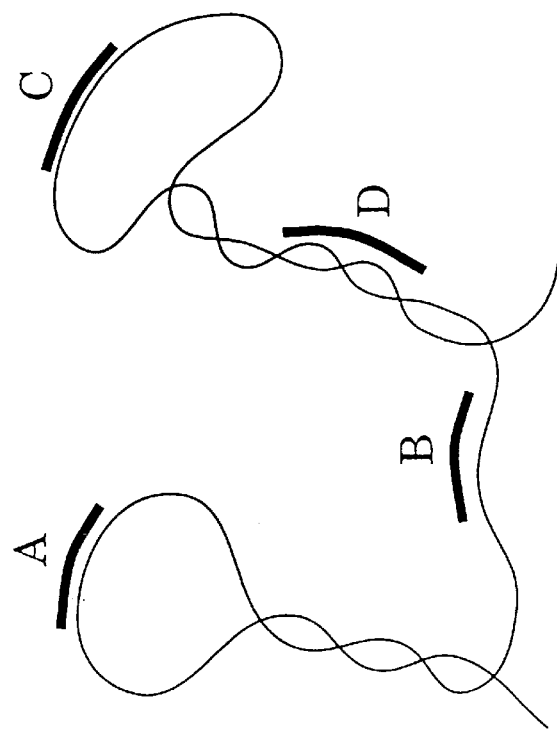
- Body-labeled transcript (not purified)
- DNA oligo (10 nM, 100 nM and 1000 nM)
- RNAse H (0.08 -1.0 u/μl)
- 37°C, 10 min

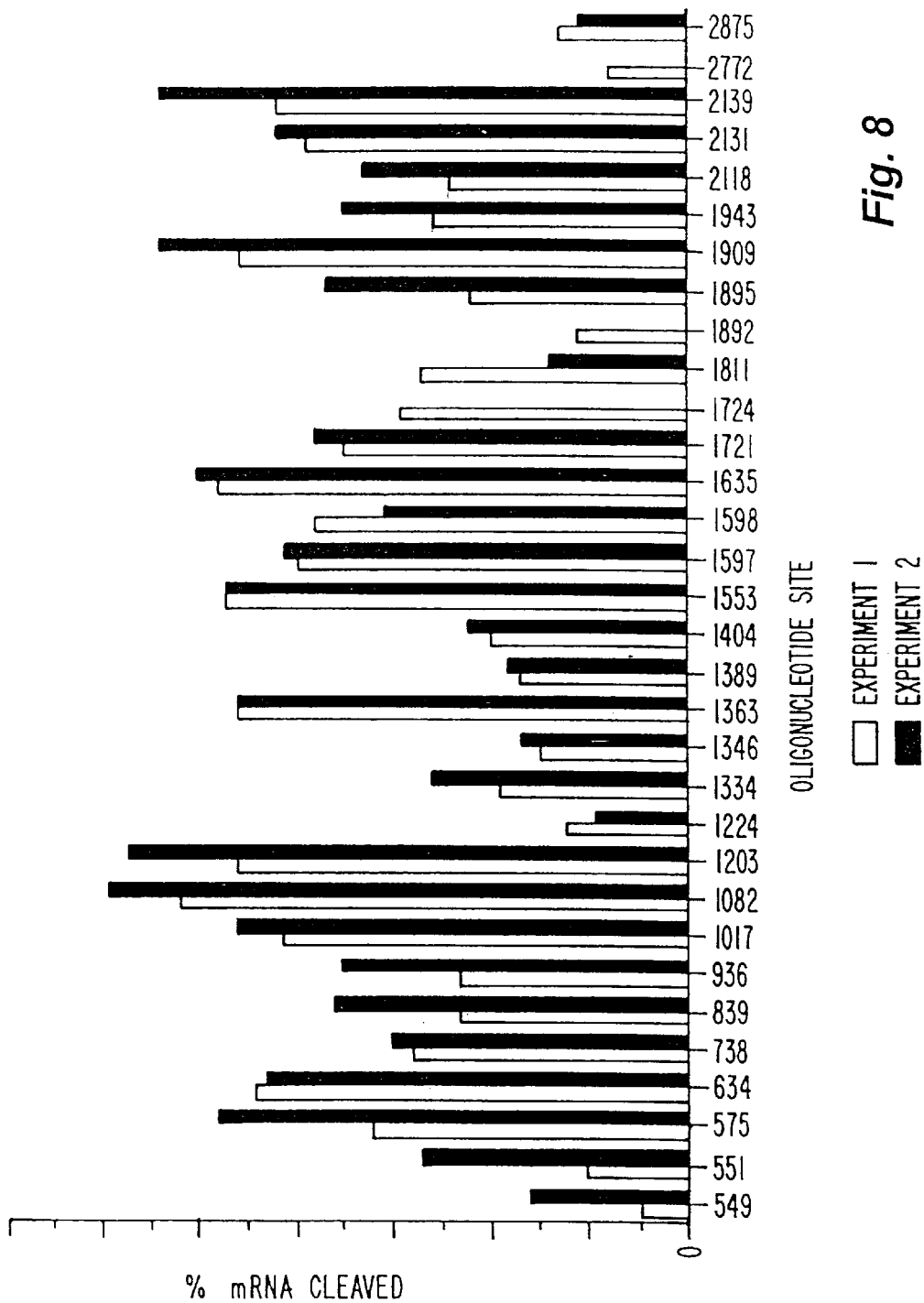

c-myb SITE 575 HAMMERHEAD RIBOZYME-SUBSTRATE COMPLEX

2'-O-Methyl Ribozyme

2'-O-Methyl P=S Ribozyme

2'-C-Allyl iT Ribozyme

2'-C-Allyl P=S Ribozyme

DOSE RESPONSE OF CHEMICALLY MODIFIED RIBOZYME

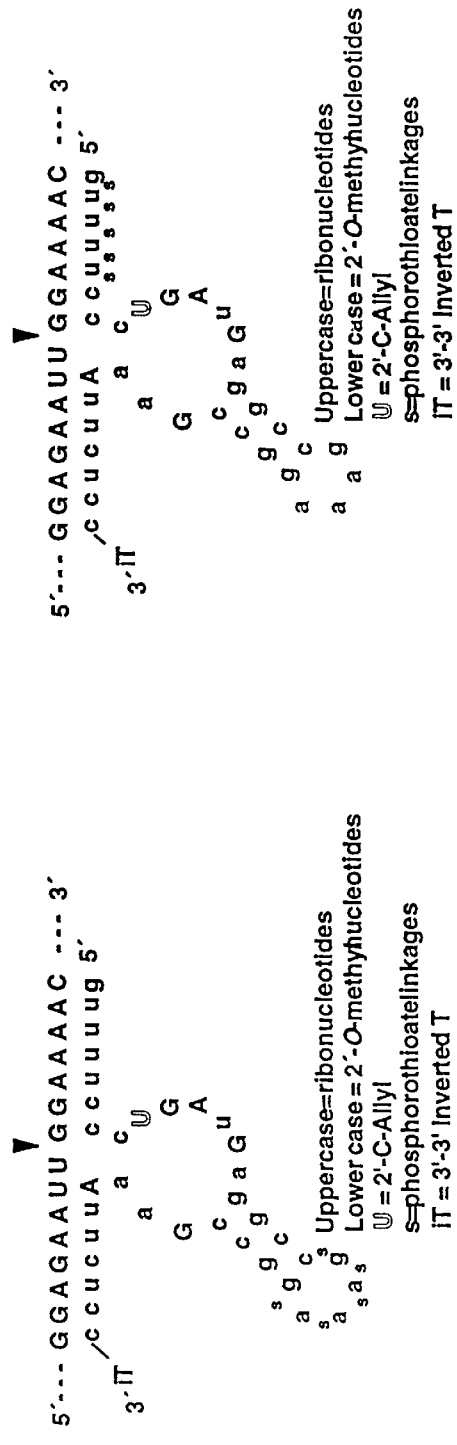
Fig. 13A c-myb TARGET SITE AND OPTIMAL RIBOZYME FOR TREATMENT OF RESTENOSIS Uppercase=ribonucleotides Lower case = 2´-O-methylnucleotides H = 3´-3´ abasic deoxyribose U = 2´C-allyl s=phosphorothioate linkages

C-MYB RIBOZYMES HAVING 2'-5'-LINKED ADENYLATE RESIDUES

This application is a division of Stinchcomb et al., U.S. Ser. No. 08/373,124, filed Jan. 13, 1995, now U.S. Pat. No. 5,646,042, and a continuation-in-part of Draper, "Method and Reagent for Treatment of a Stenotic Condition", filed Dec. 7, 1992, U.S. Ser. No. 07/987,132, now abandoned; Thompson et al, "Method and Reagent for Treatment of diseases caused by expression of the c-myc gene," U.S. Ser. No. 08/192,943, filed Feb. 7, 1994, which is a continuation of U.S. Ser. No. 07/936,422, filed Aug. 26, 1992, now abandoned, and Stinchcomb et al., "Methods and compositions for the treatment of restenosis and cancer using ribozymes," U.S. Ser. No. 08/245,466, now abandoned, filed May 18, 1994, all hereby incorporated by reference herein in their totality.

BACKGROUND OF THE INVENTION

The present invention concerns therapeutic compositions and methods for the treatment of restenosis and cancer.

The following is a brief description of the physiology, cellular pathology and treatment of restenosis. The discussion is not meant to be complete and is provided only for understanding of the invention that follows. This summary is not an admission that any of the work described below is prior art to the claimed invention.

Coronary angioplasty is one of the major surgical treatments for heart disease. Its use has been accelerating rapidly; over 450,000 procedures are performed in the U.S. annually. The short term success rate of angioplasty is 80 to 90%. However, in spite of a number of technical improvements in the procedure, post-operative occlusions of the arteries, or restenosis, still occur. Thirty-five to forty-five percent of patients who have undergone a single vessel angioplasty develop clinically significant restenosis within 6 months of the procedure. The rate of restenosis is even higher (50 to 60%) in patients who have undergone multivessel angioplasty (Califf, R. M., et al., 1990, in *Textbook of Interventional Cardiology*., E. J. Topol, ed., W. B. Saunders, Philadelphia, pp 363–394.).

Histopathological studies have shown that restenosis after angioplasty is characterized by migration of medial smooth muscle cells to the intima and a striking hyper-proliferative response of these neointimal cells (Garratt, K. N., et al., 1991, *J. Am. Coll. Cardio.*, 17, 442–428; Austin, G. E., et al., 1985, *J. Am. Coll. Cardiol.*, 6, 369–375). Smooth muscle cell proliferation could be an overly robust response to injury. Alternatively, the intimal smooth muscle cells within atherosclerotic lesions are already in an activated or "synthetic" state (Sjolund, M., et al., 1988, *J. Cell. Biol.*, 106, 403–413 and thus may be poised to proliferate. One recent study demonstrated a positive correlation between the presence of activated smooth muscle cells in coronary lesions and the extent of subsequent luminal narrowing after atherectomy (Simons, M., et al., 1993, *New Engl. J. Med.*, 328, 608–613). In any case, slowing smooth muscle cell proliferation after angioplasty could prevent intimal thickening and restenosis.

The presently preferred therapeutic treatment for restenosis is the use of streptokinase, urokinase or other thrombolytic compounds, such as fish oil, anticoagulants, ACE (angiotensin converting enzyme) inhibitors, aspirin and cholesterol lowering compounds. Alternative treatment includes the surgical incorporation of endoluminal stents. The occurrence of pharmacologic side-effects (particularly bleeding disorders associated with anti-coagulants and platelet inhibitors) is an issue with current therapies. Popoma, J. J., et al., report that the current therapies have not significantly impacted the rates of restenosis occurrence.(*Circulation*, 84, 1426–1436, 1991).

Recently, the results of a clinical trial of the efficacy of an anti-platelet therapy have been reported. Patients undergoing coronary angioplasty were given a single bolus injection followed by a 12 hour infusion of an antibody directed against the platelet adhesion molecule, gpIIb/gpIIIa. After six months, patients with the treatment showed a 23% reduction in the occurrence of restenosis than patients receiving placebo (27 vs. 35%; p=0.001).

A number of growth factors have been shown to induce smooth muscle cell proliferation. In vitro, platelet-derived growth factor (PDGF) is a potent smooth muscle cell mitogen (Ross, R., et al., 1974, *Proc. Natl. Acad. Sci. USA*, 71, 1207–1210) and a smooth muscle cell chemoattractant (Grotendorst, G., et al., 1982, *Proc. Natl. Acad. Sci. USA*, 71, 3669–3672.). In vivo, when PDGF is expressed ectopically in porcine arteries, it induces intimal hyperplasia (Nabel, E. B., et al., 1993, *J. Clin. Invest.*, 91, 1822–1829). Furthermore, antibodies to PDGF have been shown to reduce intimal thickening after arterial injury (Ferns, G. A. A., et al., 1991, *Science*, 253, 1129–1132). Analysis of $^3$H-thymidine incorporation in the lesions indicates that the anti-PDGF antibodies primarily inhibit smooth muscle cell migration.

Basic fibroblast growth factor (bFGF) is another smooth muscle cell mitogen in vitro (Klagsbrun, M. and Edelman, E. R., 1989, *Arteriosclerosis*, 9, 269–278). In a rat model, anti-bFGF antibodies inhibit the proliferation of medial smooth muscle cells 24 to 48 hours after balloon catheter injury (Lidner, V. and Reidy, M. A., 1991, *Proc. Natl, Acad. Sci. USA*, 88, 3739–3743). In addition to bFGF, heparin binding epidermal growth factor (HB-EGF) (Higashiyama, S., et al., 1991, *Science*, 251, 936–939.), insulin-like growth factor I (IGF-I) (Banskota, N. K., et al., 1989, *Molec. Endocrinol.*, 3, 1183–1190) and endothelin (Komuro, I., et al., 1988, *FEBS Letters*, 238, 249–252) have been shown to induce smooth muscle cell proliferation. A number of other factors (such as interleukin-1 and tumor necrosis factor-α) may indirectly affect smooth muscle cell proliferation by inducing the expression of PDGF (Hajjar, K. A., et al., 1987, *J. Exp. Med.*, 166, 235–245; Raines, E. W., et al., 1989, *Science*, 243, 393–396).

When whole serum is added to serum-starved smooth muscle cells in vitro, the oncogenes, c-myc, c-fos, and c-myb, are induced (Kindy, M. S. and Sonenshein, G. E., 1986, *J. Bio. Chem.*, 261, 12865–12868; Brown, K. E., et al., 1992, *J. Bio. Chem.*, 267, 4625–4630) and cell proliferation ensues. Blocking c-myb with an antisense oligonucleotide prevents cells from entering S phase (Brown, K. E., et al., 1992, *J. Biol. Chem.*, 267, 4625–4630.). Thus, c-myb is required for the $G_1$ to S transition after stimulation by the multitude of growth factors present in serum. In vivo, a c-myb antisense oligonucleotide inhibits restenosis when applied to rat arteries after balloon angioplasty (Simons, M., et al., 1992, *Nature*, 359, 67–70). Similarly, an antisense oligonucleotide directed against mRNA of the oncogene c-myc was shown to inhibit human smooth muscle cell proliferation (Shi, Y., et al., 1993, *Circulation*, 88, 1190–5) and migration (Biro, S., et al., 1993, *Proc. Natl. Acad. Sci. USA*, 90, 654–8).

Ohno et al., 1994 *Science* 265, 781, have shown that a combination of viral thymidine kinase enzyme expression (gene therapy) and treatment with anti-viral drug ganciclovir inhibits smooth muscle cell proliferation in pigs, following baloon angioplasty.

Epstein et al., "Inhibition of non-transformed cell proliferation using antisense oligonucleotides," NTIS publication 1992 discusses use of antisense oligonucleotides to c-myc, PCNA or cyclin B. Fung et al., PCT WO91/15580, describes gene therapy for cell proliferative disease and mentions administration of a ribozyme construct against a PGR element. Mention is made of inactivation of c-myb. Rosenberg et al., WO93/08845, Calabretta et al., WO92/20348 and Gewirtz WO93/09789 concern c-myb antisense oligonucleotides for treatment of melanoma or colorectal cancer, and administration locally. Sytkowski, PCT WO 93/02654, describe the uses of antisense oligonucleotides to inhibit c-myb gene expression in red blood cells to stimulate hemoglobin synthesis.

Nabel and Nabel, U.S. Pat. No. 5,328,470, describe a method for the treatment of diseases by delivering therapeutic reagents directly to the sites of disease. They state that " . . . Method is based on the delivery of proteins by catheterization to discrete blood vessel segments using genetically modified or normal cells or other vector systems . . . In addition, catalytic RNAs, called ribozymes, can specifically degrade RNA sequences . . . The requirements for a successful RNA cleavage include a hammerhead structure with conserved RNA sequence at the region flanking this structure . . . any GUG sequence within the RNA transcript can serve as a target for degradation by the ribozyme . . . gene transfer using vectors expressing such proteins as tPA for the treatment of thrombosis and restenosis, angiogenesis or growth factors for the purpose of revascularization . . . "

SUMMARY OF THE INVENTION

This invention relates to ribozymes, or enzymatic RNA molecules, directed to cleave mRNA species that are required for cellular growth responses. In particular, applicant describes the selection and function of ribozymes capable of cleaving RNA encoded by the oncogene, c-myb. Such ribozymes may be used to inhibit the hyperproliferation of smooth muscle cells in restenosis and of tumor cells in numerous cancers. To block restenosis, a target molecule required for the induction of smooth muscle cell proliferation by a number of different growth factors is preferred. To this end c-myc, c-fos, and c-myb are useful targets in this invention.

Other transcription factors involved in the response to growth and proliferation signals include NF-κB, oct-1 and SRF. NF-κB protein activates cellular transcription and induces increases in cellular synthetic pathways. In a resting cell, this protein is found in the cytoplasm, complexed with its inhibitor, I-κB. Upon phosphorylation of the I-κB molecule, the complex dissociates and NF-κB is released for transport to the nucleus, where it binds DNA and induces transcriptional activity in (NF-κB)-responsive genes. One of the (NF-κB)-responsive genes is the NF-κB gene itself. Thus, release of the NF-κB protein from the inhibitory complex results in a cascade of gene expression which is auto-induced. Early inhibition of NF-κB can reduce expression of a number of genes required for growth and proliferation, such as c-myb.

Two other transcription factors, oct-1 and serum response factor (SRF) have been shown to be expressed selectively in dividing cells. Both oct-1 and SRF are expressed ubiquitously in cultured cells, including smooth muscle cells. However, R. Majack and his colleagues have recently shown that these transcription factors are not expressed by the smooth muscle cells in intact vessels. Both oct-1 and SRF are rapidly expressed upon dispersal of tissue into single cell suspensions. Thus, these transcription factors are thought to be regulated by their interactions with the extracellular matrix (Weiser, M. C. M., et al., 1994, *J. Cell. Biochem.*, S18A, 282; Belknap, J. K., et al., 1994, *J. Cell. Biochem.*, S18A, 277). Upon injury during angioplasty, the expression of oct-1 and SRF may be enhanced, leading to increased smooth muscle cell proliferation. Treatment with ribozymes that block the expression of these transcription factors can alleviate the smooth muscle cell proliferation associated with restenosis.

While some of the above mentioned studies demonstrated that antisense oligonucleotides can efficiently reduce the expression of factors required for smooth muscle cell proliferation, enzymatic RNAs, or ribozymes have yet to be demonstrated to inhibit smooth muscle cell proliferation. Such ribozymes, with their catalytic activity and increased site specificity (as described below), represent more potent and safe therapeutic molecules than antisense oligonucleotides. In the present invention, ribozymes that cleave c-myb mRNA are described. Moreover, applicant shows that these ribozymes are able to inhibit smooth muscle cell proliferation and that the catalytic activity of the ribozymes is required for their inhibitory effect. From those of ordinary skill in the art, it is clear from the examples described, that other ribozymes that cleave target mRNAs required for smooth muscle cell proliferation may be readily designed and are within the invention.

By "inhibit" is meant that the activity of c-myb or level of mRNAs encoded by c-myb is reduced below that observed in the absence of the nucleic acid, particularly, inhibition with ribozymes and preferably is below that level observed in the presence of an inactive RNA molecule able to bind to the same site on the mRNA, but unable to cleave that RNA.

By "enzymatic nucleic acid molecule" it is meant a nucleic acid molecule which has complementarity in a substrate binding region to a specified gene target, and also has an enzymatic activity which is active to specifically cleave RNA in that target. That is, the enzymatic nucleic acid molecule is able to intermolecularly cleave RNA and thereby inactivate a target RNA molecule. This complementarity functions to allow sufficient hybridization of the enzymatic nucleic acid molecule to the target RNA to allow the cleavage to occur. One hundred percent complementarity is preferred, but complementarity as low as 50–75% may also be useful in this invention. By "equivalent" RNA to c-myb is meant to include those naturally occurring RNA molecules associated with restenosis and cancer in various animals, including human, rat and pig. Such a molecule will generally contain some ribonucleotides, but the other nucleotides may be substituted at the 2'-hydroxyl position and in other locations with other moeities as discussed below.

By "complementarity" is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, *Proc. Natl. Acad. Sci. USA*, 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al, 1992, *Aids Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al, U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of a target mRNAs encoding c-myb proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. USA* 89, 10802–6; Chen et al., 1992 *Nucleic Acids Res.*, 20, 4581–9; Sarver et al., 1990 *Science* 247, 1222–1225). Those skilled in the art realize that any ribozyme can be expressed in eukaryotic cells from the appropriate DNA/RNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856)

Thus, in a first aspect, the invention features ribozymes that inhibit cell proliferation. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target mRNAs, preventing translation and protein accumulation. In the absence of the expression of the target gene, cell proliferation is inhibited.

In a preferred embodiment, the enzymatic RNA molecules cleave c-myb mRNA and inhibit smooth muscle cell proliferation. Such ribozymes are useful for the prevention of restenosis after coronary angioplasty. Ribozymes are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. The ribozymes, similarly delivered, also are useful for inhibiting proliferation of certain cancers associated with elevated levels of the c-myb oncogene, particularly leukemias, neuroblastomas, and lung, colon, and breast carcinomas. Using the methods described herein, other enzymatic RNA molecules that cleave c-myb, c-myc, oct-1, SRF, NF-κB, PDGF receptor, bFGF receptor, angiotensin II, and endothelium-derived relaxing factor and thereby inhibit smooth muscle cell proliferation and/or tumor cell proliferation may be derived and used as described above. Specific examples are provided below in the Tables.

Such ribozymes are useful for the prevention of the diseases and conditions discussed above, and any other diseases or conditions that are related to the level of c-myb activity in a cell or tissue. By "related" is meant that the inhibition of c-myb mRNAs and thus reduction in the level of protein activity will relieve to some extent the symptoms of the disease or condition.

Ribozymes are added directly, or can be complexed with cationic lipids, packaged within liposomes, or otherwise delivered to target cells. The nucleic acid or nucleic acid, complexes can be locally administered to relevant tissues ex vivo, or in vivo through injection, infusion pump or stent, with or without their incorporation in biopolymers.

In another aspect of the invention, ribozymes that cleave target molecules and inhibit c-myb activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

In preferred embodiments, the ribozymes have binding arms which are complementary to the sequences in the tables, shown as Seq. I.D. Nos. 1–100. Examples of such ribozymes are shown as Seq. I.D. Nos. 101–129. Those in the art will recognize that while such examples are designed to mouse RNA, similar ribozymes can be made complementary to human RNA. By complementary is thus meant that the binding arms are able to cause cleavage of a human or mouse mRNA target. Examples of such ribozymes consist essentially of sequences defined as Seq. I.D. Nos. 101–129 below. By "consists essentially of" is meant that the active ribozyme contains an enzymatic center equivalent to those in the examples, and binding arms able to bind human mRNA such that cleavage at the target site occurs. Other sequences may be present which do not interfere with such cleavage.

In another aspect of the invention, ribozymes that cleave target molecules and inhibit cell proliferation are expressed from transcription units inserted into DNA, RNA, or viral vectors. Preferably, the recombinant vectors capable of expressing the ribozymes are locally delivered as described above, and transiently persist in smooth muscle cells. Once expressed, the ribozymes cleave their target mRNAs and prevent proliferation of their host cells. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.
Drawings FIG. 1 is a diagrammatic representation of the hammerhead ribozyme domain known in the art. Stem II can be $\geq 2$ base-pair long.

FIG. 2a is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H refers to bases A, U, or C. Y refers to pyrimidine bases. "_____" refers to a covalent bond.

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Figure 7:
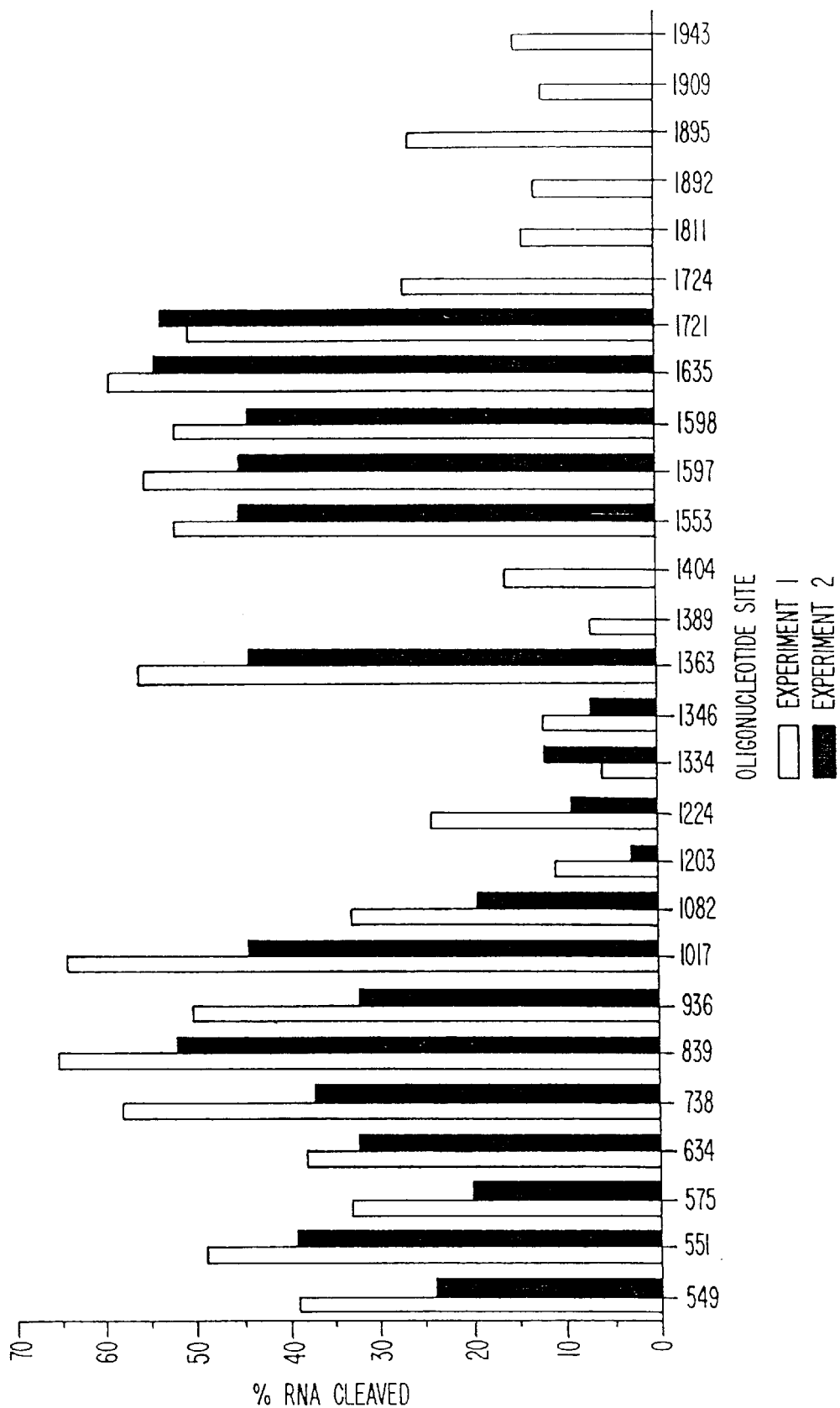

FIG. 7 is a graph of the results of an RNAseH accessibility assay of murine c-myb RNA. On the abscissa is the sequence number of the DNA oligonucleotide that is homologous to the ribozyme target site. The ordinate represents the percentage of the intact transcript that was cleaved by RNAse H.

FIG. 8 is a graph of the outcome of an RNAseH accessibility assay of human c-myb mRNA. The graphs are labeled as in FIG. 7.

FIG. 9 shows the effect of chemical modifications on the catalytic activity of hammerhead ribozyme targeted to c-myb site 575. A) diagrammatic representation of 575 hammerhead ribozyme•substrate complex. 2'-O-methyl ribozyme represents a hammerhead (HH) ribozyme containing 2'-O-methyl substitutions at five nucleotides in the 5' and 3' termini. 2'-O-methyl P=S ribozyme represents a hammerhead (HH) ribozyme containing 2'-O-methyl and phosphorothioate substitutions at five nucleotides in the 5' and 3' termini. 2'-C-allyl iT ribozyme represents a hammerhead containing ribose residues at five positions. The remaining 31 nucleotide positions contain 2'-hydroxyl group substitutions, wherein 30 nucleotides contain 2'-O-methyl substitutions and one nucleotide ($U_4$) contains 2'-C-allyl substitution. Additionally, 3' end of this ribozyme contains a 3'—3' linked inverted T. 2'-C-allyl P=S ribozyme is similar to 2'-C-allyl iT ribozyme with the following changes: five nucleotides at the 5' and 3' termini contain phosphorothioate substitutions and the ribozyme lacks the 3'-end inverted T modification. B) shows the ability of ribozymes described in FIG. 9A to inhibit smooth muscle cell proliferation.

Figure 10:
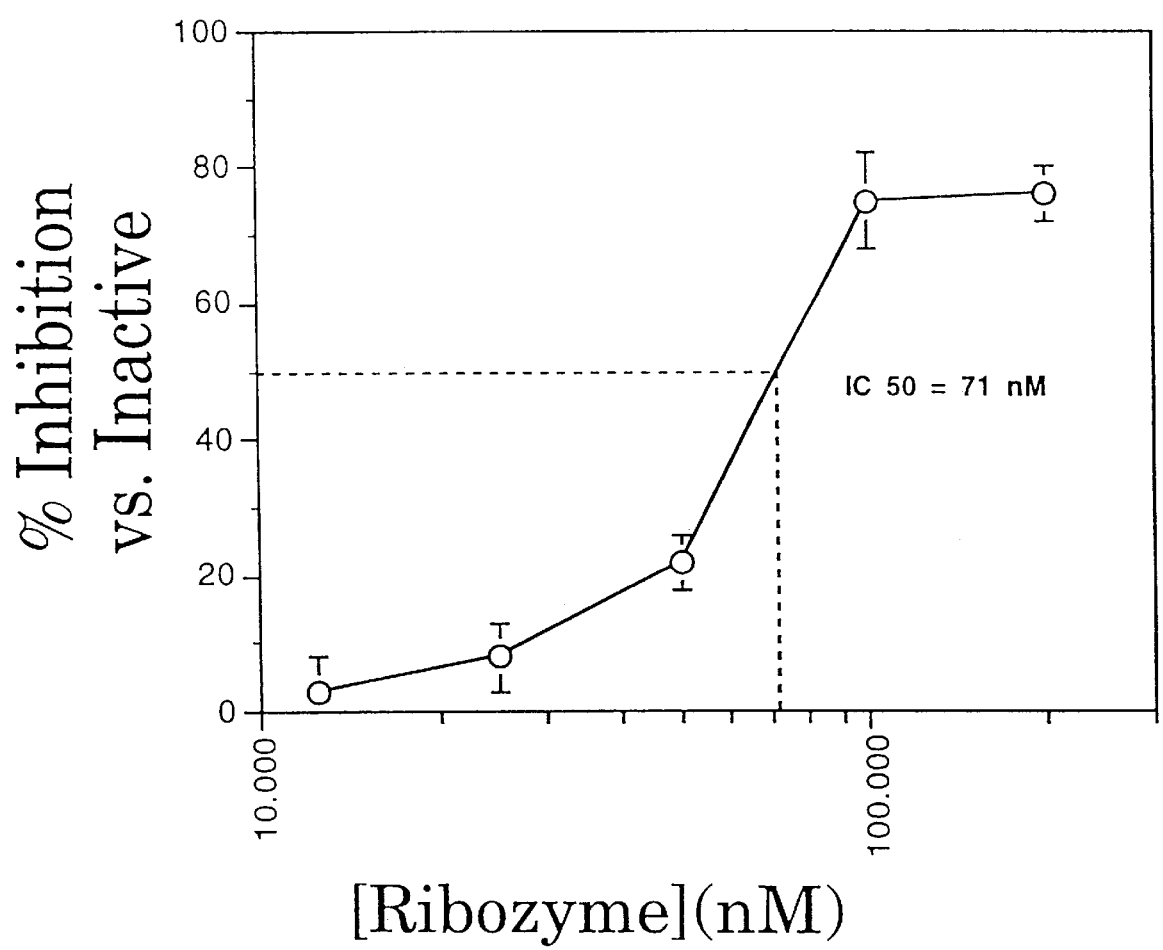

FIG. 10 shows the effect of 2'-C-allyl P=S 575 HH ribozyme concentration on smooth muscle cell proliferation. A plot of percent inhibition of smooth muscle cell proliferation (normalized to the effect of a catalytically inactive ribozyme) as a function of ribozyme concentration is shown.

Figure 11:
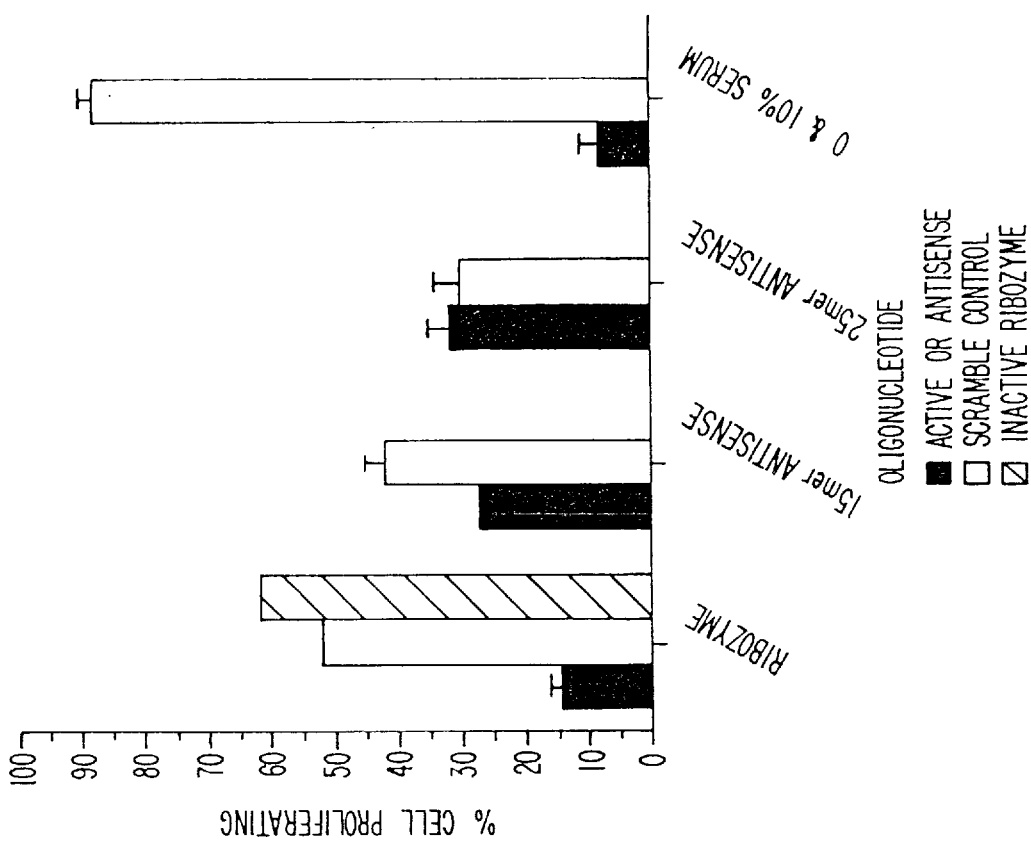

FIG. 11 shows a comparison of the effects of 2'-C-allyl P=S 575 HH ribozyme and phosphorothioate antisense DNA on the proliferation of smooth muscle cells.

Figure 12:
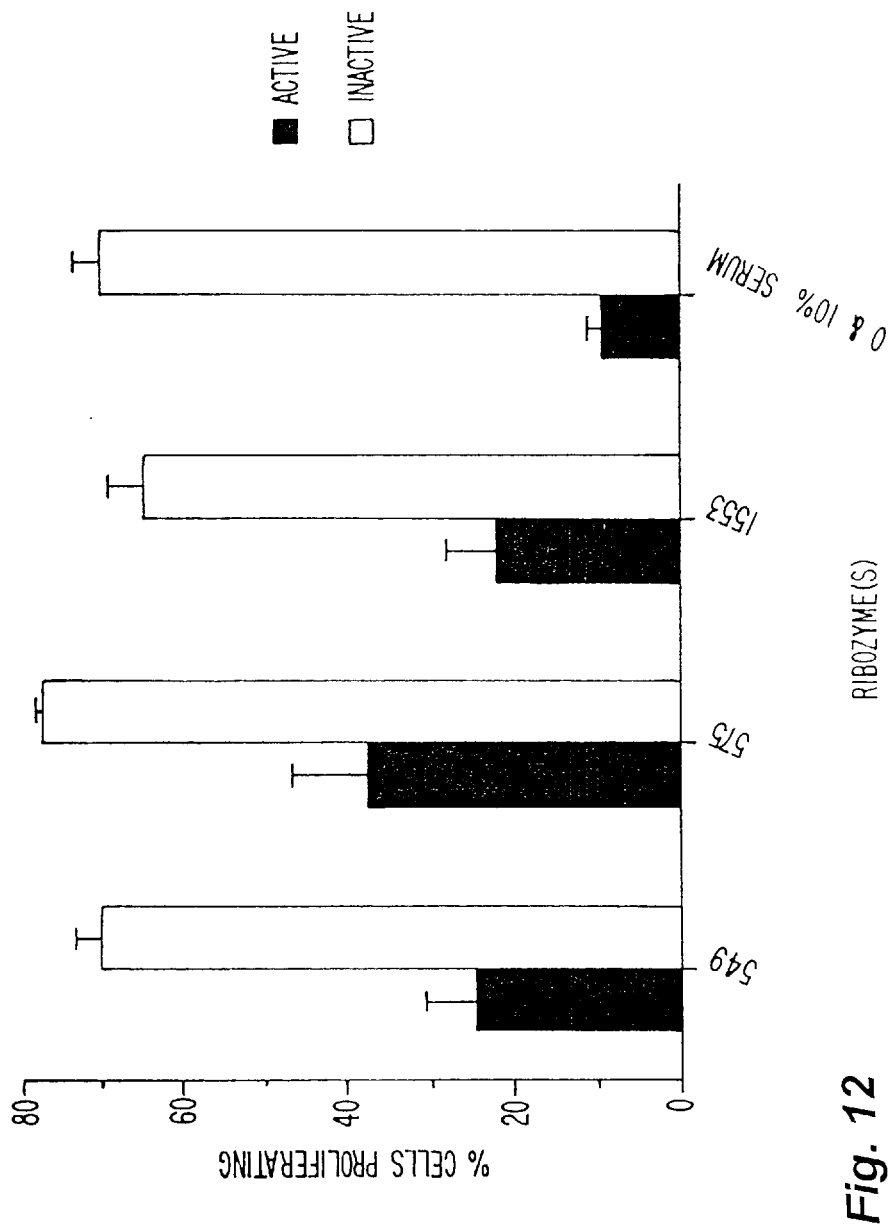

FIG. 12 shows the inhibition of smooth muscle cell proliferation catalyzed by 2'-C-allyl P=S HH ribozymes targeted to sites 549, 575, and 1533 within c-myb mRNA.

FIG. 13 shows the effect of phosphorthioate substitutions on the catalytic activity of 2'-C-allyl 575 HH ribozyme. A) diagrammatic representation of 575 hammerhead ribozyme•substrate complex. 10 P=S 5' and 3' ribozyme is identical to the 2'-C-allyl P=S ribozyme described in FIG. 9. 5 P=S 3' ribozyme is same as 10 P=S 5' and 3' ribozyme, with the exception that only five nucleotides at the 3' termini contain phosphorothioate substitutions. 5 P=S Loop ribozyme is similar to 2'-C-allyl iT described in FIG. 9, with the exception that five nucleotides within loop 11 of this ribozyme contain phosphorothioate substitutions. 5 P=S 5' ribozyme is same as 10 P=S 5' and 3' ribozyme, with the exception that only five nucleotides at the 5' termini contain phosphorothioate substitutions. Additionally, this ribozyme contains a 3'—3' linked inverted T at its 3' end. B) shows the ability of ribozymes described in FIG. 13A to inhibit smooth muscle cell proliferation.

Figure 14:
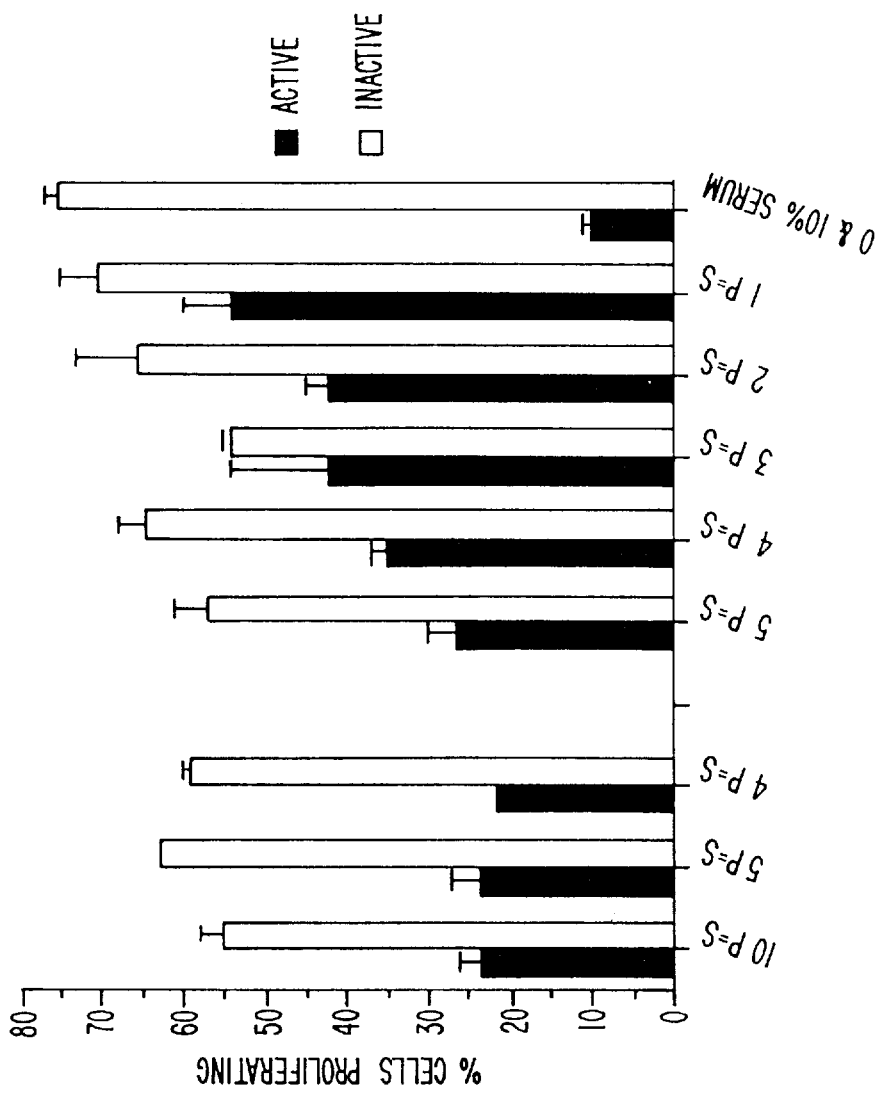

FIG. 14 shows the minimum number of phosphorothioate substitutions required at the 5' termini of 575 HH ribozyme to achieve efficient inhibition of smooth muscle cell proliferation.

Figure 15:
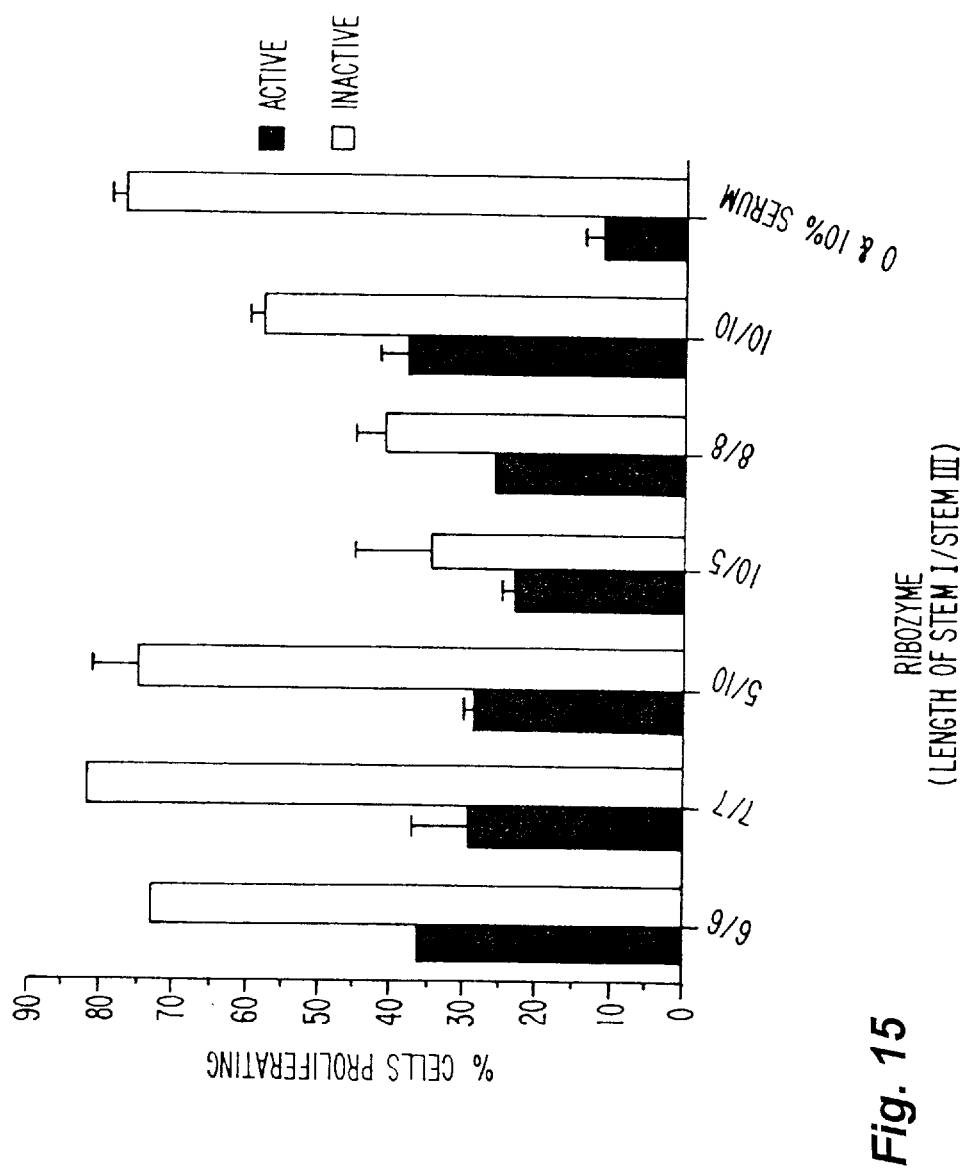

FIG. 15 shows the effect of varying the length of substrate binding arm of 575 HH ribozyme on the inhibition of smooth muscle cell proliferation.

Figure 16:
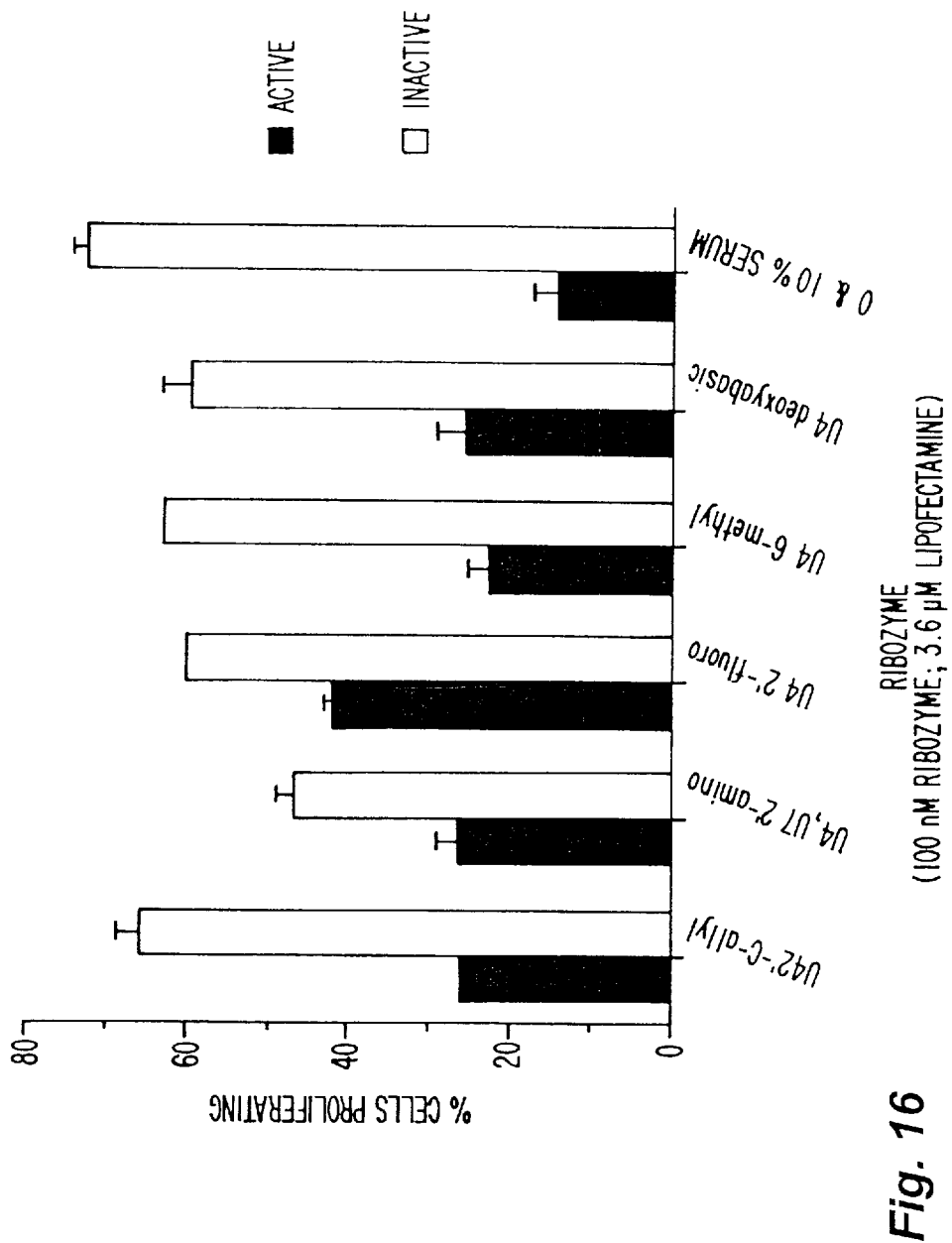

FIG. 16 shows the effect of various chemical modifications, at $U_4$ and/or $U_7$ positions within 575 HH ribozyme core, on the ability of the ribozyme to inhibit smooth muscle cell proliferation.

Figure 17:
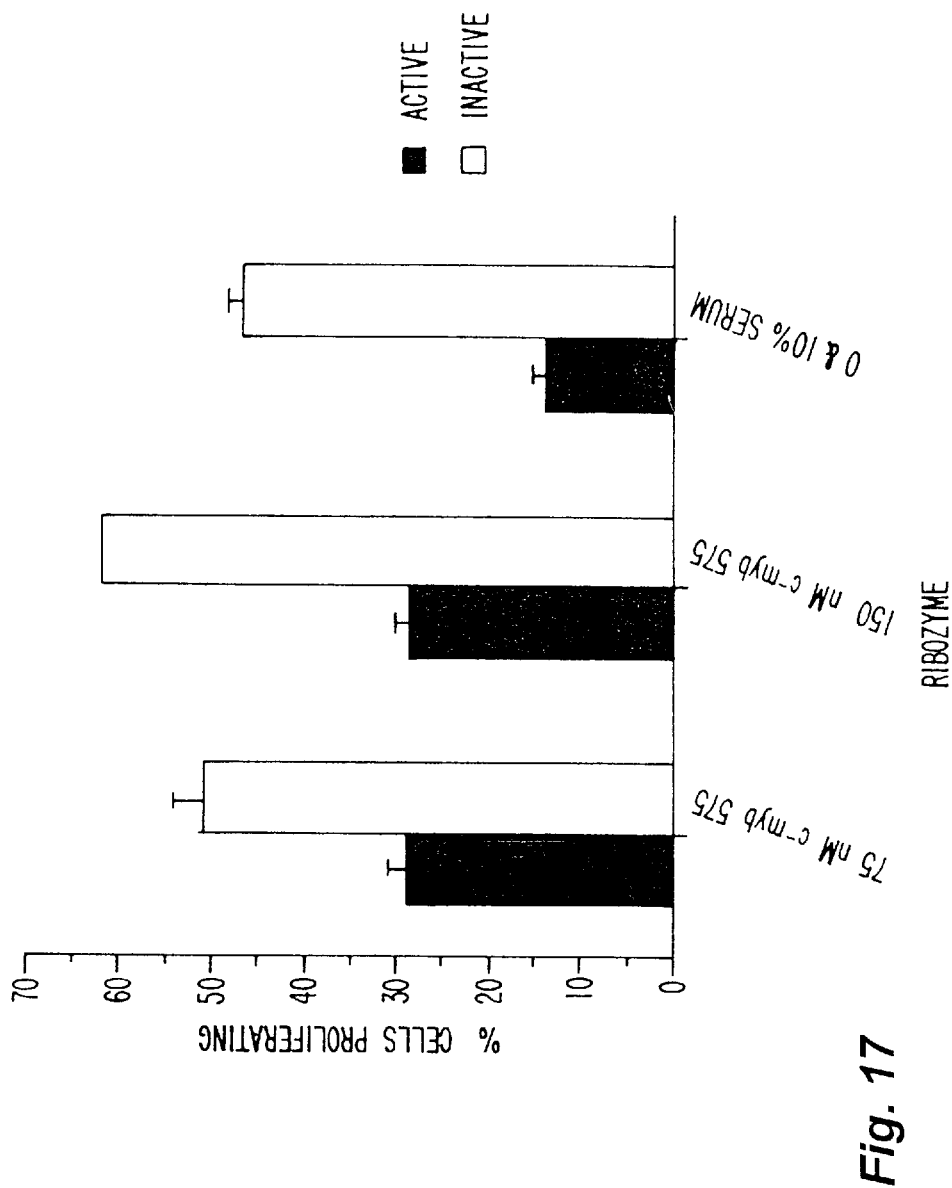

FIG. 17 shows the inhibition of pig smooth muscle cell proliferation by active c-myb 575 HH ribozyme.

Figure 18:
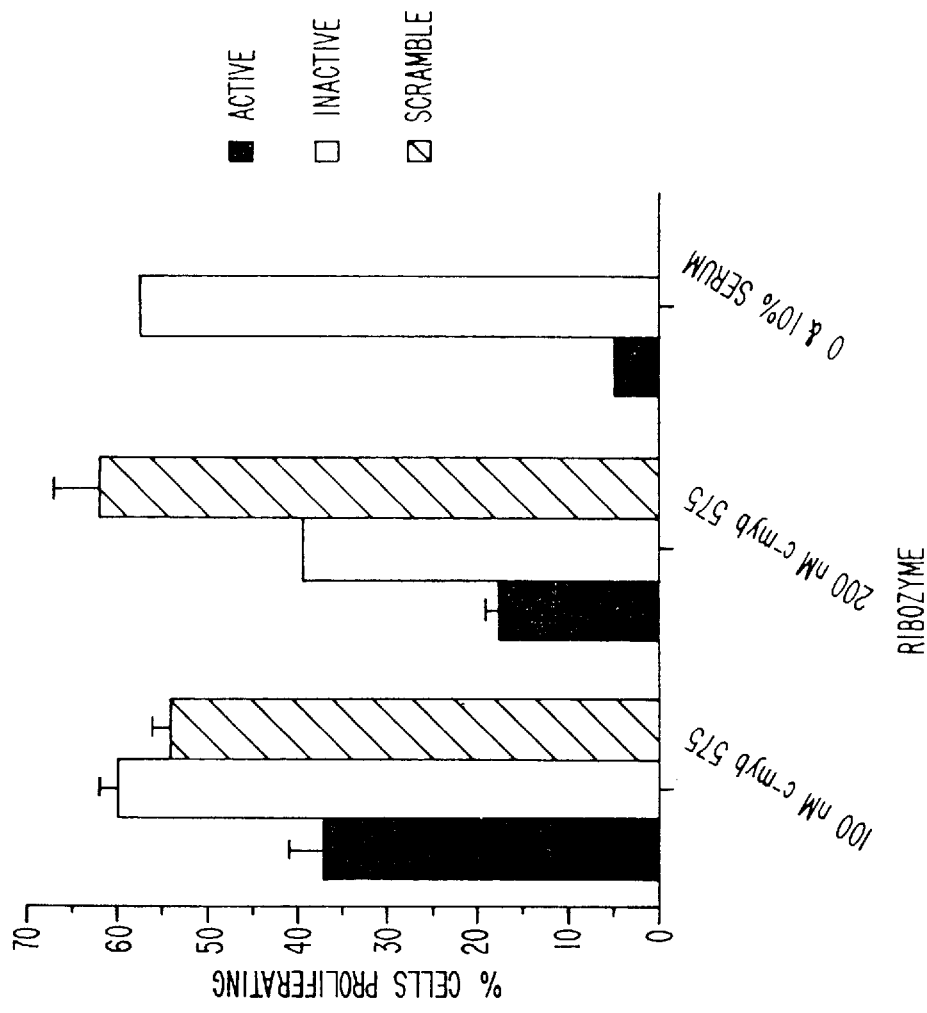

FIG. 18 shows the inhibition of human smooth muscle cell proliferation by active c-myb 575 HH ribozyme.

Figure 19:
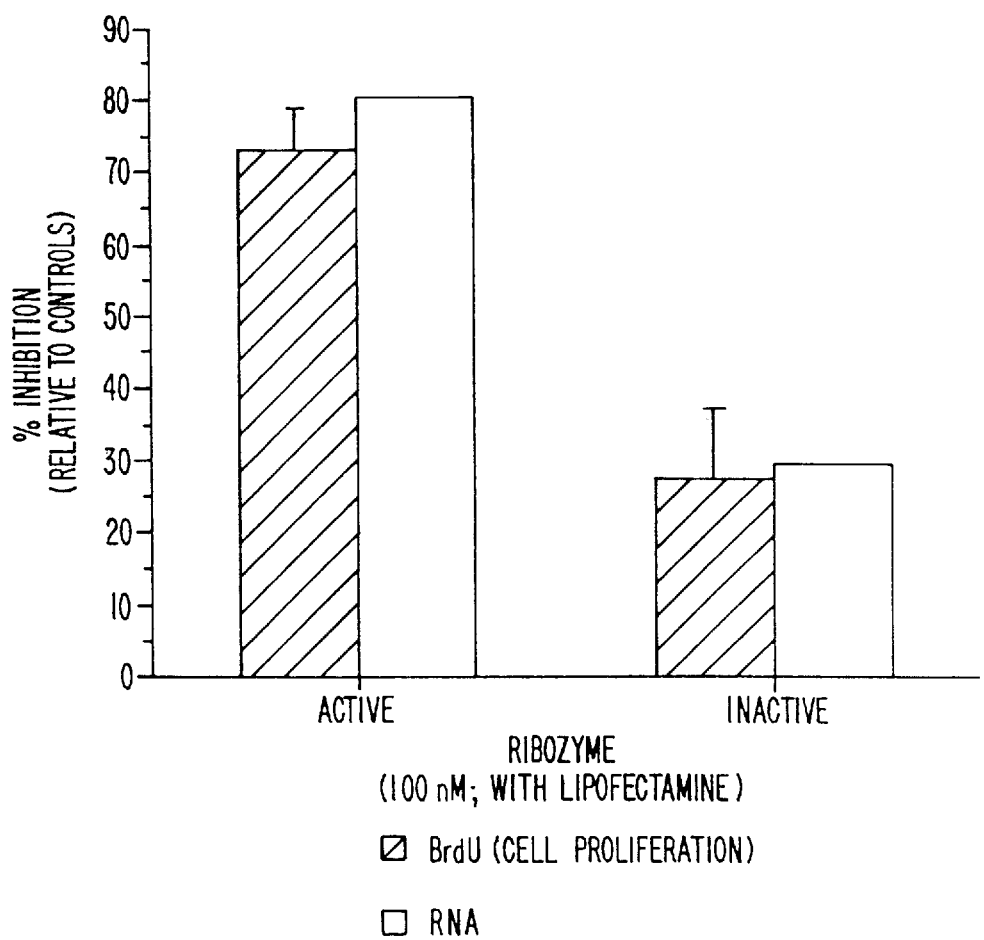

FIG. 19 shows inhibition of intimal hyperplasia in injured pig vessels by locally delivered synthetic RNA.

Figure 20:
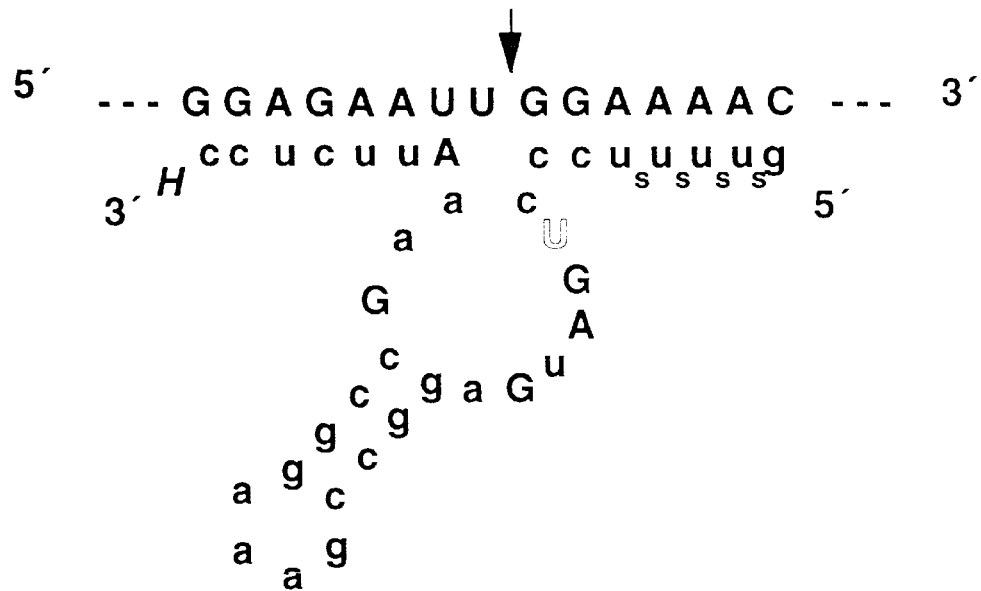

FIG. 20 is digrammatic representation of an optimal c-myb HH ribozyme that can be used to treat diseases like restenosis.

Figure 21:
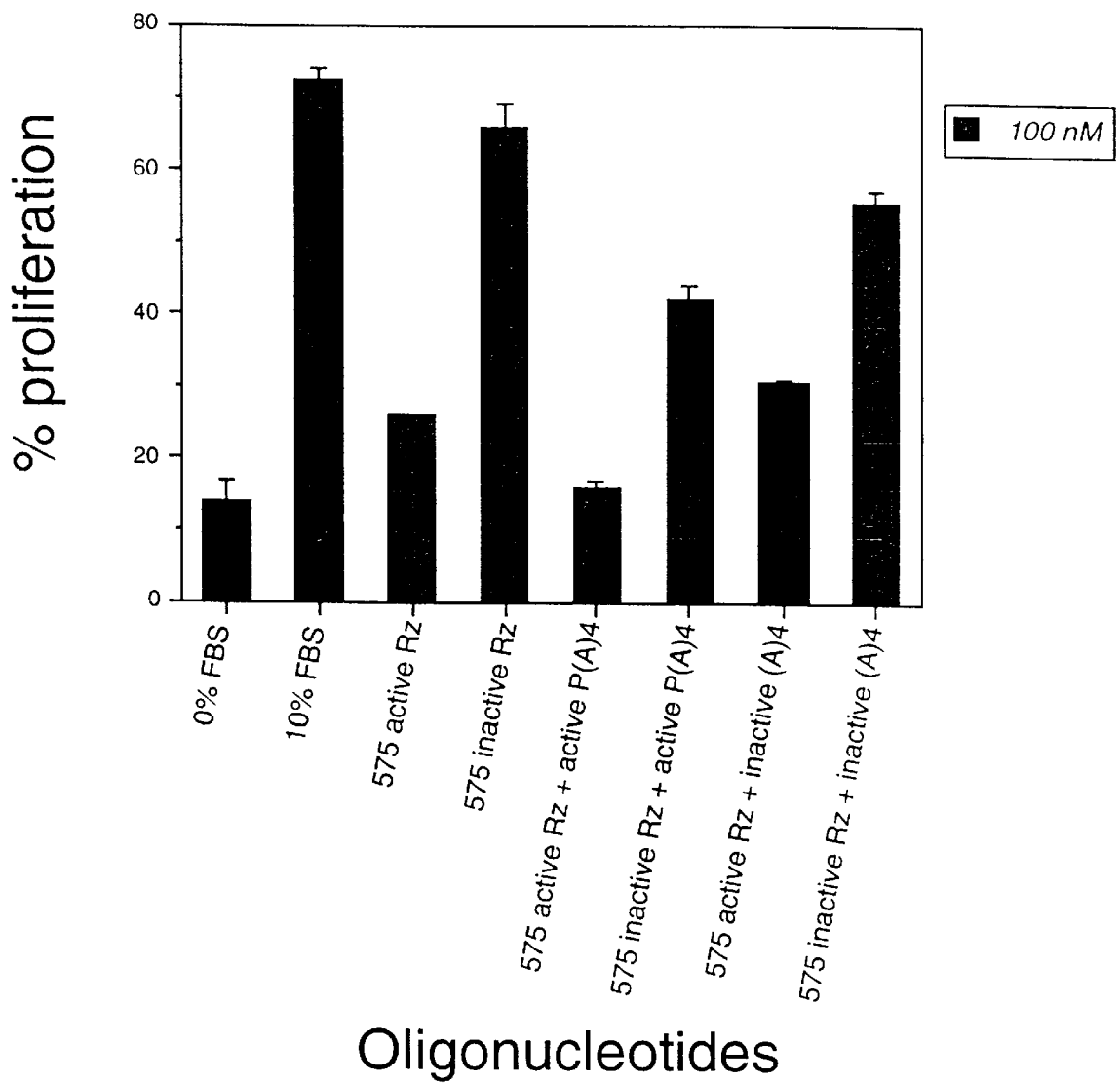

FIG. 21 shows the inhibition of Rat smooth muscle cells by 2–5A containing nucleic acids.

Target sites

Targets for useful ribozymes can be determined as disclosed in Draper et al supra. Sullivan et al., supra, as well as by Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to mouse RNA are provided, those in the art will recognize that equivalent human RNA targets can be used as described below. Thus, the same target may be used, but binding arms suitable for targetting human RNA sequences are present in the ribozyme. Such targets may also be selected as described below.

The sequence of human, pig and murine c-myb mRNAs were screened for optimal ribozyme target sites using a computer folding algorithm. Hammerhead or hairpin ribozyme cleavage sites were identified. These sites are shown in Tables II and IV (All sequences are 5' to 3' in the tables) The nucleotide base position is noted in the Tables as that site to be cleaved by the designated type of ribozyme. While murine, pig and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, murine and pig targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes were designed that could bind and were individually analyzed by computer folding (Jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

The sequences of the ribozymes that are chemically synthesized, useful in this study, are shown in Table III. Those in the art will recognize that these sequences are representative only of many more such sequences where the enzymatic portion of the ribozyme (all but the binding arms) is altered to affect activity. For example, stem-loop II sequence of hammerhead ribozymes listed in Table III (5'-GGCCGAAAGGCC-3') can be altered (substitution, deletion, and/or insertion) to contain any sequences provided a minimum of two base-paired stem structure can form. Similarly, stem-loop IV sequence of hairpin ribozymes listed in Table III (5'-CACGUUGUG-3') can be altered (substitution, deletion, and/or insertion) to contain any sequence, provided a minimum of two base-paired stem structure can form. The sequences listed in Table III may be formed of ribonucleotides or other nucleotides or non-nucleotides. Such ribozymes are equivalent to the ribozymes described specifically in the Tables.

Optimizing Ribozyme Activity

Figure 2:
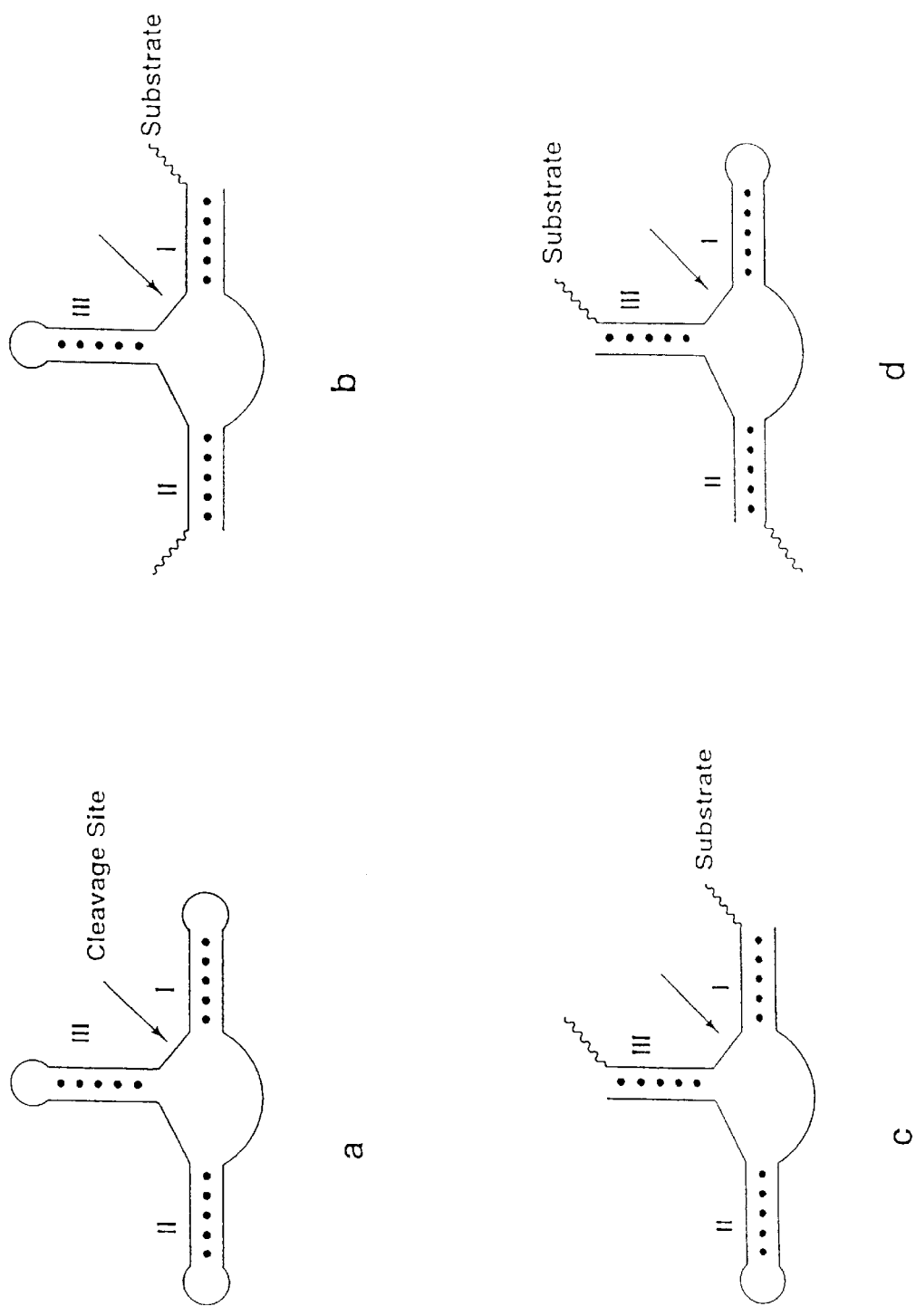

Ribozyme activity can be optimized as described in this application. These include altering the length of the ribozyme binding arms (stems I and III, see FIG. 2c), or chemically synthesizing ribozymes with modifications that prevent their degradation by serum ribonucleases (see e.g., Eckstein et al, International Publication No. WO 92/07065;

Perrault et al, 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application Ser. No. 07/829,729, and Sproat, European Patent Application 92110298.4 which describe various chemical modifications that can be made to the sugar moieties of enzymatic RNA molecules, modifications which enhance their efficacy in cells, and removal of stem II bases to shorten RNA synthesis times and reduce chemical requirements. (All these publications are hereby incorporated by reference herein.), Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al, supra which have been incorporated by reference herein.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. U.S.A.*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves mRNAs encoded by c-myb is inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech.* 3, 533).

The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo.

In another preferred embodiment, the ribozyme is administered to the site of c-myb expression (e.g., smooth muscle cells) in an appropriate liposomal vesicle.

EXAMPLES

Ability Of Exogenously-Delivered Ribozymes Directed Against c-myb To Inhibit Vascular Smooth Muscle Cell Proliferation The following examples demonstrate the selection of ribozymes that cleave c-myb mRNA. The methods described herein represent a scheme by which ribozymes may be derived that cleave other mRNA targets required for cell division. Also provided is a description of how such ribozymes may be delivered to smooth muscle cells. The examples demonstrate that upon delivery, the ribozymes inhibit cell proliferation in culture. Moreover, no inhibition is observed if mutated ribozymes that are catalytically inactive are applied to the cells. Thus, inhibition requires the catalytic activity of the ribozymes. The cell division assay used represents a model system for smooth muscle cell hyperproliferation in restenotic lesions.

Example 1

Identification of Potential Ribozyme Cleavage Sites in Human c-myb mRNA

The sequence of human c-myb mRNA was screened for accessible sites using a computer folding algorithm. Regions of the mRNA that did not form secondary folding structures and contained potential hammerhead ribozyme cleavage sites were identified. These sites are shown in Table II and are identical to Table I of Draper, "Method and Reagent for Treatment of a Stenotic Condition", U.S. Ser. No. 07/987, 132. (All sequences are 5' to 3' in the tables.) In the original, the sites were identified using nucleotide numbers from (Majello, B., et al., 1986, *Proc. Natl. Acad. Sci. USA*, 83, 9636–9640) (GenBank Accession No. M15024). Here, we report sites using the sequence numbers from (Westin, E. H., et al., 1990, *Oncogene*, 5, 1117–1124) (GenBank Accession No. X52125); the latter sequence is derived from a longer c-myb cDNA isolate and thus is more representative of the full-length RNA.

Example 2

Selection of Ribozyme Cleavage Sites in Murine and Human c-myb mRNA

To test whether the sites predicted by the computer-based RNA folding algorithm corresponded to accessible sites in c-myb RNA, 41 hammerhead sites were selected for analysis. Ribozyme target sites were chosen by comparing cDNA sequences of mouse and human c-myb (GenBank Accession No. X02774 and GenBank Accession No. X52125, repsectively) and prioritizing the sites on the basis of overall nucleotide sequence homology. Hammerhead ribozymes were designed that could bind each target (see FIG. 2C) and were individually analyzed by computer folding (Jaeger, J. A., et al., 1989, *Proc. Natl. Acad. Sci. USA*, 86, 7706–7710)

to assess whether the ribozyme sequences fold into the appropriate secondary structure. Those ribozymes with unfavorable intramolecular interactions between the binding arms and the catalytic core were eliminated from consideration. As noted below, varying binding arm lengths can be chosen to optimize activity. Generally, at least 5 bases on each arm are able to bind to, or otherwise interact with, the target RNA.

Example 3
Screening Ribozyme Cleavage Sites by RNaseH Protection

Murine and human mRNA was screened for accessible cleavage sites by the method described generally in McSwiggen, U.S. patent application Ser. No. 07/883,849 filed May 1, 1992, entitled "Assay for ribozyme target site," hereby incorporated by reference herein. Briefly, DNA oligonucleotides representing 41 potential hammerhead ribozyme cleavage sites were synthesized. A polymerase chain reaction was used to generate a substrate for T7 RNA polymerase transcription from human or murine c-myb cDNA clones. Labeled RNA transcripts were synthesized in vitro from the two templates. The oligonucleotides and the labeled transcripts were annealed, RNAseH was added and the mixtures were incubated for the designated times at 37° C. Reactions were stopped and RNA separated on sequencing polyacrylamide gels. The percentage of the substrate cleaved was determined by autoradiographic quantitation using a phosphor imaging system. The results are shown in FIGS. 7 and 8. From these data, 20 hammerhead ribozyme sites were chosen as the most accessible (see Table III). Eighteen of the twenty sites chosen overlap sequences shown in Table II; thus, the RNA folding is predictive of accessible regions in the RNA.

Example 4
Chemical Synthesis and Purification of Ribozymes for Efficient Cleavage of c-myb RNA Ribozymes of the hammerhead or hairpin motif were designed to anneal to various sites in the mRNA message. The binding arms are complementary to the target site sequences described above. The ribozymes were chemically synthesized. The method of synthesis used followed the procedure for normal RNA synthesis as described in Usman et al., 1987 *J. Am. Chem. Soc.*, 109, 7845 and in Scaringe et al., 1990 *Nucleic Acids Res.*, 18, 5433 and made use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.*, 20, 3252). Hairpin ribozymes were synthesized in two parts and annealed to reconstruct the active ribozyme (Chowrira and Burke, 1992 *Nucleic Acids Res.*, 20, 2835–2840). Ribozymes were also synthesized from DNA templates using bacteriophage T7 RNA polymerase (Milligan and Uhlenbeck, 1989, *Methods Enzymol.* 180, 51). All ribozymes were modified extensively to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34). Ribozymes were purified by gel electrophoresis using general methods or were purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and were resuspended in water. The sequences of the chemically synthesized ribozymes used in this study are shown below in Table III.

Example 5
Ribozyme Cleavage of Long Substrate RNA Corresponding to c-myb mRNA Target Hammerhead-type ribozymes which were targeted to the murine c-myb mRNA were designed and synthesized to test the cleavage activity at the 20 most accessible sites in in vitro transcripts of both mouse and human c-myb RNAs. The target sequences and the nucleotide location within the c-myb mRNA are given in Table IV. All hammerhead ribozymes were synthesized with binding arm (Stems I and II; see FIG. 2C) lengths of seven nucleotides. Two hairpin ribozymes were synthesized to sites 1632 and 2231. The relative abilities of these ribozymes to cleave both murine and human RNAs is summarized in Table IV. Ribozymes (1 $\mu$M) were incubated with $^{32}$P-labeled substrate RNA (prepared as described in Example 3, approximately 20 nM) for 60 minutes at 37° C. using buffers described previously. Intact RNA and cleavage products were separated by electrophoresis through polyacrylamide gels. The percentage of cleavage was determined by Phosphor Imager® quantitation of bands representing the intact substrate and the cleavage products.

Five hammerhead ribozymes (directed against sites 549, 575, 1553, 1597, and 1635) and one hairpin ribozyme (directed against site 1632) were very active; they cleaved >70% of both murine and human c-myb RNA in 60 minutes. Nine of the hammerhead ribozymes (directed against sites 551, 634, 936, 1082, 1597, 1721, 1724, 1895, and 1943) were intermediate in activity, cleaving >50% of both murine and human c-myb RNA in 60 minutes. All of the sites cleaved by these active ribozymes were predicted to be accessible to ribozyme cleavage in Table 2. Six hammerhead ribozymes and one hairpin ribozyme showed low activity on at least one of the substrates. The observed differences in accessibility between the two species of c-myb RNA demonstrate the sensitivity of ribozyme action to RNA structure and suggest that even when homologous target sequences exist, ribozymes may be excluded from cleaving that RNA by structural constraints. This level of specificity minimizes non-specific toxicity of ribozymes within cells.

Example 6
Ability of Hammerhead Ribozymes to Inhibit Smooth Muscle Cell Proliferation.

The ribozymes that cleaved c-myb RNA described above were assayed for their effect on smooth muscle cell proliferation. Rat vascular smooth muscle cells were isolated and cultured as follows. Aortas from adult Sprague-Dawley rats were dissected, connective tissue was removed under a dissecting microscope, and 1 mm$^2$ pieces of the vessel were placed, intimal side up, in a Petri dish in Modified Eagle's Medium (MEM) with the following additives: 10% FBS, 2% tryptose phosphate broth, 1% penicillin/streptomycin and 2 mM L-Glutamine. The smooth muscle cells were allowed to migrate and grow to confluence over a 3–4 week period. These primary cells were frozen and subsequent passages were grown at 37° C. in 5% CO2 in Dulbecco's modified Eagle's medium (DMEM), 10% fetal bovine serum (FBS), and the following additives: 2 mM L-Glutamine, 1% penicillin/streptomycin, 1 mM sodium pyruvate, non-essential amino acids (0.1 mM of each amino acid), and 20 mM Hepes pH 7.4. Cells passed four to six times were used in proliferation assays. For the cell proliferation assays, 24-well tissue culture plates were prepared by coating the wells with 0.2% gelatin and washing once with phosphate-buffered saline (PBS). RASMC were inoculated at 1×10$^4$ cells per well in 1 ml of DMEM plus 10% FBS and additives and incubated for 24 hours. The cells were subconfluent when plated at this density. The cells were serum-starved by removing the medium, washing once with PBS, and incubating 48–72 hours in DMEM containing 0.5% FBS plus additives.

In several other systems, cationic lipids have been shown to enhance the bioavailability of oligonucleotides to cells in culture (Bennet, C. F., et al., 1992, *Mol. Pharmacology*, 41, 1023–1033). In many of the following experiments, ribozymes were complexed with cationic lipids. The cationic lipid, Lipofectamine (a 3:1 (w/w) formulation of DOSPA (2,3-dioleyloxy-N-[2(sperminecarboxamido)ethyl]-N,N-dimethyl-1-propanaminium trifluoroacetate) and dioleoyl phosphatidylethanolamine (DOPE)), was purchased from Life Technologies, Inc. DMRIE (N-[1-(2, 3-ditetradecyloxy)propyl]-N,N-dimethyl-N-hydroxyethylammonium bromide) was obtained from VICAL. DMRIE was resuspended in $CHCl_3$ and mixed at a 1:1 molar ratio with dioleoyl phosphatidylethanolamine (DOPE). The $CHCl_3$ was evaporated, the lipid was resuspended in water, vortexed for 1 minute and bath sonicated for 5 minutes. Ribozyme and cationic lipid mixtures were prepared in serum-free DMEM immediately prior to addition to the cells. DMEM plus additives was warmed to room temperature (about 20–25° C.), cationic lipid was added to the final desired concentration and the solution was vortexed briefly. RNA oligonucleotides were added to the final desired concentration and the solution was again vortexed briefly and incubated for 10 minutes at room temperature. In dose response experiments, the RNA/lipid complex was serially diluted into DMEM following the 10 minute incubation.

Serum-starved smooth muscle cells were washed twice with PBS, and the RNA/lipid complex was added. The plates were incubated for 4 hours at 37° C. The medium was then removed and DMEM containing 10% FBS, additives and 10 $\mu$M bromodeoxyuridine (BrdU) was added. In some wells, FBS was omitted to determine the baseline of unstimulated proliferation. The plates were incubated at 37° C. for 20–24 hours, fixed with 0.3% $H_2O_2$ in 100% methanol, and stained for BrdU incorporation by standard methods. In this procedure, cells that have proliferated and incorporated BrdU stain brown; non-proliferating cells are counterstained a light purple. Both BrdU positive and BrdU negative cells were counted under the microscope. 300–600 total cells per well were counted. In the following experiments, the percentage of the total cells that have incorporated BrdU (% cell proliferation) is presented. Errors represent the range of duplicate wells. Percent inhibition then is calculated from the % cell proliferation values as follows: % inhibition= 100–100((Ribozyme –0% serum)/(Control–0% serum)).

Six hammerhead ribozymes, including the best five ribozymes from the in vitro RNA cleavage test (directed against sites 549, 575, 1553, 1598, and 1635) and one with intermediate cleavage levels (directed against site 1597) and their catalytically inactive controls were synthesized and purified as described above. The ribozymes were delivered at a concentration of 0.3 $\mu$M, complexed with DMRIE/DOPE such that the cationic lipid charges and the anionic RNA charges were at 1:1 molar ratio. The results, shown in Table V, demonstrate a considerable range in the efficacy of ribozymes directed against different sites. Five of the six hammerhead ribozymes (directed against sites 549, 575, 1553, 1597, and 1598) significantly inhibit smooth muscle cell proliferation. The control, inactive ribozymes that cannot cleave c-myb RNA due to alterations in their catalytic core sequence fail to inhibit rat smooth muscle cell proliferation. Thus, inhibition of cell proliferation by these five hammerhead sequences is due to their ability to cleave c-myb RNA, and not because of any antisense activity. The sixth ribozyme (directed against site 1635) fails to function in smooth muscle cells. This ribozyme cleaved c-myb RNA very efficiently in vitro. In this experiment, 10% FBS (no ribozyme added) induced 64±1% proliferation; 0% FBS produced a background of 9±1% proliferation.

Example 7

Ability of exogenously delivered hairpin ribozyme against c-myb to inhibit vascular smooth muscle cell proliferation In addition to the hammerhead ribozymes tested above, a bipartite hairpin ribozyme (Chowrira, B. M., supra, 1992, *Nucleic Acids Res.*, 20, 2835–2840) was identified that also cleaves c-myb RNA. The effect of this ribozyme on smooth muscle cell proliferation was tested. Ribozymes were delivered at the indicated doses with Lipofectamine at a 1:1 charge ratio. In this experiment, 10% FBS (no ribozyme) induced 87±1%. proliferation; 0% FBS produced 5±1% proliferation. The results of a dose-response experiment are shown in Table VI. In this example, the control was an irrelevant hammerhead ribozyme. The irrelevant ribozyme control contains the same catalytic core sequences, but has binding arms that are directed to a cellular RNA that is not required for smooth muscle cell proliferation. This control failed to significantly inhibit cell proliferation, demonstrating the sequence specificity of these ribozymes. Another control that could be run is an irrelevant catalytically active ribozyme having the same GC content as the test ribozyme.

Example 8

Ribozymes inhibit proliferation of rat smooth muscle cells in a dose-dependent fashion.

If the inhibition of proliferation observed in Example 6 is caused by the ribozymes, the level of inhibition should be proportional to the dose of RNA added. Rat aortic smooth muscle cells were assayed for proliferation in the presence of differing doses of two hammerhead ribozymes. The results shown in Table VII indicate that two hammerhead ribozymes that cleave c-myb RNA at sites 575 and 549 inhibit SMC proliferation in a dose-dependent fashion. Ribozymes were delivered with the cationic lipid, Lipofectamine at a 1:1 charge ratio. In this experiment, 10% FBS (no ribozyme) gave 92 i 1% proliferation; 0% FBS gave 6±1% proliferation. The control is an active ribozyme directed against an irrelevant mRNA target and shows no inhibition over the dose range tested. The control ribozyme contains the same catalytic core sequences as the active ribozymes but differs in its binding arm sequences (stems I and III in FIG. 2c). Thus, ribozyme inhibition of smooth muscle cell proliferation requires sequence-specific binding by the hammerhead arms to c-myb mRNA.

Example 9

Delivery of a c-myb Ribozyme With Different Cationic Lipids

The experiment in Table VIII shows the response of rat smooth muscle cells to a hammerhead ribozyme that cleaves c-myb RNA at site 575 delivered with two different cationic lipids, DMRIE and Lipofectamine.

Similar efficacy is observed with either lipid. 10% FBS (no ribozyme) induced 78±2% proliferation; 0% FBS produced a background of 6±1% proliferation.

Example 10

Effect of varying arm-lengths on ribozyme activity.

The exact configuration of each ribozyme can be optimized by altering the length of the binding arms (stems I and III, see FIG. 2C). The length of the binding arms may have an effect on both the binding and the catalytic cleavage step (Herschlag, D., 1991, *Proc. Natl. Acad. Sci. USA*, 88, 6921–5). For example, Table IX shows the ability of arm length variants of c-myb hammerhead 575 to inhibit SMC proliferation. Note that the dose used in this experiment (0.1 μM) is 3-fold lower than in previous experiments. At this concentration, the 7/7 arm variant gives relatively little inhibition. In this case, the degree of inhibition increases with concomitant increases in arm length.

The optimum arm length may be site-specific and should be determined empirically for each ribozyme. Towards this end, hammerhead ribozymes target with 7 nucleotide binding arms (7/7) and ribozymes with 12 nucleotide binding arms (12/12) targeted to three different cleavage sites were compared.

Ribozymes were delivered at 0.2 μM with the cationic lipid DMRIE at a 1:1 charge ratio of oligonucleotide to cationic lipid as described in Example 6. The data are shown below in Table X. As can be seen, all three ribozymes demonstrated enhanced inhibition of smooth muscle cell proliferation with twelve nucleotide binding arms. Each ribozyme showed greater inhibition than its catalytically inactive control, again demonstrating that the ribozymes function via their ability to cleave c-myb RNA. In this experiment, 10% stimulation resulted in 54±2% cell proliferation;

unstimulated cells showed 8±0.5% cell proliferation.

Example 11
Effect of chloroquine on ribozyme activity.

A number of substances that effect the trafficking of macromolecules through the endosome have been shown to enhance the efficacy of DNA delivery to cells. These include, but are not limited to, ammonium chloride, carbonyl cyanide p-trifluoromethoxy phenyl hydrazone (FCCP), chloroquine, monensin, colchicine, and viral particles (Cotten, M. et al., 1990, *Proc. Natl. Acad. Sci. USA*, 87, 4033–4037; Cotten, M. et al., 1993, *J. Virol.*, 67, 3777–3785; Cotten, M. et al., 1992, *Proc. Natl. Acad. Sci.* 89, 6094–6098; Cristiano, R. J. et al., 1993, *Proc. Natl. Acad. Sci. USA*, 90, 2122–6; Curiel, D. T. et al., 1991, *Proc. Nat. Acad. Sci. USA*, 88, 8850–8854; Ege, T. et al., 1984, *Exp. Cell Res.*, 155, 9–16; Harris, C. E. et al., 1993, *Am. J. Respir. Cell Mol. Biol.*, 9, 441–7; Seth, P. et al., 1994, *J. Virol.*, 68, 933–40; Zenke, M. et al., 1990, *Proc. Natl. Acad. Sci. USA*, 87, 3655–3659). It is thought that DNA is taken up by cells by endocytosis, resulting in DNA accumulation in endosomes (Akhtar, S. and Juliano, R. L., 1992, *Trends Cell Biol.*, 2, 139–144). Thus, the above agents may enhance DNA expression by promoting DNA release from endosomes. To determine whether such agents may augment the functional delivery of RNA and ribozymes to smooth muscle cells, the effects of chloroquine on ribozyme inhibition of smooth muscle cell proliferation were assessed. A ribozyme with twelve nucleotide binding arms that cleaves c-mby RNA was delivered to rat smooth muscle cells as described in Example 6 (0.2 μM ribozyme complexed with DMRIE/DOPE at a 1:1 charge ratio). In some cases, 10 μM chloroquine was added upon stimulation of the cells. The addition of choloroquine had no effect on untreated cells (stimulation with 10% serum in the presence or absence of chloroquine resulted in 80.5±1.5% and 83±2% cell proliferation, respectively; unstimulated cells with and without chloroquine showed 7±0.5% and 7±1% cell proliferation, respectively). As shown in Table Xl below, addition of chloroquine augments ribozyme inhibition of smooth muscle cell proliferation two- to three-fold.

Example 12
Effect of a hammerhead ribozyme on human smooth muscle cell proliferation.

The hammerhead ribozyme that cleaves human c-myb RNA at site 549 was tested for its ability to inhibit human aortic smooth muscle cell proliferation. The binding site for this ribozyme is completely conserved between the mouse and human cDNA sequences. Human aortic smooth muscle cells (AOSMC) were obtained from Clonetics and were grown in SmGM (Clonetics®). Cells from passage five or six were used for assays. Conditions for the proliferation assay were the same as for the rat cells (see Example 6), except that the cells were plated in SmGM and starved in SmBM plus 0.5% FBS. The ribozyme that cleaves site 549 was delivered at varying doses complexed with the cationic lipid DMRIE at a 1:1 charge ratio. In this experiment, 10% FBS (no ribozyme) induced 57±7% proliferation; the uninduced background was 6±1% proliferation. The results in Table XII show that inhibition is observed over a similar concentration range as was seen with rat smooth muscle cells.

Example 13
Inhibition by direct addition of a modified, stabilized ribozyme.

Figure 1:
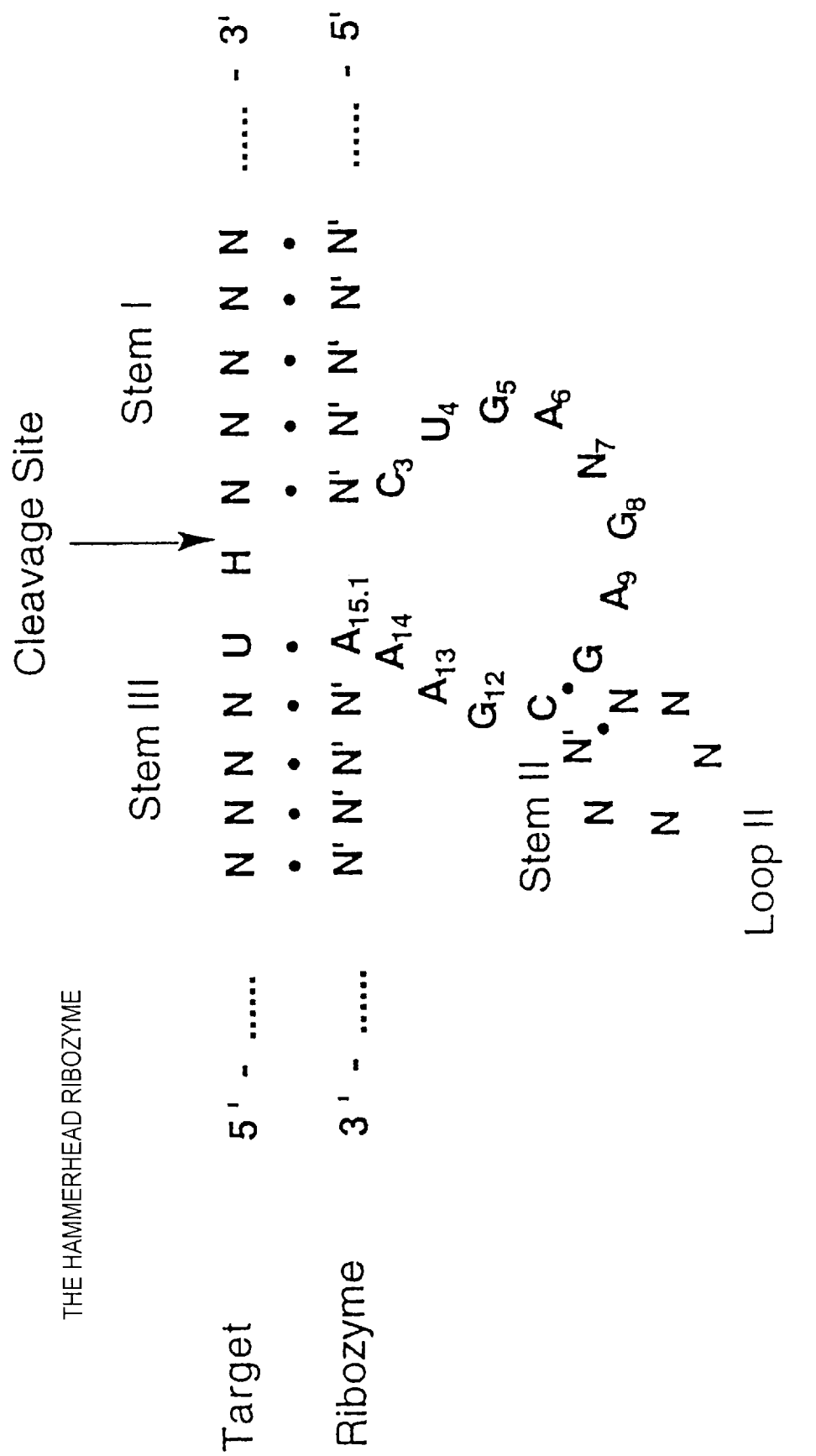

A hammerhead ribozyme that cleaves site 575 was chemically synthesized with 12 nucleotide binding arms (sequence ID NO. 127, in Table III). Chemically modified nucleotides were incorporated into this ribozyme that have been shown to enhance ribozyme stability in serum without greatly impacting catalytic activity. (See Eckstein et al., International Publication No. WO 92/07065, Perrault et al., 1990, *Nature*, 344, 565–568, Pieken, W. et al. 1991, *Science*, 253, 314–317, Usman, N.; Cedergren, R. J., 1992, *Trends in Biochem. Sci.*, 17, 334–339, Usman, N. et al. U.S. patent application Ser. No. 07/829,729 and Sproat, B. European Patent Application 92110298.4 describe various chemical modifications that can be made to the sugar moieties of enzymatic RNA molecules. All these publications are hereby incorporated by reference herein.) The modifications used were as follows. All the nucleotides of the ribozyme contained 2'-O-methyl groups with the following exceptions: $U_4$ and $U_7$ contained 2'-amino substitutions; $G_5$, $A_6$, $G_8$, $G_{12}$, and $A_{15.1}$ were 2'-OH ribonucleotides (numbering as in FIG. 1). An inactive ribozyme was chemically synthesized in which $G_5$ and $A_{14}$ were substituted with 2'-O-methyl U. Ribozymes were added to rat smooth muscle cells at the indicated concentrations as per Example 6 except that cationic lipids were omitted. Proliferation was assessed by BrdU incorporation and staining. Table XII shows that the modified ribozyme is capable of inhibiting rat smooth muscle cell proliferation without addition of cationic lipids. In this experiment, 10% serum induced 45±2% proliferation while uninduced cells showed a background of 2.3±0.1% proliferation.

Optimizing Ribozyme Activity

As demonstrated in the above examples, ribozymes that cleave c-myb RNA are capable of inhibiting 50% of the smooth muscle cells from proliferating in response to serum. This level of inhibition does not represent the maximal effect obtainable with the ribozymes; in each dose response experiment, the highest dose produced the greatest extent of inhibition. Thus, optimizing activity of the ribozyme within the cells and/or optimizing the delivery of the ribozyme to the cells is expected to increase the extent of inhibition.

Tables IX and X demonstrate one means of optimizing ribozyme activity. By altering the length of the ribozyme binding arms (stems I and III, see FIG. 2c), the ability of the ribozyme to inhibit smooth muscle cell proliferation is greatly enhanced. Ribozymes with increasing arm lengths will be synthesized either chemically in one or two parts (see above and see Mamone, U.S. Ser. No. 07/882,689, filed May 11, 1992, hereby incorporated by reference herein) or by in vitro transcription (see Cech et al., U.S. Pat. No. 4,987,071). Ribozymes are chemically synthesized with modifications that prevent their degradation by serum ribonucleases (as described in Example 13, above). When synthesized in two parts, the fragments are ligated or otherwise juxtaposed as described (see original application and Mamone, supra). The effects of the ribozymes on smooth muscle cell proliferation are assessed as in Examples 6 and 12, above. As the length of stems I and III can affect both hybridization to the target and the catalytic rate, the arm length of each ribozyme will be optimized for maximal inhibitory effect in cells. Similarly, the precise sequence of modified nucleotides in the stabilized ribozyme will affect the activity in cells. The nature of the stabilizing modifications will be optimized for maximal inhibitory effect in cells. In each case, activity of the ribozyme that cleaves c-myb RNA will be compared to the activity of its catalytically inactive control (substitution of 2'-O-methyl U for $G_5$ and a 2'-O-methyl U for $A_{14}$) and to a ribozyme targeted to an irrelevant RNA (same catalytic core, with appropriate modifications, but different binding arm sequences).

Sullivan, et al., supra, describes the general methods for delivery of enzymatic RNA molecules. The data presented in Example 9 indicate that different cationic lipids can deliver active ribozymes to rat smooth muscle cells. In this example, 0.6 μM ribozyme delivered with Lipofectamine produced the same inhibitory effect as 0.3 μM ribozyme delivered with DMRIE. Thus, DMRIE is twice as efficacious as Lipofectamine at delivering active ribozymes to smooth muscle cells. There are a number of other cationic lipids known to those skilled in the art that can be used to deliver nucleic acid to cells, including but not limited to dioctadecylamidoglycylspermine (DOGS), dioleoxltrimetylammonium propane (DOTAP), N-[1-(2,3-dioleoyloxy)-propyl]-n,n,n-trimethylammoniumchloride (DOTMA), N-[1-(2,3-dioleoyloxy)-propyl]-N,N-dimethyl-N-hydroxyethylammonium bromide (DORIE), and N-[1-(2,3-dioleoyloxy)propyl]-N,N-dimethyl-N-hydroxypropylammonium bromide (DORIE-HP). Experiments similar to those performed in Example 9 are used to determine which lipids give optimal delivery of ribozymes to smooth muscle cells. Other such delivery methods are known in the art and can be utilized in this invention.

The data described in Example 11 show that ribozyme delivery and efficacy may be augmented by agents that disrupt or alter cellular endosome metabolism. Chloroquine was shown to increase the ability of a ribozyme to inhibit smooth muscle cell proliferation by 2- to 3-fold. Experiments similar to those described in Example 11 can be performed to determine the optimal concentration of chloroquine to be used to augment delivery of ribozymes alone (as in Example 13), or delivery in the presence different cationic lipids (as in Example 9 and described above) or with other delivery agents (as described below). Other agents that disrupt or alter endosomes known to those familiar with the art can be used to similarly augment ribozyme effects. These agents may include, but are not limited to, ammonium chloride, carbonyl cyanide p-trifluoromethoxy phenyl hydrazone (FCCP), chloroquine, monensin, colchicine, amphipathic peptides, viral proteins, and viral particles. Such compounds may be used in conjunction with ribozymes as described above, may be chemically conjugated directly to ribozymes may be chemically conjugated to liposomes, or may be incorporated with ribozymes in liposome particles (see Sullivan, et al, supra, incorporated by reference herein).

The data presented in Example 13 indicate that the proliferation of smooth muscle cells can be inhibited by the direct addition of chemically stabilized ribozymes. Presumably, uptake is mediated by passive diffusion of the anionic nucleic acid across the cell membrane. In this case, efficacy could be greatly enhanced by directly coupling a ligand to the ribozyme. The ribozymes are then delivered to the cells by receptor-mediated uptake. Using such conjugated adducts, cellular uptake can be increased by several orders of magnitude without having to alter the phosphodiester linkages necessary for ribozyme cleavage activity.

Alternatively, ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. The RNA/ vehicle combination is locally delivered by direct injection or by use of a catheter, infusion pump or stent. Alternative routes of delivery include, but are not limited to, intramuscular injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Example 14

Phosphorothioate linkages enhance the ability of ribozymes to inhibit smooth muscle cell proliferation.

As the applicant had shown in Example 13, the hammerhead (HH) ribozyme that cleaves c-myb RNA at site 575 can be modified to confer resistance to nucleases while maintaining catalytic activity (see also Usman et al., supra). To identify ribozymes with optimal activity in cells, several different chemically-modified ribozymes were directly compared for inhibition of rat smooth muscle cell proliferation. Chemically-modified ribozymes used are diagrammed in FIG. 9A. One ribozyme (designated "2'-O-methyl") contains ribonucleotide residues at all positions except the 5 terminal nucleotides of each target binding arm (Stems I and III). The ribozyme designated "2'-O-methyl P=S" in addition contains five phosphorothioate linkages between the terminal nucleotides in each target binding arm. The ribozyme termed "2'-C-allyl iT" contains thirty 2'-O-methyl nucleotides as specified in Example 13. The ribozyme also contains 2'-C-allyl U (Usman et al., 1994 Nucleic Acids Symp. Ser. 31, 163) at the U4 position and 2'-O-methyl U at the U7 position and a 3'—3'-linked inverted thymidine (Ortigao et al., 1992 Antisense Res. & Development 2, 129; Seliger et al., Canadian Patent Application No. 2,106,819) at the 3' end of the molecule (referred to as 2'-C-allyl iT). The fourth ribozyme contains the same 2'-O-methyl and 2'-C-allyl residues described above with the addition of 5 phosphorothioate linkages between the terminal nucleotides in each target binding arm (referred to as "2'-C-allyl P=S").

Figures 1, 9A:
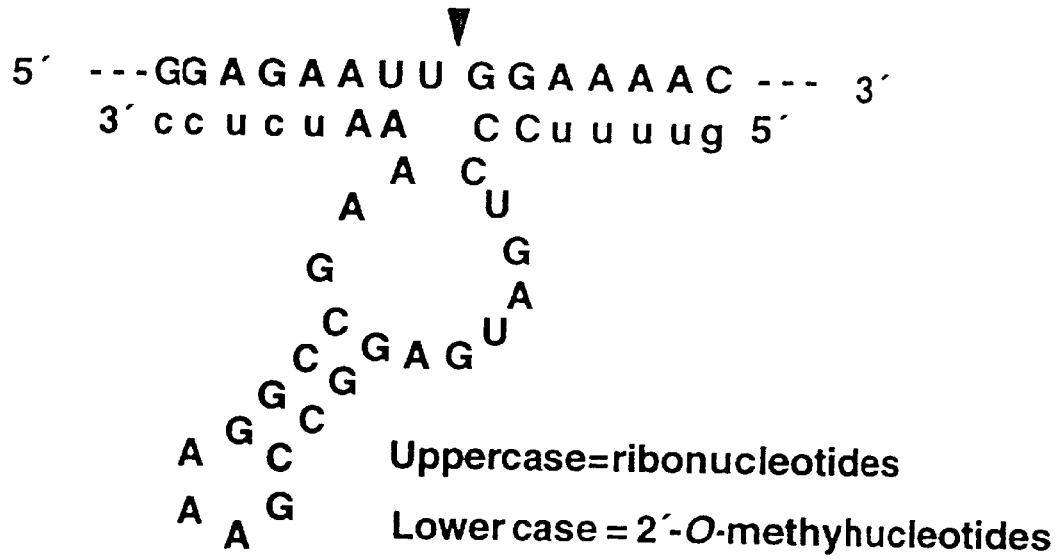
Figures 2, 9A:
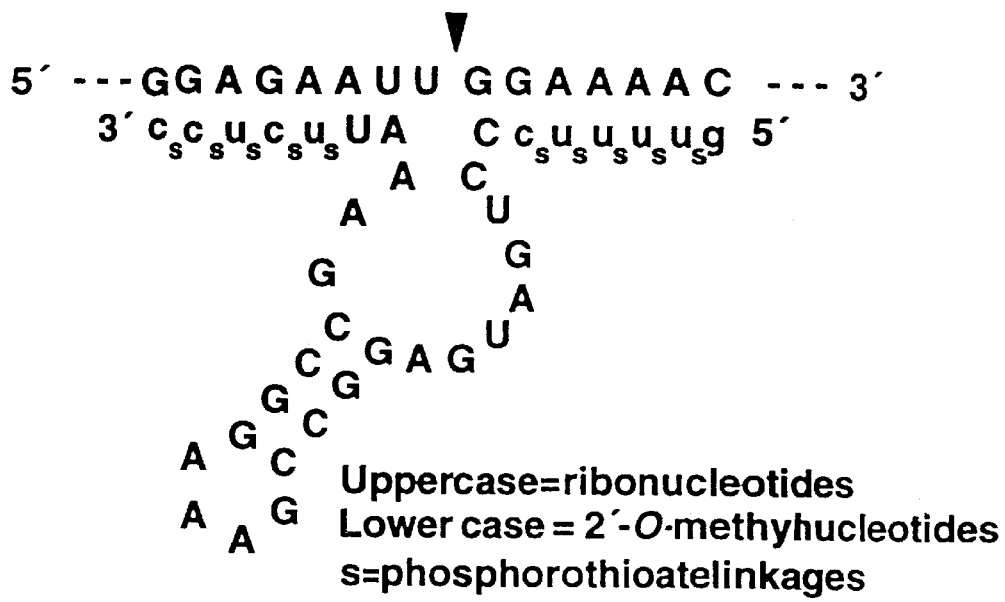
Figures 3, 9A:
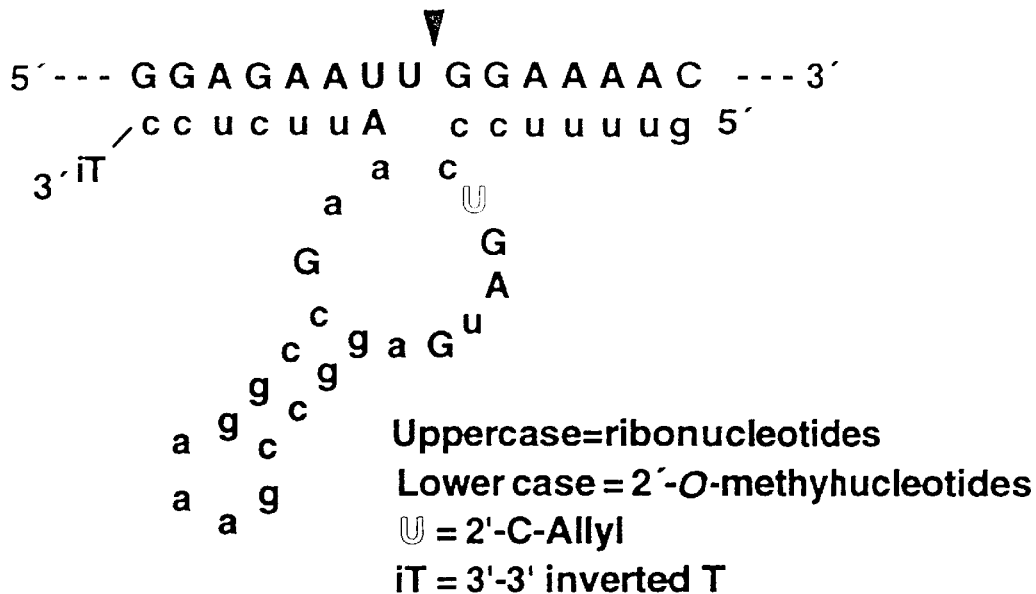
Figures 4, 9A:
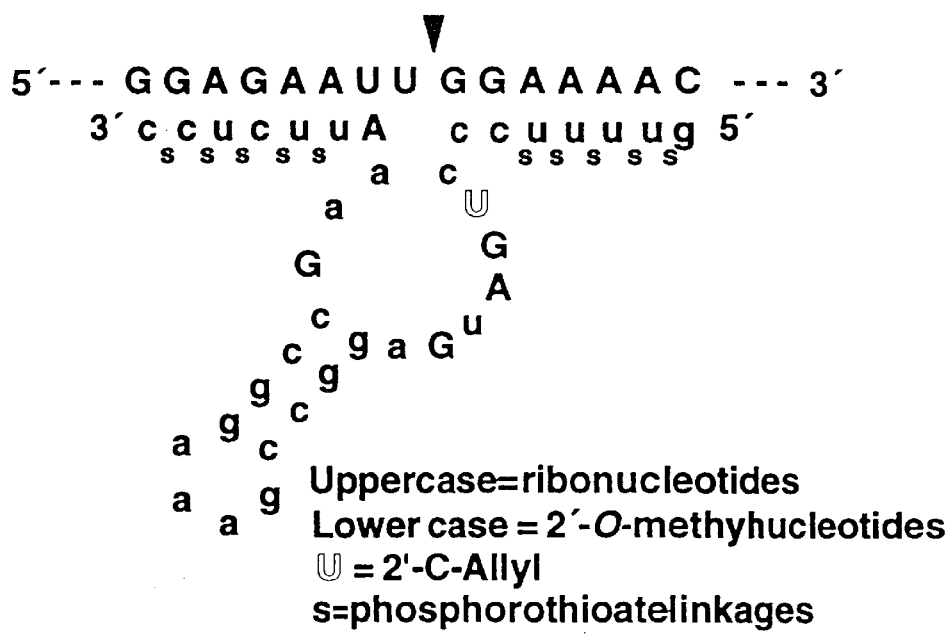
Figure 9B:
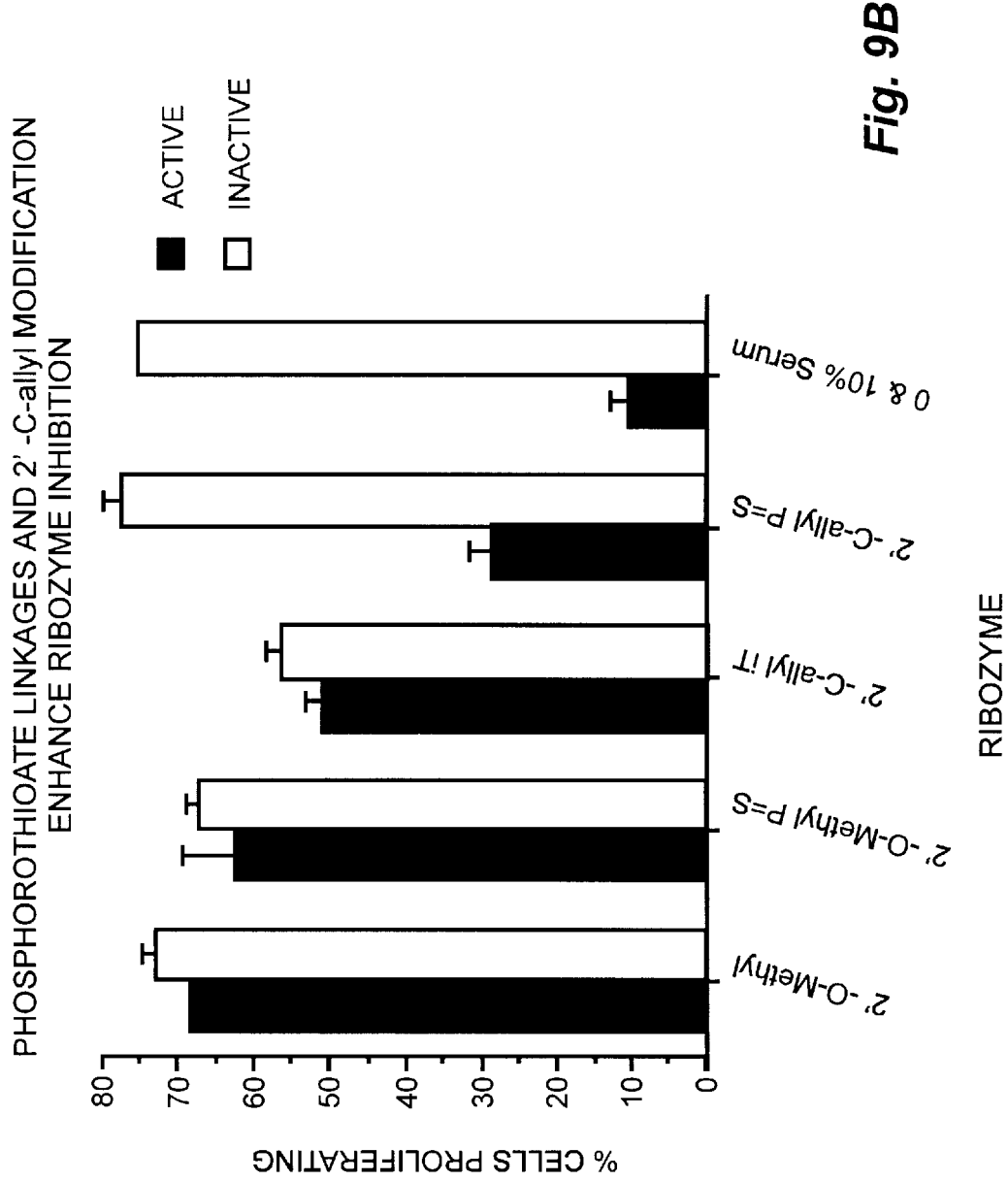

Ribozymes were delivered to smooth muscle cells as cationic lipid complexes (Sullivan et al., supra). In this example, the cationic lipid, Lipofectamine (GIBCO-BRL), was used at a charged lipid concentration of 3.6 μM (see Examples 6 and 9). Active versus inactive forms of each ribozyme were compared to determined whether inhibition is mediated specifically by ribozyme cleavage. As shown in FIG. 9B, the ribozyme synthesized with the 2'-C-allyl modification and the phosphorothioate linkages demonstrated enhanced inhibition of smooth muscle cell proliferation. The catalytically inactive form of the ribozyme had little effect on cell proliferation; thus, the inhibition observed requires the catalytic activity of the ribozyme. In contrast, ribozymes without the stable 2'-O-methyl- and 2'-C-allyl-modified catalytic core (2'-O-methyl and 2'-O-methyl P=S) at best showed only modest inhibition of smooth muscle cell proliferation. The stable core chemistry alone was not sufficient to greatly enhance ribozyme-mediated inhibition; without terminal P=S linkages, the 2'-C-allyl-modified ribozyme showed very little specific inhibition when compared to its inactive ribozyme control. These results demonstrate that certain chemical modifications greatly enhance the ability of exogenously-delivered ribozymes to cleave c-myb RNA and impact cell proliferation.

Example 15

Dose response of the chemically modified ribozyme.

Varying doses of the 2'-C-allyl P=S-modified ribozyme were delivered to rat aortic smooth muscle cells as described above. As in previous examples, percent inhibition was calculated by comparing the effects of the active ribozyme to the effects of the inactive ribozyme. As shown in FIG. 10, the ribozyme concentration at which cell proliferation is inhibited by 50% ($IC_{50}$) is approximately 70 nM. From day to day, the $IC_{50}$ varies between 25 and 100 nM.

Example 16

Direct comparison of the effects of ribozymes and antisense DNA.

Ribozymes are thought to be more specific reagents for the inhibition of gene expression than antisense oligonucleotides due to their catalytic activity and strict sequence requirements around the site of cleavage (Castanotto et al., 1994 *Adv. in Pharmacol.* 25, 289). To test this hypothesis, ribozyme activity was directly compared to the activity of phosphorothioate DNA oligonucleotides that target the same site in the c-myb mRNA. The ribozyme used was the 2'-C-allyl P=S-modified ribozyme described in Example 14, above. This ribozyme binds to a 15 nucleotide long region of the c-myb mRNA. Thus, a 15 nucleotide antisense phosphorothioate DNA molecule was prepared. A phosphorothioate DNA oligonucleotide with a randomly scrambled sequence of the same 15 nucleotides and a 2'-C-allyl P=S-modified ribozyme with randomly scrambled target binding arm sequences were synthesized as controls (by comparison to the murine c-myb cDNA sequence, the scrambled controls would not be expected to bind any region of the c-myb mRNA). Since longer phosphorothioate DNA oligonucleotides are often utilized as antisense inhibitors (for a review see Wagner, 1994 *Science* 372, 333), a symmetrically placed, 25 nucleotide phosphorothioate DNA antisense oligonucleotide and its scrambled sequence control were also synthesized. The ribozymes and the antisense oligonucleotides were delivered to rat smooth muscle cells as complexes with the cationic lipid, Lipofectamine, and serum-stimulated smooth muscle cell proliferation was measured subsequently.

As shown in FIG. 11, the 2'-C-allyl P=S-modified ribozyme demonstrated greater inhibition of smooth muscle cell proliferation than either of the antisense oligonucleotides. Furthermore, the scrambled arm ribozyme and inactive ribozyme controls demonstrated less non-specific inhibition than either of the scrambled sequence antisense control oligonucleotides. In fact, the non-specific inhibition demonstrated by the 25 nucleotide phosphorothioate molecule completely masked any specific effect of the antisense molecule. Similar results have been obtained with phosphorothioate DNA targeting other sites in the c-myb mRNA. Thus, a ribozyme that cleaves c-myb RNA is a more potent and more specific inhibitor of smooth muscle cell proliferation than phosphorothioate antisense DNA molecules.

Example 17

Chemically-modified ribozymes targeting different sites in the c-myb mRNA specifically inhibit smooth muscle cell proliferation.

If the observed inhibition of smooth muscle cell proliferation is mediated by ribozyme cleavage of c-myb mRNA, then other ribozymes that target the same mRNA should have the same effect. Two other ribozymes targeting two disparate sites in the c-myb mRNA (sites 549 and 1553, ribozyme Seq. ID Nos. 102 and 112) were synthesized with the 2'-C-allyl P=S modifications as described in Example 14. Inactive ribozyme controls also were synthesized corresponding to each new target sequence. Chemically-modified ribozymes targeting sites 549, 575, and 1553 were delivered to rat smooth muscle cells and their ability to inhibit serum-stimulated cell proliferation was assessed. Equivalent levels of inhibition are obtained with active ribozymes targeting sites 549, 575 and 1553 (see FIG. 12). None of the inactive ribozymes inhibited cell proliferation. Active ribozymes targeting other mRNA sequences not present in c-myb or ribozymes with scrambled arm sequences also fail to inhibit smooth muscle cell proliferation (see FIG. 12). Thus, inhibition of cell proliferation requires a catalytically active ribozyme that can bind to accessible c-myb mRNA sequences and is likely due to the reduction of c-myb mRNA levels by ribozyme cleavage.

Examples 18 and 19 describe experiments designed to determine the position and minimum number of phosphorothioate residues required for efficacy.

Example 18

Effect of position of phosphorothioate linkages on ribozyme inhibition.

Ribozymes targeting c-myb site 575 were synthesized with the 2'-C-allyl modification and with phosphorothioate linkages between various nucleotides in the ribozyme. One ribozyme contained a total of 10 phosphorothioate linkages, 5 in Stem I and 5 in Stem III, identical to the ribozyme described in Examples 14 through 17 above (referred to as 10 P=S 5' and 3' in FIG. 13A). One ribozyme contained only 5 phosphorothioate linkages in Stem III (5 P=S 3' in FIG. 13A). Another ribozyme contained 5 phosphorothioate linkages between the 6 nucleotides comprising the last base pair of stem 11 and the GAAA loop (5 P=S loop in FIG. 13A). The fourth ribozyme contained 5 phosphorothioate linkages in stem 1 (5 P=S 5' in FIG. 13A). The latter two ribozymes also were synthesized with the 3'—3' thymidine at the 3'end to help protect the ribozyme from 3' exonucleases (Ortigao et al., 1992 *Antisense Res. & Development* 2, 129; Seliger et al., Canadian Patent Application No. 2,106,819). The structure of these four different ribozymes is diagrammed in FIG. 13A. Inactive ribozyme controls were synthesized for each individual ribozyme. The active and inactive ribozymes were applied to rat smooth muscle cells as RNA/Lipofectamine complexes and their effects on cell proliferation were measured.

Figure 13B:
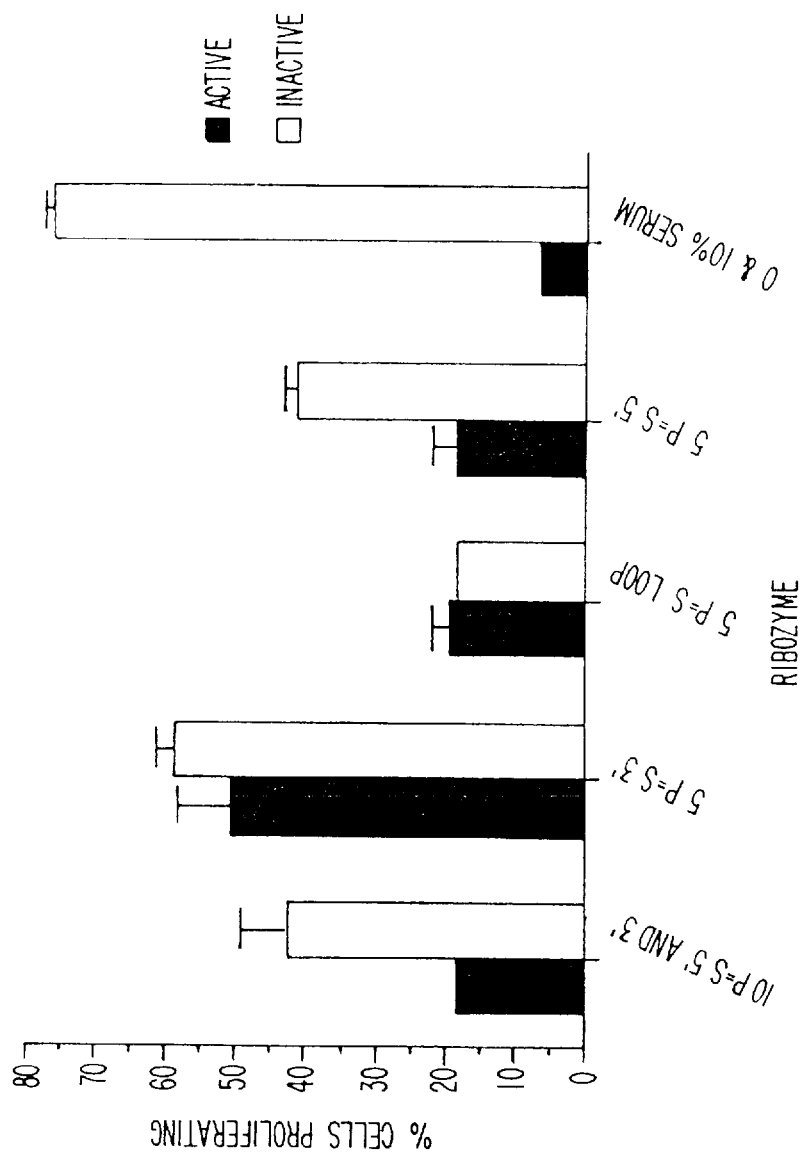

Referring to FIG. 13B, the ribozyme containing 5 phosphorothioate linkages in Stem I and the 3' inverted thymidine inhibited smooth muscle cell proliferation as well as the parent ribozyme with 10 total phosphorothioate linkages. None of the other ribozymes demonstrated significant differences between active and inactive controls. Therefore, the 3' inverted T can effectively substitute for the 5 phosphorothioate linkages in Stem III. Phosphorothioate linkages in the loop position lead to non-specific inhibition of smooth muscle cell proliferation, while phosphorothioate linkages in Stem I are necessary for enhanced efficacy in cells. Additionally, these results suggest that 3'-end modifications, such as iT, is desirable to minimize the amount of phosphorothioate contained in the ribozymes in order to minimize toxicity and facilitate chemical synthesis, while maintaining protection from endogenous 3'-exonuclease digestion.

Example 19
Minimizing phosphorothioate linkages in Stem I.

Fewer phosphorothioate linkages in the ribozyme will reduce the complexity and cost of chemical synthesis. Furthermore, phosphorothioate DNA molecules are known to have some undesirable and non-specific effects on cellular functions (for a review see Wagner, supra); reducing the phosphorothioate linkages in these RNA molecules is expected to enhance their specificity. A series of ribozymes targeting c-myb were synthesized to determine how many phosphorothioate linkages in Stem I are required for optimal ribozyme activity. The ribozymes contained 5, 4, 3, 2, or 1 phosphorothioate linkage(s) in Stem I, beginning with the phosphodiester bond between the first and second nucleotides and proceeding 3'. Each ribozyme contained the 2'-O-methyl modifications, the $U_4$ 2'-C-allyl nucleotide, and the inverted T nucleotide at the 3' end as described above. Activity of each of these ribozymes was compared to the activity of the ribozyme with 10 phosphorothioate linkages, 5 each in Stems I and III (referred to as 10 P=S in FIG. 14). Active and inactive ribozymes were applied to rat smooth muscle cells as complexes with Lipofectamine and their effects on smooth muscle cell proliferation were measured in two separate experiments. The results are diagrammed in FIG. 14. Ribozymes with 10, 5, and 4 phosphorothioate linkages showed equivalent efficacy. Ribozymes with fewer than four phosphorothioate linkages also showed efficacy, but the level of inhibition of smooth muscle cell proliferation was modestly reduced.

Example 20
Varying the length of Stems I and III

Ribozymes that cleave c-myb RNA at position 575 were synthesized with varying arm lengths. Each ribozyme contained 4 phosphorothioate linkages at the 5' end, 2'-O-methyl and 2'-C-allyl modifications and an inverted thymidine nucleotide at the 3'end as described above. FIG. 15 shows the effects of these ribozymes upon rat smooth muscle cell proliferation. Ribozymes were delivered at 100 nM with cationic lipid. Ribozymes with 6/6, 7/7 and 5/10 arms (where x/y denotes the nucleotides in Stem I/nucleotides in Stem III; see FIG. 2) all showed comparable efficacy. As shown in FIG. 15, ribozymes with longer arm lengths tended to demonstrate more non-specific inhibition (the inactive ribozyme controls with longer binding arms inhibited smooth muscle cell proliferation) when compared to ribozymes with shorter binding arms. From these data, it appears that ribozymes with 6/6, 7/7, 5/10, 10/5, 8/8 and 10/10 nucleotide arms all specifically inhibit smooth muscle cell proliferation, optimal inhibition, however, is observed with 6/6, 7/7 and 5/10 nucleotide arms.

Example 21
Ribozymes with different modified nucleotides inhibit smooth muscle cell proliferation.

Ribozymes containing seven nucleotides in both Stems I and II, four phosphorothioate residues at the 5' end and a 3'—3' inverted thymidine at the 3' end, were synthesized with various modified nucleotides at the $U_4$ and $U_7$ positions within the core of a HH ribozyme. All of the modified catalytic core chemistries retained ribozyme activity and demonstrated enhanced stability to serum nucleases (Usman et al., 1994 supra). The ribozyme termed U4 2'-C-allyl contains a 2'-C-allyl uridine at the $U_4$ position and a 2'-O-methyl nucleotide at the $U_7$ position. The ribozyme termed U4,U7 2'-amino contains a 2'-amino nucleotide at both U4 and U7. The ribozyme termed U4 2'-fluoro contains a 2'-fluoro-modified nucleotide at U4 and 2'-O-methyl at U7. The ribozyme termed U4 6-methyl contains a 6-methyl uridine nucleotide at U4 and 2'-O-methyl at U7. The ribozyme termed U4 deoxyabasic contains a deoxyribose moeity and lacks a base at U4 (Beigelman et al., 1994 *Bioorganic & Med. Chem. Letters* 4, 1715) and 2'-O-methyl at U7. Active and inactive versions of each of the chemically-modified ribozymes were applied to rat smooth muscle cells using Lipofectamine as described above. As diagrammed in FIG. 16, all of the nuclease-stable, chemically-modified ribozymes demonstrated significant inhibition of rat smooth muscle cell proliferation. Thus, the requirements for ribozyme activity in smooth muscle cells appear to be a catalytically core that is modified to minimize endonucleolytic degradation and modifications at the 5' and 3' ends which may prevent exonucleolytic degradation.

Chemical modifications described in this invention are meant to be non-limiting examples, and those skilled in the art will recognize that other modifications (base, sugar and phosphate modifications) to enhance nuclease stability of a ribozyme can be readily generated using standard techniques and are hence within the scope of this invention.

Example 22
Ribozyme inhibition of pig smooth muscle cell proliferation.

Of the commonly used animal models of intimal hyperplasia after balloon angioplasty, the pig model is believed to be most predictive of human disease (Steele et al., 1985 *Circ. Res.* 57, 105; Ohno et al., 1994 *Science* 265, 781; Baringa, 1994 *Science* 265, 738). Therefore, we wished to assess the ability of c-myb ribozymes to inhibit pig smooth muscle cell proliferation. Yucatan pig smooth muscle cells (YSM) were obtained from Dr. Elizabeth Nabel (University of Michigan Medical Center) and were grown in Dulbecco's modified Eagle's medium as described (see Example 6). The YSM cells were starved for 72 hours in DMEM with 0.1% FBS. Active and inactive ribozymes (four phosphorothioate linkages at the 5' end, 2'-C-allyl-modified core and 3'—3' inverted thymidine at the 3' end) were applied as RNA/Lipofectamine® complexes as described in the above examples. Proliferation was stimulated with serum and assessed by BrdU incorporation. FIG. 17 shows that a ribozyme dose of as low as 75 nM can inhibit pig smooth muscle cell proliferation by as much as 60%. The same chemical modifications of the ribozymes (2'-modified, stable core, 5' phosphorothioate linkages and 3' inverted thymidine) are required to obtain significant and reproducible inhibition of pig smooth muscle cell proliferation as were shown to be required for inhibition of rat cells in the above Examples.

Example 23
Ribozyme inhibition of human smooth muscle cell proliferation.

In Example 12, we demonstrated that a minimally modified ribozyme directed against c-myb site 549 could significantly inhibit human smooth muscle cell proliferation. The 2'-C-allyl and phosphorothioate-modified ribozyme targeting c-myb site 575 characterized above was applied to human smooth muscle cells as RNA/Lipofectamine® complexes. Inactive ribozyme and inactive, scrambled arm ribozymes were applied as controls. At 200 nM, the active ribozyme inhibits human smooth muscle proliferation by greater than 75% while the inactive ribozyme inhibits proliferation by only 38%. The ribozyme with scrambled binding arm sequences fails to inhibit. At 100 nM, the active ribozyme still demonstrates significant inhibition while neither the inactive or scramble controls inhibit cell proliferation (see FIG. 18). Thus, the active ribozyme identified in these studies mediates significant inhibition of human smooth muscle cell proliferation and represents a novel therapeutic for restenosis and/or vascular disease.

Example 24

Delivery of c-myb ribozymes to vessels in vivo.

The ribozyme that cleaves c-myb RNA at site 575 was synthesized in two parts (Mamone, supra), the internal 5' end was labeled with $^{33}$P using polynucleotide kinase and the two fragments were ligated with RNA ligase. The resulting RNA was an intact ribozyme with an internal $^{33}$P label. This internally-labeled ribozyme was delivered to balloon injured rat carotid arteries as described (Simons et al., 1992 *Nature* 359, 67). Rats were anesthetized and the carotid artery was surgically exposed. The external carotid was dissected and a 2F Fogarty balloon catheter was inserted and directed into the carotid artery. Injury was caused by repeated (3 times) inflation and retraction of the balloon. The injured region was isolated by ligatures and a cannula was inserted in the external carotid. Ribozymes alone (two rat vessels) or ribozyme/Lipofectamine® complexes (two rat vessels) were applied to the injured vessel through the cannula and were left in the vessel for twenty minutes. After application, blood flow was restored by removal of the ligatures for five minutes and the vessels were harvested and processed as described below.

Half of the vessel was frozen in liquid nitrogen, crushed into a fine powder, and RNA was extracted using standard protocols. The extracted RNA was applied to a denaturing polyacrylamide gels and subjected to electrophoresis. Autoradiography of the gel permitted detection of the $^{33}$P label; the amount of radioactivity in each band was quantitated using a Phosphor-imaging system. The amount of extracted and intact ribozyme was calculated by direct comparison to labeled ribozyme controls run on the same gel. The percentage of the ribozyme delivered intact could be estimated by quantifying the percentage of label that co-migrates with the intact ribozyme controls. After delivery of ribozymes in phosphate-buffered saline (PBS), 3% of the $^{33}$P label was recovered from the rat vessels and >90% of the label was present in the form of intact ribozyme. After delivery of ribozyme in RNA/Lipofectamine complexes, 10 to 11% of the $^{33}$P label was recovered from the rat vessels and 20 to 90% of the label was present in the form of intact ribozyme. The significant uptake of the intact ribozyme demonstrates that local delivery of modified ribozymes to arterial walls is feasible.

The other half of each vessel was fixed in PBS-buffered 2% glutaraldehyde, sectioned onto slides and coated with emulsion. After autoradiography for four days, the emulsion was developed and the sections were stained with hematoxylin and eosin by standard techniques (Simons et al., 1992 supra). Inspection of the sections showed a majority of the grains present over the medial smooth muscle cells after application of the ribozyme. Some $^{33}$P label could be detected in the underlying adventitia as well. Similar density and distribution of grains was observed when the ribozyme was delivered with or without Lipofectamine. These data demonstrate that ribozyme can penetrate the injured vessel wall and is in close apposition or within the underlying medial smooth muscle cells. Thus, therapeutic ribozymes can be locally delivered to vessels for the treatment of vascular disease.

Similar experiments were performed in pig iliofemoral vessels. After balloon injury, a ribozyme, internally labeled with $^{33}$P as described above, was delivered with a double balloon catheter device (Nabel and Nabel, supra; Ohno et al., 1994 supra). After 20 minutes, blood flow was restored by deflating the balloons. The vessels were harvested after an additional hour or the surgical injuries were sutured and the vessels harvested one day later. Harvested vessels were sectioned, subjected to autoradiography and stained. One hour after delivery, the majority of the $^{33}$P label could be detected in the media, overlying or within smooth muscle cells. Some label was also detected at the luminal surface of the vessel and in the adventitial tissue. One day after delivery, grains could be still be detected associated with remaining medial smooth muscle cells. No major differences in density or distribution was observed between ribozymes delivered with or without Lipofectamine®. These data demonstrate that ribozymes can be locally delivered to smooth muscle cells of injured vessels in a large animal model that is clinically relevant to human vascular disease.

Example 25

Ribozyme-mediated decrease in the level of c-myb RNA in rat smooth muscle cells.

To determine whether a ribozyme catalyzes the cleavage of c-myb RNA in a mammalian cell, applicant has used a sensitive quantitative competitive polymerase chain reaction (QCPCR) to assay the level of c-myb RNA in rat smooth muscle cells treated with either catalytically active or inactive ribozyme.

Rat smooth muscle cells (RASMC) were treated with ribozymes as described above. Following the ribozyme treatment for 4 h, cells were stimulated with 10% serum (in the presence or absence of BrdU). After 24 h, cells were harvested for further analysis. Cells, that were treated with BrdU, were assayed for proliferation as described above. Cells, that were not treated with BrdU, were used for the QCPCR assay.

The following is a brief description of the QCPCR technique used to quantitate levels of c-myb mRNA from RASMC, normalizing to the housekeeping gene, GAPDH. This method was adapted from Thompson et al, *Blood* 79:1692, 1992. Briefly, total RNA was isolated from RASMC using the Guanidinium isothiocyanate technique of Chomczynski and Sacchi (*Analytical Biochemistry*, 162:156, 1987). In order to construct a deletion competitor and control wild-type RNA, a cDNA clone of the rat c-myb message, referred to as pc8myb, was used. The competitor RNA comprises a deletion of 50 bases, making it smaller than the wild-type cellular RNA, and spansfrom nucleotide 428 to nucleotide 753.

A house-keeping gene, GAPDH, that is constitutively expressed by the RASMC, was used as an internal control for QCPCR assay. A deletion competitor and wild-type controls for GAPDH were made the same way as for c-myb. GAPDH-containing plasmid (pTri-GAPDH) was purchased from Ambion. The GAPDH competitor is also a deletion mutant, lacking 50 bases. The GAPDH competitor was used to quantitate the amount of this housekeeping gene in each sample, thus allowing for a confirmation of cellular RNA's integrity and for the efficiency of RNA isolation. All quantitations for the level of c-myb expression were normalized to the level of GAPDH expression in the same sample of cells.

Referring to FIG. 19, RASMC that were treated with a stabilized catalytically active 575 HH ribozyme did not proliferate well. There was greater than 70% inhibition of RASMC proliferation when compared with approximately 25% inhibition of cell proliferation by a catalytically inactive version of the 575 HH ribozyme. The level of inhibition of RASMC proliferation correlates very well with the greater than 70% decrease in the level of c-myb RNA. This shows that the inhibition of smooth muscle cell proliferation is directly mediated by the cleavage of c-myb RNA by a ribozyme in RASMC.

FIG. 20 shows what Applicant presently believes is an optimal ribozyme configuration.

Example 26

Inhibition of smooth muscle cell proliferation by 2-5A antisense chimera.

By "2-5A antisense chimera" is meant, an antisense oligonucleotide containing a 5' phosphorylated 2'-5'-linked adenylate residues. These chimeras bind to target RNA in a sequence-specific manner and activate a cellular 2-5A-dependent ribonuclease which in turn cleaves the target RNA (Torrence et al., 1993 Proc. Natl. Acad. Sci. USA 90, 1300).

RNAs containing 2'-5' Adenosine with a terminal 5' phosphate has been shown to activate RNAse L (Torrence et al., 1993 Proc. Natl. Acad. Sci. USA 90, 1300). The terminal phosphate is required for efficient activation of RNAse L. Ribozymes targeting c-myb site 575 were synthesized with 2-5A moieties on the 5' end, with and without the terminal 5' phosphate. The ribozyme-2-5A chimera was complexed with LipofectAMINE and assayed on rat aortic smooth muscle cells (RASMC) as described above.

As shown in FIG. 21, when no terminal phosphate is present, the active ribozyme [575 active Rz+inactive (A)4] functions similarly to a normal active ribozyme lacking a 2-5A modification (575 active Rz). An inactive ribozyme core with 5' phosphate-2-5A [575 inactive Rz+active P(A)4] shows significant inhibition relative to the controls, but has significantly lower activity when compared with an active ribozyme. A molecule that contains both an active ribozyme core and 5' phosphate-continuing 2-5A [575 active Rz+active P (A)4] shows even greater inhibition than that obtained by either mechanism individually, inhibiting the smooth muscle cell proliferation to baseline levels (0% FBS). Thus the ribozyme and 2-5A anitisense chimera together show an additive effect in inhibiting RASMC proliferation.

Use of Ribozymes That Cleave c-myb RNA to Treat Restenosis.

The above discussion demonstrates, by way of example, how ribozymes that inhibit smooth muscle cell proliferation are delivered directly, or through the use of expression vectors, to vessels. Preferably, ribozymes cleaving c-myb RNA are delivered to vessels at the time of coronary angioplasty. Local delivery during intervention can be achieved through the use of double balloon catheters, porous balloon catheters, balloon catheters coated with polymers (Riessen, R., et al., 1993, *Human Gene Therapy*, 4, 749–758), or biopolymer stents (Slepian and Schindler, U.S. Pat. No. 5,213,580). In the above examples, ribozymes were identified that could inhibit roughly half of the smooth muscle cells in culture from proliferating in response to the growth factors present in serum. A corresponding 50% (or even lower) reduction in intimal thickening will significantly improve the outcome of patients undergoing coronary angioplasty.

Use of Ribozymes Targeting c-myb to Treat Cancer

Overexpression of the c-myb oncogene has been reported in a number of cancers, including leukemias, neuroblastomas, and lung, colon, and breast carcinomas (Torelli, G., et al., 1987, *Cancer Res.*, 47, 5266–5269; Slamon, D. J., et al., 1986, *Science*, 233, 203–206; Slamon, D. J., et al., 1984, *Science*, 224, 256–262; Thiele, C. J., et al., 1988, *Mol. Cell. Biol.*, 8, 1677–1683; Griffin, C. A. and Baylin, S. B., 1985, *Cancer Res.*, 45, 272–275; Alitalo, K., et al., 1984, *Proc, Natl. Acad. Sci. USA*, 81, 4534–4538). Thus, inhibition of c-myb expression can reduce cell proliferation of a number of cancers. Indeed, in tissue culture, treatment of colon adenocarcinoma, neurectodermal, and myeloid leukemia cell lines with antisense c-myb oligonucleotides inhibits their proliferation (Melani, C., et al., 1991, *Cancer Res.*, 51, 2897–2901; Raschella, F., et al., 1992, *Cancer Res.*, 52, 4221–4226; Anfossi, G., et al., 1989, *Proc. Natl. Acad. Sci. USA*, 86, 3379–3383). Furthermore, myeloid cells from patients with chronic myelogenous leukemia and acute myelogenous leukemia are differentially sensitive to c-myb antisense oligonucleotides (Calabretta, B., et al., 1991, *Proc. Natl. Acad. Sci. USA*, 88, 2351–2355). Ratajczak, et al. (1992, *Proc. Natl. Acad, Sci. USA*, 89, 11823–11827) treated mice bearing human leukemia cells with c-myb antisense oligonucleotides and significantly prolonged their survival and reduced their tumor burden. Thus, reduction of c-myb expression in leukemic cells in tissue culture and in vivo can reduce their proliferative potential.

While the above studies demonstrated that antisense oligonucleotides can efficiently reduce the expression of c-myb in cancer cells and reduce their ability to proliferate and spread, this invention describes the first enzymatic RNAs, or ribozymes, shown to cleave c-myb RNA. Such ribozymes, with their catalytic activity and increased site specificity (see above), are likely to represent more potent and safe therapeutic molecules than antisense oligonucleotides for the treatment of cancer as well as restenosis. In the present invention, ribozymes are shown to inhibit smooth muscle cell proliferation. From those practiced in the art, it is clear from the examples described, that the same ribozymes may be delivered in a similar fashion to cancer cells to block their proliferation.

In a preferred embodiment, autologous bone marrow from patients suffering with acute myelogenous leukemia or chronic myelogenous leukemia are treated with ribozymes that cleave c-myb RNA. Ribozymes will be delivered to the autologous bone marrow cells ex vivo at 0.1 to 50 μM with or without forming complexes of the ribozymes with cationic lipids, encapsulating in liposomes or alternative delivery agents. After several days, the proliferative capacity of the leukemic cells in the patients bone marrow will be reduced. The patient's endogenous bone marrow cells will be depleted by chemical or radiation treatments and their bone marrow reconstituted with the ex vivo treated cells. In such autologous bone marrow reconstitution treatments of leukemic patients, recurrence of the disease can be caused by proliferation of leukemic cells present in the transplanted bone marrow. Significantly reducing the proliferative potential of the leukemic cells by treating with ribozymes that cleave c-myb RNA will reduce the risk of recurrent leukemia.

Diagnostic uses

Ribozymes of this invention may be used as diagnostic tools to examine genetic drift and mutations within diseased cells or to detect the presence of c-myb RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with c-myb related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., c-myb) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T41 blue-green algae, and others.
RNAseP RNA (M1 RNA)

Size: ~290 to 400 nucleotides.

TABLE I-continued

Characteristics of Ribozymes

RNA portion of a ribonucleoprotein enzyme. Cleaves tRNA precursors to form mature tRNA.
Roughly 10 known members of this group all are bacterial in origin.
Hammerhead Ribozyme

Figure 3:
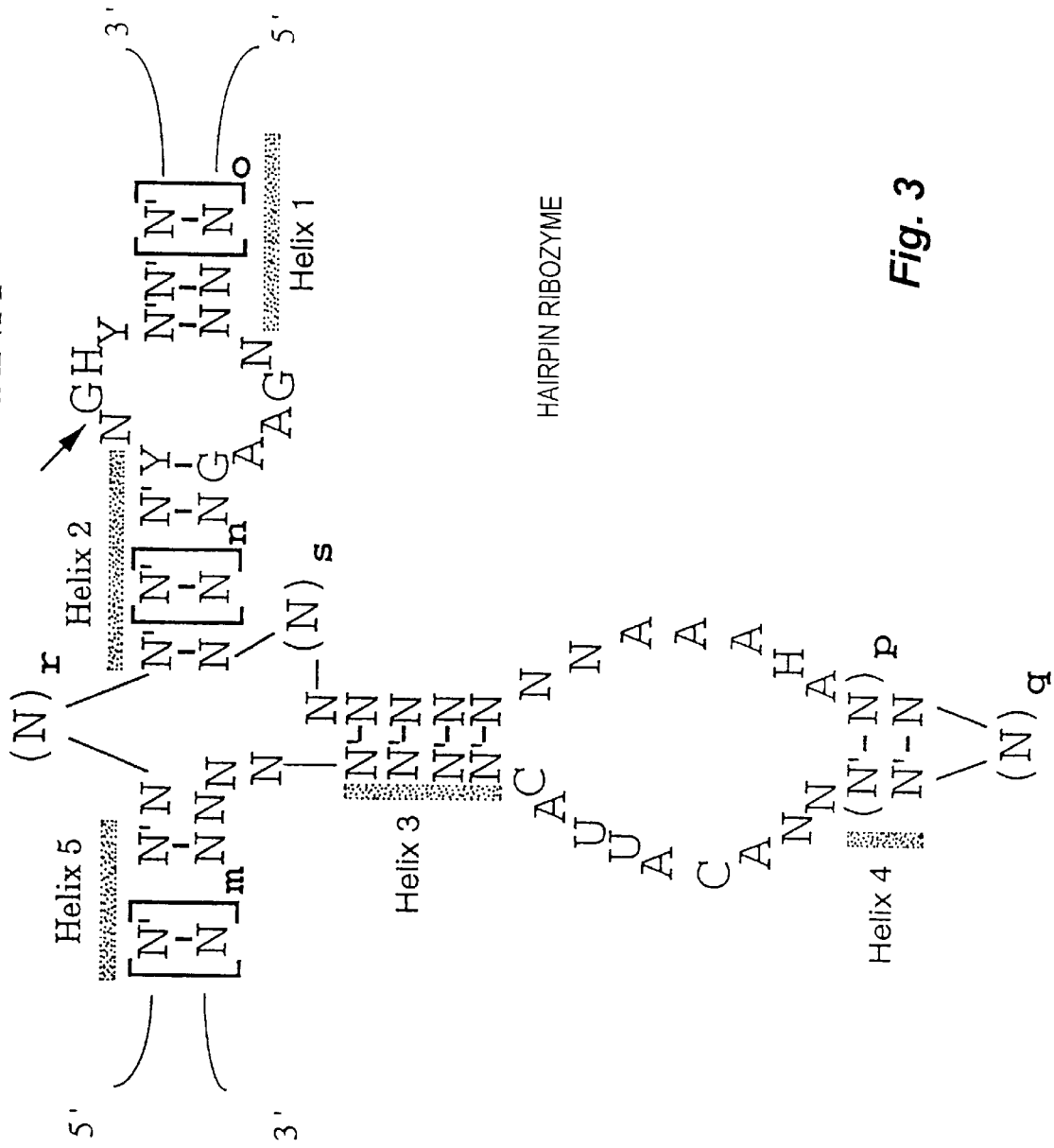
Figure 4:
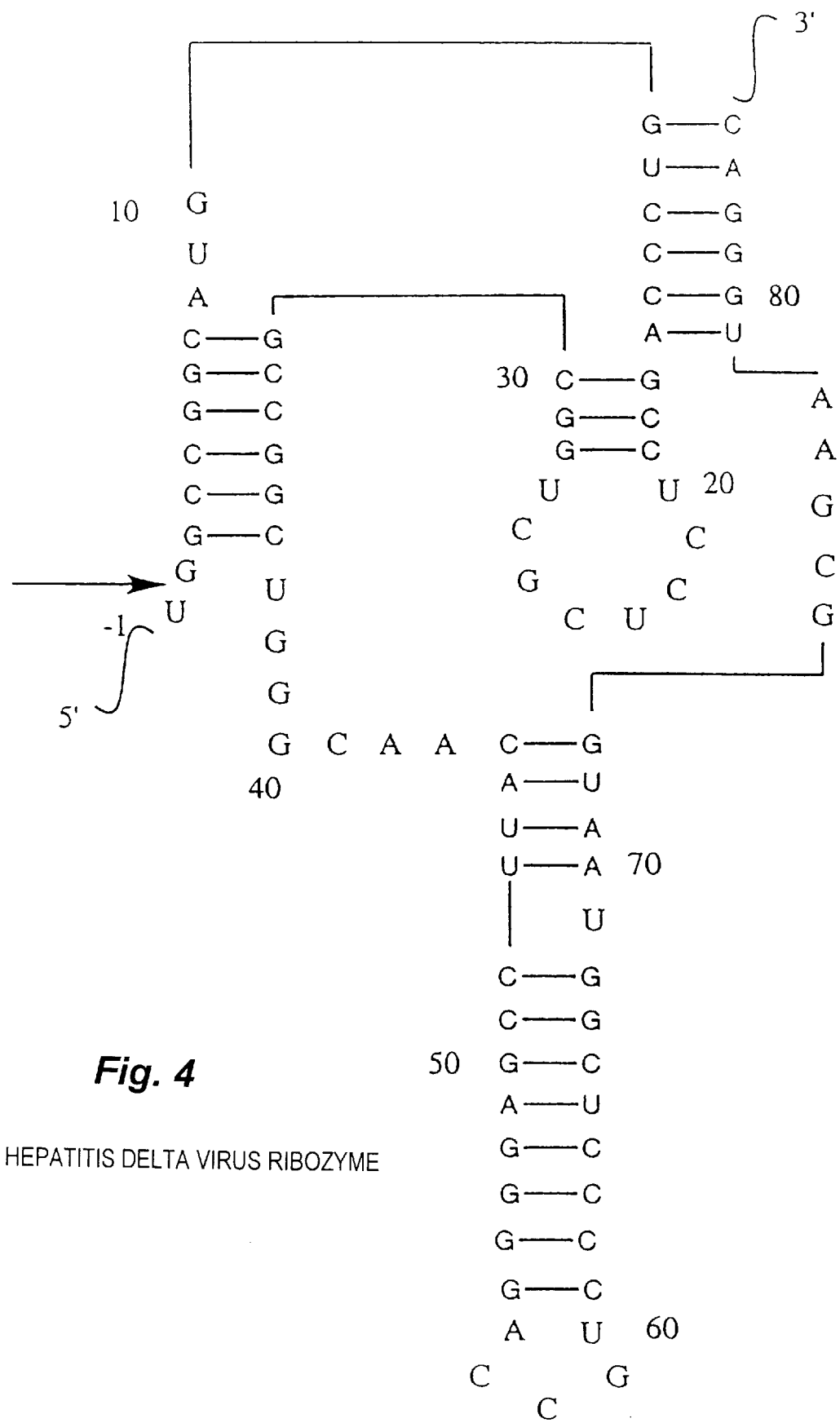
FIG. 4 is a representation of the general structure of the hepatitis delta virus ribozyme domain known in the art.
Figure 5:
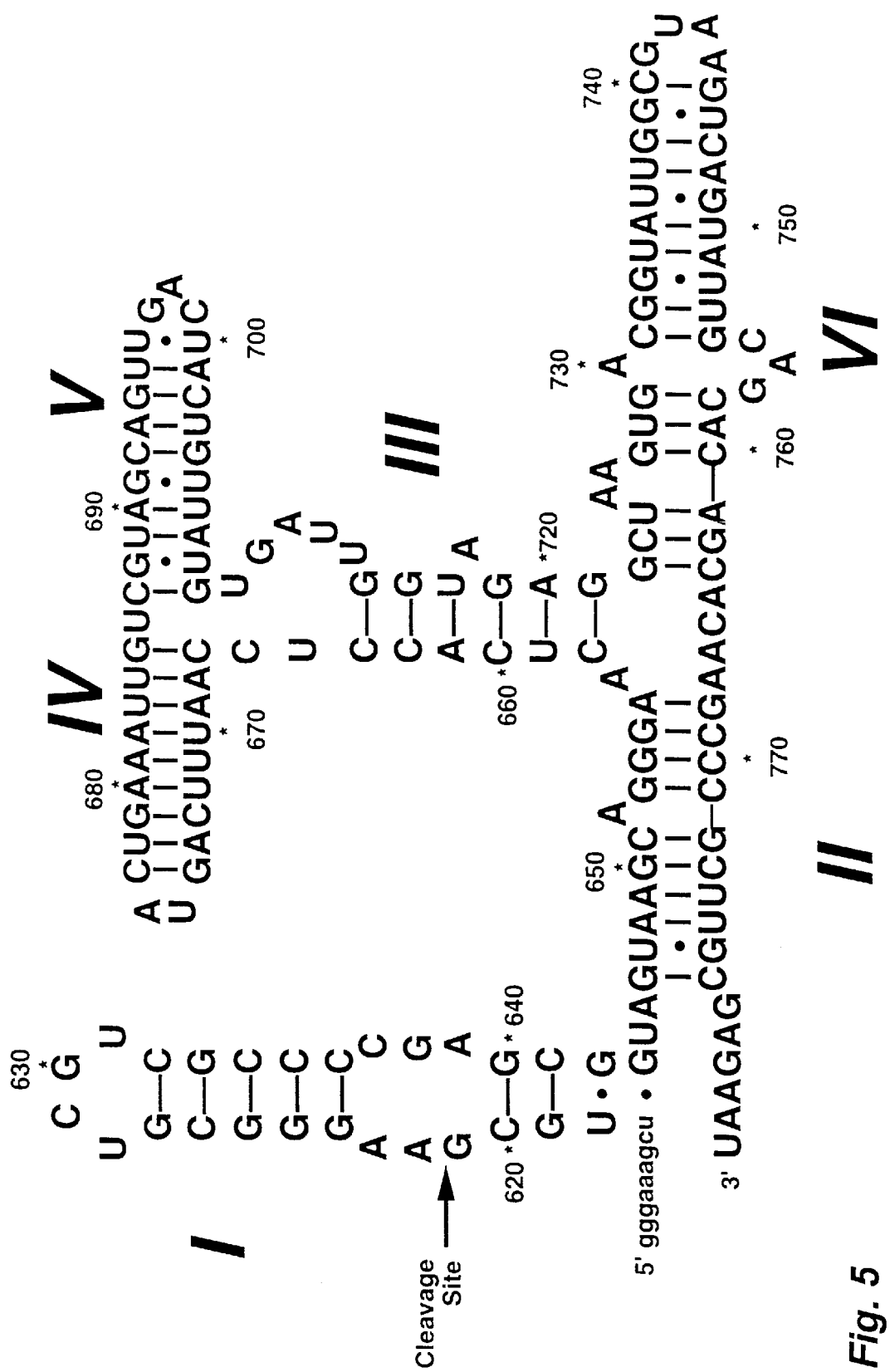
FIG. 5 is a representation of the general structure of the self-cleaving VS RNA ribozyme domain.

*Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)
Hairpin Ribozyme Size: ~50 nucleotides.
Requires the target sequence GUO immediately 3' of the cleavage site.
Binds 4–6 nucleotides at 5' side of the cleavage site and a variable number to the 3' side of the cleavage site
Only 3 known member of this class. Found in three plant pathogen (satellite RNAs of the tobacco ringspot virus, arabis mosaic virus and chicory yellow mottle virus) which uses RNA as the infectious agent (FIG. 3).
Hepatitis Delta Virus (HDV) Ribozyme Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).
Neuraspora VS RNA Ribozyme Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Human c-myb Target Sequence

| Site | Target Sequence | Sequence I.D. No. |
|---|---|---|
| 86 | GGCGGCAGCGCCCUGCCGACGCCGGGG | ID. NO. 01 |
| 162 | CCGCGGCUCUCGGC | ID. NO. 02 |
| 195 | GCCAUGGCCCGAA | ID. NO. 03 |
| 213 | CGGCACAGCAUAUAUAGCAGUGACGAGGA | ID. NO. 04 |
| 249 | GACUUUGAGAUGUGUGACCAUGACUAUGAUGGG | ID. NO. 05 |
| 295 | CUGGAAAGCGUC | ID. NO. 06 |
| 332 | GGAAGAGGAUGAAAAACUGAAGAAG | ID. NO. 07 |

TABLE II-continued

Human c-myb Target Sequence

| Site | Target Sequence | Sequence I.D. No. |
|---|---|---|
| 350 | GAAGAACUGGUGGAACAGAAUGGAAC | ID. NO. 08 |
| 383 | CUGGAAAGUUAUUGCCAA | ID. NO. 09 |
| 407 | CCCGAAUCGAACAGAUGUGCAG | ID. NO. 10 |
| 446 | GAAAGUACUAAACCCUGAG | ID. NO. 11 |
| 478 | CUUGGACCAAAGAAGAAGAUCAGAGAGUGAUA | ID. NO. 12 |
| 518 | ACAGAAAUACGGUCCGAAACGUUGGUCUG | ID. NO. 13 |
| 547 | UUAUUGCCAAGCACUUAAAGGGGAGAAUUGGAA | ID. NO. 14 |
| 611 | GAAUCCAGAAGUUAAGAA | ID. NO. 15 |
| 647 | GGAAGACAGAAUUAUUUACCAGGCACA | ID. NO. 16 |
| 674 | CAAGAGACUGGGGAACAGAU | ID. NO. 17 |
| 700 | AAAUCGCAAAGCUA | ID. NO. 18 |
| 720 | GGACGAACUGAUAAUGCUAUCAAGAACC | ID. NO. 19 |
| 748 | ACUGGAAUUCUACAAUGCGUCGGAAGGUCAACA | ID. NO. 20 |
| 816 | CAGCCAGCAGUGGCCACAA | ID. NO. 21 |
| 852 | CAUUUGAUGGGUUUUGCUCAGGCUCCGCCUACA | ID. NO. 22 |
| 885 | GCUCAACUCCCUGCCACUGGCCAGCCC | ID. NO. 23 |
| 918 | AACAACGACUAUUCCUAUUACCACA | ID. NO. 24 |
| 954 | CAAAAUGUCUCCAGUCAUGUUCCAUACCCU | ID. NO. 2S |
| 998 | AAAUAUAGUCAAUGUCCCUCAGCCAGCUGCCGCA | ID. NO. 26 |
| 1039 | AGAGACACUAUAAUGAUGAAGACCCUGAGAAGGA | ID. NO. 27 |
| 1073 | AAAGCGAAUAAAGGAAUUAGAAUUG | ID. NO. 28 |
| 1098 | CUCCUAAUGUCAACCGA | ID. NO. 29 |
| 1120 | AGCUAAAAGGACAGCAGGUGCUACCAACACAGAA | ID. NO. 30 |
| 1161 | CCCGGGUGGCACAGCACCACCAUUGCCGACCACA | ID. NO. 31 |
| 1237 | AACACCACUCCACUCCAUCUCUGCCAGCGGAUCC | ID. NO. 32 |
| 1279 | UACCUGAAGAAA | ID. NO. 33 |
| 1311 | AUGAUCGUCCACCAGGGCACCAUU | ID. NO. 34 |
| 1366 | CAGAAACACUCCAAUUUA | ID. NO. 35 |
| 1418 | AAACUCAGACU | ID. NO. 36 |
| 1434 | AUGCCUUCUUUAAC | ID. NO. 37 |
| 1480 | UUACAACACCA | ID. NO. 38 |
| 1515 | ACUCAAAAGGAAAAUACUGUUUUUAGAACCC | ID. NO. 39 |
| 1546 | CAGCUAUCAAAAGGUCAAUCUUAGAAAGCU | ID. NO. 40 |
| 1576 | CUCCAAGAACUCCUACACCAUUCAA | ID. NO. 41 |
| 1601 | ACAUGCACUUGCAGCUCAAGAA | ID. NO. 42 |
| 1630 | UACGGUCCCCUGAAGAUGCUACCUCAGA | ID. NO. 43 |
| 1657 | CACCCUCUCAUCUAGUAGAAGAUCUGCAGGA | ID. NO. 44 |
| 1693 | UCAAACAGGAAUCUGAUGAAUCUGGA | ID. NO. 45 |
| 1735 | AAGAAAAUGGA | ID. NO. 46 |
| 1751 | CUUACUGAAGAAAAUCAAACAAGA | ID. NO. 47 |
| 1780 | AAUCUCCAACUGAUAAAUCAG | ID. NO. 48 |
| 1813 | GCUCACACCACUGGGA | ID. NO. 49 |
| 1864 | CCUCGCCUGUGCGAGAUGCACCGAAUAUUC | ID. NO. 50 |
| 1913 | GGCACCAGCAUCAGAAGAUGAAGAC | ID. NO. 51 |
| 1951 | CAUUUACAGUACC | ID. NO. 52. |
| 1975 | CCCUGGCGAGCCCCUUGCA | ID. NO. 53 |
| 1994 | GCCUUGUAGCAGUACCUGGGA | ID. NO. 54 |
| 2059 | GUCAAGCUCGUAAAUACGUGAA | ID. NO. 55 |
| 2142 | GAACAGUUCAA | ID. NO. 56 |
| 2181 | AUGAAACUUUUCAU | ID. NO. 57 |
| 2304 | AAAAUAAAUAACAGUC | ID. NO. 58 |
| 2340 | UGAAUUGUAGCC | ID. NO. 59 |
| 2357 | UUAAUAUCUUAAU | ID. NO. 60 |
| 2399 | AUUUAUCUGGUAUUUUAAAGGAUCCAACAGAUC | ID. NO. 61 |
| 2483 | CCAGUAUUUCA | ID. NO. 62 |
| 2499 | CUCGAUCACUAAACAUAUG | ID. NO. 63 |
| 2518 | CAUAUAUUUUUAAAAAUC | ID. NO. 64 |
| 2767 | UGCUAUGGUCUUAGCCU | ID. NO. 65 |
| 2799 | AGUAUCAGAGG | ID. NO. 66 |
| 2849 | UAGGUAAUUGACUAU | ID. NO. 67 |
| 2871 | UAUUUCAGACUUUUUAAUUUUAUAUAUAUAUACA | ID. NO. 6B |
| 2920 | CAAUACAUUUGAAAACUUGUUUGGGAGACUCUGC | ID. NO. 69 |
| 2964 | GUGGUUUUUUGUUAUUGUUGGUUU | ID. NO. 70 |
| 3008 | UUCUUUUUUGGGAGAU | ID. NO. 71 |
| 3040 | CUAUGUUUUGUUUUG | ID. NO. 72 |
| 3660 | AGCCUGACUGUUUUAUA | ID. NO. 73 |
| 3089 | UCGAUUUGAUC | ID. NO. 74 |
| 3145 | UGGAUCCUGUGUU | ID. NO. 75 |
| 3184 | UUGAUAGCCAGUCACUGCCUUAAGA | ID. NO. 76 |
| 3209 | ACAUUUGAUGCAAGAUGGCCAGCACU | ID. NO. 77 |
| 3252 | CGGUGUACUUACUGCC | ID. NO. 78 |

TABLE III

Sequences of ribozymes used in these studies.

| Target Site | Sequence ID No. | Ribozyme Sequence |
|---|---|---|
| Hammerhead ribozymes with 7 nucleotide binding arms | | |
| 310 | 101 | UUUCCCCCUGAUGAGGCCGAAAGGCCGAAAGUGACG |
| 549 | 102 | UUGGCAACUGAUGAGGCCGAAAGGCCGAAAACAGAC |
| 551 | 103 | GCUUGGCCUGAUGAGGCCGAAAGGCCGAAAUAACAG |
| 575 | 104 | GCUUUCCCUGAUGAGGCCGAAAGGCCGAAAUUCUCC |
| 634 | 105 | UGUCCAGCUGAUGAGGCCGAAAGGCCGAAAGGUUUU |
| 738 | 106 | UUCUUGACUGAUGAGGCCGAAAGGCCGAAAGCAUUA |
| 839 | 107 | UCUUCUGCUGAUGAGGCCGAAAGGCCGAAAAGCUCG |
| 936 | 108 | AUGUGGUCUGAUGAGGCCGAAAGGCCGAAAUAGGAA |
| 1017 | 109 | GCCGGCUCUGAUGAGGCCGAAAGGCCGAAAGGGACG |
| 1082 | 110 | GCUCCUUCUGAUGAGGCCGAAAGGCCGAAAUUCGCU |
| 1363 | 111 | UUCUGCACUGAUGAGGCCGAAAGGCCGAAAUUCUAA |
| 1553 | 112 | ACCUUUUCUGAUGAGGCCGAAAGGCCGAAAUAGCUG |
| 1597 | 113 | AUGUUUGCUGAUGAGGCCGAAAGGCCGAAAUGGUGU |
| 1598 | 114 | CAUGUUUCUGAUGAGGCCGAAAGGCCGAAAAUGGUG |
| 1635 | 115 | UUCAGGGCUGAUGAGGCCGAAAGGCCGAAACCGUAU |
| 1721 | 116 | CAGCAAACUGAUGAGGCCGAAAGGCCGAAAUUCCAG |
| 1724 | 117 | ACUCAGCCUGAUGAGGCCGAAAGGCCGAAACAAUUC |
| 1895 | 118 | AGCUUGUCUGAUGAGGCCGAAAGGCCGAAAGAAUAU |
| 1909 | 119 | UGUCAUUCUGAUGAGGCCGAAAGGCCGAAAAACAGA |
| 1943 | 120 | CUUUGAGCUGAUGAGGCCGAAAGGCCGAAACAUUGU |
| Bimolecular Hairpin Ribozymes | | |
| 1632[a] | 121 | 5' Fragment: UCAGGGAGAAGUAUACCAGAGAAACACACGCG<br>3' Fragment: CGCGUGGUACAUUACCUGGUA |
| 2231[a] | 122 | 5' Fragment: GCUCUCAGAAGUUGACCAGAGAAACACACGCG<br>3' Fragment: CGCGUGGUACAUUACCUGGUA |
| Hammerhead ribozymes with 6, 8, 9, 10, and 12 nucleotide binding arms | | |
| 575 6/6[b] | 123 | CUUUCCCUGAUGAGGCCGAAAGGCCGAA AUUCUC |
| 575 8/8 | 124 | UGCUUUCCCUGAUGAGGCCGAAAGGCCGAA AUUCUCCC |
| 575 9/9 | 125 | CUGCUUUCCCUGAUGAGGCCGAAAGGCCGAA AUUCUCCCU |
| 575 9/9 | 126 | ACUGCUUUCCCUGAUGAGGCCGAAAGGCCGAA AUUCUCCCUU |
| 575 12/12 | 127 | ACACUGCUUUCCCUGAUGAGGCCGAAAGGCCGAA AUUCUCCCUU |
| 549 12/12 | 128 | AGUGCUUGGCAACUGAUGAGGCCGAAAGGCCGAA AACAGACCAACG |
| 1553 12/12 | 129 | GAUUGACCUUUUCUGAUGAGGCCGAAAGGCCGAA AUAGCUGGAGUU |

[a]The hairpin ribozymes were synthesized in two pieces as indicated. The two oligonucleotides were annealed and tested for activity against the c-myb RNA as described above. See Mamone, Ribozyme synthesis, filed May 11, 1992, U.S.S.N. 07/882,689, hereby incorporated by reference herein.
[b]Designation of the ribozymes with different arm lengths is a/b where (a) represents the nucleotides in stem I and (b) represents the nucleotides in stem III (see FIG. 1).

TABLE IV

Ribozyme catalyzed cleavage of c-myb RNA

| Cleavage Site | Sequence ID No. | Target sequence | % Cleavage Mouse c-myb RNA | % Cleavage Human c-myb RNA |
|---|---|---|---|---|
| Hammerhead Sites | | | | |
| 310 | 79 | CGUCACU U GGGGAAA | 28.5 | 0.1 |
| 549 | 80 | GUCUGUU A UUGCCAA | 87.4 | 91.6 |
| 551 | 81 | CUGUUAU U GCCAAGC | 56.8 | 82.4 |
| 575 | 82 | GGAGAAU U GGAAAAC | 93.9 | 91.3 |
| 634 | 83 | AAAACCU C CUGGACA | 68.4 | 87.1 |
| 738 | 84 | UAAUGCU A UCAAGAA | 78.1 | 0.01 |
| 839 | 85 | CAAGCUU C CAGAAGA | 27.2 | 0.01 |
| 936 | 86 | UUCCUAU U ACCACAU | 61.8 | 60.6 |
| 1017 | 87 | UGUCCCU C AGCCAGC | 40.3 | 0.1 |
| 1082 | 88 | AGCGAAU A AAGGAAU | 55.2 | 89.2 |
| 1363 | 89 | UUAGAAU U UGCAGAA | 11.6 | 0.1 |
| 1553 | 90 | CAGCUAU C AAAAGGU | 87.1 | 92.5 |
| 1597 | 91 | ACACCAU U CAAACAU | 71.2 | 62.7 |
| 1598 | 92 | CACCAUU C AAACAUG | 79.6 | 85.5 |
| 1635 | 93 | AUACGGU C CCCUGAA | 84.4 | 82.3 |
| 1721 | 94 | CUGGAAU U GUUGCUG | 62.1 | 79.3 |
| 1724 | 95 | GAAUUGU U GCUGAGU | 65.6 | 86 |
| 1895 | 96 | AUAUUCU U ACAAGCU | 79.1 | 66.2 |
| 1909 | 97 | UCCGUUU U AAUGGCA | 31.1 | 0.1 |
| 1943 | 98 | ACAAUGU U CUCAAAG | 66.1 | 80 |
| Hairpin Ribozymes | | | | |
| 1632 | 99 | ACG GUCC CCUGAAG | 92.8 | 84.6 |
| 2231 | 100 | ACA GUUG AGAGCAG | 0.1 | 0.1 |

TABLE IV-continued

Ribozyme catalyzed cleavage of c-myb RNA

| Cleavage Site | Sequence ID No. | Target sequence | % Cleavage Mouse c-myb RNA | % Cleavage Human c-myb RNA |
|---|---|---|---|---|

[a]The nucleotide numbers given correspond to the nucleotide just 5' of the ribozyme cleavage site in the human c-myb sequence taken from Westin, et al., supra (GenBank Accession No. X52125). All but two of the sequences (310; I.D. No. 79 and 2231; I. D. No. 100) overlap sequences in Table I.

TABLE V

Comparison of the effects six hammerhead ribozymes, that cleave c-myb RNA, on smooth muscle cell proliferation.

| Ribozyme Site | Inactive Ribozyme % Cell Proliferation | Active Ribozyme % Cell Proliferation | % Inhibition (Active vs. Inactive) |
|---|---|---|---|
| 549 | 68 ± 1 | 59.5 ± 1.5 | 14 ± 4 |
| 575 | 66.5 ± 0.5 | 54.5 ± 1.5 | 21 ± 3 |
| 1553 | 68.5 ± 0.5 | 52 ± 1 | 28 ± 1 |
| 1597 | 66 ± 1 | 57 ± 3 | 16 ± 7 |
| 1598 | 67 ± 1 | 58.5 ± 0.5 | 15 ± 1 |
| 1635 | 62.5 ± 2.5 | 64 ± 1 | 0 |

TABLE VI

Dose Response of c-myb Hairpin Ribozyme 1632

| Ribozyme Dose ($\mu$M) | Control Ribozyme % Proliferation | Ribozyme 1632 % Proliferation | % Inhibition (vs. control) |
|---|---|---|---|
| 0.05 | 86.5 ± 1.5 | 88 ± 5 | 0 |
| 0.15 | 89.5 ± 1.5 | 78.5 ± 2.5 | 10 ± 5 |
| 0.45 | 87.5 ± 1 | 66.5 ± 1.5 | 25 ± 4 |

TABLE VII

Dose Response of c-myb Hammerhead Ribozymes 575 and 549

| Ribozyme Dose ($\mu$M) | Ribozyme 575 Control Ribozyme % cells in S phase | Ribozyme 575 % cells in S phase | Ribozyme 575 % Inhibition (vs. control) | Ribozyme 549 % cells in S phase | Ribozyme 549 % Inhibition (vs. control) |
|---|---|---|---|---|---|
| 0.05 | 89 ± 5 | 77.5 ± 1.5 | 14 ± 8 | 92 ± 1 | 0 |
| 0.15 | 90 ± 1 | 68.5 ± 1.5 | 26 ± 2 | 84 ± 2 | 9 ± 4 |
| 0.45 | 91.5 ± 0.5 | 59 ± 5 | 38 ± 7 | 76.5 ± 2.5 | 18 ± 5 |

TABLE VIII

Delivery of c-myb Ribozyme 575 by Two Different Cationic Lipids

| Ribozyme Dose ($\mu$M) | Inactive Ribozyme 575 % cells is S phase | Active Ribozyme 575 % cells in S phase | % inhibition (vs. inactive) |
|---|---|---|---|
| Delivery with DMRIE/DOPE | | | |
| 0.075 | 79 ± 6 | 74.5 ± 1.5 | 6 ± 6 |
| 0.15 | 79.5 ± 0.5 | 67 ± 1 | 17 ± 4 |
| 0.30 | 77 ± 1 | 57 ± 2 | 28 ± 5 |

TABLE VIII-continued

Delivery of c-myb Ribozyme 575 by Two Different Cationic Lipids

| Ribozyme Dose ($\mu$M) | Inactive Ribozyme 575 % cells is S phase | Active Ribozyme 575 % cells in S phase | % inhibition (vs. inactive) |
|---|---|---|---|
| Delivery with Lipofectamine | | | |
| 0.075 | 81 ± 1 | 83 ± 1 | 0 |
| 0.15 | 79 ± 3 | 71 ± 1 | 11 ± 4 |
| 0.30 | 82 ± 1 | 68.5 ± 1.5 | 18 ± 4 |
| 0.60 | 75 ± 1 | 59.5 ± 3.5 | 22 ± 7 |

TABLE IX

Arm Length Variations of c-myb Hammerhead Ribozyme 575

| Arm Length (base-pairs) | % cells in S phase | % Inhibition (vs. Inactive 7/7) |
|---|---|---|
| 6/6 | 62 ± 1 | 4 ± 4 |
| 7/7 | 60 ± 1 | 7 ± 3 |
| 8/8 | 60.5 ± 0.5 | 6 ± 2 |
| 9/9 | 53.5 ± 0.5 | 18 ± 2 |
| 10/10 | 55 ± 1 | 16 ± 4 |
| 12/12 | 48 ± 1 | 28 ± 3 |

TABLE X

Hammerhead ribozymes with 7 vs. 12-nucleotide binding arms targeting three different sites.

| Ribozyme Target Site | Length of Binding Arms | Inactive Ribozyme (% Cell Proliferation) | Active Ribozyme (% Cell Proliferation) | % Inhibition (Active vs. Inactive) |
|---|---|---|---|---|
| 575 | 7/7 | 51.5 ± 0.5 | 43 ± 0.5 | 24 ± 5 |
| 575 | 12/12 | 50.5 ± 3.5 | 37 ± 0.5 | 37 ± 4 |
| 549 | 7/7 | 49.5 ± 0.5 | 44.5 ± 1.5 | 21 ± 7 |
| 549 | 12/12 | 48.5 ± 1.5 | 35 ± 2 | 41 ± 7 |
| 1553 | 7/7 | 49.5 ± 0.5 | 43.5 ± 2.5 | 23 ± 9 |
| 1553 | 12/12 | 49 ± 1 | 33.5 ± 1.5 | 45 ± 6 |

TABLE XI

Effect of chloroquine on ribozyme inhibition of smooth muscle cell proliferation.

| Ribozyme | Chloroquine ($\mu$M) | Inactive Ribozyme (% Cell Proliferation) | Active Ribozyme (% Cell Proliferation) | % Inhibition (Active vs. Inactive) |
|---|---|---|---|---|
| 575, 12/12 | 0 | 81.8 ± 0.5 | 74 ± 1 | 10 ± 2 |
| 575, 12/12 | 10 | 83 ± 4 | 62.5 ± 0.5 | 28 ± 6 |

TABLE XII

Inhibition of Human Aortic Smooth Muscle Cells by c-myb Ribozyme 549

| Ribozyme Dose ($\mu$M) | Inactive Ribozyme % Proliferation | Active Ribozyme % Proliferation | % Inhibition (active vs. inactive) |
|---|---|---|---|
| 0.075 | 55 ± 2 | 40.5 ± 4.5 | 30 ± 13 |
| 0.15 | 53 ± 10 | 42 ± 1 | 23 ± 23 |
| 0.30 | 53 ± 7 | 32.5 ± 4.5 | 44 ± 22 |

TABLE XIII

Inhibition of Rat Smooth Muscle Cell Proliferation by Direct Addition of a Chemically-Modified c-myb Ribozyme 575

| Ribozyme Dose ($\mu$M) | Inactive Ribozyme % Proliferation | Active Ribozyme % Proliferation | % Inhibition (active vs. inactive) |
|---|---|---|---|
| 0.22 | 42 ± 3 | 36 ± 0.5 | 15 ± 8 |
| 0.67 | 48 ± 3 | 35 ± 2 | 28 ± 9 |
| 2.0 | 52 ± 5 | 25 ± 1 | 54 ± 7 |

TABLE XIV

Human c-myb Hairpin Ribozyme and Target Sequences

| nt | Ribozyme Sequence | Seq. ID No. | Target | Seq. ID No. |
|---|---|---|---|---|
| 104 | CCCUCCCC AGAA GCGC ACCAGAGAAACACACGUUGUGGUACAUUACCUGGUA | 149 | GCGCA GCC GGGGAGGG | 130 |
| 148 | ACCGACCG AGAA GCCG ACCAGAGAAACACACGUUGUGGUACAUUACCUGGUA | 150 | CGGCA GCC CGGUCGGU | 131 |
| 185 | GCGCGGCG AGAA GCGG ACCAGAGAAACACACGUUGUGGUACAUUACCUGGUA | 151 | CCGCC GCC CGCCGCGC | 132 |
| 528 | ACGUUUCG AGAA GUAU ACCAGAGAAACACACGUUGUGGUACAUUACCUGGUA | 152 | AUACG GUC CGAAACGU | 133 |
| 715 | UUCGUCCA AGAA GUAG ACCAGAGAAACACACGUUGUGGUACAUUACCUGGUA | 153 | CUACU GCC UGGACGAA | 134 |
| 1025 | AUGGCUGC AGAA GCUG ACCAGAGAAACACACGUUGUGGUACAUUACCUGGUA | 154 | CAGCU GCC GCAGCCAU | 135 |
| 1187 | CUGGUGUG AGAA GCAA ACCAGAGAAACACACGUUGUGGUACAUUACCUGGUA | 155 | UUGCC GAC CACACCAG | 136 |
| 1532 | GUUCUAAA AGAA GUAU ACCAGAGAAACACACGUUGUGGUACAUUACCUGGUA | 156 | AUACU GUU UUUAGAAC | 137 |
| 1632 | CUUCAGGG AGAA GUAU ACCAGAGAAACACACGUUGUGGUACAUUACCUGGUA | 157 | AUACG GUC CCCUGAAG | 138 |
| 1836 | GGUAUUCA AGAA GUCC ACCAGAGAAACACACGUUGUGGUACAUUACCUGGUA | 158 | GGACA GUC UGAAUACC | 139 |
| 1852 | UCUGCGUG AGAA GUUG ACCAGAGAAACACACGUUGUGGUACAUUACCUGGUA | 159 | CAACU GUU CACGCAGA | 140 |
| 1861 | CAGGCGAG AGAA GCGU ACCAGAGAAACACACGUUGUGGUACAUUACCUGGUA | 160 | ACGCA GAC CUCGCCUG | 141 |
| 1993 | UGCUACAA AGAA GCAA ACCAGAGAAACACACGUUGUGGUACAUUACCUGGUA | 161 | UUGCA GCC UUGUAGCA | 142 |
| 2231 | CUGCUCUC AGAA GUUG ACCAGAGAAACACACGUUGUGGUACAUUACCUGGUA | 162 | CAACA GUU GAGAGCAG | 143 |
| 2316 | UUAGGUAA AGAA GUUA ACCAGAGAAACACACGUUGUGGUACAUUACCUGGUA | 163 | UAACA GUC UUACCUAA | 144 |
| 3068 | AAUUAUAA AGAA GUCA ACCAGAGAAACACACGUUGUGGUACAUUACCUGGUA | 164 | UGACU GUU UUAUAAUU | 145 |
| 3138 | AUCCAUGC AGAA GUUC ACCAGAGAAACACACGUUGUGGUACAUUACCUGGUA | 165 | GAACU GUU GCAUGGAU | 146 |
| 3199 | GUUCUUAA AGAA GUGA ACCAGAGAAACACACGUUGUGGUACAUUACCUGGUA | 166 | UCACU GCC UUAAGAAC | 147 |
| 3264 | UGCUACAA AGAA GUAA ACCAGAGAAACACACGUUGUGGUACAUUACCUGGUA | 167 | UUACU GCC UUGUAGCA | 148 |

TABLE XV

Human c-myb Hammerhead Ribozyme and Target Sequences
(REVISED)

| nt. | Target Sequence | Seq. ID No. | HH Ribozyme Sequence | Seq. ID No. |
|---|---|---|---|---|
| 15 | AACCUGUU U CCUCCUCC | 170 | GGAGGAGG CUGAUGAGGCCGAAAGGCCGAA AACAGGUU | 171 |
| 16 | ACCUGUUU C CUCCUCCU | 172 | AGGAGGAG CUGAUGAGGCCGAAAGGCCGAA AAACAGGU | 173 |
| 19 | UGUUUCCU C CUCCUCCU | 174 | AGGAGGAG CUGAUGAGGCCGAAAGGCCGAA AGGAAACA | 175 |
| 22 | UUCCUCCU C CUCCUUCU | 176 | AGAAGGAG CUGAUGAGGCCGAAAGGCCGAA AGGAGGAA | 177 |
| 25 | CUCCUCCU C CUUCUCCU | 178 | AGGAGAAG CUGAUGAGGCCGAAAGGCCGAA AGGAGGAG | 179 |
| 28 | CUCCUCCU U CUCCUCCU | 180 | AGGAGGAG CUGAUGAGGCCGAAAGGCCGAA AGGAGGAG | 161 |
| 29 | UCCUCCUU C UCCUCCUC | 182 | GAGGAGGA CUGAUGAGGCCGAAAGGCCGAA AAGGAGGA | 183 |
| 31 | CUCCUUCU C UCCUCCUU | 184 | AGGAGGAG CUGAUGAGGCCGAAAGGCCGAA AGAAGGAG | 165 |
| 34 | CUUCUCCU C CUCCUCCG | 186 | CGGAGGAG CUGAUGAGGCCGAAAGGCCGAA AGGAGAAG | 187 |
| 37 | CUCCUCCU C CUCCGUGA | 188 | UCACGGAG CUGAUGAGGCCGAAAGGCCGAA AGGAGGAG | 189 |
| 40 | CUCCUCCU C CGUGACCU | 190 | AGGUCACG CUGAUGAGGCCGAAAGGCCGAA AGGAGGAG | 191 |
| 49 | CGUGACCU C CUCCUCCU | 192 | AGGAGGAG CUGAUGAGGCCGAAAGGCCGAA AGGUCACG | 193 |
| 52 | GACCUCCU C CUCCUCUU | 194 | AAGAGGAG CUGAUGAGGCCGAAAGGCCGAA AGGAGGUC | 195 |
| 55 | CUCCUCCU C CUCUUUCU | 196 | AGAAAGAG CUGAUGAGGCCGAAAGGCCGAA AGGAGGAG | 197 |
| 58 | CUCCUCCU C UUUCUCCU | 198 | AGGAGAAA CUGAUGAGGCCGAAAGGCCGAA AGGAGGAG | 199 |
| 60 | CCUCCUCU U UCUCCUGA | 200 | UCAGGAGA CUGAUGAGGCCGAAAGGCCGAA AGAGGAGG | 201 |
| 61 | CUCCUCUU U UCUCCUGAG | 202 | CUCAGGAG CUGAUGAGGCCGAAAGGCCGAA AAGAGGAG | 203 |
| 62 | UCCUCUUU C UCCUGAGA | 204 | UCUCAGGA CUGAUGAGGCCGAAAGGCCGAA AAAGAGGA | 205 |
| 64 | CUCUUUCU C CUGAGAAA | 206 | UUUCUCAG CUGAUGAGGCCGAAAGGCCGAA AGAAAGAG | 207 |
| 75 | GAGAAACU U CGCCCAG | 208 | CUGGGGCG CUGAUGAGGCCGAAAGGCCGAA AGUUUCUC | 209 |
| 76 | AGAAACUU C GCCCAGC | 210 | GCUGGGGC CUGAUGAGGCCGAAAGGCCGAA AAGUUUCU | 211 |
| 170 | CCGCGGCU C UCGCGGAG | 212 | CUCCGCGA CUGAUGAGGCCGAAAGGCCGAA AGCCGCGG | 213 |
| 172 | GCGGCUCU C GCGGAGCC | 214 | GGCUCCGC CUGAUGAGGCCGAAAGGCCGAA AGAGCCGC | 215 |
| 224 | CACAGCAU A UAUAGCAG | 216 | CUGCUAUA CUGAUGAGGCCGAAAGGCCGAA AUGCUGUG | 217 |
| 226 | CAGCAUAU A UAGCAGUG | 218 | CACUGCUA CUGAUGAGGCCGAAAGGCCGAA AUAUGCUG | 219 |

TABLE XV-continued

Human c-myb Hammerhead Ribozyme and Target Sequences
(REVISED)

| nt. | Target Sequence | Seq. ID No. | HH Ribozyme Sequence | Seq. ID No. |
|---|---|---|---|---|
| 226 | GCAUAUAU A GCAGUGAC | 220 | GUCACUGC CUGAUGAGGCCGAAAGGCCGAA AUAUAUGC | 221 |
| 253 | UGAGGACU U UGAGAUGU | 222 | ACAUCUCA CUGAUGAGGCCGAAAGGCCGAA AGUCCUCA | 223 |
| 254 | GAGGACUU U GAGAUGUG | 224 | CACAUCUC CUGAUGAGGCCGAAAGGCCGAA AAGUCCUC | 225 |
| 274 | CCAUGACU A UGAUGGGC | 226 | GCCCAUCA CUGAUGAGGCCGAAAGGCCGAA AGUCAUGG | 227 |
| 287 | GGGCUGCU U CCCAAGUC | 228 | GACUUGGG CUGAUGAGGCCGAAAGGCCGAA AGCAGCCC | 229 |
| 268 | GGCUGCUU C CCAAGUCU | 230 | AGACUUGG CUGAUGAGGCCGAAAGGCCGAA AAGCAGCC | 231 |
| 310 | GCGUCACU U GGGGAAAA | 232 | UUUUCCCC CUGAUGAGGCCGAAAGGCCGAA AGUGACGC | 233 |
| 393 | GGAAAGUU A UUGCCAAU | 234 | AUUGGCAA CUGAUGAGGCCGAAAGGCCGAA AACUUUCC | 235 |
| 395 | AAAGUUAU U GCCAAUUA | 236 | UAAUUGGC CUGAUGAGGCCGAAAGGCCGAA AUAACUUU | 237 |
| 402 | UUGCCAAU U AUCUCCCG | 238 | CGGGAGAU CUGAUGAGGCCGAAAGGCCGAA AUUGGCAA | 239 |
| 403 | UGCCAAUU A UCUCCCGA | 240 | UCGGGAGA CUGAUGAGGCCGAAAGGCCGAA AAUUGGCA | 241 |
| 405 | CCAAUUAU C UCCCGAAU | 242 | AUUCGGGA CUGAUGAGGCCGAAAGGCCGAA AUAAUUGG | 243 |
| 407 | AAUUAUCU C CCGAAUCG | 244 | CGAUUCGG CUGAUGAGGCCGAAAGGCCGAA AGAUAAUU | 245 |
| 414 | UCCCGAAU C GAACAGAU | 246 | AUCUGUUC CUGAUGAGGCCGAAAGGCCGAA AUUCGGGA | 247 |
| 455 | AAAGUACU A AACCCUGA | 248 | UCAGGGUU CUGAUGAGGCCGAAAGGCCGAA AGUACUUU | 249 |
| 467 | CCUGAGCU C AUCAAGGG | 250 | CCCUUGAU CUGAUGAGGCCGAAAGGCCGAA AGCUCAGG | 251 |
| 470 | GAGCUCAU C AAGGGUCC | 252 | GGACCCUU CUGAUGAGGCCGAAAGGCCGAA AUGAGCUC | 253 |
| 480 | AGGGUCCU U GGACCAAA | 254 | UUUGGUCC CUGAUGAGGCCGAAAGGCCGAA AGGACCCU | 255 |
| 498 | AAGAAGAU C AGAGAGUG | 256 | CACUCUCU CUGAUGAGGCCGAAAGGCCGAA AUCUUCUU | 257 |
| 509 | AGAGUGAU A GAGCUUGU | 258 | ACAAGCUC CUGAUGAGGCCGAAAGGCCGAA AUCACUCU | 259 |
| 515 | AUAGAGCU U GUACAGAA | 260 | UUCGUAC CUGAUGAGGCCGAAAGGCCGAA AGCUCUAU | 261 |
| 526 | ACAGAAAU A CGGUCCGA | 262 | UCGGACCG CUGAUGAGGCCGAAAGGCCGAA AUUUCUGU | 263 |
| 549 | GGUCUGUU A UUGCCAAG | 264 | CUUGGCAA CUGAUGAGGCCGAAAGGCCGAA AACAGACC | 265 |
| 551 | UCUGUUAU U GCCAAGCA | 266 | UGCUUGGC CUGAUGAGGCCGAAAGGCCGAA AUAACAGA | 267 |
| 562 | CAAGCACU U AAAGGGGA | 268 | UCCCCUUU CUGAUGAGGCCGAAAGGCCGAA AGUGCUUG | 269 |
| 563 | AAGCACUU A AAGGGGAG | 270 | CUCCCCUU CUGAUGAGGCCGAAAGGCCGAA AAGUGCUU | 271 |
| 575 | GGGAGAAU U GGAAAACA | 272 | UGUUUUCC CUGAUGAGGCCGAAAGGCCGAA AUUCUCCC | 273 |
| 603 | GGUGGCAU A ACCACUUG | 274 | CAAGUGGU CUGAUGAGGCCGAAAGGCCGAA AUGCCACC | 275 |
| 610 | UAACCACU U GAAUCCAG | 276 | CUGGAUUC CUGAUGAGGCCGAAAGGCCGAA AGUGGUUA | 277 |
| 615 | ACUUGAAU C CAGAAGUU | 278 | AACUUCUG CUGAUGAGGCCGAAAGGCCGAA AUUCAAGU | 279 |
| 624 | CAGAAGUU A AGAAAACC | 280 | GGUUUUCU CUGAUGAGGCCGAAAGGCCGAA AACUUCUG | 281 |
| 634 | GAAAACCU C CUGGACAG | 282 | CUGUCCAG CUGAUGAGGCCGAAAGGCCGAA AGGUUUUC | 283 |
| 659 | GACAGAAU U AUUUACCA | 284 | UGGUAAAU CUGAUGAGGCCGAAAGGCCGAA AUUCUGUC | 285 |
| 660 | ACAGAAUU A UUUACCAG | 286 | CUGGUAAA CUGAUGAGGCCGAAAGGCCGAA AAUUCUGU | 287 |
| 662 | AGAAUUAU U UACCAGGC | 288 | GCCUGGUA CUGAUGAGGCCGAAAGGCCGAA AUAAUUCU | 289 |
| 663 | GAAUUAUU U ACCAGGCA | 290 | UGCCUGGU CUGAUGAGGCCGAAAGGCCGAA AAUAAUUC | 291 |
| 664 | AAUUAUUU A CCAGGCAC | 292 | GUGCCUGG CUGAUGAGGCCGAAAGGCCGAA AAAUAAUU | 293 |
| 704 | GCAGAAAU C GCAAAGCU | 294 | AGCUUUGC CUGAUGAGGCCGAAAGGCCGAA AUUUCUGC | 295 |
| 713 | GCAAAGCU A CUGCCUGG | 296 | CCAGGCAG CUGAUGAGGCCGAAAGGCCGAA AGCUUUGC | 297 |
| 732 | GAACUGAU A AUGCUAUC | 298 | GAUAGCAU CUGAUGAGGCCGAAAGGCCGAA AUCAGUUC | 299 |
| 738 | AUAAUGCU A UCAAGAAC | 300 | GUUCUUGA CUGAUGAGGCCGAAAGGCCGAA AGCAUUAU | 301 |
| 740 | AAUGCUAU C AAGAACCA | 302 | UGGUUCUU CUGAUGAGGCCGAAAGGCCGAA AUAGCAUU | 303 |
| 756 | ACUGGAAU U CUACAAUG | 304 | CAUUGUAG CUGAUGAGGCCGAAAGGCCGAA AUUCCAGU | 305 |
| 757 | CUGGAAUU C UACAAUGC | 306 | GCAUUGUA CUGAUGAGGCCGAAAGGCCGAA AAUUCCAG | 307 |
| 759 | GGAAUUCU A CAAUGCGU | 308 | ACGCAUUG CUGAUGAGGCCGAAAGGCCGAA AGAAUUCC | 309 |
| 790 | GGAAGGUU A UCUGCAGG | 310 | CCUGCAGA CUGAUGAGGCCGAAAGGCCGAA AACCUUCC | 311 |
| 792 | AAGGUUAU C UGCAGGAG | 312 | CUCCUGCA CUGAUGAGGCCGAAAGGCCGAA AUAACCUU | 313 |
| 804 | AGGAGUCU U CAAAAGCC | 314 | GGCUUUUG CUGAUGAGGCCGAAAGGCCGAA AGACUCCU | 315 |
| 805 | GGAGUCUU C AAAAGCCA | 316 | UGGCUUUU CUGAUGAGGCCGAAAGGCCGAA AAGACUCC | 317 |
| 838 | CACAAGCU U CCAGAAGA | 318 | UCUUCUGG CUGAUGAGGCCGAAAGGCCGAA AGCUUGUG | 319 |
| 839 | ACAAGCUU C CAGAAGAA | 320 | UUCUUCUG CUGAUGAGGCCGAAAGGCCGAA AAGCUUGU | 321 |
| 855 | ACAGUCAU U UGAUGGGU | 322 | ACCCAUCA CUGAUGAGGCCGAAAGGCCGAA AUGACUGU | 323 |
| 856 | CAGUCAUU U GAUGGGUU | 324 | AACCCAUC CUGAUGAGGCCGAAAGGCCGAA AAUGACUG | 325 |
| 865 | GAUGGGUU U UGCUCAGG | 326 | CCUGAGCA CUGAUGAGGCCGAAAGGCCGAA AACCCAUC | 327 |
| 866 | AUGGGUUU U GCUCAGGC | 328 | GCCUGAGC CUGAUGAGGCCGAAAGGCCGAA AAACCCAU | 329 |
| 870 | GUUUUGCU C AGGCUCCG | 330 | CGGAGCCU CUGAUGAGGCCGAAAGGCCGAA AGCAAAAC | 331 |
| 876 | CUCAGGCU C CGCCUACA | 332 | UGUAGGCG CUGAUGAGGCCGAAAGGCCGAA AGCCUGAG | 333 |
| 882 | CUCCGCCU A CAGCUCAA | 334 | UUGAGCUG CUGAUGAGGCCGAAAGGCCGAA AGGCGGAG | 335 |
| 888 | CUACAGCU C AACUCCCU | 336 | AGGGAGUU CUGAUGAGGCCGAAAGGCCGAA AGCUGUAG | 337 |
| 893 | GCUCAACU C CCUGCCAC | 338 | GUGGCAGG CUGAUGAGGCCGAAAGGCCGAA AGUUGAGC | 339 |
| 918 | CCACUGUU A ACAACGAC | 340 | GUCGUUGU CUGAUGAGGCCGAAAGGCCGAA AACAGUGG | 341 |
| 928 | CAACGACU A UUCCUAUU | 342 | AAUAGGAA CUGAUGAGGCCGAAAGGCCGAA AGUCGUUG | 343 |
| 930 | ACGACUAU U CCUAUUAC | 344 | GUAAUAGG CUGAUGAGGCCGAAAGGCCGAA AUAGUCGU | 345 |
| 931 | CGACUAUU C CUAUUACC | 346 | GGUAAUAG CUGAUGAGGCCGAAAGGCCGAA AAUAGUCG | 347 |
| 934 | CUAUUCCU A UUACCACA | 348 | UGUGGUAA CUGAUGAGGCCGAAAGGCCGAA AGGAAUAG | 349 |
| 936 | AUUCCUAU U ACCACAUU | 350 | AAUGUGGU CUGAUGAGGCCGAAAGGCCGAA AUAGGAAU | 351 |
| 937 | UUCCUAUU A CCACAUUU | 352 | AAAUGUGG CUGAUGAGGCCGAAAGGCCGAA AAUAGGAA | 353 |
| 944 | UACCACAU U UCUGAAGC | 354 | GCUUCAGA CUGAUGAGGCCGAAAGGCCGAA AUGUGGUA | 355 |
| 945 | ACCACAUU U CUGAAGCA | 356 | UGCUUCAG CUGAUGAGGCCGAAAGGCCGAA AAUGUGGU | 357 |
| 946 | CCACAUUU C UGAAGCAC | 358 | GUGCUUCA CUGAUGAGGCCGAAAGGCCGAA AAAUGUGG | 359 |
| 964 | AAAUGUCU C CAGUCAUG | 360 | CAUGACUG CUGAUGAGGCCGAAAGGCCGAA AGACAUUU | 361 |
| 975 | GUCAUGUU C CAUACCCU | 362 | AGGGUAUG CUGAUGAGGCCGAAAGGCCGAA AACAUGAC | 363 |
| 979 | UGUUCCAU A CCCUGUAG | 364 | CUACAGGG CUGAUGAGGCCGAAAGGCCGAA AUGGAACA | 365 |

TABLE XV-continued

Human c-myb Hammerhead Ribozyme and Target Sequences
(REVISED)

| nt. | Target Sequence | Seq. ID No. | HH Ribozyme Sequence | Seq. ID No. |
|---|---|---|---|---|
| 992 | GUAGCGUU A CAUGUAAA | 366 | UUUACAUG CUGAUGAGGCCGAAAGGCCGAA AACGCUAC | 367 |
| 998 | UUACAUGU A AAUAUAGU | 368 | ACUAUAUU CUGAUGAGGCCGAAAGGCCGAA ACAUGUAA | 369 |
| 1002 | AUGUAAAU A UAGUCAAU | 370 | AUUGACUA CUGAUGAGGCCGAAAGGCCGAA AUUUACAU | 371 |
| 1004 | GUAAAUAU A GUCAAUGU | 372 | ACAUUGAC CUGAUGAGGCCGAAAGGCCGAA AUAUUUAC | 373 |
| 1017 | AUGUCCCU C AGCCAGCU | 374 | AGCUGGCU CUGAUGAGGCCGAAAGGCCGAA AGGGACAU | 375 |
| 1037 | GCAdCCAU U CAGAGACA | 376 | UGUCUCUG CUGAUGAGGCCGAAAGGCCGAA AUGGCUGC | 377 |
| 1038 | CAGCCAUU C ACAGACAC | 378 | GUGUCUCU CUGAUGAGGCCGAAAGGCCGAA AAUGGCUG | 379 |
| 1048 | GAGACACU A UAAUGAUG | 380 | CAUCAUUA CUGAUGAGGCCGAAAGGCCGAA AGUGUCUC | 381 |
| 1050 | GACACUAU A AUGAUGAA | 382 | UUCAUCAU CUGAUGAGGCCGAAAGGCCGAA AUAGUGUC | 383 |
| 1082 | AAGCGAAU A AAGGAAUU | 364 | AAUUCCUU CUGAUGAGGCCGAAAGGCCGAA AUUCGCUU | 385 |
| 1090 | AAAGGAAU U AGAAUUGC | 386 | GCAAUUCU CUGAUGAGGCCGAAAGGCCGAA AUUCCUUU | 387 |
| 1091 | AAGGAAUU A GAAUUGCU | 388 | AGCAAUUC CUGAUGAGGCCGAAAGGCCGAA AAUUCCUU | 389 |
| 1096 | AUUAGAAU U GCUCCUAA | 390 | UUAGGAGC CUGAUGAGGCCGAAAGGCCGAA AUUCUAAU | 391 |
| 1100 | GAAUUGCU C CUAAUGUC | 392 | GACAUUAG CUGAUGAGGCCGAAAGGCCGAA AGCAAUUC | 393 |
| 1103 | UUGCUCCU A AUGUCAAC | 394 | GUUGACAU CUGAUGAGGCCGAAAGGCCGAA AGGAGCAA | 395 |
| 1124 | AAUGAGCU A AAAGGACA | 396 | UGUCCUUU CUGAUGAGGCCGAAAGGCCGAA AGCUCAUU | 397 |
| 1159 | AUGCAGCU A CCCCGGGU | 398 | ACCCGGGG CUGAUGAGGCCGAAAGGCCGAA AGCUGCAU | 399 |
| 1184 | ACCACCAU U GCCGACCA | 400 | UGGUCGGC CUGAUGAGGCCGAAAGGCCGAA AUGGUGGU | 401 |
| 1203 | CCAGACCU C AUGGAGAC | 402 | GUCUCCAU CUGAUGAGGCCGAAAGGCCGAA AGGUCUGG | 403 |
| 1224 | CACCUGUU U CCUGUUUG | 404 | CAAACAGG CUGAUGAGGCCGAAAGGCCGAA AACAGGUG | 405 |
| 1225 | ACCUGUUU C CUGUUUGG | 406 | CCAAACAG CUGAUGAGGCCGAAAGGCCGAA AAACAGGU | 407 |
| 1231 | UUCCUGUU U GGGAGAAC | 408 | GUUCUCCC CUGAUGAGGCCGAAAGGCCGAA AACAGGAA | 409 |
| 1246 | ACACCACU C CACUCCAU | 410 | AUGGAGUG CUGAUGAGGCCGAAAGGCCGAA AGUGGUGU | 411 |
| 1251 | ACUCCACU C CAUCUCUG | 412 | CAGAGAUG CUGAUGAGGCCGAAAGGCCGAA AGUGGAGU | 413 |
| 1255 | CACUCCAU C UCUGCCAG | 414 | CUGGCAGA CUGAUGAGGCCGAAAGGCCGAA AUGGAGUG | 415 |
| 1257 | CUCCAUCU C UGCCAGCG | 416 | CGCUGGCA CUGAUGAGGCCGAAAGGCCGAA AGAUGGAG | 417 |
| 1269 | CAGCGGAU C CUGGCUCC | 418 | GGAGCCAG CUGAUGAGGCCGAAAGGCCGAA AUCCGCUG | 419 |
| 1276 | UCCUGGCU C CCUACCUG | 420 | CAGGUAGG CUGAUGAGGCCGAAAGGCCGAA AGCCAGGA | 421 |
| 1280 | GGCUCCCU A CCUGAAGA | 422 | UCUUCAGG CUGAUGAGGCCGAAAGGCCGAA AGGGAGCC | 423 |
| 1297 | AAGCGCCU C GCCAGCAA | 424 | UUGCUGGC CUGAUGAGGCCGAAAGGCCGAA AGGCGCUU | 425 |
| 1316 | UGCAUGAU C GUCCACCA | 426 | UGGUGGAC CUGAUGAGGCCGAAAGGCCGAA AUCAUGCA | 427 |
| 1334 | GGCACCAU U CUGGAUAA | 428 | UUAUCCAG CUGAUGAGGCCGAAAGGCCGAA AUGGUGCC | 429 |
| 1335 | GCACCAUU C UGGAUAAU | 430 | AUUAUCCA CUGAUGAGGCCGAAAGGCCGAA AAUGGUGC | 431 |
| 1341 | UUCUGGAU A AUGUUAAG | 432 | CUUAACAU CUGAUGAGGCCGAAAGGCCGAA AUCCAGAA | 433 |
| 1347 | AUAAUGUU A AGAACCUC | 434 | GAGGUUCU CUGAUGAGGCCGAAAGGCCGAA AACAUUAU | 435 |
| 1355 | AAGAACCU C UUAGAAUU | 436 | AAUUCUAA CUGAUGAGGCCGAAAGGCCGAA AGGUUCUU | 437 |
| 1357 | GAACCUCU U AGAAUUUG | 438 | CAAAUUCU CUGAUGAGGCCGAAAGGCCGAA AGAGGUUC | 439 |
| 1358 | AACCUCUU A GAAUUUGC | 440 | GCAAAUUC CUGAUGAGGCCGAAAGGCCGAA AAGAGGUU | 441 |
| 1363 | CUUAGAAU U UGCAGAAA | 442 | UUUCUGCA CUGAUGAGGCCGAAAGGCCGAA AUUCUAAG | 443 |
| 1364 | UUAGAAUU U GCAGAAAC | 444 | GUUUCUGC CUGAUGAGGCCGAAAGGCCGAA AAUUCUAA | 445 |
| 1376 | GAAACACU C CAAUUUAU | 446 | AUAAAUUG CUGAUGAGGCCGAAAGGCCGAA AGUGUUUC | 447 |
| 1381 | ACUCCAAU U UAUAGAUU | 448 | AAUCUAUA CUGAUGAGGCCGAAAGGCCGAA AAUUGGAG | 449 |
| 1382 | CUCCAAUU U AUAGAUUC | 450 | GAAUCUAU CUGAUGAGGCCGAAAGGCCGAA AAUUGGAG | 451 |
| 1383 | UCCAAUUU A UAGAUUCU | 452 | AGAAUCUA CUGAUGAGGCCGAAAGGCCGAA AAAUUGGA | 453 |
| 1385 | CAAUUUAU A GAUUCUUU | 454 | AAAGAAUC CUGAUGAGGCCGAAAGGCCGAA AUAAAUUG | 455 |
| 1389 | UUAUAGAU U CUUUCUUA | 456 | UAAGAAAG CUGAUGAGGCCGAAAGGCCGAA AUCUAUAA | 457 |
| 1390 | UAUAGAUU C UUUCUUAA | 458 | UUAAGAAA CUGAUGAGGCCGAAAGGCCGAA AAUCUAUA | 459 |
| 1392 | UAGAUUCU U UCUUAAAC | 460 | GUUUAAGA CUGAUGAGGCCGAAAGGCCGAA AGAAUCUA | 461 |
| 1393 | AGAUUCUU U CUUAAACA | 462 | UGUUUAAG CUGAUGAGGCCGAAAGGCCGAA AAGAAUCU | 463 |
| 1394 | GAUUCUUU C UUAAACAC | 464 | GUGUUUAA CUGAUGAGGCCGAAAGGCCGAA AAAGAAUC | 465 |
| 1396 | UUCUUUCU U AAACACUU | 466 | AAGUGUUU CUGAUGAGGCCGAAAGGCCGAA AGAAAGAA | 467 |
| 1397 | UCUUUCUU A AACACUUC | 468 | GAAGUGUU CUGAUGAGGCCGAAAGGCCGAA AAGAAAGA | 469 |
| 1404 | UAAACACU U CCAGUAAC | 470 | GUUACUGG CUGAUGAGGCCGAAAGGCCGAA AGUGUUUA | 471 |
| 1405 | AAACACUU C CAGUAACC | 472 | GGUUACUG CUGAUGAGGCCGAAAGGCCGAA AAGUGUUU | 473 |
| 1423 | UGAAACUC A GACUUGG | 474 | CCAAGUCU CUGAUGAGGCCGAAAGGCCGAA AGUUUUCA | 475 |
| 1429 | CUCAGACU U GGAAAUGC | 476 | GCAUUUCC CUGAUGAGGCCGAAAGGCCGAA AGUCUGAG | 477 |
| 1440 | AAAUGCCU U CUUUAACU | 478 | AGUUAAAG CUGAUGAGGCCGAAAGGCCGAA AGGCAUUU | 479 |
| 1441 | AAUGCCUU C UUUAACUU | 480 | AAGUUAAA CUGAUGAGGCCGAAAGGCCGAA AAGGCAUU | 481 |
| 1443 | UGCCUUCU U UAACUUCC | 482 | GGAAGUUA CUGAUGAGGCCGAAAGGCCGAA AGAAGGCA | 483 |
| 1444 | GCCUUCUU U AACUUCCA | 484 | UGGAAGUU CUGAUGAGGCCGAAAGGCCGAA AAGAAGGC | 485 |
| 1445 | CCUUCUUU A ACUUCCAC | 486 | GUGGAAGU CUGAUGAGGCCGAAAGGCCGAA AAAGAAGG | 487 |
| 1449 | CUUUAACU U CCACCCCC | 488 | GGGGGUGG CUGAUGAGGCCGAAAGGCCGAA AGUUAAAG | 489 |
| 1450 | UUUAACUU C CACCCCCC | 490 | GGGGGGUG CUGAUGAGGCCGAAAGGCCGAA AAGUUAAA | 491 |
| 1460 | ACCCCCCU C AUUGGUCA | 492 | UGACCAAU CUGAUGAGGCCGAAAGGCCGAA AGGGGGGU | 493 |
| 1463 | CCCCUCAU U GGUCACAA | 494 | UUGUGACC CUGAUGAGGCCGAAAGGCCGAA AUGAGGGG | 495 |
| 1474 | UCACAAAU U GACUGUUA | 496 | UAACAGUC CUGAUGAGGCCGAAAGGCCGAA AUUUGUGA | 497 |
| 1482 | UGACUGUU A CAACACCA | 498 | UGGUGUUG CUGAUGAGGCCGAAAGGCCGAA AACAGUCA | 499 |
| 1492 | AACACCAU U UCAUAGAG | 500 | CUCUAUGA CUGAUGAGGCCGAAAGGCCGAA AUGGUGUU | 501 |
| 1493 | ACACCAUU U CAUAGAGA | 502 | UCUCUAUG CUGAUGAGGCCGAAAGGCCGAA AAUGGUGU | 503 |
| 1494 | CACCAUUU C AUAGAGAC | 504 | GUCUCUAU CUGAUGAGGCCGAAAGGCCGAA AAAUGGUG | 505 |
| 1497 | CAUUUCAU A GAGACCAG | 506 | CUGGUCUC CUGAUGAGGCCGAAAGGCCGAA AUGAAAUG | 507 |
| 1518 | UGAAACU C AAAAGGAA | 508 | UUCCUUUU CUGAUGAGGCCGAAAGGCCGAA AGUUUUCA | 509 |
| 1530 | AGGAAAAU A CUGUUUUU | 510 | AAAAACAG CUGAUGAGGCCGAAAGGCCGAA AUUUUCCU | 511 |

TABLE XV-continued

Human c-myb Hammerhead Ribozyme and Target Sequences
(REVISED)

| nt. | Target Sequence | Seq. ID No. | HH Ribozyme Sequence | Seq. ID No. |
|---|---|---|---|---|
| 1536 | AUACUGUU U UUAGAACC | 512 | GGUUCUAA CUGAUGAGGCCGAAAGGCCGAA AACAGUAU | 513 |
| 1537 | UACUGUUU U UAGAACCC | 514 | GGGUUCUA CUGAUGAGGCCGAAAGGCCGAA AAACAGUA | 515 |
| 1538 | ACUGUUUU U AGAACCCC | 516 | GGGGUUCU CUGAUGAGGCCGAAAGGCCGAA AAAACAGU | 517 |
| 1539 | CUGUUUUU A GAACCCCA | 518 | UGGGGUUC CUGAUGAGGCCGAAAGGCCGAA AAAAACAG | 519 |
| 1551 | CCCCAGCU A UCAAAAGG | 520 | CCUUUUGA CUGAUGAGGCCGAAAGGCCGAA AGCUGGGG | 521 |
| 1553 | CCAGCUAU C AAAAGGUC | 522 | GACCUUUU CUGAUGAGGCCGAAAGGCCGAA AUAGCUGG | 523 |
| 1565 | AGGUCAAU C UUAGAAAG | 524 | CUUUCUAA CUGAUGAGGCCGAAAGGCCGAA AUUGACCU | 525 |
| 1567 | GUCAAUCU U AGAAAGCU | 526 | AGCUUUCU CUGAUGAGGCCGAAAGGCCGAA AGAUUGAC | 527 |
| 1568 | UCAAUCUU A GAAAGCUC | 528 | GAGCUUUC CUGAUGAGGCCGAAAGGCCGAA AAGAUUGA | 529 |
| 1576 | AGAAAGCU C UCCAAGAA | 530 | UUCUUGGA CUGAUGAGGCCGAAAGGCCGAA AGCUUUCU | 531 |
| 1578 | AAAGCUCU C CAAGAACU | 532 | AGUUCUUG CUGAUGAGGCCGAAAGGCCGAA AGAGCUUU | 533 |
| 1587 | CAAGAACU C CUACACCA | 534 | UGGUGUAG CUGAUGAGGCCGAAAGGCCGAA AGUUCUUG | 535 |
| 1590 | GAACUCCU A CACCAUUC | 536 | GAAUGGUG CUGAUGAGGCCGAAAGGCCGAA AGGAGUUC | 537 |
| 1597 | UACACCAU U CAAACAUG | 538 | CAUGUUUG CUGAUGAGGCCGAAAGGCCGAA AUGGUGUA | 539 |
| 1598 | ACACCAUU C AAACAUGC | 540 | GCAUGUUU CUGAUGAGGCCGAAAGGCCGAA AUGGUGU | 541 |
| 1610 | CAUGCACU U GCAGCUCA | 542 | UGAGCUGC CUGAUGAGGCCGAAAGGCCGAA AGUGCAUG | 543 |
| 1617 | UUGCAGCU C AAGAAAUU | 544 | AAUUUCUU CUGAUGAGGCCGAAAGGCCGAA AGCUGCAA | 545 |
| 1625 | CAAGAAAU U AAAUACGG | 546 | CCGUAUUU CUGAUGAGGCCGAAAGGCCGAA AUUUCUUG | 547 |
| 1626 | AAGAAAUU A AAUACGGU | 548 | ACCGUAUU CUGAUGAGGCCGAAAGGCCGAA AAUUUCUU | 549 |
| 1630 | AAUUAAAU A CGGUCCCC | 550 | GGGGACCG CUGAUGAGGCCGAAAGGCCGAA AUUUAAUU | 551 |
| 1649 | AAGAUGCU A CCUCAGAC | 552 | GUCUGAGG CUGAUGAGGCCGAAAGGCCGAA AGCAUCUU | 553 |
| 1653 | UGCUACCU C AGACACCC | 554 | GGGUGUCU CUGAUGAGGCCGAAAGGCCGAA AGGUAGCA | 555 |
| 1663 | GACACCCU C UCAUCUAG | 556 | CUAGAUGA CUGAUGAGGCCGAAAGGCCGAA AGGGUGUC | 557 |
| 1665 | CACCCUCU C AUCUAGUA | 558 | UACUAGAU CUGAUGAGGCCGAAAGGCCGAA AGAGGGUG | 559 |
| 1668 | CCUCUCAU C UAGUAGAA | 560 | UUCUACUA CUGAUGAGGCCGAAAGGCCGAA AUGAGAGG | 561 |
| 1670 | UCUCAUCU A GUAGAAGA | 562 | UCUUCUAC CUGAUGAGGCCGAAAGGCCGAA AGAUGAGA | 563 |
| 1680 | UAGAAGAU C UGCAGGAU | 564 | AUCCUGCA CUGAUGAGGCCGAAAGGCCGAA AUCUUCUA | 565 |
| 1694 | GAUGUGAU C AAACAGGA | 566 | UCCUGUUU CUGAUGAGGCCGAAAGGCCGAA AUCACAUC | 567 |
| 1705 | ACAGGAAU C UGAUGAAU | 568 | AUUCAUCA CUGAUGAGGCCGAAAGGCCGAA AUUCCUGU | 569 |
| 1714 | UGAUGAAU C UGGAAUUG | 570 | CAAUUCCA CUGAUGAGGCCGAAAGGCCGAA AUUCAUCA | 571 |
| 1721 | UCUGGAAU U GUUGCUGA | 572 | UCAGCAAC CUGAUGAGGCCGAAAGGCCGAA AUUCCAGA | 573 |
| 1733 | GCUGAGUU U CAAGAAAA | 574 | UUUUCUUG CUGAUGAGGCCGAAAGGCCGAA AACUCAGC | 575 |
| 1734 | CUGAGUUU C AAGAAAAU | 576 | AUUUUCUU CUGAUGAGGCCGAAAGGCCGAA AAACUCAG | 577 |
| 1753 | ACCACCCU U ACUGAAGA | 578 | UCUUCAGU CUGAUGAGGCCGAAAGGCCGAA AGGGUGGU | 579 |
| 1754 | CCACCCUU A CUGAAGAA | 580 | UUCUUCAG CUGAUGAGGCCGAAAGGCCGAA AAGGGUGG | 581 |
| 1766 | AAGAAAAU C AAACAAGA | 582 | UCUUGUUU CUGAUGAGGCCGAAAGGCCGAA AUUUUCUU | 583 |
| 1783 | GGUGGAAU C UCCAACUG | 584 | CAGUUGGA CUGAUGAGGCCGAAAGGCCGAA AUUCCACC | 585 |
| 1785 | UGGAAUCU C CAACUGAU | 586 | AUCAGUUG CUGAUGAGGCCGAAAGGCCGAA AGAUUCCA | 587 |
| 1794 | CAACUGAU A AAUCAGGA | 588 | UCCUGAUU CUGAUGAGGCCGAAAGGCCGAA AUCAGUUG | 589 |
| 1798 | UGAUAAAU C AGGAAACU | 590 | AGUUUCCU CUGAUGAGGCCGAAAGGCCGAA AUUUAUCA | 591 |
| 1807 | AGGAAACU U CUUCUGCU | 592 | AGCAGAAG CUGAUGAGGCCGAAAGGCCGAA AGUUUCCU | 593 |
| 1808 | GGAAACUU C UUCUGCUC | 594 | GAGCAGAA CUGAUGAGGCCGAAAGGCCGAA AGUUUCC | 595 |
| 1810 | AAACUUCU U CUGCUCAC | 596 | GUGAGCAG CUGAUGAGGCCGAAAGGCCGAA AGAAGUUU | 597 |
| 1811 | AACUUCUU C UGCUCACA | 598 | UGUGAGCA CUGAUGAGGCCGAAAGGCCGAA AAGAAGUU | 599 |
| 1816 | CUUCUGCU C ACACCACU | 600 | AGUGGUGU CUGAUGAGGCCGAAAGGCCGAA AGCAGAAG | 601 |
| 1845 | GUCUGAAU A CCCAACUG | 602 | CAGUUGGG CUGAUGAGGCCGAAAGGCCGAA AUUCAGAC | 603 |
| 1856 | CAACUGUUC ACGCAGAC | 604 | GUCUGCGU CUGAUGAGGCCGAAAGGCCGAA AACAGUUG | 605 |
| 1867 | GCAGACCU C GCCUGUGG | 606 | CCACAGGC CUGAUGAGGCCGAAAGGCCGAA AGGUCUGC | 607 |
| 1890 | CACCGAAU A UUCUUACA | 608 | UGUAAGAA CUGAUGAGGCCGAAAGGCCGAA AUUCGGUG | 609 |
| 1892 | CCGAAUAU U CUUACAAG | 619 | CUUGUAAG CUGAUGAGGCCGAAAGGCCGAA AUAUUCGG | 611 |
| 1893 | CGAAUAUU C UUACAAGC | 612 | GCUUGUAA CUGAUGAGGCCGAAAGGCCGAA AUAUUCG | 613 |
| 1895 | AAUAUUCU U ACAAGCUC | 614 | GAGCUUGU CUGAUGAGGCCGAAAGGCCGAA AGAAUAUU | 615 |
| 1896 | AUAUUCUU A CAAGCUCC | 616 | GGAGCUUG CUGAUGAGGCCGAAAGGCCGAA AAGAAUAU | 617 |
| 1903 | UACAAGCU C CGUUUUAA | 618 | UUAAAACG CUGAUGAGGCCGAAAGGCCGAA AGCUUGUA | 619 |
| 1908 | GCUCCGUU U UAAUGGCA | 620 | UGCCAUUA CUGAUGAGGCCGAAAGGCCGAA AACGGAGC | 621 |
| 1909 | CUCCGUUU U AAUGGCAC | 622 | GUGCCAUU CUGAUGAGGCCGAAAGGCCGAA AAACGGAG | 623 |
| 1910 | UCCGUUUU A AUGGCACC | 624 | GGUGCCAU CUGAUGAGGCCGAAAGGCCGAA AAAACGGA | 625 |
| 1924 | ACCAGCAU C AGAAGAUG | 626 | CAUCUUCU CUGAUGAGGCCGAAAGGCCGAA AUGCUGGU | 627 |
| 1944 | ACAAUGUU U UCAAAGCA | 626 | UGCUUUGA CUGAUGAGGCCGAAAGGCCGAA AACAUUGU | 629 |
| 1946 | AAUGUUCU C AAAGCAUU | 630 | AAUGCUUU CUGAUGAGGCCGAAAGGCCGAA AGAACAUU | 631 |
| 1954 | CAAAGCAU U UACAGUAC | 632 | GUACUGUA CUGAUGAGGCCGAAAGGCCGAA AUGCUUUG | 633 |
| 1955 | AAAGCAUU U ACAGUACC | 634 | GGUACUGU CUGAUGAGGCCGAAAGGCCGAA AAUGCUUU | 635 |
| 1956 | AAGCAUUU A CAGUACCU | 636 | AGGUACUG CUGAUGAGGCCGAAAGGCCGAA AAAUGCUU | 637 |
| 1965 | CAGUACCU A AAAACAGG | 638 | CCUGUUUU CUGAUGAGGCCGAAAGGCCGAA AGGUACUG | 639 |
| 1990 | GAGCCCCU U GCAGCCUU | 640 | AAGGCUGC CUGAUGAGGCCGAAAGGCCGAA AGGGGCUC | 641 |
| 1998 | UGCAGCCU U GUAGCAGU | 642 | ACUGCUAC CUGAUGAGGCCGAAAGGCCGAA AGGCUGCA | 643 |
| 2023 | ACCUGCAU C CUGUGGAA | 644 | UUCCACAG CUGAUGAGGCCGAAAGGCCGAA AUGCAGGU | 645 |
| 2053 | GAUGACAU C UUCCAGUC | 646 | GACUGGAA CUGAUGAGGCCGAAAGGCCGAA AUGUCAUC | 647 |
| 2055 | UGACACUC U UCCAGUCAA | 648 | UUGACUGG CUGAUGAGGCCGAAAGGCCGAA AGAUGUCA | 649 |
| 2056 | GACAUCUU C CAGUCAAG | 650 | CUUGACUG CUGAUGAGGCCGAAAGGCCGAA AAGAUGUC | 651 |
| 2061 | CUUCCAGU C AAGCUCGU | 652 | ACGAGCUU CUGAUGAGGCCGAAAGGCCGAA ACUGGAAG | 653 |
| 2067 | GUCAAGCU C GUAAAUAC | 654 | GUAUUUAC CUGAUGAGGCCGAAAGGCCGAA AGCUUGAC | 655 |
| 2074 | UCGUAAAU A CGUGAAUG | 656 | CAUUCACG CUGAUGAGGCCGAAAGGCCGAA AUUUACGA | 657 |

TABLE XV-continued

Human c-myb Hammerhead Ribozyme and Target Sequences
(REVISED)

| nt. | Target Sequence | Seq. ID No. | HH Ribozyme Sequence | Seq. ID No. |
|---|---|---|---|---|
| 2086 | GAAUGCAU U CUCAGCCC | 656 | GGGCUGAG CUGAUGAGGCCGAAAGGCCGAA AUGCAUUC | 659 |
| 2087 | AAUGCAUU C UCAGCCCG | 660 | CGGGCUGA CUGAUGAGGCCGAAAGGCCGAA AAUGCAUU | 661 |
| 2089 | UGCAUUCU C AGCCCGGA | 662 | UCCGGGCU CUGAUGAGGCCGAAAGGCCGAA AGAAUGCA | 663 |
| 2117 | UGAGACAU U CCAGAAA | 664 | UUUCUGGA CUGAUGAGGCCGAAAGGCCGAA AUGUCUCA | 665 |
| 2118 | GAGACAUU U CCAGAAAA | 666 | UUUUCUGG CUGAUGAGGCCGAAAGGCCGAA AAUGUCUC | 667 |
| 2119 | AGACAUUU C CAGAAAAG | 666 | CUUUUCUG CUGAUGAGGCCGAAAGGCCGAA AAAUGUCU | 669 |
| 2131 | AAAAGCAU U AUGGUUUU | 670 | AAAACCAU CUGAUGAGGCCGAAAGGCCGAA AUGCUUUU | 671 |
| 2132 | AAAGCAUU A UGGUUUUC | 672 | GAAAACCA CUGAUGAGGCCGAAAGGCCGAA AAUGCUUU | 673 |
| 2138 | UUAUGGUU U UCAGAACA | 674 | UGUUCUGA CUGAUGAGGCCGAAAGGCCGAA AACCAUAA | 675 |
| 2139 | UAUGGUUU U CAGAACAC | 676 | GUGUUCUG CUGAUGAGGCCGAAAGGCCGAA AAACCAUA | 677 |
| 2140 | AUGGUUUU C AGAACACU | 678 | AGUGUUCU CUGAUGAGGCCGAAAGGCCGAA AAAACCAU | 679 |
| 2149 | AGAACACU U CAAGUUGA | 680 | UCAACUUG CUGAUGAGGCCGAAAGGCCGAA AGUGUUCU | 681 |
| 2150 | GAACACUU C AAGUUGAC | 682 | GUCAACUU CUGAUGAGGCCGAAAGGCCGAA AAGUGUUC | 683 |
| 2155 | CUUCAAGU U GACUUGGG | 684 | CCCAAGUC CUGAUGAGGCCGAAAGGCCGAA ACUUGAAG | 685 |
| 2160 | AGUUGACU U GGGAUAUA | 686 | UAUAUCCC CUGAUGAGGCCGAAAGGCCGAA AGUCAACU | 687 |
| 2166 | CUUGGGAU A UAUCAUUC | 688 | GAAUGAUA CUGAUGAGGCCGAAAGGCCGAA AUCCCAAG | 689 |
| 2168 | UGGGAUAU A UCAUUCCU | 690 | AGGAAUGA CUGAUGAGGCCGAAAGGCCGAA AUAUCCCA | 691 |
| 2170 | GGAUAUAU C AUUCCUCA | 692 | UGAGGAAU CUGAUGAGGCCGAAAGGCCGAA AUAUAUCC | 693 |
| 2173 | UAUAUCAU U CCUCAACA | 694 | UGUUGAGG CUGAUGAGGCCGAAAGGCCGAA AUGAUAUA | 695 |
| 2174 | AUAUCAUU C CUCAACAU | 696 | AUGUUGAG CUGAUGAGGCCGAAAGGCCGAA AAUGAUAU | 697 |
| 2177 | UCAUUCCU C AACAUGAA | 698 | UUCAUGUU CUGAUGAGGCCGAAAGGCCGAA AGGAAUGA | 699 |
| 2189 | AUGAACU U UCAUGAA | 700 | UUCAUGAA CUGAUGAGGCCGAAAGGCCGAA AGUUUCAU | 701 |
| 2190 | UGAACUU U UCAUGAAU | 702 | AUUCAUGA CUGAUGAGGCCGAAAGGCCGAA AAGUUUCA | 703 |
| 2191 | GAAACUUU U CAUGAAUG | 704 | CAUUCAUG CUGAUGAGGCCGAAAGGCCGAA AAAGUUUC | 705 |
| 2192 | AAACUUUU C AUGAAUGG | 706 | CCAUUCAU CUGAUGAGGCCGAAAGGCCGAA AAAAGUUU | 707 |
| 2212 | AAGAACCU A UUUUGUU | 708 | AACAAAAA CUGAUGAGGCCGAAAGGCCGAA AGGUUCUU | 709 |
| 2214 | GAACCUAU U UUUGUUGU | 710 | ACAACAAA CUGAUGAGGCCGAAAGGCCGAA AUAGGUUC | 711 |
| 2215 | AACCUAUU U UUGUUGUG | 712 | CACAACAA CUGAUGAGGCCGAAAGGCCGAA AAUAGGUU | 713 |
| 2216 | ACCUAUUU U UGUUGUGG | 714 | CCACAACA CUGAUGAGGCCGAAAGGCCGAA AAAUAGGU | 715 |
| 2217 | CCUAUUUU U GUUGUGGU | 716 | ACCACAAC CUGAUGAGGCCGAAAGGCCGAA AAUUAGG | 717 |
| 2255 | AAGUGCAU U UAGUUGAA | 718 | UUCAACUA CUGAUGAGGCCGAAAGGCCGAA AUGCACUU | 719 |
| 2256 | AGUGCAUU U AGUUGAAU | 720 | AUUCAACU CUGAUGAGGCCGAAAGGCCGAA AAUGCACU | 721 |
| 2257 | GUGCAUUU A GUUGAAUG | 722 | CAUUCAAC CUGAUGAGGCCGAAAGGCCGAA AAAUGCAC | 723 |
| 2272 | UGAAGUCU U CUUGGAUU | 724 | AAUCCAAG CUGAUGAGGCCGAAAGGCCGAA AGACUUCA | 725 |
| 2273 | GAAGUCUU C UUGGAUUU | 726 | AAAUCCAA CUGAUGAGGCCGAAAGGCCGAA AAGACUUC | 727 |
| 2275 | AGUCUUCU U GGAUUUCA | 728 | UGAAAUCC CUGAUGAGGCCGAAAGGCCGAA AGAAGACU | 729 |
| 2280 | UCUUGGAU U UCACCCAA | 730 | UUGGGUGA CUGAUGAGGCCGAAAGGCCGAA AUCCAAGA | 731 |
| 2281 | CUUGGAUU U CACCAAC | 732 | GUUGGGUG CUGAUGAGGCCGAAAGGCCGAA AAUCCAAG | 733 |
| 2282 | UUGGAUUU C ACCCAACU | 734 | AGUUGGGU CUGAUGAGGCCGAAAGGCCGAA AAAUCCAA | 735 |
| 2291 | ACCCAACU A AAAGGAUU | 736 | AAUCCUUU CUGAUGAGGCCGAAAGGCCGAA AGUUGGGU | 737 |
| 2299 | AAAAGGAU U UUUAAAAA | 736 | UUUUUAAA CUGAUGAGGCCGAAAGGCCGAA AUCCUUUU | 739 |
| 2300 | AAAGGAUU U UUAAAAAU | 740 | AUUUUUAA CUGAUGAGGCCGAAAGGCCGAA AAUCCUUU | 741 |
| 2301 | AAGGAUUU U UAAAAAUA | 742 | UAUUUUUA CUGAUGAGGCCGAAAGGCCGAA AAAUCCUU | 743 |
| 2302 | AGGAUUUU U AAAAAUAA | 744 | UUAUUUUU CUGAUGAGGCCGAAAGGCCGAA AAAAUCCU | 745 |
| 2303 | GGAUUUUU A AAAAUAAA | 746 | UUUAUUUU CUGAUGAGGCCGAAAGGCCGAA AAAAAUCC | 747 |
| 2309 | UUAAAAAU A AAUAACAG | 748 | CUGUUAUU CUGAUGAGGCCGAAAGGCCGAA AUUUUUAA | 749 |
| 2313 | AAAUAAAU A ACAGUCUU | 750 | AAGACUGU CUGAUGAGGCCGAAAGGCCGAA AUUUAUUU | 751 |
| 2321 | AACAGUCU U ACCUAAAU | 752 | AUUUAGGU CUGAUGAGGCCGAAAGGCCGAA AGACUGUU | 753 |
| 2322 | ACAGUCUU A CCUAAAUU | 754 | AAUUUAGG CUGAUGAGGCCGAAAGGCCGAA AAGACUGU | 755 |
| 2326 | UCUUACCU A AAUUAUUA | 756 | UAAUAAUU CUGAUGAGGCCGAAAGGCCGAA AGGUAAGA | 757 |
| 2330 | ACCUAAAU U AUUAGGUA | 758 | UACCUAAU CUGAUGAGGCCGAAAGGCCGAA AUUUAGGU | 759 |
| 2331 | CCUAAAUU A UUAGGUAA | 760 | UUACCUAA CUGAUGAGGCCGAAAGGCCGAA AAUUUAGG | 761 |
| 2333 | UAAAUUAU U AGGUAAUG | 762 | CAUUACCU CUGAUGAGGCCGAAAGGCCGAA AUAAUUUA | 763 |
| 2334 | AAAUUAUU A GGUAAUGA | 764 | UCAUUACC CUGAUGAGGCCGAAAGGCCGAA AAUAAUUU | 765 |
| 2345 | UAAUGAAU U GUAGCCAG | 766 | CUGGCUAC CUGAUGAGGCCGAAAGGCCGAA AUUCAUUA | 767 |
| 2359 | CAGUUGUU A AUAUCUUA | 768 | UAAGAUAU CUGAUGAGGCCGAAAGGCCGAA AACAACUG | 769 |
| 2362 | UUGUUAAU A UCUUAAUG | 770 | CAUUAAGA CUGAUGAGGCCGAAAGGCCGAA AUUAACAA | 771 |
| 2364 | GUUAAUAU C UUAAUGCA | 772 | UGCAUUAA CUGAUGAGGCCGAAAGGCCGAA AUAUUAAC | 773 |
| 2366 | UAAUAUCU U AAUGCAGA | 774 | UCUGCAUU CUGAUGAGGCCGAAAGGCCGAA AGAUAUUA | 775 |
| 2367 | AAUAUCUU A AUGCAGAU | 776 | AUCUGCAU CUGAUGAGGCCGAAAGGCCGAA AAGAUAUU | 777 |
| 2376 | AUGCAGAU U UUUUAAA | 778 | UUUAAAAA CUGAUGAGGCCGAAAGGCCGAA AUCUGCAU | 779 |
| 2377 | UGCAGAUU U UUUAAAA | 780 | UUUUAAAA CUGAUGAGGCCGAAAGGCCGAA AAUCUGCA | 781 |
| 2378 | GCAGAUUU U UUAAAAA | 782 | UUUUUAAA CUGAUGAGGCCGAAAGGCCGAA AAAUCUGC | 783 |
| 2379 | CAGAUUUU U UAAAAAA | 784 | UUUUUUAA CUGAUGAGGCCGAAAGGCCGAA AAAAUCUG | 785 |
| 2380 | AGAUUUUU U AAAAAAA | 786 | UUUUUUUA CUGAUGAGGCCGAAAGGCCGAA AAAAAUCU | 787 |
| 2381 | GAUUUUUU U AAAAAAAA | 788 | UUUUUUUU CUGAUGAGGCCGAAAGGCCGAA AAAAAAUC | 789 |
| 2382 | AUUUUUUU A AAAAAAC | 790 | GUUUUUUU CUGAUGAGGCCGAAAGGCCGAA AAAAAAAU | 791 |
| 2393 | AAAAACAU A AAAUGAUU | 792 | AAUCAUUU CUGAUGAGGCCGAAAGGCCGAA AUGUUUUU | 793 |
| 2401 | AAAAUGAU U UAUCUGUA | 794 | UACAGAUA CUGAUGAGGCCGAAAGGCCGAA AUCAUUUU | 795 |
| 2402 | AAAUGAUU U AUCUGUAU | 796 | AUACAGAU CUGAUGAGGCCGAAAGGCCGAA AAUCAUUU | 797 |
| 2403 | AAUGAUUU A UCUGUAUU | 798 | AAUACAGA CUGAUGAGGCCGAAAGGCCGAA AAAUCAUU | 799 |
| 2405 | UGAUUUAU C UGUAUUUU | 800 | AAAAUACA CUGAUGAGGCCGAAAGGCCGAA AUAAAUCA | 801 |
| 2411 | AUCUGUAU U UUAAAGGA | 802 | UCCUUUAA CUGAUGAGGCCGAAAGGCCGAA AUACAGAU | 803 |

TABLE XV-continued

Human c-myb Hammerhead Ribozyme and Target Sequences
(REVISED)

| nt. | Target Sequence | Seq. ID No. | HH Ribozyme Sequence | Seq. ID No. |
|---|---|---|---|---|
| 2412 | UCUGUAUU U UAAAGGAU | 804 | AUCCUUUA CUGAUGAGGCCGAAAGGCCGAA AAUACAGA | 805 |
| 2413 | CUGUAUUU U AAAGGAUC | 806 | GAUCCUUU CUGAUGAGGCCGAAAGGCCGAA AAAUACAG | 807 |
| 2414 | UGUAUUUU A AAGGAUCC | 808 | GGAUCCUU CUGAUGAGGCCGAAAGGCCGAA AAAAUACA | 809 |
| 2421 | UAAAGGAU C CAACAGAU | 810 | AUCUGUUG CUGAUGAGGCCGAAAGGCCGAA AUCCUUUA | 811 |
| 2430 | CAACAGAU C AGUAUUUU | 812 | AAAAUACU CUGAUGAGGCCGAAAGGCCGAA AUCUGUUG | 813 |
| 2436 | AUCAGUAU U UUUUCCUG | 814 | CAGGAAAA CUGAUGAGGCCGAAAGGCCGAA AUACUGAU | 815 |
| 2437 | UCAGUAUU U UUUCCUGU | 816 | ACAGGAAA CUGAUGAGGCCGAAAGGCCGAA AAUACUGA | 817 |
| 2438 | CAGUAUUU U UUCCUGUG | 818 | CACAGGAA CUGAUGAGGCCGAAAGGCCGAA AAAUACUG | 819 |
| 2439 | AGUAUUUU U UCCUGUGA | 820 | UCACAGGA CUGAUGAGGCCGAAAGGCCGAA AAAAUACU | 821 |
| 2440 | GUAUUUUU U CCUGUGAU | 822 | AUCACAGG CUGAUGAGGCCGAAAGGCCGAA AAAAAUAC | 823 |
| 2441 | UAUUUUUU C CUGUGAUG | 824 | CAUCACAG CUGAUGAGGCCGAAAGGCCGAA AAAAAAUA | 825 |
| 2454 | GAUGGGUU U UUUGAAAU | 826 | AUUUCAAA CUGAUGAGGCCGAAAGGCCGAA AACCCAUC | 827 |
| 2455 | AUGGGUUU U UUGAAAUU | 828 | AAUUUCAA CUGAUGAGGCCGAAAGGCCGAA AAACCCAU | 829 |
| 2456 | UGGGUUUU U UGAAAUUU | 830 | AAAUUUCA CUGAUGAGGCCGAAAGGCCGAA AAAACCCA | 831 |
| 2457 | GGGUUUUU U GAAAUUUG | 832 | CAAAUUUC CUGAUGAGGCCGAAAGGCCGAA AAAAACCC | 833 |
| 2463 | UUUGAAAU U UGACACAU | 834 | AUGUGUCA CUGAUGAGGCCGAAAGGCCGAA AUUUCAAA | 835 |
| 2464 | UUGAAAUU U GACACAUU | 836 | AAUGUGUC CUGAUGAGGCCGAAAGGCCGAA AAUUUCAA | 837 |
| 2472 | UGACACAU U AAAAGGUA | 838 | UACCUUUU CUGAUGAGGCCGAAAGGCCGAA AUGUGUCA | 839 |
| 2473 | GACACAUU A AAAGGUAC | 840 | GUACCUUU CUGAUGAGGCCGAAAGGCCGAA AAUGUGUC | B41 |
| 2483 | AAGGUACU C CAGUAUUU | 842 | AAAUACUG CUGAUGAGGCCGAAAGGCCGAA AGUACCUU | 843 |
| 2490 | UCCAGUAU U UCACUUUU | 844 | AAAAGUGA CUGAUGAGGCCGAAAGGCCGAA AUACUGGA | 845 |
| 2491 | CCAGUAUU U CACUUUUC | 846 | GAAAAGUG CUGAUGAGGCCGAAAGGCCGAA AAUACUGG | 847 |
| 2492 | CAGUAUUU C ACUUUUCU | 848 | AGAAAAGU CUGAUGAGGCCGAAAGGCCGAA AAAUACUG | 849 |
| 2496 | AUUUCACU U UUCUCGAU | 850 | AUCGAGAA CUGAUGAGGCCGAAAGGCCGAA AGUGAAAU | 851 |
| 2497 | UUUCACUU U UCUCGAUC | 852 | GAUCGAGA CUGAUGAGGCCGAAAGGCCGAA AAGUGAAA | 853 |
| 2498 | UUCACUUU U CUCGAUCA | 854 | UGAUCGAG CUGAUGAGGCCGAAAGGCCGAA AAAGUGAA | 855 |
| 2499 | UCACUUUU C UCGAUCAC | 856 | GUGAUCGA CUGAUGAGGCCGAAAGGCCGAA AAAAGUGA | 857 |
| 2501 | ACUUUUCU C GAUCACUA | 858 | UAGUGAUC CUGAUGAGGCCGAAAGGCCGAA AGAAAAGU | 859 |
| 2505 | UUCUCGAU C ACUAAACA | 860 | UGUUUAGU CUGAUGAGGCCGAAAGGCCGAA AUCGAGAA | 861 |
| 2509 | CGAUCACU A AACAUAUG | 862 | CAUAUGUU CUGAUGAGGCCGAAAGGCCGAA AGUGAUCG | 863 |
| 2515 | CUAAACAU A UGCAUAUA | 864 | UAUAUGCA CUGAUGAGGCCGAAAGGCCGAA AUGUUUAG | 865 |
| 2521 | AUAUGCAU A UAUUUUUA | 866 | UAAAAAUA CUGAUGAGGCCGAAAGGCCGAA AUGCAUAU | 867 |
| 2523 | AUGCAUAU A UUUUUAAA | 868 | UUUAAAAA CUGAUGAGGCCGAAAGGCCGAA AUAUGCAU | 869 |
| 2525 | GCAUAUAU U UUUAAAAA | 870 | UUUUUAAA CUGAUGAGGCCGAAAGGCCGAA AUAUAUGC | 871 |
| 2526 | CAUAUAUU U UUAAAAAU | 872 | AUUUUUAA CUGAUGAGGCCGAAAGGCCGAA AAUAUAUG | 873 |
| 2527 | AUAUAUUU U UAAAAAUC | 874 | GAUUUUUA CUGAUGAGGCCGAAAGGCCGAA AAAUAUAU | 875 |
| 2528 | UAUAUUUU U AAAAAUCA | 876 | UGAUUUUU CUGAUGAGGCCGAAAGGCCGAA AAAAUAUA | 877 |
| 2529 | AUAUUUUU A AAAAUCAG | 878 | CUGAUUUU CUGAUGAGGCCGAAAGGCCGAA AAAAAUAU | 879 |
| 2535 | UUAAAAAU C AGUAAAAG | 880 | CUUUUACU CUGAUGAGGCCGAAAGGCCGAA AUUUUUAA | 881 |
| 2547 | AAAAGCAU U ACUCUAAG | 882 | CUUAGAGU CUGAUGAGGCCGAAAGGCCGAA AUGCUUUU | 883 |
| 2548 | AAAGCAUU A CUCUAAGU | 884 | ACUUAGAG CUGAUGAGGCCGAAAGGCCGAA AAUGCUUU | 885 |
| 2551 | GCAUUACU C UAAGUGUA | 886 | UACACUUA CUGAUGAGGCCGAAAGGCCGAA AGUAAUGC | 887 |
| 2553 | AUUACUCU A AGUGUAGA | 888 | UCUACACU CUGAUGAGGCCGAAAGGCCGAA AGAGUAAU | 889 |
| 2559 | CUAAGUGU A GACUUAAU | 890 | AUUAAGUC CUGAUGAGGCCGAAAGGCCGAA ACACUUAG | 891 |
| 2564 | UGUAGACU U AAUACCAU | 892 | AUGGUAUU CUGAUGAGGCCGAAAGGCCGAA AGUCUACA | 893 |
| 2565 | GUAGACUU A AUACCAUG | 894 | CAUGGUAU CUGAUGAGGCCGAAAGGCCGAA AAGUCUAC | 895 |
| 2568 | GACUUAAU A CCAUGUGA | 896 | UCACAUGG CUGAUGAGGCCGAAAGGCCGAA AUUAAGUC | 897 |
| 2580 | UGUGACAU U UAAUCCAG | 898 | CUGGAUUA CUGAUGAGGCCGAAAGGCCGAA AUGUCACA | 899 |
| 2581 | GUGACAUU U AAUCCAGA | 900 | UCUGGAUU CUGAUGAGGCCGAAAGGCCGAA AAUGUCAC | 901 |
| 2582 | UGACAUUU A AUCCAGAU | 902 | AUCUGGAU CUGAUGAGGCCGAAAGGCCGAA AAAUGUCA | 903 |
| 2585 | CAUUUAAU C CAGAUUGU | 904 | ACAAUCUG CUGAUGAGGCCGAAAGGCCGAA AUUAAAUG | 905 |
| 2591 | AUCCAGAU U GUAAAUGC | 906 | GCAUUUAC CUGAUGAGGCCGAAAGGCCGAA AUCUGGAU | 907 |
| 2601 | UAAAUGCU C AUUUAUGG | 908 | CCAUAAAU CUGAUGAGGCCGAAAGGCC9AA AGCAUUUA | 909 |
| 2604 | AUGCUCAU U UAUGGUUA | 910 | UAACCAUA CUGAUGAGGCCGAAAGGCCGAA AUGAGCAU | 911 |
| 2605 | UGCUCAUU U AUGGUUAA | 912 | UUAACCAU CUGAUGAGGCCGAAAGGCCGAA AAUGAGCA | 913 |
| 2606 | GCUCAUUU A UGGUUAAU | 914 | AUUAACCA CUGAUGAGGCCGAAAGGCCGAA AAAUGAGC | 915 |
| 2612 | UUAUGGUU A AUGACAUU | 916 | AAUGUCAU CUGAUGAGGCCGAAAGGCCGAA AACCAUAA | 917 |
| 2620 | AAUGACAU U GAAGGUAC | 918 | GUACCUUC CUGAUGAGGCCGAAAGGCCGAA AUGUCAUU | 919 |
| 2631 | AGGUACAU U UAUUGUAC | 920 | GUACAAUA CUGAUGAGGCCGAAAGGCCGAA AUGUACCU | 921 |
| 2632 | GGUACAUU U AUUGUACC | 922 | GGUACAAU CUGAUGAGGCCGAAAGGCCGAA AAUGUACC | 923 |
| 2633 | GUACAUUU A UUGUACCA | 924 | UGGUACAA CUGAUGAGGCCGAAAGGCCGAA AAAUGUAC | 925 |
| 2635 | ACAUUUAU U GUACCAAA | 926 | UUUGGUAC CUGAUGAGGCCGAAAGGCCGAA AUAAAUGU | 927 |
| 2648 | CAAACCAU U UUAUGAGU | 928 | ACUCAUAA CUGAUGAGGCCGAAAGGCCGAA AUGGUUUG | 929 |
| 2649 | AAACCAUU U UAUGAGUU | 930 | AACUCAUA CUGAUGAGGCCGAAAGGCCGAA AAUGGUUU | 931 |
| 2650 | AACCAUUU U AUGAGUUU | 932 | AAACUCAU CUGAUGAGGCCGAAAGGCCGAA AAAUGGUU | 933 |
| 2651 | ACCAUUUU A UGAGUUUU | 934 | AAAACUCA CUGAUGAGGCCGAAAGGCCGAA AAAAUGGU | 935 |
| 2658 | UAUGAGUU U UCUGUUAG | 936 | CUAACAGA CUGAUGAGGCCGAAAGGCCGAA AACUCAUA | 937 |
| 2659 | AUGAGUUU U CUGUUAGC | 938 | GCUAACAG CUGAUGAGGCCGAAAGGCCGAA AAACUCAU | 939 |
| 2660 | UGAGUUUU C UGUUAGCU | 940 | AGCUAACA CUGAUGAGGCCGAAAGGCCGAA AAAACUCA | 941 |
| 2665 | UUUCUGUU A GCUUGCUU | 942 | AAGCAAGC CUGAUGAGGCCGAAAGGCCGAA AACAGAAA | 943 |
| 2669 | UGUUAGCU U GCUUUAAA | 944 | UUUAAAGC CUGAUGAGGCCGAAAGGCCGAA AGCUAACA | 945 |
| 2673 | AGCUUGCU U UAAAAAUU | 946 | AAUUUUUA CUGAUGAGGCCGAAAGGCCGAA AGCAAGCU | 947 |
| 2674 | GCUUGCUU U AAAAAUUA | 948 | UAAUUUUU CUGAUGAGGCCGAAAGGCCGAA AAGCAAGC | 949 |

TABLE XV-continued

Human c-myb Hammerhead Ribozyme and Target Sequences
(REVISED)

| nt. | Target Sequence | Seq. ID No. | HH Ribozyme Sequence | Seq. ID No. |
|---|---|---|---|---|
| 2675 | CUUGCUUU A AAAAUUAU | 950 | AUAAUUUU CUGAUGAGGCCGAAAGGCCGAA AAAGCAAG | 951 |
| 2681 | UUAAAAAU U AUUACUGU | 952 | ACAGUAAU CUGAUGAGGCCGAAAGGCCGAA AUUUUUAA | 953 |
| 2682 | UAAAAAUU A UUACUGUA | 954 | UACAGUAA CUGAUGAGGCCGAAAGGCCGAA AAUUUUUA | 955 |
| 2684 | AAAAUUAU U ACUGUAAG | 956 | CUUACAGU CUGAUGAGGCCGAAAGGCCGAA AUAAUUUU | 957 |
| 2685 | AAAUUAUU A CUGUAAGA | 958 | UCUUACAG CUGAUGAGGCCGAAAGGCCGAA AAUAAUUU | 959 |
| 2697 | UAAGAAAU A GUUUUAUA | 960 | UAUAAAAC CUGAUGAGGCCGAAAGGCCGAA AUUUCUUA | 961 |
| 2701 | AAAUAGUU U UAUAAAAA | 962 | UUUUUAUA CUGAUGAGGCCGAAAGGCCGAA AACUAUUU | 963 |
| 2702 | AAUAGUUU U AUAAAAAA | 964 | UUUUUUAU CUGAUGAGGCCGAAAGGCCGAA AAACUAUU | 965 |
| 2703 | AUAGUUUU A UAAAAAAU | 966 | AUUUUUUA CUGAUGAGGCCGAAAGGCCGAA AAAACUAU | 967 |
| 2705 | AGUUUUAU A AAAAAUUA | 968 | UAAUUUUU CUGAUGAGGCCGAAAGGCCGAA AUAAAACU | 969 |
| 2712 | UAAAAAAU U AUAUUUUU | 970 | AAAAAAUAU CUGAUGAGGCCGAAAGGCCGAA AUUUUUUA | 971 |
| 2713 | AAAAAAUU A UAUUUUUA | 972 | UAAAAAUA CUGAUGAGGCCGAAAGGCCGAA AAUUUUUU | 973 |
| 2715 | AAAAUUAU A UUUUUAUU | 974 | AAUAAAAA CUGAUGAGGCCGAAAGGCCGAA AUAAUUUU | 975 |
| 2717 | AAUUAUAU U UUUAUUCA | 976 | UGAAUAAA CUGAUGAGGCCGAAAGGCCGAA AUAUAAUU | 977 |
| 2718 | AUUAUAUU U UUAUUCAG | 978 | CUGAAUAA CUGAUGAGGCCGAAAGGCCGAA AAUAUAAU | 979 |
| 2719 | UUAUAUUU U UAUUCAGU | 980 | ACUGAAUA CUGAUGAGGCCGAAAGGCCGAA AAAUAUAA | 981 |
| 2720 | UAUAUUUU U AUUCAGUA | 982 | UACUGAAU CUGAUGAGGCCGAAAGGCCGAA AAAAUAUA | 983 |
| 2721 | AUAUUUUU A UUCAGUAA | 984 | UUACUGAA CUGAUGAGGCCGAAAGGCCGAA AAAAAUAU | 985 |
| 2723 | AUUUUUAU U CAGUAAUU | 986 | AAUUACUG CUGAUGAGGCCGAAAGGCCGAA AUAAAAAU | 987 |
| 2724 | UUUUUAUU C AGUAAUUU | 988 | AAAUUACU CUGAUGAGGCCGAAAGGCCGAA AAUAAAAA | 989 |
| 2731 | UCAGUAAU U UAAUUUUG | 990 | CAAAAUUA CUGAUGAGGCCGAAAGGCCGAA AUUACUGA | 991 |
| 2732 | CAGUAAUU U AAUUUUGU | 992 | ACAAAAUU CUGAUGAGGCCGAAAGGCCGAA AAUUACUG | 993 |
| 2733 | AGUAAUUU A AUUUUGUA | 994 | UACAAAAU CUGAUGAGGCCGAAAGGCCGAA AAAUUACU | 995 |
| 2736 | AAUUUAAU U UUGUAAAU | 996 | AUUUACAA CUGAUGAGGCCGAAAGGCCGAA AUUAAAUU | 997 |
| 2737 | AUUUAAUU U UGUAAAUG | 998 | CAUUUACA CUGAUGAGGCCGAAAGGCCGAA AAUUAAAU | 999 |
| 2738 | UUUAAUUUU GUAAAUGC | 1000 | GCAUUUAC CUGAUGAGGCCGAAAGGCCGAA AAAUUAAA | 1001 |
| 2762 | AAAACGUU U UUUGCUGC | 1002 | GCAGCAAA CUGAUGAGGCCGAAAGGCCGAA AACGUUUU | 1003 |
| 2763 | AAACGUUU U UUGCUGCU | 1004 | AGCAGCAA CUGAUGAGGCCGAAAGGCCGAA AAACGUUU | 1005 |
| 2764 | AACGUUUU U UGCUGCUA | 1006 | UAGCAGCA CUGAUGAGGCCGAAAGGCCGAA AAAACGUU | 1007 |
| 2765 | ACGUUUUU U GCUGCUAU | 1008 | AUAGCAGC CUGAUGAGGCCGAAAGGCCGAA AAAAACGU | 1009 |
| 2772 | UUGCUGCU A UGGUCUUA | 1010 | UAAGACCA CUGAUGAGGCCGAAAGGCCGAA AGCAGCAA | 1011 |
| 2779 | UAUGGUCU U AGCCUGUA | 1012 | UACAGGCU CUGAUGAGGCCGAAAGGCCGAA AGACCAUA | 1013 |
| 2780 | AUGGUCUU A GCCUGUAG | 1014 | CUACAGGC CUGAUGAGGCCGAAAGGCCGAA AAGACCAU | 1015 |
| 2799 | AUGCUGCU A GUAUCAGA | 1016 | UCUGAUAC CUGAUGAGGCCGAAAGGCCGAA AGCAGCAU | 1017 |
| 2804 | GCUAGUAU C AGAGGGGC | 1018 | GCCCCUCU CUGAUGAGGCCGAAAGGCCGAA AUACUAGC | 1019 |
| 2822 | GUAGAGCU U GGACAGAA | 1020 | UUCUGUCC CUGAUGAGGCCGAAAGGCCGAA AGCUCUAC | 1021 |
| 2843 | AAGAAACU U GGUGUUAG | 1022 | CUAACACC CUGAUGAGGCCGAAAGGCCGAA AGUUUCUU | 1023 |
| 2850 | UUGGUGUU A GGUAAUUG | 1024 | CAAUUACC CUGAUGAGGCCGAAAGGCCGAA AACACCAA | 1025 |
| 2857 | UAGGUAAU U GACUAUGC | 1026 | GCAUAGUC CUGAUGAGGCCGAAAGGCCGAA AUUACCUA | 1027 |
| 2862 | AAUUGACU A UGCACUAG | 1028 | CUAGUGCA CUGAUGAGGCCGAAAGGCCGAA AGUCAAUU | 1029 |
| 2869 | UAUGCACU A GUAUUUCA | 1030 | UGAAAUAC CUGAUGAGGCCGAAAGGCCGAA AGUGCAUA | 1031 |
| 2874 | ACUAGUAU U UCAGACUU | 1032 | AAGUCUGA CUGAUGAGGCCGAAAGGCCGAA AAUACUAGU | 1033 |
| 2875 | CUAGUAUU U CAGACUUU | 1034 | AAAGUCUG CUGAUGAGGCCGAAAGGCCGAA AAUACUAG | 1035 |
| 2876 | UAGUAUUU C AGACUUUU | 1036 | AAAAGUCU CUGAUGAGGCCGAAAGGCCGAA AAAUACUA | 1037 |
| 2882 | UUCAGACU U UUUAAUUU | 1038 | AAAUUAAA CUGAUGAGGCCGAAAGGCCGAA AGUCUGAA | 1039 |
| 2883 | UCAGACUU U UUAAUUUU | 1040 | AAAAUUAA CUGAUGAGGCCGAAAGGCCGAA AAGUCUGA | 1041 |
| 2884 | CAGACUUU U UAAUUUUA | 1042 | UAAAAUUA CUGAUGAGGCCGAAAGGCCGAA AAAGUCUG | 1043 |
| 2885 | AGACUUUU U AAUUUUAU | 1044 | AUAAAAUU CUGAUGAGGCCGAAAGGCCGAA AAAAGUCU | 1045 |
| 2886 | GACUUUUU A AUUUUAUA | 1046 | UAUAAAAU CUGAUGAGGCCGAAAGGCCGAA AAAAAGUC | 1047 |
| 2889 | UUUUUAAU U UUAUAUAU | 1048 | AUAUAUAA CUGAUGAGGCCGAAAGGCCGAA AUUAAAAA | 1049 |
| 2890 | UUUUUAAU U UAUAUAUA | 1050 | UAUAUAUA CUGAUGAGGCCGAAAGGCCGAA AAUUAAAA | 1051 |
| 2891 | UUUUAAUU U AUAUAUAU | 1052 | AUAUAUAU CUGAUGAGGCCGAAAGGCCGAA AAAUUAAA | 1053 |
| 2892 | UUAAUUUU A UAUAUAUA | 1054 | UAUAUAUA CUGAUGAGGCCGAAAGGCCGAA AAAAUUAA | 1055 |
| 2894 | AAUUUUAU A UAUAUAUA | 1056 | UAUAUAUA CUGAUGAGGCCGAAAGGCCGAA AUAAAAUU | 1057 |
| 2896 | UUUUAUAU A UAUAUACA | 1058 | UGUAUAUA CUGAUGAGGCCGAAAGGCCGAA AUAUAAAA | 1059 |
| 2898 | UUAUAUAU A UAUACAUU | 1060 | AAUGUAUA CUGAUGAGGCCGAAAGGCCGAA AUAUAUAA | 1061 |
| 2900 | AUAUAUAU A UACAUUUU | 1062 | AAAAUGUA CUGAUGAGGCCGAAAGGCCGAA AUAUAUAU | 1063 |
| 2902 | AUAUAUAU A CAUUUUUU | 1064 | AAAAAAUG CUGAUGAGGCCGAAAGGCCGAA AUAUAUAU | 1065 |
| 2906 | AUAUACAU U UUUUUCCU | 1066 | GGAAAAAA CUGAUGAGGCCGAAAGGCCGAA AUGUAUAU | 1067 |
| 2907 | UAUACAUU U UUUUCCUU | 1068 | AGGAAAAA CUGAUGAGGCCGAAAGGCCGAA AAUGUAUA | 1069 |
| 2906 | AUACAUUU U UUUCCUUU | 1070 | AAGGAAAA CUGAUGAGGCCGAAAGGCCGAA AAAUGUAU | 1071 |
| 2909 | UACAUUUU U UUCCUUUC | 1072 | GAAGGAAA CUGAUGAGGCCGAAAGGCCGAA AAAAUGUA | 1073 |
| 2910 | ACAUUUUU U UCCUUCU | 1074 | AGAAGGAA CUGAUGAGGCCGAAAGGCCGAA AAAAUGU | 1075 |
| 2911 | CAUUUUUU U CCUUCUG | 1076 | CAGAAGGA CUGAUGAGGCCGAAAGGCCGAA AAAAAAUG | 1077 |
| 2912 | AUUUUUUU U CCUUCUGC | 1078 | GCAGAAGG CUGAUGAGGCCGAAAGGCCGAA AAAAAAU | 1079 |
| 2913 | UUUUUUUU C CUUCUGCA | 1060 | UGCAGAAG CUGAUGAGGCCGAAAGGCCGAA AAAAAAA | 1081 |
| 2916 | UUUUUCCU U CUGCAAUA | 1062 | UAUUGCAG CUGAUGAGGCCGAAAGGCCGAA AGGAAAAA | 1083 |
| 2917 | UUUUCCUU C UGCAAUAC | 1084 | GUAUUGCA CUGAUGAGGCCGAAAGGCCGAA AAGGAAAA | 1085 |
| 2924 | UCUGCAAU A CAUUUGAA | 1086 | UUCAAAUG CUGAUGAGGCCGAAAGGCCGAA AUUGCAGA | 1067 |
| 2926 | CAAUACAU U UGAAAACU | 1088 | AGUUUUCA CUGAUGAGGCCGAAAGGCCGAA AUGUAUUG | 1069 |
| 2929 | AAUACAUU U GAAAACUU | 1090 | AAGUUUUC CUGAUGAGGCCGAAAGGCCGAA AAUGUAUU | 1091 |
| 2937 | UGAAAACU U GUUUGGGA | 1092 | UCCCAAAC CUGAUGAGGCCGAAAGGCCGAA AGUUUUCA | 1093 |
| 2941 | AACUUGUU U GGGAGACU | 1094 | AGUCUCCC CUGAUGAGGCCGAAAGGCCGAA AACAAGUU | 1095 |

TABLE XV-continued

Human c-myb Hammerhead Ribozyme and Target Sequences
(REVISED)

| nt. | Target Sequence | Seq. ID No. | HH Ribozyme Sequence | Seq. ID No. |
|---|---|---|---|---|
| 2950 | GGGAGACU C UGCAUUUU | 1096 | AAAAUGCA CUGAUGAGGCCGAAAGGCCGAA AGUCUCCC | 1097 |
| 2956 | CUCUGCAU U UUUUAUUG | 1098 | CAAUAAAA CUGAUGAGGCCGAAAGGCCGAA AUGCAGAG | 1099 |
| 2957 | UCUGCAUU U UUUAUUGU | 1100 | ACAAUAAA CUGAUGAGGCCGAAAGGCCGAA AAUGCAGA | 1101 |
| 2958 | CUGCAUUU U UUAUUGUG | 1102 | CACAAUAA CUGAUGAGGCCGAAAGGCCGAA AAAUGCAG | 1103 |
| 2959 | UGCAUUUU U UAUUGUGG | 1104 | CCACAAUA CUGAUGAGGCCGAAAGGCCGAA AAAAUGCA | 1105 |
| 2960 | GCAUUUUU U AUUGUGGU | 1106 | ACCACAAU CUGAUGAGGCCGAAAGGCCGAA AAAAAUGC | 1107 |
| 2961 | CAUUUUUU A UUGUGGUU | 1108 | AACCACAA CUGAUGAGGCCGAAAGGCCGAA AAAAAAUG | 1109 |
| 2963 | UUUUUUAU U GUGGUUUU | 1110 | AAAACCAC CUGAUGAGGCCGAAAGGCCGAA AUAAAAAA | 1111 |
| 2970 | UUGUGGUU U UUUUGUUA | 1112 | UAACAAAA CUGAUGAGGCCGAAAGGCCGAA AACCACAA | 1113 |
| 2971 | UGUGGUUU U UUUGUUAU | 1114 | AUAACAAA CUGAUGAGGCCGAAAGGCCGAA AAACCACA | 1115 |
| 2972 | GUGGUUUU U UUGUUAUU | 1116 | AAUAACAA CUGAUGAGGCCGAAAGGCCGAA AAAACCAC | 1117 |
| 2973 | UGGUUUUU U UGUUAUUG | 1118 | CAAUAACA CUGAUGAGGCCGAAAGGCCGAA AAAAACCA | 1119 |
| 2974 | GGUUUUUU U GUUAUUGU | 1120 | ACAAUAAC CUGAUGAGGCCGAAAGGCCGAA AAAAAACC | 1121 |
| 2977 | UUUUUUGU U AUUGUUGG | 1122 | CCAACAAU CUGAUGAGGCCGAAAGGCCGAA ACAAAAAA | 1123 |
| 2978 | UUUUUGUU A UUGUUGGU | 1124 | ACCAACAA CUGAUGAGGCCGAAAGGCCGAA AACAAAAA | 1125 |
| 2980 | UUUGUUAU U GUUGGUUU | 1126 | AAACCAAC CUGAUGAGGCCGAAAGGCCGAA AUAACAAA | 1127 |
| 2986 | UGUUGGUU U AUACAAGC | 1128 | GCUUGUAU CUGAUGAGGCCGAAAGGCCGAA AACCAACA | 1129 |
| 2989 | GUUGGUUU A UACAAGCA | 1130 | UGCUUGUA CUGAUGAGGCCGAAAGGCCGAA AAACCAAC | 1131 |
| 2991 | UGGUUUAU A CAAGCAUG | 1132 | CAUGCUUG CUGAUGAGGCCGAAAGGCCGAA AUAAACCA | 1133 |
| 3009 | GUUGCACU U CUUUUUUG | 1134 | CAAAAAAG CUGAUGAGGCCGAAAGGCCGAA AGUGCAAC | 1135 |
| 3010 | UUGCACUU C UUUUUUGG | 1136 | CCAAAAAA CUGAUGAGGCCGAAAGGCCGAA AAGUGCAA | 1137 |
| 3012 | GCACUUCU U UUUUGGGA | 1138 | UCCCAAAA CUGAUGAGGCCGAAAGGCCGAA AGAAGUGC | 1139 |
| 3013 | CACUUCUU U UUUGGGAG | 1140 | CUCCCAAA CUGAUGAGGCCGAAAGGCCCAA AAGAAGUG | 1141 |
| 3014 | ACUUCUUU U UUGGGAGA | 1142 | UCUCCCAA CUGAUGAGGCCGAAAGGCCGAA AAAGAAGU | 1143 |
| 3015 | CUUCUUUU U UGGGAGAU | 1144 | AUCUCCCA CUGAUGAGGCCGAAAGGCCGAA AAAAGAAG | 1145 |
| 3016 | UUCUUUUU U GGGAGAUG | 1146 | CAUCUCCC CUGAUGAGGCCGAAAGGCCGAA AAAAAGAA | 1147 |
| 3040 | UUGAUGUU C UAUGUUUU | 1146 | AAAACAUA CUGAUGAGGCCGAAAGGCCGAA AACAUCAA | 1149 |
| 3042 | GAUGUUCU A UGUUUUGU | 1150 | ACAAAACA CUGAUGAGGCCGAAAGGCCGAA AGAACAUC | 1151 |
| 3047 | UCUAUGUU U UGUUUUGA | 1152 | UCAAAACA CUGAUGAGGCCGAAAGGCCGAA AACAUAGA | 1153 |
| 3048 | CUAUGUUU U GUUUUGAG | 1154 | CUCAAAAC CUGAUGAGGCCGAAAGGCCGAA AAACAUAG | 1155 |
| 3052 | GUUUUGUU U UGAGUGUA | 1156 | UACACUCA CUGAUGAGGCCGAAAGGCCGAA AACAAAAC | 1157 |
| 3053 | UUUUGUUU U GAGUGUAG | 1158 | CUACACUC CUGAUGAGGCCGAAAGGCCGAA AAACAAAA | 1159 |
| 3072 | UGACUGUU U UAUAAUUU | 1160 | AAAUUAUA CUGAUGAGGCCGAAAGGCCGAA AACAGUCA | 1161 |
| 3073 | GACUGUUU U AUAAUUUG | 1162 | CAAAUUAU CUGAUGAGGCCGAAAGGCCGAA AAACAGUC | 1163 |
| 3074 | ACUGUUUU A UAAUUUGG | 1164 | CCAAAUUA CUGAUGAGGCCGAAAGGCCGAA AAAACAGU | 1165 |
| 3076 | UGUUUUAU A AUUUGGGA | 1166 | UCCCAAAU CUGAUGAGGCCGAAAGGCCGAA AUAAAACA | 1167 |
| 3079 | UUUAUAAU U UGGGAGUU | 1168 | AACUCCCA CUGAUGAGGCCGAAAGGCCGAA AUUAUAAA | 1169 |
| 3080 | UUAUAAUU U GGGAGUUC | 1170 | GAACUCCC CUGAUGAGGCCGAAAGGCCGAA AAUUAUAA | 1171 |
| 3088 | UGGGAGUU C UGCAUUUG | 1172 | CAAAUGCA CUGAUGAGGCCGAAAGGCCGAA AACUCCCA | 1173 |
| 3094 | UUCUGCAU U UGAUCCGC | 1174 | GCGGAUCA CUGAUGAGGCCGAAAGGCCGAA AUGCAGAA | 1175 |
| 3095 | UCUGCAUU U GAUCCGCA | 1176 | UGCaGAUC CUGAUGAGdCCGAAAGGCCGAA AAUGCAGA | 1177 |
| 3099 | CAUUUGAU C CGCAUCCC | 1178 | GGGAUGCG CUGAUGAGGCCGAAAGGCCGAA AUCAAAUG | 1179 |
| 3105 | AUCCGCAU C CCCUGUGG | 1180 | CCACAGGG CUGAUGAGGCCGAAAGGCCGAA AUGCGGAU | 1181 |
| 3116 | CUGUGGUU U CUAAGUGU | 1182 | ACACUUAG CUGAUGAGGCCGAAAGGCCGAA AACCACAG | 1183 |
| 3117 | UGUGGUUU C UAAGUGUA | 1184 | UACACUUA CUGAUGAGGCCGAAAGGCCGAA AAACCACA | 1185 |
| 3119 | UGGUUUCU A AGUGUAUG | 1186 | CAUACACU CUGAUGAGGCCGAAAGGCCGAA AGAAACCA | 1187 |
| 3132 | UAUGGUCU C AGAACUGU | 1188 | ACAGUUCU CUGAUGAGGCCGAAAGGCCGAA AGACCAUA | 1189 |
| 3150 | GCAUGGAU C CUGUGUUU | 1190 | AAACACAG CUGAUGAGGCCGAAAGGCCGAA AUCCAUGC | 1191 |
| 3157 | UCCUGUGU U UGCAACUG | 1192 | CAGUUGCA CUGAUGAGGCCGAAAGGCCGAA ACACAGGA | 1193 |
| 3158 | CCUGUGUU U GCAACUGG | 1194 | CCAGUUGC CUGAUGAGGCCGAAAGGCCGAA AACACAGG | 1195 |
| 3189 | UGGUUGAU A GCCAGUCA | 1196 | UGACUGGC CUGAUGAGGCCGAAAGGCCGAA AUCAACCA | 1197 |
| 3204 | CACUGCCU U AAGAACAU | 1198 | AUGUUCUU CUGAUGAGGCCGAAAGGCCGAA AGGCAGUG | 1199 |
| 3205 | ACUGCCUU A AGAACAUU | 1200 | AAUGUUCU CUGAUGAGGCCGAAAGGCCGAA AAGGCAGU | 1201 |
| 3213 | AAGAACAU U UGAUGCAA | 1202 | UUGCAUCA CUGAUGAGGCCGAAAGGCCGAA AUGUUCUU | 1203 |
| 3214 | AGAACAUU U GAUGCAAG | 1204 | CUUGCAUC CUGAUGAGGCCGAAAGGCCGAA AAUGUUCU | 1205 |
| 3240 | ACUGAACU U UGAGAUA | 1206 | UAUCUCAA CUGAUGAGGCCGAAAGGCCGAA AGUUCAGU | 1207 |
| 3241 | CUGAACUU U UGAGAUAU | 1206 | AUAUCUCA CUGAUGAGGCCGAAAGGCCGAA AAGUUCAG | 1209 |
| 3242 | UGAACUUU U GAGAUAUG | 1210 | CAUAUCUC CUGAUGAGGCCGAAAGGCCGAA AAAGUUCA | 1211 |
| 3248 | UUUGAGAU A UGACGGUG | 1212 | CACCGUCA CUGAUGAGGCCGAAAGGCCGAA AUCUCAAA | 1213 |
| 3261 | GGUGACU U ACUGCCUU | 1214 | AAGGCAGU CUGAUGAGGCCGAAAGGCCGAA AGUACACC | 1215 |
| 3262 | GUGUACUU A CUGCCUUG | 1216 | CAAGGCAG CUGAUGAGGCCGAAAGGCCGAA AAGUACAC | 1217 |
| 3269 | UACUGCCU U GUAGCAAA | 1216 | UUUGCUAC CUGAUGAGGCCGAAAGGCCGAA AGGCAGUA | 1219 |
| 3280 | AGCAAAAU A AAGAUGUG | 1220 | CACAUCUU CUGAUGAGGCCGAAAGGCCGAA AUUUUGCU | 1221 |
| 3293 | UGUGCCCU U AUUUUACC | 1222 | GGUAAAAU CUGAUGAGGCCGAAAGGCCGAA AGGGCACA | 1223 |
| 3294 | GUGCCCUU A UUUUACCU | 1224 | AGGUAAAA CUGAUGAGGCCGAAAGGCCGAA AAGGGCAC | 1225 |

TABLE XVI

Mouse c-myb Hammerhead Ribozyme and Target Sequences
(REVISED)

| nt | HH Ribozyme Sequence | Seq ID No. | Target | Seq ID No. |
|---|---|---|---|---|
| 10 | UCCGCCAA CUGAUGAGGCCGAAAGGCCGAA AGCCCCGG | 1226 | CCGGGGCUC UUGGCGGA | 1227 |
| 12 | GCUCCGCC CUGAUGAGGCCGAAAGGCCGAA AGAGCCCC | 1228 | GGGGCUCUU GGCGGAGC | 1229 |
| 33 | GCCAUGGC CUGAUGAGGCCGAAAGGCCGAA AGGCGGGC | 1230 | GCCCGCCUC GCCAUGGC | 1231 |
| 63 | CUACUGUA CUGAUGAGGCCGAAAGGCCGAA AUGCUGUG | 1232 | CACAGCAUC UACAGUAG | 1233 |
| 65 | CGCUACUG CUGAUGAGGCCGAAAGGCCGAA AGAUGCUG | 1234 | CAGCAUCUA CAGUAGCG | 1235 |
| 70 | UUCAUCGC CUGAUGAGGCCGAAAGGCCGAA ACUGUAGA | 1236 | UCUACAGUA GCGAUGAA | 1237 |
| 93 | CACAUCUC CUUAUGAGGCCGAAAGGCCGAA AUGUCUUC | 1238 | GAAGACAUU GAGAUGUG | 1239 |
| 113 | GCCCAUCG CUGAUGAGGCCGAAAGGCCGAA AGUCAUGG | 1240 | CCAUGACUA CGAUGGGC | 1241 |
| 134 | CCUUUCCA CUGAUGAGGCCGAAAGGCCGAA AUUUGGGC | 1242 | GCCCAAAUC UGGAAAGC | 1243 |
| 145 | CCCCAAGU CUGAUGAGGCCGAAAGGCCGAA ACGCUUUC | 1244 | GAAAGCGUC ACUUGGGG | 1245 |
| 149 | UUUUCCCC CUGAUGAGGCCGAAAGGCCGAA AGUGACGC | 1246 | GCGUCACUU GGGGAAAA | 1247 |
| 160 | UGUCCACC CUGAUGAGGCCGAAAGGCCGAA AGUUUUCC | 1248 | GGAAAACUA GGUGGACA | 1249 |
| 231 | UUGGCAAU CUGAUGAGGCCGAAAGGCCGAA ACUUUCCA | 1250 | UGGAAAGUC AUUGCCAA | 1251 |
| 234 | UAAUUGGC CUGAUGAGGCCGAAAGGCCGAA AUGACUUU | 1252 | AAAGUCAUU GCCAAUUA | 1253 |
| 241 | GGGCAGAU CUGAUGAGGCCGAAAGGCCGAA AUUGGCAA | 1254 | UUGCCAAUU AUCUGCCC | 1255 |
| 242 | UGGGCAGA CUGAUGAGGCCGAAAGGCCGAA AAUUGGCA | 1256 | UGCCAAUUA UCUGCCCA | 1257 |
| 244 | GUUGGGCA CUCAUGAGGCCGAAAGGCCGAA AUAAUUGG | 1258 | CCAAUUAUC UGCCCAAC | 1259 |
| 264 | UGGCACUG CUGAUCAGCCCGAAAGGCCGAA ACAUCUGU | 1260 | ACAGAUGUA CAGUGCCA | 1261 |
| 306 | CCUUUGAU CUGAUGAGGCCGAAAGGCCGAA AGUUCAGG | 1262 | CCUGAACUC AUCAAAGG | 1263 |
| 309 | GGACCUUU CUGAUGAGGCCGAAAGGCCGAA AUGAGUUC | 1264 | GAACUCAUC AAAGGUCC | 1265 |
| 316 | GGUCCAGG CUGAUGAGGCCGAAAGGCCGAA ACCUUUGA | 1266 | UCAAAGGUC CCUGGACC | 1267 |
| 337 | CACUCUCU CUGAUGAGGCCGAAAGGCCGAA AUCUUCUU | 1268 | AAGAAGAUC AGAGAGUC | 1269 |
| 345 | AGCUUUAU CUGAUGAGGCCGAAAGGCCGAA ACUCUCUG | 1270 | CAGAGAGUC AUAAAGCU | 1271 |
| 348 | ACAAGCUU CUGAUGAGGCCGAAAGGCCGAA AUGACUCU | 1272 | AGAGUCAUA AAGCUUGU | 1273 |
| 354 | UUCUGGAC CUGAUGAGGCCGAAAGGCCGAA AGCUUUAU | 1274 | AUAAAGCUU GUCCAGAA | 1275 |
| 357 | UAUUUCUG CUGAUGAGGCCGAAAGGCCGAA ACAAGCUU | 1276 | AAGCUUGUC CAGAAAUA | 1277 |
| 365 | UCGGACCA CUGAUGAGGCCGAAAGGCCGAA AUUUCUGG | 1278 | CCAGAAAUA UGGUCCGA | 1279 |
| 370 | ACGCUUCG CUGAUGAGGCCGAAAGGCCGAA ACCAUAUU | 1280 | AAUAUGGUC CGAAGCGU | 1281 |
| 379 | AACAGACC CUGAUGAGGCCGAAAGGCCGAA ACGCUUCG | 1282 | CGAAGCGUU GGUCUGUU | 1283 |
| 383 | CAAUAACA CUUAUGAGGCCGAAAGGCCGAA ACCAACGC | 1264 | GCGUUGGUC UGUUAUUG | 1285 |
| 387 | UUGGCAAU CUGAUGAGGCCGAAAGGCCGAA ACAGACCA | 1286 | UGGUCUGUU AUUGCCAA | 1287 |
| 388 | CUUGGCAA CUGAUGAGGCCGAAAGGCCGAA AACAGACC | 1288 | GGUCUGUA UUGCCAAG | 1289 |
| 390 | UGCUUGGC CUGAUGAGGCCGAAAGGCCGAA AUAACAGA | 1290 | UCUGUUAUU GCCAAGCA | 1291 |
| 401 | UCCCUUUU CUGAUGAGGCCGAAAGGCCGAA AGUGCUUG | 1292 | CAAGCACUU AAAAGGGA | 1293 |
| 402 | CUCCCUUU CUGAUGAGGCCGAAAGGCCGAA AAGUGCUU | 1294 | AAGCACUUA AAAGGGAG | 1295 |
| 414 | UGCUUUCC CUGAUGAGGCCGAAAGGCCGAA AUUCUCCC | 1296 | GGGAGAAUU GGAAAGCA | 1297 |
| 427 | CCUCUCCC CUGAUGAGGCCGAAAGGCCGAA ACACUGCU | 1298 | AGCAGUGUC GGGAGAGG | 1299 |
| 448 | UGGAUUCA CUGAUGAGGCCGAAAGGCCGAA AUGGUUGU | 1300 | ACAACCAUU UGAAUCCA | 1301 |
| 449 | CUGGAUUC CUGAUGAGGCCGAAAGGCCGAA AAUGGUUG | 1302 | CAACCAUUU GAAUCCAG | 1303 |
| 454 | AACUUCUG CUGAUGAGGCCGAAAGGCCGAA AUUCAAAU | 1304 | AUUUGAAUC CAGAAGUU | 1305 |
| 462 | GUUUUCUU CUGAUGAGGCCGAAAGGCCGAA ACUUCUGG | 1306 | CCAGAAGUU AAGAAAAC | 1307 |
| 463 | GGUUUUCU CUGAUGAGGCCGAAAGGCCGAA AACUUCUG | 1308 | CAGAAGUUA AGAAAACC | 1309 |
| 473 | CUCUCCAG CUGAUGAGGCCGAAAGGCCGAA AGGUUUUC | 1310 | GAAAACCUC CUGGACAG | 1311 |
| 498 | UGGUAAAU CUGAUGAGGCCGAAAGGCCGAA AUUCUGUC | 1312 | GACAGAAUC AUUUACCA | 1313 |
| 501 | GCCUGGUA CUGAUGAGGCCGAAAGGCCGAA AUGAUUCU | 1314 | AGAAUCAUU UACCAGGC | 1315 |
| 502 | UGCCUGGU CUGAUGAGGCCGAAAGGCCGAA AAUGAUUC | 1316 | GAAUCAUUU ACCAGGCA | 1317 |
| 503 | GUGCCUGG CUGAUGAGGCCGAAAGGCCGAA AAAUGAUU | 1318 | AAUCAUUUA CCAGGCAC | 1319 |
| 520 | GUUCCCCA CUGAUGAGGCCCAAAGGCCGAA ACGCUUGU | 1320 | ACAAGCGUC UGGGGAAC | 1321 |
| 543 | AGCUUUGC CUGAUGAGGCCGAAAGGCCGAA AUCUCUGC | 1322 | GCAGAGAUC GCAAAGCU | 1323 |
| 571 | GAUAGCAU CUGAUGAGGCCGAAAGGCCGAA AUCAGUCC | 1324 | GGACUGAUA AUGCUAUC | 1325 |
| 577 | GUUCUUGA CUGAUGAGGCCGAAAGGCCGAA AGCAUUAU | 1326 | AUAAUGCUA UCAAGAAC | 1327 |
| 579 | UGGUUCUU CUGAUGAGGCCGAAAGGCCGAA AUAGCAUU | 1328 | AAUGCUAUC AAGAACCA | 1329 |
| 595 | CAUGGUGG CUGAUGAGGCCGAAAGGCCGAA AUUCCAGU | 1330 | ACUGGAAUU CCACCAUG | 1331 |
| 596 | GCAUGGUG CUGAUGAGGCCGAAAGGCCGAA AAUUCCAG | 1332 | CUGGAAUUC CACCAUGC | 1333 |
| 607 | CACCUUGC CUGAUGAGGCCGAAAGGCCGAA ACGCAUGG | 1334 | CCAUGCGUC GCAAGGUG | 1335 |
| 629 | UCUGCAGG CUGAUGAGGCCGAAAGGCCGAAAGCCUUCC | 1336 | GGAAGGCUA CCUGCAGA | 1337 |
| 643 | GGCUUUGG CUGAUGAGGCCGAAAGGCCGAA AGGCUUCU | 1338 | AGAAGCCUU CCAAAGCC | 1339 |
| 644 | UGGCUUUG CUGAUGAGGCCGAAAGGCCGAA AAGGCUUC | 1340 | GAAGCCUUC CAAAGCCA | 1341 |
| 677 | UCUUCUGG CUGAUGAGGCCGAAAGGCCGAA AGCUCGUG | 1342 | CACGAGCUU CCAGAAGA | 1343 |
| 678 | UUCUUCUG CUGAUGAGGCCGAAAGGCCGAA AAGCUCGU | 1344 | ACGAGCUUC CAGAAGAA | 1345 |
| 691 | CAUCAAAU CUGAUGAGGCCGAAAGGCCGAA AUUGUUCU | 1346 | AGAACAAUC AUUUGAUG | 1347 |
| 694 | CCCCAUCA CUGAUGAGGCCGAAAGGCCGAA AUGAUUGU | 1348 | ACAAUCAUU UGAUGGGG | 1349 |
| 695 | ACCCCAUC CUGAUGAGGCCGAAAGGCCGAA AAUGAUUG | 1350 | CAAUCAUUU GAUGGGGU | 1351 |
| 704 | CAUGCCCA CUGAUGAGGCCGAAAGGCCGAA ACCCCAUC | 1352 | GAUGGGGUU GGGCAUG | 1353 |
| 705 | GCAUGCCC CUGAUGAGGCCGAAAGGCCGAA AACCCCAU | 1354 | AUGGGGUUU GGGCAUGC | 1355 |
| 716 | AUGGAGGU CUGAUGAGGCCGAAAGGCCGAA AGGCAUGC | 1356 | GCAUGCCUC ACCUCCAU | 1357 |
| 721 | CUGAGAUG CUGAUGAGGCCGAAAGGCCGAA AGGUGAGG | 1358 | CCUCACCUC CAUCUCAG | 1359 |
| 725 | AGAGCUGA CUGAUGAGGCCGAAAGGCCGAA AUGGAGGU | 1360 | ACCUCCAUC UCAGCUCU | 1361 |
| 727 | AGAGAGCU CUGAUGAGGCCGAAAGGCCGAA AGAUGGAG | 1362 | CUCCAUCUC AGCUCUCU | 1363 |
| 732 | CUUGGAGA CUGAUGAGGCCGAAAGGCCGAA AGCUGAGA | 1364 | UCUCAGCUC UCUCCAAG | 1365 |
| 734 | CACUGGAA CUGAUGAGGCCGAAAGGCCGAA AGAGCUGA | 1366 | UCAGCUCUC UCCAAGUG | 1367 |
| 736 | GCCACUUG CUGAUGAGGCCGAAAGGCCGAA AGAGAGCU | 1368 | AGCUCUCUC CAAGUGGC | 1369 |
| 749 | UGACGGAG CUGAUGAGGCCGAAAGGCCGAA ACUGGCCA | 1370 | UGGCCAGUC CUCCGUCA | 1371 |

TABLE XVI-continued

Mouse c-myb Hammerhead Ribozyme and Target Sequences
(REVISED)

| nt | HH Ribozyme Sequence | Seq ID No. | Target | Seq ID No. |
|---|---|---|---|---|
| 752 | UGUUGACG CUGAUGAGGCCGAAAGGCCGAA AGGACUGG | 1372 | CCAGUCCUC CGUCAACA | 1373 |
| 756 | UCGCUGUU CUGAUGAGGCCGAAAGGCCGAA ACGGAGGA | 1374 | UCCUCCGUC AACAGCGA | 1375 |
| 767 | AAUAGGGA CUGAUGAGGCCGAAAGGCCGAA AUUCGCUG | 1376 | CAGCGAAUA UCCCUAUU | 1377 |
| 769 | GUAAUAGG CUGAUGAGGCCGAAAGGCCGAA AUAUUCGC | 1378 | GCGAAUAUC CCUAUUAC | 1379 |
| 773 | UGUGGUAA CUGAUGAGGCCGAAAGGCCGAA AGGGAUAU | 1380 | AUAUCCCUA UUACCACA | 1381 |
| 775 | GAUGUGGU CUGAUGAGGCCGAAAGGCCGAA AUAGGGAU | 1382 | AUCCCUAUU ACCACAUC | 1383 |
| 776 | CGAUGUGG CUGAUGAGGCCGAAAGGCCGAA AAUAGGGA | 1384 | UCCCUAUUA CCACAUCG | 1385 |
| 783 | GCUUCGGC CUGAUGAGGCCGAAAGGCCGAA AUGUGGUA | 1386 | UACCACAUC GCCGAAGC | 1387 |
| 801 | GGACUGGA CUGAUGAGGCCGAAAGGCCGAA AUGUUUUG | 1388 | CAAAACAUC UCCAGUCA | 1389 |
| 803 | CGUGACUG CUGAUGAGGCCGAAAGGCCGAA AGAUGUUU | 1390 | AAACAUCUC CAGUCACG | 1391 |
| 808 | GGGAACGU CUGAUGAGGCCGAAAGGCCGAA ACUGGAGA | 1392 | UCUCCAGUC ACGUUCCC | 1393 |
| 813 | GGAUAGGG CUGAUGAGGCCGAAAGGCCGAA ACGUGACU | 1394 | AGUCACGUU CCCUAUCC | 1395 |
| 814 | AGGAUAGG CUGAUGAGGCCGAAAGGCCGAA AACGUGAC | 1396 | GUCACGUUC CCUAUCCU | 1397 |
| 818 | CGACAGGA CUGAUGAGGCCGAAAGGCCGAA AGGGAACG | 1398 | CGUUCCCUA UCCUGUCG | 1399 |
| 820 | UGCGACAG CUGAUGAGGCCGAAAGGCCGAA AUAGGGAA | 1400 | UUCCCUAUC CUGUCGCA | 1401 |
| 825 | UGCAAUGC CUGAUGAGGCCGAAAGGCCGAA ACAGGAUA | 1402 | UAUCCUGUC GCAUUGCA | 1403 |
| 830 | UAACAUGC CUGAUGAGGCCGAAAGGCCGAA AUGCGACA | 1404 | UGUCGCAUU GCAUGUUA | 1405 |
| 837 | ACUAUAUU CUGAUGAGGCCGAAAGGCCGAA ACAUGCAA | 1406 | UUGCAUGUU AAUAUAGU | 1407 |
| 838 | GACUAUAU CUGAUGAGGCCGAAAGGCCGAA AACAUGCA | 1408 | UGCAUGUUA AUAUAGUC | 1409 |
| 841 | GUUGACUA CUGAUGAGGCCGAAAGGCCGAA AUUAACAU | 1410 | AUGUUAAUA UAGUCAAC | 1411 |
| 843 | ACGUUGAC CUGAUGAGGCCGAAAGGCCGAA AUAUUAAC | 1412 | GUUAAUAUA GUCAACGU | 1413 |
| 846 | GGGACGUU CUGAUGAGGCCGAAAGGCCGAA ACUAUAUU | 1414 | AAUAUAGUC AACGUCCC | 1415 |
| 852 | GGCUGAGG CUGAUGAGGCCGAAAGGCCGAA ACGUUGAC | 1416 | GUCAACGUC CCUCAGCC | 1417 |
| 856 | AGCCGGCU CUGAUGAGGCCGAAAGGCCGAA AGGGACGU | 1418 | ACGUCCCUC AGCCGGCU | 1419 |
| 876 | UGUCUCUG CUGAUGAGGCCGAAAGGCCGAA AUGGCUGC | 1420 | GCAGCCAUC CAGAGACA | 1421 |
| 887 | CGUCGUUA CUGAUGAGGCCGAAAGGCCGAA AGUGCUC | 1422 | GAGACACUA UAACGACG | 1423 |
| 889 | UUCGUCGU CUGAUGAGGCCGAAAGGCCGAA AUAGUGUC | 1424 | GACACUAUA ACGACGAA | 1425 |
| 921 | AGCUCCUU CUGAUGAGGCCGAAAGGCCGAA AUUCGCUU | 1426 | AAGCGAAUA AAGGAGCU | 1427 |
| 935 | UCAGGAGC CUGAUGAGGCCGAAAGGCCGAA ACUCCAGC | 1428 | GCUGGAGUU GCUCCUGA | 1429 |
| 939 | GACAUCAG CUGAUGAGGCCGAAAGGCCGAA AGCAACUC | 1430 | GAGUUGCUC CUGAUGUC | 1431 |
| 947 | UCUCUGUU CUGAUGAGGCCGAAAGGCCGAA ACAUCAGG | 1432 | CCUGAUGUC AACAGAGA | 1433 |
| 980 | GUGUUGGU CUGAUGAGGCCGAAAGGCCGAA AUGCCUGC | 1434 | GCAGGCAUU ACCAACAC | 1435 |
| 981 | UGUGUUGG CUGAUGAGGCCGAAAGGCCGAA AAUGCCUG | 1436 | CAGGCAUUA CCAACACA | 1437 |
| 1000 | GUAGCUGC CUGAUGAGGCCGAAAGGCCGAA AGUGUGGU | 1438 | ACCACACUU GCAGCUAC | 1439 |
| 1007 | ACCCGGGG CUGAUGAGGCCGAAAGGCCGAA AGCUGCAA | 1440 | UUGCAGCUA CCCCGGGU | 1441 |
| 1028 | CCACAAUG CUGAUGAGGCCGAAAGGCCGAA A9GUGCUG | 1442 | CAGCACCUC CAUUGUGG | 1443 |
| 1032 | UGGUCCAC CUGAUGAGGCCGAAAGGCCGAA AUGGAGGU | 1444 | ACCUCCAUU GUGGACCA | 1445 |
| 1051 | AUCCCCAU CUGAUGAGGCCGAAAGGCCGAA AGGUCUGG | 1446 | CCAGACCUC AUGGGGAU | 1447 |
| 1060 | AGGUGCAC CUGAUGAGGCCGAAAGGCCGAA AUCCCCAU | 1448 | AUGGGGAUA GUGCACCU | 1449 |
| 1071 | AAACAGGA CUGAUGAGGCCGAAAGGCCGAA ACAGGUGC | 1450 | GCACCUGUU UCCUGUUU | 1451 |
| 1072 | CAAACAGG CUGAUGAGGCCGAAAGGCCGAA AACAGGUG | 1452 | CACCUGUUU CCUGUUUG | 1453 |
| 1073 | CCAAACAG CUGAUGAGGCCGAAAGGCCGAA AAACAGGU | 1454 | ACCUGUUUC CUGUUUGG | 1455 |
| 1078 | UUCUCCCA CUGAUGAGGCCGAAAGGCCGAA ACAGGAAA | 1456 | UUUCCUGUU UGGGAGAA | 1457 |
| 1079 | GUUCUCCC CUGAUGAGGCCGAAAGGCCGAA AACAGGAA | 1458 | UUCCUGUUU GGGAGAAC | 1459 |
| 1103 | CAGGCAGA CUGAUGAGGCCGAAAGGCCGAA AUGGGGUG | 1460 | CACCCCAUC UCUGCCUG | 1461 |
| 1105 | GUCAGGCA CUGAUGAGGCCGAAAGGCCGAA AGAUGGGG | 1462 | CCCCAUCUC UGCCUGCA | 1463 |
| 1117 | GGAGCCGG CUGAUGAGGCCGAAAGGCCGAA AUCUGCAG | 1464 | CUGCAGAUC CCGGCUCC | 1465 |
| 1124 | CAaGUAGG CUGAUGAGGCCGAAAGGCCGAA AGCCGGGA | 1466 | UCCCGGCUC CUACCUG | 1467 |
| 1128 | UCUUCAGG CUGAUGAGGCCGAAAGGCCGAA AGGGAGCC | 1468 | AGCUCCCUA CCUGAAGA | 1469 |
| 1145 | UUGCUGGU CUGAUGAGGCCGAAAGGCCGAA AGGCACUU | 1470 | AAGUGCCUC ACCAGCAA | 1471 |
| 1164 | UGGUGGAC CUGAUGAGGCCGAAAGGCCGAA AUCAUGCA | 1472 | UGCAUGAUC GUCCACCA | 1473 |
| 1167 | CCCUGGUG CUGAUGAGGCCGAAAGGCCGAA ACGAUCAU | 1474 | AUGAUCGUC CACCAGGG | 1475 |
| 1182 | UUGUCCAG CUGAUGAGGCCGAAAGGCCGAA AUGGUGCC | 1476 | GGCACCAUU CUGGACAA | 1477 |
| 1183 | AUUGUCCA CUGAUAAGGCCGAAAGGCCGAA AAUGGUGC | 1478 | GCACCAUUC UGGACAAU | 1479 |
| 1194 | AGGUUCUU CUGAUGAGGCCGAAAGGCCGAA ACAUUGUC | 1480 | GACAAUGUU AAGAACCU | 1481 |
| 1195 | GAGAUUCU CUGAUGAGGCCGAAAGGCCGAA AACAUUGU | 1482 | ACAAUGUUA AGAACCUC | 1483 |
| 1203 | AAUUCUAA CUGAUGAGGCCGAAAGGCCGAA AGGUUCUU | 1484 | AAGAACCUC UUAGAAUU | 1485 |
| 1205 | CAAAUUCU CUGAUGAGGCCGAAAGGCCGAA AGAGGUUC | 1486 | GAACCUCUU AGAAUUUG | 1487 |
| 1206 | GCAAAUUC CUGAUGAGGCCGAAAGGCCGAA AAGAGGUU | 1488 | AACCUCUUA GAAUUUGC | 1489 |
| 1211 | UUUCUGCA CUGAUGAGGCCGAAAGGCCGAA AUUCUAAG | 1490 | CUUAGAAUU UGCAGAAA | 1491 |
| 1212 | GUUUCUGC CUGAUGAGGCCGAAAGGCCGAA AAUUCUAA | 1492 | UUAGAAUUU GCAGAAAC | 1493 |
| 1224 | AUAAACUG CUGAUGAGGCCGAAAGGCCGAA AGUGUUUC | 1494 | GAAACACUC AGUUUAUU | 1495 |
| 1229 | AAUCUAUA CUGAUGAGGCCGAAAGGCCGAA ACUGGAGU | 1496 | ACUCCAGUU UAUAGAUU | 1497 |
| 1230 | GAAUCUAU CUGAUGAGGCCGAAAGGCCGAA AACUGGAG | 1498 | CUCCAGUUU AUAGAUUC | 1499 |
| 1231 | AGAAUCUA CUGAUGAGGCCGAAAGGCCGAA AAACUGGA | 1500 | UCCAGUUUA UAGAUUCU | 1501 |
| 1233 | AAAGAAUC CUGAUGAGGCCGAAAGGCCGAA AUAAACUG | 1502 | CAGUUUAUA GAUUCUUU | 1503 |
| 1237 | CAAGAAAG CUGAUGAGGCCGAAAGGCCGAA AUCUAUAA | 1504 | UUAUAGAUU CUUCUUG | 1505 |
| 1238 | UCAAGAAA CUGAUGAGGCCGAAAGGCCGAA AAUCUAUA | 1506 | UAUAGAUUC UUUCUUGA | 1507 |
| 1240 | GUUCAAGA CUGAUGAGGCCGAAAGGCCGAA AGAAUCUA | 1508 | UAGAUUCUU UCUUGAAC | 1509 |
| 1241 | UGUUCAAG CUGAUGAGGCCGAAAGGCCGAA AAGAAUCU | 1510 | AGAUUCUUU CUUGAACA | 1511 |
| 1242 | GUGUUCAA CUGAUGAGGCCGAAAGGCCGAA AAAGAAUC | 1512 | GAUUCUUUC UUGAACAC | 1513 |
| 1244 | AAGUGUUC CUGAUGAGGCCGAAAGGCCGAA AGAAAGAA | 1514 | UUCUUUCU GAACACUU | 1515 |
| 1252 | GUUGCUGG CUGAUGAGGCCGAAAGGCCGAA AGUGUUCA | 1516 | UGAACACUU CCAGCAAC | 1517 |

TABLE XVI-continued

Mouse c-myb Hammerhead Ribozyme and Target Sequences
(REVISED)

| nt | HH Ribozyme Sequence | Seq ID No. | Target | Seq ID No. |
|---|---|---|---|---|
| 1253 | GGUUGCUG CUGAUGAGGCCGAAAGGCCGAA AAGUGUUC | 1518 | GAACACUUC CAGCAACC | 1519 |
| 1271 | CUAAGCCC CUGAUGAGGCCGAAAGGCCGAA AGUUUUCA | 1520 | UGAAAACUC GGGCUUAG | 1521 |
| 1277 | GUGCAUCU CUGAUGAGGCCGAAAGGCCGAA AGCCCGAG | 1522 | CUCGGGCUU AGAUGCAC | 1523 |
| 1278 | GGUGCAUC CUGAUGAGGCCGAAAGGCCGAA AAGCCCGA | 1524 | UCGGGCUUA GAUGCACC | 1525 |
| 1288 | GGGUAAGG CUGAUGAGGCCGAAAGGCCGAA AGGUGCAU | 1526 | AUGCACCUA CCUUACCC | 1527 |
| 1292 | UGGAGGGU CUGAUGAGGCCGAAAGGCCGAA AGGUAGGU | 1528 | ACCUACCUU ACCCUCCA | 1529 |
| 1293 | GUGGAGGG CUGAUGAGGCCGAAAGGCCGAA AAGAUAGG | 1530 | CCUACCUUA CCCUCCAC | 1531 |
| 1298 | GAGGAGUG CUGAUGAGGCCGAAAGGCCGAA AGGGUAAG | 1532 | CUUACCCUC CACUCCUC | 1533 |
| 1303 | AAUGAGAG CUGAUGAGGCCGAAAGGCCGAA AGGGUAGG | 1534 | CCUCCACUC CUCUCAUU | 1535 |
| 1306 | ACCAAUGA CUGAUGAGGCCGAAAGGCCGAA AGGAGUGG | 1536 | CCACUCCUC UCAUUGGU | 1537 |
| 1308 | UGACCAAU CUGAUGAGGCCGAAAGGCCGAA AGAGGAGU | 1538 | ACUCCUCUC AUUGGUCA | 1539 |
| 1311 | UUGUGACC CUGAUGAGGCCGAAAGGCCGAA AUGAGAGG | 1540 | CCUCUCAUU GGUCACAA | 1541 |
| 1315 | CAGUUUGU CUGAUGAGGCCGAAAGGCCGAA ACCAAUGA | 1542 | UCAUUGGUC ACAAACUG | 1543 |
| 1333 | CUGGUCUC CUGAUGAGGCCGAAAGGCCGAA ACAUGGUG | 1544 | CACCAUGUC GAGACCAG | 1545 |
| 1366 | AAAGAUGG CUGAUGAGGCCGAAAGGCCGAA AUUUUCCU | 1546 | AGGAAAAUU CCAUCUUU | 1547 |
| 1367 | UAAAGAUG CUGAUGAGGCCGAAAGGCCGAA AAUUUUCC | 1548 | GGAAAAUUC CAUCUUUA | 1549 |
| 1371 | GUUCUAAA CUGAUGAGGCCGAAAGGCCGAA AUGGAAUU | 1550 | AAUUCCAUC UUUAGAAC | 1551 |
| 1373 | GAGUUCUA CUGAUGAGGCCGAAAGGCCGAA AGAUGGAA | 1552 | UUCCAUCUU UAGAACUC | 1553 |
| 1374 | GGAGUUCU CUGAUGAGGCCGAAAG0CCGAA AAGAUGGA | 1554 | UCCAUCUUU AGAACUCC | 1555 |
| 1375 | UGGAGUUC CUGAUGAGGCCGAAAGGCCGAA AAAGAUGG | 1556 | CCAUCUUUA GAACUCCA | 1557 |
| 1361 | GAUAGCUG CUGAUGAGGCCGAAAGGCCGAA AGUUCUAA | 1556 | UUAGAACUC CAGCUAUC | 1559 |
| 1387 | CCUUUUGA CUGAUGAGGCCGAAAGGCCGAA AGCUGGAG | 1560 | CUCCAGCUA UCAAAAGG | 1561 |
| 1389 | GACCUUUU CUGAUGAGGCCGAAAGGCCGAA AUAGCUGG | 1562 | CCAGCUAUC AAAAGGUC | 1563 |
| 1397 | CGAGGAUU CUGAUGAGGCCGAAAGGCCGAA ACCUUUUG | 1564 | CAAAAGGUC AAUCCUCG | 1565 |
| 1401 | CUUUCGAG CUGAUGAGGCCGAAAGGCCGAA AUUGACCU | 1566 | AGGUCAAUC CUCGAAAG | 1567 |
| 1404 | GAGCUUUC CUGAUGAGGCCGAAAGGCCGAA AUUGACCU | 1566 | UCAAUCCUC GAAAGCUC | 1569 |
| 1412 | UUCGAGGA CUGAUGAGGCCGAAAGGCCGAA AGCUUUCG | 1570 | CGAAAGCUC UCCUCGAA | 1571 |
| 1414 | AGUUCGAG CUGAUGAGGCCGAAAGGCCGAA AGAGCUUU | 1572 | AAAGCUCUC CUCGAACU | 1573 |
| 1417 | GGGAGUUC CUGAUGAGGCCGAAAGGCCGAA AGGAGAGC | 1574 | GCUCUCCUC GAACUCCC | 1575 |
| 1423 | UGGUGUGG CUGAUGAGGCCGAAAGGCCGAA AGUUCGAG | 1576 | CUCGAACUC CCACACCA | 1577 |
| 1433 | CAUGUUUG CUGAUGAGGCCGAAAGGCCGAA AUGGUGUG | 1578 | CACACCAUU CAAACAUG | 1579 |
| 1434 | GCAUGUUU CUGAUGAGGCCGAAAGGCCGAA AAUGGUGU | 1560 | ACACCAUUC AAACAUGC | 1581 |
| 1446 | UGAGCUGC CUGAUGAGGCCGAAAGGCCGAA AGGGCAUG | 1582 | CAUGCCCUU GCAGCUCA | 1583 |
| 1453 | AAUUUCUU CUGAUGAGGCCGAAAGGCCGAA AGCUGCAA | 1584 | UUGCAGCUC AAGAAAUU | 1585 |
| 1461 | CCGUAUUU CUGAUGAGGCCGAAAGGCCGAA AUUUCUUG | 1586 | CAAGAAAUU AAAUACGG | 1567 |
| 1462 | ACCGUAUU CUGAUGAGGCCGAAAGGCCGAA AAUUUCUU | 1588 | AAGAAAUUA AAUACGGU | 1589 |
| 1466 | GGGGACCG CUGAUGAGGCCGAAAGGCCGAA AUUUAAUU | 1590 | AAUUAAAUA CGGUCCCC | 1591 |
| 1471 | CUUCAGGG CUGAUGAGGCCGAAAGGCCGAA ACCGUAUU | 1592 | AAUACGGUC CCCUGAAG | 1593 |
| 1485 | GUCUGAGG CUGAUGAGGCCGAAAGGCCGAA AGCAUCUU | 1594 | AAGAUGCUA CCUCAGAC | 1595 |
| 1489 | GGGGGUCU CUGAUGAGGCCGAAAGGCCGAA AGGUAGCA | 1596 | UGCUACCUC AGACCCCC | 1597 |
| 1499 | CUGCAUGG CUGAUGAGGCCGAAAGGCCGAA AGGGGGUC | 1598 | GACCCCCUC CAUGCAG | 1599 |
| 1518 | ACAUCUUG CUGAUGAGGCCGAAAGGCCGAA AGUCCUC | 1600 | GAGGACCUA CAAGAUGU | 1601 |
| 1530 | UCCCGCUU CUGAUGAGGCCGAAAGGCCGAA AUCACAUC | 1602 | GAUGUGAUU AAGCGGGA | 1603 |
| 1531 | UUCCCGCU CUGAUGAGGCCGAAAGGCCGAA AAUCACAU | 1604 | AUGUGAUUA AGCGGGAA | 1605 |
| 1541 | AUUCAUCC CUGAUGAGGCCGAAAGGCCGAA AUUCCCGC | 1606 | GCGGGAAUC GGAUGAAU | 1607 |
| 1550 | CAAUUCCA CUGAUGAGGCCGAAAGGCCGAA AUUCAUCC | 1608 | GGAUGAAUC UGGAAUUG | 1609 |
| 1557 | UCAGCAAC CUGAUGAGGCCGAAAGGCCGAA AUUCCAGA | 1610 | UCUGGAAUU GUUGCUGA | 1611 |
| 1560 | AACUCAGC CUGAUGAGGCCGAAAGGCCGAA ACAAUUCC | 1612 | GGAAUUGUU GCUGAGUU | 1613 |
| 1566 | UCUCUUGA CUGAUGAGGCCGAAAGGCCGAA ACUCAGCA | 1614 | UACUGAGUU CAAGAGA | 1615 |
| 1569 | CUCUCUUG CUGAUGAGGCCGAAAGGCCGAA AACUCAGC | 1616 | GCUGAGUUU CAAGAGAG | 1617 |
| 1570 | ACUCUCUU CUGAUGAGGCCGAAAGGCCGAA AAACUCAG | 1618 | CUGAGUUUC AAGAGAGU | 1619 |
| 1589 | UUUUCAGU CUGAUGAGGCCGAAAGGCCGAA ACGGUGGU | 1620 | ACCACCGUU ACUGAAAA | 1621 |
| 1590 | UUUUUCAG CUGAUGAGGCCGAAAGGCCGAA AACGGUGG | 1622 | CCACCGUUA CUGAAAAA | 1623 |
| 1602 | GCCUGCUU CUGAUGAGGCCGAAAGGCCGAA AUUUUUUU | 1624 | AAAAAAAUC AAGCAGGC | 1625 |
| 1619 | CAGUUGGC CUGAUGAGGCCGAAAGGCCGAA ACUCCACC | 1626 | GGGGGAGUC GCCAACUG | 1627 |
| 1634 | AGUUUCCC CUGAUGAGGCCGAAAGGCCGAA AUUUCUCA | 1628 | UGAGAAAUC GGGAAACU | 1629 |
| 1643 | AACAGAAG CUGAUGAGGCCGAAAGGCCGAA AGUUUCCC | 1630 | GGGAAACUU CUUCUGCU | 1631 |
| 1644 | GAGCAGAA CUGAUGAGGCCGAAAGGCCGAA AAGUUUCC | 1632 | GGAAACUUC UUCUGCUC | 1633 |
| 1646 | UUGAGCAG CUGAUGAGGCCGAAAGGCCGAA AGAAGUUU | 1634 | AAACUUCUU CUGCUCAA | 1635 |
| 1647 | UUUGAGCA CUGAUGAGGCCGAAAGGCCGAA AAGAAGUU | 1636 | AACUUCUUC UGCUCAAA | 1637 |
| 1652 | AGUGGUUU CUGAUGAGGCCGAAAGGCCGAA AGCAGAAG | 1638 | CUUCUGCUC AAACCACU | 1639 |
| 1691 | CCUGCGAG CUGAUGAGGCCGAAAGGCCGAA ACAGUUGG | 1640 | CCAACUGUU CUCGCAGG | 1641 |
| 1692 | GCCUGCGA CUUAUGAGGCCGAAAGGCCGAA AACAGUUG | 1642 | CAAGGGUUC UCGCAGGC | 1643 |
| 1694 | ACGCCUGC CUGAUGAGGCCGAAAGGCCGAA AGAACAGU | 1644 | ACUGUUCUC GCAGGCGU | 1645 |
| 1703 | CCACAGGA CUGAUGAGGCCGAAAGGCCGAA ACGCCUGC | 1646 | GCAGGCGUC UCCUGUGG | 1647 |
| 1705 | UACCACAG CUGAUGAGGCCGAAAGGCCGAA AGACGCCU | 1648 | AGGCGUCUC CUGUGGCA | 1649 |
| 1726 | UGUAAGAA CUGAUGAGGCCGAAAGGCCGAA AUUUUGGG | 1650 | CCCCAAAUA UUCUUACA | 1651 |
| 1728 | CUUGUAAG CUGAUGAGGCCGAAAGGCCGAA AUAUUUGG | 1652 | CCAAAUAUU CUUACAAG | 1653 |
| 1729 | GCUUGUAA CUGAUGAGGCCGAAAGGCCGAA AAUAUUUG | 1G54 | CAAAUAUUC UUACAAGC | 1655 |
| 1731 | GAGCUUGU CUGAUGAGGCCGAAAGGCCGAA AGAAUAUU | 1656 | AAUAUUCUU ACAAGCUC | 1657 |
| 1732 | AGAGCUUG CUGAUGAGGCCGAAAGGCCGAA AAGAAUAU | 1658 | AUAUUCUUA CAAGCUCU | 1659 |
| 1739 | UUAAAACA CUGAUGAGGCCGAAAGGCCGAA AGCUUGUA | 1660 | UACAAGCUC UGUUUUAA | 1661 |
| 1743 | GUCAUUAA CUGAUGAGGCCGAAAGGCCGAA ACAGAGCU | 1662 | AGCUCUGUU UUAAUGAC | 1663 |

TABLE XVI-continued

Mouse c-myb Hammerhead Ribozyme and Target Sequences
(REVISED)

| nt | HH Ribozyme Sequence | Seq ID No. | Target | Seq ID No. |
|---|---|---|---|---|
| 1744 | UGUCAUUA CUGAUGAGGCCGAAAGGCCGAA AACAGAGC | 1664 | GCUCUGUUU UAAUGACA | 1665 |
| 1745 | GUGUCAUU CUGAUGAGGCCGAAAGGCCGAA AAACAGAG | 1666 | CUCUGUUUU AAUGACAC | 1667 |
| 1746 | GGUGUCAU CUGAUGAGGCCGAAAGGCCGAA AAAACAGA | 1668 | UCUGUUUUA AUGACACC | 1669 |
| 1758 | UCUUCUGA CUGAUGAGGCCGAAAGGCCGAA ACAGGUGU | 1670 | ACACCUGUA UCAGAAGA | 1671 |
| 1760 | CAUCUUCU CUGAUGAGGCCGAAAGGCCGAA AUACAGGU | 1672 | ACCUGUAUC AGAAGAUG | 1673 |
| 1779 | GCUUUGAG CUGAUGAGGCCGAAAGGCCGAA ACAUUGUC | 1674 | GACAAUGUC CUCAAAGC | 1675 |
| 1782 | AAGGCUUU CUGAUGAGGCCGAAAGGCCGAA AGGACAUU | 1676 | AAUCUCCUC AAAGCCUU | 1677 |
| 1790 | GUACGGUA CUGAUGAGGCCGAAAGGCCGAA AGGCUUUG | 1678 | CAAAGCCUU UACCGUAC | 1679 |
| 1791 | GGUACGGU CUGAUGAGGCCGAAAGGCCGAA AAGGCUUU | 1680 | AAAGCCUUU ACCGUACC | 1681 |
| 1792 | AGGUACGG CUGAUGAGGCCGAAAGGCCGAA AAAGGCUU | 1682 | AAGCCUUUA CCGUACCU | 1683 |
| 1797 | UUCUUAGG CUGAUGAGGCCGAAAGGCCGAA ACGGUAAA | 1684 | UUUACCGUA CCUAAGAA | 1685 |
| 1801 | CCUGUUCU CUGAUGAGGCCGAAAGGCCGAA AGGUACGG | 1686 | CCGUACCUA AGAACAGG | 1687 |
| 1822 | CUGCAAGG CUGAUGAGGCCGAAAGGCCGAA ACCCACCA | 1688 | UGGUGGGUC CCUUGCAG | 1689 |
| 1826 | AUGGCUGC CUGAUGAGGCCGAAAGGCCGAA AGGGACCC | 1690 | GGGUCCCUU GCAGCCAU | 1691 |
| 1859 | UCCCACAC CUGAUGAGGCCGAAAGGCCGAA AUGCUGGC | 1692 | GCCAGCAUC CUGUGGGA | 1693 |
| 1892 | CCGGACCG CUGAUGAGGCCGAAAGGCCGAA AGGCCGUC | 1694 | GACGGCCUC CGGUCCGG | 1695 |
| 1897 | CCGAGCCG CUGAUGAGGCCGAAAGGCCGAA ACCGGAGG | 1696 | CCUCCGGUC CGGCUCGG | 1697 |
| 1903 | GUAUUUCC CUGAUGAGGCCGAAAGGCCGAA AGCCGGAC | 1698 | GUCCGGCUC GGAAAUAC | 1699 |
| 1910 | CCUUCACG CUGAUGAGGCCGAAAGGCCGAA AUUUCCGA | 1700 | UCGGAAAUA CGUGAACG | 1701 |
| 1922 | GAGCUGAG CUGAUGAGGCCGAAAGGCCGAA ACGCGUUC | 1702 | CAACGCGUU CUCAGCUC | 1703 |
| 1923 | CCAGCUGA CUGAUGAGGCCGAAAGGCCGAA AACGCGUU | 1704 | AACGCGUUC UCAGCUCG | 1705 |
| 1925 | UUCGAGCU CUGAUGAGGCCGAAAGGCCGAA AGAACGCG | 1706 | CGCGUUCUC AGCUCGAA | 1707 |
| 1930 | CAGAGUUC CUGAUGAGGCCGAAAGGCCGAA AGCUGAGA | 1708 | UCUCACCUC GAACUCUG | 1709 |
| 1936 | CAUGACCA CUGAUGAGGCCGAAAGGCCGAA AGUUCGAG | 1710 | CUCGAACUC UGGUCAUG | 1711 |
| 1941 | UCUCACAU CUGAUGAGGCCGAAAGGCCGAA ACCAGAGU | 1712 | ACUCUGGUC AUGUGAGA | 1713 |
| 1953 | UUUCUGGA CUGAUGAGGCCGAAAGGCCGAA AUGUCUCA | 1714 | UGAGACAUU UCCAGAAA | 1715 |
| 1954 | UUUUCUGG CUGAUGAGGCCGAAAGGCCGAA AAUGUCUC | 1716 | GAGACAUUU CCAGAAAA | 1717 |
| 1955 | CUUUUCUG CUGAUGAGGCCGAAAGGCCGAA AAAUGUCU | 1718 | AGACAUUUC CAGAAAAG | 1719 |
| 1967 | AAAACCAU CUGAUGAGGCCGAAAGGCCGAA AUGCUUUU | 1720 | AAAAGCAUU AUGGUUUU | 1721 |
| 1968 | GAAAACCA CUGAUGAGGCCGAAAGGCCGAA AAUGCUUU | 1722 | AAAGCAUUA UGGUUUUC | 1723 |
| 1973 | GUUCUGAA CUGAUGAGGCCGAAAGGCCGAA ACCAUAAU | 1724 | AUUAUGGUU UCAGAAC | 1725 |
| 1974 | UGUUCUGA CUGAUGAGGCCGAAAGGCCGAA AACCAUAA | 1726 | UUAUGGUUU UCAGAACA | 1727 |
| 1975 | GUGUUCUG CUGAUGAGGCCGAAAGGCCGAA AAACCAUA | 1728 | UAUGGUUUU CAGAACAC | 1729 |
| 1976 | AGUGUUCU CUGAUGAGGCCGAAAGGCCGAA AAAACCAU | 1730 | AUGGUUUUC AGAACACU | 1731 |
| 1985 | CAACUUUU CUGAUGAGGCCGAAAGGCCGAA AGUGUUCU | 1732 | AGAACACUU AAAAGUUG | 1733 |
| 1986 | UCAACUUU CUGAUGAGGCCGAAAGGCCGAA AAGUGUUC | 1734 | CAACACUUA AAAGUUGA | 1735 |
| 1992 | CGAAAGUC CUGAUGAGGCCGAAAGGCCGAA ACUUUUAA | 1736 | UUAAAAGUU GACUUUCG | 1737 |
| 1997 | UGUGUCGA CUGAUGAGGCCGAAAGGCCGAA AGUCAACU | 1738 | AGUUCACUU UCGACACA | 1739 |
| 1998 | AUGUGUCG CUGAUGAGGCCGAAAGGCCGAA AAGUCAAC | 1740 | CUUGACUUU CGACACAU | 1741 |
| 1999 | CAUGUGUC CUGAUGAGGCCGAAAGGCCGAA AAAGUCAA | 1742 | UUGACUUUC GACACAUG | 1743 |
| 2011 | ACGCUGAG CUGAUGAGGCCGAAAGGCCGAA AGCCAUGU | 1744 | ACAUGGCUC CUCAGCGU | 1745 |
| 2014 | UCCACGCU CUGAUGAGGCCGAAAGGCCGAA AGGAGCCA | 1746 | UGGCUCCUC AGCGUGGA | 1747 |
| 2028 | CACCCAUG CUGAUGAGGCCCAAAGGCCGAA AGCGCUCC | 1748 | GGAGCGCUC CAUGGCUG | 1749 |
| 2052 | CACAACAA CUGAUGAGGCCGAAAGGCCGAA AUCAGGCU | 1750 | AGCCUGAUU UGUUGUG | 1751 |
| 2053 | CCACAACA CUGAUGAGGCCGAAAGGCCGAA AAUCAGGC | 1752 | GCCUGAUUU GUUGUGG | 1753 |
| 2054 | ACCACAAC CUGAUGAGGCCGAAAACGCCGAA AAAUCAGG | 1754 | CCUGAUUUU GUUGUGGU | 1755 |
| 2057 | UCUACCAC CUGAUGAGGCCGAAAGGCCGAA ACAAAAUC | 1756 | GAUUUUGUU GUGGUACA | 1757 |
| 2063 | AACUGUUG CUGAUGAGGCCGAAAGGCCGAA ACCACAAC | 1758 | GUUGUGGUA CAACAGUU | 1759 |
| 2071 | CUGCUCUC CUGAUGAGGCCGAAAGGCCGAA ACUGUUGU | 1760 | ACAACAGUU GAGAGCAG | 1761 |
| 2092 | CAACUAAA CUGAUGAGGCCGAAAGGCCGAA AUGCACUU | 1762 | AAGUGCAUU UUUACUUG | 1763 |
| 2093 | GCAACUAA CUGAUGAGGCCGAAAGGCCGAA AAUGCACU | 1764 | AGUGCAUUU UUAGUUGC | 1765 |
| 2094 | AGCAACUA CUGAUGAGGCCGAAAGGCCGAA AAAUGCAC | 1766 | GUGCAUUUU UAGUUGCU | 1767 |
| 2095 | AAGCAACU CUGAUGAGGCCGAAAGGCCGAA AAAAUGCA | 1768 | UGCAUUUUU AGUUGCUU | 1769 |
| 2096 | CAAGCAAC CUGAUGAGGCCGAAAGGCCGAA AAAAAUGC | 1770 | GCAUUUUUA GUUGCUUG | 1771 |
| 2099 | UCUCAAGC CUGAUGAGGCCGAAAGGCCGAA ACUAAAAA | 1772 | UUUUUAGUU GCUUGAGA | 1773 |
| 2103 | GAGAUCUC CUGAUGAG0CCGAAAGGCCGAA AGCAACUA | 1774 | UAGUUGCUU GAGAUCUC | 1775 |
| 2109 | UCAAGUGA CUGAUGAGGCCGAAAGGCC0AA AUCUCAAG | 1776 | CUUGAGAUC UCACUUGA | 1777 |
| 2111 | AAUCAAGU CUGAUGAGGCCGAAAGGCCGAA A0AUCUCA | 1778 | UGAGAUCUC ACUUGAUU | 1779 |
| 2115 | GUGAAAUC CUGAUGAGGCCGAAAGGCCGAA AGUGAGAU | 1780 | AUCUCACUU GAUUUCAC | 1781 |
| 2119 | UUGUGUGA CUGAUGAGGCCGAAAGGCCGAA AUCAAGUG | 1782 | CACUUGAUU UCACACAA | 1783 |
| 2120 | GUUGUGUG CUGAUGAGGCCGAAAGGCCGAA AAUCAAGU | 1784 | ACUUGAUUU CACACAAC | 1785 |
| 2121 | AGUUGUGU CUGAUGAGGCCGAAAGGCCGAA AAAUCAAG | 1786 | CUUGAUUUC ACACAACU | 1787 |
| 2130 | AUCCUUUU CUGAUGAGGCCGAAAGGCCGAA AGUUGUGU | 1788 | ACACAACUA AAAAGGAU | 1789 |
| 2139 | AAAAAAAA CUGAUGAGGCCGAAAGGCCGAA AUCCUUUU | 1790 | AAAAGGAUU UUUUUUUU | 1791 |
| 2140 | UAAAAAAA CUGAUGAGGCCGAAAGGCCGAA AAUCCUUU | 1792 | AAAGGAUUU UUUUUUA | 1793 |
| 2141 | UUAAAAAA CUGAUGAGGCCGAAAGGCCGAA AAAUCCUU | 1794 | AAGGAUUUU UUUUUAA | 1795 |
| 2142 | UUUAAAAA CUGAUGAGGCCGAAAGGCCGAA AAAAUCCU | 1796 | AGGAUUUUU UUUUAAA | 1797 |
| 2143 | UUUUAAAA CUGAUGAGGCCGAAAGGCCGAA AAAAAUCC | 1798 | GGAUUUUUU UUUAAAA | 1799 |
| 2144 | UUUUUAAA CUGAUGAGGCCGAAAGGCCGAA AAAAAAUC | 1800 | GAUUUUUUU UUAAAAA | 1801 |
| 2145 | AUUUUUAA CUGAUGAGGCCGAAAGGCCGAA AAAAAAAU | 1802 | AUUUUUUU UAAAAAU | 1803 |
| 2146 | UAUUUUUA CUGAUGAGGCCGAAAGGCCGAA AAAAAAAA | 1804 | UUUUUUUU UAAAAAUA | 1805 |
| 2147 | UUAUUUUU CUGAUGAGGCCGAAAGGCCGAA AAAAAAAA | 1806 | UUUUUUUU AAAAAUAA | 1807 |
| 2148 | AUUAUUUU CUGAUGAGGCCGAAAGGCCGAA AAAAAAAA | 1808 | UUUUUUUA AAAAUAAU | 1809 |

TABLE XVI-continued

Mouse c-myb Hammerhead Ribozyme and Target Sequences
(REVISED)

| nt | HH Ribozyme Sequence | Seq ID No. | Target | Seq ID No. |
|---|---|---|---|---|
| 2154 | AUUAUUAU CUGAUGAGGCCGAAAGGCCGAA AUUUUUAA | 1810 | UUAAAAAUA AUAAUAAU | 1811 |
| 2157 | UUCAUUAU CUGAUGAGGCCGAAAGGCCGAA AUUAUUUU | 1812 | AAAAUAAUA AUAAUGAA | 1813 |
| 2160 | UUAUUCAU CUGAUGAGGCCGAAAGGCCGAA AUUAUUAU | 1814 | AUAAUAAUA AUGAAUAA | 1815 |
| 2167 | AAGACUGU CUGAUGAGGCCGAAAGGCCGAA AUUCAUUA | 1816 | UAAUGAAUA ACAGUCUU | 1817 |
| 2173 | UUAGGUAA CUGAUGAGGCCGAAAGGCCGAA ACUGUUAU | 1818 | AUAACAGUC UUACCUAA | 1819 |
| 2175 | AUUUAGGU CUGAUGAGGCCGAAAGGCCGAA AGACUGUU | 1820 | AACAGUCUU ACCUAAAU | 1821 |
| 2176 | AAUUUAGG CUGAUGAGGCCGAAAGGCCGAA AAGACUGU | 1822 | ACAGUCUUA CCUAAAUU | 1823 |
| 2180 | UAAUAAUU CUGAUGAGGCCGAAAGGCCGAA AGGUAAGA | 1824 | UCUUACCUA AAUUAUUA | 1825 |
| 2184 | UACCUAAU CUGAUGAGGCCGAAAGGCCGAA AUUUAGGU | 1826 | ACCUAAAUU AUUAGGUA | 1827 |
| 2185 | UUACCUAA CUGAUGAGGCCGAAAGGCCGAA AAUUUAGG | 1828 | CCUAAAUUA UUAGGUAA | 1829 |
| 2187 | CAUUACCU CUGAUGAGGCCGAAAGGCCGAA AUAAUUUA | 1830 | UAAAUUAUU AGGUAAUG | 1831 |
| 2188 | UCAUUACC CUGAUGAGGCCGAAAGGCCGAA AAUAAUUU | 1832 | AAAUUAUUA GGUAAUGA | 1833 |
| 2192 | CAAUUCAU CUGAUGAGGCCGAAAGGCCGAA ACCUAAUA | 1834 | UAUUAGGUA AUGAAUUG | 1835 |
| 2199 | AUGGUCAC CUGAUGAGGCCGAAAGGCCGAA AUUCAUUA | 1836 | UAAUGAAUU GUGACCAU | 1837 |
| 2208 | UAUUAACA CUGAUGAGGCCGAAAGGCCGAA AUGGUCAC | 1838 | GUGACCAUU UGUUAAUA | 1839 |
| 2209 | AUAUUAAC CUGAUGAGGCCGAAAGGCCGAA AAUGGUCA | 1840 | UGACCAUUU GUUAAUAU | 1841 |
| 2212 | AUGAUAUU CUGAUGAGGCCGAAAGGCCGAA ACAAAUGG | 1842 | CCAUUUGUU AAUAUCAU | 1843 |
| 2213 | UAUGAUAU CUGAUGAGGCCGAAAGGCCGAA AACAAAUG | 1844 | CAUUUGUUA AUAUCAUA | 1845 |
| 2216 | GAUUAUGA CUGAUGAGGCCGAAAGGCCGAA AUUAACAA | 1846 | UUGUUAAUA UCAUAAUC | 1847 |
| 2218 | CUGAUUAU CUGAUGAGGCCGAAAGGCCGAA AUAUUAAC | 1848 | GUUAAUAUC AUAAUCAG | 1849 |
| 2221 | AAUCUGAU CUGAUGAGGCCGAAAGGCCGAA AUGAUAUU | 1850 | AAUAUCAUA AUCAGAUU | 1851 |
| 2224 | AAAAAUCU CUGAUGAGGCCGAAAGGCCGAA AUUAUGAU | 1852 | AUCAUAAUC AGAUUUUU | 1853 |
| 2229 | UUUUAAAA CUGAUGAGGCCGAAAGGCCGAA AUCUGAUU | 1854 | AAUCAGAUU UUUAAAA | 1855 |
| 2230 | UUUUUAAA CUGAUGAGGCCGAAAGGCCGAA AAUCUGAU | 1856 | AUCAGAUUU UUUAAAAA | 1857 |
| 2231 | UUUUUUAA CUGAUGAGGCCGAAAGGCCGAA AAAUCUGA | 1858 | UCAGAUUUU UUAAAAAA | 1859 |
| 2232 | UUUUUUUA CUGAUGAGGCCGAAAGGCCGAA AAAAUCUG | 1860 | CAGAUUUUU UAAAAAAA | 1861 |
| 2233 | UUUUUUUU CUGAUGAGGCCGAAAGGCCGAA AAAAAUCU | 1862 | AGAUUUUUU AAAAAAAA | 1863 |
| 2234 | AUUUUUUU CUGAUGAGGCCGAAAGGCCGAA AAAAAAUC | 1864 | GAUUUUUUA AAAAAAAU | 1865 |
| 2243 | AAUCAUUU CUGAUGAGGCCGAAAGGCCGAA AUUUUUUU | 1866 | AAAAAAAUA AAAUGAUU | 1867 |
| 2251 | UACAAAUA CUGAUGAGGCCGAAAGGCCGAA AUCAUUUU | 1868 | AAAAUGAUU UAUUUGUA | 1869 |
| 2252 | AUACAAAU CUGAUGAGGCCGAAAGGCCGAA AAUCAUUU | 1870 | AAAUGAUUU AUUUGUAU | 1871 |
| 2253 | AAUACAAA CUGAUGAGGCCGAAAGGCCGAA AAAUCAUU | 1872 | AAUGAUUUA UUUGUAUU | 1873 |
| 2255 | AAAAUACA CUGAUGAGGCCGAAAGGCCGAA AUAAAUCA | 1874 | UGAUUUAUU UGUAUUUU | 1875 |
| 2256 | UAAAAUAC CUGAUGAGGCCGAAAGGCCGAA AAUAAAUC | 1876 | GAUUUAUUU GUAUUUUA | 1877 |
| 2259 | CUCUAAAA CUGAUGAGGCCGAAAGGCCGAA ACAAAUAA | 1878 | UUAUUUGUA UUUUAGAG | 1879 |
| 2261 | UUCUCUAA CUGAUGAGGCCGAAAGGCCGAA AUACAAAU | 1880 | AUUUGUAUU UUAGAGAA | 1881 |
| 2262 | AUUCUCUA CUGAUGAGGCCGAAAGGCCGAA AAUACAAA | 1882 | UUUGUAUUU UAGAGAAU | 1883 |
| 2263 | UAUUCUCU CUGAUGAGGCCGAAAGGCCGAA AAAUACAA | 1884 | UUGUAUUUU AGAGAAUA | 1885 |
| 2264 | GUAUUCUC CUCAUGAGGCCAAAAGGCCGAA AAAAUACA | 1886 | UUUAUUUUA GAGAAUAC | 1887 |
| 2271 | AUCUGUUA CUGAUGAGGCCGAAAGGCCGAA AUUCUCUA | 1888 | UAGAGAAUA CAACAGAU | 1889 |
| 2280 | AAAAUACU CUGAUGAGGCCGAAAGGCCGAA AUCUGUUG | 1890 | CAACAGAUC AGUAUUUU | 1891 |
| 2284 | GUCAAAAA CUGAUGAGGCCGAAAGGCCGAA ACUGAUCU | 1892 | AAAUCAGUA UUUUUGAC | 1893 |
| 2286 | CAGUCAAA CUGAUGAGGCCGAAAGGCCGAA AUACUGAU | 1894 | AUCAGUAUU UUUGACUG | 1895 |
| 2287 | ACAGUCAA CUGAUGAGGCCGAAAGGCCGAA AAUACUGA | 1896 | UCAGUAUUU UUGACUGU | 1897 |
| 2288 | CACAGUCA CUGAUGAGGCCGAAAGGCCGAA AAAUACUG | 1898 | CAGUAUUUU UGACUGUG | 1899 |
| 2289 | CCACAGUC CUGAUGAGGCCGAAAGGCCGAA AAAAUACU | 1900 | AGUAUUUUU GACUGUGG | 1901 |
| 2303 | UUUUUUUA CUGAUGAGGCCGAAAGGCCGAA AUUCACCA | 1902 | UGGUGAAUU UAAAAAAA | 1903 |
| 2304 | UUUUUUUU CUGAUGAGGCCGAAAGGCCGAA AAUUCACC | 1904 | GGUGAAUUU AAAAAAAA | 1905 |
| 2305 | UUUUUUUU CUGAUGAGGCCGAAAGGCCGAA AAAUUCAC | 1906 | GUGAAUUUA AAAAAAAA | 1907 |
| 2316 | UUUGUGUA CUGAUGAGGCCGAAAGGCCGAA AUUUUUUU | 1908 | AAAAAAAUU UACACAAA | 1909 |
| 2317 | CUUUGUGU CUGAUGAGGCCGAAAGGCCGAA AAUUUUUU | 1910 | AAAAAAUUU ACACAAAG | 1911 |
| 2318 | UCUUUGUG CUGAUGAGGCCGAAAGGCCGAA AAAUUUUU | 1912 | AAAAAUUUA CACAAAGA | 1913 |
| 2330 | UACUGGGA CUGAUGAGGCCGAAAGGCCGAA AUUUCUUU | 1914 | AAAGAAAUA UCCCAGUA | 1915 |
| 2332 | AAUACUGG CUGAUGAGGCCGAAAGGCCGAA AUAUUUCU | 1916 | AGAAAUAUC CAGUAUUU | 1917 |
| 2338 | ACAUGGAA CUGAUGAGGCCGAAAGGCCGAA ACUGGGAU | 1918 | AUCCCAGUA UUCCAUGU | 1919 |
| 2340 | AUACAUGG CUGAUGAGGCCGAAAGGCCGAA AUACUGGG | 1920 | CCCAGUAUU CCAUGUAU | 1921 |
| 2341 | GAUACAUG CUGAUGAGGCCGAAAGGCCGAA AAUACUGG | 1922 | CCAGUAUUC CAUGUAUC | 1923 |
| 2347 | GACUGAGA CUGAUGAGGCCGAAAGGCCGAA ACAUGGAA | 1924 | UUCCAUGUA UCUCAGUC | 1925 |
| 2349 | AUGACUGA CUGAUGAGGCCGAAAGGCCGAA AUACAUGG | 1926 | CCAUGUAUC UCAGUCAU | 1927 |
| 2351 | UAGUGACU CUGAUGAGGCCGAAAGGCCGAA AGAUACAU | 1928 | AUGUAUCUC AGUCACUA | 1929 |
| 2355 | UGUUUAGU CUGAUGAGGCCGAAAGGCCGAA ACUGAGAU | 1930 | AUCUCAGUCACUAAACA | 1931 |
| 2359 | UGUAUGUU CUGAUGAGGCCGAAAGGCCGAA AGUGACUG | 1932 | CAGUCACUA AACAUACA | 1933 |
| 2365 | UCUCUGUG CUGAUGAGGCCGAAAGGCCGAA AUGUUUAG | 1934 | CUAAACAUA CACAGAGA | 1935 |
| 2377 | UUUUUAAA CUGAUGAGGCCGAAAGGCCGAA AUCUCUCU | 1936 | AGAGAGAUU UUUAAAAA | 1937 |
| 2378 | GUUUUUAA CUGAUGAGGCCGAAAGGCCGAA AAUCUCUC | 1938 | GAGAGAUUU UUAAAAAC | 1939 |
| 2379 | GGUUUUUA CUGAUGAGGCCGAAAGGCCGAA AAAUCUCU | 1940 | AGAGAUUUU UAAAAACC | 1941 |
| 2380 | UGGUUUUU CUGAUGAGGCCGAAAGGCCGAA AAAAUCUC | 1942 | GAGAUUUUU AAAAACCA | 1943 |
| 2381 | CUGGUUUU CUGAUGAGGCCGAAAGGCCGAA AAAAAUCU | 1944 | AGAUUUUUU AAAACCAG | 1945 |
| 2399 | UUCAAAAU CUGAUGAGGCCGAAAGGCCGAA AUGCUUCU | 1946 | AGAAGCAUU AUUUUGAA | 1947 |
| 2400 | AUUCAAAA CUGAUGAGGCCGAAAGGCCGAA AAUGCUUC | 1948 | AAAGCAUUA UUUUGAAU | 1949 |
| 2402 | ACAUUCAA CUGAUGAGGCCGAAAGGCCGAA AUAAUGCU | 1950 | AGCAUUAUU UUGAAUGU | 1951 |
| 2403 | AACAUUCA CUGAUGAGGCCGAAAGGCCGAA AAUAAUGC | 1952 | GCAUUAUUU UGAAUGUU | 1953 |
| 2404 | UAACAUUC CUGAUGAGGCCGAAAGGCCGAA AAAUAAUG | 1954 | CAUUAUUUU GAAUGUUA | 1955 |

TABLE XVI-continued

Mouse c-myb Hammerhead Ribozyme and Target Sequences
(REVISED)

| nt | HH Ribozyme Sequence | Seq ID No. | Target | Seq ID No. |
|---|---|---|---|---|
| 2411 | AUUUAGCU CUGAUGAGGCCGAAAGGCCGAA ACAUUCAA | 1956 | UUGAAUGUU AGCUAAAU | 1957 |
| 2412 | GAUUUAGC CUGAUGAGGCCGAAAGGCCGAA AACAUUCA | 1958 | UCAAUGUUA GCUAAAUC | 1959 |
| 2416 | UUCGGAUU CUGAUGAGGCCGAAAGGCCGAA AGCUAACA | 1960 | UGUUAGCUA AAUCCCAA | 1961 |
| 2420 | UUACUUGG CUGAUGAGGCCGAAAGGCCGAA AUUUAGCU | 1962 | AACUAAAUC CCAAGUAA | 1963 |
| 2427 | UUAAGUAU CUGAUGAGGCCGAAAGGCCGAA ACUUGGGA | 1964 | UCCCAAGUA AUACUUAA | 1965 |
| 2430 | GCAUUAAG CUGAUGAGGCCGAAAGGCCGAA AUUACUUG | 1966 | CAAGUAAUA CUUAAUGC | 1967 |
| 2433 | GUUGCAUU CUGAUGAGGCCGAAAGGCCGAA AGUAUUAC | 1968 | AUAAUACUU AAUGCAAC | 1969 |
| 2434 | GGUUGCAU CUGAUGAGGCCGAAAGGCCGAA AAGUAUUA | 1970 | UAAUACUUA AUGCAACC | 1971 |
| 2445 | AGCUCCUA CUGAUGAGGCCGAAAGGCCGAA AGGGUUGC | 1972 | GCAACCCUC UAGGAGCU | 1973 |
| 2447 | UGAGCUCC CUGAUGAGGCCGAAAGGCCGAA AGAGGGUU | 1974 | AACCCUCUA GGAGCUCA | 1975 |
| 2454 | CCACAAAU CUGAUGAGGCCGAAAGGCCGAA AGCUCCUA | 1976 | UAGGAGCUC AUUUGUGG | 1977 |
| 2457 | UAGCCACA CUGAUGAGGCCGAAAGGCCGAA AUGAGCUC | 1978 | GAGCUCAUU UGUGGCUA | 1979 |
| 2458 | UUAGCCAC CUGAUGAGGCCGAAAGGCCGAA AAUGAGCU | 1980 | AGCUCAUUU GUGGCUAA | 1981 |
| 2465 | AAGAUUAU CUGAUGAGGCCGAAAGGCCGAA AGCCACAA | 1982 | UUGUGGCUA AUAAUCUU | 1983 |
| 2468 | UCCAAGAU CUGAUGAGGCCGAAAGGCCGAA AUUAGCCA | 1984 | UGGCUAAUA AUCUUGGA | 1985 |
| 2471 | AUUUCCAA CUGAUGAGGCCGAAAGGCCGAA AUUAUUAG | 1986 | CUAAUAAUC UUGGAAAU | 1987 |
| 2473 | AUAUUUCC CUGAUGAGGCCGAAAGGCCGAA AGAUUAUU | 1988 | AAUAAUCUU GGAAAUAU | 1989 |
| 2480 | AAUAAAGA CUGAUGAGGCCGAAAGGCCGAA AUUUCCAA | 1990 | UUGGAAAUA UCUUUAUU | 1991 |
| 2482 | AUAAUAAA CUGAUGAGGCCGAAAGGCCGAA AUAUUUCC | 1992 | GGAAAUAUC UUUAUUAU | 1993 |
| 2484 | AUAUAAUA CUGAUGAGGCCGAAAGGCCGAA AGAUAUUU | 1994 | AAAUAUCUU UAUUAUAU | 1995 |
| 2485 | UAUAUAAU CUGAUGAGGCCGAAAGGCCGAA AAGAUAUU | 1996 | AAUAUCUUU AUUAUAUA | 1997 |
| 2486 | CUAUAUAA CUGAUGAGGCCGAAAGGCCGAA AAAGAUAU | 1998 | AUAUCUUUA UUAUAUAG | 1999 |
| 2488 | UGCUAUAU CUGAUGAGGCCGAAAGGCCGAA AUAAAGAU | 2000 | AUCUUUAUU AUAUAGCA | 2001 |
| 2489 | AUGCUAUA CUGAUGAGGCCGAAAGGCCGAA AAUAAAGA | 2002 | UCUUUAUUA UAUAGCAU | 2003 |
| 2491 | AAAUGCUA CUGAUGAGGCCGAAAGGCCGAA AUAAUAAA | 2004 | UUUAUUAUA UAGCAUUU | 2005 |
| 2493 | AUAAAUGC CUGAUGAGGCCGAAAGGCCGAA AUAUAAUA | 2006 | UAUUAUAUA GCAUUUAU | 2007 |
| 2498 | UCCUCAUA CUGAUGAGGCCGAAAGGCCGAA AUGCUAUA | 2008 | UAUAGCAUU UAUGAGGA | 2009 |
| 2499 | CUCCUCAU CUGAUGAGGCCGAAAGGCCGAA AAUGCUAU | 2010 | AUAGCAUUU AUGAGGAG | 2011 |
| 2500 | UCUCCUCA CUGAUGAGGCCGAAAGGCCGAA AAAUGCUA | 2012 | UAGCAUUUA UGAGGAGA | 2013 |
| 2510 | GACAACAA CUGAUGAGGCCGAAAGGCCGAA AUCUCCUC | 2014 | GAGGAGAUU UUGUUGUC | 2015 |
| 2511 | UGACAACA CUGAUGAGGCCGAAAGGCCGAA AAUCUCCU | 2016 | ACGAGAUUU UGUUGUCA | 2017 |
| 2512 | CUGACAAC CUGAUGAGGCCGAAAGGCCGAA AAAUCUCC | 2018 | GGAGAUUUU GUUGUCAG | 2019 |
| 2515 | AAGCUGAC CUGAUGAGGCCGAAAGGCCGAA ACAAAAUC | 2020 | GAUUUUGUU GUCAGCUU | 2021 |
| 2518 | AGCAAGCU CUGAUGAGGCCGAAAGGCCGAA ACAACAAA | 2022 | UUUGUUGUC AGCUUGCU | 2023 |
| 2523 | UUUCAAGC CUGAUGAGGCCGAAAGGCCGAA AGCUGACA | 2024 | UGUCAGCUU GCUUGAAA | 2025 |
| 2527 | UAACUUUC CUGAUGAGGCCGAAAGGCCGAA AGCAAGCU | 2026 | AGCUUGCUU GAAAGUUA | 2027 |
| 2534 | UACAUAAU CUGAUGAGGCCGAAAGGCCGAA ACUUUCAA | 2028 | UUGAAAGUU AUUAUGUA | 2029 |
| 2535 | AUACAUAA CUGAUGAGGCCGAAAGGCCGAA AACUUUCA | 2030 | UGAAAGUUA UUAUGUAU | 2031 |
| 2537 | UCAUACAU CUGAUGAGGCCGAAAGGCCGAA AUAACUUU | 2032 | AAAGUUAUU AUGUAUGA | 2033 |
| 2538 | UUCAUACA CUGAUGAGGCCGAAAGGCCGAA AAUAACUU | 2034 | AAGUUAUUA UGUAUGAA | 2035 |
| 2542 | ACUAUUCA CUGAUGAGGCCGAAAGGCCGAA ACAUAAUA | 2036 | UAUUAUGUA UGAAUAGU | 2037 |
| 2548 | AAUAAAAC CUGAUGAGGCCGAAAGGCCGAA AUUCAUAC | 2038 | GUAUGAAUA GUUUUAUU | 2039 |
| 2551 | UUCAAUAA CUGAUGAGGCCGAAAGGCCGAA ACUAUUCA | 2040 | UGAAUAGUU UUAUUGAA | 2041 |
| 2552 | UUUCAAUA CUGAUGAGGCCGAAAGGCCGAA AACUAUUC | 2042 | GAAUAGUUU UAUUGAAA | 2043 |
| 2553 | UUUUCAAU CUGAUGAGGCCGAAAGGCCGAA AAACUAUU | 2044 | AAUAGUUUU AUUGAAAA | 2045 |
| 2554 | UUUUUCAA CUGAUGAGGCCGAAAGGCCGAA AAAACUAU | 2046 | AUAGUUUUA UUGAAAAA | 2047 |
| 2556 | AUUUUUUC CUGAUGAGGCCGAAAGGCCGAA AUAAAACU | 2048 | AGUUUUAUU GAAAAAAU | 2049 |
| 2565 | AAAAAUAU CUGAUGAGGCCGAAAGGCCGAA AUUUUUUC | 2050 | GAAAAAAUU AUAUUUUU | 2051 |
| 2566 | UAAAAAUA CUGAUGAGGCCGAAAGGCCGAA AAUUUUUU | 2052 | AAAAAAUUA UAUUUUUA | 2053 |
| 2568 | AAUAAAAA CUGAUGAGGCCGAAAGGCCGAA AUAAUUUU | 2054 | AAAAUUAUA UUUUAUU | 2055 |
| 2570 | UGAAUAAA CUGAUGAGGCCGAAAGGCCGAA AUAUAAUU | 2056 | AAUUAUAUU UUAUUCA | 2057 |
| 2571 | CUGAAUAA CUGAUGAGGCCGAAAGGCCGAA AAUAUAAU | 2058 | AUUAUAUUU UAUUCAG | 2059 |
| 2572 | ACUGAAUA CUGAUGAGGCCGAAAGGCCGAA AAAUAUAA | 2060 | UUAUAUUUU UAUUCAGU | 2061 |
| 2573 | UACUGAAU CUGAUGAGGCCGAAAGGCCGAA AAAAUAUA | 2062 | UAUAUUUUU AUUCAGUA | 2063 |
| 2574 | UUACUGAA CUGAUGAGGCCGAAAGGCCGAA AAAAAUAU | 2064 | AUAUUUUUA UUCAGUAA | 2065 |
| 2576 | AAUUACUG CUGAUGAGGCCGAAAGGCCGAA AUAAAAAU | 2066 | AUUUUUAUU CAGUAAUU | 2067 |
| 2577 | AAAUUACU CUGAUGAGGCCGAAAGGCCGAA AAUAAAAA | 2068 | UUUUAUUC AGUAAUUU | 2069 |
| 2581 | AAUUAAAU CUGAUGAGGCCGAAAGGCCGAA ACUGAAUA | 2070 | UAUUCAGUA AUUUAAUU | 2071 |
| 2584 | CAAAAUUA CUGAUGAGGCCGAAAGGCCGAA AUUACUGA | 2072 | UCAGUAAUU UAAUUUUG | 2073 |
| 2585 | ACAAAAUU CUGAUGAGGCCGAAAGGCCGAA AAUUACUG | 2074 | CAGUAAUUU AAUUUUGU | 2075 |
| 2586 | UACAAAAU CUGAUGAGGCCGAAAGGCCGAA AAAUUACU | 2076 | AGUAAUUUA AUUUUGUA | 2077 |
| 2589 | AUUUACAA CUGAUGAGGCCGAAAGGCCGAA AUUAAAUU | 2078 | AAUUUAAUU UGUAAAUU | 2079 |
| 2590 | CAUUUACA CUGAUGAGGCCGAAAGGCCGAA AAUUAAAU | 2080 | AUUUAAUUU UGUAAAUG | 2081 |
| 2591 | GCAUUUAC CUGAUGAGGCCGAAAGGCCGAA AAAUUAAA | 2082 | UUUAAUUUU GUAAAUGC | 2083 |
| 2594 | UUGGCAUU CUGAUGAGGCCGAAAGGCCGAA ACAAAAUU | 2084 | AAUUUGUA AAUGCCAA | 2085 |
| 2617 | UAGCAGCG CUGAUGAGGCCGAAAGGCCGAA ACACAUUU | 2086 | AAAUGUGUU CGCUGCUA | 2087 |
| 2618 | AUAGCAGC CUGAUGAGGCCGAAAGGCCGAA AACACAUU | 2086 | AAUGUGUUC GCUGCUAU | 2089 |
| 2625 | UAAAACCA CUGAUGAGGCCGAAAGGCCGAA AGCAGCGA | 2090 | UCGCUGCUA UGGUUUUA | 2091 |
| 2630 | UAGGCUAA CUGAUGAGGCCGAAAGGCCGAA ACCAUAGC | 2092 | GCUAUGGUU UUAGCCUA | 2093 |
| 2631 | AUAGGCUA CUGAUGAGGCCGAAAGGCCGAA AACCAUAG | 2094 | CUAUGGUUU UAGCCUAU | 2095 |
| 2632 | UAUAGGCU CUGAUGAGGCCGAAAGGCCGAA AAACCAUA | 2096 | UAUGGUUUU AGCCUAUA | 2097 |
| 2633 | CUAUAGGC CUGAUGAGGCCGAAAGGCCGAA AAAACCAU | 2098 | AUGGUUUUA GCCUAUAG | 2099 |
| 2638 | CAUGACUA CUGAUGAGGCCGAAAGGCCGAA AGGCUAAA | 2100 | UUUAGCCUA UAGUCAUG | 2101 |

TABLE XVI-continued

Mouse c-myb Hammerhead Ribozyme and Target Sequences (REVISED)

| nt | HH Ribozyme Sequence | Seq ID No. | Target | Seq ID No. |
|---|---|---|---|---|
| 2640 | AGCAUGAC CUGAUGAGGCCGAAAGGCCGAA AUAGGCUA | 2102 | UAGCCUAUA GUCAUGCU | 2103 |
| 2643 | AGCAGCAU CUGAUGAGGCCGAAAGGCCGAA ACUAUAGG | 2104 | CCUAUAGUC AUGCUGCU | 2105 |
| 2652 | ACACUAGC CUGAUGAGGCCGAAAGGCCGAA AGCAGCAU | 2106 | AUGCUGCUA GCUAGUGU | 2107 |
| 2656 | CCUGACAC CUGAUGAGGCCGAAAGGCCGAA AGCUAGCA | 2108 | UGCUAGCUA GUGUCAGG | 2109 |
| 2661 | UGCCCCCU CUGAUGAGGCCGAAAGGCCGAA ACACUAGC | 2110 | GCUAGUGUC AGGGGGCA | 2111 |
| 2672 | CUAAGCUC CUGAUGAGGCCGAAAGGCCGAA AUUGCCCC | 2112 | GGGGCAAUA GAGCUUAG | 2113 |
| 2678 | UUCCAUCU CUGAUGAGGCCGAAAGGCCGAA AGCUCUAU | 2114 | AUAGAGCUU AGAUGGAA | 2115 |
| 2679 | UUUCCAUC CUGAUGAGGCCGAAAGGCCGAA AAGCUCUA | 2116 | UAGAGCUUA GAUGGAAA | 2117 |
| 2703 | CUAACACC CUGAUGAGGCCGAAAGGCCGAA AGUCUCUU | 2118 | AAGAGACUC GGUGUUAG | 2119 |
| 2709 | CGUUAUCU CUGAUGAGGCCGAAAGGCCGAA ACACCGAG | 2120 | CUCGGUGUU AGAUAACG | 2121 |
| 2710 | CCGUUAUC CUGAUGAGGCCGAAAGGCCGAA AACACCGA | 2122 | UCGGUGUUA GAUAACGG | 2123 |
| 2714 | UAGUCCGU CUGAUGAGGCCGAAAGGCCGAA AUCUAACA | 2124 | UGUUAGAUA ACGGACUA | 2125 |
| 2722 | CUAGUGCA CUGAUGAGGCCGAAAGGCCGAA AGUCCGUU | 2126 | AACGGACUA UGCACUAG | 2127 |
| 2729 | UGGAAUAC CUGAUGAGGCCGAAAGGCCGAA AGUGCAUA | 2128 | UAUGCACUA GUAUUCCA | 2129 |
| 2732 | GUCUGGAA CUGAUGAGGCCGAAAGGCCGAA ACUAGUGC | 2130 | GCACUAGUA UUCCAGAC | 2131 |
| 2734 | AAGUCUGG CUGAUGAGGCCGAAAGGCCGAA AUACUAGU | 2132 | ACUAGUAUU CCAGACUU | 2133 |
| 2735 | AAAGUCUG CUGAUGAGGCCGAAAGGCCGAA AAUACUAG | 2134 | CUAGUAUUC CAGACUUU | 2135 |
| 2742 | AAAUAAAA CUGAUGAGGCCGAAAGGCCGAA AGUCUGGA | 2136 | UCCAGACUU UUUUAUUU | 2137 |
| 2743 | AAAAUAAA CUGAUGAGGCCGAAAGGCCGAA AAGUCUGG | 2138 | CCAGACUUU UUUAUUUU | 2139 |
| 2744 | AAAAAUAA CUGAUGAGGCCGAAAGGCCGAA AAAGUCUG | 2140 | CAGACUUUU UUAUUUUU | 2141 |
| 2746 | UAAAAAAU CUGAUGAGGCCGAAAGGCCGAA AAAAAGUC | 2144 | GACUUUUUU AUUUUUUA | 2145 |
| 2747 | AUAAAAAA CUGAUGAGGCCGAAAGGCCGAA AAAAAAGU | 2146 | ACUUUUUUA UUUUUUAU | 2147 |
| 2749 | AUAUAAAA CUGAUGAGGCCGAAAGGCCGAA AUAAAAAA | 2148 | UUUUUUAUU UUUUAUAU | 2149 |
| 2750 | UAUAUAAA CUGAUGAGGCCGAAAGGCCGAA AAUAAAAA | 2150 | UUUUUAUUU UUUAUAUA | 2151 |
| 2751 | AUAUAUAA CUGAUGAGGCCGAAAGGCCGAA AAAUAAAA | 2152 | UUUUAUUUU UUAUAUAU | 2153 |
| 2752 | UAUAUAUA CUGAUGAGGCCGAAAGGCCGAA AAAAUAAA | 2154 | UUUAUUUUU UAUAUAUA | 2155 |
| 2753 | AUAUAUAU CUGAUGAGGCCGAAAGGCCGAA AAAAAUAA | 2156 | UUAUUUUUU AUAUAUAU | 2157 |
| 2754 | CAUAUAUA CUGAUGAGGCCGAAAGGCCGAA AAAAAAUA | 2158 | UAUUUUUUA UAUAUAUG | 2159 |
| 2756 | UACAUAUA CUGAUGAGGCCGAAAGGCCGAA AUAAAAAA | 2160 | UUUUUUAUA UAUAUGUA | 2161 |
| 2758 | GGUACAUA CUGAUGAGGCCGAAAGGCCGAA AUAUAAAA | 2162 | UUUUAUAUA UAUGUACC | 2163 |
| 2760 | AAGGUACA CUGAUGAGGCCGAAAGGCCGAA AUAUAUAA | 2164 | UUAUAUAUA UGUACCUU | 2165 |
| 2764 | GGAAAAGG CUGAUGAGGCCGAAAGGCCGAA ACAUAUAU | 2166 | AUAUAUGUA CCUUUUCC | 2167 |
| 2768 | AAAAGGAA CUGAUGAGGCCGAAAGGCCGAA AGGUACAU | 2168 | AUGUACCUU UUCCUUUU | 2169 |
| 2769 | CAAAAGGA CUGAUGAGGCCGAAAGGCCGAA AAGGUACA | 2170 | UGUACCUUU UCCUUUUG | 2171 |
| 2770 | ACAAAAGG CUGAUGAGGCCGAAAGGCCGAA AAAGGUAC | 2172 | GUACCUUUU CCUUUUGU | 2173 |
| 2771 | GACAAAAG CUGAUGAGGCCGAAAGGCCGAA AAAAGGUA | 2174 | UACCUUUUC CUUUUGUC | 2175 |
| 2774 | AUUGACAA CUGAUGAGGCCGAAAGGCCGAA AGGAAAAG | 2176 | CUUUUCCUU UUGUCAAU | 2177 |
| 2775 | AAUUGACA CUGAUGAGGCCGAAAGGCCGAA AAGGAAAA | 2178 | UUUUCCUUU UGUCAAUU | 2179 |
| 2776 | CAAUUGAC CUGAUGAGGCCGAAAGGCCGAA AAAGGAAA | 2180 | UUUCCUUUU GUCAAUUG | 2181 |

TABLE XVII

Mouse c-myb Hairpin ribozyme and target sequences (REVISED)

| Position | Ribozyme | Seq. ID No. |
|---|---|---|
| 24 | GCGAGGCG AGAA GGGGCU ACCAGAGAAACACACGUUGUGGUACAUUACCUGGUA | 2182 |
| 28 | CAUGGCGA AGAA GGCCGG ACCAGAGAAACACACGUUGUGGUACAUUACCUGGUA | 2184 |
| 122 | AUUUGGGC AGAA GCCCAU ACCAGAGAAACACACGUUGUGGUACAUUACCUGGUA | 2186 |
| 125 | CAGAUUUG AGAA GCAGCC ACCAGAGAAACACACGUUGUGGUACAUUACCUGGUA | 2188 |
| 216 | UUCCAGUC AGAA GUUCCG ACCAGAGAAACACACGUUGUGGUACAUUACCUGGUA | 2190 |
| 245 | UCCGGUUG AGAA GAUAAU ACCAGAGAAACACACGUUGUGGUACAUUACCUGGUA | 2192 |
| 258 | CACUGUAC AGAA GUCCGG ACCAGAGAAACACACGUUGUGGUACAUUACCUGGUA | 2194 |
| 529 | CUCUGCCC AGAA GUUCCC ACCAGAGAAACACACGUUGUGGUACAUUACCUGGUA | 2196 |
| 551 | GUCCGGGC AGAA GCUUUG ACCAGAGAAACACACGUUGUGGUACAUUACCUGGUA | 2198 |
| 554 | UCCGUCCG AGAA GCAGCU ACCAGAGAAACACACGUUGUGGUACAUUACCUGGUA | 2200 |
| 559 | AUCAGUCC AGAA GGGCAG ACCAGAGAAACACACGUUGUGGUACAUUACCUGGUA | 2202 |
| 563 | CAUUAUCA AGAA GUCCGG ACCAGAGAAACACACGUUGUGGUACAUUACCUGGUA | 2204 |
| 656 | CCACUGGC AGAA GGCUGG ACCAGAGAAACACACGUUGUGGUACAUUACCUGGUA | 2206 |
| 728 | UUGGAGAA AGAA GAGAUG ACCAGAGAAACACACGUUGUGGUACAUUACCUGGUA | 2208 |
| 746 | UGACGGAG AGAA GGCCAC ACCAGAGAAACACACGUUGUGGUACAUUACCUGGUA | 2210 |
| 822 | UGCAAUGC AGAA GGAUAG ACCAGAGAAACACACGUUGUGGUACAUUACCUGGUA | 2212 |
| 857 | CCGCAGCC AGAA GAGGGA ACCAGAGAAACACACGUUGUGGUACAUUACCUGGUA | 2214 |
| 861 | GCUGCCGC AGAA GGCUGA ACCAGAGAAACACACGUUGUGGUACAUUACCUGGUA | 2216 |
| 941 | CUGUUGAC AGAA GGAGCA ACCAGAGAAACACACGUUGUGGUACAUUACCUGGUA | 2218 |
| 1040 | GAGGUCUG AGAA GGUCCA ACCAGAGAAACACACGUUGUGGUACAUUACCUGGUA | 2220 |
| 1045 | CCCAUGAG AGAA GGUCUG ACCAGAGAAACACACGUUGUGGUACAUUACCUGGUA | 2222 |
| 1068 | AAACAGGA AGAA GGUGCA ACCAGAGAAACACACGUUGUGGUACAUUACCUGGUA | 2224 |
| 1075 | UUCUCCCA AGAA GGAAAC ACCAGAGAAACACACGUUGUGGUACAUUACCUGGUA | 2226 |
| 1106 | GAUCUGCA AGAA GAGAUG ACCAGAGAAACACACGUUGUGGUACAUUACCUGGUA | 2228 |

TABLE XVII-continued

| Mouse c-myb Hairpin ribozyme and target sequences (REVISED) |||
|---|---|---|
| 1113 | GAGCCGGG AGAA GCAGGC ACCAGAGAAACACACGUUGUGGUACAUUACCUGGUA | 2230 |
| 1120 | AGGUAGGG AGAA GGGAUC ACCAGAGAAACACACGUUGUGGUACAUUACCUGGUA | 2232 |
| 1226 | AAUCUAUA AGAA GGAGUG ACCAGAGAAACACACGUUGUGGUACAUUACCUGGUA | 2234 |
| 1340 | UUUUCACA AGAA GGUCUC ACCAGAGAAACACACGUUGUGGUACAUUACCUGGUA | 2236 |
| 1449 | AUUUCUUG AGAA GCAAGG ACCAGAGAAACACACGUUGUGGUACAUUACCUGGUA | 2238 |
| 1468 | CUUCAGGG AGAA GUAUUU ACCAGAGAAACACACGUUGUGGUACAUUACCUGGUA | 2240 |
| 1490 | GGGAGGGG AGAA GAGGUA ACCAGAGAAACACACGUUGUGGUACAUUACCUGGUA | 2242 |
| 1542 | CCAGAUUC AGAA GAUUCC ACCAGAGAAACACACGUUGUGGUACAUUACCUGGUA | 2244 |
| 1648 | GUGGUUUG AGAA GAAGAA ACCAGAGAAACACACGUUGUGGUACAUUACCUGGUA | 2246 |
| 1672 | GGUGCUCA AGAA GUUCUC ACCAGAGAAACACACGUUGUGGUACAUUACCUGGUA | 2248 |
| 1688 | CCUGCGAG AGAA GUUGGG ACCAGAGAAACACACGUUGUGGUACAUUACCUGGUA | 2250 |
| 1713 | UUUGGGGC AGAA GCCACA ACCAGAGAAACACACGUUGUGGUACAUUACCUGGUA | 2252 |
| 1740 | GUCAUUAA AGAA GAGCUU ACCAGAGAAACACACGUUGUGGUACAUUACCUGGUA | 2254 |
| 1880 | AGGCCGUC AGAA GGUCCU ACCAGAGAAACACACGUUGUGGUACAUUACCUGGUA | 2256 |
| 1887 | GGACCGGA AGAA GUCAUC ACCAGAGAAACACACGUUGUGGUACAUUACCUGGUA | 2258 |
| 1894 | CCGAGCCG AGAA GGAGGC ACCAGAGAAACACACGUUGUGGUACAUUACCUGGUA | 2260 |
| 1899 | UAUUUCCG AGAA GGACCG ACCAGAGAAACACACGUUGUGGUACAUUACCUGGUA | 2262 |
| 1926 | AGAGUUCG AGAA GAGAAC ACCAGAGAAACACACGUUGUGGUACAUUACCUGGUA | 2264 |
| 2048 | ACAACAAA AGAA GGCUCU ACCAGAGAAACACACGUUGUGGUACAUUACCUGGUA | 2266 |
| 2068 | CUGCUCUC AGAA GUUGUA ACCAGAGAAACACACGUUGUGGUACAUUACCUGGUA | 2268 |
| 2170 | UUAGGUAA AGAA GUUAUU ACCAGAGAAACACACGUUGUGGUACAUUACCUGGUA | 2270 |
| 2225 | UUUAAAAA AGAA GAUUAU ACCAGAGAAACACACGUUGUGGUACAUUACCUGGUA | 2272 |
| 2276 | AAAUACUG AGAA GUUGUA ACCAGAGAAACACACGUUGUGGUACAUUACCUGGUA | 2274 |
| 2519 | UUCAAGCA AGAA GACAAC ACCAGAGAAACACACGUUGUGGUACAUUACCUGGUA | 2276 |
| 2717 | AGUGCAUA AGAA GUUAUC ACCAGAGAAACACACGUUGUGGUACAUUACCUGGUA | 2278 |
| 2737 | AUAAAAAA AGAA GGAAUA ACCAGAGAAACACACGUUGUGGUACAUUACCUGGUA | 2280 |

| Position | Substrate | Seq. ID No. |
|---|---|---|
| 24 | AGCCCCG GCC CGCCUCGC | 2183 |
| 28 | CCGGCCC GCC UCGCCAUG | 2185 |
| 122 | AUGGGCU GCU GCCCAAAU | 2187 |
| 125 | GGCUGCU GCC CAAAUCUG | 2189 |
| 216 | CGGAACA GAC GACUGGAA | 2191 |
| 245 | AUUAUCU GCC CAACCGGA | 2193 |
| 258 | CCGGACA GAU GUACAGUG | 2195 |
| 529 | GGGAACA GAU GGGCAGAG | 2197 |
| 551 | CAAAGCU GCU GCCCGGAC | 2199 |
| 554 | AGCUGCU GCC CGGACGGA | 2201 |
| 559 | CUGCCCG GAC GGACUGAU | 2203 |
| 563 | CCGGACG GAC UGAUAAUG | 2205 |
| 656 | CCAGCCA GAC GCCAGUGG | 2207 |
| 728 | CAUCUCA GCU CUCUCCAA | 2209 |
| 746 | GUGGCCA GUC CUCCGUCA | 2211 |
| 822 | CUAUCCU GUC GCAUUGCA | 2213 |
| 857 | UCCCUCA GCC GGCUGCGG | 2215 |
| 861 | UCAGCCG GCU GCGGCAGC | 2217 |
| 941 | UGCUCCU GAU GUCAACAG | 2218 |
| 1040 | UGGACCA GAC CAGACCUC | 2221 |
| 1045 | CAGACCA GAC CUCAUGGG | 2223 |
| 1068 | UGCACCU GUU UCCUGUUU | 2225 |
| 1075 | GUUUCCU GUU UGGGAGAA | 2227 |
| 1106 | CAUCUCU GCC UGCAGAUC | 2229 |
| 1113 | GCCUGCA GAU CCCGGCUC | 2231 |
| 1120 | GAUCCCG GCU CCCUACCU | 2233 |
| 1226 | CACUCCA GUU UAUAGAUU | 2235 |
| 1340 | GAGACCA GAC UGUGAAAA | 2237 |
| 1449 | CCUUGCA GCU CAAGAAAU | 2239 |
| 1468 | AAAUACG GUC CCCUGAAG | 2241 |
| 1490 | UACCUCA GAC CCCCUCCC | 2243 |
| 1542 | GGAAUCG GAU GAAUCUGG | 2245 |
| 1648 | UUCUUCU GCU CAAACCAC | 2247 |
| 1672 | GAGAACA GCC UGAGCACC | 2249 |
| 1688 | CCCAACU GUU CUCGCAGG | 2251 |
| 1713 | UGUGGCA GAU GCCCAAA | 2253 |
| 1740 | AAGCUCU GUU UUAAUGAC | 2255 |
| 1880 | AGGACCA GAU GACGGCCU | 2257 |
| 1887 | GAUGACG GCC UCCGGUCC | 2259 |
| 1894 | GCCUCCG GUC CGGCUCGG | 2261 |
| 1899 | CGGUCCG GCU CGGAAAUA | 2263 |
| 1926 | GUUCUCA GCU CGAACUCU | 2265 |
| 2048 | AGAGCCU GAU UUUGUUGU | 2267 |
| 2068 | UACAACA GUU GAGAGCAG | 2269 |
| 2170 | AAUAACA GUC UUACCUAA | 2271 |
| 2225 | AUAAUCA GAU UUUUUAAA | 2273 |
| 2276 | UACAACA GAU CAGUAUUU | 2275 |
| 2519 | GUUGUCA GCU UGCUUGAA | 2277 |

TABLE XVII-continued

Mouse c-myb Hairpin ribozyme and target sequences (REVISED)

| | | |
|---|---|---|
| 2717 | GAUAACG GAC UAUGCACU | 2279 |
| 2737 | UAUUCCA GAC UUUUUUAU | 2281 |

TABLE XVIII

Porcine c-myb (region A) Hammerhead Ribozyme and Target Sequence (266 bp; nt. 458 start; Human numbering system) (REVISED)

| Position | HH Ribozyme | Seq. ID No. | Substrate | Seq. ID No. |
|---|---|---|---|---|
| 467 | CCCUUGAU CUGAUGAGGCCGAAAGGCCGAA AGAUNAGG | 2282 | CCUNAUCUC AUCAAGGG | 2283 |
| 470 | GGACCCUU CUGAUGAGGCCGAAAGGCCGAA AUGAGAUN | 2284 | NAUCUCAUC AAGGGUCC | 2285 |
| 477 | GGUCCAAG CUGAUGAGGCCGAAAGGCCGAA ACCCUUGA | 2286 | UCAAGGGUC CUUGGACC | 2287 |
| 480 | UUUGGUCC CUGAUGAGGCCGAAAGGCCGAA AGGACCCU | 2288 | AGGGUCCUU GGACCAAA | 2289 |
| 498 | CACUCUCU CUGAUGAGGCCGAAAGGCCGAA AUCUUCUU | 2290 | AAGAAGAUC AGAGAGUG | 2291 |
| 509 | ACAAGCUC CUGAUGAGGCCGAAAGGCCGAA AUCACUCU | 2292 | AGAGUGAUA GAGCUUGU | 2293 |
| 515 | UUCUGUAC CUGAUGAGGCCGAAAGGCCGAA AGCUCUAU | 2294 | AUAGAGCUU GUACAGAA | 2295 |
| 518 | UAUUUCUG CUGAUGAGGCCGAAAGGCCGAA ACAAGCUC | 2296 | GAGCUUGUA CAGAAAUA | 2297 |
| 526 | UCGGACCG CUGAUGAGGCCGAAAGGCCGAA AUUUCUGU | 2298 | ACAGAAAUA CGGUCCGA | 2299 |
| 531 | ACGUUUCG CUGAUGAGGCCGAAAGGCCGAA ACCGUAUU | 2300 | AAUACGGUC CGAAACGU | 2301 |
| 540 | AACAGACC CUGAUGAGGCCGAAAGGCCGAA ACGUUUCG | 2302 | CGAAACGUU GGUCUGUU | 2303 |
| 544 | CAAUAACA CUGAUGAGGCCGAAAGGCCGAA ACCAACGU | 2304 | ACGUUGGUC UGUUAUUG | 2305 |
| 548 | UUGGCAAU CUGAUGAGGCCGAAAGGCCGAA ACAGACCA | 2306 | UGGUCUGUU AUUGCCAA | 2307 |
| 549 | CUUGGCAA CUGAUGAGGCCGAAAGGCCGAA AACAGACC | 2308 | GGUCUGUUA UUGCCAAG | 2309 |
| 551 | UGCUUGGC CUGAUGAGGCCGAAAGGCCGAA AUAACAGA | 2310 | UCUGUUAUU GCCAAGCA | 2311 |
| 562 | UCCCCUUU CUGAUGAGGCCGAAAGGCCGAA AGUGCUUG | 2312 | CAAGCACUU AAAGGGGA | 2313 |
| 563 | CUCCCCUU CUGAUGAGGCCGAAAGGCCGAA AAGUGCUU | 2314 | AAGCACUUA AGGGGAG | 2315 |
| 575 | UGUUUUCC CUGAUGAGGCCGAAAGGCCGAA AUUCUCCC | 2316 | GGGAGAAUU GGAAAACA | 2317 |
| 588 | CCUCUCCC CUGAUGAGGCCGAAAGGCCGAA ACAUUGUU | 2318 | AACAAUGUA GGGAGAGG | 2319 |
| 603 | CAAGUGGU CUGAUGAGGCCGAAAGGCCGAA AUGCCACC | 2320 | GGUGGCAUA ACCACUUG | 2321 |
| 610 | CUGGAUUC CUGAUGAGGCCGAAAGGCCGAA AGUGGUUA | 2322 | UAACCACUU GAAUCCAG | 2323 |
| 615 | AACUUCUG CUGAUGAGGCCGAAAGGCCGAA AUUCAAGU | 2324 | ACUUGAAUC CAGAAGUU | 2325 |
| 623 | GUUUUCUU CUGAUGAGGCCGAAAGGCCGAA ACUUCUGG | 2326 | CCAGAAGUU AAGAAAAC | 2327 |
| 624 | GGUUUUCU CUGAUGAGGCCGAAAGGCCGAA AACUUCUG | 2328 | CAGAAGUUA AGAAAACC | 2329 |
| 634 | CUGUCCAG CUGAUGAGGCCGAAAGGCCGAA AGGUUUUC | 2330 | GAAAACCUC CUGGACAG | 2331 |
| 659 | UGGUAAAU CUGAUGAGGCCGAAAGGCCGAA AUUCUGUC | 2332 | GACAGAAUU AUUUACCA | 2333 |
| 660 | CUGGUAAA CUGAUGAGGCCGAAAGGCCGAA AAUUCUGU | 2334 | ACAGAAUUA UUUACCAG | 2335 |
| 662 | GCCUGGUA CUGAUGAGGCCGAAAGGCCGAA AUAAUUCU | 2336 | AGAAUUAUU UACCAGGC | 2337 |
| 663 | UGCCUGGU CUGAUGAGGCCGAAAGGCCGAA AAUAAUUC | 2338 | GAAUUAUUU ACCAGGCA | 2339 |
| 664 | GUGCCUGG CUGAUGAGGCCGAAAGGCCGAA AAAUAAUU | 2340 | AAUUAUUUA CCAGGCAC | 2341 |
| 704 | AGCUUUGC CUGAUGAGGCCGAAAGGCCGAA AUUUCCGC | 2342 | GCGGAAAUC GCAAAGCU | 2343 |
| 713 | CCAGGCAG CUGAUGAGGCCGAAAGGCCGAA AGCUUUGC | 2344 | GCAAAGCUA CUGCCUGG | 2345 |

TABLE XIX

Porcine c-myb (region B) Hammerhead Ribozyme and Target Sequence (308 bp; nt. 1386 start; Human numbering system) (REVISED)

| Position | Ribozyme | Seq. ID No. | Substrate | Seq. ID No. |
|---|---|---|---|---|
| 1394 | GUGUUUAA CUGAUGAGGCCGAAAGGCCGAA AAAGAAUC | 2346 | GAUUCUUUC UUAAACAC | 2347 |
| 1396 | AAGUGUUU CUGAUGAGGCCGAAAGGCCGAA AGAAAGAA | 2348 | UUCUUUCUU AAACACUU | 2349 |
| 1397 | GAAGUGUU CUGAUGAGGCCGAAAGGCCGAA AAGAAAGA | 2350 | UCUUUCUUA AACACUUC | 2351 |
| 1404 | GUUAUGG CUGAUGAGGCCGAAAGGCCGAA AGUGUUUA | 2352 | UAAACACUU CCAAUAAC | 2353 |
| 1405 | GGUUAUUG CUGAUGAGGCCGAAAGGCCGAA AAGUGUUU | 2354 | AAACACUUC CAAUAACC | 2355 |
| 1410 | UUCAUGGU CUGAUGAGGCCGAAAGGCCGAA AUUGGAAG | 2356 | CUUCCAAUA ACCAUGAA | 2357 |
| 1423 | CCAAGUCU CUGAUGAGGCCGAAAGGCCGAA AGUUUUCA | 2358 | UGAAAACUU AGACUUGG | 2359 |
| 1424 | UCCAAGUC CUGAUGAGGCCGAAAGGCCGAA AAGUUUUC | 2360 | GAAAACUUA GACUUGGA | 2361 |
| 1429 | GCAUUCC CUGAUGAGGCCGAAAGGCCGAA AGUCUAAG | 2362 | CUUAGACUU GGAAAUGC | 2363 |
| 1440 | CGUUAAAG CUGAUGAGGCCGAAAGGCCGAA AGGCAUUU | 2364 | AAAUGCCUU CUUUAACG | 2365 |
| 1441 | ACGUUAAA CUGAUGAGGCCGAAAGGCCGAA AAGGCAUU | 2366 | AAUGCCUUC UUUAACGU | 2367 |
| 1443 | GGACGUUA CUGAUGAGGCCGAAAGGCCGAA AGAAGGCA | 2368 | UGCCUUCUU UAACGUCC | 2369 |
| 1444 | UGGACGUU CUGAUGAGGCCGAAAGGCCGAA AAGAAGGC | 2370 | GCCUUCUUU AACGUCCA | 2371 |
| 1445 | GUGGACGU CUGAUGAGGCCGAAAGGCCGAA AAAGAAGG | 2372 | CCUUCUUUA ACGUCCAC | 2373 |
| 1450 | GAGGCGUG CUGAUGAGGCCGAAAGGCCGAA ACGUUAAA | 2374 | UUUAACGUC CACGCCUC | 2375 |
| 1458 | ACCACUGA CUGAUGAGGCCGAAAGGCCGAA AGGCGUGG | 2376 | CCACGCCUC UCAGUGGU | 2377 |
| 1460 | UGACCACU CUGAUGAGGCCGAAAGGCCGAA AGAGGCGU | 2378 | ACGCCUCUC AGUGGUCA | 2379 |
| 1467 | CAAUUUGU CUGAUGAGGCCGAAAGGCCGAA ACCACUGA | 2380 | UCAGUGGUC ACAAAUUG | 2381 |
| 1474 | UAACAGUC CUGAUGAGGCCGAAAGGCCGAA AUUUGUGA | 2382 | UCACAAAUU GACUGUUA | 2383 |
| 1481 | GGUGUUGU CUGAUGAGGCCGAAAGGCCGAA ACAGUCAA | 2384 | UUGACUGUU ACAACACC | 2385 |
| 1482 | UGGUGUUG CUGAUGAGGCCGAAAGGCCGAA AACAGUCA | 2386 | UGACUGUUA CAACACCA | 2387 |

TABLE XIX-continued

Porcine c-myb (region B) Hammerhead Ribozyme and Target Sequence (308 bp; nt. 1386 start; Human numbering system) (REVISED)

| Position | Ribozyme | Seq. ID No. | Substrate | Seq. ID No. |
|---|---|---|---|---|
| 1492 | CUCUAUGA CUGAUGAGGCCGAAAGGCCGAA AUGGUGUU | 2388 | AACACCAUU UCAUAGAG | 2389 |
| 1493 | UCUCUAUG CUGAUGAGGCCGAAAGGCCGAA AAUGGUGU | 2390 | ACACCAUUU CAUAGAGA | 2391 |
| 1494 | GUCUCUAU CUGAUGAGGCCGAAAGGCCGAA AAAUGGUG | 2392 | CACCAUUUC AUAGAGAC | 2393 |
| 1497 | CUGGUCUC CUGAUGAGGCCGAAAGGCCGAA AUGAAAUG | 2394 | CAUUUCAUA GAGACCAG | 2395 |
| 1530 | AAAAUAUG CUGAUGAGGCCGAAAGGCCGAA AUUUUCCU | 2396 | AGGAAAAUA CAUAUUUU | 2397 |
| 1534 | UUCAAAAA CUGAUGAGGCCGAAAGGCCGAA AUGUAUUU | 2398 | AAAUACAUA UUUUUGAA | 2399 |
| 1536 | AGUUCAAA CUGAUGAGGCCGAAAGGCCGAA AUAUGUAU | 2400 | AUACAUAUU UUUGAACU | 2401 |
| 1537 | GAGUUCAA CUGAUGAGGCCGAAAGGCCGAA AAUAUGUA | 2402 | UACAUAUUU UUGAACUC | 2403 |
| 1538 | GGAGUUCA CUGAUGAGGCCGAAAGGCCGAA AAAUAUGU | 2404 | ACAUAUUUU UGAACUCC | 2405 |
| 1539 | CGGAGUUC CUGAUGAGGCCGAAAGGCCGAA AAAAUAUG | 2406 | CAUAUUUUU GAACUCCG | 2407 |
| 1545 | GAUAGCCG CUGAUGAGGCCGAAAGGCCGAA AGUUCAAA | 2408 | UUUGAACUC CGGCUAUC | 2409 |
| 1551 | CCUUUUGA CUGAUGAGGCCGAAAGGCCGAA AGCCGGAG | 2410 | CUCCGGCUA UCAAAAGG | 2411 |
| 1553 | GACCUUUU CUGAUGAGGCCGAAAGGCCGAA AUAGCCGG | 2412 | CCGGCUAUC AAAAGGUC | 2413 |
| 1561 | CCAGGAUU CUGAUGAGGCCGAAAGGCCGAA ACCUUUUG | 2414 | CAAAAGGUC AAUCCUGG | 2415 |
| 1565 | CUUUCCAG CUGAUGAGGCCGAAAGGCCGAA AUUGACCU | 2416 | AGGUCAAUC CUGGAAAG | 2417 |
| 1576 | UUCUUGGA CUGAUGAGGCCGAAAGGCCGAA AGCUUUCC | 2418 | GGAAAGCUC UCCAAGAA | 2419 |
| 1578 | AGUUCUUG CUGAUGAGGCCGAAAGGCCGAA AGAGCUUU | 2420 | AAAGCUCUC CAAGAACU | |
| 1587 | CGGUGUAG CUGAUGAGGCCGAAAGGCCGAA AGUUCUUG | 2422 | CAAGAACUC CUACACCG | 2423 |
| 1590 | GAACGGUG CUGAUGAGGCCGAAAGGCCGAA AGGAGUUC | 2424 | GAACUCCUA CACCGUUC | 2425 |
| 1597 | CAUGUUUG CUGAUGAGGCCGAAAGGCCGAA ACGGUGUA | 2426 | UACACCGUU CAAACAUG | 2427 |
| 1598 | GCAUGUUU CUGAUGAGGCCGAAAGGCCGAA AACGGUGU | 2428 | ACACCGUUC AAACAUGC | 2429 |
| 1610 | UGAGCUGC CUGAUGAGGCCGAAAGGCCGAA AGUGCAUG | 2430 | CAUGCACUC GCAGCUCA | 2431 |
| 1617 | AAUUCUU CUGAUGAGGCCGAAAGGCCGAA AGCUGCGA | 2432 | UCGCAGCUC AAGAAAUU | 2433 |
| 1625 | CCAUAUUU CUGAUGAGGCCGAAAGGCCGAA AUUUCUUG | 2434 | CAAGAAAUU AAAUAUGG | 2435 |
| 1626 | ACCAUAUU CUGAUGAGGCCGAAAGGCCGAA AAUUUCUU | 2436 | AAGAAAUUA AAUAUGGU | 2437 |
| 1630 | GGGGACCA CUGAUGAGGCCGAAAGGCCGAA AUUUAAUU | 2438 | AAUUAAAUA UGGUCCCC | 2439 |
| 1635 | CUUCAGGG CUGAUGAGGCCGAAAGGCCGAA ACCAUAUU | 2440 | AAUAUGGUC CCCUGAAG | 244i |
| 1649 | GUCUGAGG CUGAUGAGGCCGAAAGGCCGAA AGCAUCUU | 2442 | AAGAUGCUA CCUCAGAC | 2443 |
| 1653 | UGGUGUCU CUGAUGAGGCCGAAAGGCCGAA AGGUAGCA | 2444 | UGCUACCUC AGACACCA | 2445 |
| 1663 | CUAAAUGA CUGAUGAGGCCGAAAGGCCGAA AUGGUGUC | 2446 | GACACCAUC UCAUUUAG | 2447 |
| 1665 | UACUAAAU CUGAUGAGGCCGAAAGGCCGAA AGAUGGUG | 2448 | CACCAUCUC AUUUAGUA | 2449 |
| 1668 | UUCUACUA CUGAUGAGGCCGAAAGGCCGAA.AUGAGAUG | 2450 | CAUCUCAUU UAGUAGAA | 2451 |
| 1669 | CUUCUACU CUGAUGAGGCCGAAAGGCCGAA AAUGAGAU | 2452 | AUCUCAUUU AGUAGAAG | 2453 |
| 1670 | UCUUCUAC CUGAUGAGGCCGAAAGGCCGAA AAAUGAGA | 2454 | UCUCAUUUA GUAGAAGA | 2455 |
| 1673 | AGGUCUUC CUGAUGAGGCCGAAAGGCCGAA ACUAAAUG | 2456 | CAUUUAGUA GAAGACCU | 2457 |

TABLE XX

Porcine c-myb (Region B) Hairpin Ribozyme and Target Sequence (308 bp; nt. 1386 start; Human numbering system) (REVISED)

| Position | Hairpin Ribozyme | Seq. ID No. | Substrate | Seq. ID No. |
|---|---|---|---|---|
| 1504 | UUUUCACA AGAA GGUCUC ACCAGAGAAACACACGUUGUGGUACAUUACCUGGUA | 2456 | GAGACCA GAC UGUGAAAA | 2459 |
| 1594 | CAUGUUUC AGAA GUGUAG ACCAGAGAAACACACGUUGUGGUACAUUACCUGGUA | 2460 | CUACACC GUU CAAACAUG | 2461 |
| 1613 | AUUUCUUG AGAA GCGAGU ACCAGAGAAACACACGUUGUGGUACAUUACCUGGUA | 2462 | ACUCGCA GCU CAAGAAAU | 2463 |

TABLE XXI

Porcine c-myb (Region A) Hairpin Ribozyme and Target Sequence (266 bp; nt. 458 start; Human numbering system) (REVISED)

| Position | RZ | Seq. ID No. |
|---|---|---|
| 528 | ACGUUUCG AGAA GUAUUU ACCAGAGAAACACACGUUGUGGUACAUUACCUGGUA | 2464 |
| 690 | UUCCGCCC AGAA GUUCCC ACCAGAGAAACACACGUUGUGGUACAUUACCUGGUA | 2466 |

| Position | Substrate | Seq. ID No. |
|---|---|---|
| 528 | AAAUACG GUC CGAAACGU | 2465 |
| 690 | GGGAACA GAU GGGCGGAA | 2467 |

TABLE XXII

Rat c-myb (Region A) Hammerhead Ribozyme and Target Sequences (282 bp; nt. 428 start; human numbering system) (REVISED)

| Position | HH Ribozyme | Seq. ID No. | Substrate | Seq. ID No. |
|---|---|---|---|---|
| 467 | CCUUUGAU CUGAUGAGGCCGAAAGGCCGAA AGCUCAGG | 2468 | CCUGAGCUC AUCAAAGG | 2469 |
| 470 | GGACCUUU CUGAUGAGGCCGAAAGGCCGAA AUGAGCUC | 2470 | GAGCUCAUC AAAGGUCC | 2471 |
| 477 | GGUCCAGG CUGAUGAGGCCGAAAGGCCGAA ACCUUUGA | 2472 | UCAAAGGUC CCUGGACC | 2473 |
| 498 | CACUCUUU CUGAUGAGGCCGAAAGGCCGAA AUCUUCUU | 2474 | AAGAAGAUC AAAGAGUG | 2475 |
| 509 | ACAAGCUC CUGAUGAGGCCGAAAGGCCGAA AUCACUCU | 2476 | AGAGUGAUA GAGCUUGU | 2477 |
| 515 | UUCUGGAC CUGAUGAGGCCGAAAGGCCGAA AGCUCUAU | 2478 | AUAGAGCUU GUCCAGAA | 2479 |
| 518 | UAUUUCUG CUGAUGAGGCCGAAAGGCCGAA ACAAGCUC | 2480 | GAGCUUGUC CAGAAAUA | 2481 |
| 526 | UCGGACCG CUGAUGAGGCCGAAAGGCCGAA AUUUCUGG | 2482 | CCAGAAAUA CGGUCCGA | 2483 |
| 531 | GCGCUUCG CUGAUGAGGCCGAAAGGCCGAA ACCGUAUU | 2484 | AAUACGGUC CGAAGCGC | 2485 |
| 544 | CAAUAACA CUGAUGAGGCCGAAAGGCCGAA ACCAGCGC | 2486 | GCGCUGGUC UGUUAUUG | 2487 |
| 548 | UUGGCAAU CUGAUGAGGCCGAAAGGCCGAA ACAGACCA | 2488 | UGGUCUGUU AUUGCCAA | 2489 |
| 549 | CUUGGCAA CUGAUGAGGCCGAAAGGCCGAA AACAGACC | 2490 | GGUCUGUUA UUGCCAAG | 2491 |
| 551 | UGCUUGGC CUGAUGAGGCCGAAAGGCCGAA AUAACAGA | 2492 | UCUGUUAUU GCCAAGCA | 2493 |
| 562 | UCCCUUUU CUGAUGAGGCCGAAAGGCCGAA AGUGCUUG | 2494 | CAAGCACUU AAAAGGGA | 2495 |
| 563 | CUCCCUUU CUGAUGAGGCCGAAAGGCCGAA AAGUGCUU | 2496 | AAGCACUUA AAAGGGAG | 2497 |
| 575 | UGUUUUCC CUGAUGAGGCCGAAAGGCCGAA AUUCUCCC | 2498 | GGGAGAAUU GGAAAACA | 2499 |
| 588 | CCUCUCCC CUGAUGAGGCCGAAAGGCCGAA ACAUUGUU | 2500 | AACAAUGUC GGGAGAGG | 2501 |
| 609 | UGGAUUCA CUGAUGAGGCCGAAAGGCCGAA AUGGUUGU | 2502 | ACAACCAUU UGAAUCCA | 2503 |
| 610 | CUGGAUUC CUGAUGAGGCCGAAAGGCCGAA AAUGGUUG | 2504 | CAACCAUUU GAAUCCAG | 2505 |
| 615 | AACUUCUG CUGAUGAGGCCGAAAGGCCGAA AUUCAAAU | 2506 | AUUUGAAUC CAGAAGUU | 2507 |
| 623 | GUUUUCUU CUGAUGAGGCCGAAAGGCCGAA ACUUCUGG | 2508 | CCAGAAGUU AAGAAAAC | 2509 |
| 624 | GGUUUUCU CUGAUGAGGCCGAAAGGCCGAA AACUUCUG | 2510 | CAGAAGUUA AGAAAACC | 2511 |
| 634 | CUGUCCAU CUGAUGAGGCCGAAAGGCCGAA AGGUUUUC | 2512 | GAAAACCUC AUGGACAG | 2513 |
| 659 | UGAUAAAU CUGAUGAGGCCGAAAGGCCGAA AUUCUGUC | 2514 | GACAGAAUC AUUUAUCA | 2515 |
| 662 | GCCUGAUA CUGAUGAGGCCGAAAGGCCGAA AUGAUUCU | 2516 | AGAAUCAUU UAUCAGGC | 2517 |
| 663 | UGCCUGAU CUGAUGAGGCCGAAAGGCCGAA AAUGAUUC | 2518 | GAAUCAUUU AUCAGGCA | 2519 |
| 664 | GUGCCUGA CUGAUGAGGCCGAAAGGCCGAA AAAUGAUU | 2520 | AAUCAUUUA UCAGGCAC | 2521 |
| 666 | GUGUGCCU CUGAUGAGGCCGAAAGGCCGAA AUAAAUGA | 2522 | UCAUUUAUC AGGCACAC | 2523 |

TABLE XXIII

Rat c-myb (Region B) Hammerhead Ribozyme and Target Sequences (262 bp; nt. 1421 start; human numbering system) (REVISED)

| Position | Ribozyme | Seq. ID No. | Substrate | Seq. ID No. |
|---|---|---|---|---|
| 1429 | GCGUAUCU CUGAUGAGGCCGAAAGGCCGAA AGCCCGAG | 2524 | CUCGGGCUU AGAUACGC | 2525 |
| 1430 | GGCGUAUC CUGAUGAGGCCGAAAGGCCGAA AAGCCCGA | 2526 | UCGGGCUUA GAUACGCC | 2527 |
| 1434 | AGUAGGCG CUGAUGAGGCCGAAAGGCCGAA AUCUAAGC | 2528 | GCUUAGAUA CGCCUACU | 2529 |
| 1440 | GGGUAAAG CUGAUGAGGCCGAAAGGCCGAA AGGCGUAU | 2530 | AUACGCCUA CUUUACCC | 2531 |
| 1443 | GGAGGGUA CUGAUGAGGCCGAAAGGCCGAA AGUAGGCG | 2532 | CGCCUACUU UACCCUCC | 2533 |
| 1444 | UGGAGGGU CUGAUGAGGCCGAAAGGCCGAA AAGUAGGC | 2534 | GCCUACUUU ACCCUCCA | 2535 |
| 1445 | GUGGAGGG CUGAUGAGGCCGAAAGGCCGAA AAAGUAGG | 2536 | CCUACUUUA CCCUCCAC | 2537 |
| 1450 | GAGGCGUG CUGAUGAGGCCGAAAGGCCGAA AGGGUAAA | 2538 | UUUACCCUC CACGCCUC | 2539 |
| 1458 | ACCAAUGA CUGAUGAGGCCGAAAGGCCGAA AGGCGUGG | 2540 | CCACGCCUC UCAUUGGU | 2541 |
| 1460 | UGACCAAU CUGAUGAGGCCGAAAGGCCGAA AGAGGCGU | 2542 | ACGCCUCUC AUUGGUCA | 2543 |
| 1463 | UUGUGACC CUGAUGAGGCCGAAAGGCCGAA AUGAGAGG | 2544 | CCUCUCAUU GGUCACAA | 2545 |
| 1467 | CAGUUUGU CUGAUGAGGCCGAAAGGCCGAA ACCAAUGA | 2546 | UCAUUGGUC ACAAACUG | 2547 |
| 1485 | GUCUCGGU CUGAUGAGGCCGAAAGGCCGAA ACACGGUG | 2548 | CACCGUGUC ACCGAGAC | 2549 |
| 1509 | UUCCUUUU CUGAUGAGGCCGAAAGGCCGAA AGUUUUCA | 2550 | UGAAAACUN AAAAGGAA | 2551 |
| 1522 | UAAAGAUN CUGAUGAGGCCGAAAGGCCGAA AGUUUUCC | 2552 | GGAAAACUC NAUCUUUA | 2553 |
| 1526 | GUUCUAAA CUGAUGAGGCCGAAAGGCCGAA AUNGAGUU | 2554 | AACUCNAUC UUUAGAAC | 2555 |
| 1528 | GAGUUCUA CUGAUGAGGCCGAAAGGCCGAA AGAUNGAG | 2556 | CUCNAUCUU UAGAACUC | 2557 |
| 1529 | GGAGUUCU CUGAUGAGGCCGAAAGGCCGAA AAGAUNGA | 2558 | UCNAUCUUU AGAACUCC | 2559 |
| 1530 | UGGAGUUC CUGAUGAGGCCGAAAGGCCGAA AAAGAUNG | 2560 | CNAUCUUUA GAACUCCA | 2561 |
| 1536 | GAUAGCUG CUGAUGAGGCCGAAAGGCCGAA AGUUCUAA | 2562 | UUAGAACUC CAGCUAUC | 2563 |
| 1542 | CCUUUUGA CUGAUGAGGCCGAAAGGCCGAA AGCUGGAG | 2564 | CUCCAGCUA UCAAAAGG | 2565 |
| 1544 | NACCUUUU CUGAUGAGGCCGAAAGGCCGAA AUAGCUGG | 2566 | CCAGCUAUC AAAAGGUN | 2567 |
| 1552 | CGAGGAUU CUGAUGAGGCCGAAAGGCCGAA ACCUUUUG | 2568 | CAAAAGGUN AAUCCUCG | 2569 |
| 1556 | CUUUCGAG CUGAUGAGGCCGAAAGGCCGAA AUUNACCU | 2570 | AGGUNAAUC CUCGAAAG | 2571 |
| 1559 | GAGCUUUC CUGAUGAGGCCGAAAGGCCGAA AGGAUUNA | 2572 | UNAAUCCUC GAAAGCUC | 2573 |
| 1567 | UUCUGGGA CUGAUGAGGCCGAAAGGCCGAA AGCUUUCG | 2574 | CGAAAGCUC UCCCAGAA | 2575 |
| 1569 | AGUUCUGG CUGAUGAGGCCGAAAGGCCGAA AGAGCUUU | 2576 | AAAGCUCUC CCAGAACU | 2577 |
| 1578 | UGGUGUGG CUGAUGAGGCCGAAAGGCCGAA AGUUCUGG | 2578 | CCAGAACUC CCACACCA | 2579 |
| 1588 | CAUGUUUG CUGAUGAGGCCGAAAGGCCGAA AUGGUGUG | 2580 | CACACCAUU CAAACAUG | 2581 |
| 1589 | GCAUGUUU CUGAUGAGGCCGAAAGGCCGAA AAUGGUGU | 2582 | ACACCAUUC AAACAUGC | 2583 |
| 1608 | AAUUUCUU CUGAUGAGGCCGAAAGGCCGAA AGCUGCCA | 2584 | UGGCAGCUC AAGAAAUU | 2585 |
| 1616 | CCGUAUUU CUGAUGAGGCCGAAAGGCCGAA AUUUCUUG | 2586 | CAAGAAAUU AAAUACGG | 2587 |
| 1617 | ACCGUAUU CUGAUGAGGCCGAAAGGCCGAA AAUUUCUU | 2588 | AAGAAAUUA AAUACGGU | 2589 |

TABLE XXIII-continued

Rat c-myb (Region B) Hammerhead Ribozyme and Target
Sequences (262 bp; nt. 1421 start; human numbering system) (REVISED)

| Position | Ribozyme | Seq. ID No. | Substrate | Seq. ID No. |
|---|---|---|---|---|
| 1621 | GGGGACCG CUGAUGAGGCCGAAAGGCCGAA AUUUAAUU | 2590 | AAUUAAAUA CGGUCCCC | 2591 |
| 1626 | CUUCAGGG CUGAUGAGGCCGAAAGGCCGAA ACCGUAUU | 2592 | AAUACGGUC CCCUGAAG | 2593 |
| 1640 | GUCUNAGG CUGAUGAGGCCGAAAGGCCGAA AGCAUCUU | 2594 | AAGAUGCUA CCUNAGAC | 2595 |
| 1644 | GGGGGUCU CUGAUGAGGCCGAAAGGCCGAA AGGUAGCA | 2596 | UGCUACCUN AGACCCCC | 2597 |
| 1654 | CUACAUNA CUGAUGAGGCCGAAAGGCCGAA AGGGGGUC | 2598 | GACCCCCUN UNAUGUAG | 2599 |
| 1656 | NACUACAU CUGAUGAGGCCGAAAGGCCGAA ANAGGGGG | 2600 | CCCCCUNUN AUGUAGUN | 2601 |
| 1661 | UNUNNNAC CUGAUGAGGCCGAAAGGCCGAA ACAUNANA | 2602 | UNUNAUGUA GUNNNANA | 2603 |
| 1664 | AGGUNUNN CUGAUGAGGCCGAAAGGCCGAA ACUACAUN | 2604 | NAUGUAGUN NNANACCU | 2605 |
| 1673 | ACAUCNUG CUGAUGAGGCCGAAAGGCCGAA AGGUNUNN | 2606 | NNANACCUN CANGAUGU | 2607 |

TABLE XXIV

Rat c-myb (Region A) Hairpin Ribozyme and Target Sequence (282 bp; nt. 428 start;
human numbering system) (REVISED)

| Position | RZ | Seq. ID No. |
|---|---|---|
| 528 | GCGCUUCG AGAA GUAUUU ACCAGAGAAACACACGUUGUGGUACAUUACCUGGUA | 2608 |
| 690 | UUCUGCCC AGAA GUUUCC ACCAGAGAAACACACGUUGUGGUACAUUACCUGGUA | 2610 |

| | Position | Substrate | Seq. ID No. |
|---|---|---|---|
| | 528 | AAAUACG GUC CGAAGCGC | 2609 |
| | 690 | GGAAACA GAU GGGCAGAA | 2611 |

TABLE XXV

Rat c-myb (Region B) Hairpin Ribozyme and Target Sequence (262 bp; nt. 1421 start;
human numbering system) (REVISED)

| Position | RZ | Seq. ID No. | Substrate | Seq. ID No. |
|---|---|---|---|---|
| 1495 | UUUUCACA AGAA GGUCUC ACCAGAGAAACACACGUUGUGGUACAUUACCUGGUA | 2612 | GAGACCA GAC UGUGAAAA | 2613 |
| 1604 | AUUUCUUG AGAA GCCAGG ACCAGAGAAACACACGUUGUGGUACAUUACCUGGUA | 2614 | CCUGGCA GCU CAAGAAAU | 2615 |
| 1623 | CUUCAGGG AGAA GUAUUU ACCAGAGAAACACACGUUGUGGUACAUUACCUGGUA | 2616 | AAAUACG GUC CCCUGAAG | 2617 |

---

We claim:

1. An enzymatic RNA molecule for the specific cleavage of c-myb RNA, wherein said enzymatic RNA molecule comprises an oligonucleotide having a 2'-5'-linked adenylate residue having a 5'-phosphate.

2. The enzymatic RNA molecule of claim 1, wherein said enzymatic RNA molecule is complementarity to c-myb RNA at a region selected from the group consisting of: SEQ ID Nos. 1–100, 130–148, and even numbered SEQ ID Nos. from SEQ ID No. 170 to 1224.

3. The enzymatic RNA molecule of claim 1, wherein said enzymatic RNA molecule is complementarity to c-myb RNA at a region other than the region consisting of nucleotides 111–140.

* * * * *

UNITED STATES PATENT AND TRADEMARK OFFICE
CERTIFICATE OF CORRECTION

PATENT NO. : 5,817,796

DATED : October 6, 1998

INVENTOR(S) : Dan T. Stinchcomb, et al.

It is certified that error appears in the above-identified patent and that said Letters Patent is hereby corrected as shown below:

Column 8, line 61, after "575." delete "A)" and insert --9A1-4)--.

Column 9, line 12, after "9A" insert --1-4--.

Column 20, line 43, after "9A" insert --1-4--

Signed and Sealed this

Twelfth Day of October, 1999

*Attest:*

Q. TODD DICKINSON

*Attesting Officer*   Acting Commissioner of Patents and Trademarks

SEQUENCE LISTING ( 1 ) GENERAL INFORMATION:

( i i i ) NUMBER OF SEQUENCES: 2627

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGCGGCAGCG   CCCUGCCGAC   GCCGGGG      27

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single (D) TOPOLOGY: linear (xi) SEQUENCE DESCRIPTION: SEQ ID NO:2:

CCGCGGCUCU CGGC  14

(2) INFORMATION FOR SEQ ID NO:3:

(i) SEQUENCE CHARACTERISTICS:
(A) LENGTH: 13 base pairs
(B) TYPE: nucleic acid
(C) STRANDEDNESS: single
(D) TOPOLOGY: linear (xi) SEQUENCE DESCRIPTION: SEQ ID NO:3:

GCCAUGGCCC GAA  13

(2) INFORMATION FOR SEQ ID NO:4:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:4:

CGGCACAGCA UAUAUAGCAG UGACGAGGA  29

(2) INFORMATION FOR SEQ ID NO:5:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:5:

GACUUUGAGA UGUGUGACCA UGACUAUGAU GGG  33

(2) INFORMATION FOR SEQ ID NO:6:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:6:

CUGGAAAGCG UC  12

(2) INFORMATION FOR SEQ ID NO:7:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:7:

GGAAGAGGAU GAAAAACUGA AGAAG  25

(2) INFORMATION FOR SEQ ID NO:8:

(i) SEQUENCE CHARACTERISTICS:
(A) LENGTH: 26 base pairs
(B) TYPE: nucleic acid
(C) STRANDEDNESS: single
(D) TOPOLOGY: linear ( x i ) SEQUENCE DESCRIPTION: SEQ ID NO:8:

GAAGAACUGG UGGAACAGAA UGGAAC 26

( 2 ) INFORMATION FOR SEQ ID NO:9:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

CUGGAAAGUU AUUGCCAA 18

( 2 ) INFORMATION FOR SEQ ID NO:10:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

CCCGAAUCGA ACAGAUGUGC AG 22

( 2 ) INFORMATION FOR SEQ ID NO:11:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

GAAAGUACUA AACCCUGAG 19

( 2 ) INFORMATION FOR SEQ ID NO:12:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

CUUGGACCAA AGAAGAAGAU CAGAGAGUGA UA 32

( 2 ) INFORMATION FOR SEQ ID NO:13:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

ACAGAAAUAC GGUCCGAAAC GUUGGUCUG 29

( 2 ) INFORMATION FOR SEQ ID NO:14:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

UUAUUGCCAA GCACUUAAAG GGGAGAAUUG GAA                33

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:15:

GAAUCCAGAA GUUAAGAA                                 18

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:16:

GGAAGACAGA AUUAUUUACC AGGCACA                       27

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

CAAGAGACUG GGGAACAGAU                               20

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:18:

AAAUCGCAAA GCUA                                     14

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:19:

GGACGAACUG AUAAUGCUAU CAAGAACC                      28

(2) INFORMATION FOR SEQ ID NO:20:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:20:

ACUGGAAUUC UACAAUGCGU CGGAAGGUCG AACA                34

( 2 ) INFORMATION FOR SEQ ID NO:21:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CAGCCAGCAG UGGCCACAA             19

( 2 ) INFORMATION FOR SEQ ID NO:22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CAUUUGAUGG GUUUUGCUCA GGCUCCGCCU ACA         33

( 2 ) INFORMATION FOR SEQ ID NO:23:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GCUCAACUCC CUGCCACUGG CCAGCCC         27

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AACAACGACU AUUCCUAUUA CCACA         25

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CAAAAUGUCU CCAGUCAUGU UCCAUACCCU         30

( 2 ) INFORMATION FOR SEQ ID NO:26:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

AAAUAUAGUC AAUGUCCCUC AGCCAGCUGC CGCA         34

( 2 ) INFORMATION FOR SEQ ID NO:27:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:27:

AGAGACACUA UAAUGAUGAA GACCCUGAGA AGGA 34

( 2 ) INFORMATION FOR SEQ ID NO:28:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:28:

AAAGCGAAUA AAGGAAUUAG AAUUG 25

( 2 ) INFORMATION FOR SEQ ID NO:29:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:29:

CUCCUAAUGU CAACCGA 17

( 2 ) INFORMATION FOR SEQ ID NO:30:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:30:

AGCUAAAAGG ACAGCAGGUG CUACCAACAC AGAA 34

( 2 ) INFORMATION FOR SEQ ID NO:31:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:31:

CCCGGGUGGC ACAGCACCAC CAUUGCCGAC CACA 34

( 2 ) INFORMATION FOR SEQ ID NO:32:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:32:

AACACCACUC CACUCCAUCU CUGCCAGCGG AUCC 34

( 2 ) INFORMATION FOR SEQ ID NO:33:

( i ) SEQUENCE CHARACTERISTICS:

(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:33:

UACCUGAAGA AA 12

(2) INFORMATION FOR SEQ ID NO:34:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:34:

AUGAUCGUCC ACCAGGGCAC CAUU 24

(2) INFORMATION FOR SEQ ID NO:35:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:35:

CAGAAACACU CCAAUUUA 18

(2) INFORMATION FOR SEQ ID NO:36:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:36:

AAACUCAGAC U 11

(2) INFORMATION FOR SEQ ID NO:37:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:37:

AUGCCUUCUU UAAC 14

(2) INFORMATION FOR SEQ ID NO:38:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:38:

UUACAACACC A 11

(2) INFORMATION FOR SEQ ID NO:39:

(i) SEQUENCE CHARACTERISTICS:
(A) LENGTH: 31 base pairs
(B) TYPE: nucleic acid ( C ) STRANDEDNESS: single
( D ) TOPOLOGY: linear ( x i ) SEQUENCE DESCRIPTION: SEQ ID NO:39:

ACUCAAAAGG AAAAUACUGU UUUUAGAACC C 31

( 2 ) INFORMATION FOR SEQ ID NO:40:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:40:

CAGCUAUCAA AAGGUCAAUC UUAGAAAGCU 30

( 2 ) INFORMATION FOR SEQ ID NO:41:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:41:

CUCCAAGAAC UCCUACACCA UUCAA 25

( 2 ) INFORMATION FOR SEQ ID NO:42:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:42:

ACAUGCACUU GCAGCUCAAG AA 22

( 2 ) INFORMATION FOR SEQ ID NO:43:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:43:

UACGGUCCCC UGAAGAUGCU ACCUCAGA 28

( 2 ) INFORMATION FOR SEQ ID NO:44:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:44:

CACCCUCUCA UCUAGUAGAA GAUCUGCAGG A 31

( 2 ) INFORMATION FOR SEQ ID NO:45:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:45:

UCAAACAGGA AUCUGAUGAA UCUGGA 26

( 2 ) INFORMATION FOR SEQ ID NO:46:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

AAGAAAAUGG A 11

( 2 ) INFORMATION FOR SEQ ID NO:47:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

CUUACUGAAG AAAAUCAAAC AAGA 24

( 2 ) INFORMATION FOR SEQ ID NO:48:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

AAUCUCCAAC UGAUAAAUCA G 21

( 2 ) INFORMATION FOR SEQ ID NO:49:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

GCUCACACCA CUGGGA 16

( 2 ) INFORMATION FOR SEQ ID NO:50:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

CCUCGCCUGU GCGAGAUGCA CCGAAUAUUC 30

( 2 ) INFORMATION FOR SEQ ID NO:51:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

GGCACCAGCA UCAGAAGAUG AAGAC                                                25

( 2 ) INFORMATION FOR SEQ ID NO:52:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

CAUUUACAGU ACC                                                             13

( 2 ) INFORMATION FOR SEQ ID NO:53:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CCCUGGCGAG CCCCUUGCA                                                       19

( 2 ) INFORMATION FOR SEQ ID NO:54:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GCCUUGUAGC AGUACCUGGG A                                                    21

( 2 ) INFORMATION FOR SEQ ID NO:55:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

GUCAAGCUCG UAAAUACGUG AA                                                   22

( 2 ) INFORMATION FOR SEQ ID NO:56:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GAACAGUUCA A                                                               11

( 2 ) INFORMATION FOR SEQ ID NO:57:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

AUGAAACUUU UCAU                                                            14

( 2 ) INFORMATION FOR SEQ ID NO:58:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

AAAAUAAAUA ACAGUC                                            16

( 2 ) INFORMATION FOR SEQ ID NO:59:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

UGAAUUGUAG CC                                                 12

( 2 ) INFORMATION FOR SEQ ID NO:60:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

UUAAUAUCUU AAU                                              13

( 2 ) INFORMATION FOR SEQ ID NO:61:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

AUUUAUCUGG UAUUUUAAAG GAUCCAACAG AUC                33

( 2 ) INFORMATION FOR SEQ ID NO:62:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

CCAGUAUUUC A                                                   11

( 2 ) INFORMATION FOR SEQ ID NO:63:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CUCGAUCACU AAACAUAUG                                      19

( 2 ) INFORMATION FOR SEQ ID NO:64:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

CAUAUAUUUU UAAAAAUC                                                                                                                                         1 8

( 2 ) INFORMATION FOR SEQ ID NO:65:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

UGCUAUGGUC UUAGCCU                                                                                                                                        1 7

( 2 ) INFORMATION FOR SEQ ID NO:66:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

AGUAUCAGAG G                                                                                                                                                1 1

( 2 ) INFORMATION FOR SEQ ID NO:67:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

UAGGUAAUUG ACUAU                                                                                                                         1 5

( 2 ) INFORMATION FOR SEQ ID NO:68:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

UAUUUCAGAC UUUUUAAUUU UAUAUAUAUA UACA                                                       3 4

( 2 ) INFORMATION FOR SEQ ID NO:69:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

CAAUACAUUU GAAAACUUGU UUGGGAGACU CUGC                                                       3 4

( 2 ) INFORMATION FOR SEQ ID NO:70:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:70:

GUGGUUUUUU UGUUAUUGUU GGUUU    25

( 2 ) INFORMATION FOR SEQ ID NO:71:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:71:

UUCUUUUUUG GGAGAU    16

( 2 ) INFORMATION FOR SEQ ID NO:72:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:72:

CUAUGUUUUG UUUUG    15

( 2 ) INFORMATION FOR SEQ ID NO:73:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:73:

AGCCUGACUG UUUUAUA    17

( 2 ) INFORMATION FOR SEQ ID NO:74:

( i ) SEQUENCE CHARACTERISTICS:
  ( A ) LENGTH: 11 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:74:

UCGAUUUGAU C    11

( 2 ) INFORMATION FOR SEQ ID NO:75:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:75:

UGGAUCCUGU GUU    13

( 2 ) INFORMATION FOR SEQ ID NO:76:

( i ) SEQUENCE CHARACTERISTICS:
  ( A ) LENGTH: 25 base pairs (B) TYPE: nucleic acid
        (C) STRANDEDNESS: single
        (D) TOPOLOGY: linear (xi) SEQUENCE DESCRIPTION: SEQ ID NO:76:

UUGAUAGCCA GUCACUGCCU UAAGA 25

(2) INFORMATION FOR SEQ ID NO:77:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:77:

ACAUUUGAUG CAAGAUGGCC AGCACU 26

(2) INFORMATION FOR SEQ ID NO:78:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:78:

CGGUGUACUU ACUGCC 16

(2) INFORMATION FOR SEQ ID NO:79:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:79:

CGUCACUUGG GGAAA 15

(2) INFORMATION FOR SEQ ID NO:80:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:80:

GUCUGUUAUU GCCAA 15

(2) INFORMATION FOR SEQ ID NO:81:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:81:

CUGUUAUUGC CAAGC 15

(2) INFORMATION FOR SEQ ID NO:82:

(i) SEQUENCE CHARACTERISTICS:
        (A) LENGTH: 15 base pairs
        (B) TYPE: nucleic acid
        (C) STRANDEDNESS: single ( D ) TOPOLOGY: linear ( x i ) SEQUENCE DESCRIPTION: SEQ ID NO:82:

GGAGAAUUGG AAAAC 15

( 2 ) INFORMATION FOR SEQ ID NO:83:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

AAAACCUCCU GGACA 15

( 2 ) INFORMATION FOR SEQ ID NO:84:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

UAAUGCUAUC AAGAA 15

( 2 ) INFORMATION FOR SEQ ID NO:85:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

CAAGCUUCCA GAAGA 15

( 2 ) INFORMATION FOR SEQ ID NO:86:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

UUCCUAUUAC CACAU 15

( 2 ) INFORMATION FOR SEQ ID NO:87:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

UGUCCCUCAG CCAGC 15

( 2 ) INFORMATION FOR SEQ ID NO:88:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

AGCGAAUAAA GGAAU  15

( 2 ) INFORMATION FOR SEQ ID NO:89:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:89:

UUAGAAUUUG CAGAA  15

( 2 ) INFORMATION FOR SEQ ID NO:90:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

CAGCUAUCAA AAGGU  15

( 2 ) INFORMATION FOR SEQ ID NO:91:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:91:

ACACCAUUCA AACAU  15

( 2 ) INFORMATION FOR SEQ ID NO:92:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:92:

CACCAUUCAA ACAUG  15

( 2 ) INFORMATION FOR SEQ ID NO:93:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:93:

AUACGGUCCC CUGAA  15

( 2 ) INFORMATION FOR SEQ ID NO:94:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:94:

CUGGAAUUGU UGCUG 15

( 2 ) INFORMATION FOR SEQ ID NO:95:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

GAAUUGUUGC UGAGU 15

( 2 ) INFORMATION FOR SEQ ID NO:96:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

AUAUUCUUAC AAGCU 15

( 2 ) INFORMATION FOR SEQ ID NO:97:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:97:

UCCGUUUUAA UGGCA 15

( 2 ) INFORMATION FOR SEQ ID NO:98:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:98:

ACAAUGUUCU CAAAG 15

( 2 ) INFORMATION FOR SEQ ID NO:99:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

ACGGUCCCCU GAAG 14

( 2 ) INFORMATION FOR SEQ ID NO:100:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:100:

ACAGUUGAGA GCAG 14

( 2 ) INFORMATION FOR SEQ ID NO:101:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:101:

UUUCCCCUG AUGAGGCCGA AAGGCCGAAA GUGACG     36

( 2 ) INFORMATION FOR SEQ ID NO:102:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:102:

UUGGCAACUG AUGAGGCCGA AAGGCCGAAA ACAGAC     36

( 2 ) INFORMATION FOR SEQ ID NO:103:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:103:

GCUUGGCCUG AUGAGGCCGA AAGGCCGAAA UAACAG     36

( 2 ) INFORMATION FOR SEQ ID NO:104:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:104:

GCUUUCCUG AUGAGGCCGA AAGGCCGAAA UUCUCC     36

( 2 ) INFORMATION FOR SEQ ID NO:105:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:105:

UGUCCAGCUG AUGAGGCCGA AAGGCCGAAA GGUUUU     36

( 2 ) INFORMATION FOR SEQ ID NO:106:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

UUCUUGACUG AUGAGGCCGA AAGGCCGAAA GCAUUA     36

( 2 ) INFORMATION FOR SEQ ID NO:107:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:107:

UCUUCUGCUG AUGAGGCCGA AAGGCCGAAA AGCUCG         36

( 2 ) INFORMATION FOR SEQ ID NO:108:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:108:

AUGUGGUCUG AUGAGGCCGA AAGGCCGAAA UAGGAA         36

( 2 ) INFORMATION FOR SEQ ID NO:109:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:109:

GCCGGCUCUG AUGAGCGCGA AAGCGCGAAA GGGACG         36

( 2 ) INFORMATION FOR SEQ ID NO:110:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:110:

GCUCCUUCUG AUGAGGCCGA AAGGCCGAAA UUCGCU         36

( 2 ) INFORMATION FOR SEQ ID NO:111:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:111:

UUCUGCACUG AUGAGGCCGA AAGGCCGAAA UUCUAA         36

( 2 ) INFORMATION FOR SEQ ID NO:112:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:112:

ACCUUUUCUG AUGAGGCCGA AAGGCCGAAA UAGCUG         36

( 2 ) INFORMATION FOR SEQ ID NO:113:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:113:

AUGUUUGCUG AUGAGGCCGA AAGGCCGAAA UGGUGU 36

( 2 ) INFORMATION FOR SEQ ID NO:114:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:114:

CAUGUUUCUG AUGAGGCCGA AAGGCCGAAA AUGGUG 36

( 2 ) INFORMATION FOR SEQ ID NO:115:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:115:

UUCAGGGCUG AUGAGGCCGA AAGGCCGAAA CCGUAU 36

( 2 ) INFORMATION FOR SEQ ID NO:116:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:116:

CAGCAACCUG AUGAGGCCGA AAGGCCGAAA UUCCAG 36

( 2 ) INFORMATION FOR SEQ ID NO:117:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:117:

ACUCAGCCUG AUGAGGCCGA AAGGCCGAAA CAAUUC 36

( 2 ) INFORMATION FOR SEQ ID NO:118:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:118:

AGCUUGUCUG AUGAGGCCGA AAGGCCGAAA GAAUAU 36

( 2 ) INFORMATION FOR SEQ ID NO:119:

( i ) SEQUENCE CHARACTERISTICS:
( A ) LENGTH: 36 base pairs
( B ) TYPE: nucleic acid ( C ) STRANDEDNESS: single
( D ) TOPOLOGY: linear ( x i ) SEQUENCE DESCRIPTION: SEQ ID NO:119:

UGUCAUUCUG AUGAGGCCGA AAGGCCGAAA AACAGA 36

( 2 ) INFORMATION FOR SEQ ID NO:120:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:120:

CUUUGAGCUG AUGAGGCCGA AAGGCCGAAA CAUUGU 36

( 2 ) INFORMATION FOR SEQ ID NO:121:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:121:

UCAGGGAGAA GUAUACCAGA GAAACACACG CG 32

( 2 ) INFORMATION FOR SEQ ID NO:122:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:122:

GCUCUCAGAA GUUGACCAGA GAAACACACG CG 32

( 2 ) INFORMATION FOR SEQ ID NO:123:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:123:

CUUUCCCUGA UGAGGCCGAA AGGCCGAAAU UCUC 34

( 2 ) INFORMATION FOR SEQ ID NO:124:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:124:

UGCUUUCCCU GAUGAGGCCG AAAGGCCGAA AUUCUCCC 38

( 2 ) INFORMATION FOR SEQ ID NO:125:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear (x i) SEQUENCE DESCRIPTION: SEQ ID NO:125:

CUGCUUUCCC UGAUGAGGCC GAAAGGCCGA AAUUCUCCCU 40

(2) INFORMATION FOR SEQ ID NO:126:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (x i) SEQUENCE DESCRIPTION: SEQ ID NO:126:

ACUGCUUUCC CUGAUGAGGC CGAAAGGCCG AAAUUCUCCC UU 42

(2) INFORMATION FOR SEQ ID NO:127:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (x i) SEQUENCE DESCRIPTION: SEQ ID NO:127:

ACACUGCUUU CCCUGAUGAG GCCGAAAGGC CGAAAUUCUC CCUUUU 46

(2) INFORMATION FOR SEQ ID NO:128:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (x i) SEQUENCE DESCRIPTION: SEQ ID NO:128:

AGUGCUUGGC AACUGAUGAG GCCGAAAGGC CGAAAACAGA CCAACG 46

(2) INFORMATION FOR SEQ ID NO:129:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (x i) SEQUENCE DESCRIPTION: SEQ ID NO:129:

GAUUGACCUU UUCUGAUGAG GCCGAAAGGC CGAAAUAGCU GGAGUU 46

(2) INFORMATION FOR SEQ ID NO:130:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO:130:

GCGCAGCCGG GGAGGG 16

(2) INFORMATION FOR SEQ ID NO:131:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO:131:

CGGCAGCCCG GUCGGU 16

( 2 ) INFORMATION FOR SEQ ID NO:132:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

CCGCCGCCCG CCGCGC 16

( 2 ) INFORMATION FOR SEQ ID NO:133:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

AUACGGUCCG AAACGU 16

( 2 ) INFORMATION FOR SEQ ID NO:134:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:134:

CUACUGCCUG GACGAA 16

( 2 ) INFORMATION FOR SEQ ID NO:135:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:135:

CAGCUGCCGC AGCCAU 16

( 2 ) INFORMATION FOR SEQ ID NO:136:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

UUGCCGACCA CACCAG 16

( 2 ) INFORMATION FOR SEQ ID NO:137:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

AUACUGUUUU UAGAAC 16

( 2 ) INFORMATION FOR SEQ ID NO:138:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

A U A C G G U C C C   C U G A A G         16

( 2 ) INFORMATION FOR SEQ ID NO:139:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

G G A C A G U C U G   A A U A C C         16

( 2 ) INFORMATION FOR SEQ ID NO:140:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

C A A C U G U U C A   C G C A G A         16

( 2 ) INFORMATION FOR SEQ ID NO:141:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

A C G C A G A C C U   C G C C U G         16

( 2 ) INFORMATION FOR SEQ ID NO:142:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:142:

U U G C A G C C U U   G U A G C A         16

( 2 ) INFORMATION FOR SEQ ID NO:143:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:143:

C A A C A G U U G A   G A G C A G         16

( 2 ) INFORMATION FOR SEQ ID NO:144:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:144:

UAACAGUCUU ACCUAA  16

( 2 ) INFORMATION FOR SEQ ID NO:145:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:145:

UGACUGUUUU AUAAUU  16

( 2 ) INFORMATION FOR SEQ ID NO:146:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:146:

GAACUGUUGC AUGGAU  16

( 2 ) INFORMATION FOR SEQ ID NO:147:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:147:

UCACUGCCUU AAGAAC  16

( 2 ) INFORMATION FOR SEQ ID NO:148:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:148:

UUACUGCCUU GUAGCA  16

( 2 ) INFORMATION FOR SEQ ID NO:149:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:149:

CCCUCCCCAG AAGCGCACCA GAGAAACACA CGUUGUGGUA CAUUACCUGG UA  52

( 2 ) INFORMATION FOR SEQ ID NO:150:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:150:

ACCGACCGAG AAGCCGACCA GAGAAACACA CGUUGUGGUA CAUUACCUGG UA                52

( 2 ) INFORMATION FOR SEQ ID NO:151:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:151:

GCGCGGCGAG AAGCGGACCA GAGAAACACA CGUUGUGGUA CAUUACCUGG UA                52

( 2 ) INFORMATION FOR SEQ ID NO:152:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:152:

ACGUUUCGAG AAGUAUACCA GAGAAACACA CGUUGUGGUA CAUUACCUGG UA                52

( 2 ) INFORMATION FOR SEQ ID NO:153:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:153:

UUCGUCCAAG AAGUAGACCA GAGAAACACA CGUUGUGGUA CAUUACCUGG UA                52

( 2 ) INFORMATION FOR SEQ ID NO:154:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:154:

AUGGCUGCAG AAGCUGACCA GAGAAACACA CGUUGUGGUA CAUUACCUGG UA                52

( 2 ) INFORMATION FOR SEQ ID NO:155:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:155:

CUGGUGUGAG AAGCAAACCA GAGAAACACA CGUUGUGGUA CAUUACCUGG UA                52

( 2 ) INFORMATION FOR SEQ ID NO:156:

( i ) SEQUENCE CHARACTERISTICS:
    ( A ) LENGTH: 52 base pairs (B) TYPE: nucleic acid
(C) STRANDEDNESS: single
(D) TOPOLOGY: linear (xi) SEQUENCE DESCRIPTION: SEQ ID NO:156:

GUUCUAAAAG AAGUAUACCA GAGAAACACA CGUUGUGGUA CAUUACCUGG UA  52

(2) INFORMATION FOR SEQ ID NO:157:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:157:

CUUCAGGGAG AAGUAUACCA GAGAAACACA CGUUGUGGUA CAUUACCUGG UA  52

(2) INFORMATION FOR SEQ ID NO:158:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:158:

GGUAUUCAAG AAGUCCACCA GAGAAACACA CGUUGUGGUA CAUUACCUGG UA  52

(2) INFORMATION FOR SEQ ID NO:159:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:159:

UCUGCGUGAG AAGUUGACCA GAGAAACACA CGUUGUGGUA CAUUACCUGG UA  52

(2) INFORMATION FOR SEQ ID NO:160:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:160:

CAGGCGAGAG AAGCGUACCA GAGAAACACA CGUUGUGGUA CAUUACCUGG UA  52

(2) INFORMATION FOR SEQ ID NO:161:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:161:

UGCUACAAAG AAGCAAACCA GAGAAACACA CGUUGUGGUA CAUUACCUGG UA  52

(2) INFORMATION FOR SEQ ID NO:162:

(i) SEQUENCE CHARACTERISTICS:
(A) LENGTH: 52 base pairs
(B) TYPE: nucleic acid
(C) STRANDEDNESS: single (D) TOPOLOGY: linear (xi) SEQUENCE DESCRIPTION: SEQ ID NO:162:

CUGCUCUCAG AAGUUGACCA GAGAAACACA CGUUGUGGUA CAUUACCUGG UA    52

(2) INFORMATION FOR SEQ ID NO:163:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:163:

UUAGGUAAAG AAGUUAACCA GAGAAACACA CGUUGUGGUA CAUUACCUGG UA    52

(2) INFORMATION FOR SEQ ID NO:164:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:164:

AAUUAUAAAG AAGUCAACCA GAGAAACACA CGUUGUGGUA CAUUACCUGG UA    52

(2) INFORMATION FOR SEQ ID NO:165:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:165:

AUCCAUGCAG AAGUUCACCA GAGAAACACA CGUUGUGGUA CAUUACCUGG UA    52

(2) INFORMATION FOR SEQ ID NO:166:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:166:

GUUCUUAAAG AAGUGAACCA GAGAAACACA CGUUGUGGUA CAUUACCUGG UA    52

(2) INFORMATION FOR SEQ ID NO:167:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:167:

UGCUACAAAG AAGUAAACCA GAGAAACACA CGUUGUGGUA CAUUACCUGG UA    52

(2) INFORMATION FOR SEQ ID NO:168:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:168:

CGCGUGGUAC AUUACCUGGU A                                        21

(2) INFORMATION FOR SEQ ID NO:169:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (x i) SEQUENCE DESCRIPTION: SEQ ID NO:169:

CGCGUGGUAC AUUACCUGGU A                                        21

(2) INFORMATION FOR SEQ ID NO:170:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:170:

AACCUGUUUC CUCCUCC                                             17

(2) INFORMATION FOR SEQ ID NO:171:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:171:

GGAGGAGGCU GAUGAGGCCG AAAGGCCGAA AACAGGUU                      38

(2) INFORMATION FOR SEQ ID NO:172:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:172:

ACCUGUUUCC UCCUCCU                                             17

(2) INFORMATION FOR SEQ ID NO:173:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:173:

AGGAGGAGCU GAUGAGGCCG AAAGGCCGAA AAACAGGU                      38

(2) INFORMATION FOR SEQ ID NO:174:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:174:

UGUUCCUCC UCCUCCU 17

(2) INFORMATION FOR SEQ ID NO:175:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:175:

AGGAGGAGCU GAUGAGGCCG AAAGGCCGAA AGGAAACA 38

(2) INFORMATION FOR SEQ ID NO:176:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:176:

UUCCUCCUCC UCCUUCU 17

(2) INFORMATION FOR SEQ ID NO:177:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:177:

AGAAGGAGCU GAUGAGGCCG AAAGGCCGAA AGGAGGAA 38

(2) INFORMATION FOR SEQ ID NO:178:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:178:

CUCCUCCUCC UUCUCCU 17

(2) INFORMATION FOR SEQ ID NO:179:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:179:

AGGAGAAGCU GAUGAGGCCG AAAGGCCGAA AGGAGGAG 38

(2) INFORMATION FOR SEQ ID NO:180:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:180:

CUCCUCCUUC UCCUCCU 17

( 2 ) INFORMATION FOR SEQ ID NO:181:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:181:

AGGAGGAGCU GAUGAGGCCG AAAGGCCGAA AGGAGGAG 38

( 2 ) INFORMATION FOR SEQ ID NO:182:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:182:

UCCUCCUUCU CCUCCUC 17

( 2 ) INFORMATION FOR SEQ ID NO:183:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:183:

GAGGAGGACU GAUGAGGCCG AAAGGCCGAA AAGGAGGA 38

( 2 ) INFORMATION FOR SEQ ID NO:184:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:184:

CUCCUUCUCC UCCUCCU 17

( 2 ) INFORMATION FOR SEQ ID NO:185:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:185:

AGGAGGAGCU GAUGAGGCCG AAAGGCCGAA AGAAGGAG 38

( 2 ) INFORMATION FOR SEQ ID NO:186:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:186:

CUUCUCCUCC UCCUCCG 17

( 2 ) INFORMATION FOR SEQ ID NO:187:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:187:

CGGAGGAGCU GAUGAGGCCG AAAGGCCGAA AGGAGAAG      3 8

( 2 ) INFORMATION FOR SEQ ID NO:188:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:188:

CUCCUCCUCC UCCGUGA      1 7

( 2 ) INFORMATION FOR SEQ ID NO:189:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:189:

UCACGGAGCU GAUGAGGCCG AAAGGCCGAA AGGAGGAG      3 8

( 2 ) INFORMATION FOR SEQ ID NO:190:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:190:

CUCCUCCUCC GUGACCU      1 7

( 2 ) INFORMATION FOR SEQ ID NO:191:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:191:

AGGUCACGCU GAUGAGGCCG AAAGGCCGAA AGGAGGAG      3 8

( 2 ) INFORMATION FOR SEQ ID NO:192:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:192:

CGUGACCUCC UCCUCCU      1 7

( 2 ) INFORMATION FOR SEQ ID NO:193:

( i ) SEQUENCE CHARACTERISTICS:

( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:193:

AGGAGGAGCU GAUGAGGCCG AAAGGCCGAA AGGUCACG                                         3 8

( 2 ) INFORMATION FOR SEQ ID NO:194:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:194:

GACCUCCUCC UCCUCUU                                                                 1 7

( 2 ) INFORMATION FOR SEQ ID NO:195:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:195:

AAGAGGAGCU GAUGAGGCCG AAAGGCCGAA AGGAGGUC                                          3 8

( 2 ) INFORMATION FOR SEQ ID NO:196:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:196:

CUCCUCCUCC UCUUUCU                                                                 1 7

( 2 ) INFORMATION FOR SEQ ID NO:197:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:197:

AGAAAGAGCU GAUGAGGCCG AAAGGCCGAA AGGAGGAG                                          3 8

( 2 ) INFORMATION FOR SEQ ID NO:198:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:198:

CUCCUCCUCU UUCUCCU                                                                 1 7

( 2 ) INFORMATION FOR SEQ ID NO:199:

( i ) SEQUENCE CHARACTERISTICS:
            ( A ) LENGTH: 38 base pairs
            ( B ) TYPE: nucleic acid ( C ) STRANDEDNESS: single
( D ) TOPOLOGY: linear ( x i ) SEQUENCE DESCRIPTION: SEQ ID NO:199:

AGGAGAAACU GAUGAGGCCG AAAGGCCGAA AGGAGGAG 38

( 2 ) INFORMATION FOR SEQ ID NO:200:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:200:

CCUCCUCUUU CUCCUGA 17

( 2 ) INFORMATION FOR SEQ ID NO:201:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:201:

UCAGGAGACU GAUGAGGCCG AAAGGCCGAA AGAGGAGG 38

( 2 ) INFORMATION FOR SEQ ID NO:202:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:202:

CUCCUCUUUC UCCUGAG 17

( 2 ) INFORMATION FOR SEQ ID NO:203:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:203:

CUCAGGAGCU GAUGAGGCCG AAAGGCCGAA AAGAGGAG 38

( 2 ) INFORMATION FOR SEQ ID NO:204:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:204:

UCCUCUUUCU CCUGAGA 17

( 2 ) INFORMATION FOR SEQ ID NO:205:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:205:

UCUCAGGACU GAUGAGGCCG AAAGGCCGAA AAAGAGGA 38

( 2 ) INFORMATION FOR SEQ ID NO:206:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:206:

CUCUUUCUCC UGAGAAA 17

( 2 ) INFORMATION FOR SEQ ID NO:207:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:207:

UUUCUCAGCU GAUGAGGCCG AAAGGCCGAA AGAAAGAG 38

( 2 ) INFORMATION FOR SEQ ID NO:208:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:208:

GAGAAACUUC GCCCCAG 17

( 2 ) INFORMATION FOR SEQ ID NO:209:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:209:

CUGGGGCGCU GAUGAGGCCG AAAGGCCGAA AGUUUCUC 38

( 2 ) INFORMATION FOR SEQ ID NO:210:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:210:

AGAAACUUCG CCCCAGC 17

( 2 ) INFORMATION FOR SEQ ID NO:211:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:211:

GCUGGGGCCU GAUGAGGCCG AAAGGCCGAA AAGUUUCU 38

( 2 ) INFORMATION FOR SEQ ID NO:212:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:212:

CCGCGGCUCU CGCGGAG 17

( 2 ) INFORMATION FOR SEQ ID NO:213:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:213:

CUCCGCGACU GAUGAGGCCG AAAGGCCGAA AGCCGCGG 38

( 2 ) INFORMATION FOR SEQ ID NO:214:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:214:

GCGGCUCUCG CGGAGCC 17

( 2 ) INFORMATION FOR SEQ ID NO:215:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:215:

GGCUCCGCCU GAUGAGGCCG AAAGGCCGAA AGAGCCGC 38

( 2 ) INFORMATION FOR SEQ ID NO:216:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:216:

CACAGCAUAU AUAGCAG 17

( 2 ) INFORMATION FOR SEQ ID NO:217:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:217:

CUGCUAUACU GAUGAGGCCG AAAGGCCGAA AUGCUGUG 38

( 2 ) INFORMATION FOR SEQ ID NO:218:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:218:

CAGCAUAUAU AGCAGUG 17

( 2 ) INFORMATION FOR SEQ ID NO:219:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:219:

CACUGCUACU GAUGAGGCCG AAAGGCCGAA AUAUGCUG 38

( 2 ) INFORMATION FOR SEQ ID NO:220:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:220:

GCAUAUAUAG CAGUGAC 17

( 2 ) INFORMATION FOR SEQ ID NO:221:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:221:

GUCACUGCCU GAUGAGGCCG AAAGGCCGAA AUAUAUGC 38

( 2 ) INFORMATION FOR SEQ ID NO:222:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:222:

UGAGGACUUU GAGAUGU 17

( 2 ) INFORMATION FOR SEQ ID NO:223:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:223:

ACAUCUCACU GAUGAGGCCG AAAGGCCGAA AGUCCUCA 38

( 2 ) INFORMATION FOR SEQ ID NO:224:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:224:

GAGGACUUUG AGAUGUG 17

( 2 ) INFORMATION FOR SEQ ID NO:225:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:225:

CACAUCUCCU GAUGAGGCCG AAAGGCCGAA AAGUCCUC 38

( 2 ) INFORMATION FOR SEQ ID NO:226:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:226:

CCAUGACUAU GAUGGGC 17

( 2 ) INFORMATION FOR SEQ ID NO:227:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:227:

GCCCAUCACU GAUGAGGCCG AAAGGCCGAA AGUCAUGG 38

( 2 ) INFORMATION FOR SEQ ID NO:228:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:228:

GGGCUGCUUC CCAAGUC 17

( 2 ) INFORMATION FOR SEQ ID NO:229:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:229:

GACUUGGGCU GAUGAGGCCG AAAGGCCGAA AGCAGCCC 38

( 2 ) INFORMATION FOR SEQ ID NO:230:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:230:

GGCUGCUUCC CAAGUCU 17

( 2 ) INFORMATION FOR SEQ ID NO:231:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:231:

AGACUUGGCU GAUGAGGCCG AAAGGCCGAA AAGCAGCC 38

( 2 ) INFORMATION FOR SEQ ID NO:232:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:232:

GCGUCACUUG GGGAAAA 17

( 2 ) INFORMATION FOR SEQ ID NO:233:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:233:

UUUUCCCCU GAUGAGGCCG AAAGGCCGAA AGUGACGC 38

( 2 ) INFORMATION FOR SEQ ID NO:234:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:234:

GGAAAGUUAU UGCCAAU 17

( 2 ) INFORMATION FOR SEQ ID NO:235:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:235:

AUUGGCAACU GAUGAGGCCG AAAGGCCGAA AACUUUCC 38

( 2 ) INFORMATION FOR SEQ ID NO:236:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:236:

AAAGUUAUUG CCAAUUA                                                          17

(2) INFORMATION FOR SEQ ID NO:237:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:237:

UAAUUGGCCU GAUGAGGCCG AAAGGCCGAA AUAACUUU                                    38

(2) INFORMATION FOR SEQ ID NO:238:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:238:

UUGCCAAUUA UCUCCCG                                                          17

(2) INFORMATION FOR SEQ ID NO:239:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:239:

CGGGAGAUCU GAUGAGGCCG AAAGGCCGAA AUUGGCAA                                    38

(2) INFORMATION FOR SEQ ID NO:240:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:240:

UGCCAAUUAU CUCCCGA                                                          17

(2) INFORMATION FOR SEQ ID NO:241:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:241:

UCGGGAGACU GAUGAGGCCG AAAGGCCGAA AAUUGGCA                                    38

(2) INFORMATION FOR SEQ ID NO:242:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO:242:

CCAAUUAUCU CCCGAAU                                                                                              17

( 2 ) INFORMATION FOR SEQ ID NO:243:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:243:

AUUCGGGACU GAUGAGGCCG AAAGGCCGAA AUAAUUGG                                                                        38

( 2 ) INFORMATION FOR SEQ ID NO:244:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:244:

AAUUAUCUCC CGAAUCG                                                                                               17

( 2 ) INFORMATION FOR SEQ ID NO:245:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:245:

CGAUUCGGCU GAUGAGGCCG AAAGGCCGAA AGAUAAUU                                                                        38

( 2 ) INFORMATION FOR SEQ ID NO:246:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:246:

UCCCGAAUCG AACAGAU                                                                                               17

( 2 ) INFORMATION FOR SEQ ID NO:247:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:247:

AUCUGUUCCU GAUGAGGCCG AAAGGCCGAA AUUCGGGA                                                                        38

( 2 ) INFORMATION FOR SEQ ID NO:248:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:248:

AAAGUACUAA ACCCUGA 17

( 2 ) INFORMATION FOR SEQ ID NO:249:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:249:

UCAGGGUUCU GAUGAGGCCG AAAGGCCGAA AGUACUUU 38

( 2 ) INFORMATION FOR SEQ ID NO:250:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:250:

CCUGAGCUCA UCAAGGG 17

( 2 ) INFORMATION FOR SEQ ID NO:251:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:251:

CCCUUGAUCU GAUGAGGCCG AAAGGCCGAA AGCUCAGG 38

( 2 ) INFORMATION FOR SEQ ID NO:252:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:252:

GAGCUCAUCA AGGGUCC 17

( 2 ) INFORMATION FOR SEQ ID NO:253:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:253:

GGACCCUUCU GAUGAGGCCG AAAGGCCGAA AUGAGCUC 38

( 2 ) INFORMATION FOR SEQ ID NO:254:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:254:

AGGGUCCUUG GACCAAA            17

( 2 ) INFORMATION FOR SEQ ID NO:255:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:255:

UUUGGUCCCU GAUGAGGCCG AAAGGCCGAA AGGACCCU            38

( 2 ) INFORMATION FOR SEQ ID NO:256:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:256:

AAGAAGAUCA GAGAGUG            17

( 2 ) INFORMATION FOR SEQ ID NO:257:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:257:

CACUCUCUCU GAUGAGGCCG AAAGGCCGAA AUCUUCUU            38

( 2 ) INFORMATION FOR SEQ ID NO:258:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:258:

AGAGUGAUAG AGCUUGU            17

( 2 ) INFORMATION FOR SEQ ID NO:259:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:259:

ACAAGCUCCU GAUGAGGCCG AAAGGCCGAA AUCACUCU            38

( 2 ) INFORMATION FOR SEQ ID NO:260:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:260:

AUAGAGCUUG UACAGAA            17

( 2 ) INFORMATION FOR SEQ ID NO:261:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:261:

UUCUGUACCU GAUGAGGCCG AAAGGCCGAA AGCUCUAU     38

( 2 ) INFORMATION FOR SEQ ID NO:262:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:262:

ACAGAAAUAC GGUCCGA     17

( 2 ) INFORMATION FOR SEQ ID NO:263:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:263:

UCGGACCGCU GAUGAGGCCG AAAGGCCGAA AUUUCUGU     38

( 2 ) INFORMATION FOR SEQ ID NO:264:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:264:

GGUCUGUUAU UGCCAAG     17

( 2 ) INFORMATION FOR SEQ ID NO:265:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:265:

CUUGGCAACU GAUGAGGCCG AAAGGCCGAA AACAGACC     38

( 2 ) INFORMATION FOR SEQ ID NO:266:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:266:

UCUGUUAUUG CCAAGCA     17

( 2 ) INFORMATION FOR SEQ ID NO:267:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:267:

UGCUUGGCCU GAUGAGGCCG AAAGGCCGAA AUAACAGA 38

( 2 ) INFORMATION FOR SEQ ID NO:268:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:268:

CAAGCACUUA AAGGGGA 17

( 2 ) INFORMATION FOR SEQ ID NO:269:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:269:

UCCCCUUUCU GAUGAGGCCG AAAGGCCGAA AGUGCUUG 38

( 2 ) INFORMATION FOR SEQ ID NO:270:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:270:

AAGCACUUAA AGGGGAG 17

( 2 ) INFORMATION FOR SEQ ID NO:271:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:271:

CUCCCCUUCU GAUGAGGCCG AAAGGCCGAA AAGUGCUU 38

( 2 ) INFORMATION FOR SEQ ID NO:272:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:272:

GGGAGAAUUG GAAAACA 17

( 2 ) INFORMATION FOR SEQ ID NO:273:

( i ) SEQUENCE CHARACTERISTICS:

( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:273:

UGUUUUCCCU GAUGAGGCCG AAAGGCCGAA AUUCUCCC     38

( 2 ) INFORMATION FOR SEQ ID NO:274:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:274:

GGUGGCAUAA CCACUUG     17

( 2 ) INFORMATION FOR SEQ ID NO:275:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:275:

CAAGUGGUCU GAUGAGGCCG AAAGGCCGAA AUGCCACC     38

( 2 ) INFORMATION FOR SEQ ID NO:276:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:276:

UAACCACUUG AAUCCAG     17

( 2 ) INFORMATION FOR SEQ ID NO:277:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:277:

CUGGAUUCCU GAUGAGGCCG AAAGGCCGAA AGUGGUUA     38

( 2 ) INFORMATION FOR SEQ ID NO:278:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:278:

ACUUGAAUCC AGAAGUU     17

( 2 ) INFORMATION FOR SEQ ID NO:279:

( i ) SEQUENCE CHARACTERISTICS:
    ( A ) LENGTH: 38 base pairs
    ( B ) TYPE: nucleic acid (C) STRANDEDNESS: single
(D) TOPOLOGY: linear (xi) SEQUENCE DESCRIPTION: SEQ ID NO:279:

AACUUCUGCU GAUGAGGCCG AAAGGCCGAA AUUCAAGU 38

(2) INFORMATION FOR SEQ ID NO:280:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:280:

CAGAAGUUAA GAAAACC 17

(2) INFORMATION FOR SEQ ID NO:281:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:281:

GGUUUUCUCU GAUGAGGCCG AAAGGCCGAA AACUUCUG 38

(2) INFORMATION FOR SEQ ID NO:282:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:282:

GAAAACCUCC UGGACAG 17

(2) INFORMATION FOR SEQ ID NO:283:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:283:

CUGUCCAGCU GAUGAGGCCG AAAGGCCGAA AGGUUUUC 38

(2) INFORMATION FOR SEQ ID NO:284:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:284:

GACAGAAUUA UUUACCA 17

(2) INFORMATION FOR SEQ ID NO:285:

(i) SEQUENCE CHARACTERISTICS:
(A) LENGTH: 38 base pairs
(B) TYPE: nucleic acid
(C) STRANDEDNESS: single
(D) TOPOLOGY: linear (x i ) SEQUENCE DESCRIPTION: SEQ ID NO:285:

UGGUAAAUCU GAUGAGGCCG AAAGGCCGAA AUUCUGUC 38

( 2 ) INFORMATION FOR SEQ ID NO:286:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:286:

ACAGAAUUAU UUACCAG 17

( 2 ) INFORMATION FOR SEQ ID NO:287:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:287:

CUGGUAAACU GAUGAGGCCG AAAGGCCGAA AAUUCUGU 38

( 2 ) INFORMATION FOR SEQ ID NO:288:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:288:

AGAAUUAUUU ACCAGGC 17

( 2 ) INFORMATION FOR SEQ ID NO:289:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:289:

GCCUGGUACU GAUGAGGCCG AAAGGCCGAA AUAAUUCU 38

( 2 ) INFORMATION FOR SEQ ID NO:290:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:290:

GAAUUAUUUA CCAGGCA 17

( 2 ) INFORMATION FOR SEQ ID NO:291:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:291:

UGCCUGGUCU GAUGAGGCCG AAAGGCCGAA AAUAAUUC     38

( 2 ) INFORMATION FOR SEQ ID NO:292:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:292:

AAUUAUUUAC CAGGCAC     17

( 2 ) INFORMATION FOR SEQ ID NO:293:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:293:

GUGCCUGGCU GAUGAGGCCG AAAGGCCGAA AAAUAAUU     38

( 2 ) INFORMATION FOR SEQ ID NO:294:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:294:

GCAGAAAUCG CAAAGCU     17

( 2 ) INFORMATION FOR SEQ ID NO:295:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:295:

AGCUUUGCCU GAUGAGGCCG AAAGGCCGAA AUUUCUGC     38

( 2 ) INFORMATION FOR SEQ ID NO:296:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:296:

GCAAAGCUAC UGCCUGG     17

( 2 ) INFORMATION FOR SEQ ID NO:297:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:297:

CCAGGCAGCU GAUGAGGCCG AAAGGCCGAA AGCUUUGC     38

( 2 ) INFORMATION FOR SEQ ID NO:298:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:298:

GAACUGAUAA UGCUAUC 17

( 2 ) INFORMATION FOR SEQ ID NO:299:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:299:

GAUAGCAUCU GAUGAGGCCG AAAGGCCGAA AUCAGUUC 38

( 2 ) INFORMATION FOR SEQ ID NO:300:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:300:

AUAAUGCUAU CAAGAAC 17

( 2 ) INFORMATION FOR SEQ ID NO:301:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:301:

GUUCUUGACU GAUGAGGCCG AAAGGCCGAA AGCAUUAU 38

( 2 ) INFORMATION FOR SEQ ID NO:302:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:302:

AAUGCUAUCA AGAACCA 17

( 2 ) INFORMATION FOR SEQ ID NO:303:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:303:

UGGUUCUUCU GAUGAGGCCG AAAGGCCGAA AUAGCAUU 38

( 2 ) INFORMATION FOR SEQ ID NO:304:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:304:

ACUGGAAUUC UACAAUG     17

( 2 ) INFORMATION FOR SEQ ID NO:305:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:305:

CAUUGUAGCU GAUGAGGCCG AAAGGCCGAA AUUCCAGU     38

( 2 ) INFORMATION FOR SEQ ID NO:306:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:306:

CUGGAAUUCU ACAAUGC     17

( 2 ) INFORMATION FOR SEQ ID NO:307:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:307:

GCAUUGUACU GAUGAGGCCG AAAGGCCGAA AAUUCCAG     38

( 2 ) INFORMATION FOR SEQ ID NO:308:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:308:

GGAAUUCUAC AAUGCGU     17

( 2 ) INFORMATION FOR SEQ ID NO:309:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:309:

ACGCAUUGCU GAUGAGGCCG AAAGGCCGAA AGAAUCC     38

( 2 ) INFORMATION FOR SEQ ID NO:310:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:310:

GGAAGGUUAU CUGCAGG 17

( 2 ) INFORMATION FOR SEQ ID NO:311:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:311:

CCUGCAGACU GAUGAGGCCG AAAGGCGAA AACCUUCC 38

( 2 ) INFORMATION FOR SEQ ID NO:312:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:312:

AAGGUUAUCU GCAGGAG 17

( 2 ) INFORMATION FOR SEQ ID NO:313:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:313:

CUCCUGCACU GAUGAGGCCG AAAGGCCGAA AUAACCUU 38

( 2 ) INFORMATION FOR SEQ ID NO:314:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:314:

AGGAGUCUUC AAAAGCC 17

( 2 ) INFORMATION FOR SEQ ID NO:315:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:315:

GGCUUUUGCU GAUGAGGCCG AAAGGCCGAA AGACUCCU 38

( 2 ) INFORMATION FOR SEQ ID NO:316:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:316:

GGAGUCUUCA AAAGCCA 17

(2) INFORMATION FOR SEQ ID NO:317:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:317:

UGGCUUUUCU GAUGAGGCCG AAAGGCCGAA AAGACUCC 38

(2) INFORMATION FOR SEQ ID NO:318:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:318:

CACAAGCUUC CAGAAGA 17

(2) INFORMATION FOR SEQ ID NO:319:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:319:

UCUUCUGGCU GAUGAGGCCG AAAGGCCGAA AGCUUGUG 38

(2) INFORMATION FOR SEQ ID NO:320:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:320:

ACAAGCUUCC AGAAGAA 17

(2) INFORMATION FOR SEQ ID NO:321:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:321:

UUCUUCUGCU GAUGAGGCCG AAAGGCCGAA AAGCUUGU 38

(2) INFORMATION FOR SEQ ID NO:322:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO:322:

ACAGUCAUUU GAUGGGU                                                                    17

( 2 ) INFORMATION FOR SEQ ID NO:323:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:323:

ACCCAUCACU GAUGAGGCCG AAAGGCCGAA AUGACUGU                                              38

( 2 ) INFORMATION FOR SEQ ID NO:324:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:324:

CAGUCAUUUG AUGGGUU                                                                    17

( 2 ) INFORMATION FOR SEQ ID NO:325:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:325:

AACCCAUCCU GAUGAGGCCG AAAGGCCGAA AAUGACUG                                              38

( 2 ) INFORMATION FOR SEQ ID NO:326:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:326:

GAUGGGUUUU GCUCAGG                                                                    17

( 2 ) INFORMATION FOR SEQ ID NO:327:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:327:

CCUGAGCACU GAUGAGGCCG AAAGGCCGAA AACCCAUC                                              38

( 2 ) INFORMATION FOR SEQ ID NO:328:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:328:

AUGGGUUUUG CUCAGGC 17

( 2 ) INFORMATION FOR SEQ ID NO:329:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:329:

GCCUGAGCCU GAUGAGGCCG AAAGGCCGAA AAACCCAU 38

( 2 ) INFORMATION FOR SEQ ID NO:330:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:330:

GUUUUGCUCA GGCUCCG 17

( 2 ) INFORMATION FOR SEQ ID NO:331:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:331:

CGGAGCCUCU GAUGAGGCCG AAAGGCCGAA AGCAAAAC 38

( 2 ) INFORMATION FOR SEQ ID NO:332:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:332:

CUCAGGCUCC GCCUACA 17

( 2 ) INFORMATION FOR SEQ ID NO:333:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:333:

UGUAGGCGCU GAUGAGGCCG AAAGGCCGAA AGCCUGAG 38

( 2 ) INFORMATION FOR SEQ ID NO:334:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:334:

CUCCGCCUAC AGCUCAA                                                                                      17

( 2 ) INFORMATION FOR SEQ ID NO:335:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:335:

UUGAGCUGCU GAUGAGGCCG AAAGGCCGAA AGGCGGAG                                                                38

( 2 ) INFORMATION FOR SEQ ID NO:336:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:336:

CUACAGCUCA ACUCCCU                                                                                      17

( 2 ) INFORMATION FOR SEQ ID NO:337:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:337:

AGGGAGUUCU GAUGAGGCCG AAAGGCCGAA AGCUGUAG                                                                38

( 2 ) INFORMATION FOR SEQ ID NO:338:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:338:

GCUCAACUCC CUGCCAC                                                                                      17

( 2 ) INFORMATION FOR SEQ ID NO:339:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:339:

GUGGCAGGCU GAUGAGGCCG AAAGGCCGAA AGUUGAGC                                                                38

( 2 ) INFORMATION FOR SEQ ID NO:340:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:340:

CCACUGUUAA CAACGAC                                                                                      17

( 2 ) INFORMATION FOR SEQ ID NO:341:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:341:

GUCGUUGUCU GAUGAGGCCG AAAGGCCGAA AACAGUGG        38

( 2 ) INFORMATION FOR SEQ ID NO:342:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:342:

CAACGACUAU UCCUAUU        17

( 2 ) INFORMATION FOR SEQ ID NO:343:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:343:

AAUAGGAACU GAUGAGGCCG AAAGGCCGAA AGUCGUUG        38

( 2 ) INFORMATION FOR SEQ ID NO:344:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:344:

ACGACUAUUC CUAUUAC        17

( 2 ) INFORMATION FOR SEQ ID NO:345:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:345:

GUAAUAGGCU GAUGAGGCCG AAAGGCCGAA AUAGUCGU        38

( 2 ) INFORMATION FOR SEQ ID NO:346:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:346:

CGACUAUUCC UAUUACC        17

( 2 ) INFORMATION FOR SEQ ID NO:347:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:347:

GGUAAUAGCU GAUGAGGCCG AAAGGCCGAA AAUAGUCG    38

( 2 ) INFORMATION FOR SEQ ID NO:348:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:348:

CUAUUCCUAU UACCACA    17

( 2 ) INFORMATION FOR SEQ ID NO:349:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:349:

UGUGGUAACU GAUGAGGCCG AAAGGCCGAA AGGAAUAG    38

( 2 ) INFORMATION FOR SEQ ID NO:350:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:350:

AUUCCUAUUA CCACAUU    17

( 2 ) INFORMATION FOR SEQ ID NO:351:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:351:

AAUGUGGUCU GAUGAGGCCG AAAGGCCGAA AUAGGAAU    38

( 2 ) INFORMATION FOR SEQ ID NO:352:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:352:

UUCCUAUUAC CACAUUU    17

( 2 ) INFORMATION FOR SEQ ID NO:353:

( i ) SEQUENCE CHARACTERISTICS:

(A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:353:

AAAUGUGGCU GAUGAGGCCG AAAGGCCGAA AAUAGGAA    38

(2) INFORMATION FOR SEQ ID NO:354:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:354:

UACCACAUUU CUGAAGC    17

(2) INFORMATION FOR SEQ ID NO:355:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:355:

GCUUCAGACU GAUGAGGCCG AAAGGCCGAA AUGUGGUA    38

(2) INFORMATION FOR SEQ ID NO:356:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:356:

ACCACAUUUC UGAAGCA    17

(2) INFORMATION FOR SEQ ID NO:357:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:357:

UGCUUCAGCU GAUGAGGCCG AAAGGCCGAA AAUGUGGU    38

(2) INFORMATION FOR SEQ ID NO:358:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:358:

CCACAUUUCU GAAGCAC    17

(2) INFORMATION FOR SEQ ID NO:359:

(i) SEQUENCE CHARACTERISTICS:
                (A) LENGTH: 38 base pairs
                (B) TYPE: nucleic acid (C) STRANDEDNESS: single
(D) TOPOLOGY: linear (xi) SEQUENCE DESCRIPTION: SEQ ID NO:359:

GUGCUUCACU GAUGAGGCCG AAAGGCCGAA AAAUGUGG  38

(2) INFORMATION FOR SEQ ID NO:360:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:360:

AAAUGUCUCC AGUCAUG  17

(2) INFORMATION FOR SEQ ID NO:361:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:361:

CAUGACUGCU GAUGAGGCCG AAAGGCCGAA AGACAUUU  38

(2) INFORMATION FOR SEQ ID NO:362:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:362:

GUCAUGUUCC AUACCCU  17

(2) INFORMATION FOR SEQ ID NO:363:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:363:

AGGGUAUGCU GAUGAGGCCG AAAGGCCGAA AACAUGAC  38

(2) INFORMATION FOR SEQ ID NO:364:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:364:

UGUUCCAUAC CCUGUAG  17

(2) INFORMATION FOR SEQ ID NO:365:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:365:

CUACAGGGCU GAUGAGGCCG AAAGGCCGAA AUGGAACA    38

(2) INFORMATION FOR SEQ ID NO:366:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:366:

GUAGCGUUAC AUGUAAA    17

(2) INFORMATION FOR SEQ ID NO:367:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:367:

UUUACAUGCU GAUGAGGCCG AAAGGCCGAA AACGCUAC    38

(2) INFORMATION FOR SEQ ID NO:368:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:368:

UUACAUGUAA AUAUAGU    17

(2) INFORMATION FOR SEQ ID NO:369:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:369:

ACUAUAUUCU GAUGAGGCCG AAAGGCCGAA ACAUGUAA    38

(2) INFORMATION FOR SEQ ID NO:370:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:370:

AUGUAAAUAU AGUCAAU    17

(2) INFORMATION FOR SEQ ID NO:371:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:371:

AUUGACUACU GAUGAGGCCG AAAGGCCGAA AUUUACAU        38

(2) INFORMATION FOR SEQ ID NO:372:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:372:

GUAAAUAUAG UCAAUGU        17

(2) INFORMATION FOR SEQ ID NO:373:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:373:

ACAUUGACCU GAUGAGGCCG AAAGGCCGAA AUAUUUAC        38

(2) INFORMATION FOR SEQ ID NO:374:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:374:

AUGUCCCUCA GCCAGCU        17

(2) INFORMATION FOR SEQ ID NO:375:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:375:

AGCUGGCUCU GAUGAGGCCG AAAGGCCGAA AGGGACAU        38

(2) INFORMATION FOR SEQ ID NO:376:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:376:

GCAGCCAUUC AGAGACA        17

(2) INFORMATION FOR SEQ ID NO:377:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:377:

UGUCUCUGCU GAUGAGGCCG AAAGGCCGAA AUGGCUGC        38

( 2 ) INFORMATION FOR SEQ ID NO:378:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:378:

CAGCCAUUCA GAGACAC            17

( 2 ) INFORMATION FOR SEQ ID NO:379:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:379:

GUGUCUCUCU GAUGAGGCCG AAAGGCCGAA AAUGGCUG    38

( 2 ) INFORMATION FOR SEQ ID NO:380:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:380:

GAGACACUAU AAUGAUG           17

( 2 ) INFORMATION FOR SEQ ID NO:381:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:381:

CAUCAUUACU GAUGAGGCCG AAAGGCCGAA AGUGUCUC    38

( 2 ) INFORMATION FOR SEQ ID NO:382:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:382:

GACACUAUAA UGAUGAA           17

( 2 ) INFORMATION FOR SEQ ID NO:383:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:383:

UUCAUCAUCU GAUGAGGCCG AAAGGCCGAA AUAGUGUC    38

( 2 ) INFORMATION FOR SEQ ID NO:384:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:384:

AAGCGAAUAA AGGAAUU                    17

( 2 ) INFORMATION FOR SEQ ID NO:385:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:385:

AAUUCCUUCU GAUGAGGCCG AAAGGCCGAA AUUCGCUU      38

( 2 ) INFORMATION FOR SEQ ID NO:386:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:386:

AAAGGAAUUA GAAUUGC                    17

( 2 ) INFORMATION FOR SEQ ID NO:387:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:387:

GCAAUUCUCU GAUGAGGCCG AAAGGCCGAA AUUCCUUU      38

( 2 ) INFORMATION FOR SEQ ID NO:388:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:388:

AAGGAAUUAG AAUUGCU                    17

( 2 ) INFORMATION FOR SEQ ID NO:389:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:389:

AGCAAUUCCU GAUGAGGCCG AAAGGCCGAA AAUUCCUU      38

( 2 ) INFORMATION FOR SEQ ID NO:390:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:390:

AUUAGAAUUG CUCCUAA                                                            17

( 2 ) INFORMATION FOR SEQ ID NO:391:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:391:

UUAGGAGCCU GAUGAGGCCG AAAGGCCGAA AUUCUAAU                                      38

( 2 ) INFORMATION FOR SEQ ID NO:392:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:392:

GAAUUGCUCC UAAUGUC                                                            17

( 2 ) INFORMATION FOR SEQ ID NO:393:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:393:

GACAUUAGCU GAUGAGGCCG AAAGGCCGAA AGCAAUUC                                      38

( 2 ) INFORMATION FOR SEQ ID NO:394:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:394:

UUGCUCCUAA UGUCAAC                                                            17

( 2 ) INFORMATION FOR SEQ ID NO:395:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:395:

GUUGACAUCU GAUGAGGCCG AAAGGCCGAA AGGAGCAA                                      38

( 2 ) INFORMATION FOR SEQ ID NO:396:

( i ) SEQUENCE CHARACTERISTICS:
        ( A ) LENGTH: 17 base pairs (B) TYPE: nucleic acid
                (C) STRANDEDNESS: single
                (D) TOPOLOGY: linear (xi) SEQUENCE DESCRIPTION: SEQ ID NO: 396:

AAUGAGCUAA AAGGACA                                                                                          17

(2) INFORMATION FOR SEQ ID NO:397:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:397:

UGUCCUUUCU GAUGAGGCCG AAAGGCCGAA AGCUCAUU                                                                    38

(2) INFORMATION FOR SEQ ID NO:398:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:398:

AUGCAGCUAC CCCGGGU                                                                                          17

(2) INFORMATION FOR SEQ ID NO:399:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:399:

ACCCGGGGCU GAUGAGGCCG AAAGGCCGAA AGCUGCAU                                                                    38

(2) INFORMATION FOR SEQ ID NO:400:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:400:

ACCACCAUUG CCGACCA                                                                                          17

(2) INFORMATION FOR SEQ ID NO:401:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:401:

UGGUCGGCCU GAUGAGGCCG AAAGGCCGAA AUGGUGGU                                                                    38

(2) INFORMATION FOR SEQ ID NO:402:

(i) SEQUENCE CHARACTERISTICS:
                (A) LENGTH: 17 base pairs
                (B) TYPE: nucleic acid
                (C) STRANDEDNESS: single ( D ) TOPOLOGY: linear ( x i ) SEQUENCE DESCRIPTION: SEQ ID NO:402:

CCAGACCUCA UGGAGAC                                                                                                17

( 2 ) INFORMATION FOR SEQ ID NO:403:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:403:

GUCUCCAUCU GAUGAGGCCG AAAGGCCGAA AGGUCUGG                                                                         38

( 2 ) INFORMATION FOR SEQ ID NO:404:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:404:

CACCUGUUUC CUGUUUG                                                                                                17

( 2 ) INFORMATION FOR SEQ ID NO:405:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:405:

CAAACAGGCU GAUGAGGCCG AAAGGCCGAA AACAGGUG                                                                         38

( 2 ) INFORMATION FOR SEQ ID NO:406:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:406:

ACCUGUUUCC UGUUUGG                                                                                                17

( 2 ) INFORMATION FOR SEQ ID NO:407:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:407:

CCAAACAGCU GAUGAGGCCG AAAGGCCGAA AAACAGGU                                                                         38

( 2 ) INFORMATION FOR SEQ ID NO:408:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (x i) SEQUENCE DESCRIPTION: SEQ ID NO:408:

UUCCUGUUUG GGAGAAC 17

(2) INFORMATION FOR SEQ ID NO:409:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:409:

GUUCUCCCCU GAUGAGGCCG AAAGGCCGAA AACAGGAA 38

(2) INFORMATION FOR SEQ ID NO:410:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:410:

ACACCACUCC ACUCCAU 17

(2) INFORMATION FOR SEQ ID NO:411:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:411:

AUGGAGUGCU GAUGAGGCCG AAAGGCCGAA AGUGGUGU 38

(2) INFORMATION FOR SEQ ID NO:412:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:412:

ACUCCACUCC AUCUCUG 17

(2) INFORMATION FOR SEQ ID NO:413:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:413:

CAGAGAUGCU GAUGAGGCCG AAAGGCCGAA AGUGGAGU 38

(2) INFORMATION FOR SEQ ID NO:414:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:414:

CACUCCAUCU CUGCCAG                                                                                      17

( 2 ) INFORMATION FOR SEQ ID NO:415:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:415:

CUGGCAGACU GAUGAGGCCG AAAGGCCGAA AUGGAGUG                                                                38

( 2 ) INFORMATION FOR SEQ ID NO:416:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:416:

CUCCAUCUCU GCCAGCG                                                                                      17

( 2 ) INFORMATION FOR SEQ ID NO:417:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:417:

CGCUGGCACU GAUGAGGCCG AAAGGCCGAA AGAUGGAG                                                                38

( 2 ) INFORMATION FOR SEQ ID NO:418:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:418:

CAGCGGAUCC UGGCUCC                                                                                      17

( 2 ) INFORMATION FOR SEQ ID NO:419:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:419:

GGAGCCAGCU GAUGAGGCCG AAAGGCCGAA AUCCGCUG                                                                38

( 2 ) INFORMATION FOR SEQ ID NO:420:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:420:

UCCUGGCUCC CUACCUG                                                                                      17

( 2 ) INFORMATION FOR SEQ ID NO:421:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:421:

CAGGUAGGCU GAUGAGGCCG AAAGGCCGAA AGCCAGGA    38

( 2 ) INFORMATION FOR SEQ ID NO:422:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:422:

GGCUCCCUAC CUGAAGA    17

( 2 ) INFORMATION FOR SEQ ID NO:423:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:423:

UCUUCAGGCU GAUGAGGCCG AAAGGCCGAA AGGGAGCC    38

( 2 ) INFORMATION FOR SEQ ID NO:424:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:424:

AAGCGCCUCG CCAGCAA    17

( 2 ) INFORMATION FOR SEQ ID NO:425:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:425:

UUGCUGGCCU GAUGAGGCCG AAAGGCCGAA AGGCGCUU    38

( 2 ) INFORMATION FOR SEQ ID NO:426:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:426:

UGCAUGAUCG UCCACCA    17

( 2 ) INFORMATION FOR SEQ ID NO:427:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:427:

UGGUGGACCU GAUGAGGCCG AAAGGCGAA AUCAUGCA 38

( 2 ) INFORMATION FOR SEQ ID NO:428:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:428:

GGCACCAUUC UGGAUAA 17

( 2 ) INFORMATION FOR SEQ ID NO:429:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:429:

UUAUCCAGCU GAUGAGGCCG AAAGGCCGAA AUGGUGCC 38

( 2 ) INFORMATION FOR SEQ ID NO:430:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:430:

GCACCAUUCU GGAUAAU 17

( 2 ) INFORMATION FOR SEQ ID NO:431:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:431:

AUUAUCCACU GAUGAGGCCG AAAGGCCGAA AAUGGUGC 38

( 2 ) INFORMATION FOR SEQ ID NO:432:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:432:

UUCUGGAUAA UGUUAAG 17

( 2 ) INFORMATION FOR SEQ ID NO:433:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:433:

CUUAACAUCU GAUGAGGCCG AAAGGCCGAA AUCCAGAA 38

(2) INFORMATION FOR SEQ ID NO:434:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:434:

AUAAUGUUAA GAACCUC 17

(2) INFORMATION FOR SEQ ID NO:435:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:435:

GAGGUUCUCU GAUGAGGCCG AAAGGCCGAA AACAUUAU 38

(2) INFORMATION FOR SEQ ID NO:436:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:436:

AAGAACCUCU UAGAAUU 17

(2) INFORMATION FOR SEQ ID NO:437:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:437:

AAUUCUAACU GAUGAGGCCG AAAGGCCGAA AGGUUCUU 38

(2) INFORMATION FOR SEQ ID NO:438:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:438:

GAACCUCUUA GAAUUUG 17

(2) INFORMATION FOR SEQ ID NO:439:

(i) SEQUENCE CHARACTERISTICS:
(A) LENGTH: 38 base pairs
(B) TYPE: nucleic acid (C) STRANDEDNESS: single
        (D) TOPOLOGY: linear (x i) SEQUENCE DESCRIPTION: SEQ ID NO:439:

CAAAUUCUCU GAUGAGGCCG AAAGGCCGAA AGAGGUUC                                38

(2) INFORMATION FOR SEQ ID NO:440:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:440:

AACCUCUUAG AAUUUGC                                                       17

(2) INFORMATION FOR SEQ ID NO:441:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:441:

GCAAAUUCCU GAUGAGGCCG AAAGGCCGAA AAGAGGUU                                38

(2) INFORMATION FOR SEQ ID NO:442:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:442:

CUUAGAAUUU GCAGAAA                                                       17

(2) INFORMATION FOR SEQ ID NO:443:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:443:

UUUCUGCACU GAUGAGGCCG AAAGGCCGAA AUUCUAAG                                38

(2) INFORMATION FOR SEQ ID NO:444:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:444:

UUAGAAUUUG CAGAAAC                                                       17

(2) INFORMATION FOR SEQ ID NO:445:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:445:

GUUUCUGCCU GAUGAGGCCG AAAGGCCGAA AAUUCUAA 38

( 2 ) INFORMATION FOR SEQ ID NO:446:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:446:

GAAACACUCC AAUUUAU 17

( 2 ) INFORMATION FOR SEQ ID NO:447:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:447:

AUAAAUUGCU GAUGAGGCCG AAAGGCCGAA AGUGUUUC 38

( 2 ) INFORMATION FOR SEQ ID NO:448:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:448:

ACUCCAAUUU AUAGAUU 17

( 2 ) INFORMATION FOR SEQ ID NO:449:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:449:

AAUCUAUACU GAUGAGGCCG AAAGGCCGAA AUUGGAGU 38

( 2 ) INFORMATION FOR SEQ ID NO:450:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:450:

CUCCAAUUUA UAGAUUC 17

( 2 ) INFORMATION FOR SEQ ID NO:451:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:451:

```
GAAUCUAUCU  GAUGAGGCCG  AAAGGCCGAA  AAUUGGAG                                      38
```

( 2 ) INFORMATION FOR SEQ ID NO:452:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:452:

```
UCCAAUUUAU  AGAUUCU                                                                17
```

( 2 ) INFORMATION FOR SEQ ID NO:453:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:453:

```
AGAAUCUACU  GAUGAGGCCG  AAAGGCCGAA  AAAUUGGA                                      38
```

( 2 ) INFORMATION FOR SEQ ID NO:454:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:454:

```
CAAUUUAUAG  AUUCUUU                                                                17
```

( 2 ) INFORMATION FOR SEQ ID NO:455:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:455:

```
AAAGAAUCCU  GAUGAGGCCG  AAAGGCCGAA  AUAAAUUG                                      38
```

( 2 ) INFORMATION FOR SEQ ID NO:456:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:456:

```
UUAUAGAUUC  UUUCUUA                                                                17
```

( 2 ) INFORMATION FOR SEQ ID NO:457:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:457:

```
UAAGAAAGCU  GAUGAGGCCG  AAAGGCCGAA  AUCUAUAA                                      38
```

( 2 ) INFORMATION FOR SEQ ID NO:458:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:458:

UAUAGAUUCU UUCUUAA        17

( 2 ) INFORMATION FOR SEQ ID NO:459:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:459:

UUAAGAAACU GAUGAGGCCG AAAGGCCGAA AAUCUAUA        38

( 2 ) INFORMATION FOR SEQ ID NO:460:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:460:

UAGAUUCUUU CUUAAAC        17

( 2 ) INFORMATION FOR SEQ ID NO:461:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:461:

GUUUAAGACU GAUGAGGCCG AAAGGCCGAA AGAAUCUA        38

( 2 ) INFORMATION FOR SEQ ID NO:462:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:462:

AGAUUCUUUC UUAAACA        17

( 2 ) INFORMATION FOR SEQ ID NO:463:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:463:

UGUUUAAGCU GAUGAGGCCG AAAGGCCGAA AAGAAUCU        38

( 2 ) INFORMATION FOR SEQ ID NO:464:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:464:

GAUUCUUUCU UAAACAC                                  17

( 2 ) INFORMATION FOR SEQ ID NO:465:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:465:

GUGUUUAACU GAUGAGGCCG AAAGGCCGAA AAAGAAUC         38

( 2 ) INFORMATION FOR SEQ ID NO:466:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:466:

UUCUUUCUUA AACACUU                                 17

( 2 ) INFORMATION FOR SEQ ID NO:467:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:467:

AAGUGUUUCU GAUGAGGCCG AAAGGCCGAA AGAAAGAA         38

( 2 ) INFORMATION FOR SEQ ID NO:468:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:468:

UCUUUCUUAA ACACUUC                                 17

( 2 ) INFORMATION FOR SEQ ID NO:469:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:469:

GAAGUGUUCU GAUGAGGCCG AAAGGCCGAA AAGAAAGA         38

( 2 ) INFORMATION FOR SEQ ID NO:470:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:470:

UAAACACUUC CAGUAAC      17

( 2 ) INFORMATION FOR SEQ ID NO:471:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:471:

GUUACUGGCU GAUGAGGCCG AAAGGCCGAA AGUGUUUA      38

( 2 ) INFORMATION FOR SEQ ID NO:472:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:472:

AAACACUUCC AGUAACC      17

( 2 ) INFORMATION FOR SEQ ID NO:473:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:473:

GGUUACUGCU GAUGAGGCCG AAAGGCCGAA AAGUGUUU      38

( 2 ) INFORMATION FOR SEQ ID NO:474:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:474:

UGAAAACUCA GACUUGG      17

( 2 ) INFORMATION FOR SEQ ID NO:475:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:475:

CCAAGUCUCU GAUGAGGCCG AAAGGCCGAA AGUUUUCA      38

( 2 ) INFORMATION FOR SEQ ID NO:476:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:476:

CUCAGACUUG GAAAUGC 17

(2) INFORMATION FOR SEQ ID NO:477:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:477:

GCAUUUCCCU GAUGAGGCCG AAAGGCCGAA AGUCUGAG 38

(2) INFORMATION FOR SEQ ID NO:478:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:478:

AAAUGCCUUC UUUAACU 17

(2) INFORMATION FOR SEQ ID NO:479:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:479:

AGUUAAAGCU GAUGAGGCCG AAAGGCCGAA AGGCAUUU 38

(2) INFORMATION FOR SEQ ID NO:480:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:480:

AAUGCCUUCU UUAACUU 17

(2) INFORMATION FOR SEQ ID NO:481:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:481:

AAGUUAAACU GAUGAGGCCG AAAGGCCGAA AAGGCAUU 38

(2) INFORMATION FOR SEQ ID NO:482:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO:482:

UGCCUUCUUU AACUUCC 17

(2) INFORMATION FOR SEQ ID NO:483:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:483:

GGAAGUUACU GAUGAGGCCG AAAGGCCGAA AGAAGGCA 38

(2) INFORMATION FOR SEQ ID NO:484:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:484:

GCCUUCUUUA ACUUCCA 17

(2) INFORMATION FOR SEQ ID NO:485:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:485:

UGGAAGUUCU GAUGAGGCCG AAAGGCCGAA AAGAAGGC 38

(2) INFORMATION FOR SEQ ID NO:486:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:486:

CCUUCUUUAA CUUCCAC 17

(2) INFORMATION FOR SEQ ID NO:487:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:487:

GUGGAAGUCU GAUGAGGCCG AAAGGCCGAA AAAGAAGG 38

(2) INFORMATION FOR SEQ ID NO:488:

(i) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:488:

CUUUAACUUC CACCCCC                                                                                          17

( 2 ) INFORMATION FOR SEQ ID NO:489:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:489:

GGGGGUGGCU GAUGAGGCCG AAAGGCCGAA AGUUAAAG                                                                    38

( 2 ) INFORMATION FOR SEQ ID NO:490:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:490:

UUUAACUUCC ACCCCCC                                                                                          17

( 2 ) INFORMATION FOR SEQ ID NO:491:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:491:

GGGGGGUGCU GAUGAGGCCG AAAGGCCGAA AAGUUAAA                                                                    38

( 2 ) INFORMATION FOR SEQ ID NO:492:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:492:

ACCCCCCUCA UUGGUCA                                                                                          17

( 2 ) INFORMATION FOR SEQ ID NO:493:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:493:

UGACCAAUCU GAUGAGGCCG AAAGGCCGAA AGGGGGGU                                                                    38

( 2 ) INFORMATION FOR SEQ ID NO:494:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:494:

CCCCUCAUUG GUCACAA                                              17

( 2 ) INFORMATION FOR SEQ ID NO:495:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:495:

UUGUGACCCU GAUGAGGCCG AAAGGCCGAA AUGAGGGG                        38

( 2 ) INFORMATION FOR SEQ ID NO:496:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:496:

UCACAAAUUG ACUGUUA                                              17

( 2 ) INFORMATION FOR SEQ ID NO:497:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:497:

UAACAGUCCU GAUGAGGCCG AAAGGCCGAA AUUUGUGA                        38

( 2 ) INFORMATION FOR SEQ ID NO:498:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:498:

UGACUGUUAC AACACCA                                              17

( 2 ) INFORMATION FOR SEQ ID NO:499:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:499:

UGGUGUUGCU GAUGAGGCCG AAAGGCCGAA AACAGUCA                        38

( 2 ) INFORMATION FOR SEQ ID NO:500:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:500:

AACACCAUUU CAUAGAG                                              17

( 2 ) INFORMATION FOR SEQ ID NO:501:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:501:

CUCUAUGACU GAUGAGGCCG AAAGGCCGAA AUGGUGUU         38

( 2 ) INFORMATION FOR SEQ ID NO:502:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:502:

ACACCAUUUC AUAGAGA         17

( 2 ) INFORMATION FOR SEQ ID NO:503:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:503:

UCUCUAUGCU GAUGAGGCCG AAAGGCCGAA AAUGGUGU         38

( 2 ) INFORMATION FOR SEQ ID NO:504:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:504:

CACCAUUUCA UAGAGAC         17

( 2 ) INFORMATION FOR SEQ ID NO:505:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:505:

GUCUCUAUCU GAUGAGGCCG AAAGGCCGAA AAAUGGUG         38

( 2 ) INFORMATION FOR SEQ ID NO:506:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:506:

CAUUUCAUAG AGACCAG         17

( 2 ) INFORMATION FOR SEQ ID NO:507:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:507:

CUGGUCUCCU GAUGAGGCCG AAAGGCCGAA AUGAAAUG                         38

( 2 ) INFORMATION FOR SEQ ID NO:508:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:508:

UGAAAACUCA AAAGGAA                                                17

( 2 ) INFORMATION FOR SEQ ID NO:509:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:509:

UUCCUUUUCU GAUGAGGCCG AAAGGCCGAA AGUUUUCA                         38

( 2 ) INFORMATION FOR SEQ ID NO:510:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:510:

AGGAAAAUAC UGUUUUU                                                17

( 2 ) INFORMATION FOR SEQ ID NO:511:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:511:

AAAAACAGCU GAUGAGGCCG AAAGGCCGAA AUUUUCCU                         38

( 2 ) INFORMATION FOR SEQ ID NO:512:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:512:

AUACUGUUUU UAGAACC                                                17

( 2 ) INFORMATION FOR SEQ ID NO:513:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:513:

GGUUCUAACU GAUGAGGCCG AAAGGCCGAA AACAGUAU                        38

(2) INFORMATION FOR SEQ ID NO:514:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:514:

UACUGUUUUU AGAACCC                                                17

(2) INFORMATION FOR SEQ ID NO:515:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:515:

GGGUUCUACU GAUGAGGCCG AAAGGCCGAA AAACAGUA                         38

(2) INFORMATION FOR SEQ ID NO:516:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:516:

ACUGUUUUA GAACCCC                                                 17

(2) INFORMATION FOR SEQ ID NO:517:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:517:
            GGGGUUCUCU GAUGAGGCCG AAAGGCCGAA AAAACAGU (2) INFORMATION FOR SEQ ID NO:518:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:518:

CUGUUUUUAG AACCCCA                                                17

(2) INFORMATION FOR SEQ ID NO:519:

(i) SEQUENCE CHARACTERISTICS:
(A) LENGTH: 38 base pairs
(B) TYPE: nucleic acid
(C) STRANDEDNESS: single
(D) TOPOLOGY: linear ( x i ) SEQUENCE DESCRIPTION: SEQ ID NO:519:

UGGGGUUCCU GAUGAGGCCG AAAGGCCGAA AAAAACAG    38

( 2 ) INFORMATION FOR SEQ ID NO:520:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:520:

CCCCAGCUAU CAAAAGG    17

( 2 ) INFORMATION FOR SEQ ID NO:521:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:521:

CCUUUUGACU GAUGAGGCCG AAAGGCCGAA AGCUGGGG    38

( 2 ) INFORMATION FOR SEQ ID NO:522:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:522:

CCAGCUAUCA AAAGGUC    17

( 2 ) INFORMATION FOR SEQ ID NO:523:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:523:

GACCUUUUCU GAUGAGGCCG AAAGGCCGAA AUAGCUGG    38

( 2 ) INFORMATION FOR SEQ ID NO:524:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:524:

AGGUCAAUCU UAGAAAG    17

( 2 ) INFORMATION FOR SEQ ID NO:525:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:525:

CUUUCUAACU GAUGAGGCCG AAAGGCCGAA AUUGACCU                                    3 8

( 2 ) INFORMATION FOR SEQ ID NO:526:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:526:

GUCAAUCUUA GAAAGCU                                                            1 7

( 2 ) INFORMATION FOR SEQ ID NO:527:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:527:

AGCUUUCUCU GAUGAGGCCG AAAGGCCGAA AGAUUGAC                                     3 8

( 2 ) INFORMATION FOR SEQ ID NO:528:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:528:

UCAAUCUUAG AAAGCUC ( 2 ) INFORMATION FOR SEQ ID NO:529:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:529:

GAGCUUUCCU GAUGAGGCCG AAAGGCCGAA AAGAUUGA                                     3 8

( 2 ) INFORMATION FOR SEQ ID NO:530:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:530:

AGAAAGCUCU CCAAGAA                                                            1 7

( 2 ) INFORMATION FOR SEQ ID NO:531:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:531:

UUCUUGGACU GAUGAGGCCG AAAGGCCGAA AGCUUUCU                                     3 8

( 2 ) INFORMATION FOR SEQ ID NO:532:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:532:

AAAGCUCUCC AAGAACU        17

( 2 ) INFORMATION FOR SEQ ID NO:533:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:533:

AGUUCUUGCU GAUGAGGCCG AAAGGCCGAA AGAGCUUU        38

( 2 ) INFORMATION FOR SEQ ID NO:534:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:534:

CAAGAACUCC UACACCA        17

( 2 ) INFORMATION FOR SEQ ID NO:535:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:535:

UGGUGUAGCU GAUGAGGCCG AAAGGCCGAA AGUUCUUG        38

( 2 ) INFORMATION FOR SEQ ID NO:536:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:536:

GAACUCCUAC ACCAUUC        17

( 2 ) INFORMATION FOR SEQ ID NO:537:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:537:

GAAUGGUGCU GAUGAGGCCG AAAGGCCGAA AGGAGUUC        38

( 2 ) INFORMATION FOR SEQ ID NO:538:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:538:

UACACCAUUC AAACAUG 17

( 2 ) INFORMATION FOR SEQ ID NO:539:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:539:

CAUGUUUGCU GAUGAGGCCG AAAGGCCGAA AUGGUGUA ( 2 ) INFORMATION FOR SEQ ID NO:540:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:540:

ACACCAUUCA AACAUGC 17

( 2 ) INFORMATION FOR SEQ ID NO:541:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:541:

GCAUGUUUCU GAUGAGGCCG AAAGGCCGAA AAUGGUGU 38

( 2 ) INFORMATION FOR SEQ ID NO:542:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:542:

CAUGCACUUG CAGCUCA 17

( 2 ) INFORMATION FOR SEQ ID NO:543:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:543:

UGAGCUGCCU GAUGAGGCCG AAAGGCCGAA AGUGCAUG 38

( 2 ) INFORMATION FOR SEQ ID NO:544:

( i ) SEQUENCE CHARACTERISTICS:
    ( A ) LENGTH: 17 base pairs
    ( B ) TYPE: nucleic acid
    ( C ) STRANDEDNESS: single (D) TOPOLOGY: linear (xi) SEQUENCE DESCRIPTION: SEQ ID NO:544:

UUGCAGCUCA AGAAAUU 17

(2) INFORMATION FOR SEQ ID NO:545:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:545:

AAUUCUUCU GAUGAGGCCG AAAGGCCGAA AGCUGCAA 38

(2) INFORMATION FOR SEQ ID NO:546:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:546:

CAAGAAAUUA AAUACGG 17

(2) INFORMATION FOR SEQ ID NO:547:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:547:

CCGUAUUUCU GAUGAGGCCG AAAGGCCGAA AUUUCUUG 38

(2) INFORMATION FOR SEQ ID NO:548:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:548:

AAGAAAUUAA AUACGGU 17

(2) INFORMATION FOR SEQ ID NO:549:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:549:

ACCGUAUUCU GAUGAGGCCG AAAGGCCGAA AAUUUCUU 38

(2) INFORMATION FOR SEQ ID NO:550:

(i) SEQUENCE CHARACTERISTICS:
    (A) LENGTH: 17 base pairs
    (B) TYPE: nucleic acid
    (C) STRANDEDNESS: single
    (D) TOPOLOGY: linear ( x i ) SEQUENCE DESCRIPTION: SEQ ID NO:550:

AAUUAAAUAC GGUCCCC ( 2 ) INFORMATION FOR SEQ ID NO:551:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:551:

GGGGACCGCU GAUGAGGCCG AAAGGCCGAA AUUUAAUU 38

( 2 ) INFORMATION FOR SEQ ID NO:552:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:552:

AAGAUGCUAC CUCAGAC 17

( 2 ) INFORMATION FOR SEQ ID NO:553:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:553:

GUCUGAGGCU GAUGAGGCCG AAAGGCCGAA AGCAUCUU 38

( 2 ) INFORMATION FOR SEQ ID NO:554:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:554:

UGCUACCUCA GACACCC 17

( 2 ) INFORMATION FOR SEQ ID NO:555:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:555:

GGGUGUCUCU GAUGAGGCCG AAAGGCCGAA AGGUAGCA 38

( 2 ) INFORMATION FOR SEQ ID NO:556:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:556:

GACACCCUCU CAUCUAG 17

( 2 ) INFORMATION FOR SEQ ID NO:557:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:557:

CUAGAUGACU GAUGAGGCCG AAAGGCCGAA AGGGUGUC    38

( 2 ) INFORMATION FOR SEQ ID NO:558:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:558:

CACCCUCUCA UCUAGUA    17

( 2 ) INFORMATION FOR SEQ ID NO:559:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:559:

UACUAGAUCU GAUGAGGCCG AAAGGCCGAA AGAGGGUG    38

( 2 ) INFORMATION FOR SEQ ID NO:560:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:560:

CCUCUCAUCU AGUAGAA    17

( 2 ) INFORMATION FOR SEQ ID NO:561:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:561:
        UUCUACUACU GAUGAGGCCG AAAGGCCGAA AUGAGAGG ( 2 ) INFORMATION FOR SEQ ID NO:562:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:562:

UCUCAUCUAG UAGAAGA    17

( 2 ) INFORMATION FOR SEQ ID NO:563:

( i ) SEQUENCE CHARACTERISTICS:

(A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:563:

UCUUCUACCU GAUGAGGCCG AAAGGCCGAA AGAUGAGA 38

(2) INFORMATION FOR SEQ ID NO:564:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:564:

UAGAAGAUCU GCAGGAU 17

(2) INFORMATION FOR SEQ ID NO:565:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:565:

AUCCUGCACU GAUGAGGCCG AAAGGCCGAA AUCUUCUA 38

(2) INFORMATION FOR SEQ ID NO:566:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:566:

GAUGUGAUCA AACAGGA 17

(2) INFORMATION FOR SEQ ID NO:567:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:567:

UCCUGUUUCU GAUGAGGCCG AAAGGCCGAA AUCACAUC 38

(2) INFORMATION FOR SEQ ID NO:568:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:568:

ACAGGAAUCU GAUGAAU 17

(2) INFORMATION FOR SEQ ID NO:569:

(i) SEQUENCE CHARACTERISTICS:
        (A) LENGTH: 38 base pairs
        (B) TYPE: nucleic acid ( C ) STRANDEDNESS: single
        ( D ) TOPOLOGY: linear ( x i ) SEQUENCE DESCRIPTION: SEQ ID NO:569:

AUUCAUCACU GAUGAGGCCG AAAGGCCGAA AUUCCUGU                    38

( 2 ) INFORMATION FOR SEQ ID NO:570:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:570:

UGAUGAAUCU GGAAUUG                    17

( 2 ) INFORMATION FOR SEQ ID NO:571:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:571:

CAAUUCCACU GAUGAGGCCG AAAGGCCGAA AUUCAUCA                    38

( 2 ) INFORMATION FOR SEQ ID NO:572:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:572:
                    UCUGGAAUUG UUGCUGA ( 2 ) INFORMATION FOR SEQ ID NO:573:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:573:

UCAGCAACCU GAUGAGGCCG AAAGGCCGAA AUUCCAGA                    38

( 2 ) INFORMATION FOR SEQ ID NO:574:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:574:

GCUGAGUUUC AAGAAAA                    17

( 2 ) INFORMATION FOR SEQ ID NO:575:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:575:

```
UUUUCUUGCU  GAUGAGGCCG  AAAGGCCGAA  AACUCAGC                                          38
```

( 2 ) INFORMATION FOR SEQ ID NO:576:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:576:

```
CUGAGUUUCA  AGAAAAU                                                                   17
```

( 2 ) INFORMATION FOR SEQ ID NO:577:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:577:

```
AUUUCUUCU  GAUGAGGCCG  AAAGGCCGAA  AAACUCAG                                           38
```

( 2 ) INFORMATION FOR SEQ ID NO:578:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:578:

```
ACCACCCUUA  CUGAAGA                                                                   17
```

( 2 ) INFORMATION FOR SEQ ID NO:579:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:579:

```
UCUUCAGUCU  GAUGAGGCCG  AAAGGCCGAA  AGGGUGGU                                          38
```

( 2 ) INFORMATION FOR SEQ ID NO:580:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:580:

```
CCACCCUUAC  UGAAGAA                                                                   17
```

( 2 ) INFORMATION FOR SEQ ID NO:581:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:581:

```
UUCUUCAGCU  GAUGAGGCCG  AAAGGCCGAA  AAGGGUGG                                          38
```

( 2 ) INFORMATION FOR SEQ ID NO:582:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:582:

AAGAAAAUCA AACAAGA 17

( 2 ) INFORMATION FOR SEQ ID NO:583:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:583:

UCUUGUUUCU GAUGAGGCCG AAAGGCCGAA AUUUCUU ( 2 ) INFORMATION FOR SEQ ID NO:584:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:584:

GGUGGAAUCU CCAACUG 17

( 2 ) INFORMATION FOR SEQ ID NO:585:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:585:

CAGUUGGACU GAUGAGGCCG AAAGGCCGAA AUUCCACC 38

( 2 ) INFORMATION FOR SEQ ID NO:586:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:586:

UGGAAUCUCC AACUGAU 17

( 2 ) INFORMATION FOR SEQ ID NO:587:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:587:

AUCAGUUGCU GAUGAGGCCG AAAGGCCGAA AGAUUCCA 38

( 2 ) INFORMATION FOR SEQ ID NO:588:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:588:

CAACUGAUAA AUCAGGA 17

( 2 ) INFORMATION FOR SEQ ID NO:589:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:589:

UCCUGAUUCU GAUGAGGCCG AAAGGCCGAA AUCAGUUG 38

( 2 ) INFORMATION FOR SEQ ID NO:590:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:590:

UGAUAAAUCA GGAAACU 17

( 2 ) INFORMATION FOR SEQ ID NO:591:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:591:

AGUUUCCUCU GAUGAGGCCG AAAGGCCGAA AUUUAUCA 38

( 2 ) INFORMATION FOR SEQ ID NO:592:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:592:

AGGAAACUUC UUCUGCU 17

( 2 ) INFORMATION FOR SEQ ID NO:593:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:593:

AGCAGAAGCU GAUGAGGCCG AAAGGCCGAA AGUUUCCU 38

( 2 ) INFORMATION FOR SEQ ID NO:594:

( i ) SEQUENCE CHARACTERISTICS:
    ( A ) LENGTH: 17 base pairs (B) TYPE: nucleic acid
                (C) STRANDEDNESS: single
                (D) TOPOLOGY: linear (xi) SEQUENCE DESCRIPTION: SEQ ID NO:594:
                        GGAAACUUCU UCUGCUC (2) INFORMATION FOR SEQ ID NO:595:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:595:

GAGCAGAACU GAUGAGGCCG AAAGGCCGAA AAGUUUCC                                    38

(2) INFORMATION FOR SEQ ID NO:596:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:596:

AAACUUCUUC UGCUCAC                                                           17

(2) INFORMATION FOR SEQ ID NO:597:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:597:

GUGAGCAGCU GAUGAGGCCG AAAGGCCGAA AGAAGUUU                                    38

(2) INFORMATION FOR SEQ ID NO:598:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:598:

AACUUCUUCU GCUCACA                                                           17

(2) INFORMATION FOR SEQ ID NO:599:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:599:

UGUGAGCACU GAUGAGGCCG AAAGGCCGAA AAGAAGUU                                    38

(2) INFORMATION FOR SEQ ID NO:600:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (x i) SEQUENCE DESCRIPTION: SEQ ID NO:600:

CUUCUGCUCA CACCACU                                                                              17

(2) INFORMATION FOR SEQ ID NO:601:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:601:

AGUGGUGUCU GAUGAGGCCG AAAGGCCGAA AGCAGAAG                                                        38

(2) INFORMATION FOR SEQ ID NO:602:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:602:

GUCUGAAUAC CCAACUG                                                                              17

(2) INFORMATION FOR SEQ ID NO:603:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:603:

CAGUUGGGCU GAUGAGGCCG AAAGGCCGAA AUUCAGAC                                                        38

(2) INFORMATION FOR SEQ ID NO:604:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:604:

CAACUGUUCA CGCAGAC                                                                              17

(2) INFORMATION FOR SEQ ID NO:605:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:605:
                GUCUGCGUCU GAUGAGGCCG AAAGGCCGAA AACAGUUG (2) INFORMATION FOR SEQ ID NO:606:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:606:

GCAGACCUCG CCUGUGG                                                                              17

( 2 ) INFORMATION FOR SEQ ID NO:607:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:607:

CCACAGGCCU GAUGAGGCCG AAAGGCCGAA AGGUCUGC        38

( 2 ) INFORMATION FOR SEQ ID NO:608:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:608:

CACCGAAUAU UCUUACA        17

( 2 ) INFORMATION FOR SEQ ID NO:609:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:609:

UGUAAGAACU GAUGAGGCCG AAAGGCCGAA AUUCGGUG        38

( 2 ) INFORMATION FOR SEQ ID NO:610:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:610:

CCGAAUAUUC UUACAAG        17

( 2 ) INFORMATION FOR SEQ ID NO:611:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:611:

CUUGUAAGCU GAUGAGGCCG AAAGGCCGAA AUAUUCGG        38

( 2 ) INFORMATION FOR SEQ ID NO:612:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:612:

CGAAUAUUCU UACAAGC        17

( 2 ) INFORMATION FOR SEQ ID NO:613:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:613:

GCUUGUAACU GAUGAGGCCG AAAGGCCGAA AAUAUUCG 38

( 2 ) INFORMATION FOR SEQ ID NO:614:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:614:

AAUAUUCUUA CAAGCUC 17

( 2 ) INFORMATION FOR SEQ ID NO:615:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:615:

GAGCUUGUCU GAUGAGGCCG AAAGGCCGAA AGAAUAUU 38

( 2 ) INFORMATION FOR SEQ ID NO:616:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:616:

AUAUUCUUAC AAGCUCC ( 2 ) INFORMATION FOR SEQ ID NO:617:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:617:

GGAGCUUGCU GAUGAGGCCG AAAGGCCGAA AAGAAUAU 38

( 2 ) INFORMATION FOR SEQ ID NO:618:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:618:

UACAAGCUCC GUUUUAA 17

( 2 ) INFORMATION FOR SEQ ID NO:619:

( i ) SEQUENCE CHARACTERISTICS:
( A ) LENGTH: 38 base pairs
( B ) TYPE: nucleic acid (C) STRANDEDNESS: single
(D) TOPOLOGY: linear (xi) SEQUENCE DESCRIPTION: SEQ ID NO:619:

UUAAAACGCU GAUGAGGCCG AAAGGCCGAA AGCUUGUA                                    38

(2) INFORMATION FOR SEQ ID NO:620:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:620:

GCUCCGUUUU AAUGGCA                                                          17

(2) INFORMATION FOR SEQ ID NO:621:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:621:

UGCCAUUACU GAUGAGGCCG AAAGGCCGAA AACGGAGC                                    38

(2) INFORMATION FOR SEQ ID NO:622:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:622:

CUCCGUUUUA AUGGCAC                                                          17

(2) INFORMATION FOR SEQ ID NO:623:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:623:

GUGCCAUUCU GAUGAGGCCG AAAGGCCGAA AAACGGAG                                    38

(2) INFORMATION FOR SEQ ID NO:624:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:624:

UCCGUUUUAA UGGCACC                                                          17

(2) INFORMATION FOR SEQ ID NO:625:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:625:

GGUGCCAUCU GAUGAGGCCG AAAGGCCGAA AAAACGGA    38

(2) INFORMATION FOR SEQ ID NO:626:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (x i) SEQUENCE DESCRIPTION: SEQ ID NO:626:

ACCAGCAUCA GAAGAUG    17

(2) INFORMATION FOR SEQ ID NO:627:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (x i) SEQUENCE DESCRIPTION: SEQ ID NO:627:

CAUCUUCUCU GAUGAGGCCG AAAGGCCGAA AUGCUGGU (2) INFORMATION FOR SEQ ID NO:628:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (x i) SEQUENCE DESCRIPTION: SEQ ID NO:628:

ACAAUGUUCU CAAAGCA    17

(2) INFORMATION FOR SEQ ID NO:629:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (x i) SEQUENCE DESCRIPTION: SEQ ID NO:629:

UGCUUUGACU GAUGAGGCCG AAAGGCCGAA AACAUUGU    38

(2) INFORMATION FOR SEQ ID NO:630:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (x i) SEQUENCE DESCRIPTION: SEQ ID NO:630:

AAUGUUCUCA AAGCAUU    17

(2) INFORMATION FOR SEQ ID NO:631:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (x i) SEQUENCE DESCRIPTION: SEQ ID NO:631:

AAUGCUUUCU GAUGAGGCCG AAAGGCCGAA AGAACAUU    38

( 2 ) INFORMATION FOR SEQ ID NO:632:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:632:

CAAAGCAUUU ACAGUAC                                        17

( 2 ) INFORMATION FOR SEQ ID NO:633:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:633:

GUACUGUACU GAUGAGGCCG AAAGGCCGAA AUGCUUUG           38

( 2 ) INFORMATION FOR SEQ ID NO:634:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:634:

AAAGCAUUUA CAGUACC                                        17

( 2 ) INFORMATION FOR SEQ ID NO:635:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:635:

GGUACUGUCU GAUGAGGCCG AAAGGCCGAA AAUGCUUU           38

( 2 ) INFORMATION FOR SEQ ID NO:636:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:636:

AAGCAUUUAC AGUACCU                                        17

( 2 ) INFORMATION FOR SEQ ID NO:637:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:637:

AGGUACUGCU GAUGAGGCCG AAAGGCCGAA AAAUGCUU           38

( 2 ) INFORMATION FOR SEQ ID NO:638:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:638:
        CAGUACCUAA AAACAGG ( 2 ) INFORMATION FOR SEQ ID NO:639:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:639:

CCUGUUUUCU GAUGAGGCCG AAAGGCCGAA AGGUACUG    38

( 2 ) INFORMATION FOR SEQ ID NO:640:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:640:

GAGCCCUUG CAGCCUU    17

( 2 ) INFORMATION FOR SEQ ID NO:641:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:641:

AAGGCUGCCU GAUGAGGCCG AAAGGCCGAA AGGGGCUC    38

( 2 ) INFORMATION FOR SEQ ID NO:642:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:642:

UGCAGCCUUG UAGCAGU    17

( 2 ) INFORMATION FOR SEQ ID NO:643:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:643:

ACUGCUACCU GAUGAGGCCG AAAGGCCGAA AGGCUGCA    38

( 2 ) INFORMATION FOR SEQ ID NO:644:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:644:

ACCUGCAUCC UGUGGAA 17

(2) INFORMATION FOR SEQ ID NO:645:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:645:

UUCCACAGCU GAUGAGGCCG AAAGGCCGAA AUGCAGGU 38

(2) INFORMATION FOR SEQ ID NO:646:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:646:

GAUGACAUCU UCCAGUC 17

(2) INFORMATION FOR SEQ ID NO:647:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:647:

GACUGGAACU GAUGAGGCCG AAAGGCCGAA AUGUCAUC 38

(2) INFORMATION FOR SEQ ID NO:648:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:648:

UGACAUCUUC CAGUCAA 17

(2) INFORMATION FOR SEQ ID NO:649:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:649:
UUGACUGGCU GAUGAGGCCG AAAGGCCGAA AGAUGUCA (2) INFORMATION FOR SEQ ID NO:650:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:650:

GACAUCUUCC AGUCAAG 17

( 2 ) INFORMATION FOR SEQ ID NO:651:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:651:

CUUGACUGCU GAUGAGGCCG AAAGGCCGAA AAGAUGUC 38

( 2 ) INFORMATION FOR SEQ ID NO:652:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:652:

CUUCCAGUCA AGCUCGU 17

( 2 ) INFORMATION FOR SEQ ID NO:653:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:653:

ACGAGCUUCU GAUGAGGCCG AAAGGCCGAA ACUGGAAG 38

( 2 ) INFORMATION FOR SEQ ID NO:654:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:654:

GUCAAGCUCG UAAAUAC 17

( 2 ) INFORMATION FOR SEQ ID NO:655:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:655:

GUAUUUACCU GAUGAGGCCG AAAGGCCGAA AGCUUGAC 38

( 2 ) INFORMATION FOR SEQ ID NO:656:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:656:

UCGUAAAUAC GUGAAUG 17

(2) INFORMATION FOR SEQ ID NO:657:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:657:

CAUUCACGCU GAUGAGGCCG AAAGGCCGAA AUUUACGA 38

(2) INFORMATION FOR SEQ ID NO:658:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:658:

GAAUGCAUUC UCAGCCC 17

(2) INFORMATION FOR SEQ ID NO:659:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:659:

GGGCUGAGCU GAUGAGGCCG AAAGGCCGAA AUGCAUUC 38

(2) INFORMATION FOR SEQ ID NO:660:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:660:

AAUGCAUUCU CAGCCCG (2) INFORMATION FOR SEQ ID NO:661:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:661:

CGGGCUGACU GAUGAGGCCG AAAGGCCGAA AAUGCAUU 38

(2) INFORMATION FOR SEQ ID NO:662:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:662:

UGCAUUCUCA GCCCGGA 17

(2) INFORMATION FOR SEQ ID NO:663:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:663:

UCCGGGCUCU GAUGAGGCCG AAAGGCCGAA AGAAUGCA 38

( 2 ) INFORMATION FOR SEQ ID NO:664:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:664:

UGAGACAUUU CCAGAAA 17

( 2 ) INFORMATION FOR SEQ ID NO:665:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:665:

UUUCUGGACU GAUGAGGCCG AAAGGCCGAA AUGUCUCA 38

( 2 ) INFORMATION FOR SEQ ID NO:666:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:666:

GAGACAUUUC CAGAAAA 17

( 2 ) INFORMATION FOR SEQ ID NO:667:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:667:

UUUUCUGGCU GAUGAGGCCG AAAGGCCGAA AAUGUCUC 38

( 2 ) INFORMATION FOR SEQ ID NO:668:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:668:

AGACAUUUCC AGAAAAG 17

( 2 ) INFORMATION FOR SEQ ID NO:669:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:669:

CUUUUCUGCU GAUGAGGCCG AAAGGCCGAA AAAUGUCU        38

(2) INFORMATION FOR SEQ ID NO:670:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:670:

AAAAGCAUUA UGGUUUU        17

(2) INFORMATION FOR SEQ ID NO:671:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:671:

AAAACCAUCU GAUGAGGCCG AAAGGCCGAA AUGCUUUU (2) INFORMATION FOR SEQ ID NO:672:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:672:

AAAGCAUUAU GGUUUUC        17

(2) INFORMATION FOR SEQ ID NO:673:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:673:

GAAAACCACU GAUGAGGCCG AAAGGCCGAA AAUGCUUU        38

(2) INFORMATION FOR SEQ ID NO:674:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:674:

UUAUGGUUUU CAGAACA        17

(2) INFORMATION FOR SEQ ID NO:675:

(i) SEQUENCE CHARACTERISTICS:
(A) LENGTH: 38 base pairs
(B) TYPE: nucleic acid
(C) STRANDEDNESS: single
(D) TOPOLOGY: linear ( x i ) SEQUENCE DESCRIPTION: SEQ ID NO:675:

UGUUCUGACU GAUGAGGCCG AAAGGCCGAA AACCAUAA 38

( 2 ) INFORMATION FOR SEQ ID NO:676:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:676:

UAUGGUUUUC AGAACAC 17

( 2 ) INFORMATION FOR SEQ ID NO:677:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:677:

GUGUUCUGCU GAUGAGGCCG AAAGGCCGAA AAACCAUA 38

( 2 ) INFORMATION FOR SEQ ID NO:678:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:678:

AUGGUUUUCA GAACACU 17

( 2 ) INFORMATION FOR SEQ ID NO:679:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:679:

AGUGUUCUCU GAUGAGGCCG AAAGGCCGAA AAAACCAU 38

( 2 ) INFORMATION FOR SEQ ID NO:680:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:680:

AGAACACUUC AAGUUGA 17

( 2 ) INFORMATION FOR SEQ ID NO:681:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:681:

UCAACUUGCU GAUGAGGCCG AAAGGCCGAA AGUGUUCU 38

( 2 ) INFORMATION FOR SEQ ID NO:682:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:682:

GAACACUUCA AGUUGAC ( 2 ) INFORMATION FOR SEQ ID NO:683:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:683:

GUCAACUUCU GAUGAGGCCG AAAGGCCGAA AAGUGUUC 38

( 2 ) INFORMATION FOR SEQ ID NO:684:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:684:

CUUCAAGUUG ACUUGGG 17

( 2 ) INFORMATION FOR SEQ ID NO:685:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:685:

CCCAAGUCCU GAUGAGGCCG AAAGGCCGAA ACUUGAAG 38

( 2 ) INFORMATION FOR SEQ ID NO:686:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:686:

AGUUGACUUG GGAUAUA 17

( 2 ) INFORMATION FOR SEQ ID NO:687:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:687:

UAUAUCCCCU GAUGAGGCCG AAAGGCCGAA AGUCAACU 38

(2) INFORMATION FOR SEQ ID NO:688:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:688:

CUUGGGAUAU AUCAUUC 17

(2) INFORMATION FOR SEQ ID NO:689:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:689:

GAAUGAUACU GAUGAGGCCG AAAGGCCGAA AUCCCAAG 38

(2) INFORMATION FOR SEQ ID NO:690:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:690:

UGGGAUAUAU CAUUCCU 17

(2) INFORMATION FOR SEQ ID NO:691:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:691:

AGGAAUGACU GAUGAGGCCG AAAGGCCGAA AUAUCCCA 38

(2) INFORMATION FOR SEQ ID NO:692:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:692:

GGAUAUAUCA UUCCUCA 17

(2) INFORMATION FOR SEQ ID NO:693:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:693:
UGAGGAAUCU GAUGAGGCCG AAAGGCCGAA AUAUAUCC (2) INFORMATION FOR SEQ ID NO:694:

(i) SEQUENCE CHARACTERISTICS:
(A) LENGTH: 17 base pairs ( B ) TYPE: nucleic acid
        ( C ) STRANDEDNESS: single
        ( D ) TOPOLOGY: linear ( x i ) SEQUENCE DESCRIPTION: SEQ ID NO:694:

UAUAUCAUUC CUCAACA                                                                                          17

( 2 ) INFORMATION FOR SEQ ID NO:695:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:695:

UGUUGAGGCU GAUGAGGCCG AAAGGCCGAA AUGAUAUA                                                                    38

( 2 ) INFORMATION FOR SEQ ID NO:696:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:696:

AUAUCAUUCC UCAACAU                                                                                          17

( 2 ) INFORMATION FOR SEQ ID NO:697:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:697:

AUGUUGAGCU GAUGAGGCCG AAAGGCCGAA AAUGAUAU                                                                    38

( 2 ) INFORMATION FOR SEQ ID NO:698:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:698:

UCAUUCCUCA ACAUGAA                                                                                          17

( 2 ) INFORMATION FOR SEQ ID NO:699:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:699:

UUCAUGUUCU GAUGAGGCCG AAAGGCCGAA AGGAAUGA                                                                    38

( 2 ) INFORMATION FOR SEQ ID NO:700:

( i ) SEQUENCE CHARACTERISTICS:
        ( A ) LENGTH: 17 base pairs
        ( B ) TYPE: nucleic acid
        ( C ) STRANDEDNESS: single (D) TOPOLOGY: linear (xi) SEQUENCE DESCRIPTION: SEQ ID NO:700:

AUGAAACUUU UCAUGAA 17

(2) INFORMATION FOR SEQ ID NO:701:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:701:

UUCAUGAACU GAUGAGGCCG AAAGGCCGAA AGUUUCAU 38

(2) INFORMATION FOR SEQ ID NO:702:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:702:

UGAAACUUUU CAUGAAU 17

(2) INFORMATION FOR SEQ ID NO:703:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:703:

AUUCAUGACU GAUGAGGCCG AAAGGCCGAA AAGUUUCA 38

(2) INFORMATION FOR SEQ ID NO:704:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:704:

GAAACUUUUC AUGAAUG (2) INFORMATION FOR SEQ ID NO:705:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:705:

CAUUCAUGCU GAUGAGGCCG AAAGGCCGAA AAAGUUUC 38

(2) INFORMATION FOR SEQ ID NO:706:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:706:

AAACUUUUCA UGAAUGG                                                                17

( 2 ) INFORMATION FOR SEQ ID NO:707:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:707:

CCAUUCAUCU GAUGAGGCCG AAAGGCCGAA AAAAGUUU                                          38

( 2 ) INFORMATION FOR SEQ ID NO:708:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:708:

AAGAACCUAU UUUUGUU                                                                17

( 2 ) INFORMATION FOR SEQ ID NO:709:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:709:

AACAAAAACU GAUGAGGCCG AAAGGCCGAA AGGUUCUU                                          38

( 2 ) INFORMATION FOR SEQ ID NO:710:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:710:

GAACCUAUUU UUGUUGU                                                                17

( 2 ) INFORMATION FOR SEQ ID NO:711:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:711:

ACAACAAACU GAUGAGGCCG AAAGGCCGAA AUAGGUUC                                          38

( 2 ) INFORMATION FOR SEQ ID NO:712:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:712:

AACCUAUUUU UGUUGUG                                                                17

( 2 ) INFORMATION FOR SEQ ID NO:713:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:713:

CACAACAACU GAUGAGGCCG AAAGGCCGAA AAUAGGUU    38

( 2 ) INFORMATION FOR SEQ ID NO:714:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:714:

ACCUAUUUUU GUUGUGG    17

( 2 ) INFORMATION FOR SEQ ID NO:715:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:715:

CCACAACACU GAUGAGGCCG AAAGGCCGAA AAAUAGGU ( 2 ) INFORMATION FOR SEQ ID NO:716:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:716:

CCUAUUUUUG UUGUGGU    17

( 2 ) INFORMATION FOR SEQ ID NO:717:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:717:

ACCACAACCU GAUGAGGCCG AAAGGCCGAA AAAAUAGG    38

( 2 ) INFORMATION FOR SEQ ID NO:718:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:718:

AAGUGCAUUU AGUUGAA    17

( 2 ) INFORMATION FOR SEQ ID NO:719:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:719:

UUCAACUACU GAUGAGGCCG AAAGGCCGAA AUGCACUU 38

(2) INFORMATION FOR SEQ ID NO:720:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:720:

AGUGCAUUUA GUUGAAU 17

(2) INFORMATION FOR SEQ ID NO:721:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:721:

AUUCAACUCU GAUGAGGCCG AAAGGCCGAA AAUGCACU 38

(2) INFORMATION FOR SEQ ID NO:722:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:722:

GUGCAUUUAG UUGAAUG 17

(2) INFORMATION FOR SEQ ID NO:723:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:723:

CAUUCAACCU GAUGAGGCCG AAAGGCCGAA AAAUGCAC 38

(2) INFORMATION FOR SEQ ID NO:724:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:724:

UGAAGUCUUC UUGGAUU 17

(2) INFORMATION FOR SEQ ID NO:725:

(i) SEQUENCE CHARACTERISTICS:
(A) LENGTH: 38 base pairs
(B) TYPE: nucleic acid (C) STRANDEDNESS: single
        (D) TOPOLOGY: linear (xi) SEQUENCE DESCRIPTION: SEQ ID NO:725:

AAUCCAAGCU GAUGAGGCCG AAAGGCCGAA AGACUUCA                                    38

(2) INFORMATION FOR SEQ ID NO:726:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:726:
                GAAGUCUUCU UGGAUUU (2) INFORMATION FOR SEQ ID NO:727:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:727:

AAAUCCAACU GAUGAGGCCG AAAGGCCGAA AAGACUUC                                    38

(2) INFORMATION FOR SEQ ID NO:728:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:728:

AGUCUUCUUG GAUUUCA                                                           17

(2) INFORMATION FOR SEQ ID NO:729:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:729:

UGAAAUCCCU GAUGAGGCCG AAAGGCCGAA AGAAGACU                                    38

(2) INFORMATION FOR SEQ ID NO:730:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:730:

UCUUGGAUUU CACCCAA                                                           17

(2) INFORMATION FOR SEQ ID NO:731:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:731:

```
UUGGGUGACU  GAUGAGGCCG  AAAGGCCGAA  AUCCAAGA                                   38
```

( 2 ) INFORMATION FOR SEQ ID NO:732:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:732:

```
CUUGGAUUUC  ACCCAAC                                                            17
```

( 2 ) INFORMATION FOR SEQ ID NO:733:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:733:

```
GUUGGGUGCU  GAUGAGGCCG  AAAGGCCGAA  AAUCCAAG                                   38
```

( 2 ) INFORMATION FOR SEQ ID NO:734:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:734:

```
UUGGAUUUCA  CCCAACU                                                            17
```

( 2 ) INFORMATION FOR SEQ ID NO:735:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:735:

```
AGUUGGGUCU  GAUGAGGCCG  AAAGGCCGAA  AAAUCCAA                                   38
```

( 2 ) INFORMATION FOR SEQ ID NO:736:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:736:

```
ACCCAACUAA  AAGGAUU                                                            17
```

( 2 ) INFORMATION FOR SEQ ID NO:737:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:737:

```
            AAUCCUUUCU  GAUGAGGCCG  AAAGGCCGAA  AGUUGGGU
```

( 2 ) INFORMATION FOR SEQ ID NO:738:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:738:

AAAAGGAUUU UUAAAAA 17

( 2 ) INFORMATION FOR SEQ ID NO:739:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:739:

UUUUUAAACU GAUGAGGCCG AAAGGCCGAA AUCCUUUU 38

( 2 ) INFORMATION FOR SEQ ID NO:740:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:740:

AAAGGAUUUU UAAAAAU 17

( 2 ) INFORMATION FOR SEQ ID NO:741:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:741:

AUUUUUAACU GAUGAGGCCG AAAGGCCGAA AAUCCUUU 38

( 2 ) INFORMATION FOR SEQ ID NO:742:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:742:

AAGGAUUUUU AAAAAUA 17

( 2 ) INFORMATION FOR SEQ ID NO:743:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:743:

UAUUUUUACU GAUGAGGCCG AAAGGCCGAA AAAUCCUU 38

( 2 ) INFORMATION FOR SEQ ID NO:744:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:744:

AGGAUUUUUA AAAAUAA      17

( 2 ) INFORMATION FOR SEQ ID NO:745:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:745:

UUAUUUUCU GAUGAGGCCG AAAGGCCGAA AAAAUCCU      38

( 2 ) INFORMATION FOR SEQ ID NO:746:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:746:

GGAUUUUUAA AAAUAAA      17

( 2 ) INFORMATION FOR SEQ ID NO:747:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:747:

UUUAUUUUCU GAUGAGGCCG AAAGGCCGAA AAAAAUCC      38

( 2 ) INFORMATION FOR SEQ ID NO:748:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:748:
UUAAAAAUAA AUAACAG ( 2 ) INFORMATION FOR SEQ ID NO:749:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:749:

CUGUUAUUCU GAUGAGGCCG AAAGGCCGAA AUUUUUAA      38

( 2 ) INFORMATION FOR SEQ ID NO:750:

( i ) SEQUENCE CHARACTERISTICS:
    ( A ) LENGTH: 17 base pairs
    ( B ) TYPE: nucleic acid
    ( C ) STRANDEDNESS: single ( D ) TOPOLOGY: linear ( x i ) SEQUENCE DESCRIPTION: SEQ ID NO:750:

AAAUAAAUAA CAGUCUU 17

( 2 ) INFORMATION FOR SEQ ID NO:751:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:751:

AAGACUGUCU GAUGAGGCCG AAAGGCCGAA AUUUAUUU 38

( 2 ) INFORMATION FOR SEQ ID NO:752:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:752:

AACAGUCUUA CCUAAAU 17

( 2 ) INFORMATION FOR SEQ ID NO:753:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:753:

AUUUAGGUCU GAUGAGGCCG AAAGGCCGAA AGACUGUU 38

( 2 ) INFORMATION FOR SEQ ID NO:754:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:754:

ACAGUCUUAC CUAAAUU 17

( 2 ) INFORMATION FOR SEQ ID NO:755:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:755:

AAUUUAGGCU GAUGAGGCCG AAAGGCCGAA AAGACUGU 38

( 2 ) INFORMATION FOR SEQ ID NO:756:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:756:

UCUUACCUAA AUUAUUA                                                                     17

( 2 ) INFORMATION FOR SEQ ID NO:757:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:757:

UAAUAAUUCU GAUGAGGCCG AAAGGCCGAA AGGUAAGA                                               38

( 2 ) INFORMATION FOR SEQ ID NO:758:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:758:

ACCUAAAUUA UUAGGUA                                                                     17

( 2 ) INFORMATION FOR SEQ ID NO:759:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:759:

UACCUAAUCU GAUGAGGCCG AAAGGCCGAA AUUUAGGU ( 2 ) INFORMATION FOR SEQ ID NO:760:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:760:

CCUAAAUUAU UAGGUAA                                                                     17

( 2 ) INFORMATION FOR SEQ ID NO:761:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:761:

UUACCUAACU GAUGAGGCCG AAAGGCCGAA AAUUUAGG                                               38

( 2 ) INFORMATION FOR SEQ ID NO:762:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:762:

UAAAUUAUUA GGUAAUG                                                                     17

( 2 ) INFORMATION FOR SEQ ID NO:763:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:763:

CAUUACCUCU GAUGAGGCCG AAAGGCCGAA AUAAUUUA    38

( 2 ) INFORMATION FOR SEQ ID NO:764:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:764:

AAAUUAUUAG GUAAUGA    17

( 2 ) INFORMATION FOR SEQ ID NO:765:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:765:

UCAUUACCCU GAUGAGGCCG AAAGGCCGAA AAUAAUUU    38

( 2 ) INFORMATION FOR SEQ ID NO:766:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:766:

UAAUGAAUUG UAGCCAG    17

( 2 ) INFORMATION FOR SEQ ID NO:767:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:767:

CUGGCUACCU GAUGAGGCCG AAAGGCCGAA AUUCAUUA    38

( 2 ) INFORMATION FOR SEQ ID NO:768:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:768:

CAGUUGUUAA UAUCUUA    17

( 2 ) INFORMATION FOR SEQ ID NO:769:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:769:

UAAGAUAUCU GAUGAGGCCG AAAGGCCGAA AACAACUG  38

( 2 ) INFORMATION FOR SEQ ID NO:770:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:770:

UUGUUAAUAU CUUAAUG ( 2 ) INFORMATION FOR SEQ ID NO:771:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:771:

CAUUAAGACU GAUGAGGCCG AAAGGCCGAA AUUAACAA  38

( 2 ) INFORMATION FOR SEQ ID NO:772:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:772:

GUUAAUAUCU UAAUGCA  17

( 2 ) INFORMATION FOR SEQ ID NO:773:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:773:

UGCAUUAACU GAUGAGGCCG AAAGGCCGAA AUAUUAAC  38

( 2 ) INFORMATION FOR SEQ ID NO:774:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:774:

UAAUAUCUUA AUGCAGA  17

( 2 ) INFORMATION FOR SEQ ID NO:775:

( i ) SEQUENCE CHARACTERISTICS:
    ( A ) LENGTH: 38 base pairs
    ( B ) TYPE: nucleic acid ( C ) STRANDEDNESS: single
( D ) TOPOLOGY: linear ( x i ) SEQUENCE DESCRIPTION: SEQ ID NO:775:

UCUGCAUUCU GAUGAGGCCG AAAGGCCGAA AGAUAUUA  38

( 2 ) INFORMATION FOR SEQ ID NO:776:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:776:

AAUAUCUUAA UGCAGAU  17

( 2 ) INFORMATION FOR SEQ ID NO:777:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:777:

AUCUGCAUCU GAUGAGGCCG AAAGGCCGAA AAGAUAUU  38

( 2 ) INFORMATION FOR SEQ ID NO:778:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:778:

AUGCAGAUUU UUUAAA  17

( 2 ) INFORMATION FOR SEQ ID NO:779:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:779:

UUUAAAAACU GAUGAGGCCG AAAGGCCGAA AUCUGCAU  38

( 2 ) INFORMATION FOR SEQ ID NO:780:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:780:

UGCAGAUUUU UUUAAAA  17

( 2 ) INFORMATION FOR SEQ ID NO:781:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:781:

UUUUAAAACU GAUGAGGCCG AAAGGCCGAA AAUCUGCA ( 2 ) INFORMATION FOR SEQ ID NO:782:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:782:

GCAGAUUUUU UUAAAAA 17

( 2 ) INFORMATION FOR SEQ ID NO:783:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:783:

UUUUUAAACU GAUGAGGCCG AAAGGCCGAA AAAUCUGC 38

( 2 ) INFORMATION FOR SEQ ID NO:784:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:784:

CAGAUUUUU UAAAAAA 17

( 2 ) INFORMATION FOR SEQ ID NO:785:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:785:

UUUUUUAACU GAUGAGGCCG AAAGGCCGAA AAAAUCUG 38

( 2 ) INFORMATION FOR SEQ ID NO:786:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:786:

AGAUUUUUU AAAAAAA 17

( 2 ) INFORMATION FOR SEQ ID NO:787:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:787:

UUUUUUUACU GAUGAGGCCG AAAGGCCGAA AAAAAUCU 38

( 2 ) INFORMATION FOR SEQ ID NO:788:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:788:

GAUUUUUUUA AAAAAAA                                                    17

( 2 ) INFORMATION FOR SEQ ID NO:789:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:789:

UUUUUUUUCU GAUGAGGCCG AAAGGCCGAA AAAAAAUC                38

( 2 ) INFORMATION FOR SEQ ID NO:790:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:790:

AUUUUUUUAA AAAAAAC                                                  17

( 2 ) INFORMATION FOR SEQ ID NO:791:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:791:

GUUUUUUUCU GAUGAGGCCG AAAGGCCGAA AAAAAAAU                38

( 2 ) INFORMATION FOR SEQ ID NO:792:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:792:

AAAAACAUAA AAUGAUU ( 2 ) INFORMATION FOR SEQ ID NO:793:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:793:

AAUCAUUUCU GAUGAGGCCG AAAGGCCGAA AUGUUUUU                38

( 2 ) INFORMATION FOR SEQ ID NO:794:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:794:

AAAAUGAUUU AUCUGUA                           17

( 2 ) INFORMATION FOR SEQ ID NO:795:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:795:

UACAGAUACU GAUGAGGCCG AAAGGCCGAA AUCAUUUU    38

( 2 ) INFORMATION FOR SEQ ID NO:796:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:796:

AAAUGAUUUA UCUGUAU                           17

( 2 ) INFORMATION FOR SEQ ID NO:797:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:797:

AUACAGAUCU GAUGAGGCCG AAAGGCCGAA AAUCAUUU    38

( 2 ) INFORMATION FOR SEQ ID NO:798:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:798:

AAUGAUUUAU CUGUAUU                           17

( 2 ) INFORMATION FOR SEQ ID NO:799:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:799:

AAUACAGACU GAUGAGGCCG AAAGGCCGAA AAAUCAUU    38

( 2 ) INFORMATION FOR SEQ ID NO:800:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:800:

UGAUUUAUCU GUAUUUU 17

(2) INFORMATION FOR SEQ ID NO:801:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:801:

AAAAUACACU GAUGAGGCCG AAAGGCCGAA AUAAAUCA 38

(2) INFORMATION FOR SEQ ID NO:802:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:802:

AUCUGUAUUU UAAAGGA 17

(2) INFORMATION FOR SEQ ID NO:803:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:803:
UCCUUUAACU GAUGAGGCCG AAAGGCCGAA AUACAGAU (2) INFORMATION FOR SEQ ID NO:804:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:804:

UCUGUAUUUU AAAGGAU 17

(2) INFORMATION FOR SEQ ID NO:805:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:805:

AUCCUUUACU GAUGAGGCCG AAAGGCCGAA AAUACAGA 38

(2) INFORMATION FOR SEQ ID NO:806:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:806:

CUGUAUUUUA AAGGAUC    17

( 2 ) INFORMATION FOR SEQ ID NO:807:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:807:

GAUCCUUUCU GAUGAGGCCG AAAGGCCGAA AAAUACAG    38

( 2 ) INFORMATION FOR SEQ ID NO:808:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:808:

UGUAUUUUAA AGGAUCC    17

( 2 ) INFORMATION FOR SEQ ID NO:809:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:809:

GGAUCCUUCU GAUGAGGCCG AAAGGCCGAA AAAAUACA    38

( 2 ) INFORMATION FOR SEQ ID NO:810:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:810:

UAAAGGAUCC AACAGAU    17

( 2 ) INFORMATION FOR SEQ ID NO:811:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:811:

AUCUGUUGCU GAUGAGGCCG AAAGGCCGAA AUCCUUUA    38

( 2 ) INFORMATION FOR SEQ ID NO:812:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:812:

CAACAGAUCA GUAUUUU                                                          17

( 2 ) INFORMATION FOR SEQ ID NO:813:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:813:

AAAAUACUCU GAUGAGGCCG AAAGGCCGAA AUCUGUUG                                    38

( 2 ) INFORMATION FOR SEQ ID NO:814:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:814:
                     AUCAGUAUUU UUUCCUG ( 2 ) INFORMATION FOR SEQ ID NO:815:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:815:

CAGGAAAACU GAUGAGGCCG AAAGGCCGAA AUACUGAU                                    38

( 2 ) INFORMATION FOR SEQ ID NO:816:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:816:

UCAGUAUUUU UUCCUGU                                                          17

( 2 ) INFORMATION FOR SEQ ID NO:817:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:817:

ACAGGAAACU GAUGAGGCCG AAAGGCCGAA AAUACUGA                                    38

( 2 ) INFORMATION FOR SEQ ID NO:818:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:818:

CAGUAUUUUU UCCUGUG                                                          17

( 2 ) INFORMATION FOR SEQ ID NO:819:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:819:

CACAGGAACU GAUGAGGCCG AAAGGCCGAA AAAUACUG  38

( 2 ) INFORMATION FOR SEQ ID NO:820:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:820:

AGUAUUUUUU CCUGUGA  17

( 2 ) INFORMATION FOR SEQ ID NO:821:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:821:

UCACAGGACU GAUGAGGCCG AAAGGCCGAA AAAAUACU  38

( 2 ) INFORMATION FOR SEQ ID NO:822:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:822:

GUAUUUUUUC CUGUGAU  17

( 2 ) INFORMATION FOR SEQ ID NO:823:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:823:

AUCACAGGCU GAUGAGGCCG AAAGGCCGAA AAAAAUAC  38

( 2 ) INFORMATION FOR SEQ ID NO:824:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:824:

UAUUUUUUCC UGUGAUG  17

( 2 ) INFORMATION FOR SEQ ID NO:825:

( i ) SEQUENCE CHARACTERISTICS:

(A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:825:

CAUCACAGCU GAUGAGGCCG AAAGGCCGAA AAAAAUA (2) INFORMATION FOR SEQ ID NO:826:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:826:

GAUGGGUUUU UUGAAAU                                                                 17

(2) INFORMATION FOR SEQ ID NO:827:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:827:

AUUUCAAACU GAUGAGGCCG AAAGGCCGAA AACCCAUC                                           38

(2) INFORMATION FOR SEQ ID NO:828:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:828:

AUGGGUUUUU UGAAAUU                                                                 17

(2) INFORMATION FOR SEQ ID NO:829:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:829:

AAUUUCAACU GAUGAGGCCG AAAGGCCGAA AAACCCAU                                           38

(2) INFORMATION FOR SEQ ID NO:830:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:830:

UGGGUUUUUU GAAAUUU                                                                 17

(2) INFORMATION FOR SEQ ID NO:831:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:831:

AAAUUUCACU GAUGAGGCCG AAAGGCCGAA AAAACCCA 38

( 2 ) INFORMATION FOR SEQ ID NO:832:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:832:

GGGUUUUUUG AAAUUUG 17

( 2 ) INFORMATION FOR SEQ ID NO:833:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:833:

CAAAUUUCCU GAUGAGGCCG AAAGGCCGAA AAAACCC 38

( 2 ) INFORMATION FOR SEQ ID NO:834:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:834:

UUUGAAAUUU GACACAU 17

( 2 ) INFORMATION FOR SEQ ID NO:835:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:835:

AUGUGUCACU GAUGAGGCCG AAAGGCCGAA AUUUCAAA 38

( 2 ) INFORMATION FOR SEQ ID NO:836:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:836:
UUGAAAUUUG ACACAUU ( 2 ) INFORMATION FOR SEQ ID NO:837:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:837:

AAUGUGUCCU GAUGAGGCCG AAAGGCCGAA AAUUUCAA 38

( 2 ) INFORMATION FOR SEQ ID NO:838:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:838:

UGACACAUUA AAAGGUA                                                                                              17

( 2 ) INFORMATION FOR SEQ ID NO:839:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:839:

UACCUUUCU GAUGAGGCCG AAAGGCCGAA AUGUGUCA                                                                        38

( 2 ) INFORMATION FOR SEQ ID NO:840:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:840:

GACACAUUAA AAGGUAC                                                                                              17

( 2 ) INFORMATION FOR SEQ ID NO:841:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:841:

GUACCUUUCU GAUGAGGCCG AAAGGCCGAA AAUGUGUC                                                                       38

( 2 ) INFORMATION FOR SEQ ID NO:842:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:842:

AAGGUACUCC AGUAUUU                                                                                              17

( 2 ) INFORMATION FOR SEQ ID NO:843:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:843:

AAAUACUGCU GAUGAGGCCG AAAGGCCGAA AGUACCUU                                                                       38

( 2 ) INFORMATION FOR SEQ ID NO:844:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:844:

UCCAGUAUUU CACUUUU                                       17

( 2 ) INFORMATION FOR SEQ ID NO:845:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:845:

AAAAGUGACU GAUGAGGCCG AAAGGCCGAA AUACUGGA            38

( 2 ) INFORMATION FOR SEQ ID NO:846:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:846:

CCAGUAUUUC ACUUUUC                                       17

( 2 ) INFORMATION FOR SEQ ID NO:847:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:847:

GAAAAGUGCU GAUGAGGCCG AAAGGCCGAA AAUACUGG ( 2 ) INFORMATION FOR SEQ ID NO:848:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:848:

CAGUAUUUCA CUUUUCU                                       17

( 2 ) INFORMATION FOR SEQ ID NO:849:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:849:

AGAAAAGUCU GAUGAGGCCG AAAGGCCGAA AAAUACUG            38

( 2 ) INFORMATION FOR SEQ ID NO:850:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:850:

AUUUCACUUU UCUCGAU                                                              17

(2) INFORMATION FOR SEQ ID NO:851:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:851:

AUCGAGAACU GAUGAGGCCG AAAGGCCGAA AGUGAAAU                                       38

(2) INFORMATION FOR SEQ ID NO:852:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:852:

UUUCACUUUU CUCGAUC                                                              17

(2) INFORMATION FOR SEQ ID NO:853:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:853:

GAUCGAGACU GAUGAGGCCG AAAGGCCGAA AAGUGAAA                                       38

(2) INFORMATION FOR SEQ ID NO:854:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:854:

UUCACUUUUC UCGAUCA                                                              17

(2) INFORMATION FOR SEQ ID NO:855:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:855:

UGAUCGAGCU GAUGAGGCCG AAAGGCCGAA AAAGUGAA                                       38

(2) INFORMATION FOR SEQ ID NO:856:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO:856:

UCACUUUUCU CGAUCAC                                                                              17

(2) INFORMATION FOR SEQ ID NO:857:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO:857:

GUGAUCGACU GAUGAGGCCG AAAGGCCGAA AAAAGUGA                                                        38

(2) INFORMATION FOR SEQ ID NO:858:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO:858:

ACUUUCUCG AUCACUA (2) INFORMATION FOR SEQ ID NO:859:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO:859:

UAGUGAUCCU GAUGAGGCCG AAAGGCCGAA AGAAAAGU                                                        38

(2) INFORMATION FOR SEQ ID NO:860:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO:860:

UUCUCGAUCA CUAAACA                                                                              17

(2) INFORMATION FOR SEQ ID NO:861:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO:861:

UGUUUAGUCU GAUGAGGCCG AAAGGCCGAA AUCGAGAA                                                        38

(2) INFORMATION FOR SEQ ID NO:862:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO:862:

CGAUCACUAA ACAUAUG                                                                                   17

( 2 ) INFORMATION FOR SEQ ID NO:863:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:863:

CAUAUGUUCU GAUGAGGCCG AAAGGCCGAA AGUGAUCG                                                             38

( 2 ) INFORMATION FOR SEQ ID NO:864:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:864:

CUAAACAUAU GCAUAUA                                                                                   17

( 2 ) INFORMATION FOR SEQ ID NO:865:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:865:

UAUAUGCACU GAUGAGGCCG AAAGGCCGAA AUGUUUAG                                                             38

( 2 ) INFORMATION FOR SEQ ID NO:866:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:866:

AUAUGCAUAU AUUUUUA                                                                                   17

( 2 ) INFORMATION FOR SEQ ID NO:867:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:867:

UAAAAAUACU GAUGAGGCCG AAAGGCCGAA AUGCAUAU                                                             38

( 2 ) INFORMATION FOR SEQ ID NO:868:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:868:

AUGCAUAUAU UUUUAAA                                                                                   17

( 2 ) INFORMATION FOR SEQ ID NO:869:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:869:
        UUUAAAAACU GAUGAGGCCG AAAGGCCGAA AUAUGCAU ( 2 ) INFORMATION FOR SEQ ID NO:870:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:870:

GCAUAUAUUU UUAAAAA                              17

( 2 ) INFORMATION FOR SEQ ID NO:871:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:871:

UUUUUAAACU GAUGAGGCCG AAAGGCCGAA AUAUAUGC        38

( 2 ) INFORMATION FOR SEQ ID NO:872:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:872:

CAUAUAUUUU UAAAAAU                             17

( 2 ) INFORMATION FOR SEQ ID NO:873:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:873:

AUUUUUAACU GAUGAGGCCG AAAGGCCGAA AAUAUAUG        38

( 2 ) INFORMATION FOR SEQ ID NO:874:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:874:

AUAUAUUUUU AAAAAUC                             17

( 2 ) INFORMATION FOR SEQ ID NO:875:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:875:

GAUUUUACU GAUGAGGCCG AAAGGCCGAA AAAUAUAU 38

(2) INFORMATION FOR SEQ ID NO:876:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:876:

UAUAUUUUUA AAAAUCA 17

(2) INFORMATION FOR SEQ ID NO:877:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:877:

UGAUUUUCU GAUGAGGCCG AAAGGCCGAA AAAAUAUA 38

(2) INFORMATION FOR SEQ ID NO:878:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:878:

AUAUUUUAA AAAUCAG 17

(2) INFORMATION FOR SEQ ID NO:879:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:879:

CUGAUUUCU GAUGAGGCCG AAAGGCCGAA AAAAAUAU 38

(2) INFORMATION FOR SEQ ID NO:880:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:880:
UUAAAAAUCA GUAAAAG (2) INFORMATION FOR SEQ ID NO:881:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:881:

CUUUUACUCU GAUGAGGCCG AAAGGCCGAA AUUUUUAA 38

(2) INFORMATION FOR SEQ ID NO:882:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:882:

AAAAGCAUUA CUCUAAG 17

(2) INFORMATION FOR SEQ ID NO:883:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:883:

CUUAGAGUCU GAUGAGGCCG AAAGGCCGAA AUGCUUUU 38

(2) INFORMATION FOR SEQ ID NO:884:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:884:

AAAGCAUUAC UCUAAGU 17

(2) INFORMATION FOR SEQ ID NO:885:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:885:

ACUUAGAGCU GAUGAGGCCG AAAGGCCGAA AAUGCUUU 38

(2) INFORMATION FOR SEQ ID NO:886:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:886:

GCAUUACUCU AAGUGUA 17

(2) INFORMATION FOR SEQ ID NO:887:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:887:

UACACUUACU GAUGAGGCCG AAAGGCCGAA AGUAAUGC 38

(2) INFORMATION FOR SEQ ID NO:888:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:888:

AUUACUCUAA GUGUAGA 17

(2) INFORMATION FOR SEQ ID NO:889:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:889:

UCUACACUCU GAUGAGGCCG AAAGGCCGAA AGAGUAAU 38

(2) INFORMATION FOR SEQ ID NO:890:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:890:

CUAAGUGUAG ACUUAAU 17

(2) INFORMATION FOR SEQ ID NO:891:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:891:

AUUAAGUCCU GAUGAGGCCG AAAGGCCGAA ACACUUAG (2) INFORMATION FOR SEQ ID NO:892:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:892:

UGUAGACUUA AUACCAU 17

(2) INFORMATION FOR SEQ ID NO:893:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:893:

AUGGUAUUCU GAUGAGGCCG AAAGGCCGAA AGUCUACA 38

( 2 ) INFORMATION FOR SEQ ID NO:894:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:894:

GUAGACUUAA UACCAUG    17

( 2 ) INFORMATION FOR SEQ ID NO:895:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:895:

CAUGGUAUCU GAUGAGGCCG AAAGGCCGAA AAGUCUAC    38

( 2 ) INFORMATION FOR SEQ ID NO:896:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:896:

GACUUAAUAC CAUGUGA    17

( 2 ) INFORMATION FOR SEQ ID NO:897:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:897:

UCACAUGGCU GAUGAGGCCG AAAGGCCGAA AUUAAGUC    38

( 2 ) INFORMATION FOR SEQ ID NO:898:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:898:

UGUGACAUUU AAUCCAG    17

( 2 ) INFORMATION FOR SEQ ID NO:899:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:899:

CUGGAUUACU GAUGAGGCCG AAAGGCCGAA AUGUCACA    38

( 2 ) INFORMATION FOR SEQ ID NO:900:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:900:

GUGACAUUUA AUCCAGA 17

( 2 ) INFORMATION FOR SEQ ID NO:901:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:901:

UCUGGAUUCU GAUGAGGCCG AAAGGCCGAA AAUGUCAC 38

( 2 ) INFORMATION FOR SEQ ID NO:902:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:902:
                UGACAUUUAA UCCAGAU ( 2 ) INFORMATION FOR SEQ ID NO:903:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:903:

AUCUGGAUCU GAUGAGGCCG AAAGGCCGAA AAAUGUCA 38

( 2 ) INFORMATION FOR SEQ ID NO:904:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:904:

CAUUUAAUCC AGAUUGU 17

( 2 ) INFORMATION FOR SEQ ID NO:905:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:905:

ACAAUCUGCU GAUGAGGCCG AAAGGCCGAA AUUAAAUG 38

( 2 ) INFORMATION FOR SEQ ID NO:906:

( i ) SEQUENCE CHARACTERISTICS:
        ( A ) LENGTH: 17 base pairs
        ( B ) TYPE: nucleic acid
        ( C ) STRANDEDNESS: single (D) TOPOLOGY: linear (xi) SEQUENCE DESCRIPTION: SEQ ID NO:906:

AUCCAGAUUG UAAAUGC                                                                                    17

(2) INFORMATION FOR SEQ ID NO:907:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:907:

GCAUUUACCU GAUGAGGCCG AAAGGCCGAA AUCUGGAU                                                              38

(2) INFORMATION FOR SEQ ID NO:908:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:908:

UAAAUGCUCA UUUAUGG                                                                                    17

(2) INFORMATION FOR SEQ ID NO:909:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:909:

CCAUAAAUCU GAUGAGGCCG AAAGGCCGAA AGCAUUUA                                                              38

(2) INFORMATION FOR SEQ ID NO:910:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:910:

AUGCUCAUUU AUGGUUA                                                                                    17

(2) INFORMATION FOR SEQ ID NO:911:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:911:

UAACCAUACU GAUGAGGCCG AAAGGCCGAA AUGAGCAU                                                              38

(2) INFORMATION FOR SEQ ID NO:912:

(i) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:912:

UGCUCAUUUA UGGUUAA 17

( 2 ) INFORMATION FOR SEQ ID NO:913:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:913:

UUAACCAUCU GAUGAGGCCG AAAGGCCGAA AAUGAGCA ( 2 ) INFORMATION FOR SEQ ID NO:914:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:914:

GCUCAUUUAU GGUUAAU 17

( 2 ) INFORMATION FOR SEQ ID NO:915:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:915:

AUUAACCACU GAUGAGGCCG AAAGGCCGAA AAAUGAGC 38

( 2 ) INFORMATION FOR SEQ ID NO:916:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:916:

UUAUGGUUAA UGACAUU 17

( 2 ) INFORMATION FOR SEQ ID NO:917:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:917:

AAUGUCAUCU GAUGAGGCCG AAAGGCCGAA AACCAUAA 38

( 2 ) INFORMATION FOR SEQ ID NO:918:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:918:

AAUGACAUUG AAGGUAC 17

( 2 ) INFORMATION FOR SEQ ID NO:919:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:919:

GUACCUUCCU GAUGAGGCCG AAAGGCCGAA AUGUCAUU 38

( 2 ) INFORMATION FOR SEQ ID NO:920:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:920:

AGGUACAUUU AUUGUAC 17

( 2 ) INFORMATION FOR SEQ ID NO:921:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:921:

GUACAAUACU GAUGAGGCCG AAAGGCCGAA AUGUACCU 38

( 2 ) INFORMATION FOR SEQ ID NO:922:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:922:

GGUACAUUUA UUGUACC 17

( 2 ) INFORMATION FOR SEQ ID NO:923:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:923:

GGUACAAUCU GAUGAGGCCG AAAGGCCGAA AAUGUACC 38

( 2 ) INFORMATION FOR SEQ ID NO:924:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:924:

GUACAUUUAU UGUACCA ( 2 ) INFORMATION FOR SEQ ID NO:925:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:925:

UGGUACAACU GAUGAGGCCG AAAGGCCGAA AAAUGUAC 38

(2) INFORMATION FOR SEQ ID NO:926:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:926:

ACAUUUAUUG UACCAAA 17

(2) INFORMATION FOR SEQ ID NO:927:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:927:

UUUGGUACCU GAUGAGGCCG AAAGGCCGAA AUAAAUGU 38

(2) INFORMATION FOR SEQ ID NO:928:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:928:

CAAACCAUUU UAUGAGU 17

(2) INFORMATION FOR SEQ ID NO:929:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:929:

ACUCAUAACU GAUGAGGCCG AAAGGCCGAA AUGGUUUG 38

(2) INFORMATION FOR SEQ ID NO:930:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:930:

AAACCAUUUU AUGAGUU 17

(2) INFORMATION FOR SEQ ID NO:931:

(i) SEQUENCE CHARACTERISTICS:
(A) LENGTH: 38 base pairs
(B) TYPE: nucleic acid (C) STRANDEDNESS: single
(D) TOPOLOGY: linear (xi) SEQUENCE DESCRIPTION: SEQ ID NO:931:

AACUCAUACU GAUGAGGCCG AAAGGCCGAA AAUGGUUU                                    38

(2) INFORMATION FOR SEQ ID NO:932:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:932:

AACCAUUUUA UGAGUUU                                                           17

(2) INFORMATION FOR SEQ ID NO:933:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:933:

AAACUCAUCU GAUGAGGCCG AAAGGCCGAA AAAUGGUU                                    38

(2) INFORMATION FOR SEQ ID NO:934:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:934:

ACCAUUUUAU GAGUUUU                                                           17

(2) INFORMATION FOR SEQ ID NO:935:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:935:
        AAAACUCACU GAUGAGGCCG AAAGGCCGAA AAAAUGGU (2) INFORMATION FOR SEQ ID NO:936:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:936:

UAUGAGUUUU CUGUUAG                                                           17

(2) INFORMATION FOR SEQ ID NO:937:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:937:

```
CUAACAGACU  GAUGAGGCCG  AAAGGCCGAA  AACUCAUA                           38
```

( 2 ) INFORMATION FOR SEQ ID NO:938:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:938:

```
AUGAGUUUUC  UGUUAGC                                                    17
```

( 2 ) INFORMATION FOR SEQ ID NO:939:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:939:

```
GCUAACAGCU  GAUGAGGCCG  AAAGGCCGAA  AAACUCAU                           38
```

( 2 ) INFORMATION FOR SEQ ID NO:940:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:940:

```
UGAGUUUUCU  GUUAGCU                                                    17
```

( 2 ) INFORMATION FOR SEQ ID NO:941:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:941:

```
AGCUAACACU  GAUGAGGCCG  AAAGGCCGAA  AAAACUCA                           38
```

( 2 ) INFORMATION FOR SEQ ID NO:942:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:942:

```
UUUCUGUUAG  CUUGCUU                                                    17
```

( 2 ) INFORMATION FOR SEQ ID NO:943:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:943:

```
AAGCAAGCCU  GAUGAGGCCG  AAAGGCCGAA  AACAGAAA                           38
```

( 2 ) INFORMATION FOR SEQ ID NO:944:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:944:

UGUUAGCUUG CUUUAAA 17

( 2 ) INFORMATION FOR SEQ ID NO:945:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:945:

UUUAAAGCCU GAUGAGGCCG AAAGGCCGAA AGCUAACA 38

( 2 ) INFORMATION FOR SEQ ID NO:946:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:946:
AGCUUGCUUU AAAAAUU ( 2 ) INFORMATION FOR SEQ ID NO:947:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:947:

AAUUUUUACU GAUGAGGCCG AAAGGCCGAA AGCAAGCU 38

( 2 ) INFORMATION FOR SEQ ID NO:948:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:948:

GCUUGCUUUA AAAAUUA 17

( 2 ) INFORMATION FOR SEQ ID NO:949:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:949:

UAAUUUUUCU GAUGAGGCCG AAAGGCCGAA AAGCAAGC 38

( 2 ) INFORMATION FOR SEQ ID NO:950:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:950:

CUUGCUUUAA AAAUUAU 17

( 2 ) INFORMATION FOR SEQ ID NO:951:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:951:

AUAAUUUUCU GAUGAGGCCG AAAGGCCGAA AAAGCAAG 38

( 2 ) INFORMATION FOR SEQ ID NO:952:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:952:

UUAAAAAUUA UUACUGU 17

( 2 ) INFORMATION FOR SEQ ID NO:953:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:953:

ACAGUAAUCU GAUGAGGCCG AAAGGCCGAA AUUUUUAA 38

( 2 ) INFORMATION FOR SEQ ID NO:954:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:954:

UAAAAAUUAU UACUGUA 17

( 2 ) INFORMATION FOR SEQ ID NO:955:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:955:

UACAGUAACU GAUGAGGCCG AAAGGCCGAA AAUUUUUA 38

( 2 ) INFORMATION FOR SEQ ID NO:956:

( i ) SEQUENCE CHARACTERISTICS:
  ( A ) LENGTH: 17 base pairs (B) TYPE: nucleic acid
(C) STRANDEDNESS: single
(D) TOPOLOGY: linear (x i) SEQUENCE DESCRIPTION: SEQ ID NO:956:

AAAAUUAUUA CUGUAAG                                                                                              17

(2) INFORMATION FOR SEQ ID NO:957:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:957:
CUUACAGUCU GAUGAGGCCG AAAGGCCGAA AUAAUUUU (2) INFORMATION FOR SEQ ID NO:958:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO:958:

AAAUUAUUAC UGUAAGA                                                                                              17

(2) INFORMATION FOR SEQ ID NO:959:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:959:

UCUUACAGCU GAUGAGGCCG AAAGGCCGAA AAUAAUUU                                                                        38

(2) INFORMATION FOR SEQ ID NO:960:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO:960:

UAAGAAAUAG UUUUAUA                                                                                              17

(2) INFORMATION FOR SEQ ID NO:961:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:961:

UAUAAAACCU GAUGAGGCCG AAAGGCCGAA AUUUCUUA                                                                        38

(2) INFORMATION FOR SEQ ID NO:962:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO:962:

AAAUAGUUUU AUAAAAA 17

(2) INFORMATION FOR SEQ ID NO:963:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:963:

UUUUUAUACU GAUGAGGCCG AAAGGCCGAA AACUAUUU 38

(2) INFORMATION FOR SEQ ID NO:964:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:964:

AAUAGUUUUA UAAAAAA 17

(2) INFORMATION FOR SEQ ID NO:965:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:965:

UUUUUUAUCU GAUGAGGCCG AAAGGCCGAA AAACUAUU 38

(2) INFORMATION FOR SEQ ID NO:966:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:966:

AUAGUUUUAU AAAAAAU 17

(2) INFORMATION FOR SEQ ID NO:967:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:967:

AUUUUUUACU GAUGAGGCCG AAAGGCCGAA AAAACUAU 38

(2) INFORMATION FOR SEQ ID NO:968:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:968:
AGUUUUAUAA AAAAUUA ( 2 ) INFORMATION FOR SEQ ID NO:969:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:969:

UAAUUUUCU GAUGAGGCCG AAAGGCCGAA AUAAAACU     38

( 2 ) INFORMATION FOR SEQ ID NO:970:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:970:

UAAAAAAUUA UAUUUUU     17

( 2 ) INFORMATION FOR SEQ ID NO:971:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:971:

AAAAAUAUCU GAUGAGGCCG AAAGGCCGAA AUUUUUUA     38

( 2 ) INFORMATION FOR SEQ ID NO:972:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:972:

AAAAAAUUAU AUUUUUA     17

( 2 ) INFORMATION FOR SEQ ID NO:973:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:973:

UAAAAAUACU GAUGAGGCCG AAAGGCCGAA AAUUUUUU     38

( 2 ) INFORMATION FOR SEQ ID NO:974:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:974:

AAAAUUAUAU UUUUAUU     17

( 2 ) INFORMATION FOR SEQ ID NO:975:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:975:

AAUAAAACU GAUGAGGCCG AAAGGCCGAA AUAAUUUU    38

(2) INFORMATION FOR SEQ ID NO:976:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:976:

AAUUAUAUUU UUAUUCA    17

(2) INFORMATION FOR SEQ ID NO:977:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:977:

UGAAUAAACU GAUGAGGCCG AAAGGCCGAA AUAUAAUU    38

(2) INFORMATION FOR SEQ ID NO:978:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:978:

AUUAUAUUUU UAUUCAG    17

(2) INFORMATION FOR SEQ ID NO:979:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:979:
CUGAAUAACU GAUGAGGCCG AAAGGCCGAA AAUAUAAU (2) INFORMATION FOR SEQ ID NO:980:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:980:

UUAUAUUUUU AUUCAGU    17

(2) INFORMATION FOR SEQ ID NO:981:

(i) SEQUENCE CHARACTERISTICS:
(A) LENGTH: 38 base pairs
(B) TYPE: nucleic acid (C) STRANDEDNESS: single
(D) TOPOLOGY: linear (xi) SEQUENCE DESCRIPTION: SEQ ID NO:981:

ACUGAAUACU GAUGAGGCCG AAAGGCCGAA AAAUAUAA 38

(2) INFORMATION FOR SEQ ID NO:982:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:982:

UAUAUUUUUA UUCAGUA 17

(2) INFORMATION FOR SEQ ID NO:983:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:983:

UACUGAAUCU GAUGAGGCCG AAAGGCCGAA AAAAUAUA 38

(2) INFORMATION FOR SEQ ID NO:984:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:984:

AUAUUUUUAU UCAGUAA 17

(2) INFORMATION FOR SEQ ID NO:985:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:985:

UUACUGAACU GAUGAGGCCG AAAGGCCGAA AAAAAUAU 38

(2) INFORMATION FOR SEQ ID NO:986:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:986:

AUUUUUAUUC AGUAAUU 17

(2) INFORMATION FOR SEQ ID NO:987:

(i) SEQUENCE CHARACTERISTICS:
(A) LENGTH: 38 base pairs
(B) TYPE: nucleic acid
(C) STRANDEDNESS: single
(D) TOPOLOGY: linear ( x i ) SEQUENCE DESCRIPTION: SEQ ID NO:987:

AAUUACUGCU GAUGAGGCCG AAAGGCCGAA AUAAAAAU 38

( 2 ) INFORMATION FOR SEQ ID NO:988:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:988:

UUUUUAUUCA GUAAUUU 17

( 2 ) INFORMATION FOR SEQ ID NO:989:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:989:

AAAUUACUCU GAUGAGGCCG AAAGGCCGAA AAUAAAAA 38

( 2 ) INFORMATION FOR SEQ ID NO:990:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:990:

UCAGUAAUUU AAUUUUG ( 2 ) INFORMATION FOR SEQ ID NO:991:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:991:

CAAAAUUACU GAUGAGGCCG AAAGGCCGAA AUUACUGA 38

( 2 ) INFORMATION FOR SEQ ID NO:992:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:992:

CAGUAAUUUA AUUUUGU 17

( 2 ) INFORMATION FOR SEQ ID NO:993:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:993:

ACAAAAUUCU GAUGAGGCCG AAAGGCCGAA AAUUACUG 38

( 2 ) INFORMATION FOR SEQ ID NO:994:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:994:

AGUAAUUUAA UUUUGUA 17

( 2 ) INFORMATION FOR SEQ ID NO:995:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:995:

UACAAAAUCU GAUGAGGCCG AAAGGCCGAA AAAUUACU 38

( 2 ) INFORMATION FOR SEQ ID NO:996:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:996:

AAUUUAAUUU UGUAAAU 17

( 2 ) INFORMATION FOR SEQ ID NO:997:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:997:

AUUUACAACU GAUGAGGCCG AAAGGCCGAA AUUAAAUU 38

( 2 ) INFORMATION FOR SEQ ID NO:998:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:998:

AUUUAAUUUU GUAAAUG 17

( 2 ) INFORMATION FOR SEQ ID NO:999:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:999:

CAUUUACACU GAUGAGGCCG AAAGGCCGAA AAUUAAAU 38

( 2 ) INFORMATION FOR SEQ ID NO:1000:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1000:

UUUAAUUUUG UAAAUGC                                                                 1 7

( 2 ) INFORMATION FOR SEQ ID NO:1001:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1001:

GCAUUUACCU GAUGAGGCCG AAAGGCCGAA AAAUUAAA ( 2 ) INFORMATION FOR SEQ ID NO:1002:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1002:

AAAACGUUUU UUGCUGC                                                               1 7

( 2 ) INFORMATION FOR SEQ ID NO:1003:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1003:

GCAGCAAACU GAUGAGGCCG AAAGGCCGAA AACGUUUU                     3 8

( 2 ) INFORMATION FOR SEQ ID NO:1004:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1004:

AAACGUUUUU UGCUGCU                                                               1 7

( 2 ) INFORMATION FOR SEQ ID NO:1005:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1005:

AGCAGCAACU GAUGAGGCCG AAAGGCCGAA AAACGUUU                     3 8

( 2 ) INFORMATION FOR SEQ ID NO:1006:

( i ) SEQUENCE CHARACTERISTICS:
    ( A ) LENGTH: 17 base pairs ( B ) TYPE: nucleic acid
    ( C ) STRANDEDNESS: single
    ( D ) TOPOLOGY: linear ( x i ) SEQUENCE DESCRIPTION: SEQ ID NO:1006:

AACGUUUUUU GCUGCUA 17

( 2 ) INFORMATION FOR SEQ ID NO:1007:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1007:

UAGCAGCACU GAUGAGGCCG AAAGGCCGAA AAAACGUU 38

( 2 ) INFORMATION FOR SEQ ID NO:1008:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1008:

ACGUUUUUG CUGCUAU 17

( 2 ) INFORMATION FOR SEQ ID NO:1009:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1009:

AUAGCAGCCU GAUGAGGCCG AAAGGCCGAA AAAAACGU 38

( 2 ) INFORMATION FOR SEQ ID NO:1010:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1010:

UUGCUGCUAU GGUCUUA 17

( 2 ) INFORMATION FOR SEQ ID NO:1011:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1011:

UAAGACCACU GAUGAGGCCG AAAGGCCGAA AGCAGCAA 38

( 2 ) INFORMATION FOR SEQ ID NO:1012:

( i ) SEQUENCE CHARACTERISTICS:
    ( A ) LENGTH: 17 base pairs
    ( B ) TYPE: nucleic acid
    ( C ) STRANDEDNESS: single (D) TOPOLOGY: linear (xi) SEQUENCE DESCRIPTION: SEQ ID NO:1012:

UAUGGUCUUA GCCUGUA (2) INFORMATION FOR SEQ ID NO:1013:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1013:

UACAGGCUCU GAUGAGGCCG AAAGGCCGAA AGACCAUA 38

(2) INFORMATION FOR SEQ ID NO:1014:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1014:

AUGGUCUUAG CCUGUAG 17

(2) INFORMATION FOR SEQ ID NO:1015:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1015:

CUACAGGCCU GAUGAGGCCG AAAGGCCGAA AAGACCAU 38

(2) INFORMATION FOR SEQ ID NO:1016:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1016:

AUGCUGCUAG UAUCAGA 17

(2) INFORMATION FOR SEQ ID NO:1017:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1017:

UCUGAUACCU GAUGAGGCCG AAAGGCCGAA AGCAGCAU 38

(2) INFORMATION FOR SEQ ID NO:1018:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1018:

```
GCUAGUAUCA GAGGGGC                                                                    17
```

( 2 ) INFORMATION FOR SEQ ID NO:1019:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1019:

```
GCCCCUCUCU GAUGAGGCCG AAAGGCCGAA AUACUAGC                                              38
```

( 2 ) INFORMATION FOR SEQ ID NO:1020:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1020:

```
GUAGAGCUUG GACAGAA                                                                    17
```

( 2 ) INFORMATION FOR SEQ ID NO:1021:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1021:

```
UUCUGUCCCU GAUGAGGCCG AAAGGCCGAA AGCUCUAC                                              38
```

( 2 ) INFORMATION FOR SEQ ID NO:1022:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1022:

```
AAGAAACUUG GUGUUAG                                                                    17
```

( 2 ) INFORMATION FOR SEQ ID NO:1023:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1023:
```
            CUAACACCCU GAUGAGGCCG AAAGGCCGAA AGUUCUU
```

( 2 ) INFORMATION FOR SEQ ID NO:1024:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1024:

```
UUGGUGUUAG GUAAUUG                                                                    17
```

( 2 ) INFORMATION FOR SEQ ID NO:1025:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1025:

CAAUUACCCU GAUGAGGCCG AAAGGCGAA AACACCAA 38

( 2 ) INFORMATION FOR SEQ ID NO:1026:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1026:

UAGGUAAUUG ACUAUGC 17

( 2 ) INFORMATION FOR SEQ ID NO:1027:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1027:

GCAUAGUCCU GAUGAGGCCG AAAGGCCGAA AUUACCUA 38

( 2 ) INFORMATION FOR SEQ ID NO:1028:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1028:

AAUUGACUAU GCACUAG 17

( 2 ) INFORMATION FOR SEQ ID NO:1029:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1029:

CUAGUGCACU GAUGAGGCCG AAAGGCCGAA AGUCAAUU 38

( 2 ) INFORMATION FOR SEQ ID NO:1030:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1030:

UAUGCACUAG UAUUUCA 17

( 2 ) INFORMATION FOR SEQ ID NO:1031:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1031:

UGAAAUACCU GAUGAGGCCG AAAGGCCGAA AGUGCAUA 38

(2) INFORMATION FOR SEQ ID NO:1032:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1032:

ACUAGUAUUU CAGACUU 17

(2) INFORMATION FOR SEQ ID NO:1033:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1033:

AAGUCUGACU GAUGAGGCCG AAAGGCCGAA AUACUAGU 38

(2) INFORMATION FOR SEQ ID NO:1034:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1034:
CUAGUAUUC AGACUUU (2) INFORMATION FOR SEQ ID NO:1035:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1035:

AAAGUCUGCU GAUGAGGCCG AAAGGCCGAA AAUACUAG 38

(2) INFORMATION FOR SEQ ID NO:1036:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1036:

UAGUAUUCA GACUUUU 17

(2) INFORMATION FOR SEQ ID NO:1037:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:1037:

AAAAGUCUCU GAUGAGGCCG AAAGGCCGAA AAAUACUA 38

(2) INFORMATION FOR SEQ ID NO:1038:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:1038:

UUCAGACUUU UUAAUUU 17

(2) INFORMATION FOR SEQ ID NO:1039:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:1039:

AAAUUAAACU GAUGAGGCCG AAAGGCCGAA AGUCUGAA 38

(2) INFORMATION FOR SEQ ID NO:1040:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:1040:

UCAGACUUUU UAAUUUU 17

(2) INFORMATION FOR SEQ ID NO:1041:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:1041:

AAAAUUAACU GAUGAGGCCG AAAGGCCGAA AAGUCUGA 38

(2) INFORMATION FOR SEQ ID NO:1042:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:1042:

CAGACUUUUU AAUUUA 17

(2) INFORMATION FOR SEQ ID NO:1043:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:1043:

UAAAAUUACU GAUGAGGCCG AAAGGCCGAA AAAGUCUG         38

( 2 ) INFORMATION FOR SEQ ID NO:1044:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1044:

AGACUUUUUA AUUUUAU         17

( 2 ) INFORMATION FOR SEQ ID NO:1045:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1045:

AUAAAAUUCU GAUGAGGCCG AAAGGCCGAA AAAAGUCU ( 2 ) INFORMATION FOR SEQ ID NO:1046:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1046:

GACUUUUUAA UUUUAUA         17

( 2 ) INFORMATION FOR SEQ ID NO:1047:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1047:

UAUAAAAUCU GAUGAGGCCG AAAGGCCGAA AAAAAGUC         38

( 2 ) INFORMATION FOR SEQ ID NO:1048:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1048:

UUUUUAAUUU UAUAUAU         17

( 2 ) INFORMATION FOR SEQ ID NO:1049:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1049:

AUAUAUAACU GAUGAGGCCG AAAGGCCGAA AUUAAAAA         38

( 2 ) INFORMATION FOR SEQ ID NO:1050:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1050:

UUUUAAUUUU AUAUAUA        17

( 2 ) INFORMATION FOR SEQ ID NO:1051:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1051:

UAUAUAUACU GAUGAGGCCG AAAGGCCGAA AAUUAAAA        38

( 2 ) INFORMATION FOR SEQ ID NO:1052:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1052:

UUUAAUUUUA UAUAUAU        17

( 2 ) INFORMATION FOR SEQ ID NO:1053:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1053:

AUAUAUAUCU GAUGAGGCCG AAAGGCCGAA AAAUUAAA        38

( 2 ) INFORMATION FOR SEQ ID NO:1054:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1054:

UUAAUUUUAU AUAUAUA        17

( 2 ) INFORMATION FOR SEQ ID NO:1055:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1055:

UAUAUAUACU GAUGAGGCCG AAAGGCCGAA AAAAUUAA        38

( 2 ) INFORMATION FOR SEQ ID NO:1056:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1056:

AAUUUUAUAU AUAUAUA ( 2 ) INFORMATION FOR SEQ ID NO:1057:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1057:

UAUAUAUACU GAUGAGGCCG AAAGGCCGAA AUAAAAUU 38

( 2 ) INFORMATION FOR SEQ ID NO:1058:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1058:

UUUUAUAUAU AUAUACA 17

( 2 ) INFORMATION FOR SEQ ID NO:1059:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1059:

UGUAUAUACU GAUGAGGCCG AAAGGCCGAA AUAUAAAA 38

( 2 ) INFORMATION FOR SEQ ID NO:1060:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1060:

UUAUAUAUAU AUACAUU 17

( 2 ) INFORMATION FOR SEQ ID NO:1061:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1061:

AAUGUAUACU GAUGAGGCCG AAAGGCCGAA AUAUAUAA 38

( 2 ) INFORMATION FOR SEQ ID NO:1062:

( i ) SEQUENCE CHARACTERISTICS:
      ( A ) LENGTH: 17 base pairs
      ( B ) TYPE: nucleic acid
      ( C ) STRANDEDNESS: single (D) TOPOLOGY: linear (xi) SEQUENCE DESCRIPTION: SEQ ID NO:1062:

AUAUAUAUAU ACAUUUU 17

(2) INFORMATION FOR SEQ ID NO:1063:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1063:

AAAAUGUACU GAUGAGGCCG AAAGGCCGAA AUAUAUAU 38

(2) INFORMATION FOR SEQ ID NO:1064:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1064:

AUAUAUAUAC AUUUUUU 17

(2) INFORMATION FOR SEQ ID NO:1065:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1065:

AAAAAUGCU GAUGAGGCCG AAAGGCCGAA AUAUAUAU 38

(2) INFORMATION FOR SEQ ID NO:1066:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1066:

AUAUACAUUU UUUUUCC 17

(2) INFORMATION FOR SEQ ID NO:1067:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1067:
GGAAAAAACU GAUGAGGCCG AAAGGCCGAA AUGUAUAU (2) INFORMATION FOR SEQ ID NO:1068:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1068:

UAUACAUUUU UUUUCCU                                                           17

( 2 ) INFORMATION FOR SEQ ID NO:1069:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1069:

AGGAAAAACU GAUGAGGCCG AAAGGCCGAA AAUGUAUA                                    38

( 2 ) INFORMATION FOR SEQ ID NO:1070:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1070:

AUACAUUUUU UUUCCUU                                                           17

( 2 ) INFORMATION FOR SEQ ID NO:1071:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1071:

AAGGAAAACU GAUGAGGCCG AAAGGCCGAA AAAUGUAU                                    38

( 2 ) INFORMATION FOR SEQ ID NO:1072:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1072:

UACAUUUUUU UUCCUUC                                                           17

( 2 ) INFORMATION FOR SEQ ID NO:1073:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1073:

GAAGGAAACU GAUGAGGCCG AAAGGCCGAA AAAAUGUA                                    38

( 2 ) INFORMATION FOR SEQ ID NO:1074:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1074:

ACAUUUUUUU UCCUUCU                                                           17

( 2 ) INFORMATION FOR SEQ ID NO:1075:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1075:

AGAAGGAACU GAUGAGGCCG AAAGGCCGAA AAAAAUGU    38

( 2 ) INFORMATION FOR SEQ ID NO:1076:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1076:

CAUUUUUUUU CCUUCUG    17

( 2 ) INFORMATION FOR SEQ ID NO:1077:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1077:

CAGAAGGACU GAUGAGGCCG AAAGGCCGAA AAAAAAUG    38

( 2 ) INFORMATION FOR SEQ ID NO:1078:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1078:
        AUUUUUUUC CUUCUGC ( 2 ) INFORMATION FOR SEQ ID NO:1079:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1079:

GCAGAAGGCU GAUGAGGCCG AAAGGCCGAA AAAAAAU    38

( 2 ) INFORMATION FOR SEQ ID NO:1080:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1080:

UUUUUUUCC UUCUGCA    17

( 2 ) INFORMATION FOR SEQ ID NO:1081:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1081:

UGCAGAAGCU GAUGAGGCCG AAAGGCCGAA AAAAAAAA 38

(2) INFORMATION FOR SEQ ID NO:1082:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1082:

UUUUUCCUUC UGCAAUA 17

(2) INFORMATION FOR SEQ ID NO:1083:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1083:

UAUUGCAGCU GAUGAGGCCG AAAGGCCGAA AGGAAAAA 38

(2) INFORMATION FOR SEQ ID NO:1084:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1084:

UUUUCCUUCU GCAAUAC 17

(2) INFORMATION FOR SEQ ID NO:1085:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1085:

GUAUUGCACU GAUGAGGCCG AAAGGCCGAA AAGGAAAA 38

(2) INFORMATION FOR SEQ ID NO:1086:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1086:

UCUGCAAUAC AUUUGAA 17

(2) INFORMATION FOR SEQ ID NO:1087:

(i) SEQUENCE CHARACTERISTICS:
(A) LENGTH: 38 base pairs
(B) TYPE: nucleic acid (C) STRANDEDNESS: single
(D) TOPOLOGY: linear (xi) SEQUENCE DESCRIPTION: SEQ ID NO:1087:

UUCAAAUGCU GAUGAGGCCG AAAGGCCGAA AUUGCAGA 38

(2) INFORMATION FOR SEQ ID NO:1088:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1088:

CAAUACAUUU GAAAACU 17

(2) INFORMATION FOR SEQ ID NO:1089:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1089:

AGUUUUCACU GAUGAGGCCG AAAGGCCGAA AUGUAUUG (2) INFORMATION FOR SEQ ID NO:1090:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1090:

AAUACAUUUG AAAACUU 17

(2) INFORMATION FOR SEQ ID NO:1091:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1091:

AAGUUUUCCU GAUGAGGCCG AAAGGCCGAA AAUGUAUU 38

(2) INFORMATION FOR SEQ ID NO:1092:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1092:

UGAAAACUUG UUUGGGA 17

(2) INFORMATION FOR SEQ ID NO:1093:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1093:

UCCCAAACCU GAUGAGGCCG AAAGGCCGAA AGUUUUCA 38

( 2 ) INFORMATION FOR SEQ ID NO:1094:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1094:

AACUUGUUUG GGAGACU 17

( 2 ) INFORMATION FOR SEQ ID NO:1095:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1095:

AGUCUCCCU GAUGAGGCCG AAAGGCCGAA AACAAGUU 38

( 2 ) INFORMATION FOR SEQ ID NO:1096:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1096:

GGGAGACUCU GCAUUUU 17

( 2 ) INFORMATION FOR SEQ ID NO:1097:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1097:

AAAAUGCACU GAUGAGGCCG AAAGGCCGAA AGUCUCCC 38

( 2 ) INFORMATION FOR SEQ ID NO:1098:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1098:

CUCUGCAUUU UUUAUUG 17

( 2 ) INFORMATION FOR SEQ ID NO:1099:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1099:

CAAUAAAACU GAUGAGGCCG AAAGGCCGAA AUGCAGAG 38

( 2 ) INFORMATION FOR SEQ ID NO:1100:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1100:

UCUGCAUUUU UUAUUGU ( 2 ) INFORMATION FOR SEQ ID NO:1101:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1101:

ACAAUAAACU GAUGAGGCCG AAAGGCCGAA AAUGCAGA 38

( 2 ) INFORMATION FOR SEQ ID NO:1102:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1102:

CUGCAUUUUU UAUUGUG 17

( 2 ) INFORMATION FOR SEQ ID NO:1103:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1103:

CACAAUAACU GAUGAGGCCG AAAGGCCGAA AAAUGCAG 38

( 2 ) INFORMATION FOR SEQ ID NO:1104:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1104:

UGCAUUUUU AUUGUGG 17

( 2 ) INFORMATION FOR SEQ ID NO:1105:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1105:

CCACAAUACU GAUGAGGCCG AAAGGCCGAA AAAAUGCA 38

( 2 ) INFORMATION FOR SEQ ID NO:1106:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1106:

GCAUUUUUUA UUGUGGU          17

( 2 ) INFORMATION FOR SEQ ID NO:1107:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1107:

ACCACAAUCU GAUGAGGCCG AAAGGCCGAA AAAAAUGC          38

( 2 ) INFORMATION FOR SEQ ID NO:1108:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1108:

CAUUUUUUAU UGUGGUU          17

( 2 ) INFORMATION FOR SEQ ID NO:1109:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1109:

AACCACAACU GAUGAGGCCG AAAGGCCGAA AAAAAUG          38

( 2 ) INFORMATION FOR SEQ ID NO:1110:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1110:

UUUUUUAUUG UGGUUUU          17

( 2 ) INFORMATION FOR SEQ ID NO:1111:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1111:
            AAAACCACCU GAUGAGGCCG AAAGGCCGAA AUAAAAAA ( 2 ) INFORMATION FOR SEQ ID NO:1112:

( i ) SEQUENCE CHARACTERISTICS:
        ( A ) LENGTH: 17 base pairs
        ( B ) TYPE: nucleic acid
        ( C ) STRANDEDNESS: single (D) TOPOLOGY: linear (xi) SEQUENCE DESCRIPTION: SEQ ID NO:1112:

UUGUGGUUUU UUUGUUA                                                                                      17

(2) INFORMATION FOR SEQ ID NO:1113:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:1113:

UAACAAAACU GAUGAGGCCG AAAGGCCGAA AACCACAA                                                               38

(2) INFORMATION FOR SEQ ID NO:1114:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:1114:

UGUGGUUUUU UUGUUAU                                                                                      17

(2) INFORMATION FOR SEQ ID NO:1115:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:1115:

AUAACAAACU GAUGAGGCCG AAAGGCCGAA AAACCACA                                                               38

(2) INFORMATION FOR SEQ ID NO:1116:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:1116:

GUGGUUUUUU UGUUAUU                                                                                      17

(2) INFORMATION FOR SEQ ID NO:1117:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:1117:

AAUAACAACU GAUGAGGCCG AAAGGCCGAA AAAACCAC                                                               38

(2) INFORMATION FOR SEQ ID NO:1118:

(i) SEQUENCE CHARACTERISTICS:
                (A) LENGTH: 17 base pairs
                (B) TYPE: nucleic acid
                (C) STRANDEDNESS: single
                (D) TOPOLOGY: linear ( x i ) SEQUENCE DESCRIPTION: SEQ ID NO:1118:

U G G U U U U U U U  G U U A U U G                                17

( 2 ) INFORMATION FOR SEQ ID NO:1119:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1119:

C A A U A A C A C U  G A U G A G G C C G  A A A G G C C G A A  A A A A A C C A                                38

( 2 ) INFORMATION FOR SEQ ID NO:1120:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1120:

G G U U U U U U U G  U U A U U G U                                17

( 2 ) INFORMATION FOR SEQ ID NO:1121:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1121:

A C A A U A A C C U  G A U G A G G C C G  A A A G G C C G A A  A A A A A C C                                38

( 2 ) INFORMATION FOR SEQ ID NO:1122:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1122:
        U U U U U U G U U A  U U G U U G G ( 2 ) INFORMATION FOR SEQ ID NO:1123:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1123:

C C A A C A A U C U  G A U G A G G C C G  A A A G G C C G A A  A C A A A A A A                                38

( 2 ) INFORMATION FOR SEQ ID NO:1124:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1124:

U U U U U G U U A U  U G U U G G U                                17

( 2 ) INFORMATION FOR SEQ ID NO:1125:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1125:

ACCAACAACU GAUGAGGCCG AAAGGCCGAA AACAAAAA 38

( 2 ) INFORMATION FOR SEQ ID NO:1126:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1126:

UUUGUUAUUG UUGGUUU 17

( 2 ) INFORMATION FOR SEQ ID NO:1127:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1127:

AAACCAACCU GAUGAGGCCG AAAGGCCGAA AUAACAAA 38

( 2 ) INFORMATION FOR SEQ ID NO:1128:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1128:

UGUUGGUUUA UACAAGC 17

( 2 ) INFORMATION FOR SEQ ID NO:1129:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1129:

GCUUGUAUCU GAUGAGGCCG AAAGGCCGAA AACCAACA 38

( 2 ) INFORMATION FOR SEQ ID NO:1130:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1130:

GUUGGUUUAU ACAAGCA 17

( 2 ) INFORMATION FOR SEQ ID NO:1131:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1131:

UGCUUGUACU GAUGAGGCCG AAAGGCCGAA AAACCAAC                38

(2) INFORMATION FOR SEQ ID NO:1132:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1132:

UGGUUUAUAC AAGCAUG                                       17

(2) INFORMATION FOR SEQ ID NO:1133:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1133:

CAUGCUUGCU GAUGAGGCCG AAAGGCCGAA AUAAACCA (2) INFORMATION FOR SEQ ID NO:1134:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1134:

GUUGCACUUC UUUUUUG                                       17

(2) INFORMATION FOR SEQ ID NO:1135:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1135:

CAAAAAGCU GAUGAGGCCG AAAGGCCGAA AGUGCAAC                 38

(2) INFORMATION FOR SEQ ID NO:1136:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1136:

UUGCACUUCU UUUUUGG                                       17

(2) INFORMATION FOR SEQ ID NO:1137:

(i) SEQUENCE CHARACTERISTICS:
    (A) LENGTH: 38 base pairs
    (B) TYPE: nucleic acid ( C ) STRANDEDNESS: single
( D ) TOPOLOGY: linear ( x i ) SEQUENCE DESCRIPTION: SEQ ID NO:1137:

CCAAAAACU GAUGAGGCCG AAAGGCCGAA AAGUGCAA    38

( 2 ) INFORMATION FOR SEQ ID NO:1138:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1138:

GCACUUCUUU UUUGGGA    17

( 2 ) INFORMATION FOR SEQ ID NO:1139:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1139:

UCCCAAAACU GAUGAGGCCG AAAGGCCGAA AGAAGUGC    38

( 2 ) INFORMATION FOR SEQ ID NO:1140:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1140:

CACUUCUUUU UUGGGAG    17

( 2 ) INFORMATION FOR SEQ ID NO:1141:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1141:

CUCCCAAACU GAUGAGGCCG AAAGGCCGAA AAGAAGUG    38

( 2 ) INFORMATION FOR SEQ ID NO:1142:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1142:

ACUUCUUUUU UGGGAGA    17

( 2 ) INFORMATION FOR SEQ ID NO:1143:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear (x i) SEQUENCE DESCRIPTION: SEQ ID NO:1143:

UCUCCCAACU GAUGAGGCCG AAAGGCCGAA AAAGAAGU  38

(2) INFORMATION FOR SEQ ID NO:1144:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (x i) SEQUENCE DESCRIPTION: SEQ ID NO:1144:

CUUCUUUUUU GGGAGAU (2) INFORMATION FOR SEQ ID NO:1145:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (x i) SEQUENCE DESCRIPTION: SEQ ID NO:1145:

AUCUCCCACU GAUGAGGCCG AAAGGCCGAA AAAAGAAG  38

(2) INFORMATION FOR SEQ ID NO:1146:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (x i) SEQUENCE DESCRIPTION: SEQ ID NO:1146:

UUCUUUUUUG GGAGAUG  17

(2) INFORMATION FOR SEQ ID NO:1147:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (x i) SEQUENCE DESCRIPTION: SEQ ID NO:1147:

CAUCUCCCCU GAUGAGGCCG AAAGGCCGAA AAAAAGAA  38

(2) INFORMATION FOR SEQ ID NO:1148:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (x i) SEQUENCE DESCRIPTION: SEQ ID NO:1148:

UUGAUGUUCU AUGUUUU  17

(2) INFORMATION FOR SEQ ID NO:1149:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (x i) SEQUENCE DESCRIPTION: SEQ ID NO:1149:

AAAACAUACU GAUGAGGCCG AAAGGCCGAA AACAUCAA  38

( 2 ) INFORMATION FOR SEQ ID NO:1150:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1150:

GAUGUUCUAU GUUUUGU 17

( 2 ) INFORMATION FOR SEQ ID NO:1151:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1151:

ACAAACACU GAUGAGGCCG AAAGGCCGAA AGAACAUC 38

( 2 ) INFORMATION FOR SEQ ID NO:1152:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1152:

UCUAUGUUUU GUUUUGA 17

( 2 ) INFORMATION FOR SEQ ID NO:1153:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1153:

UCAAAACACU GAUGAGGCCG AAAGGCCGAA AACAUAGA 38

( 2 ) INFORMATION FOR SEQ ID NO:1154:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1154:

CUAUGUUUUG UUUUGAG 17

( 2 ) INFORMATION FOR SEQ ID NO:1155:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1155:
        CUCAAAACCU GAUGAGGCCG AAAGGCCGAA AAACAUAG ( 2 ) INFORMATION FOR SEQ ID NO:1156:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1156:

GUUUUGUUUU GAGUGUA 17

( 2 ) INFORMATION FOR SEQ ID NO:1157:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1157:

UACACUCACU GAUGAGGCCG AAAGGCCGAA AACAAAAC 38

( 2 ) INFORMATION FOR SEQ ID NO:1158:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1158:

UUUUGUUUUG AGUGUAG 17

( 2 ) INFORMATION FOR SEQ ID NO:1159:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1159:

CUACACUCCU GAUGAGGCCG AAAGGCCGAA AAACAAAA 38

( 2 ) INFORMATION FOR SEQ ID NO:1160:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1160:

UGACUGUUUU AUAAUUU 17

( 2 ) INFORMATION FOR SEQ ID NO:1161:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1161:

AAAUUAUACU GAUGAGGCCG AAAGGCCGAA AACAGUCA 38

( 2 ) INFORMATION FOR SEQ ID NO:1162:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:1162:

GACUGUUUUA UAAUUUG                                                    17

(2) INFORMATION FOR SEQ ID NO:1163:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1163:

CAAAUUAUCU GAUGAGGCCG AAAGGCCGAA AAACAGUC                              38

(2) INFORMATION FOR SEQ ID NO:1164:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1164:

ACUGUUUUAU AAUUUGG                                                    17

(2) INFORMATION FOR SEQ ID NO:1165:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1165:

CCAAAUUACU GAUGAGGCCG AAAGGCCGAA AAAACAGU                              38

(2) INFORMATION FOR SEQ ID NO:1166:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1166:
UGUUUUAUAA UUUGGGA (2) INFORMATION FOR SEQ ID NO:1167:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1167:

UCCCAAAUCU GAUGAGGCCG AAAGGCCGAA AUAAAACA                              38

(2) INFORMATION FOR SEQ ID NO:1168:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:1168:

UUUAUAAUUU GGGAGUU 17

( 2 ) INFORMATION FOR SEQ ID NO:1169:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1169:

AACUCCCACU GAUGAGGCCG AAAGGCCGAA AUUAUAAA 38

( 2 ) INFORMATION FOR SEQ ID NO:1170:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1170:

UUAUAAUUUG GGAGUUC 17

( 2 ) INFORMATION FOR SEQ ID NO:1171:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1171:

GAACUCCCCU GAUGAGGCCG AAAGGCCGAA AAUUAUAA 38

( 2 ) INFORMATION FOR SEQ ID NO:1172:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1172:

UGGGAGUUCU GCAUUUG 17

( 2 ) INFORMATION FOR SEQ ID NO:1173:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1173:

CAAAUGCACU GAUGAGGCCG AAAGGCCGAA AACUCCCA 38

( 2 ) INFORMATION FOR SEQ ID NO:1174:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1174:

UUCUGCAUUU GAUCCGC                                                                                        17

( 2 ) INFORMATION FOR SEQ ID NO:1175:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1175:

GCGGAUCACU GAUGAGGCCG AAAGGCCGAA AUGCAGAA                                                                 38

( 2 ) INFORMATION FOR SEQ ID NO:1176:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1176:

UCUGCAUUUG AUCCGCA                                                                                        17

( 2 ) INFORMATION FOR SEQ ID NO:1177:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1177:

UGCGGAUCCU GAUGAGGCCG AAAGGCCGAA AAUGCAGA ( 2 ) INFORMATION FOR SEQ ID NO:1178:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1178:

CAUUUGAUCC GCAUCCC                                                                                        17

( 2 ) INFORMATION FOR SEQ ID NO:1179:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1179:

GGGAUGCGCU GAUGAGGCCG AAAGGCCGAA AUCAAAUG                                                                 38

( 2 ) INFORMATION FOR SEQ ID NO:1180:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1180:

AUCCGCAUCC CCUGUGG                                                                                        17

( 2 ) INFORMATION FOR SEQ ID NO:1181:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1181:

CCACAGGGCU GAUGAGGCCG AAAGGCCGAA AUGCGGAU 38

( 2 ) INFORMATION FOR SEQ ID NO:1182:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1182:

CUGUGGUUUC UAAGUGU 17

( 2 ) INFORMATION FOR SEQ ID NO:1183:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1183:

ACACUUAGCU GAUGAGGCCG AAAGGCCGAA AACCACAG 38

( 2 ) INFORMATION FOR SEQ ID NO:1184:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1184:

UGUGGUUUCU AAGUGUA 17

( 2 ) INFORMATION FOR SEQ ID NO:1185:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1185:

UACACUUACU GAUGAGGCCG AAAGGCCGAA AAACCACA 38

( 2 ) INFORMATION FOR SEQ ID NO:1186:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1186:

UGGUUUCUAA GUGUAUG 17

( 2 ) INFORMATION FOR SEQ ID NO:1187:

( i ) SEQUENCE CHARACTERISTICS:

( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1187:

CAUACACUCU GAUGAGGCCG AAAGGCCGAA AGAAACCA 38

( 2 ) INFORMATION FOR SEQ ID NO:1188:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1188:

UAUGGUCUCA GAACUGU ( 2 ) INFORMATION FOR SEQ ID NO:1189:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1189:

ACAGUUCUCU GAUGAGGCCG AAAGGCCGAA AGACCAUA 38

( 2 ) INFORMATION FOR SEQ ID NO:1190:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1190:

GCAUGGAUCC UGUGUUU 17

( 2 ) INFORMATION FOR SEQ ID NO:1191:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1191:

AAACACAGCU GAUGAGGCCG AAAGGCCGAA AUCCAUGC 38

( 2 ) INFORMATION FOR SEQ ID NO:1192:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1192:

UCCUGUGUUU GCAACUG 17

( 2 ) INFORMATION FOR SEQ ID NO:1193:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1193:

CAGUUGCACU GAUGAGGCCG AAAGGCCGAA ACACAGGA 38

( 2 ) INFORMATION FOR SEQ ID NO:1194:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1194:

CCUGUGUUUG CAACUGG 17

( 2 ) INFORMATION FOR SEQ ID NO:1195:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1195:

CCAGUUGCCU GAUGAGGCCG AAAGGCCGAA AACACAGG 38

( 2 ) INFORMATION FOR SEQ ID NO:1196:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1196:

UGGUUGAUAG CCAGUCA 17

( 2 ) INFORMATION FOR SEQ ID NO:1197:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1197:

UGACUGGCCU GAUGAGGCCG AAAGGCCGAA AUCAACCA 38

( 2 ) INFORMATION FOR SEQ ID NO:1198:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1198:

CACUGCCUUA AGAACAU 17

( 2 ) INFORMATION FOR SEQ ID NO:1199:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1199:

```
       AUGUUCUUCU GAUGAGGCCG AAAGGCCGAA AGGCAGUG
```

( 2 ) INFORMATION FOR SEQ ID NO:1200:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1200:

```
ACUGCCUUAA GAACAUU                                                              17
```

( 2 ) INFORMATION FOR SEQ ID NO:1201:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1201:

```
AAUGUUCUCU GAUGAGGCCG AAAGGCCGAA AAGGCAGU                                       38
```

( 2 ) INFORMATION FOR SEQ ID NO:1202:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1202:

```
AAGAACAUUU GAUGCAA                                                              17
```

( 2 ) INFORMATION FOR SEQ ID NO:1203:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1203:

```
UUGCAUCACU GAUGAGGCCG AAAGGCCGAA AUGUUCUU                                       38
```

( 2 ) INFORMATION FOR SEQ ID NO:1204:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1204:

```
AGAACAUUUG AUGCAAG                                                              17
```

( 2 ) INFORMATION FOR SEQ ID NO:1205:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1205:

```
CUUGCAUCCU GAUGAGGCCG AAAGGCCGAA AAUGUUCU                                       38
```

(2) INFORMATION FOR SEQ ID NO:1206:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1206:

ACUGAACUUU UGAGAUA         17

(2) INFORMATION FOR SEQ ID NO:1207:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1207:

UAUCUCAACU GAUGAGGCCG AAAGGCCGAA AGUUCAGU         38

(2) INFORMATION FOR SEQ ID NO:1208:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1208:

CUGAACUUUU GAGAUAU         17

(2) INFORMATION FOR SEQ ID NO:1209:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1209:

AUAUCUCACU GAUGAGGCCG AAAGGCCGAA AAGUUCAG         38

(2) INFORMATION FOR SEQ ID NO:1210:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1210:

UGAACUUUUG AGAUAUG (2) INFORMATION FOR SEQ ID NO:1211:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1211:

CAUAUCUCCU GAUGAGGCCG AAAGGCCGAA AAAGUUCA         38

(2) INFORMATION FOR SEQ ID NO:1212:

(i) SEQUENCE CHARACTERISTICS:
        (A) LENGTH: 17 base pairs (B) TYPE: nucleic acid
        (C) STRANDEDNESS: single
        (D) TOPOLOGY: linear (xi) SEQUENCE DESCRIPTION: SEQ ID NO:1212:

UUUGAGAUAU GACGGUG                                                              17

(2) INFORMATION FOR SEQ ID NO:1213:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1213:

CACCGUCACU GAUGAGGCCG AAAGGCCGAA AUCUCAAA                                        38

(2) INFORMATION FOR SEQ ID NO:1214:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1214:

GGUGUACUUA CUGCCUU                                                              17

(2) INFORMATION FOR SEQ ID NO:1215:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1215:

AAGGCAGUCU GAUGAGGCCG AAAGGCCGAA AGUACACC                                        38

(2) INFORMATION FOR SEQ ID NO:1216:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1216:

GUGUACUUAC UGCCUUG                                                              17

(2) INFORMATION FOR SEQ ID NO:1217:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1217:

CAAGGCAGCU GAUGAGGCCG AAAGGCCGAA AAGUACAC                                        38

(2) INFORMATION FOR SEQ ID NO:1218:

(i) SEQUENCE CHARACTERISTICS:
        (A) LENGTH: 17 base pairs
        (B) TYPE: nucleic acid
        (C) STRANDEDNESS: single (D) TOPOLOGY: linear (x i) SEQUENCE DESCRIPTION: SEQ ID NO:1218:

UACUGCCUUG UAGCAAA 17

(2) INFORMATION FOR SEQ ID NO:1219:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1219:

UUUGCUACCU GAUGAGGCCG AAAGGCCGAA AGGCAGUA 38

(2) INFORMATION FOR SEQ ID NO:1220:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1220:

AGCAAAAUAA AGAUGUG 17

(2) INFORMATION FOR SEQ ID NO:1221:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1221:

CACAUCUUCU GAUGAGGCCG AAAGGCCGAA AUUUUGCU (2) INFORMATION FOR SEQ ID NO:1222:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1222:

UGUGCCCUUA UUUUACC 17

(2) INFORMATION FOR SEQ ID NO:1223:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1223:

GGUAAAAUCU GAUGAGGCCG AAAGGCCGAA AGGGCACA 38

(2) INFORMATION FOR SEQ ID NO:1224:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1224:

GUGCCCUUAU UUUACCU                                                                17

( 2 ) INFORMATION FOR SEQ ID NO:1225:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1225:

AGGUAAAACU GAUGAGGCCG AAAGGCCGAA AAGGGCAC                                         38

( 2 ) INFORMATION FOR SEQ ID NO:1226:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1226:

UCCGCCAACU GAUGAGGCCG AAAGGCCGAA AGCCCGG                                          38

( 2 ) INFORMATION FOR SEQ ID NO:1227:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1227:

CCGGGGCUCU UGGCGGA                                                                17

( 2 ) INFORMATION FOR SEQ ID NO:1228:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1228:

GCUCCGCCCU GAUGAGGCCG AAAGGCCGAA AGAGCCCC                                         38

( 2 ) INFORMATION FOR SEQ ID NO:1229:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1229:

GGGGCUCUUG GCGGAGC                                                                17

( 2 ) INFORMATION FOR SEQ ID NO:1230:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1230:

GCCAUGGCCU GAUGAGGCCG AAAGGCCGAA AGGCGGGC                                         38

( 2 ) INFORMATION FOR SEQ ID NO:1231:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1231:

GCCCGCCUCG CCAUGGC 17

( 2 ) INFORMATION FOR SEQ ID NO:1232:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1232:

CUACUGUACU GAUGAGGCCG AAAGGCCGAA AUGCUGUG ( 2 ) INFORMATION FOR SEQ ID NO:1233:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1233:

CACAGCAUCU ACAGUAG 17

( 2 ) INFORMATION FOR SEQ ID NO:1234:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1234:

CGCUACUGCU GAUGAGGCCG AAAGGCCGAA AGAUGCUG 38

( 2 ) INFORMATION FOR SEQ ID NO:1235:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1235:

CAGCAUCUAC AGUAGCG 17

( 2 ) INFORMATION FOR SEQ ID NO:1236:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1236:

UUCAUCGCCU GAUGAGGCCG AAAGGCCGAA ACUGUAGA 38

( 2 ) INFORMATION FOR SEQ ID NO:1237:

( i ) SEQUENCE CHARACTERISTICS:

(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1237:

UCUACAGUAG CGAUGAA 17

(2) INFORMATION FOR SEQ ID NO:1238:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1238:

CACAUCUCCU GAUGAGGCCG AAAGGCCGAA AUGUCUUC 38

(2) INFORMATION FOR SEQ ID NO:1239:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1239:

GAAGACAUUG AGAUGUG 17

(2) INFORMATION FOR SEQ ID NO:1240:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1240:

GCCCAUCGCU GAUGAGGCCG AAAGGCCGAA AGUCAUGG 38

(2) INFORMATION FOR SEQ ID NO:1241:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1241:

CCAUGACUAC GAUGGGC 17

(2) INFORMATION FOR SEQ ID NO:1242:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1242:

GCUUUCCACU GAUGAGGCCG AAAGGCCGAA AUUUGGGC 38

(2) INFORMATION FOR SEQ ID NO:1243:

(i) SEQUENCE CHARACTERISTICS:
(A) LENGTH: 17 base pairs
(B) TYPE: nucleic acid (C) STRANDEDNESS: single
(D) TOPOLOGY: linear (xi) SEQUENCE DESCRIPTION: SEQ ID NO:1243:

GCCCAAAUCU GGAAAGC (2) INFORMATION FOR SEQ ID NO:1244:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1244:

CCCCAAGUCU GAUGAGGCCG AAAGGCCGAA ACGCUUUC 38

(2) INFORMATION FOR SEQ ID NO:1245:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1245:

GAAAGCGUCA CUUGGGG 17

(2) INFORMATION FOR SEQ ID NO:1246:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1246:

UUUUCCCCU GAUGAGGCCG AAAGGCCGAA AGUGACGC 38

(2) INFORMATION FOR SEQ ID NO:1247:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1247:

GCGUCACUUG GGGAAAA 17

(2) INFORMATION FOR SEQ ID NO:1248:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1248:

UGUCCACCCU GAUGAGGCCG AAAGGCCGAA AGUUUUCC 38

(2) INFORMATION FOR SEQ ID NO:1249:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1249:

GGAAAACUAG GUGGACA 17

( 2 ) INFORMATION FOR SEQ ID NO:1250:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1250:

UUGGCAAUCU GAUGAGGCCG AAAGGCCGAA ACUUUCCA 38

( 2 ) INFORMATION FOR SEQ ID NO:1251:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1251:

UGGAAAGUCA UUGCCAA 17

( 2 ) INFORMATION FOR SEQ ID NO:1252:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1252:

UAAUUGGCCU GAUGAGGCCG AAAGGCCGAA AUGACUUU 38

( 2 ) INFORMATION FOR SEQ ID NO:1253:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1253:

AAAGUCAUUG CCAAUUA 17

( 2 ) INFORMATION FOR SEQ ID NO:1254:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1254:
        GGGCAGAUCU GAUGAGGCCG AAAGGCCGAA AUUGGCAA ( 2 ) INFORMATION FOR SEQ ID NO:1255:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1255:

UUGCCAAUUA UCUGCCC 17

( 2 ) INFORMATION FOR SEQ ID NO:1256:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1256:

UGGGCAGACU GAUGAGGCCG AAAGGCCGAA AAUUGGCA 38

( 2 ) INFORMATION FOR SEQ ID NO:1257:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1257:

UGCCAAUUAU CUGCCCA 17

( 2 ) INFORMATION FOR SEQ ID NO:1258:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1258:

GUUGGGCACU GAUGAGGCCG AAAGGCCGAA AUAAUUGG 38

( 2 ) INFORMATION FOR SEQ ID NO:1259:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1259:

CCAAUUAUCU GCCCAAC 17

( 2 ) INFORMATION FOR SEQ ID NO:1260:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1260:

UGGCACUGCU GAUGAGGCCG AAAGGCCGAA ACAUCUGU 38

( 2 ) INFORMATION FOR SEQ ID NO:1261:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1261:

ACAGAUGUAC AGUGCCA 17

( 2 ) INFORMATION FOR SEQ ID NO:1262:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1262:

CCUUUGAUCU GAUGAGGCCG AAAGGCCGAA AGUUCAGG        38

( 2 ) INFORMATION FOR SEQ ID NO:1263:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1263:

CCUGAACUCA UCAAAGG        17

( 2 ) INFORMATION FOR SEQ ID NO:1264:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1264:

GGACCUUUCU GAUGAGGCCG AAAGGCCGAA AUGAGUUC        38

( 2 ) INFORMATION FOR SEQ ID NO:1265:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1265:
            GAACUCAUCA AAGGUCC ( 2 ) INFORMATION FOR SEQ ID NO:1266:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1266:

GGUCCAGGCU GAUGAGGCCG AAAGGCCGAA ACCUUUGA        38

( 2 ) INFORMATION FOR SEQ ID NO:1267:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1267:

UCAAAGGUCC CUGGACC        17

( 2 ) INFORMATION FOR SEQ ID NO:1268:

( i ) SEQUENCE CHARACTERISTICS:
    ( A ) LENGTH: 38 base pairs
    ( B ) TYPE: nucleic acid
    ( C ) STRANDEDNESS: single (D) TOPOLOGY: linear (xi) SEQUENCE DESCRIPTION: SEQ ID NO:1268:

GACUCUCUCU GAUGAGGCCG AAAGGCCGAA AUCUUCUU 38

(2) INFORMATION FOR SEQ ID NO:1269:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1269:

AAGAAGAUCA GAGAGUC 17

(2) INFORMATION FOR SEQ ID NO:1270:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1270:

AGCUUUAUCU GAUGAGGCCG AAAGGCCGAA ACUCUCUG 38

(2) INFORMATION FOR SEQ ID NO:1271:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1271:

CAGAGAGUCA UAAAGCU 17

(2) INFORMATION FOR SEQ ID NO:1272:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1272:

ACAAGCUUCU GAUGAGGCCG AAAGGCCGAA AUGACUCU 38

(2) INFORMATION FOR SEQ ID NO:1273:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1273:

AGAGUCAUAA AGCUUGU 17

(2) INFORMATION FOR SEQ ID NO:1274:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:1274:

UUCUGGACCU GAUGAGGCCG AAAGGCCGAA AGCUUUAU 38

( 2 ) INFORMATION FOR SEQ ID NO:1275:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1275:

AUAAAGCUUG UCCAGAA 17

( 2 ) INFORMATION FOR SEQ ID NO:1276:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1276:

UAUUUCUGCU GAUGAGGCCG AAAGGCCGAA ACAAGCUU 38

( 2 ) INFORMATION FOR SEQ ID NO:1277:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1277:

AAGCUUGUCC AGAAAUA 17

( 2 ) INFORMATION FOR SEQ ID NO:1278:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1278:

UCGGACCACU GAUGAGGCCG AAAGGCCGAA AUUUCUGG 38

( 2 ) INFORMATION FOR SEQ ID NO:1279:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1279:

CCAGAAAUAU GGUCCGA 17

( 2 ) INFORMATION FOR SEQ ID NO:1280:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1280:

ACGCUUCGCU GAUGAGGCCG AAAGGCCGAA ACCAUAUU 38

( 2 ) INFORMATION FOR SEQ ID NO:1281:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1281:

AAUAUGGUCC GAAGCGU                               17

( 2 ) INFORMATION FOR SEQ ID NO:1282:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1282:

AACAGACCCU GAUGAGGCCG AAAGGCCGAA ACGCUUCG           38

( 2 ) INFORMATION FOR SEQ ID NO:1283:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1283:

CGAAGCGUUG GUCUGUU                               17

( 2 ) INFORMATION FOR SEQ ID NO:1284:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1284:

CAAUAACACU GAUGAGGCCG AAAGGCCGAA ACCAACGC           38

( 2 ) INFORMATION FOR SEQ ID NO:1285:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1285:

GCGUUGGUCU GUUAUUG                              17

( 2 ) INFORMATION FOR SEQ ID NO:1286:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1286:

UUGGCAAUCU GAUGAGGCCG AAAGGCCGAA ACAGACCA           38

( 2 ) INFORMATION FOR SEQ ID NO:1287:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1287:

UGGUCUGUUA UUGCCAA ( 2 ) INFORMATION FOR SEQ ID NO:1288:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1288:

CUUGGCAACU GAUGAGGCCG AAAGGCCGAA AACAGACC 38

( 2 ) INFORMATION FOR SEQ ID NO:1289:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1289:

GGUCUGUUAU UGCCAAG 17

( 2 ) INFORMATION FOR SEQ ID NO:1290:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1290:

UGCUUGGCCU GAUGAGGCCG AAAGGCCGAA AUAACAGA 38

( 2 ) INFORMATION FOR SEQ ID NO:1291:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1291:

UCUGUUAUUG CCAAGCA 17

( 2 ) INFORMATION FOR SEQ ID NO:1292:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1292:

UCCCUUUUCU GAUGAGGCCG AAAGGCCGAA AGUGCUUG 38

( 2 ) INFORMATION FOR SEQ ID NO:1293:

( i ) SEQUENCE CHARACTERISTICS:
   ( A ) LENGTH: 17 base pairs
   ( B ) TYPE: nucleic acid (C) STRANDEDNESS: single
(D) TOPOLOGY: linear (xi) SEQUENCE DESCRIPTION: SEQ ID NO:1293:

CAAGCACUUA AAAGGGA                                                                                              17

(2) INFORMATION FOR SEQ ID NO:1294:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:1294:

CUCCCUUUCU GAUGAGGCCG AAAGGCCGAA AAGUGCUU                                                                        38

(2) INFORMATION FOR SEQ ID NO:1295:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:1295:

AAGCACUUAA AAGGGAG                                                                                              17

(2) INFORMATION FOR SEQ ID NO:1296:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:1296:

UGCUUUCCCU GAUGAGGCCG AAAGGCCGAA AUUCUCCC                                                                        38

(2) INFORMATION FOR SEQ ID NO:1297:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:1297:

GGGAGAAUUG GAAAGCA                                                                                              17

(2) INFORMATION FOR SEQ ID NO:1298:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:1298:
                    CCUCUCCCCU GAUGAGGCCG AAAGGCCGAA ACACUGCU (2) INFORMATION FOR SEQ ID NO:1299:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:1299:

```
AGCAGUGUCG GGAGAGG                                                                  17
```

( 2 ) INFORMATION FOR SEQ ID NO:1300:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1300:

```
UGGAUUCACU GAUGAGGCCG AAAGGCCGAA AUGGUUGU                                            38
```

( 2 ) INFORMATION FOR SEQ ID NO:1301:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1301:

```
ACAACCAUUU GAAUCCA                                                                  17
```

( 2 ) INFORMATION FOR SEQ ID NO:1302:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1302:

```
CUGGAUUCCU GAUGAGGCCG AAAGGCCGAA AAUGGUUG                                            38
```

( 2 ) INFORMATION FOR SEQ ID NO:1303:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1303:

```
CAACCAUUUG AAUCCAG                                                                  17
```

( 2 ) INFORMATION FOR SEQ ID NO:1304:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1304:

```
AACUUCUGCU GAUGAGGCCG AAAGGCCGAA AUUCAAAU                                            38
```

( 2 ) INFORMATION FOR SEQ ID NO:1305:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1305:

```
AUUUGAAUCC AGAAGUU                                                                  17
```

( 2 ) INFORMATION FOR SEQ ID NO:1306:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1306:

GUUUUCUUCU GAUGAGGCCG AAAGGCCGAA ACUUCUGG　　　　　　　　　　　　38

( 2 ) INFORMATION FOR SEQ ID NO:1307:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1307:

CCAGAAGUUA AGAAAAC　　　　　　　　　　　　　　　　　　　　　　17

( 2 ) INFORMATION FOR SEQ ID NO:1308:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1308:

GGUUUUCUCU GAUGAGGCCG AAAGGCCGAA AACUUCUG　　　　　　　　　　　　38

( 2 ) INFORMATION FOR SEQ ID NO:1309:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1309:

CAGAAGUUAA GAAAACC ( 2 ) INFORMATION FOR SEQ ID NO:1310:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1310:

CUGUCCAGCU GAUGAGGCCG AAAGGCCGAA AGGUUUUC　　　　　　　　　　　　38

( 2 ) INFORMATION FOR SEQ ID NO:1311:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1311:

GAAAACCUCC UGGACAG　　　　　　　　　　　　　　　　　　　　　　17

( 2 ) INFORMATION FOR SEQ ID NO:1312:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1312:

UGGUAAAUCU GAUGAGGCCG AAAGGCCGAA AUUCUGUC  38

( 2 ) INFORMATION FOR SEQ ID NO:1313:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1313:

GACAGAAUCA UUUACCA  17

( 2 ) INFORMATION FOR SEQ ID NO:1314:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1314:

GCCUGGUACU GAUGAGGCCG AAAGGCCGAA AUGAUUCU  38

( 2 ) INFORMATION FOR SEQ ID NO:1315:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1315:

AGAAUCAUUU ACCAGGC  17

( 2 ) INFORMATION FOR SEQ ID NO:1316:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1316:

UGCCUGGUCU GAUGAGGCCG AAAGGCCGAA AAUGAUUC  38

( 2 ) INFORMATION FOR SEQ ID NO:1317:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1317:

GAAUCAUUUA CCAGGCA  17

( 2 ) INFORMATION FOR SEQ ID NO:1318:

( i ) SEQUENCE CHARACTERISTICS:
    ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO:1318:

GUGCCUGGCU GAUGAGGCCG AAAGGCCGAA AAAUGAUU 38

(2) INFORMATION FOR SEQ ID NO:1319:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1319:

AAUCAUUUAC CAGGCAC 17

(2) INFORMATION FOR SEQ ID NO:1320:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1320:
GUUCCCACU GAUGAGGCCG AAAGGCCGAA ACGCUUGU (2) INFORMATION FOR SEQ ID NO:1321:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1321:

ACAAGCGUCU GGGGAAC 17

(2) INFORMATION FOR SEQ ID NO:1322:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1322:

AGCUUUGCCU GAUGAGGCCG AAAGGCCGAA AUCUCUGC 38

(2) INFORMATION FOR SEQ ID NO:1323:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1323:

GCAGAGAUCG CAAAGCU 17

(2) INFORMATION FOR SEQ ID NO:1324:

(i) SEQUENCE CHARACTERISTICS:
(A) LENGTH: 38 base pairs
(B) TYPE: nucleic acid
(C) STRANDEDNESS: single
(D) TOPOLOGY: linear -continued ( x i ) SEQUENCE DESCRIPTION: SEQ ID NO:1324:

GAUAGCAUCU GAUGAGGCCG AAAGGCCGAA AUCAGUCC 38

( 2 ) INFORMATION FOR SEQ ID NO:1325:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1325:

GGACUGAUAA UGCUAUC 17

( 2 ) INFORMATION FOR SEQ ID NO:1326:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1326:

GUUCUUGACU GAUGAGGCCG AAAGGCCGAA AGCAUUAU 38

( 2 ) INFORMATION FOR SEQ ID NO:1327:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1327:

AUAAUGCUAU CAAGAAC 17

( 2 ) INFORMATION FOR SEQ ID NO:1328:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1328:

UGGUUCUUCU GAUGAGGCCG AAAGGCCGAA AUAGCAUU 38

( 2 ) INFORMATION FOR SEQ ID NO:1329:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1329:

AAUGCUAUCA AGAACCA 17

( 2 ) INFORMATION FOR SEQ ID NO:1330:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1330:

CAUGGUGGCU GAUGAGGCCG AAAGGCCGAA AUUCCAGU 38

( 2 ) INFORMATION FOR SEQ ID NO:1331:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1331:

ACUGGAAUUC CACCAUG 17

( 2 ) INFORMATION FOR SEQ ID NO:1332:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1332:

GCAUGGUGCU GAUGAGGCCG AAAGGCCGAA AAUUCCAG 38

( 2 ) INFORMATION FOR SEQ ID NO:1333:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1333:

CUGGAAUUCC ACCAUGC 17

( 2 ) INFORMATION FOR SEQ ID NO:1334:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1334:

CACCUUGCCU GAUGAGGCCG AAAGGCCGAA ACGCAUGG 38

( 2 ) INFORMATION FOR SEQ ID NO:1335:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1335:

CCAUGCGUCG CAAGGUG 17

( 2 ) INFORMATION FOR SEQ ID NO:1336:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1336:

UCUGCAGGCU GAUGAGGCCG AAAGGCCGAA AGCCUUCC 38

( 2 ) INFORMATION FOR SEQ ID NO:1337:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1337:

GGAAGGCUAC CUGCAGA    17

( 2 ) INFORMATION FOR SEQ ID NO:1338:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1338:

GGCUUUGGCU GAUGAGGCCG AAAGGCCGAA AGGCUUCU    38

( 2 ) INFORMATION FOR SEQ ID NO:1339:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1339:

AGAAGCCUUC CAAAGCC    17

( 2 ) INFORMATION FOR SEQ ID NO:1340:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1340:

UGGCUUUGCU GAUGAGGCCG AAAGGCCGAA AAGGCUUC    38

( 2 ) INFORMATION FOR SEQ ID NO:1341:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1341:

GAAGCCUUCC AAAGCCA    17

( 2 ) INFORMATION FOR SEQ ID NO:1342:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1342:
UCUUCUGGCU GAUGAGGCCG AAAGGCCGAA AGCUCGUG ( 2 ) INFORMATION FOR SEQ ID NO:1343:

( i ) SEQUENCE CHARACTERISTICS:
    ( A ) LENGTH: 17 base pairs
    ( B ) TYPE: nucleic acid (C) STRANDEDNESS: single
(D) TOPOLOGY: linear (xi) SEQUENCE DESCRIPTION: SEQ ID NO:1343:

CACGAGCUUC CAGAAGA                                                               17

(2) INFORMATION FOR SEQ ID NO:1344:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1344:

UUCUUCUGCU GAUGAGGCCG AAAGGCCGAA AAGCUCGU                                         38

(2) INFORMATION FOR SEQ ID NO:1345:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1345:

ACGAGCUUCC AGAAGAA                                                                17

(2) INFORMATION FOR SEQ ID NO:1346:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1346:

CAUCAAAUCU GAUGAGGCCG AAAGGCCGAA AUUGUUCU                                         38

(2) INFORMATION FOR SEQ ID NO:1347:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1347:

AGAACAAUCA UUUGAUG                                                                17

(2) INFORMATION FOR SEQ ID NO:1348:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1348:

CCCCAUCACU GAUGAGGCCG AAAGGCCGAA AUGAUUGU                                         38

(2) INFORMATION FOR SEQ ID NO:1349:

(i) SEQUENCE CHARACTERISTICS:
    (A) LENGTH: 17 base pairs
    (B) TYPE: nucleic acid
    (C) STRANDEDNESS: single
    (D) TOPOLOGY: linear ( x i ) SEQUENCE DESCRIPTION: SEQ ID NO:1349:

ACAAUCAUUU GAUGGGG 17

( 2 ) INFORMATION FOR SEQ ID NO:1350:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1350:

ACCCCAUCCU GAUGAGGCCG AAAGGCCGAA AAUGAUUG 38

( 2 ) INFORMATION FOR SEQ ID NO:1351:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1351:

CAAUCAUUUG AUGGGGU 17

( 2 ) INFORMATION FOR SEQ ID NO:1352:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1352:

CAUGCCCACU GAUGAGGCCG AAAGGCCGAA ACCCCAUC 38

( 2 ) INFORMATION FOR SEQ ID NO:1353:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1353:
GAUGGGGUUU GGGCAUG ( 2 ) INFORMATION FOR SEQ ID NO:1354:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1354:

GCAUGCCCCU GAUGAGGCCG AAAGGCCGAA AACCCCAU 38

( 2 ) INFORMATION FOR SEQ ID NO:1355:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1355:

AUGGGGUUUG GGCAUGC 17

( 2 ) INFORMATION FOR SEQ ID NO:1356:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1356:

AUGGAGGUCU GAUGAGGCCG AAAGGCCGAA AGGCAUGC        38

( 2 ) INFORMATION FOR SEQ ID NO:1357:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1357:

GCAUGCCUCA CCUCCAU        17

( 2 ) INFORMATION FOR SEQ ID NO:1358:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1358:

CUGAGAUGCU GAUGAGGCCG AAAGGCCGAA AGGUGAGG        38

( 2 ) INFORMATION FOR SEQ ID NO:1359:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1359:

CCUCACCUCC AUCUCAG        17

( 2 ) INFORMATION FOR SEQ ID NO:1360:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1360:

AGAGCUGACU GAUGAGGCCG AAAGGCCGAA AUGGAGGU        38

( 2 ) INFORMATION FOR SEQ ID NO:1361:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1361:

ACCUCCAUCU CAGCUCU        17

-continued ( 2 ) INFORMATION FOR SEQ ID NO:1362:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1362:

AGAGAGCUCU GAUGAGGCCG AAAGGCCGAA AGAUGGAG     38

( 2 ) INFORMATION FOR SEQ ID NO:1363:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1363:

CUCCAUCUCA GCUCUCU     17

( 2 ) INFORMATION FOR SEQ ID NO:1364:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1364:

CUUGGAGACU GAUGAGGCCG AAAGGCCGAA AGCUGAGA ( 2 ) INFORMATION FOR SEQ ID NO:1365:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1365:

UCUCAGCUCU CUCCAAG     17

( 2 ) INFORMATION FOR SEQ ID NO:1366:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1366:

CACUUGGACU GAUGAGGCCG AAAGGCCGAA AGAGCUGA     38

( 2 ) INFORMATION FOR SEQ ID NO:1367:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1367:

UCAGCUCUCU CCAAGUG     17

( 2 ) INFORMATION FOR SEQ ID NO:1368:

( i ) SEQUENCE CHARACTERISTICS:
        ( A ) LENGTH: 38 base pairs (B) TYPE: nucleic acid
                (C) STRANDEDNESS: single
                (D) TOPOLOGY: linear (xi) SEQUENCE DESCRIPTION: SEQ ID NO:1368:

GCCACUUGCU GAUGAGGCCG AAAGGCCGAA AGAGAGCU                                       38

(2) INFORMATION FOR SEQ ID NO:1369:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:1369:

AGCUCUCUCC AAGUGGC                                                              17

(2) INFORMATION FOR SEQ ID NO:1370:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:1370:

UGACGGAGCU GAUGAGGCCG AAAGGCCGAA ACUGGCCA                                       38

(2) INFORMATION FOR SEQ ID NO:1371:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:1371:

UGGCCAGUCC UCCGUCA                                                              17

(2) INFORMATION FOR SEQ ID NO:1372:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:1372:

UGUUGACGCU GAUGAGGCCG AAAGGCCGAA AGGACUGG                                       38

(2) INFORMATION FOR SEQ ID NO:1373:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:1373:

CCAGUCCUCC GUCAACA                                                              17

(2) INFORMATION FOR SEQ ID NO:1374:

(i) SEQUENCE CHARACTERISTICS:
                (A) LENGTH: 38 base pairs
                (B) TYPE: nucleic acid
                (C) STRANDEDNESS: single (D) TOPOLOGY: linear (xi) SEQUENCE DESCRIPTION: SEQ ID NO:1374:

UCGCUGUUCU GAUGAGGCCG AAAGGCCGAA ACGGAGGA                38

(2) INFORMATION FOR SEQ ID NO:1375:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1375:

UCCUCCGUCA ACAGCGA (2) INFORMATION FOR SEQ ID NO:1376:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1376:

AAUAGGGACU GAUGAGGCCG AAAGGCCGAA AUUCGCUG                38

(2) INFORMATION FOR SEQ ID NO:1377:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1377:

CAGCGAAUAU CCCUAUU                17

(2) INFORMATION FOR SEQ ID NO:1378:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1378:

GUAAUAGGCU GAUGAGGCCG AAAGGCCGAA AUAUUCGC                38

(2) INFORMATION FOR SEQ ID NO:1379:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1379:

GCGAAUAUCC CUAUUAC                17

(2) INFORMATION FOR SEQ ID NO:1380:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1380:

UGUGGUAACU GAUGAGGCCG AAAGGCCGAA AGGGAUAU    38

( 2 ) INFORMATION FOR SEQ ID NO:1381:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1381:

AUAUCCCUAU UACCACA    17

( 2 ) INFORMATION FOR SEQ ID NO:1382:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1382:

GAUGUGGUCU GAUGAGGCCG AAAGGCCGAA AUAGGGAU    38

( 2 ) INFORMATION FOR SEQ ID NO:1383:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1383:

AUCCCUAUUA CCACAUC    17

( 2 ) INFORMATION FOR SEQ ID NO:1384:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1384:

CGAUGUGGCU GAUGAGGCCG AAAGGCCGAA AAUAGGGA    38

( 2 ) INFORMATION FOR SEQ ID NO:1385:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1385:

UCCCUAUUAC CACAUCG    17

( 2 ) INFORMATION FOR SEQ ID NO:1386:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1386:
    GCUUCGGCCU GAUGAGGCCG AAAGGCCGAA AUGUGGUA ( 2 ) INFORMATION FOR SEQ ID NO:1387:

( i ) SEQUENCE CHARACTERISTICS:
　　　　( A ) LENGTH: 17 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1387:

UACCACAUCG CCGAAGC　　　　　　　　　　　　　　　　　　　　　　　　　17

( 2 ) INFORMATION FOR SEQ ID NO:1388:

( i ) SEQUENCE CHARACTERISTICS:
　　　　( A ) LENGTH: 38 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1388:

UGACUGGACU GAUGAGGCCG AAAGGCCGAA AUGUUUUG　　　　　　　　　　　　　38

( 2 ) INFORMATION FOR SEQ ID NO:1389:

( i ) SEQUENCE CHARACTERISTICS:
　　　　( A ) LENGTH: 17 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1389:

CAAAACAUCU CCAGUCA　　　　　　　　　　　　　　　　　　　　　　　　　17

( 2 ) INFORMATION FOR SEQ ID NO:1390:

( i ) SEQUENCE CHARACTERISTICS:
　　　　( A ) LENGTH: 38 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1390:

CGUGACUGCU GAUGAGGCCG AAAGGCCGAA AGAUGUUU　　　　　　　　　　　　　38

( 2 ) INFORMATION FOR SEQ ID NO:1391:

( i ) SEQUENCE CHARACTERISTICS:
　　　　( A ) LENGTH: 17 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1391:

AAACAUCUCC AGUCACG　　　　　　　　　　　　　　　　　　　　　　　　　17

( 2 ) INFORMATION FOR SEQ ID NO:1392:

( i ) SEQUENCE CHARACTERISTICS:
　　　　( A ) LENGTH: 38 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1392:

GGGAACGUCU GAUGAGGCCG AAAGGCCGAA ACUGGAGA　　　　　　　　　　　　　38

( 2 ) INFORMATION FOR SEQ ID NO:1393:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1393:

UCUCCAGUCA CGUUCCC 17

( 2 ) INFORMATION FOR SEQ ID NO:1394:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1394:

GGAUAGGGCU GAUGAGGCCG AAAGGCCGAA ACGUGACU 38

( 2 ) INFORMATION FOR SEQ ID NO:1395:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1395:

AGUCACGUUC CCUAUCC 17

( 2 ) INFORMATION FOR SEQ ID NO:1396:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1396:

AGGAUAGGCU GAUGAGGCCG AAAGGCCGAA AACGUGAC 38

( 2 ) INFORMATION FOR SEQ ID NO:1397:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1397:
GUCACGUUCC CUAUCCU ( 2 ) INFORMATION FOR SEQ ID NO:1398:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1398:

CGACAGGACU GAUGAGGCCG AAAGGCCGAA AGGGAACG 38

( 2 ) INFORMATION FOR SEQ ID NO:1399:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1399:

CGUUCCCUAU CCUGUCG  17

( 2 ) INFORMATION FOR SEQ ID NO:1400:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1400:

UGCGACAGCU GAUGAGGCCG AAAGGCCGAA AUAGGGAA  38

( 2 ) INFORMATION FOR SEQ ID NO:1401:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1401:

UUCCCUAUCC UGUCGCA  17

( 2 ) INFORMATION FOR SEQ ID NO:1402:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1402:

UGCAAUGCCU GAUGAGGCCG AAAGGCCGAA ACAGGAUA  38

( 2 ) INFORMATION FOR SEQ ID NO:1403:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1403:

UAUCCUGUCG CAUUGCA  17

( 2 ) INFORMATION FOR SEQ ID NO:1404:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1404:

UAACAUGCCU GAUGAGGCCG AAAGGCCGAA AUGCGACA  38

( 2 ) INFORMATION FOR SEQ ID NO:1405:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1405:

UGUCGCAUUG CAUGUUA 17

( 2 ) INFORMATION FOR SEQ ID NO:1406:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1406:

ACUAUAUUCU GAUGAGGCCG AAAGGCCGAA ACAUGCAA 38

( 2 ) INFORMATION FOR SEQ ID NO:1407:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1407:

UUGCAUGUUA AUAUAGU 17

( 2 ) INFORMATION FOR SEQ ID NO:1408:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1408:

GACUAUAUCU GAUGAGGCCG AAAGGCCGAA AACAUGCA ( 2 ) INFORMATION FOR SEQ ID NO:1409:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1409:

UGCAUGUUAA UAUAGUC 17

( 2 ) INFORMATION FOR SEQ ID NO:1410:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1410:

GUUGACUACU GAUGAGGCCG AAAGGCCGAA AUUAACAU 38

( 2 ) INFORMATION FOR SEQ ID NO:1411:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1411:

AUGUUAAUAU AGUCAAC 17

( 2 ) INFORMATION FOR SEQ ID NO:1412:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1412:

ACGUUGACCU GAUGAGGCCG AAAGGCCGAA AUAUUAAC        38

( 2 ) INFORMATION FOR SEQ ID NO:1413:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1413:

GUUAAUAUAG UCAACGU        17

( 2 ) INFORMATION FOR SEQ ID NO:1414:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1414:

GGGACGUUCU GAUGAGGCCG AAAGGCCGAA ACUAUAUU        38

( 2 ) INFORMATION FOR SEQ ID NO:1415:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1415:

AAUAUAGUCA ACGUCCC        17

( 2 ) INFORMATION FOR SEQ ID NO:1416:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1416:

GGCUGAGGCU GAUGAGGCCG AAAGGCCGAA ACGUUGAC        38

( 2 ) INFORMATION FOR SEQ ID NO:1417:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1417:

GUCAACGUCC CUCAGCC        17

( 2 ) INFORMATION FOR SEQ ID NO:1418:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1418:

AGCCGGCUCU GAUGAGGCCG AAAGGCCGAA AGGGACGU      38

( 2 ) INFORMATION FOR SEQ ID NO:1419:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1419:

ACGUCCCUCA GCCGGCU      17

( 2 ) INFORMATION FOR SEQ ID NO:1420:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1420:

UGUCUCUGCU GAUGAGGCCG AAAGGCCGAA AUGGCUGC      38

( 2 ) INFORMATION FOR SEQ ID NO:1421:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1421:

GCAGCCAUCC AGAGACA      17

( 2 ) INFORMATION FOR SEQ ID NO:1422:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1422:

CGUCGUUACU GAUGAGGCCG AAAGGCCGAA AGUGUCUC      38

( 2 ) INFORMATION FOR SEQ ID NO:1423:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1423:

GAGACACUAU AACGACG      17

( 2 ) INFORMATION FOR SEQ ID NO:1424:

( i ) SEQUENCE CHARACTERISTICS:
        ( A ) LENGTH: 38 base pairs
        ( B ) TYPE: nucleic acid
        ( C ) STRANDEDNESS: single (D) TOPOLOGY: linear (x i) SEQUENCE DESCRIPTION: SEQ ID NO:1424:

UUCGUCGUCU GAUGAGGCCG AAAGGCCGAA AUAGUGUC                    38

(2) INFORMATION FOR SEQ ID NO:1425:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1425:

GACACUAUAA CGACGAA                                           17

(2) INFORMATION FOR SEQ ID NO:1426:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1426:

AGCUCCUUCU GAUGAGGCCG AAAGGCCGAA AUUCGCUU                    38

(2) INFORMATION FOR SEQ ID NO:1427:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1427:

AAGCGAAUAA AGGAGCU                                           17

(2) INFORMATION FOR SEQ ID NO:1428:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1428:

UCAGGAGCCU GAUGAGGCCG AAAGGCCGAA ACUCCAGC                    38

(2) INFORMATION FOR SEQ ID NO:1429:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1429:

GCUGGAGUUG CUCCUGA                                           17

(2) INFORMATION FOR SEQ ID NO:1430:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:1430:

GACAUCAGCU GAUGAGGCCG AAAGGCCGAA AGCAACUC ( 2 ) INFORMATION FOR SEQ ID NO:1431:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1431:

GAGUUGCUCC UGAUGUC 17

( 2 ) INFORMATION FOR SEQ ID NO:1432:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1432:

UCUCUGUUCU GAUGAGGCCG AAAGGCCGAA ACAUCAGG 38

( 2 ) INFORMATION FOR SEQ ID NO:1433:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1433:

CCUGAUGUCA ACAGAGA 17

( 2 ) INFORMATION FOR SEQ ID NO:1434:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1434:

GUGUUGGUCU GAUGAGGCCG AAAGGCCGAA AUGCCUGC 38

( 2 ) INFORMATION FOR SEQ ID NO:1435:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1435:

GCAGGCAUUA CCAACAC 17

( 2 ) INFORMATION FOR SEQ ID NO:1436:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1436:

UGUGUUGGCU GAUGAGGCCG AAAGGCCGAA AAUGCCUG 38

( 2 ) INFORMATION FOR SEQ ID NO:1437:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1437:

CAGGCAUUAC CAACACA 17

( 2 ) INFORMATION FOR SEQ ID NO:1438:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1438:

GUAGCUGCCU GAUGAGGCCG AAAGGCCGAA AGUGUGGU 38

( 2 ) INFORMATION FOR SEQ ID NO:1439:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1439:

ACCACACUUG CAGCUAC 17

( 2 ) INFORMATION FOR SEQ ID NO:1440:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1440:

ACCCGGGGCU GAUGAGGCCG AAAGGCCGAA AGCUGCAA 38

( 2 ) INFORMATION FOR SEQ ID NO:1441:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1441:
UUGCAGCUAC CCCGGGU ( 2 ) INFORMATION FOR SEQ ID NO:1442:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1442:

CCACAAUGCU GAUGAGGCCG AAAGGCCGAA AGGUGCUG 38

( 2 ) INFORMATION FOR SEQ ID NO:1443:

( i ) SEQUENCE CHARACTERISTICS:

```
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1443:

CAGCACCUCC AUUGUGG                                                          17

( 2 ) INFORMATION FOR SEQ ID NO:1444:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1444:

UGGUCCACCU GAUGAGGCCG AAAGGCCGAA AUGGAGGU                                   38

( 2 ) INFORMATION FOR SEQ ID NO:1445:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1445:

ACCUCCAUUG UGGACCA                                                          17

( 2 ) INFORMATION FOR SEQ ID NO:1446:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1446:

AUCCCAUCU GAUGAGGCCG AAAGGCCGAA AGGUCUGG                                    38

( 2 ) INFORMATION FOR SEQ ID NO:1447:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1447:

CCAGACCUCA UGGGGAU                                                          17

( 2 ) INFORMATION FOR SEQ ID NO:1448:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1448:

AGGUGCACCU GAUGAGGCCG AAAGGCCGAA AUCCCCAU                                   38

( 2 ) INFORMATION FOR SEQ ID NO:1449:

( i ) SEQUENCE CHARACTERISTICS:
            ( A ) LENGTH: 17 base pairs
            ( B ) TYPE: nucleic acid
```

(C) STRANDEDNESS: single
(D) TOPOLOGY: linear (xi) SEQUENCE DESCRIPTION: SEQ ID NO:1449:

AUGGGGAUAG UGCACCU                                                                                      17

(2) INFORMATION FOR SEQ ID NO:1450:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1450:

AAACAGGACU GAUGAGGCCG AAAGGCCGAA ACAGGUGC                                                                 38

(2) INFORMATION FOR SEQ ID NO:1451:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1451:

GCACCUGUUU CCUGUUU                                                                                       17

(2) INFORMATION FOR SEQ ID NO:1452:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1452:
         CAAACAGGCU GAUGAGGCCG AAAGGCCGAA AACAGGUG (2) INFORMATION FOR SEQ ID NO:1453:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1453:

CACCUGUUUC CUGUUUG                                                                                       17

(2) INFORMATION FOR SEQ ID NO:1454:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1454:

CCAAACAGCU GAUGAGGCCG AAAGGCCGAA AAACAGGU                                                                 38

(2) INFORMATION FOR SEQ ID NO:1455:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1455:

ACCUGUUUCC UGUUUGG                                                              17

( 2 ) INFORMATION FOR SEQ ID NO:1456:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1456:

UUCUCCCACU GAUGAGGCCG AAAGGCCGAA ACAGGAAA                                       38

( 2 ) INFORMATION FOR SEQ ID NO:1457:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1457:

UUUCCUGUUU GGGAGAA                                                              17

( 2 ) INFORMATION FOR SEQ ID NO:1458:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1458:

GUUCUCCCCU GAUGAGGCCG AAAGGCCGAA AACAGGAA                                       38

( 2 ) INFORMATION FOR SEQ ID NO:1459:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1459:

UUCCUGUUUG GGAGAAC                                                              17

( 2 ) INFORMATION FOR SEQ ID NO:1460:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1460:

CAGGCAGACU GAUGAGGCCG AAAGGCCGAA AUGGGGUG                                       38

( 2 ) INFORMATION FOR SEQ ID NO:1461:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1461:

CACCCCAUCU CUGCCUG                                                              17

( 2 ) INFORMATION FOR SEQ ID NO:1462:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1462:

UGCAGGCACU GAUGAGGCCG AAAGGCCGAA AGAUGGGG    38

( 2 ) INFORMATION FOR SEQ ID NO:1463:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1463:

CCCCAUCUCU GCCUGCA ( 2 ) INFORMATION FOR SEQ ID NO:1464:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1464:

GGAGCCGGCU GAUGAGGCCG AAAGGCCGAA AUCUGCAG    38

( 2 ) INFORMATION FOR SEQ ID NO:1465:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1465:

CUGCAGAUCC CGGCUCC    17

( 2 ) INFORMATION FOR SEQ ID NO:1466:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1466:

CAGGUAGGCU GAUGAGGCCG AAAGGCCGAA AGCCGGGA    38

( 2 ) INFORMATION FOR SEQ ID NO:1467:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1467:

UCCCGGCUCC CUACCUG    17

( 2 ) INFORMATION FOR SEQ ID NO:1468:

( i ) SEQUENCE CHARACTERISTICS:
     ( A ) LENGTH: 38 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:1468:

UCUUCAGGCU GAUGAGGCCG AAAGGCCGAA AGGGAGCC                    38

( 2 ) INFORMATION FOR SEQ ID NO:1469:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1469:

GGCUCCCUAC CUGAAGA                                           17

( 2 ) INFORMATION FOR SEQ ID NO:1470:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1470:

UUGCUGGUCU GAUGAGGCCG AAAGGCCGAA AGGCACUU                    38

( 2 ) INFORMATION FOR SEQ ID NO:1471:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1471:

AAGUGCCUCA CCAGCAA                                           17

( 2 ) INFORMATION FOR SEQ ID NO:1472:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1472:

UGGUGGACCU GAUGAGGCCG AAAGGCCGAA AUCAUGCA                    38

( 2 ) INFORMATION FOR SEQ ID NO:1473:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1473:

UGCAUGAUCG UCCACCA                                           17

( 2 ) INFORMATION FOR SEQ ID NO:1474:

( i ) SEQUENCE CHARACTERISTICS:
         ( A ) LENGTH: 38 base pairs ( B ) TYPE: nucleic acid
        ( C ) STRANDEDNESS: single
        ( D ) TOPOLOGY: linear ( x i ) SEQUENCE DESCRIPTION: SEQ ID NO:1474:

CCCUGGUGCU GAUGAGGCCG AAAGGCCGAA ACGAUCAU ( 2 ) INFORMATION FOR SEQ ID NO:1475:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1475:

AUGAUCGUCC ACCAGGG                                                                 17

( 2 ) INFORMATION FOR SEQ ID NO:1476:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1476:

UUGUCCAGCU GAUGAGGCCG AAAGGCCGAA AUGGUGCC                                           38

( 2 ) INFORMATION FOR SEQ ID NO:1477:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1477:

GGCACCAUUC UGGACAA                                                                 17

( 2 ) INFORMATION FOR SEQ ID NO:1478:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1478:

AUUGUCCACU GAUGAGGCCG AAAGGCCGAA AAUGGUGC                                           38

( 2 ) INFORMATION FOR SEQ ID NO:1479:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1479:

GCACCAUUCU GGACAAU                                                                 17

( 2 ) INFORMATION FOR SEQ ID NO:1480:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1480:

AGGUUCUUCU GAUGAGGCCG AAAGGCCGAA ACAUUGUC 38

( 2 ) INFORMATION FOR SEQ ID NO:1481:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1481:

GACAAUGUUA AGAACCU 17

( 2 ) INFORMATION FOR SEQ ID NO:1482:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1482:

GAGGUUCUCU GAUGAGGCCG AAAGGCCGAA AACAUUGU 38

( 2 ) INFORMATION FOR SEQ ID NO:1483:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1483:

ACAAUGUUAA GAACCUC 17

( 2 ) INFORMATION FOR SEQ ID NO:1484:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1484:

AAUUCUAACU GAUGAGGCCG AAAGGCCGAA AGGUUCUU 38

( 2 ) INFORMATION FOR SEQ ID NO:1485:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1485:
        AAGAACCUCU UAGAAUU ( 2 ) INFORMATION FOR SEQ ID NO:1486:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1486:

CAAAUUCUCU GAUGAGGCCG AAAGGCCGAA AGAGGUUC 38

( 2 ) INFORMATION FOR SEQ ID NO:1487:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1487:

GAACCUCUUA GAAUUUG        17

( 2 ) INFORMATION FOR SEQ ID NO:1488:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1488:

GCAAAUUCCU GAUGAGGCCG AAAGGCCGAA AAGAGGUU        38

( 2 ) INFORMATION FOR SEQ ID NO:1489:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1489:

AACCUCUUAG AAUUUGC        17

( 2 ) INFORMATION FOR SEQ ID NO:1490:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1490:

UUUCUGCACU GAUGAGGCCG AAAGGCCGAA AUUCUAAG        38

( 2 ) INFORMATION FOR SEQ ID NO:1491:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1491:

CUUAGAAUUU GCAGAAA        17

( 2 ) INFORMATION FOR SEQ ID NO:1492:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1492:

GUUUCUGCCU GAUGAGGCCG AAAGGCCGAA AAUUCUAA        38

( 2 ) INFORMATION FOR SEQ ID NO:1493:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1493:

UUAGAAUUUG CAGAAAC      17

( 2 ) INFORMATION FOR SEQ ID NO:1494:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1494:

AUAAACUGCU GAUGAGGCCG AAAGGCCGAA AGUGUUUC      38

( 2 ) INFORMATION FOR SEQ ID NO:1495:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1495:

GAAACACUCC AGUUUAU      17

( 2 ) INFORMATION FOR SEQ ID NO:1496:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1496:

AAUCUAUACU GAUGAGGCCG AAAGGCCGAA ACUGGAGU ( 2 ) INFORMATION FOR SEQ ID NO:1497:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1497:

ACUCCAGUUU AUAGAUU      17

( 2 ) INFORMATION FOR SEQ ID NO:1498:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1498:

GAAUCUAUCU GAUGAGGCCG AAAGGCCGAA AACUGGAG      38

( 2 ) INFORMATION FOR SEQ ID NO:1499:

( i ) SEQUENCE CHARACTERISTICS:
    ( A ) LENGTH: 17 base pairs
    ( B ) TYPE: nucleic acid ( C ) STRANDEDNESS: single
        ( D ) TOPOLOGY: linear ( x i ) SEQUENCE DESCRIPTION: SEQ ID NO:1499:

CUCCAGUUUA UAGAUUC                                                                                          17

( 2 ) INFORMATION FOR SEQ ID NO:1500:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1500:

AGAAUCUACU GAUGAGGCCG AAAGGCCGAA AAACUGGA                                                                    38

( 2 ) INFORMATION FOR SEQ ID NO:1501:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1501:

UCCAGUUUAU AGAUUCU                                                                                          17

( 2 ) INFORMATION FOR SEQ ID NO:1502:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1502:

AAAGAAUCCU GAUGAGGCCG AAAGGCCGAA AUAAACUG                                                                    38

( 2 ) INFORMATION FOR SEQ ID NO:1503:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1503:

CAGUUUAUAG AUUCUUU                                                                                          17

( 2 ) INFORMATION FOR SEQ ID NO:1504:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1504:

CAAGAAAGCU GAUGAGGCCG AAAGGCCGAA AUCUAUAA                                                                    38

( 2 ) INFORMATION FOR SEQ ID NO:1505:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1505:

UUAUAGAUUC UUUCUUG                                                                                      17

( 2 ) INFORMATION FOR SEQ ID NO:1506:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1506:

UCAAGAAACU GAUGAGGCCG AAAGGCCGAA AAUCUAUA                                                                38

( 2 ) INFORMATION FOR SEQ ID NO:1507:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1507:

UAUAGAUUCU UUCUUGA ( 2 ) INFORMATION FOR SEQ ID NO:1508:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1508:

GUUCAAGACU GAUGAGGCCG AAAGGCCGAA AGAAUCUA                                                                38

( 2 ) INFORMATION FOR SEQ ID NO:1509:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1509:

UAGAUUCUUU CUUGAAC                                                                                      17

( 2 ) INFORMATION FOR SEQ ID NO:1510:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1510:

UGUUCAAGCU GAUGAGGCCG AAAGGCCGAA AAGAAUCU                                                                38

( 2 ) INFORMATION FOR SEQ ID NO:1511:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1511:

AGAUUCUUUC UUGAACA                                                                                      17

( 2 ) INFORMATION FOR SEQ ID NO:1512:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1512:

GUGUUCAACU GAUGAGGCCG AAAGGCCGAA AAAGAAUC      38

( 2 ) INFORMATION FOR SEQ ID NO:1513:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1513:

GAUUCUUUCU UGAACAC      17

( 2 ) INFORMATION FOR SEQ ID NO:1514:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1514:

AAGUGUUCCU GAUGAGGCCG AAAGGCCGAA AGAAAGAA      38

( 2 ) INFORMATION FOR SEQ ID NO:1515:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1515:

UUCUUUCUUG AACACUU      17

( 2 ) INFORMATION FOR SEQ ID NO:1516:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1516:

GUUGCUGGCU GAUGAGGCCG AAAGGCCGAA AGUGUUCA      38

( 2 ) INFORMATION FOR SEQ ID NO:1517:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1517:

UGAACACUUC CAGCAAC      17

( 2 ) INFORMATION FOR SEQ ID NO:1518:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1518:
        GGUUGCUGCU GAUGAGGCCG AAAGGCCGAA AAGUGUUC ( 2 ) INFORMATION FOR SEQ ID NO:1519:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1519:

GAACACUUCC AGCAACC                            17

( 2 ) INFORMATION FOR SEQ ID NO:1520:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1520:

CUAAGCCCCU GAUGAGGCCG AAAGGCCGAA AGUUUUCA        38

( 2 ) INFORMATION FOR SEQ ID NO:1521:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1521:

UGAAAACUCG GGCUUAG                            17

( 2 ) INFORMATION FOR SEQ ID NO:1522:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1522:

GUGCAUCUCU GAUGAGGCCG AAAGGCCGAA AGCCCGAG        38

( 2 ) INFORMATION FOR SEQ ID NO:1523:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1523:

CUCGGGCUUA GAUGCAC                            17

( 2 ) INFORMATION FOR SEQ ID NO:1524:

( i ) SEQUENCE CHARACTERISTICS:
        ( A ) LENGTH: 38 base pairs (B) TYPE: nucleic acid
        (C) STRANDEDNESS: single
        (D) TOPOLOGY: linear (xi) SEQUENCE DESCRIPTION: SEQ ID NO:1524:

GGUGCAUCCU GAUGAGGCCG AAAGGCCGAA AAGCCCGA 38

(2) INFORMATION FOR SEQ ID NO:1525:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1525:

UCGGGCUUAG AUGCACC 17

(2) INFORMATION FOR SEQ ID NO:1526:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1526:

GGGUAAGGCU GAUGAGGCCG AAAGGCCGAA AGGUGCAU 38

(2) INFORMATION FOR SEQ ID NO:1527:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1527:

AUGCACCUAC CUUACCC 17

(2) INFORMATION FOR SEQ ID NO:1528:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1528:

UGGAGGGUCU GAUGAGGCCG AAAGGCCGAA AGGUAGGU 38

(2) INFORMATION FOR SEQ ID NO:1529:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1529:
                ACCUACCUUA CCCUCCA (2) INFORMATION FOR SEQ ID NO:1530:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:1530:

GUGGAGGGCU GAUGAGGCCG AAAGGCCGAA AAGGUAGG 38

( 2 ) INFORMATION FOR SEQ ID NO:1531:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1531:

CCUACCUUAC CCUCCAC 17

( 2 ) INFORMATION FOR SEQ ID NO:1532:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1532:

GAGGAGUGCU GAUGAGGCCG AAAGGCCGAA AGGGUAAG 38

( 2 ) INFORMATION FOR SEQ ID NO:1533:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1533:

CUUACCCUCC ACUCCUC 17

( 2 ) INFORMATION FOR SEQ ID NO:1534:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1534:

AAUGAGAGCU GAUGAGGCCG AAAGGCCGAA AGUGGAGG 38

( 2 ) INFORMATION FOR SEQ ID NO:1535:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1535:

CCUCCACUCC UCUCAUU 17

( 2 ) INFORMATION FOR SEQ ID NO:1536:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1536:

ACCAAUGACU GAUGAGGCCG AAAGGCCGAA AGGAGUGG    38

( 2 ) INFORMATION FOR SEQ ID NO:1537:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1537:

CCACUCCUCU CAUUGGU    17

( 2 ) INFORMATION FOR SEQ ID NO:1538:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1538:

UGACCAAUCU GAUGAGGCCG AAAGGCCGAA AGAGGAGU    38

( 2 ) INFORMATION FOR SEQ ID NO:1539:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1539:

ACUCCUCUCA UUGGUCA    17

( 2 ) INFORMATION FOR SEQ ID NO:1540:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1540:
UUGUGACCCU GAUGAGGCCG AAAGGCCGAA AUGAGAGG ( 2 ) INFORMATION FOR SEQ ID NO:1541:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1541:

CCUCUCAUUG GUCACAA    17

( 2 ) INFORMATION FOR SEQ ID NO:1542:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1542:

CAGUUUGUCU GAUGAGGCCG AAAGGCCGAA ACCAAUGA    38

( 2 ) INFORMATION FOR SEQ ID NO:1543:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1543:

UCAUUGGUCA CAAACUG 17

( 2 ) INFORMATION FOR SEQ ID NO:1544:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1544:

CUGGUCUCCU GAUGAGGCCG AAAGGCGAA ACAUGGUG 38

( 2 ) INFORMATION FOR SEQ ID NO:1545:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1545:

CACCAUGUCG AGACCAG 17

( 2 ) INFORMATION FOR SEQ ID NO:1546:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1546:

AAAGAUGGCU GAUGAGGCCG AAAGGCCGAA AUUUUCCU 38

( 2 ) INFORMATION FOR SEQ ID NO:1547:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1547:

AGGAAAAUUC CAUCUUU 17

( 2 ) INFORMATION FOR SEQ ID NO:1548:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1548:

UAAAGAUGCU GAUGAGGCCG AAAGGCCGAA AAUUUUCC 38

( 2 ) INFORMATION FOR SEQ ID NO:1549:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1549:

GGAAAAUUCC AUCUUUA 17

( 2 ) INFORMATION FOR SEQ ID NO:1550:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1550:

GUUCUAAACU GAUGAGGCCG AAAGGCCGAA AUGGAAUU 38

( 2 ) INFORMATION FOR SEQ ID NO:1551:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1551:

AAUUCCAUCU UUAGAAC ( 2 ) INFORMATION FOR SEQ ID NO:1552:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1552:

GAGUUCUACU GAUGAGGCCG AAAGGCCGAA AGAUGGAA 38

( 2 ) INFORMATION FOR SEQ ID NO:1553:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1553:

UUCCAUCUUU AGAACUC 17

( 2 ) INFORMATION FOR SEQ ID NO:1554:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1554:

GGAGUUCUCU GAUGAGGCCG AAAGGCCGAA AAGAUGGA 38

( 2 ) INFORMATION FOR SEQ ID NO:1555:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1555:

UCCAUCUUUA GAACUCC                                                                17

( 2 ) INFORMATION FOR SEQ ID NO:1556:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1556:

UGGAGUUCCU GAUGAGGCCG AAAGGCCGAA AAAGAUGG                                          38

( 2 ) INFORMATION FOR SEQ ID NO:1557:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1557:

CCAUCUUUAG AACUCCA                                                                17

( 2 ) INFORMATION FOR SEQ ID NO:1558:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1558:

GAUAGCUGCU GAUGAGGCCG AAAGGCCGAA AGUUCUAA                                          38

( 2 ) INFORMATION FOR SEQ ID NO:1559:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1559:

UUAGAACUCC AGCUAUC                                                                17

( 2 ) INFORMATION FOR SEQ ID NO:1560:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1560:

CCUUUUGACU GAUGAGGCCG AAAGGCCGAA AGCUGGAG                                          38

( 2 ) INFORMATION FOR SEQ ID NO:1561:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1561:

CUCCAGCUAU CAAAAGG                                                                                                        17

( 2 ) INFORMATION FOR SEQ ID NO:1562:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1562:

GACCUUUUCU GAUGAGGCCG AAAGGCCGAA AUAGCUGG ( 2 ) INFORMATION FOR SEQ ID NO:1563:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1563:

CCAGCUAUCA AAAGGUC                                                                                                        17

( 2 ) INFORMATION FOR SEQ ID NO:1564:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1564:

CGAGGAUUCU GAUGAGGCCG AAAGGCCGAA ACCUUUUG                                                                                  38

( 2 ) INFORMATION FOR SEQ ID NO:1565:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1565:

CAAAAGGUCA AUCCUCG                                                                                                        17

( 2 ) INFORMATION FOR SEQ ID NO:1566:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1566:

CUUUCGAGCU GAUGAGGCCG AAAGGCCGAA AUUGACCU                                                                                  38

( 2 ) INFORMATION FOR SEQ ID NO:1567:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1567:

AGGUCAAUCC UCGAAAG                                                                                                        17

( 2 ) INFORMATION FOR SEQ ID NO:1568:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1568:

GAGCUUUCCU GAUGAGGCCG AAAGGCCGAA AGGAUUGA　　　　　　　　　　38

( 2 ) INFORMATION FOR SEQ ID NO:1569:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1569:

UCAAUCCUCG AAAGCUC　　　　　　　　　　17

( 2 ) INFORMATION FOR SEQ ID NO:1570:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1570:

UUCGAGGACU GAUGAGGCCG AAAGGCCGAA AGCUUUCG　　　　　　　　　　38

( 2 ) INFORMATION FOR SEQ ID NO:1571:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1571:

CGAAAGCUCU CCUCGAA　　　　　　　　　　17

( 2 ) INFORMATION FOR SEQ ID NO:1572:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1572:

AGUUCGAGCU GAUGAGGCCG AAAGGCCGAA AGAGCUUU　　　　　　　　　　38

( 2 ) INFORMATION FOR SEQ ID NO:1573:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1573:
        AAAGCUCUCC UCGAACU ( 2 ) INFORMATION FOR SEQ ID NO:1574:

( i ) SEQUENCE CHARACTERISTICS:
        ( A ) LENGTH: 38 base pairs ( B ) TYPE: nucleic acid
( C ) STRANDEDNESS: single
( D ) TOPOLOGY: linear ( x i ) SEQUENCE DESCRIPTION: SEQ ID NO:1574:

GGGAGUUCCU GAUGAGGCCG AAAGGCCGAA AGGAGAGC 38

( 2 ) INFORMATION FOR SEQ ID NO:1575:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1575:

GCUCCUCG AACUCCC 17

( 2 ) INFORMATION FOR SEQ ID NO:1576:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1576:

UGGUGUGGCU GAUGAGGCCG AAAGGCCGAA AGUUCGAG 38

( 2 ) INFORMATION FOR SEQ ID NO:1577:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1577:

CUCGAACUCC CACACCA 17

( 2 ) INFORMATION FOR SEQ ID NO:1578:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1578:

CAUGUUUGCU GAUGAGGCCG AAAGGCCGAA AUGGUGUG 38

( 2 ) INFORMATION FOR SEQ ID NO:1579:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1579:

CACACCAUUC AAACAUG 17

( 2 ) INFORMATION FOR SEQ ID NO:1580:

( i ) SEQUENCE CHARACTERISTICS:
( A ) LENGTH: 38 base pairs
( B ) TYPE: nucleic acid
( C ) STRANDEDNESS: single -continued ( D ) TOPOLOGY: linear ( x i ) SEQUENCE DESCRIPTION: SEQ ID NO:1580:

GCAUGUUUCU GAUGAGGCCG AAAGGCCGAA AAUGGUGU                    38

( 2 ) INFORMATION FOR SEQ ID NO:1581:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1581:

ACACCAUUCA AACAUGC                    17

( 2 ) INFORMATION FOR SEQ ID NO:1582:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1582:

UGAGCUGCCU GAUGAGGCCG AAAGGCCGAA AGGGCAUG                    38

( 2 ) INFORMATION FOR SEQ ID NO:1583:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1583:

CAUGCCCUUG CAGCUCA                    17

( 2 ) INFORMATION FOR SEQ ID NO:1584:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1584:
AAUUUCUUCU GAUGAGGCCG AAAGGCCGAA AGCUGCAA ( 2 ) INFORMATION FOR SEQ ID NO:1585:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1585:

UUGCAGCUCA AGAAAUU                    17

( 2 ) INFORMATION FOR SEQ ID NO:1586:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1586:

CCGUAUUUCU GAUGAGGCCG AAAGGCCGAA AUUUCUUG                    38

( 2 ) INFORMATION FOR SEQ ID NO:1587:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1587:

CAAGAAAUUA AAUACGG                                            17

( 2 ) INFORMATION FOR SEQ ID NO:1588:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1588:

ACCGUAUUCU GAUGAGGCCG AAAGGCCGAA AAUUUCUU                     38

( 2 ) INFORMATION FOR SEQ ID NO:1589:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1589:

AAGAAAUUAA AUACGGU                                            17

( 2 ) INFORMATION FOR SEQ ID NO:1590:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1590:

GGGGACCGCU GAUGAGGCCG AAAGGCCGAA AUUUAAUU                     38

( 2 ) INFORMATION FOR SEQ ID NO:1591:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1591:

AAUUAAAUAC GGUCCCC                                            17

( 2 ) INFORMATION FOR SEQ ID NO:1592:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1592:

CUUCAGGGCU GAUGAGGCCG AAAGGCCGAA ACCGUAUU                     38

(2) INFORMATION FOR SEQ ID NO:1593:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1593:

AAUACGGUCC CCUGAAG 17

(2) INFORMATION FOR SEQ ID NO:1594:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1594:

GUCUGAGGCU GAUGAGGCCG AAAGGCCGAA AGCAUCUU 38

(2) INFORMATION FOR SEQ ID NO:1595:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1595:

AAGAUGCUAC CUCAGAC (2) INFORMATION FOR SEQ ID NO:1596:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1596:

GGGGGUCUCU GAUGAGGCCG AAAGGCCGAA AGGUAGCA 38

(2) INFORMATION FOR SEQ ID NO:1597:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1597:

UGCUACCUCA GACCCCC 17

(2) INFORMATION FOR SEQ ID NO:1598:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1598:

CUGCAUGGCU GAUGAGGCCG AAAGGCCGAA AGGGGGUC 38

(2) INFORMATION FOR SEQ ID NO:1599:

(i) SEQUENCE CHARACTERISTICS:

(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1599:

GACCCCUCC CAUGCAG                                                                  17

(2) INFORMATION FOR SEQ ID NO:1600:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1600:

ACAUCUUGCU GAUGAGGCCG AAAGGCCGAA AGGUCCUC                                           38

(2) INFORMATION FOR SEQ ID NO:1601:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1601:

GAGGACCUAC AAGAUGU                                                                 17

(2) INFORMATION FOR SEQ ID NO:1602:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1602:

UCCCGCUUCU GAUGAGGCCG AAAGGCCGAA AUCACAUC                                           38

(2) INFORMATION FOR SEQ ID NO:1603:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1603:

GAUGUGAUUA AGCGGGA                                                                 17

(2) INFORMATION FOR SEQ ID NO:1604:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1604:

UUCCCGCUCU GAUGAGGCCG AAAGGCCGAA AAUCACAU                                           38

(2) INFORMATION FOR SEQ ID NO:1605:

(i) SEQUENCE CHARACTERISTICS:
(A) LENGTH: 17 base pairs
(B) TYPE: nucleic acid ( C ) STRANDEDNESS: single
        ( D ) TOPOLOGY: linear ( x i ) SEQUENCE DESCRIPTION: SEQ ID NO:1605:

AUGUGAUUAA GCGGGAA                                                                                    17

( 2 ) INFORMATION FOR SEQ ID NO:1606:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1606:
                    AUUCAUCCCU GAUGAGGCCG AAAGGCCGAA AUUCCCGC ( 2 ) INFORMATION FOR SEQ ID NO:1607:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1607:

GCGGGAAUCG GAUGAAU                                                                                    17

( 2 ) INFORMATION FOR SEQ ID NO:1608:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1608:

CAAUUCCACU GAUGAGGCCG AAAGGCCGAA AUUCAUCC                                                              38

( 2 ) INFORMATION FOR SEQ ID NO:1609:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1609:

GGAUGAAUCU GGAAUUG                                                                                    17

( 2 ) INFORMATION FOR SEQ ID NO:1610:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1610:

UCAGCAACCU GAUGAGGCCG AAAGGCCGAA AUUCCAGA                                                              38

( 2 ) INFORMATION FOR SEQ ID NO:1611:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1611:

UCUGGAAUUG UUGCUGA 17

(2) INFORMATION FOR SEQ ID NO:1612:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1612:

AACUCAGCCU GAUGAGGCCG AAAGGCCGAA ACAAUUCC 38

(2) INFORMATION FOR SEQ ID NO:1613:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1613:

GGAAUUGUUG CUGAGUU 17

(2) INFORMATION FOR SEQ ID NO:1614:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1614:

UCUCUUGACU GAUGAGGCCG AAAGGCCGAA ACUCAGCA 38

(2) INFORMATION FOR SEQ ID NO:1615:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1615:

UGCUGAGUUU CAAGAGA 17

(2) INFORMATION FOR SEQ ID NO:1616:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1616:

CUCUCUUGCU GAUGAGGCCG AAAGGCCGAA AACUCAGC 38

(2) INFORMATION FOR SEQ ID NO:1617:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1617:

GCUGAGUUUC AAGAGAG

-continued ( 2 ) INFORMATION FOR SEQ ID NO:1618:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1618:

ACUCUCUUCU GAUGAGGCCG AAAGGCCGAA AAACUCAG      38

( 2 ) INFORMATION FOR SEQ ID NO:1619:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1619:

CUGAGUUUCA AGAGAGU      17

( 2 ) INFORMATION FOR SEQ ID NO:1620:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1620:

UUUUCAGUCU GAUGAGGCCG AAAGGCCGAA ACGGUGGU      38

( 2 ) INFORMATION FOR SEQ ID NO:1621:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1621:

ACCACCGUUA CUGAAAA      17

( 2 ) INFORMATION FOR SEQ ID NO:1622:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1622:

UUUUUCAGCU GAUGAGGCCG AAAGGCCGAA AACGGUGG      38

( 2 ) INFORMATION FOR SEQ ID NO:1623:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1623:

CCACCGUUAC UGAAAAA      17

( 2 ) INFORMATION FOR SEQ ID NO:1624:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1624:

GCCUGCUUCU GAUGAGGCCG AAAGGCCGAA AUUUUUUU     38

( 2 ) INFORMATION FOR SEQ ID NO:1625:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1625:

AAAAAAAUCA AGCAGGC     17

( 2 ) INFORMATION FOR SEQ ID NO:1626:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1626:

CAGUUGGCCU GAUGAGGCCG AAAGGCCGAA ACUCCACC     38

( 2 ) INFORMATION FOR SEQ ID NO:1627:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1627:

GGUGGAGUCG CCAACUG     17

( 2 ) INFORMATION FOR SEQ ID NO:1628:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1628:
AGUUCCCCU GAUGAGGCCG AAAGGCCGAA AUUUCUCA ( 2 ) INFORMATION FOR SEQ ID NO:1629:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1629:

UGAGAAAUCG GGAAACU     17

( 2 ) INFORMATION FOR SEQ ID NO:1630:

( i ) SEQUENCE CHARACTERISTICS:
( A ) LENGTH: 38 base pairs
( B ) TYPE: nucleic acid
( C ) STRANDEDNESS: single ( D ) TOPOLOGY: linear ( x i ) SEQUENCE DESCRIPTION: SEQ ID NO:1630:

AGCAGAAGCU GAUGAGGCCG AAAGGCCGAA AGUUCCC 38

( 2 ) INFORMATION FOR SEQ ID NO:1631:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1631:

GGGAAACUUC UUCUGCU 17

( 2 ) INFORMATION FOR SEQ ID NO:1632:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1632:

GAGCAGAACU GAUGAGGCCG AAAGGCCGAA AAGUUCC 38

( 2 ) INFORMATION FOR SEQ ID NO:1633:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1633:

GGAAACUUCU UCUGCUC 17

( 2 ) INFORMATION FOR SEQ ID NO:1634:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1634:

UUGAGCAGCU GAUGAGGCCG AAAGGCCGAA AGAAGUUU 38

( 2 ) INFORMATION FOR SEQ ID NO:1635:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1635:

AAACUUCUUC UGCUCAA 17

( 2 ) INFORMATION FOR SEQ ID NO:1636:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1636:

UUUGAGCACU GAUGAGGCCG AAAGGCCGAA AAGAAGUU                              38

( 2 ) INFORMATION FOR SEQ ID NO:1637:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1637:

AACUUCUUCU GCUCAAA                                                     17

( 2 ) INFORMATION FOR SEQ ID NO:1638:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1638:

AGUGGUUUCU GAUGAGGCCG AAAGGCCGAA AGCAGAAG                              38

( 2 ) INFORMATION FOR SEQ ID NO:1639:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1639:
        CUUCUGCUCA AACCACU ( 2 ) INFORMATION FOR SEQ ID NO:1640:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1640:

CCUGCGAGCU GAUGAGGCCG AAAGGCCGAA ACAGUUGG                              38

( 2 ) INFORMATION FOR SEQ ID NO:1641:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1641:

CCAACUGUUC UCGCAGG                                                     17

( 2 ) INFORMATION FOR SEQ ID NO:1642:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1642:

GCCUGCGACU GAUGAGGCCG AAAGGCCGAA AACAGUUG                              38

( 2 ) INFORMATION FOR SEQ ID NO:1643:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1643:

CAACUGUUCU CGCAGGC                                            17

( 2 ) INFORMATION FOR SEQ ID NO:1644:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1644:

ACGCCUGCCU GAUGAGGCCG AAAGGCCGAA AGAACAGU            38

( 2 ) INFORMATION FOR SEQ ID NO:1645:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1645:

ACUGUUCUCG CAGGCGU                                            17

( 2 ) INFORMATION FOR SEQ ID NO:1646:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1646:

CCACAGGACU GAUGAGGCCG AAAGGCCGAA ACGCCUGC            38

( 2 ) INFORMATION FOR SEQ ID NO:1647:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1647:

GCAGGCGUCU CCUGUGG                                            17

( 2 ) INFORMATION FOR SEQ ID NO:1648:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1648:

UGCCACAGCU GAUGAGGCCG AAAGGCCGAA AGACGCCU            38

( 2 ) INFORMATION FOR SEQ ID NO:1649:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1649:

AGGCGUCUCC UGUGGCA                                                                                           17

( 2 ) INFORMATION FOR SEQ ID NO:1650:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1650:

UGUAAGAACU GAUGAGGCCG AAAGGCCGAA AUUUGGGG ( 2 ) INFORMATION FOR SEQ ID NO:1651:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1651:

CCCCAAAUAU UCUUACA                                                                                           17

( 2 ) INFORMATION FOR SEQ ID NO:1652:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1652:

CUUGUAAGCU GAUGAGGCCG AAAGGCCGAA AUAUUUGG                                                                    38

( 2 ) INFORMATION FOR SEQ ID NO:1653:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1653:

CCAAAUAUUC UUACAAG                                                                                           17

( 2 ) INFORMATION FOR SEQ ID NO:1654:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1654:

GCUUGUAACU GAUGAGGCCG AAAGGCCGAA AAUAUUUG                                                                    38

( 2 ) INFORMATION FOR SEQ ID NO:1655:

( i ) SEQUENCE CHARACTERISTICS:
  ( A ) LENGTH: 17 base pairs
  ( B ) TYPE: nucleic acid ( C ) STRANDEDNESS: single
( D ) TOPOLOGY: linear ( x i ) SEQUENCE DESCRIPTION: SEQ ID NO:1655:

CAAAUAUUCU UACAAGC                                                                                  17

( 2 ) INFORMATION FOR SEQ ID NO:1656:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1656:

GAGCUUGUCU GAUGAGGCCG AAAGGCCGAA AGAAUAUU                                                           38

( 2 ) INFORMATION FOR SEQ ID NO:1657:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1657:

AAUAUUCUUA CAAGCUC                                                                                  17

( 2 ) INFORMATION FOR SEQ ID NO:1658:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1658:

AGAGCUUGCU GAUGAGGCCG AAAGGCCGAA AAGAAUAU                                                           38

( 2 ) INFORMATION FOR SEQ ID NO:1659:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1659:

AUAUUCUUAC AAGCUCU                                                                                  17

( 2 ) INFORMATION FOR SEQ ID NO:1660:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1660:

UUAAAACACU GAUGAGGCCG AAAGGCCGAA AGCUUGUA                                                           38

( 2 ) INFORMATION FOR SEQ ID NO:1661:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1661:

UACAAGCUCU GUUUUAA ( 2 ) INFORMATION FOR SEQ ID NO:1662:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1662:

GUCAUUAACU GAUGAGGCCG AAAGGCCGAA ACAGAGCU 38

( 2 ) INFORMATION FOR SEQ ID NO:1663:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1663:

AGCUCUGUUU UAAUGAC 17

( 2 ) INFORMATION FOR SEQ ID NO:1664:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1664:

UGUCAUUACU GAUGAGGCCG AAAGGCCGAA AACAGAGC 38

( 2 ) INFORMATION FOR SEQ ID NO:1665:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1665:

GCUCUGUUUU AAUGACA 17

( 2 ) INFORMATION FOR SEQ ID NO:1666:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1666:

GUGUCAUUCU GAUGAGGCCG AAAGGCCGAA AAACAGAG 38

( 2 ) INFORMATION FOR SEQ ID NO:1667:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1667:

CUCUGUUUUA AUGACAC 17

( 2 ) INFORMATION FOR SEQ ID NO:1668:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1668:

GGUGUCAUCU GAUGAGGCCG AAAGGCCGAA AAAACAGA  38

( 2 ) INFORMATION FOR SEQ ID NO:1669:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1669:

UCUGUUUUAA UGACACC  17

( 2 ) INFORMATION FOR SEQ ID NO:1670:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1670:

UCUUCGACU GAUGAGGCCG AAAGGCCGAA ACAGGUGU  38

( 2 ) INFORMATION FOR SEQ ID NO:1671:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1671:

ACACCUGUAU CAGAAGA  17

( 2 ) INFORMATION FOR SEQ ID NO:1672:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1672:
CAUCUUCUCU GAUGAGGCCG AAAGGCCGAA AUACAGGU ( 2 ) INFORMATION FOR SEQ ID NO:1673:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1673:

ACCUGUAUCA GAAGAUG  17

( 2 ) INFORMATION FOR SEQ ID NO:1674:

( i ) SEQUENCE CHARACTERISTICS:
- ( A ) LENGTH: 38 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:1674:

GCUUUGAGCU GAUGAGGCCG AAAGGCCGAA ACAUUGUC 38

( 2 ) INFORMATION FOR SEQ ID NO:1675:

( i ) SEQUENCE CHARACTERISTICS:
- ( A ) LENGTH: 17 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:1675:

GACAAUGUCC UCAAAGC 17

( 2 ) INFORMATION FOR SEQ ID NO:1676:

( i ) SEQUENCE CHARACTERISTICS:
- ( A ) LENGTH: 38 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:1676:

AAGGCUUUCU GAUGAGGCCG AAAGGCCGAA AGGACAUU 38

( 2 ) INFORMATION FOR SEQ ID NO:1677:

( i ) SEQUENCE CHARACTERISTICS:
- ( A ) LENGTH: 17 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:1677:

AAUGUCCUCA AAGCCUU 17

( 2 ) INFORMATION FOR SEQ ID NO:1678:

( i ) SEQUENCE CHARACTERISTICS:
- ( A ) LENGTH: 38 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:1678:

GUACGGUACU GAUGAGGCCG AAAGGCCGAA AGGCUUUG 38

( 2 ) INFORMATION FOR SEQ ID NO:1679:

( i ) SEQUENCE CHARACTERISTICS:
- ( A ) LENGTH: 17 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:1679:

CAAAGCCUUU ACCGUAC 17

( 2 ) INFORMATION FOR SEQ ID NO:1680:

( i ) SEQUENCE CHARACTERISTICS:
- ( A ) LENGTH: 38 base pairs ( B ) TYPE: nucleic acid
        ( C ) STRANDEDNESS: single
        ( D ) TOPOLOGY: linear ( x i ) SEQUENCE DESCRIPTION: SEQ ID NO:1680:

GGUACGGUCU GAUGAGGCCG AAAGGCCGAA AAGGCUUU 38

( 2 ) INFORMATION FOR SEQ ID NO:1681:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1681:

AAAGCCUUUA CCGUACC 17

( 2 ) INFORMATION FOR SEQ ID NO:1682:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1682:

AGGUACGGCU GAUGAGGCCG AAAGGCCGAA AAAGGCUU 38

( 2 ) INFORMATION FOR SEQ ID NO:1683:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1683:
                AAGCCUUUAC CGUACCU ( 2 ) INFORMATION FOR SEQ ID NO:1684:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1684:

UUCUUAGGCU GAUGAGGCCG AAAGGCCGAA ACGGUAAA 38

( 2 ) INFORMATION FOR SEQ ID NO:1685:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1685:

UUUACCGUAC CUAAGAA 17

( 2 ) INFORMATION FOR SEQ ID NO:1686:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear (x i) SEQUENCE DESCRIPTION: SEQ ID NO:1686:

CCUGUUCUCU GAUGAGGCCG AAAGGCCGAA AGGUACGG                      38

(2) INFORMATION FOR SEQ ID NO:1687:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1687:

CCGUACCUAA GAACAGG                                             17

(2) INFORMATION FOR SEQ ID NO:1688:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1688:

CUGCAAGGCU GAUGAGGCCG AAAGGCCGAA ACCCACCA                      38

(2) INFORMATION FOR SEQ ID NO:1689:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1689:

UGGUGGGUCC CUUGCAG                                             17

(2) INFORMATION FOR SEQ ID NO:1690:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1690:

AUGGCUGCCU GAUGAGGCCG AAAGGCCGAA AGGGACCC                      38

(2) INFORMATION FOR SEQ ID NO:1691:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1691:

GGGUCCCUUG CAGCCAU                                             17

(2) INFORMATION FOR SEQ ID NO:1692:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1692:

UCCCACAGCU GAUGAGGCCG AAAGGCCGAA AUGCUGGC 38

( 2 ) INFORMATION FOR SEQ ID NO:1693:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1693:

GCCAGCAUCC UGUGGGA 17

( 2 ) INFORMATION FOR SEQ ID NO:1694:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1694:

CCGGACCGCU GAUGAGGCCG AAAGGCCGAA AGGCCGUC ( 2 ) INFORMATION FOR SEQ ID NO:1695:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1695:

GACGGCCUCC GGUCCGG 17

( 2 ) INFORMATION FOR SEQ ID NO:1696:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1696:

CCGAGCCGCU GAUGAGGCCG AAAGGCCGAA ACCGGAGG 38

( 2 ) INFORMATION FOR SEQ ID NO:1697:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1697:

CCUCCGGUCC GGCUCGG 17

( 2 ) INFORMATION FOR SEQ ID NO:1698:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1698:

GUAUUCCCU GAUGAGGCCG AAAGGCCGAA AGCCGGAC 38

( 2 ) INFORMATION FOR SEQ ID NO:1699:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1699:

GUCCGGCUCG GAAAUAC                                                                          17

( 2 ) INFORMATION FOR SEQ ID NO:1700:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1700:

CGUUCACGCU GAUGAGGCCG AAAGGCCGAA AUUCCGA                                                     38

( 2 ) INFORMATION FOR SEQ ID NO:1701:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1701:

UCGGAAAUAC GUGAACG                                                                          17

( 2 ) INFORMATION FOR SEQ ID NO:1702:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1702:

GAGCUGAGCU GAUGAGGCCG AAAGGCCGAA ACGCGUUC                                                    38

( 2 ) INFORMATION FOR SEQ ID NO:1703:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1703:

GAACGCGUUC UCAGCUC                                                                          17

( 2 ) INFORMATION FOR SEQ ID NO:1704:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1704:

CGAGCUGACU GAUGAGGCCG AAAGGCCGAA AACGCGUU                                                    38

( 2 ) INFORMATION FOR SEQ ID NO:1705:

( i ) SEQUENCE CHARACTERISTICS:

( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1705:
                        A A C G C G U U C U   C A G C U C G ( 2 ) INFORMATION FOR SEQ ID NO:1706:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1706:

U U C G A G C U C U   G A U G A G G C C G   A A A G G C C G A A   A G A A C G C G                                   3 8

( 2 ) INFORMATION FOR SEQ ID NO:1707:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1707:

C G C G U U C U C A   G C U C G A A                                                                                 1 7

( 2 ) INFORMATION FOR SEQ ID NO:1708:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1708:

C A G A G U U C C U   G A U G A G G C C G   A A A G G C C G A A   A G C U G A G A                                   3 8

( 2 ) INFORMATION FOR SEQ ID NO:1709:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1709:

U C U C A G C U C G   A A C U C U G                                                                                 1 7

( 2 ) INFORMATION FOR SEQ ID NO:1710:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1710:

C A U G A C C A C U   G A U G A G G C C G   A A A G G C C G A A   A G U U C G A G                                   3 8

( 2 ) INFORMATION FOR SEQ ID NO:1711:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1711:

CUCGAACUCU GGUCAUG                                                                 17

( 2 ) INFORMATION FOR SEQ ID NO:1712:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1712:

UCUCACAUCU GAUGAGGCCG AAAGGCCGAA ACCAGAGU                                           38

( 2 ) INFORMATION FOR SEQ ID NO:1713:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1713:

ACUCGGUCA UGUGAGA                                                                  17

( 2 ) INFORMATION FOR SEQ ID NO:1714:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1714:

UUUCUGGACU GAUGAGGCCG AAAGGCCGAA AUGUCUCA                                           38

( 2 ) INFORMATION FOR SEQ ID NO:1715:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1715:

UGAGACAUUU CCAGAAA                                                                 17

( 2 ) INFORMATION FOR SEQ ID NO:1716:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1716:
    UUUCUGGCU GAUGAGGCCG AAAGGCCGAA AAUGUCUC ( 2 ) INFORMATION FOR SEQ ID NO:1717:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1717:

GAGACAUUUC CAGAAAA                                                                 17

( 2 ) INFORMATION FOR SEQ ID NO:1718:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1718:

CUUUUCUGCU GAUGAGGCCG AAAGGCCGAA AAAUGUCU 38

( 2 ) INFORMATION FOR SEQ ID NO:1719:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1719:

AGACAUUUCC AGAAAAG 17

( 2 ) INFORMATION FOR SEQ ID NO:1720:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1720:

AAAACCAUCU GAUGAGGCCG AAAGGCCGAA AUGCUUUU 38

( 2 ) INFORMATION FOR SEQ ID NO:1721:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1721:

AAAAGCAUUA UGGUUUU 17

( 2 ) INFORMATION FOR SEQ ID NO:1722:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1722:

GAAAACCACU GAUGAGGCCG AAAGGCCGAA AAUGCUUU 38

( 2 ) INFORMATION FOR SEQ ID NO:1723:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1723:

AAAGCAUUAU GGUUUUC 17

( 2 ) INFORMATION FOR SEQ ID NO:1724:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1724:

GUUCUGAACU GAUGAGGCCG AAAGGCCGAA ACCAUAAU 38

( 2 ) INFORMATION FOR SEQ ID NO:1725:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1725:

AUUAUGGUUU UCAGAAC 17

( 2 ) INFORMATION FOR SEQ ID NO:1726:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1726:

UGUUCUGACU GAUGAGGCCG AAAGGCCGAA AACCAUAA 38

( 2 ) INFORMATION FOR SEQ ID NO:1727:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1727:

UUAUGGUUUU CAGAACA ( 2 ) INFORMATION FOR SEQ ID NO:1728:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1728:

GUGUUCUGCU GAUGAGGCCG AAAGGCCGAA AAACCAUA 38

( 2 ) INFORMATION FOR SEQ ID NO:1729:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1729:

UAUGGUUUUC AGAACAC 17

( 2 ) INFORMATION FOR SEQ ID NO:1730:

( i ) SEQUENCE CHARACTERISTICS:
        ( A ) LENGTH: 38 base pairs ( B ) TYPE: nucleic acid
                    ( C ) STRANDEDNESS: single
                    ( D ) TOPOLOGY: linear ( x i ) SEQUENCE DESCRIPTION: SEQ ID NO:1730:

AGUGUUCUCU GAUGAGGCCG AAAGGCCGAA AAAACCAU                                              38

( 2 ) INFORMATION FOR SEQ ID NO:1731:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1731:

AUGGUUUUCA GAACACU                                                                     17

( 2 ) INFORMATION FOR SEQ ID NO:1732:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1732:

CAACUUUUCU GAUGAGGCCG AAAGGCCGAA AGUGUUCU                                              38

( 2 ) INFORMATION FOR SEQ ID NO:1733:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1733:

AGAACACUUA AAAGUUG                                                                     17

( 2 ) INFORMATION FOR SEQ ID NO:1734:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1734:

UCAACUUUCU GAUGAGGCCG AAAGGCCGAA AAGUGUUC                                              38

( 2 ) INFORMATION FOR SEQ ID NO:1735:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1735:

GAACACUUAA AAGUUGA                                                                     17

( 2 ) INFORMATION FOR SEQ ID NO:1736:

( i ) SEQUENCE CHARACTERISTICS:
                    ( A ) LENGTH: 38 base pairs
                    ( B ) TYPE: nucleic acid
                    ( C ) STRANDEDNESS: single (D) TOPOLOGY: linear (x i) SEQUENCE DESCRIPTION: SEQ ID NO:1736:

CGAAAGUCCU GAUGAGGCCG AAAGGCCGAA ACUUUUAA    38

(2) INFORMATION FOR SEQ ID NO:1737:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1737:

UUAAAGUUG ACUUCG    17

(2) INFORMATION FOR SEQ ID NO:1738:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1738:

UGUGUCGACU GAUGAGGCCG AAAGGCCGAA AGUCAACU (2) INFORMATION FOR SEQ ID NO:1739:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1739:

AGUUGACUUU CGACACA    17

(2) INFORMATION FOR SEQ ID NO:1740:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1740:

AUGUGUCGCU GAUGAGGCCG AAAGGCCGAA AAGUCAAC    38

(2) INFORMATION FOR SEQ ID NO:1741:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1741:

GUUGACUUUC GACACAU    17

(2) INFORMATION FOR SEQ ID NO:1742:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1742:

```
CAUGUGUCCU GAUGAGGCCG AAAGGCCGAA AAAGUCAA                                    3 8
```

( 2 ) INFORMATION FOR SEQ ID NO:1743:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1743:

```
UUGACUUUCG ACACAUG                                                            1 7
```

( 2 ) INFORMATION FOR SEQ ID NO:1744:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1744:

```
ACGCUGAGCU GAUGAGGCCG AAAGGCCGAA AGCCAUGU                                    3 8
```

( 2 ) INFORMATION FOR SEQ ID NO:1745:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1745:

```
ACAUGGCUCC UCAGCGU                                                            1 7
```

( 2 ) INFORMATION FOR SEQ ID NO:1746:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1746:

```
UCCACGCUCU GAUGAGGCCG AAAGGCCGAA AGGAGCCA                                    3 8
```

( 2 ) INFORMATION FOR SEQ ID NO:1747:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1747:

```
UGGCUCCUCA GCGUGGA                                                            1 7
```

( 2 ) INFORMATION FOR SEQ ID NO:1748:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1748:

```
CAGCCAUGCU GAUGAGGCCG AAAGGCCGAA AGCGCUCC                                    3 8
```

( 2 ) INFORMATION FOR SEQ ID NO:1749:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1749:

GGAGCGCUCC AUGGCUG ( 2 ) INFORMATION FOR SEQ ID NO:1750:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1750:

CACAACAACU GAUGAGGCCG AAAGGCCGAA AUCAGGCU           38

( 2 ) INFORMATION FOR SEQ ID NO:1751:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1751:

AGCCUGAUUU UGUUGUG           17

( 2 ) INFORMATION FOR SEQ ID NO:1752:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1752:

CCACAACACU GAUGAGGCCG AAAGGCCGAA AAUCAGGC           38

( 2 ) INFORMATION FOR SEQ ID NO:1753:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1753:

GCCUGAUUUU GUUGUGG           17

( 2 ) INFORMATION FOR SEQ ID NO:1754:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1754:

ACCACAACCU GAUGAGGCCG AAAGGCCGAA AAAUCAGG           38

( 2 ) INFORMATION FOR SEQ ID NO:1755:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1755:

CCUGAUUUUG UUGUGGU                                                                                          17

(2) INFORMATION FOR SEQ ID NO:1756:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1756:

UGUACCACCU GAUGAGGCCG AAAGGCCGAA ACAAAAUC                                                                    38

(2) INFORMATION FOR SEQ ID NO:1757:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1757:

GAUUUUGUUG UGGUACA                                                                                          17

(2) INFORMATION FOR SEQ ID NO:1758:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1758:

AACUGUUGCU GAUGAGGCCG AAAGGCCGAA ACCACAAC                                                                    38

(2) INFORMATION FOR SEQ ID NO:1759:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1759:

GUUGUGGUAC AACAGUU                                                                                          17

(2) INFORMATION FOR SEQ ID NO:1760:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1760:
            CUGCUCUCCU GAUGAGGCCG AAAGGCCGAA ACUGUUGU (2) INFORMATION FOR SEQ ID NO:1761:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1761:

ACAACAGUUG AGAGCAG 17

(2) INFORMATION FOR SEQ ID NO:1762:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1762:

CAACUAAACU GAUGAGGCCG AAAGGCCGAA AUGCACUU 38

(2) INFORMATION FOR SEQ ID NO:1763:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1763:

AAGUGCAUUU UUAGUUG 17

(2) INFORMATION FOR SEQ ID NO:1764:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1764:

GCAACUAACU GAUGAGGCCG AAAGGCCGAA AAUGCACU 38

(2) INFORMATION FOR SEQ ID NO:1765:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1765:

AGUGCAUUUU UAGUUGC 17

(2) INFORMATION FOR SEQ ID NO:1766:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1766:

AGCAACUACU GAUGAGGCCG AAAGGCCGAA AAAUGCAC 38

(2) INFORMATION FOR SEQ ID NO:1767:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1767:

GUGCAUUUUU AGUUGCU 17

( 2 ) INFORMATION FOR SEQ ID NO:1768:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1768:

AAGCAACUCU GAUGAGGCCG AAAGGCCGAA AAAAUGCA 38

( 2 ) INFORMATION FOR SEQ ID NO:1769:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1769:

UGCAUUUUUA GUUGCUU 17

( 2 ) INFORMATION FOR SEQ ID NO:1770:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1770:

CAAGCAACCU GAUGAGGCCG AAAGGCCGAA AAAAUGC 38

( 2 ) INFORMATION FOR SEQ ID NO:1771:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1771:
                GCAUUUUAG UUGCUUG ( 2 ) INFORMATION FOR SEQ ID NO:1772:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1772:

UCUCAAGCCU GAUGAGGCCG AAAGGCCGAA ACUAAAAA 38

( 2 ) INFORMATION FOR SEQ ID NO:1773:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1773:

UUUUUAGUUG CUUGAGA 17

( 2 ) INFORMATION FOR SEQ ID NO:1774:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1774:

GAGAUCUCCU GAUGAGGCCG AAAGGCCGAA AGCAACUA      38

( 2 ) INFORMATION FOR SEQ ID NO:1775:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1775:

UAGUUGCUUG AGAUCUC      17

( 2 ) INFORMATION FOR SEQ ID NO:1776:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1776:

UCAAGUGACU GAUGAGGCCG AAAGGCCGAA AUCUCAAG      38

( 2 ) INFORMATION FOR SEQ ID NO:1777:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1777:

CUUGAGAUCU CACUUGA      17

( 2 ) INFORMATION FOR SEQ ID NO:1778:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1778:

AAUCAAGUCU GAUGAGGCCG AAAGGCCGAA AGAUCUCA      38

( 2 ) INFORMATION FOR SEQ ID NO:1779:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1779:

UGAGAUCUCA CUUGAUU      17

( 2 ) INFORMATION FOR SEQ ID NO:1780:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1780:

GUGAAAUCCU GAUGAGGCCG AAAGGCCGAA AGUGAGAU                        38

( 2 ) INFORMATION FOR SEQ ID NO:1781:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1781:

AUCUCACUUG AUUUCAC                                               17

( 2 ) INFORMATION FOR SEQ ID NO:1782:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1782:
UUGUGUGACU GAUGAGGCCG AAAGGCCGAA AUCAAGUG ( 2 ) INFORMATION FOR SEQ ID NO:1783:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1783:

CACUUGAUUU CACACAA                                               17

( 2 ) INFORMATION FOR SEQ ID NO:1784:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1784:

GUUGUGUGCU GAUGAGGCCG AAAGGCCGAA AAUCAAGU                        38

( 2 ) INFORMATION FOR SEQ ID NO:1785:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1785:

ACUUGAUUUC ACACAAC                                               17

( 2 ) INFORMATION FOR SEQ ID NO:1786:

( i ) SEQUENCE CHARACTERISTICS:
        ( A ) LENGTH: 38 base pairs
        ( B ) TYPE: nucleic acid
        ( C ) STRANDEDNESS: single (D) TOPOLOGY: linear (xi) SEQUENCE DESCRIPTION: SEQ ID NO:1786:

AGUUGUGUCU GAUGAGGCCG AAAGGCCGAA AAAUCAAG 38

(2) INFORMATION FOR SEQ ID NO:1787:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1787:

CUUGAUUUCA CACAACU 17

(2) INFORMATION FOR SEQ ID NO:1788:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1788:

AUCCUUUUCU GAUGAGGCCG AAAGGCCGAA AGUUGUGU 38

(2) INFORMATION FOR SEQ ID NO:1789:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1789:

ACACAACUAA AAAGGAU 17

(2) INFORMATION FOR SEQ ID NO:1790:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1790:

AAAAAAACU GAUGAGGCCG AAAGGCCGAA AUCCUUUU 38

(2) INFORMATION FOR SEQ ID NO:1791:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1791:

AAAAGGAUUU UUUUUUU 17

(2) INFORMATION FOR SEQ ID NO:1792:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:1792:

UAAAAAAACU GAUGAGGCCG AAAGGCCGAA AAUCCUUU 38

( 2 ) INFORMATION FOR SEQ ID NO:1793:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1793:

AAAGGAUUUU UUUUUUA ( 2 ) INFORMATION FOR SEQ ID NO:1794:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1794:

UUAAAAAACU GAUGAGGCCG AAAGGCCGAA AAAUCCUU 38

( 2 ) INFORMATION FOR SEQ ID NO:1795:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1795:

AAGGAUUUUU UUUUUAA 17

( 2 ) INFORMATION FOR SEQ ID NO:1796:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1796:

UUUAAAAACU GAUGAGGCCG AAAGGCCGAA AAAAUCCU 38

( 2 ) INFORMATION FOR SEQ ID NO:1797:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1797:

AGGAUUUUUU UUUUAAA 17

( 2 ) INFORMATION FOR SEQ ID NO:1798:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1798:

UUUUAAAACU GAUGAGGCCG AAAGGCCGAA AAAAAUCC 38

( 2 ) INFORMATION FOR SEQ ID NO:1799:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1799:

GGAUUUUUUU UUUAAAA                                    17

( 2 ) INFORMATION FOR SEQ ID NO:1800:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1800:

UUUUUAAACU GAUGAGGCCG AAAGGCCGAA AAAAAAUC                38

( 2 ) INFORMATION FOR SEQ ID NO:1801:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1801:

GAUUUUUUU UUAAAAA                                     17

( 2 ) INFORMATION FOR SEQ ID NO:1802:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1802:

AUUUUUAACU GAUGAGGCCG AAAGGCCGAA AAAAAAAU                38

( 2 ) INFORMATION FOR SEQ ID NO:1803:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1803:

AUUUUUUUUU UAAAAAU                                    17

( 2 ) INFORMATION FOR SEQ ID NO:1804:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1804:
                UAUUUUUACU GAUGAGGCCG AAAGGCCGAA AAAAAAA ( 2 ) INFORMATION FOR SEQ ID NO:1805:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1805:

UUUUUUUUUU AAAAAUA                                                                                      17

(2) INFORMATION FOR SEQ ID NO:1806:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1806:

UUAUUUUCU GAUGAGGCCG AAAGGCCGAA AAAAAAAA                                                                38

(2) INFORMATION FOR SEQ ID NO:1807:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1807:

UUUUUUUUA AAAAUAA                                                                                       17

(2) INFORMATION FOR SEQ ID NO:1808:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1808:

AUUAUUUUCU GAUGAGGCCG AAAGGCCGAA AAAAAAAA                                                               38

(2) INFORMATION FOR SEQ ID NO:1809:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1809:

UUUUUUUAA AAAUAAU                                                                                       17

(2) INFORMATION FOR SEQ ID NO:1810:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1810:

AUUAUUAUCU GAUGAGGCCG AAAGGCCGAA AUUUUUAA                                                               38

(2) INFORMATION FOR SEQ ID NO:1811:

(i) SEQUENCE CHARACTERISTICS:
        (A) LENGTH: 17 base pairs
        (B) TYPE: nucleic acid (C) STRANDEDNESS: single
        (D) TOPOLOGY: linear (xi) SEQUENCE DESCRIPTION: SEQ ID NO:1811:

UUAAAAAUAA UAAUAAU                                                                                      17

(2) INFORMATION FOR SEQ ID NO:1812:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1812:

UUCAUUAUCU GAUGAGGCCG AAAGGCCGAA AUUAUUUU                                                                38

(2) INFORMATION FOR SEQ ID NO:1813:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1813:

AAAAUAAUAA UAAUGAA                                                                                      17

(2) INFORMATION FOR SEQ ID NO:1814:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1814:

UUAUUCAUCU GAUGAGGCCG AAAGGCCGAA AUUAUUAU                                                                38

(2) INFORMATION FOR SEQ ID NO:1815:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1815:
                AUAAUAAUAA UGAAUAA (2) INFORMATION FOR SEQ ID NO:1816:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1816:

AAGACUGUCU GAUGAGGCCG AAAGGCCGAA AUUCAUUA                                                                38

(2) INFORMATION FOR SEQ ID NO:1817:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1817:

UAAUGAAUAA CAGUCUU 17

(2) INFORMATION FOR SEQ ID NO:1818:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1818:

UUAGGUAACU GAUGAGGCCG AAAGGCCGAA ACUGUUAU 38

(2) INFORMATION FOR SEQ ID NO:1819:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1819:

AUAACAGUCU UACCUAA 17

(2) INFORMATION FOR SEQ ID NO:1820:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1820:

AUUUAGGUCU GAUGAGGCCG AAAGGCCGAA AGACUGUU 38

(2) INFORMATION FOR SEQ ID NO:1821:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1821:

AACAGUCUUA CCUAAAU 17

(2) INFORMATION FOR SEQ ID NO:1822:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1822:

AAUUUAGGCU GAUGAGGCCG AAAGGCCGAA AAGACUGU 38

(2) INFORMATION FOR SEQ ID NO:1823:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1823:

ACAGUCUUAC CUAAAUU 17

( 2 ) INFORMATION FOR SEQ ID NO:1824:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1824:

UAAUAAUUCU GAUGAGGCCG AAAGGCCGAA AGGUAAGA     38

( 2 ) INFORMATION FOR SEQ ID NO:1825:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1825:

UCUUACCUAA AUUAUUA     17

( 2 ) INFORMATION FOR SEQ ID NO:1826:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1826:

UACCUAAUCU GAUGAGGCCG AAAGGCCGAA AUUUAGGU ( 2 ) INFORMATION FOR SEQ ID NO:1827:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1827:

ACCUAAAUUA UUAGGUA     17

( 2 ) INFORMATION FOR SEQ ID NO:1828:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1828:

UUACCUAACU GAUGAGGCCG AAAGGCCGAA AAUUUAGG     38

( 2 ) INFORMATION FOR SEQ ID NO:1829:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1829:

CCUAAAUUAU UAGGUAA     17

( 2 ) INFORMATION FOR SEQ ID NO:1830:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1830:

CAUUACCUCU GAUGAGGCCG AAAGGCCGAA AUAAUUUA 38

( 2 ) INFORMATION FOR SEQ ID NO:1831:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1831:

UAAAUUAUUA GGUAAUG 17

( 2 ) INFORMATION FOR SEQ ID NO:1832:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1832:

UCAUUACCCU GAUGAGGCCG AAAGGCCGAA AAUAAUUU 38

( 2 ) INFORMATION FOR SEQ ID NO:1833:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1833:

AAAUUAUUAG GUAAUGA 17

( 2 ) INFORMATION FOR SEQ ID NO:1834:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1834:

CAAUCAUCU GAUGAGGCCG AAAGGCCGAA ACCUAAUA 38

( 2 ) INFORMATION FOR SEQ ID NO:1835:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1835:

UAUUAGGUAA UGAAUUG 17

( 2 ) INFORMATION FOR SEQ ID NO:1836:

( i ) SEQUENCE CHARACTERISTICS:
      ( A ) LENGTH: 38 base pairs (B) TYPE: nucleic acid
        (C) STRANDEDNESS: single
        (D) TOPOLOGY: linear (x i) SEQUENCE DESCRIPTION: SEQ ID NO:1836:

AUGGUCACCU GAUGAGGCCG AAAGGCCGAA AUUCAUUA 38

(2) INFORMATION FOR SEQ ID NO:1837:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1837:
            UAAUGAAUUG UGACCAU (2) INFORMATION FOR SEQ ID NO:1838:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1838:

UAUUAACACU GAUGAGGCCG AAAGGCCGAA AUGGUCAC 38

(2) INFORMATION FOR SEQ ID NO:1839:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1839:

GUGACCAUUU GUUAAUA 17

(2) INFORMATION FOR SEQ ID NO:1840:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1840:

AUAUUAACCU GAUGAGGCCG AAAGGCCGAA AAUGGUCA 38

(2) INFORMATION FOR SEQ ID NO:1841:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1841:

UGACCAUUUG UUAAUAU 17

(2) INFORMATION FOR SEQ ID NO:1842:

(i) SEQUENCE CHARACTERISTICS:
        (A) LENGTH: 38 base pairs
        (B) TYPE: nucleic acid
        (C) STRANDEDNESS: single
        (D) TOPOLOGY: linear -continued (xi) SEQUENCE DESCRIPTION: SEQ ID NO:1842:

AUGAUAUUCU GAUGAGGCCG AAAGGCCGAA ACAAAUGG 38

(2) INFORMATION FOR SEQ ID NO:1843:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1843:

CCAUUUGUUA AUAUCAU 17

(2) INFORMATION FOR SEQ ID NO:1844:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1844:

UAUGAUAUCU GAUGAGGCCG AAAGGCCGAA AACAAAUG 38

(2) INFORMATION FOR SEQ ID NO:1845:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1845:

CAUUUGUUAA UAUCAUA 17

(2) INFORMATION FOR SEQ ID NO:1846:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1846:

GAUUAUGACU GAUGAGGCCG AAAGGCCGAA AUUAACAA 38

(2) INFORMATION FOR SEQ ID NO:1847:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1847:

UUGUUAAUAU CAUAAUC 17

(2) INFORMATION FOR SEQ ID NO:1848:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1848:

CUGAUUAUCU GAUGAGGCCG AAAGGCCGAA AUAUUAAC ( 2 ) INFORMATION FOR SEQ ID NO:1849:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1849:

GUUAAUAUCA UAAUCAG 17

( 2 ) INFORMATION FOR SEQ ID NO:1850:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1850:

AAUCGAUCU GAUGAGGCCG AAAGGCCGAA AUGAUAUU 38

( 2 ) INFORMATION FOR SEQ ID NO:1851:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1851:

AAUAUCAUAA UCAGAUU 17

( 2 ) INFORMATION FOR SEQ ID NO:1852:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1852:

AAAAUCUCU GAUGAGGCCG AAAGGCCGAA AUUAUGAU 38

( 2 ) INFORMATION FOR SEQ ID NO:1853:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1853:

AUCAUAAUCA GAUUUUU 17

( 2 ) INFORMATION FOR SEQ ID NO:1854:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1854:

UUUUAAAACU GAUGAGGCCG AAAGGCCGAA AUCUGAUU 38

( 2 ) INFORMATION FOR SEQ ID NO:1855:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1855:

AAUCAGAUUU UUUAAAA 17

( 2 ) INFORMATION FOR SEQ ID NO:1856:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1856:

UUUUUAAACU GAUGAGGCCG AAAGGCCGAA AAUCUGAU 38

( 2 ) INFORMATION FOR SEQ ID NO:1857:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1857:

AUCAGAUUUU UUAAAAA 17

( 2 ) INFORMATION FOR SEQ ID NO:1858:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1858:

UUUUUUAACU GAUGAGGCCG AAAGGCCGAA AAAUCUGA 38

( 2 ) INFORMATION FOR SEQ ID NO:1859:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1859:

UCAGAUUUUU UAAAAAA ( 2 ) INFORMATION FOR SEQ ID NO:1860:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1860:

UUUUUUUACU GAUGAGGCCG AAAGGCCGAA AAAAUCUG 38

( 2 ) INFORMATION FOR SEQ ID NO:1861:

( i ) SEQUENCE CHARACTERISTICS:
    ( A ) LENGTH: 17 base pairs
    ( B ) TYPE: nucleic acid ( C ) STRANDEDNESS: single
        ( D ) TOPOLOGY: linear ( x i ) SEQUENCE DESCRIPTION: SEQ ID NO:1861:

CAGAUUUUUU AAAAAAA                                                                                    17

( 2 ) INFORMATION FOR SEQ ID NO:1862:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1862:

UUUUUUUUCU GAUGAGGCCG AAAGGCCGAA AAAAAUCU                                                              38

( 2 ) INFORMATION FOR SEQ ID NO:1863:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1863:

AGAUUUUUUA AAAAAAA                                                                                    17

( 2 ) INFORMATION FOR SEQ ID NO:1864:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1864:

AUUUUUUUCU GAUGAGGCCG AAAGGCCGAA AAAAAAUC                                                              38

( 2 ) INFORMATION FOR SEQ ID NO:1865:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1865:

GAUUUUUUAA AAAAAAU                                                                                    17

( 2 ) INFORMATION FOR SEQ ID NO:1866:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1866:

AAUCAUUUCU GAUGAGGCCG AAAGGCCGAA AUUUUUUU                                                              38

( 2 ) INFORMATION FOR SEQ ID NO:1867:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1867:

AAAAAAAUAA AAUGAUU                                                                          17

( 2 ) INFORMATION FOR SEQ ID NO:1868:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1868:

UACAAAUACU GAUGAGGCCG AAAGGCCGAA AUCAUUUU                                                    38

( 2 ) INFORMATION FOR SEQ ID NO:1869:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1869:

AAAAUGAUUU AUUUGUA                                                                          17

( 2 ) INFORMATION FOR SEQ ID NO:1870:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1870:

AUACAAAUCU GAUGAGGCCG AAAGGCCGAA AAUCAUUU ( 2 ) INFORMATION FOR SEQ ID NO:1871:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1871:

AAAUGAUUUA UUUGUAU                                                                          17

( 2 ) INFORMATION FOR SEQ ID NO:1872:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1872:

AAUACAAACU GAUGAGGCCG AAAGGCCGAA AAAUCAUU                                                   38

( 2 ) INFORMATION FOR SEQ ID NO:1873:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1873:

AAUGAUUUAU UUGUAUU                                                                          17

( 2 ) INFORMATION FOR SEQ ID NO:1874:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1874:

AAAAUACACU GAUGAGGCCG AAAGGCCGAA AUAAAUCA        38

( 2 ) INFORMATION FOR SEQ ID NO:1875:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1875:

UGAUUUAUUU GUAUUUU        17

( 2 ) INFORMATION FOR SEQ ID NO:1876:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1876:

UAAAAUACCU GAUGAGGCCG AAAGGCCGAA AAUAAAUC        38

( 2 ) INFORMATION FOR SEQ ID NO:1877:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1877:

GAUUUAUUUG UAUUUUA        17

( 2 ) INFORMATION FOR SEQ ID NO:1878:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1878:

CUCUAAAACU GAUGAGGCCG AAAGGCCGAA ACAAAUAA        38

( 2 ) INFORMATION FOR SEQ ID NO:1879:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1879:

UUAUUUGUAU UUUAGAG        17

( 2 ) INFORMATION FOR SEQ ID NO:1880:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1880:

UUCUCUAACU GAUGAGGCCG AAAGGCCGAA AUACAAAU        38

( 2 ) INFORMATION FOR SEQ ID NO:1881:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1881:

AUUUGUAUUU UAGAGAA ( 2 ) INFORMATION FOR SEQ ID NO:1882:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1882:

AUUCUCUACU GAUGAGGCCG AAAGGCCGAA AAUACAAA        38

( 2 ) INFORMATION FOR SEQ ID NO:1883:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1883:

UUUGUAUUUU AGAGAAU        17

( 2 ) INFORMATION FOR SEQ ID NO:1884:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1884:

UAUUCUCUCU GAUGAGGCCG AAAGGCCGAA AAAUACAA        38

( 2 ) INFORMATION FOR SEQ ID NO:1885:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1885:

UUGUAUUUUA GAGAAUA        17

( 2 ) INFORMATION FOR SEQ ID NO:1886:

( i ) SEQUENCE CHARACTERISTICS:
        ( A ) LENGTH: 38 base pairs (B) TYPE: nucleic acid
        (C) STRANDEDNESS: single
        (D) TOPOLOGY: linear (xi) SEQUENCE DESCRIPTION: SEQ ID NO:1886:

GUAUUCUCCU GAUGAGGCCG AAAGGCCGAA AAAAUACA                                    38

(2) INFORMATION FOR SEQ ID NO:1887:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1887:

UGUAUUUUAG AGAAUAC                                                           17

(2) INFORMATION FOR SEQ ID NO:1888:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1888:

AUCUGUUGCU GAUGAGGCCG AAAGGCCGAA AUUCUCUA                                    38

(2) INFORMATION FOR SEQ ID NO:1889:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1889:

UAGAGAAUAC AACAGAU                                                           17

(2) INFORMATION FOR SEQ ID NO:1890:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1890:

AAAAUACUCU GAUGAGGCCG AAAGGCCGAA AUCUGUUG                                    38

(2) INFORMATION FOR SEQ ID NO:1891:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1891:

CAACAGAUCA GUAUUUU                                                           17

(2) INFORMATION FOR SEQ ID NO:1892:

(i) SEQUENCE CHARACTERISTICS:
        (A) LENGTH: 38 base pairs
        (B) TYPE: nucleic acid
        (C) STRANDEDNESS: single ( D ) TOPOLOGY: linear ( x i ) SEQUENCE DESCRIPTION: SEQ ID NO:1892:

GUCAAAAACU GAUGAGGCCG AAAGGCCGAA ACUGAUCU ( 2 ) INFORMATION FOR SEQ ID NO:1893:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1893:

AGAUCAGUAU UUUUGAC 17

( 2 ) INFORMATION FOR SEQ ID NO:1894:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1894:

CAGUCAAACU GAUGAGGCCG AAAGGCCGAA AUACUGAU 38

( 2 ) INFORMATION FOR SEQ ID NO:1895:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1895:

AUCAGUAUUU UUGACUG 17

( 2 ) INFORMATION FOR SEQ ID NO:1896:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1896:

ACAGUCAACU GAUGAGGCCG AAAGGCCGAA AAUACUGA 38

( 2 ) INFORMATION FOR SEQ ID NO:1897:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1897:

UCAGUAUUUU UGACUGU 17

( 2 ) INFORMATION FOR SEQ ID NO:1898:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1898:

```
CACAGUCACU  GAUGAGGCCG  AAAGGCCGAA  AAAUACUG                                                38
```

( 2 ) INFORMATION FOR SEQ ID NO:1899:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1899:

```
CAGUAUUUUU  GACUGUG                                                                         17
```

( 2 ) INFORMATION FOR SEQ ID NO:1900:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1900:

```
CCACAGUCCU  GAUGAGGCCG  AAAGGCCGAA  AAAAUACU                                                38
```

( 2 ) INFORMATION FOR SEQ ID NO:1901:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1901:

```
AGUAUUUUUG  ACUGUGG                                                                         17
```

( 2 ) INFORMATION FOR SEQ ID NO:1902:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1902:

```
UUUUUUUACU  GAUGAGGCCG  AAAGGCCGAA  AUUCACCA                                                38
```

( 2 ) INFORMATION FOR SEQ ID NO:1903:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1903:
```
            UGGUGAAUUU  AAAAAAA
```

( 2 ) INFORMATION FOR SEQ ID NO:1904:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1904:

```
UUUUUUUUCU  GAUGAGGCCG  AAAGGCCGAA  AAUUCACC                                                38
```

( 2 ) INFORMATION FOR SEQ ID NO:1905:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1905:

GGUGAAUUUA AAAAAAA 17

( 2 ) INFORMATION FOR SEQ ID NO:1906:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1906:

UUUUUUUUCU GAUGAGGCCG AAAGGCCGAA AAAUUCAC 38

( 2 ) INFORMATION FOR SEQ ID NO:1907:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1907:

GUGAAUUUAA AAAAAAA 17

( 2 ) INFORMATION FOR SEQ ID NO:1908:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1908:

UUUGUGUACU GAUGAGGCCG AAAGGCCGAA AUUUUUUU 38

( 2 ) INFORMATION FOR SEQ ID NO:1909:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1909:

AAAAAAAUUU ACACAAA 17

( 2 ) INFORMATION FOR SEQ ID NO:1910:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1910:

CUUUGUGUCU GAUGAGGCCG AAAGGCCGAA AAUUUUUU 38

( 2 ) INFORMATION FOR SEQ ID NO:1911:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1911:

AAAAAUUUA CACAAAG                                                      17

( 2 ) INFORMATION FOR SEQ ID NO:1912:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1912:

UCUUUGUGCU GAUGAGGCCG AAAGGCCGAA AAAUUUUU                               38

( 2 ) INFORMATION FOR SEQ ID NO:1913:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1913:

AAAAUUUAC ACAAAGA                                                      17

( 2 ) INFORMATION FOR SEQ ID NO:1914:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1914:
UACUGGGACU GAUGAGGCCG AAAGGCCGAA AUUUCUUU ( 2 ) INFORMATION FOR SEQ ID NO:1915:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1915:

AAAGAAAUAU CCCAGUA                                                     17

( 2 ) INFORMATION FOR SEQ ID NO:1916:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1916:

AAUACUGGCU GAUGAGGCCG AAAGGCCGAA AUAUUUCU                               38

( 2 ) INFORMATION FOR SEQ ID NO:1917:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1917:

AGAAAUAUCC CAGUAUU                       17

( 2 ) INFORMATION FOR SEQ ID NO:1918:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1918:

ACAUGGAACU GAUGAGGCCG AAAGGCCGAA ACUGGGAU                       38

( 2 ) INFORMATION FOR SEQ ID NO:1919:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1919:

AUCCCAGUAU UCCAUGU                       17

( 2 ) INFORMATION FOR SEQ ID NO:1920:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1920:

AUACAUGGCU GAUGAGGCCG AAAGGCCGAA AUACUGG                       38

( 2 ) INFORMATION FOR SEQ ID NO:1921:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1921:

CCCAGUAUUC CAUGUAU                       17

( 2 ) INFORMATION FOR SEQ ID NO:1922:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1922:

GAUACAUGCU GAUGAGGCCG AAAGGCCGAA AAUACUGG                       38

( 2 ) INFORMATION FOR SEQ ID NO:1923:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1923:

CCAGUAUUCC AUGUAUC                                                                  17

( 2 ) INFORMATION FOR SEQ ID NO:1924:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1924:

GACUGAGACU GAUGAGGCCG AAAGGCCGAA ACAUGGAA                                            38

( 2 ) INFORMATION FOR SEQ ID NO:1925:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1925:

UUCCAUGUAU CUCAGUC ( 2 ) INFORMATION FOR SEQ ID NO:1926:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1926:

GUGACUGACU GAUGAGGCCG AAAGGCCGAA AUACAUGG                                            38

( 2 ) INFORMATION FOR SEQ ID NO:1927:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1927:

CCAUGUAUCU CAGUCAC                                                                  17

( 2 ) INFORMATION FOR SEQ ID NO:1928:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1928:

UAGUGACUCU GAUGAGGCCG AAAGGCCGAA AGAUACAU                                            38

( 2 ) INFORMATION FOR SEQ ID NO:1929:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1929:

AUGUAUCUCA GUCACUA                                                                  17

( 2 ) INFORMATION FOR SEQ ID NO:1930:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1930:

UGUUUAGUCU GAUGAGGCCG AAAGGCCGAA ACUGAGAU     38

( 2 ) INFORMATION FOR SEQ ID NO:1931:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1931:

AUCUCAGUCA CUAAACA     17

( 2 ) INFORMATION FOR SEQ ID NO:1932:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1932:

UGUAUGUUCU GAUGAGGCCG AAAGGCCGAA AGUGACUG     38

( 2 ) INFORMATION FOR SEQ ID NO:1933:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1933:

CAGUCACUAA ACAUACA     17

( 2 ) INFORMATION FOR SEQ ID NO:1934:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1934:

UCUCUGUGCU GAUGAGGCCG AAAGGCCGAA AUGUUUAG     38

( 2 ) INFORMATION FOR SEQ ID NO:1935:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1935:

CUAAACAUAC ACAGAGA     17

( 2 ) INFORMATION FOR SEQ ID NO:1936:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1936:

UUUUUAACU GAUGAGGCCG AAAGGCCGAA AUCUCUCU ( 2 ) INFORMATION FOR SEQ ID NO:1937:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1937:

AGAGAGAUUU UUAAAAA 17

( 2 ) INFORMATION FOR SEQ ID NO:1938:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1938:

GUUUUUAACU GAUGAGGCCG AAAGGCCGAA AAUCUCUC 38

( 2 ) INFORMATION FOR SEQ ID NO:1939:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1939:

GAGAGAUUUU UAAAAAC 17

( 2 ) INFORMATION FOR SEQ ID NO:1940:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1940:

GGUUUUUACU GAUGAGGCCG AAAGGCCGAA AAAUCUCU 38

( 2 ) INFORMATION FOR SEQ ID NO:1941:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1941:

AGAGAUUUUU AAAAACC 17

( 2 ) INFORMATION FOR SEQ ID NO:1942:

( i ) SEQUENCE CHARACTERISTICS:
    ( A ) LENGTH: 38 base pairs
    ( B ) TYPE: nucleic acid
    ( C ) STRANDEDNESS: single (D) TOPOLOGY: linear (x i) SEQUENCE DESCRIPTION: SEQ ID NO:1942:

UGGUUUUUCU GAUGAGGCCG AAAGGCCGAA AAAAUCUC 38

(2) INFORMATION FOR SEQ ID NO:1943:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1943:

GAGAUUUUUA AAAACCA 17

(2) INFORMATION FOR SEQ ID NO:1944:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1944:

CUGGUUUUCU GAUGAGGCCG AAAGGCCGAA AAAAAUCU 38

(2) INFORMATION FOR SEQ ID NO:1945:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1945:

AGAUUUUUAA AAACCAG 17

(2) INFORMATION FOR SEQ ID NO:1946:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1946:

UUCAAAAUCU GAUGAGGCCG AAAGGCCGAA AUGCUUCU 38

(2) INFORMATION FOR SEQ ID NO:1947:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1947:
                AGAAGCAUUA UUUUGAA (2) INFORMATION FOR SEQ ID NO:1948:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1948:

AUUCAAAACU GAUGAGGCCG AAAGGCCGAA AAUGCUUC            38

( 2 ) INFORMATION FOR SEQ ID NO:1949:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1949:

GAAGCAUUAU UUUGAAU            17

( 2 ) INFORMATION FOR SEQ ID NO:1950:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1950:

ACAUUCAACU GAUGAGGCCG AAAGGCCGAA AUAAUGCU            38

( 2 ) INFORMATION FOR SEQ ID NO:1951:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1951:

AGCAUUAUUU UGAAUGU            17

( 2 ) INFORMATION FOR SEQ ID NO:1952:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1952:

AACAUUCACU GAUGAGGCCG AAAGGCCGAA AAUAAUGC            38

( 2 ) INFORMATION FOR SEQ ID NO:1953:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1953:

GCAUUAUUUU GAAUGUU            17

( 2 ) INFORMATION FOR SEQ ID NO:1954:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1954:

UAACAUUCCU GAUGAGGCCG AAAGGCCGAA AAAUAAUG            38

( 2 ) INFORMATION FOR SEQ ID NO:1955:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1955:

CAUUAUUUUG AAUGUUA 17

( 2 ) INFORMATION FOR SEQ ID NO:1956:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1956:

AUUUAGCUCU GAUGAGGCCG AAAGGCCGAA ACAUUCAA 38

( 2 ) INFORMATION FOR SEQ ID NO:1957:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1957:

UUGAAUGUUA GCUAAAU 17

( 2 ) INFORMATION FOR SEQ ID NO:1958:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1958:

GAUUUAGCCU GAUGAGGCCG AAAGGCCGAA AACAUUCA ( 2 ) INFORMATION FOR SEQ ID NO:1959:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1959:

UGAAUGUUAG CUAAAUC 17

( 2 ) INFORMATION FOR SEQ ID NO:1960:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1960:

UUGGGAUUCU GAUGAGGCCG AAAGGCCGAA AGCUAACA 38

( 2 ) INFORMATION FOR SEQ ID NO:1961:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1961:

UGUUAGCUAA AUCCCAA                                                                                      17

(2) INFORMATION FOR SEQ ID NO:1962:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1962:

UUACUUGGCU GAUGAGGCCG AAAGGCCGAA AUUUAGCU                                                               38

(2) INFORMATION FOR SEQ ID NO:1963:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1963:

AGCUAAAUCC CAAGUAA                                                                                      17

(2) INFORMATION FOR SEQ ID NO:1964:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1964:

UUAAGUAUCU GAUGAGGCCG AAAGGCCGAA ACUUGGGA                                                               38

(2) INFORMATION FOR SEQ ID NO:1965:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1965:

UCCCAAGUAA UACUUAA                                                                                      17

(2) INFORMATION FOR SEQ ID NO:1966:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1966:

GCAUUAAGCU GAUGAGGCCG AAAGGCCGAA AUUACUUG                                                               38

(2) INFORMATION FOR SEQ ID NO:1967:

(i) SEQUENCE CHARACTERISTICS:
        (A) LENGTH: 17 base pairs
        (B) TYPE: nucleic acid -continued ( C ) STRANDEDNESS: single
            ( D ) TOPOLOGY: linear ( x i ) SEQUENCE DESCRIPTION: SEQ ID NO:1967:

CAAGUAAUAC UUAAUGC                                                                17

( 2 ) INFORMATION FOR SEQ ID NO:1968:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1968:

GUUGCAUUCU GAUGAGGCCG AAAGGCCGAA AGUAUUAC                                         38

( 2 ) INFORMATION FOR SEQ ID NO:1969:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1969:
                    GUAAUACUUA AUGCAAC ( 2 ) INFORMATION FOR SEQ ID NO:1970:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1970:

GGUUGCAUCU GAUGAGGCCG AAAGGCCGAA AAGUAUUA                                         38

( 2 ) INFORMATION FOR SEQ ID NO:1971:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1971:

UAAUACUUAA UGCAACC                                                                17

( 2 ) INFORMATION FOR SEQ ID NO:1972:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1972:

AGCUCCUACU GAUGAGGCCG AAAGGCCGAA AGGGUUGC                                         38

( 2 ) INFORMATION FOR SEQ ID NO:1973:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1973:

GCAACCCUCU AGGAGCU                                                      17

( 2 ) INFORMATION FOR SEQ ID NO:1974:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1974:

UGAGCUCCCU GAUGAGGCCG AAAGGCCGAA AGAGGGUU                                38

( 2 ) INFORMATION FOR SEQ ID NO:1975:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1975:

AACCCUCUAG GAGCUCA                                                      17

( 2 ) INFORMATION FOR SEQ ID NO:1976:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1976:

CCACAAAUCU GAUGAGGCCG AAAGGCCGAA AGCUCCUA                                38

( 2 ) INFORMATION FOR SEQ ID NO:1977:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1977:

UAGGAGCUCA UUUGUGG                                                      17

( 2 ) INFORMATION FOR SEQ ID NO:1978:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1978:

UAGCCACACU GAUGAGGCCG AAAGGCCGAA AUGAGCUC                                38

( 2 ) INFORMATION FOR SEQ ID NO:1979:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1979:

GAGCUCAUUU GUGGCUA                                                      17

( 2 ) INFORMATION FOR SEQ ID NO:1980:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1980:

UUAGCCACCU GAUGAGGCCG AAAGGCCGAA AAUGAGCU ( 2 ) INFORMATION FOR SEQ ID NO:1981:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1981:

AGCUCAUUUG UGGCUAA 17

( 2 ) INFORMATION FOR SEQ ID NO:1982:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1982:

AAGAUUAUCU GAUGAGGCCG AAAGGCCGAA AGCCACAA 38

( 2 ) INFORMATION FOR SEQ ID NO:1983:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1983:

UUGUGGCUAA UAAUCUU 17

( 2 ) INFORMATION FOR SEQ ID NO:1984:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1984:

UCCAAGAUCU GAUGAGGCCG AAAGGCCGAA AUUAGCCA 38

( 2 ) INFORMATION FOR SEQ ID NO:1985:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1985:

UGGCUAAUAA UCUUGGA 17

( 2 ) INFORMATION FOR SEQ ID NO:1986:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1986:

AUUUCCAACU GAUGAGGCCG AAAGGCCGAA AUUAUUAG    38

( 2 ) INFORMATION FOR SEQ ID NO:1987:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1987:

CUAAUAAUCU UGGAAAU    17

( 2 ) INFORMATION FOR SEQ ID NO:1988:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1988:

AUAUUUCCCU GAUGAGGCCG AAAGGCCGAA AGAUUAUU    38

( 2 ) INFORMATION FOR SEQ ID NO:1989:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1989:

AAUAAUCUUG GAAAUAU    17

( 2 ) INFORMATION FOR SEQ ID NO:1990:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1990:

AAUAAAGACU GAUGAGGCCG AAAGGCCGAA AUUCCAA    38

( 2 ) INFORMATION FOR SEQ ID NO:1991:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1991:
    UUGGAAAUAU CUUUAUU ( 2 ) INFORMATION FOR SEQ ID NO:1992:

( i ) SEQUENCE CHARACTERISTICS:
    ( A ) LENGTH: 38 base pairs
    ( B ) TYPE: nucleic acid
    ( C ) STRANDEDNESS: single -continued ( D ) TOPOLOGY: linear ( x i ) SEQUENCE DESCRIPTION: SEQ ID NO:1992:

AUAAUAAACU GAUGAGGCCG AAAGGCCGAA AUAUUUCC 38

( 2 ) INFORMATION FOR SEQ ID NO:1993:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1993:

GGAAAUAUCU UUAUUAU 17

( 2 ) INFORMATION FOR SEQ ID NO:1994:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1994:

AUAUAAUACU GAUGAGGCCG AAAGGCCGAA AGAUAUUU 38

( 2 ) INFORMATION FOR SEQ ID NO:1995:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1995:

AAAUAUCUUU AUUAUAU 17

( 2 ) INFORMATION FOR SEQ ID NO:1996:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1996:

UAUAUAAUCU GAUGAGGCCG AAAGGCCGAA AAGAUAUU 38

( 2 ) INFORMATION FOR SEQ ID NO:1997:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1997:

AAUAUCUUUA UUAUAUA 17

( 2 ) INFORMATION FOR SEQ ID NO:1998:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1998:

CUAUAUAACU GAUGAGGCCG AAAGGCCGAA AAAGAUAU 38

( 2 ) INFORMATION FOR SEQ ID NO:1999:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1999:

AUAUCUUUAU UAUAUAG 17

( 2 ) INFORMATION FOR SEQ ID NO:2000:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2000:

UGCUAUAUCU GAUGAGGCCG AAAGGCCGAA AUAAAGAU 38

( 2 ) INFORMATION FOR SEQ ID NO:2001:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2001:

AUCUUUAUUA UAUAGCA 17

( 2 ) INFORMATION FOR SEQ ID NO:2002:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2002:
      AUGCUAUACU GAUGAGGCCG AAAGGCCGAA AAUAAAGA ( 2 ) INFORMATION FOR SEQ ID NO:2003:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2003:

UCUUUAUUAU AUAGCAU 17

( 2 ) INFORMATION FOR SEQ ID NO:2004:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2004:

AAAUGCUACU GAUGAGGCCG AAAGGCCGAA AUAAUAAA 38

( 2 ) INFORMATION FOR SEQ ID NO:2005:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2005:

UUUAUUAUAU AGCAUUU           17

( 2 ) INFORMATION FOR SEQ ID NO:2006:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2006:

AUAAAUGCCU GAUGAGGCCG AAAGGCCGAA AUAUAAUA           38

( 2 ) INFORMATION FOR SEQ ID NO:2007:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2007:

UAUUAUAUAG CAUUUAU           17

( 2 ) INFORMATION FOR SEQ ID NO:2008:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2008:

UCCUCAUACU GAUGAGGCCG AAAGGCCGAA AUGCUAUA           38

( 2 ) INFORMATION FOR SEQ ID NO:2009:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2009:

UAUAGCAUUU AUGAGGA           17

( 2 ) INFORMATION FOR SEQ ID NO:2010:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2010:

CUCCUCAUCU GAUGAGGCCG AAAGGCCGAA AAUGCUAU           38

( 2 ) INFORMATION FOR SEQ ID NO:2011:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2011:

AUAGCAUUUA UGAGGAG     17

( 2 ) INFORMATION FOR SEQ ID NO:2012:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2012:

UCUCCUCACU GAUGAGGCCG AAAGGCCGAA AAAUGCUA     38

( 2 ) INFORMATION FOR SEQ ID NO:2013:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2013:
        UAGCAUUUAU GAGGAGA ( 2 ) INFORMATION FOR SEQ ID NO:2014:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2014:

GACAACAACU GAUGAGGCCG AAAGGCCGAA AUCUCCUC     38

( 2 ) INFORMATION FOR SEQ ID NO:2015:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2015:

GAGGAGAUUU UGUUGUC     17

( 2 ) INFORMATION FOR SEQ ID NO:2016:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2016:

UGACAACACU GAUGAGGCCG AAAGGCCGAA AAUCUCCU     38

( 2 ) INFORMATION FOR SEQ ID NO:2017:

( i ) SEQUENCE CHARACTERISTICS:
    ( A ) LENGTH: 17 base pairs
    ( B ) TYPE: nucleic acid ( C ) STRANDEDNESS: single
            ( D ) TOPOLOGY: linear ( x i ) SEQUENCE DESCRIPTION: SEQ ID NO:2017:

AGGAGAUUUU GUUGUCA                                                                    17

( 2 ) INFORMATION FOR SEQ ID NO:2018:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2018:

CUGACAACCU GAUGAGGCCG AAAGGCCGAA AAAUCUCC                                              38

( 2 ) INFORMATION FOR SEQ ID NO:2019:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2019:

GGAGAUUUUG UUGUCAG                                                                    17

( 2 ) INFORMATION FOR SEQ ID NO:2020:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2020:

AAGCUGACCU GAUGAGGCCG AAAGGCCGAA ACAAAAUC                                              38

( 2 ) INFORMATION FOR SEQ ID NO:2021:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2021:

GAUUUUGUUG UCAGCUU                                                                    17

( 2 ) INFORMATION FOR SEQ ID NO:2022:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2022:

AGCAAGCUCU GAUGAGGCCG AAAGGCCGAA ACAACAAA                                              38

( 2 ) INFORMATION FOR SEQ ID NO:2023:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2023:

UUUGUUGUCA GCUUGCU 17

( 2 ) INFORMATION FOR SEQ ID NO:2024:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2024:

UUUCAAGCCU GAUGAGGCCG AAAGGCCGAA AGCUGACA ( 2 ) INFORMATION FOR SEQ ID NO:2025:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2025:

UGUCAGCUUG CUUGAAA 17

( 2 ) INFORMATION FOR SEQ ID NO:2026:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2026:

UAACUUUCCU GAUGAGGCCG AAAGGCCGAA AGCAAGCU 38

( 2 ) INFORMATION FOR SEQ ID NO:2027:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2027:

AGCUUGCUUG AAAGUUA 17

( 2 ) INFORMATION FOR SEQ ID NO:2028:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2028:

UACAUAAUCU GAUGAGGCCG AAAGGCCGAA ACUUCAA 38

( 2 ) INFORMATION FOR SEQ ID NO:2029:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2029:

UUGAAAGUUA UUAUGUA 17

( 2 ) INFORMATION FOR SEQ ID NO:2030:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2030:

AUACAUAACU GAUGAGGCCG AAAGGCCGAA AACUUUCA        38

( 2 ) INFORMATION FOR SEQ ID NO:2031:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2031:

UGAAAGUUAU UAUGUAU        17

( 2 ) INFORMATION FOR SEQ ID NO:2032:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2032:

UCAUACAUCU GAUGAGGCCG AAAGGCCGAA AUAACUUU        38

( 2 ) INFORMATION FOR SEQ ID NO:2033:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2033:

AAAGUUAUUA UGUAUGA        17

( 2 ) INFORMATION FOR SEQ ID NO:2034:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2034:

UUCAUACACU GAUGAGGCCG AAAGGCCGAA AAUAACUU        38

( 2 ) INFORMATION FOR SEQ ID NO:2035:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2035:
        AAGUUAUUAU GUAUGAA ( 2 ) INFORMATION FOR SEQ ID NO:2036:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2036:

ACUAUUCACU GAUGAGGCCG AAAGGCCGAA ACAUAAUA 38

( 2 ) INFORMATION FOR SEQ ID NO:2037:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2037:

UAUUAUGUAU GAAUAGU 17

( 2 ) INFORMATION FOR SEQ ID NO:2038:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2038:

AAUAAAACCU GAUGAGGCCG AAAGGCCGAA AUUCAUAC 38

( 2 ) INFORMATION FOR SEQ ID NO:2039:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2039:

GUAUGAAUAG UUUUAUU 17

( 2 ) INFORMATION FOR SEQ ID NO:2040:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2040:

UUCAAUAACU GAUGAGGCCG AAAGGCCGAA ACAUUCA 38

( 2 ) INFORMATION FOR SEQ ID NO:2041:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2041:

UGAAUAGUUU UAUUGAA 17

( 2 ) INFORMATION FOR SEQ ID NO:2042:

( i ) SEQUENCE CHARACTERISTICS:
  ( A ) LENGTH: 38 base pairs (B) TYPE: nucleic acid
        (C) STRANDEDNESS: single
        (D) TOPOLOGY: linear (xi) SEQUENCE DESCRIPTION: SEQ ID NO:2042:

UUUCAAUACU GAUGAGGCCG AAAGGCCGAA AACUAUUC                                           38

(2) INFORMATION FOR SEQ ID NO:2043:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2043:

GAAUAGUUUU AUUGAAA                                                                  17

(2) INFORMATION FOR SEQ ID NO:2044:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2044:

UUUUCAAUCU GAUGAGGCCG AAAGGCCGAA AAACUAUU                                           38

(2) INFORMATION FOR SEQ ID NO:2045:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2045:

AAUAGUUUUA UUGAAAA                                                                  17

(2) INFORMATION FOR SEQ ID NO:2046:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2046:
                    UUUUUCAACU GAUGAGGCCG AAAGGCCGAA AAAACUAU (2) INFORMATION FOR SEQ ID NO:2047:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2047:

AUAGUUUUAU UGAAAAA                                                                  17

(2) INFORMATION FOR SEQ ID NO:2048:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:2048:

AUUUUUUCCU GAUGAGGCCG AAAGGCCGAA AUAAAACU 38

(2) INFORMATION FOR SEQ ID NO:2049:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2049:

AGUUUUAUUG AAAAAAU 17

(2) INFORMATION FOR SEQ ID NO:2050:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2050:

AAAAAUAUCU GAUGAGGCCG AAAGGCCGAA AUUUUUUC 38

(2) INFORMATION FOR SEQ ID NO:2051:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2051:

GAAAAAAUUA UAUUUUU 17

(2) INFORMATION FOR SEQ ID NO:2052:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2052:

UAAAAUACU GAUGAGGCCG AAAGGCCGAA AAUUUUUU 38

(2) INFORMATION FOR SEQ ID NO:2053:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2053:

AAAAAAUUAU AUUUUUA 17

(2) INFORMATION FOR SEQ ID NO:2054:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2054:

AAUAAAAACU GAUGAGGCCG AAAGGCCGAA AUAAUUUU                         38

( 2 ) INFORMATION FOR SEQ ID NO:2055:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2055:

AAAAUUAUAU UUUUAUU                                                17

( 2 ) INFORMATION FOR SEQ ID NO:2056:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2056:

UGAAUAAACU GAUGAGGCCG AAAGGCCGAA AUAUAAUU                         38

( 2 ) INFORMATION FOR SEQ ID NO:2057:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2057:

AAUUAUAUUU UUAUUCA ( 2 ) INFORMATION FOR SEQ ID NO:2058:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2058:

CUGAAUAACU GAUGAGGCCG AAAGGCCGAA AAUAUAAU                         38

( 2 ) INFORMATION FOR SEQ ID NO:2059:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2059:

AUUAUAUUUU UAUUCAG                                                17

( 2 ) INFORMATION FOR SEQ ID NO:2060:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2060:

ACUGAAUACU GAUGAGGCCG AAAGGCCGAA AAAUAUAA                         38

( 2 ) INFORMATION FOR SEQ ID NO:2061:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2061:

UUAUAUUUUU AUUCAGU      17

( 2 ) INFORMATION FOR SEQ ID NO:2062:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2062:

UACUGAAUCU GAUGAGGCCG AAAGGCCGAA AAAAUAUA      38

( 2 ) INFORMATION FOR SEQ ID NO:2063:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2063:

UAUAUUUUUA UUCAGUA      17

( 2 ) INFORMATION FOR SEQ ID NO:2064:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2064:

UUACUGAACU GAUGAGGCCG AAAGGCCGAA AAAAAUAU      38

( 2 ) INFORMATION FOR SEQ ID NO:2065:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2065:

AUAUUUUUAU UCAGUAA      17

( 2 ) INFORMATION FOR SEQ ID NO:2066:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2066:

AAUUACUGCU GAUGAGGCCG AAAGGCCGAA AUAAAAAU      38

( 2 ) INFORMATION FOR SEQ ID NO:2067:

( i ) SEQUENCE CHARACTERISTICS:

(A) LENGTH: 17 base pairs
            (B) TYPE: nucleic acid
            (C) STRANDEDNESS: single
            (D) TOPOLOGY: linear (x i) SEQUENCE DESCRIPTION: SEQ ID NO:2067:

AUUUUUAUUC AGUAAUU                                                                                   17

(2) INFORMATION FOR SEQ ID NO:2068:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (x i) SEQUENCE DESCRIPTION: SEQ ID NO:2068:
                    AAAUUACUCU GAUGAGGCCG AAAGGCCGAA AAUAAAAA (2) INFORMATION FOR SEQ ID NO:2069:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (x i) SEQUENCE DESCRIPTION: SEQ ID NO:2069:

UUUUUAUUCA GUAAUUU                                                                                   17

(2) INFORMATION FOR SEQ ID NO:2070:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (x i) SEQUENCE DESCRIPTION: SEQ ID NO:2070:

AAUUAAAUCU GAUGAGGCCG AAAGGCCGAA ACUGAAUA                                                             38

(2) INFORMATION FOR SEQ ID NO:2071:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (x i) SEQUENCE DESCRIPTION: SEQ ID NO:2071:

UAUUCAGUAA UUUAAUU                                                                                   17

(2) INFORMATION FOR SEQ ID NO:2072:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (x i) SEQUENCE DESCRIPTION: SEQ ID NO:2072:

CAAAAUUACU GAUGAGGCCG AAAGGCCGAA AUUACUGA                                                             38

(2) INFORMATION FOR SEQ ID NO:2073:

(i) SEQUENCE CHARACTERISTICS:
            (A) LENGTH: 17 base pairs
            (B) TYPE: nucleic acid
            (C) STRANDEDNESS: single
            (D) TOPOLOGY: linear ( x i ) SEQUENCE DESCRIPTION: SEQ ID NO:2073:

UCAGUAAUUU AAUUUUG 17

( 2 ) INFORMATION FOR SEQ ID NO:2074:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2074:

ACAAAAUUCU GAUGAGGCCG AAAGGCCGAA AAUUACUG 38

( 2 ) INFORMATION FOR SEQ ID NO:2075:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2075:

CAGUAAUUUA AUUUUGU 17

( 2 ) INFORMATION FOR SEQ ID NO:2076:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2076:

UACAAAAUCU GAUGAGGCCG AAAGGCCGAA AAAUUACU 38

( 2 ) INFORMATION FOR SEQ ID NO:2077:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2077:

AGUAAUUUAA UUUUGUA 17

( 2 ) INFORMATION FOR SEQ ID NO:2078:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2078:

AUUUACAACU GAUGAGGCCG AAAGGCCGAA AUUAAAUU 38

( 2 ) INFORMATION FOR SEQ ID NO:2079:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2079:

AAUUUAAUUU UGUAAAU ( 2 ) INFORMATION FOR SEQ ID NO:2080:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2080:

CAUUUACACU GAUGAGGCCG AAAGGCCGAA AAUUAAAU     38

( 2 ) INFORMATION FOR SEQ ID NO:2081:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2081:

AUUUAAUUUU GUAAAUG     17

( 2 ) INFORMATION FOR SEQ ID NO:2082:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2082:

GCAUUUACCU GAUGAGGCCG AAAGGCCGAA AAAUUAAA     38

( 2 ) INFORMATION FOR SEQ ID NO:2083:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2083:

UUUAAUUUUG UAAAUGC     17

( 2 ) INFORMATION FOR SEQ ID NO:2084:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2084:

UUGGCAUUCU GAUGAGGCCG AAAGGCCGAA ACAAAAUU     38

( 2 ) INFORMATION FOR SEQ ID NO:2085:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2085:

AAUUUUGUAA AUGCCAA     17

( 2 ) INFORMATION FOR SEQ ID NO:2086:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2086:

UAGCAGCGCU GAUGAGGCCG AAAGGCCGAA ACACAUUU 38

( 2 ) INFORMATION FOR SEQ ID NO:2087:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2087:

AAAUGUGUUC GCUGCUA 17

( 2 ) INFORMATION FOR SEQ ID NO:2088:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2088:

AUAGCAGCCU GAUGAGGCCG AAAGGCCGAA AACACAUU 38

( 2 ) INFORMATION FOR SEQ ID NO:2089:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2089:

AAUGUGUUCG CUGCUAU 17

( 2 ) INFORMATION FOR SEQ ID NO:2090:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2090:

UAAAACCACU GAUGAGGCCG AAAGGCCGAA AGCAGCGA ( 2 ) INFORMATION FOR SEQ ID NO:2091:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2091:

UCGCUGCUAU GGUUUUA 17

( 2 ) INFORMATION FOR SEQ ID NO:2092:

( i ) SEQUENCE CHARACTERISTICS:
        ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO:2092:

UAGGCUAACU GAUGAGGCCG AAAGGCCGAA ACCAUAGC 38

(2) INFORMATION FOR SEQ ID NO:2093:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2093:

GCUAUGGUUU UAGCCUA 17

(2) INFORMATION FOR SEQ ID NO:2094:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2094:

AUAGGCUACU GAUGAGGCCG AAAGGCCGAA AACCAUAG 38

(2) INFORMATION FOR SEQ ID NO:2095:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2095:

CUAUGGUUUU AGCCUAU 17

(2) INFORMATION FOR SEQ ID NO:2096:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2096:

UAUAGGCUCU GAUGAGGCCG AAAGGCCGAA AAACCAUA 38

(2) INFORMATION FOR SEQ ID NO:2097:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2097:

UAUGGUUUUA GCCUAUA 17

(2) INFORMATION FOR SEQ ID NO:2098:

(i) SEQUENCE CHARACTERISTICS:
(A) LENGTH: 38 base pairs
(B) TYPE: nucleic acid
(C) STRANDEDNESS: single (D) TOPOLOGY: linear (xi) SEQUENCE DESCRIPTION: SEQ ID NO:2098:

CUAUAGGCCU GAUGAGGCCG AAAGGCCGAA AAAACCAU 38

(2) INFORMATION FOR SEQ ID NO:2099:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2099:

AUGGUUUUAG CCUAUAG 17

(2) INFORMATION FOR SEQ ID NO:2100:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2100:

CAUGACUACU GAUGAGGCCG AAAGGCCGAA AGGCUAAA 38

(2) INFORMATION FOR SEQ ID NO:2101:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2101:

UUUAGCCUAU AGUCAUG (2) INFORMATION FOR SEQ ID NO:2102:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2102:

AGCAUGACCU GAUGAGGCCG AAAGGCCGAA AUAGGCUA 38

(2) INFORMATION FOR SEQ ID NO:2103:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2103:

UAGCCUAUAG UCAUGCU 17

(2) INFORMATION FOR SEQ ID NO:2104:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2104:

AGCAGCAUCU GAUGAGGCCG AAAGGCCGAA ACUAUAGG                                                                38

( 2 ) INFORMATION FOR SEQ ID NO:2105:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2105:

CCUAUAGUCA UGCUGCU                                                                                         17

( 2 ) INFORMATION FOR SEQ ID NO:2106:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2106:

ACACUAGCCU GAUGAGGCCG AAAGGCCGAA AGCAGCAU                                                                  38

( 2 ) INFORMATION FOR SEQ ID NO:2107:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2107:

AUGCUGCUAG CUAGUGU                                                                                         17

( 2 ) INFORMATION FOR SEQ ID NO:2108:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2108:

CCUGACACCU GAUGAGGCCG AAAGGCCGAA AGCUAGCA                                                                  38

( 2 ) INFORMATION FOR SEQ ID NO:2109:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2109:

UGCUAGCUAG UGUCAGG                                                                                         17

( 2 ) INFORMATION FOR SEQ ID NO:2110:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2110:

UGCCCCCUCU GAUGAGGCCG AAAGGCCGAA ACACUAGC                                                                  38

( 2 ) INFORMATION FOR SEQ ID NO:2111:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2111:

GCUAGUGUCA GGGGGCA                                                  17

( 2 ) INFORMATION FOR SEQ ID NO:2112:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2112:

CUAAGCUCCU GAUGAGGCCG AAAGGCCGAA AUUGCCCC        38

( 2 ) INFORMATION FOR SEQ ID NO:2113:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2113:

GGGGCAAUAG AGCUUAG                                                  17

( 2 ) INFORMATION FOR SEQ ID NO:2114:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2114:

UUCCAUCUCU GAUGAGGCCG AAAGGCCGAA AGCUCUAU        38

( 2 ) INFORMATION FOR SEQ ID NO:2115:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2115:

AUAGAGCUUA GAUGGAA                                                  17

( 2 ) INFORMATION FOR SEQ ID NO:2116:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2116:

UUUCCAUCCU GAUGAGGCCG AAAGGCCGAA AAGCUCUA        38

( 2 ) INFORMATION FOR SEQ ID NO:2117:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2117:

UAGAGCUUAG AUGGAAA                                                                                      17

(2) INFORMATION FOR SEQ ID NO:2118:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2118:

CUAACACCCU GAUGAGGCCG AAAGGCCGAA AGUCUCUU                                                               38

(2) INFORMATION FOR SEQ ID NO:2119:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2119:

AAGAGACUCG GUGUUAG                                                                                      17

(2) INFORMATION FOR SEQ ID NO:2120:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2120:

CGUUAUCUCU GAUGAGGCCG AAAGGCCGAA ACACCGAG                                                               38

(2) INFORMATION FOR SEQ ID NO:2121:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2121:

CUCGGUGUUA GAUAACG                                                                                      17

(2) INFORMATION FOR SEQ ID NO:2122:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2122:

CCGUUAUCCU GAUGAGGCCG AAAGGCCGAA AACACCGA                                                               38

(2) INFORMATION FOR SEQ ID NO:2123:

(i) SEQUENCE CHARACTERISTICS:
        (A) LENGTH: 17 base pairs
        (B) TYPE: nucleic acid (C) STRANDEDNESS: single
(D) TOPOLOGY: linear (xi) SEQUENCE DESCRIPTION: SEQ ID NO:2123:

UCGGUGUUAG AUAACGG (2) INFORMATION FOR SEQ ID NO:2124:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2124:

UAGUCCGUCU GAUGAGGCCG AAAGGCCGAA AUCUAACA 38

(2) INFORMATION FOR SEQ ID NO:2125:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2125:

UGUUAGAUAA CGGACUA 17

(2) INFORMATION FOR SEQ ID NO:2126:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2126:

CUAGUGCACU GAUGAGGCCG AAAGGCCGAA AGUCCGUU 38

(2) INFORMATION FOR SEQ ID NO:2127:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2127:

AACGGACUAU GCACUAG 17

(2) INFORMATION FOR SEQ ID NO:2128:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2128:

UGGAAUACCU GAUGAGGCCG AAAGGCCGAA AGUGCAUA 38

(2) INFORMATION FOR SEQ ID NO:2129:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2129:

UAUGCACUAG UAUUCCA 17

(2) INFORMATION FOR SEQ ID NO:2130:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2130:

GUCUGGAACU GAUGAGGCCG AAAGGCCGAA ACUAGUGC 38

(2) INFORMATION FOR SEQ ID NO:2131:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2131:

GCACUAGUAU UCCAGAC 17

(2) INFORMATION FOR SEQ ID NO:2132:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2132:

AAGUCUGGCU GAUGAGGCCG AAAGGCCGAA AUACUAGU 38

(2) INFORMATION FOR SEQ ID NO:2133:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2133:

ACUAGUAUUC CAGACUU 17

(2) INFORMATION FOR SEQ ID NO:2134:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2134:
        AAAGUCUGCU GAUGAGGCCG AAAGGCCGAA AAUACUAG (2) INFORMATION FOR SEQ ID NO:2135:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2135:

CUAGUAUUCC AGACUUU 17

( 2 ) INFORMATION FOR SEQ ID NO:2136:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2136:

AAAUAAAACU GAUGAGGCCG AAAGGCCGAA AGUCUGGA        38

( 2 ) INFORMATION FOR SEQ ID NO:2137:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2137:

UCCAGACUUU UUUAUUU        17

( 2 ) INFORMATION FOR SEQ ID NO:2138:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2138:

AAAAUAAACU GAUGAGGCCG AAAGGCCGAA AAGUCUGG        38

( 2 ) INFORMATION FOR SEQ ID NO:2139:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2139:

CCAGACUUUU UUAUUUU        17

( 2 ) INFORMATION FOR SEQ ID NO:2140:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2140:

AAAAAUAACU GAUGAGGCCG AAAGGCCGAA AAAGUCUG        38

( 2 ) INFORMATION FOR SEQ ID NO:2141:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2141:

CAGACUUUUU UAUUUUU        17

( 2 ) INFORMATION FOR SEQ ID NO:2142:

( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:2142:

AAAAAUACU GAUGAGGCCG AAAGGCCGAA AAAAGUCU 38

( 2 ) INFORMATION FOR SEQ ID NO:2143:

: ( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:2143:

AGACUUUUUU AUUUUUU 17

( 2 ) INFORMATION FOR SEQ ID NO:2144:

: ( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:2144:

UAAAAAUCU GAUGAGGCCG AAAGGCCGAA AAAAGUC 38

( 2 ) INFORMATION FOR SEQ ID NO:2145:

: ( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:2145:

GACUUUUUUA UUUUUUA ( 2 ) INFORMATION FOR SEQ ID NO:2146:

: ( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:2146:

AUAAAAACU GAUGAGGCCG AAAGGCCGAA AAAAAGU 38

( 2 ) INFORMATION FOR SEQ ID NO:2147:

: ( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:2147:

ACUUUUUUAU UUUUUAU 17

( 2 ) INFORMATION FOR SEQ ID NO:2148:

: ( i ) SEQUENCE CHARACTERISTICS:
: ( A ) LENGTH: 38 base pairs
: ( B ) TYPE: nucleic acid
: ( C ) STRANDEDNESS: single ( D ) TOPOLOGY: linear ( x i ) SEQUENCE DESCRIPTION: SEQ ID NO:2148:

AUAUAAAACU GAUGAGGCCG AAAGGCCGAA AUAAAAAA 38

( 2 ) INFORMATION FOR SEQ ID NO:2149:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2149:

UUUUUUAUUU UUUAUAU 17

( 2 ) INFORMATION FOR SEQ ID NO:2150:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2150:

UAUAUAAACU GAUGAGGCCG AAAGGCCGAA AAUAAAAA 38

( 2 ) INFORMATION FOR SEQ ID NO:2151:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2151:

UUUUUAUUUU UUAUAUA 17

( 2 ) INFORMATION FOR SEQ ID NO:2152:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2152:

AUAUAUAACU GAUGAGGCCG AAAGGCCGAA AAAUAAAA 38

( 2 ) INFORMATION FOR SEQ ID NO:2153:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2153:

UUUUAUUUUU UAUAUAU 17

( 2 ) INFORMATION FOR SEQ ID NO:2154:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear (x i) SEQUENCE DESCRIPTION: SEQ ID NO:2154:

UAUAUAUACU GAUGAGGCCG AAAGGCCGAA AAAAUAAA                                38

(2) INFORMATION FOR SEQ ID NO:2155:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2155:

UUUAUUUUUU AUAUAUA                                                         17

(2) INFORMATION FOR SEQ ID NO:2156:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2156:

AUAUAUAUCU GAUGAGGCCG AAAGGCCGAA AAAAAUAA (2) INFORMATION FOR SEQ ID NO:2157:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2157:

UUAUUUUUUA UAUAUAU                                                         17

(2) INFORMATION FOR SEQ ID NO:2158:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2158:

CAUAUAUACU GAUGAGGCCG AAAGGCCGAA AAAAAAUA                                38

(2) INFORMATION FOR SEQ ID NO:2159:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2159:

UAUUUUUUAU AUAUAUG                                                         17

(2) INFORMATION FOR SEQ ID NO:2160:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2160:

UACAUAUACU GAUGAGGCCG AAAGGCCGAA AUAAAAA                                 38

( 2 ) INFORMATION FOR SEQ ID NO:2161:

( i ) SEQUENCE CHARACTERISTICS:
　　　　　　　　( A ) LENGTH: 17 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:2161:

UUUUUUAUAU AUAUGUA　　　　　　　　　　　　　　　　　　　　　　　　　　　　　　　　　　17

( 2 ) INFORMATION FOR SEQ ID NO:2162:

( i ) SEQUENCE CHARACTERISTICS:
　　　　　　　　( A ) LENGTH: 38 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:2162:

GGUACAUACU GAUGAGGCCG AAAGGCCGAA AUAUAAAA　　　　　　　　　　　　　　　　　　38

( 2 ) INFORMATION FOR SEQ ID NO:2163:

( i ) SEQUENCE CHARACTERISTICS:
　　　　　　　　( A ) LENGTH: 17 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:2163:

UUUUAUAUAU AUGUACC　　　　　　　　　　　　　　　　　　　　　　　　　　　　　　　　　　17

( 2 ) INFORMATION FOR SEQ ID NO:2164:

( i ) SEQUENCE CHARACTERISTICS:
　　　　　　　　( A ) LENGTH: 38 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:2164:

AAGGUACACU GAUGAGGCCG AAAGGCCGAA AUAUAUAA　　　　　　　　　　　　　　　　　　38

( 2 ) INFORMATION FOR SEQ ID NO:2165:

( i ) SEQUENCE CHARACTERISTICS:
　　　　　　　　( A ) LENGTH: 17 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:2165:

UUAUAUAUAU GUACCUU　　　　　　　　　　　　　　　　　　　　　　　　　　　　　　　　　　17

( 2 ) INFORMATION FOR SEQ ID NO:2166:

( i ) SEQUENCE CHARACTERISTICS:
　　　　　　　　( A ) LENGTH: 38 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:2166:

GGAAAAGGCU GAUGAGGCCG AAAGGCCGAA ACAUAUAU　　　　　　　　　　　　　　　　　　38

( 2 ) INFORMATION FOR SEQ ID NO:2167:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2167:
AUAUAUGUAC CUUUUCC ( 2 ) INFORMATION FOR SEQ ID NO:2168:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2168:

AAAAGGAACU GAUGAGGCCG AAAGGCCGAA AGGUACAU 38

( 2 ) INFORMATION FOR SEQ ID NO:2169:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2169:

AUGUACCUUU UCCUUUU 17

( 2 ) INFORMATION FOR SEQ ID NO:2170:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2170:

CAAAAGGACU GAUGAGGCCG AAAGGCCGAA AAGGUACA 38

( 2 ) INFORMATION FOR SEQ ID NO:2171:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2171:

UGUACCUUUU CCUUUUG 17

( 2 ) INFORMATION FOR SEQ ID NO:2172:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2172:

ACAAAAGGCU GAUGAGGCCG AAAGGCCGAA AAAGGUAC 38

( 2 ) INFORMATION FOR SEQ ID NO:2173:

( i ) SEQUENCE CHARACTERISTICS:
( A ) LENGTH: 17 base pairs
( B ) TYPE: nucleic acid ( C ) STRANDEDNESS: single
( D ) TOPOLOGY: linear ( x i ) SEQUENCE DESCRIPTION: SEQ ID NO:2173:

GUACCUUUUC CUUUUGU 17

( 2 ) INFORMATION FOR SEQ ID NO:2174:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2174:

GACAAAAGCU GAUGAGGCCG AAAGGCCGAA AAAAGGUA 38

( 2 ) INFORMATION FOR SEQ ID NO:2175:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2175:

UACCUUUUCC UUUUGUC 17

( 2 ) INFORMATION FOR SEQ ID NO:2176:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2176:

AUUGACAACU GAUGAGGCCG AAAGGCCGAA AGGAAAAG 38

( 2 ) INFORMATION FOR SEQ ID NO:2177:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2177:

CUUUUCCUUU UGUCAAU 17

( 2 ) INFORMATION FOR SEQ ID NO:2178:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2178:
AAUUGACACU GAUGAGGCCG AAAGGCCGAA AAGGAAAA ( 2 ) INFORMATION FOR SEQ ID NO:2179:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2179:

UUUCCUUUU GUCAAUU 17

(2) INFORMATION FOR SEQ ID NO:2180:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2180:

CAAUUGACCU GAUGAGGCCG AAAGGCCGAA AAAGGAAA 38

(2) INFORMATION FOR SEQ ID NO:2181:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2181:

UUUCCUUUUG UCAAUUG 17

(2) INFORMATION FOR SEQ ID NO:2182:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2182:

GCGAGGCGAG AAGGGCUAC CAGAGAAACA CACGUUGUGG UACAUUACCU GGUA 54

(2) INFORMATION FOR SEQ ID NO:2183:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2183:

AGCCCCGGCC CGCCUCGC 18

(2) INFORMATION FOR SEQ ID NO:2184:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2184:

CAUGGCGAAG AAGGCCGGAC CAGAGAAACA CACGUUGUGG UACAUUACCU GGUA 54

(2) INFORMATION FOR SEQ ID NO:2185:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2185:

CCGGCCCGCC UCGCCAUG 18

( 2 ) INFORMATION FOR SEQ ID NO:2186:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2186:

AUUUGGGCAG AAGCCCAUAC CAGAGAAACA CACGUUGUGG UACAUUACCU GGUA 54

( 2 ) INFORMATION FOR SEQ ID NO:2187:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2187:

AUGGGCUGCU GCCCAAAU 18

( 2 ) INFORMATION FOR SEQ ID NO:2188:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2188:

CAGAUUUGAG AAGCAGCCAC CAGAGAAACA CACGUUGUGG UACAUUACCU GGUA 54

( 2 ) INFORMATION FOR SEQ ID NO:2189:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2189:
GGCUGCUGCC CAAAUCUG ( 2 ) INFORMATION FOR SEQ ID NO:2190:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2190:

UUCCAGUCAG AAGUUCCGAC CAGAGAAACA CACGUUGUGG UACAUUACCU GGUA 54

( 2 ) INFORMATION FOR SEQ ID NO:2191:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2191:

CGGAACAGAC GACUGGAA 18

( 2 ) INFORMATION FOR SEQ ID NO:2192:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2192:

UCCGGUUGAG AAGAUAAUAC CAGAGAAACA CACGUUGUGG UACAUUACCU GGUA    54

( 2 ) INFORMATION FOR SEQ ID NO:2193:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2193:

AUUAUCUGCC CAACCGGA    18

( 2 ) INFORMATION FOR SEQ ID NO:2194:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2194:

CACUGUACAG AAGUCCGGAC CAGAGAAACA CACGUUGUGG UACAUUACCU GGUA    54

( 2 ) INFORMATION FOR SEQ ID NO:2195:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2195:

CCGGACAGAU GUACAGUG    18

( 2 ) INFORMATION FOR SEQ ID NO:2196:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2196:

CUCUGCCCAG AAGUUCCCAC CAGAGAAACA CACGUUGUGG UACAUUACCU GGUA    54

( 2 ) INFORMATION FOR SEQ ID NO:2197:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2197:

GGGAACAGAU GGGCAGAG    18

( 2 ) INFORMATION FOR SEQ ID NO:2198:

( i ) SEQUENCE CHARACTERISTICS:
    ( A ) LENGTH: 54 base pairs (B) TYPE: nucleic acid
(C) STRANDEDNESS: single
(D) TOPOLOGY: linear (xi) SEQUENCE DESCRIPTION: SEQ ID NO:2198:

GUCCGGGCAG AAGCUUUGAC CAGAGAAACA CACGUUGUGG UACAUUACCU GGUA  54

(2) INFORMATION FOR SEQ ID NO:2199:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2199:

CAAAGCUGCU GCCCGGAC  18

(2) INFORMATION FOR SEQ ID NO:2200:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:2200:

UCCGUCCGAG AAGCAGCUAC CAGAGAAACA CACGUUGUGG UACAUUACCU GGUA  54

(2) INFORMATION FOR SEQ ID NO:2201:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2201:

AGCUGCUGCC CGGACGGA  18

(2) INFORMATION FOR SEQ ID NO:2202:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:2202:

AUCAGUCCAG AAGGGCAGAC CAGAGAAACA CACGUUGUGG UACAUUACCU GGUA  54

(2) INFORMATION FOR SEQ ID NO:2203:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2203:

CUGCCCGGAC GGACUGAU  18

(2) INFORMATION FOR SEQ ID NO:2204:

(i) SEQUENCE CHARACTERISTICS:
(A) LENGTH: 54 base pairs
(B) TYPE: nucleic acid
(C) STRANDEDNESS: single (D) TOPOLOGY: linear (xi) SEQUENCE DESCRIPTION: SEQ ID NO:2204:

CAUUAUCAAG AAGUCCGGAC CAGAGAAACA CACGUUGUGG UACAUUACCU GGUA 54

(2) INFORMATION FOR SEQ ID NO:2205:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:2205:

CCGGACGGAC UGAUAAUG 18

(2) INFORMATION FOR SEQ ID NO:2206:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (xi) SEQUENCE DESCRIPTION: SEQ ID NO:2206:

CCACUGGCAG AAGGCUGGAC CAGAGAAACA CACGUUGUGG UACAUUACCU GGUA 54

(2) INFORMATION FOR SEQ ID NO:2207:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:2207:

CCAGCCAGAC GCCAGUGG 18

(2) INFORMATION FOR SEQ ID NO:2208:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (xi) SEQUENCE DESCRIPTION: SEQ ID NO:2208:

UUGGAGAGAG AAGAGAUGAC CAGAGAAACA CACGUUGUGG UACAUUACCU GGUA 54

(2) INFORMATION FOR SEQ ID NO:2209:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:2209:

CAUCUCAGCU CUCUCCAA 18

(2) INFORMATION FOR SEQ ID NO:2210:

(i) SEQUENCE CHARACTERISTICS:
    (A) LENGTH: 54 base pairs
    (B) TYPE: nucleic acid
    (C) STRANDEDNESS: single
    (D) TOPOLOGY: linear ( x i ) SEQUENCE DESCRIPTION: SEQ ID NO:2210:

UGACGGAGAG AAGGCCACAC CAGAGAAACA CACGUUGUGG UACAUUACCU GGUA    54

( 2 ) INFORMATION FOR SEQ ID NO:2211:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2211:

GUGGCCAGUC CUCCGUCA ( 2 ) INFORMATION FOR SEQ ID NO:2212:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2212:

UGCAAUGCAG AAGGAUAGAC CAGAGAAACA CACGUUGUGG UACAUUACCU GGUA    54

( 2 ) INFORMATION FOR SEQ ID NO:2213:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2213:

CUAUCCUGUC GCAUUGCA    18

( 2 ) INFORMATION FOR SEQ ID NO:2214:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2214:

CCGCAGCCAG AAGAGGGAAC CAGAGAAACA CACGUUGUGG UACAUUACCU GGUA    54

( 2 ) INFORMATION FOR SEQ ID NO:2215:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2215:

UCCCUCAGCC GGCUGCGG    18

( 2 ) INFORMATION FOR SEQ ID NO:2216:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2216:

GCUGCCGCAG AAGGCUGAAC CAGAGAAACA CACGUUGUGG UACAUUACCU GGUA    54

( 2 ) INFORMATION FOR SEQ ID NO:2217:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2217:

UCAGCCGGCU GCGGCAGC        18

( 2 ) INFORMATION FOR SEQ ID NO:2218:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2218:

CUGUUGACAG AAGGAGCAAC CAGAGAAACA CACGUUGUGG UACAUUACCU GGUA    54

( 2 ) INFORMATION FOR SEQ ID NO:2219:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2219:

UGCUCCUGAU GUCAACAG        18

( 2 ) INFORMATION FOR SEQ ID NO:2220:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2220:

GAGGUCUGAG AAGGUCCAAC CAGAGAAACA CACGUUGUGG UACAUUACCU GGUA    54

( 2 ) INFORMATION FOR SEQ ID NO:2221:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2221:

UGGACCAGAC CAGACCUC        18

( 2 ) INFORMATION FOR SEQ ID NO:2222:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2222:

CCCAUGAGAG AAGGUCUGAC CAGAGAAACA CACGUUGUGG UACAUUACCU GGUA    54

( 2 ) INFORMATION FOR SEQ ID NO:2223:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:2223:

CAGACCAGAC CUCAUGGG      18

(2) INFORMATION FOR SEQ ID NO:2224:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (xi) SEQUENCE DESCRIPTION: SEQ ID NO:2224:

AAACAGGAAG AAGGUGCAAC CAGAGAAACA CACGUUGUGG UACAUUACCU GGUA      54

(2) INFORMATION FOR SEQ ID NO:2225:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:2225:

UGCACCUGUU UCCUGUUU      18

(2) INFORMATION FOR SEQ ID NO:2226:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (xi) SEQUENCE DESCRIPTION: SEQ ID NO:2226:

UUCUCCCAAG AAGGAAACAC CAGAGAAACA CACGUUGUGG UACAUUACCU GGUA      54

(2) INFORMATION FOR SEQ ID NO:2227:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:2227:

GUUUCCUGUU UGGGAGAA      18

(2) INFORMATION FOR SEQ ID NO:2228:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (xi) SEQUENCE DESCRIPTION: SEQ ID NO:2228:

GAUCUGCAAG AAGAGAUGAC CAGAGAAACA CACGUUGUGG UACAUUACCU GGUA      54

(2) INFORMATION FOR SEQ ID NO:2229:

(i) SEQUENCE CHARACTERISTICS:

(A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2229:

CAUCUCUGCC UGCAGAUC                                                                                      18

(2) INFORMATION FOR SEQ ID NO:2230:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2230:

GAGCCGGGAG AAGCAGGCAC CAGAGAAACA CACGUUGUGG UACAUUACCU GGUA                                               54

(2) INFORMATION FOR SEQ ID NO:2231:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2231:

GCCUGCAGAU CCCGGCUC                                                                                      18

(2) INFORMATION FOR SEQ ID NO:2232:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2232:

AGGUAGGGAG AAGGGAUCAC CAGAGAAACA CACGUUGUGG UACAUUACCU GGUA                                               54

(2) INFORMATION FOR SEQ ID NO:2233:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2233:

GAUCCCGGCU CCCUACCU                                                                                      18

(2) INFORMATION FOR SEQ ID NO:2234:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2234:

AAUCUAUAAG AAGGAGUGAC CAGAGAAACA CACGUUGUGG UACAUUACCU GGUA                                               54

(2) INFORMATION FOR SEQ ID NO:2235:

(i) SEQUENCE CHARACTERISTICS:
        (A) LENGTH: 18 base pairs
        (B) TYPE: nucleic acid ( C ) STRANDEDNESS: single
        ( D ) TOPOLOGY: linear ( x i ) SEQUENCE DESCRIPTION: SEQ ID NO:2235:

CACUCCAGUU UAUAGAUU                                                                                        18

( 2 ) INFORMATION FOR SEQ ID NO:2236:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2236:

UUUUCACAAG AAGGUCUCAC CAGAGAAACA CACGUUGUGG UACAUUACCU GGUA                                                  54

( 2 ) INFORMATION FOR SEQ ID NO:2237:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2237:

GAGACCAGAC UGUGAAAA                                                                                        18

( 2 ) INFORMATION FOR SEQ ID NO:2238:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2238:

AUUCUUGAG AAGCAAGGAC CAGAGAAACA CACGUUGUGG UACAUUACCU GGUA                                                   54

( 2 ) INFORMATION FOR SEQ ID NO:2239:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2239:

CCUUGCAGCU CAAGAAAU                                                                                        18

( 2 ) INFORMATION FOR SEQ ID NO:2240:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2240:

CUUCAGGGAG AAGUAUUUAC CAGAGAAACA CACGUUGUGG UACAUUACCU GGUA                                                  54

( 2 ) INFORMATION FOR SEQ ID NO:2241:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2241:

AAAUACGGUC CCCUGAAG                                                                                      18

( 2 ) INFORMATION FOR SEQ ID NO:2242:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2242:

GGGAGGGGAG AAGAGGUAAC CAGAGAAACA CACGUUGUGG UACAUUACCU GGUA            54

( 2 ) INFORMATION FOR SEQ ID NO:2243:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2243:

UACCUCAGAC CCCCUCCC                                                                                      18

( 2 ) INFORMATION FOR SEQ ID NO:2244:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2244:

CCAGAUUCAG AAGAUUCCAC CAGAGAAACA CACGUUGUGG UACAUUACCU GGUA            54

( 2 ) INFORMATION FOR SEQ ID NO:2245:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2245:

GGAAUCGGAU GAAUCUGG                                                                                      18

( 2 ) INFORMATION FOR SEQ ID NO:2246:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2246:

GUGGUUUGAG AAGAAGAAAC CAGAGAAACA CACGUUGUGG UACAUUACCU GGUA            54

( 2 ) INFORMATION FOR SEQ ID NO:2247:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2247:

```
UUCUUCUGCU CAAACCAC                                                                                    18
```

( 2 ) INFORMATION FOR SEQ ID NO:2248:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2248:

```
GGUGCUCAAG AAGUUCUCAC CAGAGAAACA CACGUUGUGG UACAUUACCU GGUA           54
```

( 2 ) INFORMATION FOR SEQ ID NO:2249:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2249:

```
GAGAACAGCC UGAGCACC                                                                                    18
```

( 2 ) INFORMATION FOR SEQ ID NO:2250:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2250:

```
CCUGCGAGAG AAGUUGGGAC CAGAGAAACA CACGUUGUGG UACAUUACCU GGUA           54
```

( 2 ) INFORMATION FOR SEQ ID NO:2251:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2251:

```
CCCAACUGUU CUCGCAGG                                                                                    18
```

( 2 ) INFORMATION FOR SEQ ID NO:2252:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2252:

```
UUUGGGGCAG AAGCCACAAC CAGAGAAACA CACGUUGUGG UACAUUACCU GGUA           54
```

( 2 ) INFORMATION FOR SEQ ID NO:2253:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2253:

```
UGUGGCAGAU GCCCCAAA                                                                                    18
```

( 2 ) INFORMATION FOR SEQ ID NO:2254:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2254:

GUCAUUAAAG AAGAGCUUAC CAGAGAAACA CACGUUGUGG UACAUUACCU GGUA     54

( 2 ) INFORMATION FOR SEQ ID NO:2255:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2255:

AAGCUCUGUU UUAAUGAC     18

( 2 ) INFORMATION FOR SEQ ID NO:2256:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2256:

AGGCCGUCAG AAGGUCCUAC CAGAGAAACA CACGUUGUGG UACAUUACCU GGUA     54

( 2 ) INFORMATION FOR SEQ ID NO:2257:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2257:

AGGACCAGAU GACGGCCU     18

( 2 ) INFORMATION FOR SEQ ID NO:2258:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2258:

GGACCGGAAG AAGUCAUCAC CAGAGAAACA CACGUUGUGG UACAUUACCU GGUA     54

( 2 ) INFORMATION FOR SEQ ID NO:2259:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2259:

GAUGACGGCC UCCGGUCC     18

( 2 ) INFORMATION FOR SEQ ID NO:2260:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2260:

CCGAGCCGAG AAGGAGGCAC CAGAGAAACA CACGUUGUGG UACAUUACCU GGUA 54

( 2 ) INFORMATION FOR SEQ ID NO:2261:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2261:

GCCUCCGGUC CGGCUCGG 18

( 2 ) INFORMATION FOR SEQ ID NO:2262:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2262:

UAUUUCCGAG AAGGACCGAC CAGAGAAACA CACGUUGUGG UACAUUACCU GGUA 54

( 2 ) INFORMATION FOR SEQ ID NO:2263:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2263:

CGGUCCGGCU CGGAAAUA 18

( 2 ) INFORMATION FOR SEQ ID NO:2264:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2264:

AGAGUUCGAG AAGAGAACAC CAGAGAAACA CACGUUGUGG UACAUUACCU GGUA 54

( 2 ) INFORMATION FOR SEQ ID NO:2265:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2265:

GUUCUCAGCU CGAACUCU 18

( 2 ) INFORMATION FOR SEQ ID NO:2266:

( i ) SEQUENCE CHARACTERISTICS:
    ( A ) LENGTH: 54 base pairs (B) TYPE: nucleic acid
                (C) STRANDEDNESS: single
                (D) TOPOLOGY: linear (xi) SEQUENCE DESCRIPTION: SEQ ID NO:2266:

ACAACAAAAG AAGGCUUAC CAGAGAAACA CACGUUGUGG UACAUUACCU GGUA        54

(2) INFORMATION FOR SEQ ID NO:2267:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:2267:

AGAGCCUGAU UUUGUUGU        18

(2) INFORMATION FOR SEQ ID NO:2268:

(i) SEQUENCE CHARACTERISTICS:
                (A) LENGTH: 54 base pairs
                (B) TYPE: nucleic acid
                (C) STRANDEDNESS: single
                (D) TOPOLOGY: linear (xi) SEQUENCE DESCRIPTION: SEQ ID NO:2268:

CUGCUCUCAG AAGUUGUAAC CAGAGAAACA CACGUUGUGG UACAUUACCU GGUA        54

(2) INFORMATION FOR SEQ ID NO:2269:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:2269:

UACAACAGUU GAGAGCAG        18

(2) INFORMATION FOR SEQ ID NO:2270:

(i) SEQUENCE CHARACTERISTICS:
                (A) LENGTH: 54 base pairs
                (B) TYPE: nucleic acid
                (C) STRANDEDNESS: single
                (D) TOPOLOGY: linear (xi) SEQUENCE DESCRIPTION: SEQ ID NO:2270:

UUAGGUAAAG AAGUUAUUAC CAGAGAAACA CACGUUGUGG UACAUUACCU GGUA        54

(2) INFORMATION FOR SEQ ID NO:2271:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:2271:

AAUAACAGUC UUACCUAA        18

(2) INFORMATION FOR SEQ ID NO:2272:

(i) SEQUENCE CHARACTERISTICS:
                (A) LENGTH: 54 base pairs
                (B) TYPE: nucleic acid
                (C) STRANDEDNESS: single
                (D) TOPOLOGY: linear ( x i ) SEQUENCE DESCRIPTION: SEQ ID NO:2272:

UUUAAAAAG AAGAUUAUAC CAGAGAAACA CACGUUGUGG UACAUUACCU GGUA     54

( 2 ) INFORMATION FOR SEQ ID NO:2273:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2273:

AUAAUCAGAU UUUUUAAA     18

( 2 ) INFORMATION FOR SEQ ID NO:2274:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2274:

AAAUACUGAG AAGUUGUAAC CAGAGAAACA CACGUUGUGG UACAUUACCU GGUA     54

( 2 ) INFORMATION FOR SEQ ID NO:2275:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2275:

UACAACAGAU CAGUAUUU     18

( 2 ) INFORMATION FOR SEQ ID NO:2276:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2276:

UUCAAGCAAG AAGACAACAC CAGAGAAACA CACGUUGUGG UACAUUACCU GGUA     54

( 2 ) INFORMATION FOR SEQ ID NO:2277:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2277:
GUUGUCAGCU UGCUUGAA ( 2 ) INFORMATION FOR SEQ ID NO:2278:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2278:

AGUGCAUAAG AAGUUAUCAC CAGAGAAACA CACGUUGUGG UACAUUACCU GGUA     54

( 2 ) INFORMATION FOR SEQ ID NO:2279:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2279:

GAUAACGGAC UAUGCACU                                    18

( 2 ) INFORMATION FOR SEQ ID NO:2280:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2280:

AUAAAAAAG AAGGAAUAAC CAGAGAAACA CACGUUGUGG UACAUUACCU GGUA    54

( 2 ) INFORMATION FOR SEQ ID NO:2281:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2281:

UAUUCCAGAC UUUUUUAU                                    18

( 2 ) INFORMATION FOR SEQ ID NO:2282:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2282:

CCCUUGAUCU GAUGAGGCCG AAAGGCCGAA AGAUNAGG                38

( 2 ) INFORMATION FOR SEQ ID NO:2283:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2283:

CCUNAUCUCA UCAAGGG                                     17

( 2 ) INFORMATION FOR SEQ ID NO:2284:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear (ix) FEATURE:
  (D) OTHER INFORMATION: The letter "N" stands for any base.

(xi) SEQUENCE DESCRIPTION: SEQ ID NO:2284:

GGACCCUUCU GAUGAGGCCG AAAGGCCGAA AUGAGAUN    38

(2) INFORMATION FOR SEQ ID NO:2285:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ix) FEATURE:
    (D) OTHER INFORMATION: The letter "N" stands for any base.

(xi) SEQUENCE DESCRIPTION: SEQ ID NO:2285:

NAUCUCAUCA AGGGUCC    17

(2) INFORMATION FOR SEQ ID NO:2286:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:2286:

GGUCCAAGCU GAUGAGGCCG AAAGGCCGAA ACCCUUGA    38

(2) INFORMATION FOR SEQ ID NO:2287:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:2287:

UCAAGGGUCC UUGGACC    17

(2) INFORMATION FOR SEQ ID NO:2288:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:2288:

UUUGGUCCCU GAUGAGGCCG AAAGGCCGAA AGGACCCU    38

(2) INFORMATION FOR SEQ ID NO:2289:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:2289:

AGGGUCCUUG GACCAAA    17

(2) INFORMATION FOR SEQ ID NO:2290:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2290:

CACUCUCUCU GAUGAGGCCG AAAGGCCGAA AUCUUCUU      38

( 2 ) INFORMATION FOR SEQ ID NO:2291:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2291:

AAGAAGAUCA GAGAGUG      17

( 2 ) INFORMATION FOR SEQ ID NO:2292:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2292:

ACAAGCUCCU GAUGAGGCCG AAAGGCCGAA AUCACUCU      38

( 2 ) INFORMATION FOR SEQ ID NO:2293:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2293:

AGAGUGAUAG AGCUUGU      17

( 2 ) INFORMATION FOR SEQ ID NO:2294:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2294:

UUCUGUACCU GAUGAGGCCG AAAGGCCGAA AGCUCUAU      38

( 2 ) INFORMATION FOR SEQ ID NO:2295:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2295:

AUAGAGCUUG UACAGAA      17

( 2 ) INFORMATION FOR SEQ ID NO:2296:

( i ) SEQUENCE CHARACTERISTICS:
        ( A ) LENGTH: 38 base pairs ( B ) TYPE: nucleic acid
          ( C ) STRANDEDNESS: single
          ( D ) TOPOLOGY: linear ( x i ) SEQUENCE DESCRIPTION: SEQ ID NO:2296:

UAUUUCUGCU GAUGAGGCCG AAAGGCCGAA ACAAGCUC                                    3 8

( 2 ) INFORMATION FOR SEQ ID NO:2297:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:2297:

GAGCUUGUAC AGAAAUA                                                           1 7

( 2 ) INFORMATION FOR SEQ ID NO:2298:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:2298:

UCGGACCGCU GAUGAGGCCG AAAGGCCGAA AUUUCUGU                                    3 8

( 2 ) INFORMATION FOR SEQ ID NO:2299:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:2299:
                    ACAGAAAUAC GGUCCGA ( 2 ) INFORMATION FOR SEQ ID NO:2300:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:2300:

ACGUUUCGCU GAUGAGGCCG AAAGGCCGAA ACCGUAUU                                    3 8

( 2 ) INFORMATION FOR SEQ ID NO:2301:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:2301:

AAUACGGUCC GAAACGU                                                           1 7

( 2 ) INFORMATION FOR SEQ ID NO:2302:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:2302:

AACAGACCCU GAUGAGGCCG AAAGGCCGAA ACGUUUCG 38

( 2 ) INFORMATION FOR SEQ ID NO:2303:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2303:

CGAAACGUUG GUCUGUU 17

( 2 ) INFORMATION FOR SEQ ID NO:2304:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2304:

CAAUAACACU GAUGAGGCCG AAAGGCCGAA ACCAACGU 38

( 2 ) INFORMATION FOR SEQ ID NO:2305:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2305:

ACGUUGGUCU GUUAUUG 17

( 2 ) INFORMATION FOR SEQ ID NO:2306:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2306:

UUGGCAAUCU GAUGAGGCCG AAAGGCCGAA ACAGACCA 38

( 2 ) INFORMATION FOR SEQ ID NO:2307:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2307:

UGGUCUGUUA UUGCCAA 17

( 2 ) INFORMATION FOR SEQ ID NO:2308:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2308:

CUUGGCAACU GAUGAGGCCG AAAGGCCGAA AACAGACC                38

( 2 ) INFORMATION FOR SEQ ID NO:2309:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2309:

GGUCUGUUAU UGCCAAG                17

( 2 ) INFORMATION FOR SEQ ID NO:2310:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2310:

UGCUUGGCCU GAUGAGGCCG AAAGGCCGAA AUAACAGA                38

( 2 ) INFORMATION FOR SEQ ID NO:2311:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2311:

UCUGUUAUUG CCAAGCA                17

( 2 ) INFORMATION FOR SEQ ID NO:2312:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2312:

UCCCCUUUCU GAUGAGGCCG AAAGGCCGAA AGUGCUUG                38

( 2 ) INFORMATION FOR SEQ ID NO:2313:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2313:

CAAGCACUUA AAGGGGA                17

( 2 ) INFORMATION FOR SEQ ID NO:2314:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2314:

CUCCCCUUCU GAUGAGGCCG AAAGGCCGAA AAGUGCUU                38

( 2 ) INFORMATION FOR SEQ ID NO:2315:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2315:

AAGCACUUAA AGGGGAG 17

( 2 ) INFORMATION FOR SEQ ID NO:2316:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2316:

UGUUUUCCCU GAUGAGGCCG AAAGGCCGAA AUUCUCCC 38

( 2 ) INFORMATION FOR SEQ ID NO:2317:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2317:

GGGAGAAUUG GAAAACA 17

( 2 ) INFORMATION FOR SEQ ID NO:2318:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2318:

CCUCUCCCCU GAUGAGGCCG AAAGGCCGAA ACAUUGUU 38

( 2 ) INFORMATION FOR SEQ ID NO:2319:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2319:

AACAAUGUAG GGAGAGG 17

( 2 ) INFORMATION FOR SEQ ID NO:2320:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2320:

CAAGUGGUCU GAUGAGGCCG AAAGGCCGAA AUGCCACC 38

( 2 ) INFORMATION FOR SEQ ID NO:2321:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2321:

GGUGGCAUAA CCACUUG                                17

( 2 ) INFORMATION FOR SEQ ID NO:2322:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2322:

CUGGAUUCCU GAUGAGGCCG AAAGGCCGAA AGUGGUUA         38

( 2 ) INFORMATION FOR SEQ ID NO:2323:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2323:

UAACCACUUG AAUCCAG                                17

( 2 ) INFORMATION FOR SEQ ID NO:2324:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2324:

AACUUCUGCU GAUGAGGCCG AAAGGCCGAA AUUCAAGU         38

( 2 ) INFORMATION FOR SEQ ID NO:2325:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2325:

ACUUGAAUCC AGAAGUU                                17

( 2 ) INFORMATION FOR SEQ ID NO:2326:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2326:

GUUUCUUCU GAUGAGGCCG AAAGGCCGAA ACUUCUGG          38

( 2 ) INFORMATION FOR SEQ ID NO:2327:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:2327:

CCAGAAGUUA AGAAAAC 17

(2) INFORMATION FOR SEQ ID NO:2328:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2328:

GGUUUUCUCU GAUGAGGCCG AAAGGCCGAA AACUUCUG 38

(2) INFORMATION FOR SEQ ID NO:2329:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2329:

CAGAAGUUAA GAAAACC 17

(2) INFORMATION FOR SEQ ID NO:2330:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2330:

CUGUCCAGCU GAUGAGGCCG AAAGGCCGAA AGGUUUUC 38

(2) INFORMATION FOR SEQ ID NO:2331:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2331:

GAAAACCUCC UGGACAG 17

(2) INFORMATION FOR SEQ ID NO:2332:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2332:

UGGUAAAUCU GAUGAGGCCG AAAGGCCGAA AUUCUGUC 38

(2) INFORMATION FOR SEQ ID NO:2333:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO:2333:

GACAGAAUUA UUUACCA 17

(2) INFORMATION FOR SEQ ID NO:2334:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2334:

CUGGUAAACU GAUGAGGCCG AAAGGCCGAA AAUUCUGU 38

(2) INFORMATION FOR SEQ ID NO:2335:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2335:

ACAGAAUUAU UUACCAG 17

(2) INFORMATION FOR SEQ ID NO:2336:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2336:

GCCUGGUACU GAUGAGGCCG AAAGGCCGAA AUAAUUCU 38

(2) INFORMATION FOR SEQ ID NO:2337:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2337:

AGAAUUAUUU ACCAGGC 17

(2) INFORMATION FOR SEQ ID NO:2338:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2338:

UGCCUGGUCU GAUGAGGCCG AAAGGCCGAA AAUAAUUC 38

(2) INFORMATION FOR SEQ ID NO:2339:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2339:

GAAUUAUUUA CCAGGCA 17

(2) INFORMATION FOR SEQ ID NO:2340:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2340:

GUGCCUGGCU GAUGAGGCCG AAAGGCCGAA AAAUAAUU 38

(2) INFORMATION FOR SEQ ID NO:2341:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2341:

AAUUAUUUAC CAGGCAC 17

(2) INFORMATION FOR SEQ ID NO:2342:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2342:

AGCUUUGCCU GAUGAGGCCG AAAGGCCGAA AUUCCGC 38

(2) INFORMATION FOR SEQ ID NO:2343:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2343:

GCGGAAAUCG CAAAGCU 17

(2) INFORMATION FOR SEQ ID NO:2344:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2344:

CCAGGCAGCU GAUGAGGCCG AAAGGCCGAA AGCUUUGC 38

(2) INFORMATION FOR SEQ ID NO:2345:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2345:

```
GCAAAGCUAC UGCCUGG                                                                    17
```

( 2 ) INFORMATION FOR SEQ ID NO:2346:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2346:

```
GUGUUUAACU GAUGAGGCCG AAAGGCCGAA AAAGAAUC                                              38
```

( 2 ) INFORMATION FOR SEQ ID NO:2347:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2347:

```
GAUUCUUUCU UAAACAC                                                                    17
```

( 2 ) INFORMATION FOR SEQ ID NO:2348:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2348:

```
AAGUGUUUCU GAUGAGGCCG AAAGGCCGAA AGAAAGAA                                              38
```

( 2 ) INFORMATION FOR SEQ ID NO:2349:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2349:

```
UUCUUUCUUA AACACUU                                                                    17
```

( 2 ) INFORMATION FOR SEQ ID NO:2350:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2350:

```
GAAGUGUUCU GAUGAGGCCG AAAGGCCGAA AAGAAAGA                                              38
```

( 2 ) INFORMATION FOR SEQ ID NO:2351:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2351:

```
UCUUUCUUAA ACACUUC                                                                    17
```

( 2 ) INFORMATION FOR SEQ ID NO:2352:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2352:

GUUAUUGGCU GAUGAGGCCG AAAGGCCGAA AGUGUUUA    38

( 2 ) INFORMATION FOR SEQ ID NO:2353:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2353:

UAAACACUUC CAAUAAC    17

( 2 ) INFORMATION FOR SEQ ID NO:2354:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2354:

GGUUAUUGCU GAUGAGGCCG AAAGGCCGAA AAGUGUUU    38

( 2 ) INFORMATION FOR SEQ ID NO:2355:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2355:

AAACACUUCC AAUAACC    17

( 2 ) INFORMATION FOR SEQ ID NO:2356:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2356:

UUCAUGGUCU GAUGAGGCCG AAAGGCCGAA AUUGGAAG    38

( 2 ) INFORMATION FOR SEQ ID NO:2357:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2357:

CUUCCAAUAA CCAUGAA    17

( 2 ) INFORMATION FOR SEQ ID NO:2358:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2358:

CCAAGUCUCU GAUGAGGCCG AAAGGCCGAA AGUUUUCA    38

( 2 ) INFORMATION FOR SEQ ID NO:2359:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2359:

UGAAAACUUA GACUUGG    17

( 2 ) INFORMATION FOR SEQ ID NO:2360:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2360:

UCCAAGUCCU GAUGAGGCCG AAAGGCCGAA AAGUUUUC    38

( 2 ) INFORMATION FOR SEQ ID NO:2361:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2361:

GAAAACUUAG ACUUGGA    17

( 2 ) INFORMATION FOR SEQ ID NO:2362:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2362:

GCAUUUCCCU GAUGAGGCCG AAAGGCCGAA AGUCUAAG    38

( 2 ) INFORMATION FOR SEQ ID NO:2363:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2363:

CUUAGACUUG GAAAUGC    17

( 2 ) INFORMATION FOR SEQ ID NO:2364:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2364:

CGUUAAAGCU GAUGAGGCCG AAAGGCCGAA AGGCAUUU                                38

(2) INFORMATION FOR SEQ ID NO:2365:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2365:

AAAUGCCUUC UUUAACG                                                       17

(2) INFORMATION FOR SEQ ID NO:2366:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2366:

ACGUUAAACU GAUGAGGCCG AAAGGCCGAA AAGGCAUU                                38

(2) INFORMATION FOR SEQ ID NO:2367:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2367:

AAUGCCUUCU UUAACGU                                                       17

(2) INFORMATION FOR SEQ ID NO:2368:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2368:

GGACGUUACU GAUGAGGCCG AAAGGCCGAA AGAAGGCA                                38

(2) INFORMATION FOR SEQ ID NO:2369:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2369:

UGCCUUCUUU AACGUCC                                                       17

(2) INFORMATION FOR SEQ ID NO:2370:

(i) SEQUENCE CHARACTERISTICS:
(A) LENGTH: 38 base pairs
(B) TYPE: nucleic acid
(C) STRANDEDNESS: single ( D ) TOPOLOGY: linear ( x i ) SEQUENCE DESCRIPTION: SEQ ID NO:2370:

UGGACGUUCU GAUGAGGCCG AAAGGCCGAA AAGAAGGC 38

( 2 ) INFORMATION FOR SEQ ID NO:2371:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2371:

GCCUUCUUUA ACGUCCA 17

( 2 ) INFORMATION FOR SEQ ID NO:2372:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2372:

GUGGACGUCU GAUGAGGCCG AAAGGCCGAA AAAGAAGG 38

( 2 ) INFORMATION FOR SEQ ID NO:2373:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2373:

CCUUCUUUAA CGUCCAC 17

( 2 ) INFORMATION FOR SEQ ID NO:2374:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2374:

GAGGCGUGCU GAUGAGGCCG AAAGGCCGAA ACGUUAAA 38

( 2 ) INFORMATION FOR SEQ ID NO:2375:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2375:

UUUAACGUCC ACGCCUC 17

( 2 ) INFORMATION FOR SEQ ID NO:2376:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2376:

ACCACUGACU GAUGAGGCCG AAAGGCCGAA AGGCGUGG 38

( 2 ) INFORMATION FOR SEQ ID NO:2377:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2377:

CCACGCCUCU CAGUGGU 17

( 2 ) INFORMATION FOR SEQ ID NO:2378:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2378:

UGACCACUCU GAUGAGGCCG AAAGGCCGAA AGAGGCGU 38

( 2 ) INFORMATION FOR SEQ ID NO:2379:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2379:

ACGCCUCUCA GUGGUCA 17

( 2 ) INFORMATION FOR SEQ ID NO:2380:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2380:

CAAUUUGUCU GAUGAGGCCG AAAGGCCGAA ACCACUGA 38

( 2 ) INFORMATION FOR SEQ ID NO:2381:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2381:

UCAGUGGUCA CAAAUUG 17

( 2 ) INFORMATION FOR SEQ ID NO:2382:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2382:

UAACAGUCCU GAUGAGGCCG AAAGGCCGAA AUUUGUGA    38

( 2 ) INFORMATION FOR SEQ ID NO:2383:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2383:

UCACAAAUUG ACUGUUA    17

( 2 ) INFORMATION FOR SEQ ID NO:2384:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2384:

GGUGUUGUCU GAUGAGGCCG AAAGGCCGAA ACAGUCAA    38

( 2 ) INFORMATION FOR SEQ ID NO:2385:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2385:

UUGACUGUUA CAACACC    17

( 2 ) INFORMATION FOR SEQ ID NO:2386:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2386:

UGGUGUUGCU GAUGAGGCCG AAAGGCCGAA AACAGUCA    38

( 2 ) INFORMATION FOR SEQ ID NO:2387:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2387:

UGACUGUUAC AACACCA    17

( 2 ) INFORMATION FOR SEQ ID NO:2388:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2388:

CUCUAUGACU GAUGAGGCCG AAAGGCCGAA AUGGUGUU    38

( 2 ) INFORMATION FOR SEQ ID NO:2389:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2389:

A A C A C C A U U U   C A U A G A G     17

( 2 ) INFORMATION FOR SEQ ID NO:2390:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2390:

U C U C U A U G C U   G A U G A G G C C G   A A A G G C C G A A   A A U G G U G U     38

( 2 ) INFORMATION FOR SEQ ID NO:2391:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2391:

A C A C C A U U U C   A U A G A G A     17

( 2 ) INFORMATION FOR SEQ ID NO:2392:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2392:

G U C U C U A U C U   G A U G A G G C C G   A A A G G C C G A A   A A A U G G U G     38

( 2 ) INFORMATION FOR SEQ ID NO:2393:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2393:

C A C C A U U U C A   U A G A G A C     17

( 2 ) INFORMATION FOR SEQ ID NO:2394:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2394:

C U G G U C U C C U   G A U G A G G C C G   A A A G G C C G A A   A U G A A A U G     38

( 2 ) INFORMATION FOR SEQ ID NO:2395:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2395:

CAUUCAUAG AGACCAG    17

( 2 ) INFORMATION FOR SEQ ID NO:2396:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2396:

AAAAUAUGCU GAUGAGGCCG AAAGGCCGAA AUUUUCCU    38

( 2 ) INFORMATION FOR SEQ ID NO:2397:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2397:

AGGAAAAUAC AUAUUUU    17

( 2 ) INFORMATION FOR SEQ ID NO:2398:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2398:

UUCAAAACU GAUGAGGCCG AAAGGCCGAA AUGUAUUU    38

( 2 ) INFORMATION FOR SEQ ID NO:2399:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2399:

AAAUACAUAU UUUUGAA    17

( 2 ) INFORMATION FOR SEQ ID NO:2400:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2400:

AGUUCAAACU GAUGAGGCCG AAAGGCCGAA AUAUGUAU    38

( 2 ) INFORMATION FOR SEQ ID NO:2401:

( i ) SEQUENCE CHARACTERISTICS:

( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2401:

AUACAUAUUU UUGAACU                                                                                                17

( 2 ) INFORMATION FOR SEQ ID NO:2402:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2402:

GAGUUCAACU GAUGAGGCCG AAAGGCCGAA AAUAUGUA                                                                          38

( 2 ) INFORMATION FOR SEQ ID NO:2403:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2403:

UACAUAUUUU UGAACUC                                                                                                 17

( 2 ) INFORMATION FOR SEQ ID NO:2404:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2404:

GGAGUUCACU GAUGAGGCCG AAAGGCCGAA AAAUAUGU                                                                          38

( 2 ) INFORMATION FOR SEQ ID NO:2405:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2405:

ACAUAUUUUU GAACUCC                                                                                                 17

( 2 ) INFORMATION FOR SEQ ID NO:2406:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2406:

CGGAGUUCCU GAUGAGGCCG AAAGGCCGAA AAAAUAUG                                                                          38

( 2 ) INFORMATION FOR SEQ ID NO:2407:

( i ) SEQUENCE CHARACTERISTICS:
            ( A ) LENGTH: 17 base pairs
            ( B ) TYPE: nucleic acid (C) STRANDEDNESS: single
(D) TOPOLOGY: linear (xi) SEQUENCE DESCRIPTION: SEQ ID NO:2407:

CAUAUUUUUG AACUCCG 17

(2) INFORMATION FOR SEQ ID NO:2408:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2408:

GAUAGCCGCU GAUGAGGCCG AAAGGCCGAA AGUUCAAA 38

(2) INFORMATION FOR SEQ ID NO:2409:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2409:

UUUGAACUCC GGCUAUC 17

(2) INFORMATION FOR SEQ ID NO:2410:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2410:

CCUUUUGACU GAUGAGGCCG AAAGGCCGAA AGCCGGAG 38

(2) INFORMATION FOR SEQ ID NO:2411:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2411:

CUCCGGCUAU CAAAAGG 17

(2) INFORMATION FOR SEQ ID NO:2412:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2412:

GACCUUUUCU GAUGAGGCCG AAAGGCCGAA AUAGCCGG 38

(2) INFORMATION FOR SEQ ID NO:2413:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:2413:

CCGGCUAUCA AAAGGUC                                                17

( 2 ) INFORMATION FOR SEQ ID NO:2414:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2414:

CCAGGAUUCU GAUGAGGCCG AAAGGCCGAA ACCUUUUG                          38

( 2 ) INFORMATION FOR SEQ ID NO:2415:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2415:

CAAAAGGUCA AUCCUGG                                                 17

( 2 ) INFORMATION FOR SEQ ID NO:2416:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2416:

CUUUCCAGCU GAUGAGGCCG AAAGGCCGAA AUUGACCU                          38

( 2 ) INFORMATION FOR SEQ ID NO:2417:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2417:

AGGUCAAUCC UGGAAAG                                                 17

( 2 ) INFORMATION FOR SEQ ID NO:2418:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2418:

UUCUUGGACU GAUGAGGCCG AAAGGCCGAA AGCUUUCC                          38

( 2 ) INFORMATION FOR SEQ ID NO:2419:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2419:

GGAAAGCUCU CCAAGAA 17

( 2 ) INFORMATION FOR SEQ ID NO:2420:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2420:

AGUUCUUGCU GAUGAGGCCG AAAGGCCGAA AGAGCUUU 38

( 2 ) INFORMATION FOR SEQ ID NO:2421:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2421:

AAAGCUCUCC AAGAACU 17

( 2 ) INFORMATION FOR SEQ ID NO:2422:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2422:

CGGUGUAGCU GAUGAGGCCG AAAGGCCGAA AGUUCUUG 38

( 2 ) INFORMATION FOR SEQ ID NO:2423:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2423:

CAAGAACUCC UACACCG 17

( 2 ) INFORMATION FOR SEQ ID NO:2424:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2424:

GAACGGUGCU GAUGAGGCCG AAAGGCCGAA AGGAGUUC 38

( 2 ) INFORMATION FOR SEQ ID NO:2425:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2425:

GAACUCCUAC ACCGUUC 17

( 2 ) INFORMATION FOR SEQ ID NO:2426:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2426:

CAUGUUUGCU GAUGAGGCCG AAAGGCCGAA ACGGUGUA      3 8

( 2 ) INFORMATION FOR SEQ ID NO:2427:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2427:

UACACCGUUC AAACAUG      1 7

( 2 ) INFORMATION FOR SEQ ID NO:2428:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2428:

GCAUGUUUCU GAUGAGGCCG AAAGGCCGAA AACGGUGU      3 8

( 2 ) INFORMATION FOR SEQ ID NO:2429:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2429:

ACACCGUUCA AACAUGC      1 7

( 2 ) INFORMATION FOR SEQ ID NO:2430:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2430:

UGAGCUGCCU GAUGAGGCCG AAAGGCCGAA AGUGCAUG      3 8

( 2 ) INFORMATION FOR SEQ ID NO:2431:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2431:

CAUGCACUCG CAGCUCA      1 7

( 2 ) INFORMATION FOR SEQ ID NO:2432:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2432:

AAUUCUUCU GAUGAGGCCG AAAGGCCGAA AGCUGCGA      3 8

( 2 ) INFORMATION FOR SEQ ID NO:2433:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2433:

UCGCAGCUCA AGAAAUU      1 7

( 2 ) INFORMATION FOR SEQ ID NO:2434:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2434:

CCAUAUUUCU GAUGAGGCCG AAAGGCCGAA AUUUCUUG      3 8

( 2 ) INFORMATION FOR SEQ ID NO:2435:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2435:

CAAGAAAUUA AAUAUGG      1 7

( 2 ) INFORMATION FOR SEQ ID NO:2436:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2436:

ACCAUAUUCU GAUGAGGCCG AAAGGCCGAA AAUUUCUU      3 8

( 2 ) INFORMATION FOR SEQ ID NO:2437:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2437:

AAGAAAUUAA AUAUGGU      1 7

( 2 ) INFORMATION FOR SEQ ID NO:2438:

( i ) SEQUENCE CHARACTERISTICS:
        ( A ) LENGTH: 38 base pairs ( B ) TYPE: nucleic acid
        ( C ) STRANDEDNESS: single
        ( D ) TOPOLOGY: linear ( x i ) SEQUENCE DESCRIPTION: SEQ ID NO:2438:

GGGGACCACU GAUGAGGCCG AAAGGCCGAA AUUUAAUU 38

( 2 ) INFORMATION FOR SEQ ID NO:2439:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2439:

AAUUAAAUAU GGUCCCC 17

( 2 ) INFORMATION FOR SEQ ID NO:2440:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2440:

CUUCAGGGCU GAUGAGGCCG AAAGGCCGAA ACCAUAUU 38

( 2 ) INFORMATION FOR SEQ ID NO:2441:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2441:

AAUAUGGUCC CCUGAAG 17

( 2 ) INFORMATION FOR SEQ ID NO:2442:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2442:

GUCUGAGGCU GAUGAGGCCG AAAGGCCGAA AGCAUCUU 38

( 2 ) INFORMATION FOR SEQ ID NO:2443:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2443:

AAGAUGCUAC CUCAGAC 17

( 2 ) INFORMATION FOR SEQ ID NO:2444:

( i ) SEQUENCE CHARACTERISTICS:
        ( A ) LENGTH: 38 base pairs
        ( B ) TYPE: nucleic acid
        ( C ) STRANDEDNESS: single ( D ) TOPOLOGY: linear ( x i ) SEQUENCE DESCRIPTION: SEQ ID NO:2444:

UGGUGUCUCU GAUGAGGCCG AAAGGCCGAA AGGUAGCA 38

( 2 ) INFORMATION FOR SEQ ID NO:2445:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2445:

UGCUACCUCA GACACCA 17

( 2 ) INFORMATION FOR SEQ ID NO:2446:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2446:

CUAAAUGACU GAUGAGGCCG AAAGGCCGAA AUGGUGUC 38

( 2 ) INFORMATION FOR SEQ ID NO:2447:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2447:

GACACCAUCU CAUUUAG 17

( 2 ) INFORMATION FOR SEQ ID NO:2448:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2448:

UACUAAAUCU GAUGAGGCCG AAAGGCCGAA AGAUGGUG 38

( 2 ) INFORMATION FOR SEQ ID NO:2449:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2449:

CACCAUCUCA UUUAGUA 17

( 2 ) INFORMATION FOR SEQ ID NO:2450:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2450:

UUCUACUACU GAUGAGGCCG AAAGGCCGAA AUGAGAUG 38

( 2 ) INFORMATION FOR SEQ ID NO:2451:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2451:

CAUCUCAUUU AGUAGAA 17

( 2 ) INFORMATION FOR SEQ ID NO:2452:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2452:

CUUCUACUCU GAUGAGGCCG AAAGGCCGAA AAUGAGAU 38

( 2 ) INFORMATION FOR SEQ ID NO:2453:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2453:

AUCUCAUUUA GUAGAAG ( 2 ) INFORMATION FOR SEQ ID NO:2454:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2454:

UCUUCUACCU GAUGAGGCCG AAAGGCCGAA AAAUGAGA 38

( 2 ) INFORMATION FOR SEQ ID NO:2455:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2455:

UCUCAUUUAG UAGAAGA 17

( 2 ) INFORMATION FOR SEQ ID NO:2456:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2456:

AGGUCUUCCU GAUGAGGCCG AAAGGCCGAA ACUAAAUG 38

( 2 ) INFORMATION FOR SEQ ID NO:2457:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2457:

CAUUUAGUAG AAGACCU                                                    17

( 2 ) INFORMATION FOR SEQ ID NO:2458:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2458:

UUUCACAAG AAGGUCUCAC CAGAGAAACA CACGUUGUGG UACAUUACCU GGUA      54

( 2 ) INFORMATION FOR SEQ ID NO:2459:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2459:

GAGACCAGAC UGUGAAAA                                                  18

( 2 ) INFORMATION FOR SEQ ID NO:2460:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2460:

CAUGUUUGAG AAGUGUAGAC CAGAGAAACA CACGUUGUGG UACAUUACCU GGUA      54

( 2 ) INFORMATION FOR SEQ ID NO:2461:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2461:

CUACACCGUU CAAACAUG                                                  18

( 2 ) INFORMATION FOR SEQ ID NO:2462:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2462:

AUUUCUUGAG AAGCGAGUAC CAGAGAAACA CACGUUGUGG UACAUUACCU GGUA      54

( 2 ) INFORMATION FOR SEQ ID NO:2463:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2463:

ACUCGCAGCU CAAGAAAU                                                                                 18

( 2 ) INFORMATION FOR SEQ ID NO:2464:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2464:

ACGUUUCGAG AAGUAUUUAC CAGAGAAACA CACGUUGUGG UACAUUACCU GGUA          54

( 2 ) INFORMATION FOR SEQ ID NO:2465:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2465:

AAAUACGGUC CGAAACGU                                                                                 18

( 2 ) INFORMATION FOR SEQ ID NO:2466:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2466:

UUCCGCCCAG AAGUUCCCAC CAGAGAAACA CACGUUGUGG UACAUUACCU GGUA          54

( 2 ) INFORMATION FOR SEQ ID NO:2467:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2467:

GGGAACAGAU GGGCGGAA                                                                                 18

( 2 ) INFORMATION FOR SEQ ID NO:2468:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2468:

CCUUUGAUCU GAUGAGGCCG AAAGGCCGAA AGCUCAGG                                                           38

( 2 ) INFORMATION FOR SEQ ID NO:2469:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2469:

CCUGAGCUCA UCAAAGG                                                              17

(2) INFORMATION FOR SEQ ID NO:2470:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2470:

GGACCUUUCU GAUGAGGCCG AAAGGCCGAA AUGAGCUC                                       38

(2) INFORMATION FOR SEQ ID NO:2471:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2471:

GAGCUCAUCA AAGGUCC                                                              17

(2) INFORMATION FOR SEQ ID NO:2472:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2472:

GGUCCAGGCU GAUGAGGCCG AAAGGCCGAA ACCUUUGA                                       38

(2) INFORMATION FOR SEQ ID NO:2473:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2473:

UCAAAGGUCC CUGGACC                                                              17

(2) INFORMATION FOR SEQ ID NO:2474:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2474:

CACUCUUUCU GAUGAGGCCG AAAGGCCGAA AUCUUCUU                                       38

(2) INFORMATION FOR SEQ ID NO:2475:

(i) SEQUENCE CHARACTERISTICS:
        (A) LENGTH: 17 base pairs
        (B) TYPE: nucleic acid ( C ) STRANDEDNESS: single
        ( D ) TOPOLOGY: linear ( x i ) SEQUENCE DESCRIPTION: SEQ ID NO:2475:

AAGAAGAUCA AAGAGUG                                                                                      17

( 2 ) INFORMATION FOR SEQ ID NO:2476:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2476:

ACAAGCUCCU GAUGAGGCCG AAAGGCCGAA AUCACUCU                                                                38

( 2 ) INFORMATION FOR SEQ ID NO:2477:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2477:

AGAGUGAUAG AGCUUGU                                                                                      17

( 2 ) INFORMATION FOR SEQ ID NO:2478:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2478:

UUCUGGACCU GAUGAGGCCG AAAGGCCGAA AGCUCUAU                                                                38

( 2 ) INFORMATION FOR SEQ ID NO:2479:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2479:

AUAGAGCUUG UCCAGAA                                                                                      17

( 2 ) INFORMATION FOR SEQ ID NO:2480:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2480:

UAUUUCUGCU GAUGAGGCCG AAAGGCCGAA ACAAGCUC                                                                38

( 2 ) INFORMATION FOR SEQ ID NO:2481:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2481:

GAGCUUGUCC AGAAAUA 17

( 2 ) INFORMATION FOR SEQ ID NO:2482:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2482:

UCGGACCGCU GAUGAGGCCG AAAGGCCGAA AUUUCUGG 38

( 2 ) INFORMATION FOR SEQ ID NO:2483:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2483:

CCAGAAAUAC GGUCCGA 17

( 2 ) INFORMATION FOR SEQ ID NO:2484:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2484:

GCGCUUCGCU GAUGAGGCCG AAAGGCCGAA ACCGUAUU 38

( 2 ) INFORMATION FOR SEQ ID NO:2485:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2485:

AAUACGGUCC GAAGCGC 17

( 2 ) INFORMATION FOR SEQ ID NO:2486:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2486:

CAAUAACACU GAUGAGGCCG AAAGGCCGAA ACCAGCGC 38

( 2 ) INFORMATION FOR SEQ ID NO:2487:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2487:

GCGCUGGUCU GUUAUUG 17

( 2 ) INFORMATION FOR SEQ ID NO:2488:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2488:

UUGGCAAUCU GAUGAGGCCG AAAGGCCGAA ACAGACCA 38

( 2 ) INFORMATION FOR SEQ ID NO:2489:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2489:

UGGUCUGUUA UUGCCAA 17

( 2 ) INFORMATION FOR SEQ ID NO:2490:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2490:

CUUGGCAACU GAUGAGGCCG AAAGGCCGAA AACAGACC 38

( 2 ) INFORMATION FOR SEQ ID NO:2491:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2491:

GGUCUGUUAU UGCCAAG 17

( 2 ) INFORMATION FOR SEQ ID NO:2492:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2492:

UGCUUGGCCU GAUGAGGCCG AAAGGCCGAA AUAACAGA 38

( 2 ) INFORMATION FOR SEQ ID NO:2493:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2493:

UCUGUUAUUG CCAAGCA 17

( 2 ) INFORMATION FOR SEQ ID NO:2494:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2494:

UCCCUUUUCU GAUGAGGCCG AAAGGCGAA AGUGCUUG         38

( 2 ) INFORMATION FOR SEQ ID NO:2495:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2495:

CAAGCACUUA AAAGGGA         17

( 2 ) INFORMATION FOR SEQ ID NO:2496:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2496:

CUCCCUUUCU GAUGAGGCCG AAAGGCCGAA AAGUGCUU         38

( 2 ) INFORMATION FOR SEQ ID NO:2497:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2497:

AAGCACUUAA AAGGGAG         17

( 2 ) INFORMATION FOR SEQ ID NO:2498:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2498:

UGUUUCCCU GAUGAGGCCG AAAGGCCGAA AUUCUCCC         38

( 2 ) INFORMATION FOR SEQ ID NO:2499:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2499:

GGGAGAAUUG GAAAACA         17

( 2 ) INFORMATION FOR SEQ ID NO:2500:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2500:

CCUCUCCCCU GAUGAGGCCG AAAGGCCGAA ACAUUGUU     38

( 2 ) INFORMATION FOR SEQ ID NO:2501:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2501:

AACAAUGUCG GGAGAGG     17

( 2 ) INFORMATION FOR SEQ ID NO:2502:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2502:

UGGAUUCACU GAUGAGGCCG AAAGGCCGAA AUGGUUGU     38

( 2 ) INFORMATION FOR SEQ ID NO:2503:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2503:

ACAACCAUUU GAAUCCA     17

( 2 ) INFORMATION FOR SEQ ID NO:2504:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2504:

CUGGAUUCCU GAUGAGGCCG AAAGGCCGAA AAUGGUUG     38

( 2 ) INFORMATION FOR SEQ ID NO:2505:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2505:

CAACCAUUUG AAUCCAG     17

( 2 ) INFORMATION FOR SEQ ID NO:2506:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2506:

AACUUCUGCU GAUGAGGCCG AAAGGCCGAA AUUCAAAU 38

( 2 ) INFORMATION FOR SEQ ID NO:2507:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2507:

AUUUGAAUCC AGAAGUU 17

( 2 ) INFORMATION FOR SEQ ID NO:2508:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2508:

GUUUCUUCU GAUGAGGCCG AAAGGCCGAA ACUUCUGG 38

( 2 ) INFORMATION FOR SEQ ID NO:2509:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2509:

CCAGAAGUUA AGAAAAC 17

( 2 ) INFORMATION FOR SEQ ID NO:2510:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2510:

GGUUUCUCU GAUGAGGCCG AAAGGCCGAA AACUUCUG 38

( 2 ) INFORMATION FOR SEQ ID NO:2511:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2511:

CAGAAGUUAA GAAAACC 17

( 2 ) INFORMATION FOR SEQ ID NO:2512:

( i ) SEQUENCE CHARACTERISTICS:
  ( A ) LENGTH: 38 base pairs ( B ) TYPE: nucleic acid
( C ) STRANDEDNESS: single
( D ) TOPOLOGY: linear ( x i ) SEQUENCE DESCRIPTION: SEQ ID NO:2512:

CUGUCCAUCU GAUGAGGCCG AAAGGCCGAA AGGUUUUC 38

( 2 ) INFORMATION FOR SEQ ID NO:2513:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2513:

GAAAACCUCA UGGACAG 17

( 2 ) INFORMATION FOR SEQ ID NO:2514:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2514:

UGAUAAAUCU GAUGAGGCCG AAAGGCCGAA AUUCUGUC 38

( 2 ) INFORMATION FOR SEQ ID NO:2515:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2515:

GACAGAAUCA UUUAUCA 17

( 2 ) INFORMATION FOR SEQ ID NO:2516:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2516:

GCCUGAUACU GAUGAGGCCG AAAGGCCGAA AUGAUUCU 38

( 2 ) INFORMATION FOR SEQ ID NO:2517:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2517:

AGAAUCAUUU AUCAGGC 17

( 2 ) INFORMATION FOR SEQ ID NO:2518:

( i ) SEQUENCE CHARACTERISTICS:
        ( A ) LENGTH: 38 base pairs
        ( B ) TYPE: nucleic acid
        ( C ) STRANDEDNESS: single ( D ) TOPOLOGY: linear ( x i ) SEQUENCE DESCRIPTION: SEQ ID NO:2518:

UGCCUGAUCU GAUGAGGCCG AAAGGCCGAA AAUGAUUC 38

( 2 ) INFORMATION FOR SEQ ID NO:2519:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2519:

GAAUCAUUUA UCAGGCA 17

( 2 ) INFORMATION FOR SEQ ID NO:2520:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2520:

GUGCCUGACU GAUGAGGCCG AAAGGCCGAA AAAUGAUU 38

( 2 ) INFORMATION FOR SEQ ID NO:2521:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2521:

AAUCAUUUAU CAGGCAC 17

( 2 ) INFORMATION FOR SEQ ID NO:2522:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2522:

GUGUGCCUCU GAUGAGGCCG AAAGGCCGAA AUAAAUGA 38

( 2 ) INFORMATION FOR SEQ ID NO:2523:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2523:

UCAUUUAUCA GGCACAC 17

( 2 ) INFORMATION FOR SEQ ID NO:2524:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2524:

GCGUAUCUCU GAUGAGGCCG AAAGGCCGAA AGCCCGAG 38

( 2 ) INFORMATION FOR SEQ ID NO:2525:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2525:

CUCGGGCUUA GAUACGC 17

( 2 ) INFORMATION FOR SEQ ID NO:2526:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2526:

GGCGUAUCCU GAUGAGGCCG AAAGGCCGAA AAGCCCGA 38

( 2 ) INFORMATION FOR SEQ ID NO:2527:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2527:

UCGGGCUUAG AUACGCC 17

( 2 ) INFORMATION FOR SEQ ID NO:2528:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2528:

AGUAGGCGCU GAUGAGGCCG AAAGGCCGAA AUCUAAGC 38

( 2 ) INFORMATION FOR SEQ ID NO:2529:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2529:

GCUUAGAUAC GCCUACU 17

( 2 ) INFORMATION FOR SEQ ID NO:2530:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2530:

GGGUAAAGCU GAUGAGGCCG AAAGGCCGAA AGGCGUAU                                38

( 2 ) INFORMATION FOR SEQ ID NO:2531:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2531:

AUACGCCUAC UUUACCC                                                       17

( 2 ) INFORMATION FOR SEQ ID NO:2532:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2532:

GGAGGGUACU GAUGAGGCCG AAAGGCCGAA AGUAGGCG                                38

( 2 ) INFORMATION FOR SEQ ID NO:2533:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2533:

CGCCUACUUU ACCCUCC                                                       17

( 2 ) INFORMATION FOR SEQ ID NO:2534:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2534:

UGGAGGGUCU GAUGAGGCCG AAAGGCCGAA AAGUAGGC                                38

( 2 ) INFORMATION FOR SEQ ID NO:2535:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2535:

GCCUACUUUA CCCUCCA                                                       17

( 2 ) INFORMATION FOR SEQ ID NO:2536:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2536:

GUGGAGGGCU GAUGAGGCCG AAAGGCCGAA AAAGUAGG                                38

( 2 ) INFORMATION FOR SEQ ID NO:2537:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2537:

CCUACUUUAC CCUCCAC                                  17

( 2 ) INFORMATION FOR SEQ ID NO:2538:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2538:

GAGGCGUGCU GAUGAGGCCG AAAGGCCGAA AGGGUAAA        38

( 2 ) INFORMATION FOR SEQ ID NO:2539:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2539:

UUUACCCUCC ACGCCUC                                  17

( 2 ) INFORMATION FOR SEQ ID NO:2540:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2540:

ACCAAUGACU GAUGAGGCCG AAAGGCCGAA AGGCGUGG        38

( 2 ) INFORMATION FOR SEQ ID NO:2541:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2541:

CCACGCCUCU CAUUGGU                                  17

( 2 ) INFORMATION FOR SEQ ID NO:2542:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2542:

UGACCAAUCU GAUGAGGCCG AAAGGCCGAA AGAGGCGU        38

( 2 ) INFORMATION FOR SEQ ID NO:2543:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2543:

ACGCCUCUCA UUGGUCA 17

( 2 ) INFORMATION FOR SEQ ID NO:2544:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2544:

UUGUGACCCU GAUGAGGCCG AAAGGCCGAA AUGAGAGG 38

( 2 ) INFORMATION FOR SEQ ID NO:2545:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2545:

CCUCUCAUUG GUCACAA 17

( 2 ) INFORMATION FOR SEQ ID NO:2546:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2546:

CAGUUUGUCU GAUGAGGCCG AAAGGCCGAA ACCAAUGA 38

( 2 ) INFORMATION FOR SEQ ID NO:2547:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2547:

UCAUUGGUCA CAAACUG 17

( 2 ) INFORMATION FOR SEQ ID NO:2548:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2548:

GUCUCGGUCU GAUGAGGCCG AAAGGCCGAA ACACGGUG 38

( 2 ) INFORMATION FOR SEQ ID NO:2549:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2549:

CACCGUGUCA CCGAGAC                                                                                         17

(2) INFORMATION FOR SEQ ID NO:2550:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2550:

UUCCUUUUCU GAUGAGGCCG AAAGGCCGAA AGUUUUCA                                                                   38

(2) INFORMATION FOR SEQ ID NO:2551:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:2551:

UGAAAACUNA AAAGGAA                                                                                         17

(2) INFORMATION FOR SEQ ID NO:2552:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:2552:

UAAAGAUNCU GAUGAGGCCG AAAGGCCGAA AGUUUUCC                                                                   38

(2) INFORMATION FOR SEQ ID NO:2553:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:2553:

GGAAAACUCN AUCUUUA                                                                                         17

(2) INFORMATION FOR SEQ ID NO:2554:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:

-continued (D) OTHER INFORMATION: The letter "N" stands for any base.

(x i) SEQUENCE DESCRIPTION: SEQ ID NO:2554:

GUUCUAAACU GAUGAGGCCG AAAGGCCGAA AUNGAGUU                    38

(2) INFORMATION FOR SEQ ID NO:2555:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i x) FEATURE:
        (D) OTHER INFORMATION: The letter "N" stands for any base.

(x i) SEQUENCE DESCRIPTION: SEQ ID NO:2555:

AACUCNAUCU UUAGAAC                                           17

(2) INFORMATION FOR SEQ ID NO:2556:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i x) FEATURE:
        (D) OTHER INFORMATION: The letter "N" stands for any base.

(x i) SEQUENCE DESCRIPTION: SEQ ID NO:2556:

GAGUUCUACU GAUGAGGCCG AAAGGCCGAA AGAUNGAG                    38

(2) INFORMATION FOR SEQ ID NO:2557:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i x) FEATURE:
        (D) OTHER INFORMATION: The letter "N" stands for any base.

(x i) SEQUENCE DESCRIPTION: SEQ ID NO:2557:

CUCNAUCUUU AGAACUC                                           17

(2) INFORMATION FOR SEQ ID NO:2558:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i x) FEATURE:
        (D) OTHER INFORMATION: The letter "N" stands for any base.

(x i) SEQUENCE DESCRIPTION: SEQ ID NO:2558:

GGAGUUCUCU GAUGAGGCCG AAAGGCCGAA AAGAUNGA                    38

(2) INFORMATION FOR SEQ ID NO:2559:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i x) FEATURE:

( D ) OTHER INFORMATION: The letter "N" stands for any base.

( x i ) SEQUENCE DESCRIPTION: SEQ ID NO:2559:

UCNAUCUUUA GAACUCC 17

( 2 ) INFORMATION FOR SEQ ID NO:2560:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2560:

UGGAGUUCCU GAUGAGGCCG AAAGGCCGAA AAAGAUNG 38

( 2 ) INFORMATION FOR SEQ ID NO:2561:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2561:

CNAUCUUUAG AACUCCA 17

( 2 ) INFORMATION FOR SEQ ID NO:2562:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2562:

GAUAGCUGCU GAUGAGGCCG AAAGGCCGAA AGUUCUAA 38

( 2 ) INFORMATION FOR SEQ ID NO:2563:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2563:

UUAGAACUCC AGCUAUC 17

( 2 ) INFORMATION FOR SEQ ID NO:2564:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2564:

CCUUUUGACU GAUGAGGCCG AAAGGCCGAA AGCUGGAG 38

( 2 ) INFORMATION FOR SEQ ID NO:2565:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:2565:

CUCCAGCUAU CAAAAGG                                                                 17

( 2 ) INFORMATION FOR SEQ ID NO:2566:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for any base.

( x i ) SEQUENCE DESCRIPTION: SEQ ID NO:2566:

NACCUUUUCU GAUGAGGCCG AAAGGCCGAA AUAGCUGG                                           38

( 2 ) INFORMATION FOR SEQ ID NO:2567:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for any base.

( x i ) SEQUENCE DESCRIPTION: SEQ ID NO:2567:

CCAGCUAUCA AAAGGUN                                                                 17

( 2 ) INFORMATION FOR SEQ ID NO:2568:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2568:

CGAGGAUUCU GAUGAGGCCG AAAGGCCGAA ACCUUUUG                                           38

( 2 ) INFORMATION FOR SEQ ID NO:2569:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for any base.

( x i ) SEQUENCE DESCRIPTION: SEQ ID NO:2569:

CAAAAGGUNA AUCCUCG                                                                 17

( 2 ) INFORMATION FOR SEQ ID NO:2570:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear -continued ( i x ) FEATURE:
        ( D ) OTHER INFORMATION: The letter "N"stands for any base.

( x i ) SEQUENCE DESCRIPTION: SEQ ID NO:2570:

CUUUCGAGCU GAUGAGGCCG AAAGGCCGAA AUUNACCU        38

( 2 ) INFORMATION FOR SEQ ID NO:2571:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2571:

AGGUNAAUCC UCGAAAG        17

( 2 ) INFORMATION FOR SEQ ID NO:2572:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2572:

GAGCUUUCCU GAUGAGGCCG AAAGGCCGAA AGGAUUNA        38

( 2 ) INFORMATION FOR SEQ ID NO:2573:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2573:

UNAAUCCUCG AAAGCUC        17

( 2 ) INFORMATION FOR SEQ ID NO:2574:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2574:

UUCUGGGACU GAUGAGGCCG AAAGGCCGAA AGCUUUCG        38

( 2 ) INFORMATION FOR SEQ ID NO:2575:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2575:

CGAAAGCUCU CCCAGAA        17

( 2 ) INFORMATION FOR SEQ ID NO:2576:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2576:

AGUUCUGGCU GAUGAGGCCG AAAGGCCGAA AGAGCUUU    38

( 2 ) INFORMATION FOR SEQ ID NO:2577:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2577:

AAAGCUCUCC CAGAACU    17

( 2 ) INFORMATION FOR SEQ ID NO:2578:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2578:

UGGUGUGGCU GAUGAGGCCG AAAGGCCGAA AGUUCUGG    38

( 2 ) INFORMATION FOR SEQ ID NO:2579:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2579:

CCAGAACUCC CACACCA    17

( 2 ) INFORMATION FOR SEQ ID NO:2580:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2580:

CAUGUUUGCU GAUGAGGCCG AAAGGCCGAA AUGGUGUG    38

( 2 ) INFORMATION FOR SEQ ID NO:2581:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2581:

CACACCAUUC AAACAUG    17

( 2 ) INFORMATION FOR SEQ ID NO:2582:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2582:

GCAUGUUUCU GAUGAGGCCG AAAGGCCGAA AAUGGUGU      38

( 2 ) INFORMATION FOR SEQ ID NO:2583:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2583:

ACACCAUUCA AACAUGC      17

( 2 ) INFORMATION FOR SEQ ID NO:2584:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2584:

AAUUUCUUCU GAUGAGGCCG AAAGGCCGAA AGCUGCCA      38

( 2 ) INFORMATION FOR SEQ ID NO:2585:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2585:

UGGCAGCUCA AGAAAUU      17

( 2 ) INFORMATION FOR SEQ ID NO:2586:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2586:

CCGUAUUUCU GAUGAGGCCG AAAGGCCGAA AUUUCUUG      38

( 2 ) INFORMATION FOR SEQ ID NO:2587:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2587:

CAAGAAAUUA AAUACGG      17

( 2 ) INFORMATION FOR SEQ ID NO:2588:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2588:

ACCGUAUUCU GAUGAGGCCG AAAGGCCGAA AAUUUCUU 38

( 2 ) INFORMATION FOR SEQ ID NO:2589:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2589:

AAGAAAUUAA AUACGGU 17

( 2 ) INFORMATION FOR SEQ ID NO:2590:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2590:

GGGGACCGCU GAUGAGGCCG AAAGGCCGAA AUUUAAUU 38

( 2 ) INFORMATION FOR SEQ ID NO:2591:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2591:

AAUUAAAUAC GGUCCCC 17

( 2 ) INFORMATION FOR SEQ ID NO:2592:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2592:

CUUCAGGGCU GAUGAGGCCG AAAGGCCGAA ACCGUAUU 38

( 2 ) INFORMATION FOR SEQ ID NO:2593:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2593:

AAUACGGUCC CCUGAAG 17

( 2 ) INFORMATION FOR SEQ ID NO:2594:

( i ) SEQUENCE CHARACTERISTICS:
    ( A ) LENGTH: 38 base pairs (B) TYPE: nucleic acid
            (C) STRANDEDNESS: single
            (D) TOPOLOGY: linear (ix) FEATURE:
            (D) OTHER INFORMATION: The letter "N"stands for any base.

(xi) SEQUENCE DESCRIPTION: SEQ ID NO:2594:

GUCUNAGGCU GAUGAGGCCG AAAGGCCGAA AGCAUCUU                                    38

(2) INFORMATION FOR SEQ ID NO:2595:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ix) FEATURE:
            (D) OTHER INFORMATION: The letter "N"stands for any base.

(xi) SEQUENCE DESCRIPTION: SEQ ID NO:2595:

AAGAUGCUAC CUNAGAC                                                           17

(2) INFORMATION FOR SEQ ID NO:2596:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ix) FEATURE:
            (D) OTHER INFORMATION: The letter "N"stands for any base.

(xi) SEQUENCE DESCRIPTION: SEQ ID NO:2596:

GGGGGUCUCU GAUGAGGCCG AAAGGCCGAA AGGUAGCA                                    38

(2) INFORMATION FOR SEQ ID NO:2597:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ix) FEATURE:
            (D) OTHER INFORMATION: The letter "N"stands for any base.

(xi) SEQUENCE DESCRIPTION: SEQ ID NO:2597:

UGCUACCUNA GACCCCC                                                           17

(2) INFORMATION FOR SEQ ID NO:2598:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ix) FEATURE:
            (D) OTHER INFORMATION: The letter "N"stands for any base.

(xi) SEQUENCE DESCRIPTION: SEQ ID NO:2598:

CUACAUNACU GAUGAGGCCG AAAGGCCGAA AGGGGGUC                                    38

(2) INFORMATION FOR SEQ ID NO:2599:

(i) SEQUENCE CHARACTERISTICS:
            (A) LENGTH: 17 base pairs (B) TYPE: nucleic acid
(C) STRANDEDNESS: single
(D) TOPOLOGY: linear (ix) FEATURE:
(D) OTHER INFORMATION: The letter "N" stands for any base.

(xi) SEQUENCE DESCRIPTION: SEQ ID NO:2599:

GACCCCCUNU NAUGUAG 17

(2) INFORMATION FOR SEQ ID NO:2600:

(i) SEQUENCE CHARACTERISTICS:
(A) LENGTH: 38 base pairs
(B) TYPE: nucleic acid
(C) STRANDEDNESS: single
(D) TOPOLOGY: linear (ix) FEATURE:
(D) OTHER INFORMATION: The letter "N" stands for any base.

(xi) SEQUENCE DESCRIPTION: SEQ ID NO:2600:

NACUACAUCU GAUGAGGCCG AAAGGCCGAA ANAGGGGG 38

(2) INFORMATION FOR SEQ ID NO:2601:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(D) OTHER INFORMATION: The letter "N" stands for any base.

(xi) SEQUENCE DESCRIPTION: SEQ ID NO:2601:

CCCCCUNUNA UGUAGUN 17

(2) INFORMATION FOR SEQ ID NO:2602:

(i) SEQUENCE CHARACTERISTICS:
(A) LENGTH: 38 base pairs
(B) TYPE: nucleic acid
(C) STRANDEDNESS: single
(D) TOPOLOGY: linear (ix) FEATURE:
(D) OTHER INFORMATION: The letter "N" stands for any base.

(xi) SEQUENCE DESCRIPTION: SEQ ID NO:2602:

UNUNNNACCU GAUGAGGCCG AAAGGCCGAA ACAUNANA 38

(2) INFORMATION FOR SEQ ID NO:2603:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(D) OTHER INFORMATION: The letter "N" stands for any base.

(xi) SEQUENCE DESCRIPTION: SEQ ID NO:2603:

UNUNAUGUAG UNNNANA 17

(2) INFORMATION FOR SEQ ID NO:2604:

(i) SEQUENCE CHARACTERISTICS:
(A) LENGTH: 38 base pairs (B) TYPE: nucleic acid
              (C) STRANDEDNESS: single
              (D) TOPOLOGY: linear (ix) FEATURE:
              (D) OTHER INFORMATION: The letter "N" stands for any base.

(xi) SEQUENCE DESCRIPTION: SEQ ID NO:2604:

AGGUNUNNCU GAUGAGGCCG AAAGGCCGAA ACUACAUN                                                    38

(2) INFORMATION FOR SEQ ID NO:2605:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ix) FEATURE:
              (D) OTHER INFORMATION: The letter "N" stands for any base.

(xi) SEQUENCE DESCRIPTION: SEQ ID NO:2605:

NAUGUAGUNN NANACCU                                                                           17

(2) INFORMATION FOR SEQ ID NO:2606:

(i) SEQUENCE CHARACTERISTICS:
              (A) LENGTH: 38 base pairs
              (B) TYPE: nucleic acid
              (C) STRANDEDNESS: single
              (D) TOPOLOGY: linear (ix) FEATURE:
              (D) OTHER INFORMATION: The letter "N" stands for any base.

(xi) SEQUENCE DESCRIPTION: SEQ ID NO:2606:

ACAUCNUGCU GAUGAGGCCG AAAGGCCGAA AGGUNUNN                                                    38

(2) INFORMATION FOR SEQ ID NO:2607:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ix) FEATURE:
              (D) OTHER INFORMATION: The letter "N" stands for any base.

(xi) SEQUENCE DESCRIPTION: SEQ ID NO:2607:

NNANACCUNC ANGAUGU                                                                           17

(2) INFORMATION FOR SEQ ID NO:2608:

(i) SEQUENCE CHARACTERISTICS:
              (A) LENGTH: 54 base pairs
              (B) TYPE: nucleic acid
              (C) STRANDEDNESS: single
              (D) TOPOLOGY: linear (xi) SEQUENCE DESCRIPTION: SEQ ID NO:2608:

GCGCUUCGAG AAGUAUUUAC CAGAGAAACA CACGUUGUGG UACAUUACCU GGUA                                  54

(2) INFORMATION FOR SEQ ID NO:2609:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (x i) SEQUENCE DESCRIPTION: SEQ ID NO:2609:

AAAUACGGUC CGAAGCGC                                                                                                    18

(2) INFORMATION FOR SEQ ID NO:2610:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (x i) SEQUENCE DESCRIPTION: SEQ ID NO:2610:

UUCUGCCCAG AAGUUCCAC CAGAGAAACA CACGUUGUGG UACAUUACCU GGUA                                                              54

(2) INFORMATION FOR SEQ ID NO:2611:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (x i) SEQUENCE DESCRIPTION: SEQ ID NO:2611:

GGAAACAGAU GGGCAGAA                                                                                                    18

(2) INFORMATION FOR SEQ ID NO:2612:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (x i) SEQUENCE DESCRIPTION: SEQ ID NO:2612:

UUUUCACAAG AAGGUCUCAC CAGAGAAACA CACGUUGUGG UACAUUACCU GGUA                                                             54

(2) INFORMATION FOR SEQ ID NO:2613:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (x i) SEQUENCE DESCRIPTION: SEQ ID NO:2613:

GAGACCAGAC UGUGAAAA                                                                                                    18

(2) INFORMATION FOR SEQ ID NO:2614:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (x i) SEQUENCE DESCRIPTION: SEQ ID NO:2614:

AUUUCUUGAG AAGCCAGGAC CAGAGAAACA CACGUUGUGG UACAUUACCU GGUA                                                             54

(2) INFORMATION FOR SEQ ID NO:2615:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (x i) SEQUENCE DESCRIPTION: SEQ ID NO:2615:

CCUGGCAGCU CAAGAAAU                                                                                      18

(2) INFORMATION FOR SEQ ID NO:2616:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2616:

CUUCAGGGAG AAGUAUUUAC CAGAGAAACA CACGUUGUGG UACAUUACCU GGUA              54

(2) INFORMATION FOR SEQ ID NO:2617:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2617:

AAAUACGGUC CCCUGAAG                                                                                      18

(2) INFORMATION FOR SEQ ID NO:2618:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ix) FEATURE:
        (D) OTHER INFORMATION: The letter "N"stands for any
            base. The letter "H"stands for
            A, U, or C.

(xi) SEQUENCE DESCRIPTION: SEQ ID NO:2618:

NNNNUHNNNN N                                                                                             11

(2) INFORMATION FOR SEQ ID NO:2619:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (D) OTHER INFORMATION: The letter "N"stands for any base.

(xi) SEQUENCE DESCRIPTION: SEQ ID NO:2619:

NNNNCUGAN GAGNNNNNNC GAAANNNN                                                                            28

(2) INFORMATION FOR SEQ ID NO:2620:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (D) OTHER INFORMATION: The letter "N"stands for any
            base. The leter "Y"stands for
            U or C. The letter "H"stands
            for A, U, or C.

(xi) SEQUENCE DESCRIPTION: SEQ ID NO:2620:

NNNNNNNYNG HYNNN                                                                                    15

( 2 ) INFORMATION FOR SEQ ID NO:2621:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
            base. The letter "H"stands for
            A, U, or C.

( x i ) SEQUENCE DESCRIPTION: SEQ ID NO:2621:

NNNNGAAGNN NNNNNNNNA AAHANNNNN NACAUUACNN NNNNNNN                                                    47

( 2 ) INFORMATION FOR SEQ ID NO:2622:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2622:

UGGCCGGCAU GGUCCCAGCC UCCUCGCUGG CGCCGGCUGG GCAACAUUCC GAGGGGACCG                                    60

UCCCCUCGGU AAUGGCGAAU GGGAC                                                                         85

( 2 ) INFORMATION FOR SEQ ID NO:2623:

( i ) SEQUENCE CHARACTERISTICS:
        ( A ) LENGTH: 176 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2623:

GGGAAAGCUU GCGAAGGGCG UCGUCGCCCC GAGCGGUAGU AAGCAGGGAA CUCACCUCCA                                    60

AUUUCAGUAC UGAAAUUGUC GUAGCAGUUG ACUACUGUUA UGUGAUUGGU AGAGGCUAAG                                    120

UGACGGUAUU GGCGUAAGUC AGUAUUGCAG CACAGCACAA GCCCGCUUGC GAGAAU                                        176

( 2 ) INFORMATION FOR SEQ ID NO:2624:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2624:

GGAGAAUUGG AAAAC                                                                                    15

( 2 ) INFORMATION FOR SEQ ID NO:2625:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2625:

GUUUUCCCUG AUGAGGCCGA AAGGCCGAAA AUCUCC                                                              36

( 2 ) INFORMATION FOR SEQ ID NO:2626:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:2626:

GGAGAAUUGG AAAAC 15

( 2 ) INFORMATION FOR SEQ ID NO:2627:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "H"stands for A, U or C.

( x i ) SEQUENCE DESCRIPTION: SEQ ID NO:2627:

GUUUUCCCUG AUGAGGCCGA AAGGCCGAAA UUCUCCH 37